(12) United States Patent
Bernett et al.

(10) Patent No.: US 10,787,518 B2
(45) Date of Patent: *Sep. 29, 2020

(54) BISPECIFIC CHECKPOINT INHIBITOR ANTIBODIES

(71) Applicant: Xencor, Inc., Monrovia, CA (US)

(72) Inventors: Matthew Bernett, Monrovia, CA (US);
Gregory Moore, Azusa, CA (US);
John Desjarlais, Pasadena, CA (US);
Michael Hedvat, Encino, CA (US);
Christine Bonzon, Los Angeles, CA (US); Alex Nisthal, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/623,314

(22) Filed: Jun. 14, 2017

(65) Prior Publication Data

US 2018/0118836 A1 May 3, 2018

Related U.S. Application Data

(60) Provisional application No. 62/350,145, filed on Jun. 14, 2016, provisional application No. 62/353,511, filed on Jun. 22, 2016, provisional application No. 62/420,500, filed on Nov. 10, 2016.

(51) Int. Cl.
| | |
|---|---|
| *C07K 16/20* | (2006.01) |
| *C07K 16/30* | (2006.01) |
| *C07K 16/40* | (2006.01) |
| *C07K 16/28* | (2006.01) |
| *C07K 14/735* | (2006.01) |
| *C12N 15/861* | (2006.01) |
| *A61K 39/00* | (2006.01) |
| *A61P 35/00* | (2006.01) |

(52) U.S. Cl.
CPC .... *C07K 16/2863* (2013.01); *C07K 14/70535* (2013.01); *C07K 16/2803* (2013.01); *C07K 16/2818* (2013.01); *C12N 15/8613* (2013.01); *A61K 2039/505* (2013.01); *A61K 2039/572* (2013.01); *A61P 35/00* (2018.01); *C07K 2317/24* (2013.01); *C07K 2317/31* (2013.01); *C07K 2317/33* (2013.01); *C07K 2317/34* (2013.01); *C07K 2317/524* (2013.01); *C07K 2317/526* (2013.01); *C07K 2317/53* (2013.01); *C07K 2317/55* (2013.01); *C07K 2317/569* (2013.01); *C07K 2317/622* (2013.01); *C07K 2317/64* (2013.01); *C07K 2317/70* (2013.01); *C07K 2317/71* (2013.01); *C07K 2317/73* (2013.01); *C07K 2317/76* (2013.01); *C07K 2317/92* (2013.01); *C07K 2317/94* (2013.01)

(58) Field of Classification Search
CPC .................................................. C07K 16/2863
USPC ................. 424/133.1, 136.1, 178.1
See application file for complete search history.

(56) References Cited

U.S. PATENT DOCUMENTS

| | | | |
|---|---|---|---|
| 3,773,919 | A | 11/1973 | Boswell et al. |
| 4,169,888 | A | 11/1979 | Hanka et al. |
| 4,179,337 | A | 12/1979 | Davis et al. |
| 4,256,746 | A | 3/1981 | Miyashita et al. |
| 4,294,757 | A | 10/1981 | Asai |
| 4,301,144 | A | 11/1981 | Iwashita et al. |
| 4,307,016 | A | 12/1981 | Asai et al. |
| 4,313,946 | A | 2/1982 | Powell et al. |
| 4,315,929 | A | 2/1982 | Freedman et al. |
| 4,364,935 | A | 2/1982 | Kung et al. |
| 4,322,348 | A | 3/1982 | Asai et al. |
| 4,331,598 | A | 5/1982 | Hasegawa et al. |
| 4,361,650 | A | 5/1982 | Hasegawa et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,880,935 | A | 11/1989 | Thorpe |
| 4,923,990 | A | 5/1990 | Nakano et al. |
| 4,943,533 | A | 7/1990 | Mendelsohn et al. |
| 4,970,198 | A | 11/1990 | Lee et al. |

(Continued)

FOREIGN PATENT DOCUMENTS

| | | |
|---|---|---|
| EP | 0425235 B1 | 9/1996 |
| EP | 1752471 | 2/2007 |

(Continued)

OTHER PUBLICATIONS

Sun et al., Anti-CD20/CD3 T cell-dependent bispecific antibody for the treatment of B cell malignancies., Science Translational Medicine May 13, 2015: vol. 7, Issue 287, pp. 287ra70DOI: 10.1126/scitranslmed.aaa480.

(Continued)

*Primary Examiner* — Lynn A Bristol

(74) *Attorney, Agent, or Firm* — Louis T. Nguyen; Robin M. Silva; Morgan, Lewis & Bockius LLP

(57) ABSTRACT

The present invention is directed to compositions that include programmed cell death 1 (PD-1) binding domains and antibodies that include such PD-1 binding domains. Also provided are nucleic acid compositions that encode the binding domains and antibodies, expression vector compositions that include the nucleic acids, and host cells that include the expression vector compositions.

19 Claims, 196 Drawing Sheets

Specification includes a Sequence Listing.

(56) References Cited

U.S. PATENT DOCUMENTS

| | | |
|---|---|---|
| 5,053,394 A | 10/1991 | Ellestad et al. |
| 5,070,092 A | 12/1991 | Kanda et al. |
| 5,084,468 A | 1/1992 | Saito et al. |
| 5,101,038 A | 3/1992 | Nakano et al. |
| 5,122,368 A | 6/1992 | Greenfield et al. |
| 5,187,186 A | 2/1993 | Kanda et al. |
| 5,208,020 A | 5/1993 | Chari et al. |
| 5,264,586 A | 11/1993 | Nicolaou et al. |
| 5,384,412 A | 1/1995 | Nicolaou et al. |
| 5,416,064 A | 5/1995 | Chari et al. |
| 5,475,092 A | 12/1995 | Chari et al. |
| 5,500,362 A | 3/1996 | Robinson et al. |
| 5,530,101 A | 6/1996 | Queen et al. |
| 5,541,087 A | 7/1996 | Lo et al. |
| 5,550,246 A | 8/1996 | Nicolaou et al. |
| 5,558,864 A | 9/1996 | Bendig et al. |
| 5,585,089 A | 12/1996 | Queen et al. |
| 5,585,097 A | 12/1996 | Bolt et al. |
| 5,585,499 A | 12/1996 | Chari et al. |
| 5,622,929 A | 4/1997 | Willner et al. |
| 5,635,483 A | 6/1997 | Pettit et al. |
| 5,641,780 A | 6/1997 | Amishiro et al. |
| 5,663,149 A | 9/1997 | Pettit et al. |
| 5,677,171 A | 10/1997 | Hudziak et al. |
| 5,693,761 A | 12/1997 | Queen et al. |
| 5,693,762 A | 12/1997 | Queen et al. |
| 5,703,080 A | 12/1997 | Nakakura et al. |
| 5,712,374 A | 1/1998 | Kuntsmann et al. |
| 5,714,586 A | 2/1998 | Kuntsmann et al. |
| 5,726,044 A | 3/1998 | Lo et al. |
| 5,731,168 A | 3/1998 | Carter et al. |
| 5,736,137 A | 4/1998 | Anderson et al. |
| 5,739,116 A | 4/1998 | Hamann et al. |
| 5,767,237 A | 6/1998 | Sakakibara et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,807,706 A | 9/1998 | Carter et al. |
| 5,892,020 A | 4/1999 | Mezes et al. |
| 5,945,311 A | 8/1999 | Lindhofer et al. |
| 5,968,509 A | 10/1999 | Gorman et al. |
| 6,054,297 A | 4/2000 | Carter et al. |
| 6,071,515 A | 6/2000 | Mezes et al. |
| 6,124,431 A | 9/2000 | Sakakibara et al. |
| 6,180,370 B1 | 1/2001 | Queen et al. |
| 6,214,345 B1 | 4/2001 | Firestone et al. |
| 6,235,883 B1 | 5/2001 | Jakobovits et al. |
| 6,329,507 B1 | 12/2001 | Mezes et al. |
| 6,407,213 B1 | 6/2002 | Carter et al. |
| 6,441,163 B1 | 8/2002 | Chari et al. |
| 6,455,677 B1 | 9/2002 | Park et al. |
| 6,506,883 B2 | 4/2003 | Mateo de Acosta del Rio et al. |
| 6,602,684 B1 | 8/2003 | Umana et al. |
| 6,632,927 B2 | 10/2003 | Adair et al. |
| 6,706,265 B1 | 3/2004 | Bolt et al. |
| 6,716,410 B1 | 4/2004 | Witztum |
| 6,723,538 B2 | 4/2004 | Mack et al. |
| 6,884,869 B2 | 4/2005 | Senter et al. |
| 6,989,452 B2 | 1/2006 | Ng et al. |
| 7,087,600 B2 | 8/2006 | Ng et al. |
| 7,112,324 B1 | 9/2006 | Dorken et al. |
| 7,129,261 B2 | 10/2006 | Ng et al. |
| 7,276,497 B2 | 10/2007 | Chari et al. |
| 7,303,749 B1 | 12/2007 | Chari |
| 7,368,565 B2 | 5/2008 | Chari et al. |
| 7,498,302 B2 | 3/2009 | Ng et al. |
| 7,507,420 B2 | 3/2009 | Ng et al. |
| 7,517,903 B2 | 4/2009 | Chen et al. |
| 7,601,354 B2 | 10/2009 | Chari |
| 7,642,228 B2 | 1/2010 | Carter et al. |
| 7,691,962 B2 | 4/2010 | Boyd et al. |
| 7,695,936 B2 | 4/2010 | Carter et al. |
| 7,696,338 B2 | 4/2010 | Neville, Jr. et al. |
| 7,728,114 B2 | 6/2010 | Mach et al. |
| 8,063,187 B2 | 11/2011 | Chu et al. |
| 8,114,967 B2 | 2/2012 | Bhatt et al. |
| 8,216,805 B2 | 7/2012 | Carter et al. |
| 8,236,308 B2 | 8/2012 | Kischel et al. |
| 8,309,690 B2 | 11/2012 | Allan et al. |
| 8,367,805 B2 | 2/2013 | Chamberlain et al. |
| 8,409,568 B2 | 4/2013 | Gao et al. |
| 8,592,562 B2 | 11/2013 | Kannan et al. |
| 8,637,641 B2 | 1/2014 | Dahiyat et al. |
| 8,946,387 B2 | 2/2015 | Koenig et al. |
| 9,822,181 B2 | 11/2017 | Bonvini et al. |
| 9,856,327 B2 | 1/2018 | Bernett et al. |
| 2001/0035606 A1 | 11/2001 | Schoen |
| 2002/0076406 A1 | 6/2002 | Leung |
| 2002/0103345 A1 | 8/2002 | Zhu |
| 2002/0131968 A1 | 9/2002 | Waldmann et al. |
| 2003/0003097 A1 | 1/2003 | Reff et al. |
| 2003/0017979 A1 | 1/2003 | Mack et al. |
| 2003/0091561 A1 | 5/2003 | Van de Winekl |
| 2003/0223999 A1 | 12/2003 | Lindhofer |
| 2004/0018191 A1 | 1/2004 | Wang |
| 2004/0071696 A1 | 4/2004 | Adams et al. |
| 2004/0162411 A1 | 8/2004 | Lanzavecchia |
| 2004/0170626 A1 | 9/2004 | Schuurman |
| 2004/0242851 A1 | 12/2004 | Zhu |
| 2005/0114037 A1 | 5/2005 | Desjarlais et al. |
| 2005/0136050 A1 | 6/2005 | Kufer et al. |
| 2005/0142133 A1 | 6/2005 | Lazar et al. |
| 2005/0176028 A1 | 8/2005 | Hofmeiser et al. |
| 2005/0191702 A1 | 9/2005 | Mack et al. |
| 2005/0238648 A1 | 10/2005 | Jacobs |
| 2005/0238649 A1 | 10/2005 | Doronina |
| 2006/0008883 A1 | 1/2006 | Lazar |
| 2006/0018897 A1 | 1/2006 | Lee et al. |
| 2006/0024298 A1 | 2/2006 | Lazar et al. |
| 2006/0024317 A1 | 2/2006 | Boyd |
| 2006/0073142 A1 | 4/2006 | Chan et al. |
| 2006/0074008 A1 | 4/2006 | Senter |
| 2006/0115481 A1 | 6/2006 | Lindhofer et al. |
| 2006/0121032 A1 | 6/2006 | Dahiyat et al. |
| 2006/0134105 A1 | 6/2006 | Lazar et al. |
| 2006/0235208 A1 | 10/2006 | Lazar |
| 2007/0071675 A1 | 3/2007 | Wu et al. |
| 2007/0105199 A1 | 5/2007 | Yan et al. |
| 2007/0123479 A1 | 5/2007 | Kufer et al. |
| 2007/0148170 A1 | 6/2007 | Desjarlais |
| 2007/0287170 A1 | 12/2007 | Davis et al. |
| 2008/0044413 A1 | 2/2008 | Hammond et al. |
| 2008/0050370 A1 | 2/2008 | Glaser et al. |
| 2008/0138335 A1 | 6/2008 | Takahashi et al. |
| 2008/0213273 A1 | 9/2008 | Burge |
| 2008/0219974 A1 | 9/2008 | Bernett et al. |
| 2008/0242845 A1 | 10/2008 | Lazar et al. |
| 2009/0082213 A1 | 3/2009 | Horowitz et al. |
| 2009/0136485 A1 | 5/2009 | Chu et al. |
| 2009/0163699 A1 | 6/2009 | Desjarlais |
| 2009/0214539 A1 | 8/2009 | Grosmaire et al. |
| 2009/0252683 A1 | 10/2009 | Kischel et al. |
| 2009/0252729 A1 | 10/2009 | Farrington et al. |
| 2009/0274692 A1 | 11/2009 | Tan et al. |
| 2009/0311253 A1 | 12/2009 | Ghayur et al. |
| 2009/0317869 A1 | 12/2009 | Senter |
| 2010/0004431 A1 | 1/2010 | Bernett et al. |
| 2010/0015133 A1 | 1/2010 | Igawa et al. |
| 2010/0080814 A1 | 4/2010 | Desjarlais et al. |
| 2010/0150918 A1 | 6/2010 | Kufer et al. |
| 2010/0174053 A1 | 7/2010 | Johnson et al. |
| 2010/0178298 A1 | 7/2010 | Lindhofer |
| 2010/0183554 A1 | 7/2010 | Mach et al. |
| 2010/0226925 A1 | 9/2010 | Dillon et al. |
| 2010/0239567 A1 | 9/2010 | Esue |
| 2010/0239582 A1 | 9/2010 | Humphreys et al. |
| 2010/0256339 A1 | 10/2010 | Bossenmaier et al. |
| 2010/0256340 A1 | 10/2010 | Brinkmann et al. |
| 2010/0298542 A1 | 11/2010 | Igawa et al. |
| 2010/0322933 A1 | 12/2010 | Lindhofer et al. |
| 2010/0330089 A1 | 12/2010 | Damle et al. |
| 2010/0331527 A1 | 12/2010 | Davis et al. |

(56) References Cited

U.S. PATENT DOCUMENTS

| | | |
|---|---|---|
| 2011/0054151 A1 | 3/2011 | Lazar et al. |
| 2011/0076275 A1 | 3/2011 | Senter |
| 2011/0177500 A1 | 7/2011 | Winther et al. |
| 2011/0189178 A1 | 8/2011 | Desjarlais et al. |
| 2011/0189209 A1 | 8/2011 | Neville, Jr. et al. |
| 2011/0201032 A1 | 8/2011 | Zeng et al. |
| 2011/0217302 A1 | 9/2011 | Odegard et al. |
| 2011/0262439 A1 | 10/2011 | Kufer et al. |
| 2011/0275787 A1 | 11/2011 | Kufer et al. |
| 2011/0293619 A1 | 12/2011 | Kufer et al. |
| 2012/0028304 A1 | 2/2012 | Dahiyat et al. |
| 2012/0034228 A1 | 2/2012 | Kufer et al. |
| 2012/0121597 A1 | 5/2012 | Ho et al. |
| 2012/0149876 A1 | 6/2012 | Von Kreudenstein et al. |
| 2012/0156207 A1 | 6/2012 | Chu et al. |
| 2012/0251531 A1 | 10/2012 | Baehner et al. |
| 2012/0251541 A1 | 10/2012 | Baurin et al. |
| 2013/0089541 A1 | 4/2013 | D'Angelo et al. |
| 2013/0095097 A1 | 4/2013 | Blakenship et al. |
| 2013/0101586 A1 | 4/2013 | Riegler et al. |
| 2013/0115208 A1 | 5/2013 | Ho et al. |
| 2013/0129723 A1 | 5/2013 | Blakenship et al. |
| 2013/0142793 A1 | 6/2013 | Ledbetter et al. |
| 2013/0171095 A1 | 7/2013 | Bernett et al. |
| 2013/0195849 A1 | 8/2013 | Von Kreudenstein et al. |
| 2013/0209355 A1 | 8/2013 | De Weers et al. |
| 2013/0267686 A1 | 10/2013 | Brinkmann |
| 2013/0336981 A1 | 12/2013 | de Kruif et al. |
| 2014/0024111 A1 | 1/2014 | Kannan et al. |
| 2014/0056879 A1 | 2/2014 | Lazar |
| 2014/0072581 A1 | 3/2014 | Dixit et al. |
| 2014/0086916 A1 | 3/2014 | Zha |
| 2014/0212435 A1 | 7/2014 | Moore et al. |
| 2014/0212436 A1 | 7/2014 | Moore et al. |
| 2014/0249297 A1 | 9/2014 | Lazar et al. |
| 2014/0288275 A1 | 9/2014 | Moore et al. |
| 2014/0294759 A1 | 10/2014 | Chu et al. |
| 2014/0294823 A1 | 10/2014 | Moore et al. |
| 2014/0294833 A1 | 10/2014 | Desjarlais et al. |
| 2014/0294835 A1 | 10/2014 | Moore et al. |
| 2014/0294836 A1 | 10/2014 | Chu et al. |
| 2014/0302064 A1 | 10/2014 | Moore |
| 2014/0322217 A1 | 10/2014 | Moore et al. |
| 2014/0356381 A1 | 12/2014 | Moore et al. |
| 2014/0363426 A1 | 12/2014 | Moore et al. |
| 2014/0370013 A1 | 12/2014 | Desjarlais et al. |
| 2014/0370020 A1 | 12/2014 | Kuramochi et al. |
| 2014/0377269 A1 | 12/2014 | Mabry et al. |
| 2014/0377270 A1 | 12/2014 | Moore et al. |
| 2015/0071948 A1 | 3/2015 | Lazar et al. |
| 2015/0307629 A1 | 10/2015 | Bernett et al. |
| 2016/0060360 A1 | 3/2016 | Moore et al. |
| 2016/0068588 A1 | 3/2016 | Bernett et al. |
| 2016/0176969 A1 | 6/2016 | Bernett et al. |
| 2016/0215063 A1 | 7/2016 | Bernett et al. |
| 2016/0229924 A1 | 8/2016 | Bernett et al. |
| 2017/0020963 A1 | 1/2017 | Qu et al. |
| 2018/0118828 A1* | 5/2018 | Bernett ............ A61P 35/00 |
| 2018/0127501 A1* | 5/2018 | Bernett ............ C07K 16/2818 |
| 2019/0270816 A1* | 9/2019 | Bernett ............ A61P 37/06 |
| 2019/0382495 A1* | 12/2019 | Bernett ............ C07K 14/70535 |
| 2019/0389954 A1* | 12/2019 | Bernett ............ C07K 16/2863 |

FOREIGN PATENT DOCUMENTS

| | | |
|---|---|---|
| EP | 1829895 | 5/2007 |
| EP | 2006381 | 12/2008 |
| EP | 2009101 A1 | 12/2008 |
| EP | 2194066 | 6/2010 |
| EP | 2202245 A1 | 6/2010 |
| EP | 2522724 | 6/2011 |
| EP | 2155788 | 2/2014 |
| EP | 3252078 | 12/2017 |
| WO | WO8705330 | 9/1987 |
| WO | WO9211018 | 7/1992 |
| WO | WO9321232 | 10/1993 |
| WO | WO9413804 | 5/1994 |
| WO | WO9520045 | 1/1995 |
| WO | WO9640210 | 6/1996 |
| WO | WO96027011 | 9/1996 |
| WO | WO98050431 | 11/1998 |
| WO | WO199937791 | 7/1999 |
| WO | WO99054440 | 10/1999 |
| WO | WO99066951 | 12/1999 |
| WO | WO200061739 A1 | 10/2000 |
| WO | WO2011005621 | 1/2001 |
| WO | WO200124763 A2 | 4/2001 |
| WO | WO200129246 A1 | 4/2001 |
| WO | WO200162931 A1 | 8/2001 |
| WO | WO200188138 | 11/2001 |
| WO | WO2001083525 | 11/2001 |
| WO | WO2001090192 | 11/2001 |
| WO | WO200216368 | 2/2002 |
| WO | WO200230954 A1 | 4/2002 |
| WO | WO200231140 A1 | 4/2002 |
| WO | WO2002088172 A2 | 7/2002 |
| WO | WO2002062850 | 8/2002 |
| WO | WO2002083180 | 10/2002 |
| WO | WO2002098883 | 12/2002 |
| WO | WO2004010957 | 2/2004 |
| WO | WO2004043493 | 5/2004 |
| WO | WO2004103272 | 12/2004 |
| WO | WO2004106383 | 12/2004 |
| WO | WO2005063816 | 7/2005 |
| WO | WO2005112919 A2 | 12/2005 |
| WO | WO2005118635 | 12/2005 |
| WO | WO2006020258 | 2/2006 |
| WO | WO2006034488 | 3/2006 |
| WO | WO2006036834 | 4/2006 |
| WO | WO2006072620 | 7/2006 |
| WO | WO2006110476 A2 | 10/2006 |
| WO | WO2006106905 | 12/2006 |
| WO | WO2007005612 | 1/2007 |
| WO | WO2007018431 A2 | 2/2007 |
| WO | WO2007033230 | 3/2007 |
| WO | WO2007042261 | 4/2007 |
| WO | WO2007046006 | 4/2007 |
| WO | WO2007047829 | 4/2007 |
| WO | WO2007059404 A2 | 5/2007 |
| WO | WO2007062037 | 5/2007 |
| WO | WO2007084342 | 7/2007 |
| WO | WO2007089149 A2 | 8/2007 |
| WO | WO2007093630 | 8/2007 |
| WO | WO2007098934 | 9/2007 |
| WO | WO2007110205 | 10/2007 |
| WO | WO2007113648 | 10/2007 |
| WO | WO2007147901 | 12/2007 |
| WO | WO20070147901 | 12/2007 |
| WO | WO2008003103 | 1/2008 |
| WO | WO2008003115 | 1/2008 |
| WO | WO2008003116 | 1/2008 |
| WO | WO2008119096 | 10/2008 |
| WO | WO2008119566 | 10/2008 |
| WO | WO2008124858 | 10/2008 |
| WO | WO2008145142 | 12/2008 |
| WO | WO2008150494 | 12/2008 |
| WO | WO2009000006 | 12/2008 |
| WO | WO2009017394 A1 | 2/2009 |
| WO | WO2009017823 | 2/2009 |
| WO | WO2009030734 | 3/2009 |
| WO | WO2009032782 | 3/2009 |
| WO | WO2013180201 | 6/2009 |
| WO | WO2009086320 | 7/2009 |
| WO | WO2009089004 | 7/2009 |
| WO | WO2009106096 | 9/2009 |
| WO | WO2009106321 | 9/2009 |
| WO | WO2010028796 | 3/2010 |
| WO | WO2010033736 | 3/2010 |
| WO | WO2010034441 | 4/2010 |
| WO | WO2010037835 | 4/2010 |
| WO | WO2010042904 | 4/2010 |
| WO | WO2010062171 A2 | 6/2010 |
| WO | WO2010085682 | 7/2010 |
| WO | WO2010106180 | 9/2010 |

(56) References Cited

FOREIGN PATENT DOCUMENTS

| | | |
|---|---|---|
| WO | WO2010115551 | 10/2010 |
| WO | WO2010115552 | 10/2010 |
| WO | WO2010115553 | 10/2010 |
| WO | WO2010115589 | 10/2010 |
| WO | WO2010119119 | 10/2010 |
| WO | WO2011133886 | 10/2010 |
| WO | WO20100112193 | 10/2010 |
| WO | WO2010136172 | 12/2010 |
| WO | WO2010151792 | 12/2010 |
| WO | WO2010151808 | 12/2010 |
| WO | WO2011036183 | 3/2011 |
| WO | WO2011066342 | 3/2011 |
| WO | WO2011051307 | 5/2011 |
| WO | WO2011063348 | 5/2011 |
| WO | WO2011066501 | 6/2011 |
| WO | WO2011121110 | 10/2011 |
| WO | WO2011131746 | 10/2011 |
| WO | WO2011143545 | 11/2011 |
| WO | WO2012016227 | 2/2012 |
| WO | WO2012018687 | 2/2012 |
| WO | WO2012032080 | 3/2012 |
| WO | WO2012058768 | 5/2012 |
| WO | WO2012062596 | 5/2012 |
| WO | WO2012107417 | 8/2012 |
| WO | WO2012116453 | 9/2012 |
| WO | WO2012125495 | 9/2012 |
| WO | WO2012125850 | 9/2012 |
| WO | WO2012131555 | 10/2012 |
| WO | WO2012146394 | 11/2012 |
| WO | WO2012146628 | 11/2012 |
| WO | WO2012162067 | 11/2012 |
| WO | WO2013006544 | 1/2013 |
| WO | WO2013016714 | 1/2013 |
| WO | WO2013026833 | 2/2013 |
| WO | WO2013033008 | 3/2013 |
| WO | WO2013047748 | 4/2013 |
| WO | WO2013055809 | 4/2013 |
| WO | WO2013063702 | 5/2013 |
| WO | WO2013096828 | 6/2013 |
| WO | WO2013125667 | 8/2013 |
| WO | WO2013164694 | 11/2013 |
| WO | WO2014004586 | 1/2014 |
| WO | WO2014012085 | 1/2014 |
| WO | WO2014047231 | 3/2014 |
| WO | WO2014056783 | 4/2014 |
| WO | WO2014079000 | 5/2014 |
| WO | WO2014110601 | 7/2014 |
| WO | WO2014113510 | 7/2014 |
| WO | WO2014145806 | 9/2014 |
| WO | WO2014145907 | 9/2014 |
| WO | WO2014164553 | 10/2014 |
| WO | WO2014207064 | 12/2014 |
| WO | WO2014209804 | 12/2014 |
| WO | WO2015018528 | 2/2015 |
| WO | WO2015026892 | 2/2015 |
| WO | WO2015063339 | 5/2015 |
| WO | WO2015095392 | 6/2015 |
| WO | WO2015095410 | 6/2015 |
| WO | WO2015095423 | 6/2015 |
| WO | WO2015103072 | 7/2015 |
| WO | WO2015143079 | 9/2015 |
| WO | WO2015149077 | 10/2015 |
| WO | WO2016014984 | 1/2016 |
| WO | WO2016028896 | 2/2016 |
| WO | WO2016079050 | 5/2016 |
| WO | WO2016086186 | 6/2016 |
| WO | WO2016086189 | 6/2016 |
| WO | WO2016086196 | 6/2016 |
| WO | WO2016105450 | 6/2016 |
| WO | WO2016110584 | 7/2016 |
| WO | WO2016115274 | 7/2016 |
| WO | WO2016120789 | 8/2016 |
| WO | WO2016182751 | 11/2016 |
| WO | WO2017112775 | 6/2017 |
| WO | WO2017210485 | 12/2017 |
| WO | WO2017214092 | 12/2017 |
| WO | WO2018041838 | 3/2018 |
| WO | WO2019050521 | 3/2019 |

OTHER PUBLICATIONS

Capizzi et al., Curative chemotherapy for acute myeloid leukemia: the development of high-dose ara-C from the laboratory to bedside., Invest New Drugs. 1996;14(3):249-56.

Giles et al., Intravenous corticosteroids to reduce gemtuzumab ozogamicin infusion reactions. Ann Pharmacother. Sep. 2003;37(9):1182-5.

Duong et al., Targeted treatment of acute myeloid leukemia in older adults: role of gemtuzumab ozogamicin., Clin Interv Aging. 2009;4:197-205. Epub May 14, 2009.

Chu et al., Immunotherapy with Long-Lived Anti-CD123 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias, Blood 2014, 124:3111.

Muramatsu et al., Production and characterization of an active single-chain variable fragment antibody recognizing CD25., Cancer Lett. Jul. 28, 2005;225(2):225-36. Epub Jan. 23, 2005.

Sforzini et al., Targeting of saporin to Hodgkin's lymphoma cells by anti-CD30 and anti-CD25 bispecific antibodies., Br J Haematol. Sep. 1998;102(4):1061-8.

Sun et al., Preclinical Characterization of Combinability and Potential Synergy of Anti-CD20/CD3 T-Cell Dependent Bispecific Antibody with Chemotherapy and PD-1/PD-L1 Blockade., Blood 2016 128:4168.

Zhang et al., The development of bispecific antibodies and their applications in tumor immune escape., Experimental Hematology & Oncology20176:12.

Krupka et al., Blockade of the PD-1/PD-L1 axis augments lysis of AML cells by the CD33/CD3 BiTE antibody construct AMG 330: reversing a T-cell-induced immune escape mechanism., Leukemia. Feb. 2016;30(2):484-91. doi: 10.1038/leu.2015.214. Epub Aug. 4, 2015.

Osada et al., CEA/CD3-bispecific T cell-engaging (BiTE) antibody-mediated T lymphocyte cytotoxicity maximized by inhibition of both PD1 and PD-L1., Cancer Immunol Immunother. Jun. 2015;64(6):677-88. doi: 10.1007/s00262-015-1671-y. Epub Mar. 6, 2015.

Masarova et al., Immune Checkpoint Approaches in AML and MDS: A Next Frontier., The Journal of Targeted Therapies in Cancer, Mar. 6, 2017 (Mar. 6, 2017), XP002784099.

Gantke et al., Trispecific antibodies for CD16A-directed NK cell engagement and dual-targeting of tumor cells., Protein Eng Des Sel. Sep. 1, 2017;30(9):673-684. doi: 10.1093/protein/gzx043.

U.S. Appl. No. 12/875,015, 2011-0054151, U.S. Pat. No. 9,493,578, filed Sep. 2, 2010, Mar. 3, 2011, Nov. 15, 2016.

U.S. Appl. No. 15/279,266, 2017-0058053, filed Sep. 28, 2016, Mar. 2, 2017.

U.S. Appl. No. 13/648,951, 2013-0171095, filed Oct. 10, 2012, Jul. 4, 2013.

U.S. Appl. No. 13/194,904, 2012-0028304, U.S. Pat. No. 8,637,641, filed Jul. 29, 2011, Feb. 2, 2012, Jan. 28, 2014.

U.S. Appl. No. 14/165,487, 2014-0249297, U.S. Pat. No. 9,605,061, filed Jan. 27, 2014, Sep. 4, 2014, Mar. 28, 2017.

U.S. Appl. No. 15/444,087, 2017-0174757, filed Feb. 27, 2017, Jun. 22, 2017.

U.S. Appl. No. 13/568,028, filed Aug. 6, 2012.

U.S. Appl. No. 14/853,622, 2016-0068588, filed Sep. 14, 2015, Mar. 10, 2016.

U.S. Appl. No. 13/887,234, filed May 3, 2013.

U.S. Appl. No. 14/156,431, 2014-0212435, filed Jan. 15, 2014, Jul. 31, 2014.

U.S. Appl. No. 14/156,432, 2014-0212436, filed Jan. 15, 2014, Jul. 31, 2014.

U.S. Appl. No. 14/808,826, 2016-0060360, U.S. Pat. No. 9,738,722, filed Jul. 24, 2015, Mar. 3, 2016, Aug. 22, 2017.

U.S. Appl. No. 15/682,380, filed Aug. 21, 2017.

(56) References Cited

OTHER PUBLICATIONS

U.S. Appl. No. 14/155,248, 2014-0322217, filed Jan. 14, 2014, Oct. 30, 2014.
U.S. Appl. No. 14/155,334, 2014-0370013, filed Jan. 14, 2014, Dec. 18, 2014.
U.S. Appl. No. 14/155,344, 2014-0294833, U.S. Pat. No. 9,701,759, filed Jan. 14, 2014, Oct. 2, 2014, Jul. 11, 2017.
U.S. Appl. No. 14/205,227, 2014-0294835, filed Mar. 11, 2014, Oct. 2, 2014.
U.S. Appl. No. 14/205,248, 2014-0288275, U.S. Pat. No. 9,650,446, filed Mar. 11, 2014, Sep. 25, 2014, May 16, 2017.
U.S. Appl. No. 15/589,908, filed May 8, 2017.
U.S. Appl. No. 14/214,418, 2014-0356381, filed Mar. 14, 2014, Dec. 4, 2014.
U.S. Appl. No. 14/214,475, 2014-0294836, filed Mar. 14, 2014, Oct. 2, 2014.
U.S. Appl. No. 14/217,166, 2014-0294759, filed Mar. 17, 2014, Oct. 2, 2014.
U.S. Appl. No. 14/200,652, 2014-0302064, filed Mar. 7, 2014, Oct. 9, 2014.
U.S. Appl. No. 14/207,489, 2014-0377270, filed Mar. 12, 2014, Dec. 25, 2014.
U.S. Appl. No. 14/200,821, 2014-0294823, U.S. Pat. No. 9,605,084, filed Mar. 7, 2014, Oct. 2, 2014, Mar. 28, 2017.
U.S. Appl. No. 14/216,705, 2014-0363426, filed Mar. 17, 2014, Dec. 11, 2014.
U.S. Appl. No. 15/444,026, 2018-0037668, filed Feb. 27, 2017, Feb. 8, 2018.
U.S. Appl. No. 14/673,695, 2015-0307629, filed Mar. 30, 2015, Oct. 29, 2015.
U.S. Appl. No. 15/786,252, 2018-0094079, filed Oct. 17, 2017, Apr. 5, 2018.
U.S. Appl. No. 14/952,705, 2016-0176969, filed Nov. 25, 2015, Jun. 23, 2016.
U.S. Appl. No. 14/952,714, 2016-0229924, filed Nov. 25, 2015, Aug. 11, 2016.
U.S. Appl. No. 15/141,350, 2016-0355608, filed Apr. 28, 2016, Dec. 8, 2016.
U.S. Appl. No. 14/952,786, 2016-0215063, filed Nov. 25, 2015, Jul. 28, 2016.
U.S. Appl. No. 14/757,809, 2016-0355600, filed Dec. 22, 2015, Dec. 8, 2016.
U.S. Appl. No. 15/063,441, 2017-0037131, filed Mar. 7, 2016, Feb. 9, 2017.
U.S. Appl. No. 15/372,360, 2017-0320947, filed Dec. 7, 2016, Nov. 9, 2017.
U.S. Appl. No. 15/623,314, 2018-0118836, filed Jun. 14, 2017, May 3, 2018.
U.S. Appl. No. 15/611,361, 2017-0349660, filed Jun. 1, 2017, Dec. 7, 2017.
U.S. Appl. No. 15/611,683, 2017-0349657, filed Jun. 1, 2017, Dec. 7, 2017.
U.S. Appl. No. 15/636,590, 2018-0118827, filed Jun. 28, 2017, May 3, 2018.
U.S. Appl. No. 15/185,958, 2017-0081420, U.S. Pat. No. 9,850,320, filed Jun. 17, 2016, Mar. 23, 2017, Dec. 26, 2017.
U.S. Appl. No. 15/186,167, 2017-0081424, U.S. Pat. No. 9,856,327, filed Jun. 17, 2016, Mar. 23, 2017, Jan. 2, 2018.
U.S. Appl. No. 15/691,665, 2018-0127501, filed Aug. 30, 2017, May 10, 2018.
U.S. Appl. No. 15/785,401, 2018-0118805, filed Oct. 16, 2017, May 3, 2018.
U.S. Appl. No. 15/785,393, 2018-0118828, filed Oct. 16, 2017, May 3, 2018.
U.S. Appl. No. 12/631,508, filed Dec. 4, 2009, Chari et al.
(No Author Name) "A method for making multispecific antibodies having heteromultimeric and common components", Expert Opinion on Therapeutic Patents, Genentech, Inc. (1999) 9(6): 785-790, pp. 785-790.
"Polythene Glycol and Derivatives for Advanced PEGylation", Catalog 2005-2006, Nektar Therapeutics.
"Xencor Provides Data Updates on XmaB Bispecific Antibody Program and Announces Presentations at Upcoming American Society of Hematology 2014 Annual Meeting", Nov. 6, 2014, XP055255549, retrieved from the internet: http://files.shareholder.com/downloads/AMDA-2B2V8N/0x0x792404/77590b72-837a-4085-bc55-78fa500638dc/XNCR_News_2014_11_6_General_Releases.pdf.
Abbott Laboratories, Strategies and Current Approaches for Improving Drug-Like-Properties During Biologics Drug Candidate Selection, AAPS Webinar—Nov. 10, 2011.
Adams, et al., Avidity-Mediated Enhancement of In vivo Tumor Targeting by Single-Chain Fv Dimers, Clin Cancer Res, 2006, vol. 12(5), pp. 1599-1605, doi:10.1158/1078-0432.CCR-05-2217.
Alberola-Ila et al., Stimulation Through the TCR/CD3 Complex Up-Regulates the CD2 Srface Expression on Human T Lymphocytes, Feb. 15, 1991.
Alibaud et al., A New Monoclonal Anti-CD3? Antibody Reactive on Paraffin Sections, Journal of Histochemistry & Cytochemistry, 2000, vol. 48, p. 1609.
An, et al., IgG2m4, an engineered antibody isotype with reduced Fc function, mAbs, 2009, vol. 1, Issue 6, pp. 572-579, www.landesbioscience.com/journals/mabs/article/10185.
Aplin et al., , Preparation, properties, and applications of carbohydrate conjugates of proteins and lipids, 1981, CRC Crit. Rev. Biochem., pp. 259-306.
Arnett, et al., Crystal structure of a human CD3-ε/δ dimer in complex with a UCHT1 single-chain antibody fragment, PNAS, 2004, vol. 101, No. 46, pp. 16268-16273.
Asano, et al., Cytotoxic enhancement of a bispecific diabody (Db) by format conversion to tandem single-chain variable fragment (taFv): The Case of the hEx3 Diabody, JBC Papers in Press, 2010, http://www.jbc.org/cgi/doi/10.1074/jbc.M110.172957.
Asano, et al., Highly Effective Recombinant Format of a Humanized IgG-like Bispecific Antibody for Cancer Immunotherapy with Retargeting of Lymphocytes to Tumor Cells, The Journal of Biological Chemistry, 2007, vol. 282, No. 38, pp. 27659-27665.
Atwell, et al., Stable Heterodimers from Remodeling the Domain Interface of a Homodimer using a Phage Display Library, J. Mol. Biol., 1997, vol. 270, pp. 26-35.
Baca et al., Antibody humanization using monovalent phage display, 1997, J. Biol. Chem. 272(16):10678-10684.
Baeuerle, et al., Response to Letter, "Correct TandAb protein," Molecular Immunology, 2007, vol. 44, p. 3084.
Baeuerle, et al., Review—Bispecific T-Cell Engaging Antibodies for Cancer Therapy, Cancer Res, 2009, vol. 69: (12), pp. 4941-4944.
Barbas, et al. In vitro evolution of a neutralizing human antibody to human immunodeficiency virus type 1 to enhance affinity and broaden strain cross-reactivity, 1994, Proc. Nat. Acad. Sci, USA 91:3809-3813.
Bargou et al., Tumor Regression in Cancer Patients by Very Low Doses of a T Cell-Engaging Antibody, Science, 2008, vol. 321, pp. 974-977.
Bhatt, Sea Lane—DDD presentation, "Surrobodies™—A Novel Approach to Bispecifics . . . ," Aug. 8, 2012.
Bibollet-Ruche et al., The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype, Jul. 30, 2008.
Biochemica, Your apoptosis specialist, 1999, No. 2, pp. 34-37 (Roche Molecular Biochemicals).
Bird et al., Single-chain antigen-binding proteins, 1988, Science 242:423-426.
Bluemel, et al., Epitope distance to the target cell membrane and antigen size determine the potency of T cell-mediated lysis by BiTE antibodies specific for a large melanoma surface antigen, Cancer Immunol Immunother, 2010, vol. 59(8), pp. 1197-1209.
Borras, et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.

(56) References Cited

OTHER PUBLICATIONS

Bortoletto, Nicola et al., "Optimizing anti-CD3 affinity for effective T cell targeting against tumor cells.", Eur J Immunol. Nov. 2002;32(11):3102-7.
Boswell et al., Effects of Charge on Antibody Tissue Distribution and Pharmacokinetics, 2010, Bioconjugate Chem, 21(21):2153-2163.
Brandl, et al., Bispecific antibody fragments with CD20 3 CD28 specificity allow effective autologous and allogeneic T-cell activation against malignant cells in peripheral blood and bone marrow cultures from patients with B-cell lineage leukemia and lymphoma, Experimental Hematology, 1999, vol. 27, pp. 1264-1270.
Brinkmann , et al., presentation slideshow—"Roche Penzberg & Roche Glycart, Schlieren: Centers of Excellence for Recombinant Proteins".
Brinkmann, et al., A recombinant immunotoxin containing a disulfide-stabilized Fv fragment, Proc. Natl. Acad. Sci. USA, 1993, vol. 90, pp. 7538-7542.
Cao, et al., Oligomerization is required for the activity of recombinant soluble LOX-1., FEBS J. Sep. 2009;276(17):4909-20. doi: 10.1111/j.1742-4658.2009.07190.x. Epub Jul. 31, 2009.
Carpenter, et al., Non-Fc Receptor-Binding Humanized Anti-CD3 Antibodies Induce Apoptosis of Activated Human T Cells, J. Immunol., 2000, vol. 165, No. 11, pp. 6205-6213.
Carter et al., Antibody-drug conjugates for cancer therapy, 2008, Cancer J. 14(3):154-169.
Carter et al., Humanization of an anti-p185HER2 antibody for human cancer therapy, 1992, Proc Natl Acad Sci USA 89:4285-9.
Castoldi, et al., Molecular characterization of novel trispecific ErbB-cMet-IGF1R antibodies and their antigen-binding properties, Protein Engineering, Design & Selection, 2012, vol. 25, No. 10, pp. 551-559.
Cemerski, et al., Suppression of mast cell degranulation through a dual-targeting tandem IgE-IgG Fc domain biologic engineered to bind with high affinity to FcγRIIb., Immunol Lett. Mar. 30, 2012;143(1):34-43. doi: 10.1016/j.imlet.2012.01.008. Epub Jan. 25, 2012.
Chames et al., Bispecific antibodies for cancer therapy—The light at the end of the tunnel?, mAbs, 2009, vol. 1, Issue 6, pp. 1-9.
Chang, et al., Monoclonal antibodies against oxidized low-density lipoprotein bind to apoptotic cells and inhibit their phagocytosis by elicited macrophages: evidence that oxidation-specific epitopes mediate macrophage recognition., Proc Natl Acad Sci U S A. May 25, 1999;96(11):6353-8.
Chari et al., Immunoconjugates containing novel maytansinoids: promising anticancer drugs, 1992, Cancer Research 52: 127-131.
Chatal, 1989, Monoclonal Antibodies in Immunoscintigraphy, CRC Press (Book Abstract).
Chelius, et al., Structural and functional characterization of the trifunctional antibody catumaxomab, mAbs, 2010, vol. 2, Issue 3, pp. 309-319.
Chothia et al., Canonical structures for the hypervariable regions of immunoglobulins, 1987, J. Mol. Biol. 196:901-917.
Chothia et al., Structural Determinants in the Sequences of Immunoglobulin Variable Domain, J. Mol. Biol., 1998, vol. 278, pp. 457-479.
Chu et al., Reduction of total IgE by targeted coengagement of IgE B-cell receptor and FcγRIIb with Fc-engineered antibody., J Allergy Clin Immunol. Apr. 2012;129(4):1102-15. doi: 10.1016/j.jaci.2011. 11.029. Epub Jan. 16, 2012.
Conrad, et al., TCR and CD3 Antibody Cross-Reactivity in 44 Species, Cytometry Part A, 2007, vol. 71A, pp. 925-933.
Conrath, et al., Antigen Binding and Solubility Effects upon the Veneering of a Camel VHH in Framework-2 to Mimic a VH, J. Mol. Biol. , 2005, vol. 350, pp. 112-125.
Counterman et al., "Volumes of Individual Amino Acid Residues in Gas-Phase Peptide Ions.", J. Am. Chem. Soc., 1999, 121 (16), pp. 4031-4039.
Cuesta, et al., Multivalent antibodies: when design surpasses evolution, Trends in Biotechnology, 2010, vol. 28, No. 7, pp. 355-362, doi:10.1016/j.tibtech.2010.03.007.
D'Argouges, et al., Combination of rituximab with blinatumomab (MT103/MEDI-538), a T cell-engaging CD19-/CD3-bispecific antibody, for highly efficient lysis of human B lymphoma cells, Leukemia Research, 2009, vol. 33, pp. 465-473.
Davies et al., Expression of GnTIII in recombinant anti-CD20 CHO production cell line: expression of antibodies with altered glycoforms leads to an increase in ADCC through higher affinity for FCγRIII, 2001, Biotechnol Bioeng 74:288-294.
Davila, et al., Efficacy and Toxicity Management of 19-28z CAR T Cell Therapy in B Cell Acute Lymphoblastic Leukemia, Sci. Transl. Med., 2014, vol. 6, Issue 224, pp. 1-10, 224ra25.
Davis, et al., SEEDbodies: fusion proteins based on strand-exchange engineered domain (SEED) $C_H3$ heterodimers in an Fc analogue platform for asymmetric binders or immunofusions and bispecific antibodies, Protein Engineering, Design & Selection, 2010, vol. 23, No. 4 pp. 195-202.
De Groot et al., De-Immunization of Therapeutic Proteins by T-Cell Epitope Modification, 2005, Dev. In Biologicals, 2005, 122:171-194.
De Pascalis et al., Grafting of "abbreviated" complementarity-determining regions containing specificity-determining residues essential for ligand contact to engineer a less immunogenic humanized monoclonal antibody, 2002, J. Immunol. 169:3076-3084.
Del Nagro et al., A critical role for complement C3d and the B cell coreceptor (CD19/CD21) complex in the initiation of inflammatory arthritis., J Immunol. Oct. 15, 2005;175(8):5379-89.
Demarest et al., Antibody therapeutics, antibody engineering, and the merits of protein stability, Current Opinin in Drug Discovery & Development, 2008 11(5): 675-587, Sep. 11, 2008.
Deyev, et al., Multivalency: the hallmark of antibodies used for optimization of tumor targeting by design, BioEssays, 2008, vol. 30, pp. 904-918.
DiGiammarino et al., Ligand association rates to the inner-variable-domain of a dual-variable-domain immunoglobulin are significantly impacted by linker design, mAbs3:5, Sep.-Oct. 1-8; 3(5):487-94, Landes Bioscience, Sep. 1, 2011.
Dixon, et al., Activation of Human T Lymphocytes by Crosslinking of Anti-CD3 Monoclonal Antibodies, Journal of Leukocyte Biology, 1989, vol. 46, pp. 214-220.
Dong et al., A stable IgG-like bispecific antibody targeting the epidermal growth factor receptor and the type I insulin-like growth factor receptor demonstrates superior anti-tumor activity, mAbs 3:3, May-Jun. 2011: 273-288, May 1, 2011.
Doronina , Development of potent monoclonal antibody auristatin conjugates for cancer therapy, 2003, Nat Biotechnol 21(7):778-784.
Dreier, et al., Extremely Potent, Rapid and Costimulation-Independent Cytotoxic T-cell Response Against Lymphoma Cells Catalyzed by a Single-Chain Bispecific Antibody, Int. J. Cancer, 2002, vol. 100, pp. 690-697.
Dreier, et al., T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Construct, The Journal of Immunology, 2003, vol. 170, pp. 4397-4402.
Dubowchik et al., Receptor-mediated and enzyme-dependent targeting of cytotoxic anticancer drugs, 1999, Pharm. Therapeutics 83:67-123.
Ducry et al., Antibody-drug conjugates: linking cytotoxic payloads to monoclonal antibodies, 2010, Bioconjugate Chem. 21:5-13.
Dudgeon, et al., General strategy for the generation of human antibody variable domains with increased aggregation resistance, PNAS Early Edition, 2012, pp. 10879-10884, www.pnas.org/cgi/doi/10.1073/pnas.1202866109 & Supporting Information.
Duke, et al., Measurement of apoptosis and other forms of cell death, 2004, Curr protocols immunol. 3.17.1-3.17.16.
DukSin et al., Relationship of the structure and biological activity of the natural homologues of tunicamycin, 1982, J. Biol. Chem. 257:3105.
Duval, et al., A Bispecific Antibody Composed of a Nonneutralizing Antibody to the gp41 Immunodominant Region and an Anti-CD89

(56) References Cited

OTHER PUBLICATIONS

Antibody Directs Broad Human Immunodeficiency Virus Destruction by Neutrophils, Journal of Virology, 2008, pp. 4671-4674, doi:10.1128/JVI.02499-07.
Edge et al., Deglycosylation of glycoproteins by trifluoromethanesulfonic acid, 1981, Anal. Biochem. 118:131.
Elliott, et al., Antiparallel Conformation of Knob and Hole Aglycosylated Half-Antibody Homodimers Is Mediated by a CH2—CH3 Hydrophobic Interaction, Journal of Molecular Biology, 2014, vol. 426, Issue 9, pp. 1947-1957.
Feldmann et al., Novel Humanized and Highly Efficient Bispecific Antibodies Mediate Killing of Prostate Stem Cell Antigen-Expressing Tumor Cells by CD8+ and CD4+ T cells, Aug. 8, 2012.
Feldmann et al., Retargeting of T Cells to Prostate Stem Cell Antigen Expressing Tumor Cells: Comparison of Different Antibody Formats, Dec. 28, 2010.
Fernandes, et al., T Cell Receptors are Structures Capable of Initiating Signaling in the Absence of Large Conformational Rearrangements, The Journal of Biological Chemistry, 2012, vol. 287, No. 16, pp. 13324-13335.
Fischer, Nicolas et al., "Bispecifc antibodies: molecules that enable novel therapeutic strategies", 2007, vol. 74, pp. 3-14.
Foreman, et al., ErbB3 Inhibitory Surrobodies Inhibit Tumor Cell Proliferation In Vitro and In Vivo, Mol Cancer Ther, 2012, vol. 11(7), pp. 1411-1420.
Foreman, et al., PEGS poster, "ErbB3 Inhibitory Surrobodies Inhibit Tumor Cell Proliferation In Vitro and In Vivo," 2012.
Fraker et al., Crystal structure of peptide cyclo-(D-VAL-L-PRO-L-VAL-D-PRO)$_3$, 1978, Biochem. Biophys. Res. Commun. 80(4):849-57.
Francois, et al., Construction of a Bispecific Antibody Reacting with the α- and β-Chains of the Human IL-2 Receptor, The Journal of Immunology, May 15, 1993, vol. 150, No. 10, pp. 4610-4619.
F-star Modular Antibodies Fact Sheet, Apr. 2008, "Modular Antibody Technology" (w/ reference to Ruker WO 2006/072620 A1).
F-star Modular Antibodies Press Release, Mar. 28, 2008, "Antibody Engineering Company F-Star Buys Back Royalty Obligations. TVM Capital Joins Investor Syndicate."
Fudenberg, et al., Serologic Demonstration of Dual Specificity of Rabbit Bivalent Hybrid Antibody, The Journal of Experimental Medicine, 1964, vol. 119(1), pp. 151-166.
Ganesan, et al., FcγRIIb on Liver Sinusoidal Endothelium Clears Small Immune Complexes, The Journal of Immunology, Nov. 15, 2012, vol. 189 No. 10, pp. 4981-4988.
GenBank AAA38124.1, immunoglobulin heavy-chain VJ region [*Mus musculus*] Protein/NCBI.
GenBank AAA39180.1, immunoglobulin light-chain VJ region [*Mus musculus*] Protein/NCBI.
Ghendler et al., One of the CD3ε Subunits within a T Cell Receptor Complex Lies in Close Proximity to the Cβ FG Loop, J. Exp. Med., 1998, vol. 187, No. 9. pp. 1529-1536.
Ghetie et al., Multiple roles for the major histocompatibility complex Class I-related receptor FcRn, 2000, Annu Rev Immunol 18:739-766.
Gilliland, et al., Universal bispecific antibody for targeting tumor cells for destruction by cytotoxic T cells, Proc. Natl. Acad. Sci. USA, 1988, vol. 85, pp. 7719-7723.
Gorman et al., Reshaping a therapeutic CD4 antibody, Proc. Natl. Acad. Sci. USA 88:4181-4185.
Grodzki & Bernstein, "Antibody Purification: Ion-Exchange Chromatography.", Methods Mol Biol 2010 ;588:27-32.
Gunasekaran et al., Enhancing Antibody Fc Heterodimer Formation through Electrostatic Steering Effects, Journal of Biological Chemimstry, vol. 285, No. 25, pp. 19637-10946, Apr. 16, 2010 & Supplementary Tables.
Haagen, et al., The Efficacy of CD3 x CD19 Bispecific Monoclonal Antibody (BsAb) in a Clonogenic Assay: The Effect of Repeated Addition of BsAb, and Interleukin-2, Blood, 1995, vol. 85, No. 11, pp. 3208-3212.

Hakimuddin et al., A chemical method for the deglycosylation of proteins, 1987, Arch. Biochem. Biophys. 259:52.
Hamel, et al., The Role of the $V_L$- and $V_H$-Segments in the Preferential Reassociation of Immunoglobulin Subunits, Molecular Immunology, 1986, vol. 23, No. 5, pp. 503-510.
Hawkins et al, Selection of phage antibodies by binding affinity mimicking affinity maturation, 1992, J. Mol. Biol. 226:889-896.
Hayden-Ledbetter, et al., CD20-Directed Small Modular Immunopharmaceutical, TRU-015, Depletes Normal and Malignant B Cells, Clin Cancer Res, 2009, vol. 15(8), pp. 2739-2746.
He et al., Humanization and pharmacokinetics of a monoclonal antibody with specificity for both E- and P-selectin, 1998, J. Immunol. 160:1029-1035.
Hennecke et al., "Non-repetitive single-chain Fv linkers selected by selectively infective phage (SIP) technology.", Protein Eng. May 1998;11(5):405-10.
Hernandez-Caselles, et al., A study of CD33 (SIGLEC-3) antigen expression and function on activated human T and NK cells: two isoforms of CD33 are generated by alternative splicing, J. Leukoc. Biol., 2006, vol. 79, pp. 46-58.
Hexham, et al., Influence of relative binding affinity on efficacy in a panel of anti-CD3 scFv immunotoxins, Molecular Immunology, 2001, vol. 38, pp. 397-408.
Hinman et al., Preparation and characterization of monoclonal antibody conjugates of the calicheamicins: a novel and potent family of antitumor antibodies, 1993 Cancer Res. 53:3336-3342.
Hoffmann, et al., Serial killing of tumor cells by cytotoxic T cells redirected with a CD19-/CD3-bispecific single-chain antibody construct, Int. J. Cancer, 2005, vol. 115, pp. 98-104.
Holliger et al., "Diabodies": Small Bivalent and bispecific antibody fragments, 1993, Proc. Natl. Acad. Sci. U.S.A. 90:6444-6448.
Holliger et al., Engineering bispecific antibodies, 1993, Current Opinion Biotechnol. 4:446-449.
Houtenbos, et al., The novel bispecific diabody αCD40/αCD28 strengthens leukaemic dendritic cell-induced T-cell reactivity, British Journal of Haematology, 2008, vol. 142, pp. 273-283.
Hu et al., Minibody: A novel engineered anti-carcinoembryonic antigen antibody fragment (single-chain Fv-$C_H$3) which exhibits rapid, high-level targeting of xenografts, 1996, Cancer Res. 56:3055-3061.
Huston et al., Protein engineering antibody binding sites: recovery of specific activity in an anti-digoxin single-chain Fv analogue produced in *Escherichia coli*, 1988, Proc. Natl. Acad. Sci. U.S.A. 85:5879-5883.
Igawa et al., Reduced elimination of IgG antibodies by engineering the variable region, 2010, PEDS. 23(5): 385-392.
Igawa, $V_H/V_L$ interface engineering to promote selective expression and inhibit conformational isomerization of thrombopoietin receptor agonist single-chain diabody, Protein Engineering, Design & Selection, 2010, vol. 23, No. 8, pp. 667-677.
Jackson et al., In vitro antibody maturation, 1995, J. Immunol. 154(7):3310-9.
Jäger, et al., The Trifunctional Antibody Ertumaxomab Destroys Tumor Cells That Express Low Levels of Human Epidermal Growth Factor Receptor 2, Cancer Res, 2009, vol. 69(10), pp. 4270-4276.
Jefferis et al., Interaction sites on human IgG-Fc for FcγR: current models, 2002, Immunol Lett 82:57-65.
Jespers, et al., Crystal Structure of HEL4, a Soluble, Refoldable Human $V_H$ Single Domain with a Germ-line Scaffold, J. Mol. Biol., 2004, vol. 337, pp. 893-903.
Jimenez, et al., A recombinant, fully human, bispecific antibody neutralizes the biological activities mediated by both vascular endothelial growth factor receptors 2 and 3, Mol Cancer Ther, 2005, vol. 4(3), pp. 427-434.
Jin, et al., MetMAb, the One-Armed 5D5 Anti-c-Met Antibody, Inhibits Orthotopic Pancreatic Tumor Growth and Improves Survival, Cancer Res 2008, vol. 68, pp. 4360-4368.
Johnson et al., Anti-tumor activity of CC49-doxorubicin immunoconguates, 1995, Anticancer Res. 15:1387-93.
Johnson, et al., Effector Cell Recruitment with Novel Fv-based Dual-affinity Re-targeting Protein Leads to Potent Tumor Cytolysis and in Vivo B-cell Depletion, J. Mol. Biol., 2010, vol. 399, pp. 436-449.

(56) References Cited

OTHER PUBLICATIONS

Jones et al., Replacing the complementarity-determining regions in a human antibody with those from a mouse, 1986, Nature 321:522-525.

Jordan et al., Structural understanding of stabilization patterns in engineered bispecific Ig-like antibody molecules, Proteins 2009; 77:832-841, Jun. 19, 2009.

Jung, et al., Design of interchain disulfide bonds in the framework region of the Fv fragment of the monoclonal antibody B3, Proteins, 1994, vol. 19(1), pp. 35-47.

Jung, et al., Target Cell-restricted Triggering of the CD95 (APO-1/Fas) Death Receptor with Bispecific Antibody Fragments, Cancer Research, 2001, vol. 61, pp. 1846-1848.

Jungbluth et al., A monoclonal antibody recognizing human cancers with amplification/overexpression of the human epidermal growth factor receptor, 2003, Proc Natl Acad Sci U S A. 100(2):639-44.

Kabat et al., 1991, Sequences of proteins of immunological interest, Department of Health and Human Services, Bethesda, vol. 1, $5^{th}$ Ed.

Kakutani et al., Accumulation of LOX-1 ligand in plasma and atherosclerotic lesions of Watanabe heritable hyperlipidemic rabbits: identification by a novel enzyme immunoassay.,Biochem Biophys Res Commun. Mar. 23, 2001;282(1):180-5.

Kanakaraj, et al., Simultaneous targeting of TNF and Ang2 with a novel bispecific antibody enhances efficacy in an in vivo model of arthritis, mAbs, 2012, vol. 4, Issue 5, pp. 600-613, http://dx.doi.org/10.4161/mabs.21227 & Supplemental Data.

Kettleborough et al., Humanization of a mouse monoclonal antibody by CDR-grafting: the importance of framework residues on loop conformation, 1991, Protein Eng. 4(7):773-83.

Keyna, et al., Surrogate Light Chain-Dependent Selection of Ig Heavy Chain V Regions, J. Immunol., 1995, vol. 155, pp. 5536-5542.

Kiewe, et al., Phase I Trial of the Trifunctional Anti-HER2 x Anti-CD3 Antibody Ertumaxomab in Metastatic Breast Cancer, Clin Cancer Res., 2006, vol. 12(10), pp. 3085-3091.

Kim et al., "Localization of the site of murine IgG1 molecule that is involved in binding the murine intestinal Fc receptor," Eur. J. Immunol., 24:2429-2434, 1994.

Kipriyanov, et al., Bispecific CD3 x CD19 Diabody for T Cell-Mediated Lysis of Malignant Human B Cells, Int. J. Cancer, 1998. vol. 77, pp. 763-772.

Kipriyanov, et al., Bispecific Tandem Diabody for Tumor Therapy with Improved Antigen Binding and Pharmacokinetics, J. Mol. Biol., 1999, vol. 293, pp. 41-56.

Kipriyanov, et al., Effect of Domain Order on the Activity of Bacterially Produced Bispecific Single-chain Fv Antibodies, J. Mol. Biol., 2003, vol. 330, pp. 99-111.

Kipriyanov, et al., Two amino acid mutations in an anti-human CD3 single chain Fv antibody fragment that affect the yield on bacterial secretion but not the affinity, Protein Engineering, 1997, vol. 10, No. 4, pp. 445-453.

Klein et al., Progression of metastatic human prostate cancer to androgen independence in immunodeficient SDIC mice, 1997, Nature Medicine 3: 402-408.

Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.

Klinger, et al., Immunopharmacologic response of patients with B-lineage acute lymphoblastic leukemia to continuous infusion of T cell-engaging CD19/CD3-bispecific BiTE antibody blinatumomab, Blood, 2012, vol. 119, No. 26, pp. 6226-6233.

Koristka, et al., Retargeting of Human Regulatory T Cells by Single-Chain Bispecific Antibodies, The Journal of Immunology, 2012, vol. 188, pp. 1551-1558, www.jimmunol.org/cgi/doi/10.4049/jimmunol.1101760.

Kostelny, et al., Formation of a Bispecific Antibody by the Use of Leucine Zippers, The Journal of Immunology 1992 vol. 148, pp. 1547-1553.

Krauss et al., Specificity grafting of human antibody frameworks selected from a phage display library: generation of a highly stable humanized anti-CD22 single-chain Fv fragment, 2003, Protein Engineering 16(10):753-759.

Krupka, et al., CD33 target validation and sustained depletion of AML blasts in long-term cultures by the bispecific T-cell-engaging antibody AMG 330, Blood, 2014, vol. 123, No. 3, pp. 356-365, Prepublished online Dec. 3, 2013; doi:10.1182/blood-2013-08-523548 & Data Supplement.

Kung, et al., Monoclonal Antibodies Defining Distinctive Human T Cell Surface Antigens, Science, 1979, vol. 206, pp. 347-349.

Kuppen, peter et al., The development and purification of a bispecific antibody for lymphokine-activated killer cell targeting against the rat colon carcinoma CC531., Cancer Immunol Immunother. Jun. 1993;36(6):403-8.

Labrijn, et al., Efficient generation of stable bispecific IgG1 by controlled Fab-arm exchange, www.pnas.org/cgi/doi/10.1073/pnas.1220145110 & Supporting Information.

Laszlo et al., Cellular determinants for preclinical activity of a novel CD33/CD3 bispecific T-cell engager (BiTE) antibody, AMG 330, against human AML, blood 2014 123: 554-561, Dec. 5, 2013.

Lau et al., Conjugation of Doxorubicin to monoclonal anti-carcinoembryonic antigen antibody via novel thiol-directed cross-linking regents, 1995, Bioorg-Med-Chem. 3(10):1299-1304.

Lau et al., Novel doxorubicin-monoclonal anti-carcinoembryonic antigen antibody immunoconjugate activity in vitro, 1995, Bioorg-Med-Chem. 3(10):1305-12.

Lazar Declaration, Dec. 27, 2010, pp. 1-4.

Lewis, et al., Generation of bispecific IgG antibodies by structure-based design of an orthogonal Fab interface, Nature Biotechnology, 2014, doi:10.1038/nbt.2797 & Supplemental Information.

Li, et al., Construction and characterization of a humanized anti-human CD3 monoclonal antibody 12F6 with effective immunoregulation functions, Immunology, 2005, vol. 116, pp. 487-498.

Lindhofer, et al., Preferential Species-Restricted Heavy/Light Chain Pairing in Rat/Mouse Quadromas: Implications for a Single-Step Purification of Bispecific Antibodies, The Journal of Immunology, 1995, vol. 155, pp. 219-225.

Ling, et al., Interspecies Scaling of Therapeutic Monoclonal Antibodies: Initial Look, J Clin Pharmacol, 2009, vol. 49, pp. 1382-1402, doi: 10.1177/0091270009337134.

Link, et al., Production and Characterization of a Bispecific IgG Capable of Inducing T-Cell-Mediated Lysis of Malignant B Cells, Blood, 1993, vol. 81, No. 12, pp. 3343-3349.

Linke, et al., Catumaxomab, Clinical development and future directions, mAbs, 2010, vol. 2, Issue 2, pp. 129-136.

Little, et al., Letter to the Editor, "Flawed TandAb production," Molecular Immunology, 2007, vol. 44, p. 3083.

Liu et al, Asymmetrical Fc Engineering Greatly Enhances Antibody-dependent Cellular Cytotoxicity (ADCC) Effector Function and Stability of the Modified Antibodies, J. Biol. Chem. 2014, 289: 3571-3590, Dec. 5, 2013.

Liu et al., Eradication of large colon tumor xenografts by targeted delivery of maytansinoids, 1996 Proc. Natl. Acad. Sci. USA 93:8618-8623.

Liu, et al., Crystallization of a Deglycosylated T Cell Receptor (TCR) Complexed with an Anti-TCR Fab Fragment, The Journal of Biological Chemistry, 1996, vol. 271, No. 52, pp. 33639-33646.

Lode et al., Targeted therapy with a novel enediyene antibiotic calicheamicins $o^{51}{}_1$ effectively suppress growth and dissemination of liver metastases in a syngeneic model of murine neuroblastoma, 1998, Cancer Res. 58:2928.

Löffler, et al., A recombinant bispecific single-chain antibody, CD19×CD3, induces rapid, and high lymphoma-directed cytotoxicity by unstimulated T lymphocytes, Blood, 2000, vol. 95, No. 6, pp. 2098-2103.

Lu, et al., A Fully Human Recombinant IgG-like Bispecific Antibody to Both the Epidermal Growth Factor Receptor and the Insulin-like Growth Factor Receptor for Enhanced Antitumor Activity, The Journal of Biological Chemistry, 2005, vol. 280, No. 20, pp. 19665-19672.

(56) References Cited

OTHER PUBLICATIONS

Lu, et al., Di-diabody: a novel tetravalent bispecific antibody molecule by design, Journal of Immunological Methods, 2003, vol. 279, pp. 219-232.
Lu, et al., Fab-scFv fusion protein: an efficient approach to production of bispecific antibody fragments, Journal of Immunological Methods, 2002, vol. 267, pp. 213-226.
Lu, et al., The effect of variable domain orientation and arrangement on the antigen-binding activity of a recombinant human bispecific diabody, Biochemical and Biophysical Research Communications, 2004, vol. 318, pp. 507-513.
Lum, et al., The new face of bispecific antibodies: targeting cancer and much more, Experimental Hematology, 2006, vol. 34, pp. 1-6.
Lutterbuese, et al., AACR Poster, "Conversion of Cetuximab, Panitumumab, Trastuzumab and Omalizumab into T Cell-engaging BiTE Antibodies Creates Novel Drug Candidates of High Potency," 2008.
Lutterbuese, et al., T cell-engaging BiTE antibodies specific for EGFR potently eliminate KRAS- and BRAF-mutated colorectal cancer cells, PNAS Early Edition, 2010, www.pnas.org/cgi/doi/10.1073/pnas.1000976107 & Supporting Information.
Ma, et al., Expression and Characterization of a Divalent Chimeric Anti-Human CD3 Single Chain Antibody, Scand.J.Immunol, 1996, vol. 43, pp. 134-139.
Mabry, et al., A dual-targeting PDGFRβ/VEGF—A molecule assembled from stable antibody fragments demonstrated anti-angiogenic activity in vitro and in vivo, mAbs, 2010, vol. 2, Issue 1, pp. 20-34; www.landesbioscience.com/journals/mabs/article/10498 & Supplemental Information.
Mabry, et al., Engineering of stable bispecific antibodies targeting IL-17A and IL-23, Protein Engineering, Design & Selection, 2009, vol. 23, No. 3, pp. 115-127; doi:10.1093/protein/gzp073 & Supplementary Figures 1-8.
Mack, et al., A small bispecific antibody construct expressed as a functional single-chain molecule with high tumor cell cytotoxicity, Proc. Natl. Acad. Sci. USA, 1995, vol. 92, pp. 7021-7025.
Mack, et al., Biologic Properties of a Bispecific Single-Chain Antibody Directed Against 17-1A (EpCAM) and CD3—Tumor Cell-Dependent T Cell Stimulation and Cytotoxic Activity, The Journal of Immunology, 1997, vol. 158, pp. 3965-3970.
MacroGenics Factsheet, Dual Affinity Re-Targeting ("DART") Platform, 2010.
Mandler et al., Immunoconjugates of geldanamycin and anti-HER2 Monoclonal antibodies: antiproliferative activity on human breast carcinoma cell lines, 2000, J. Nat. Cancer Inst. 92(19):1573-1581.
Mandler et al., Modifications in synthesis strategy improve the yield and efficacy of geldanamycin-herceptin immunoconjugates, 2002, Bioconjugate Chem. 13:786-791).
Mandler et al., Synthesis and evaluation of antiproliferative activity of a geldanaymcin-herceptin™ immunoconjugates, 2000, Bioorganic & Med. Chem. Letters 10:1025-1028.
Mandy, et al., Effect of Reduction of Several Disulfide Bonds on the Properties and Recombination of Univalent Fragments of Rabbit Antibody, The Journal of Biological Chemistry, 1963, vol. 238, No. 1, pp. 206-213.
Mandy, et al., Recombination of Univalent Subunits Derived from Rabbit Antibody, The Journal of Biological Chemistry, 1961, vol. 236, No. 12, pp. 3221-3226.
Marks et al., By-passing immunization: building high affinity human antibodies by chain shuffling, 1992, Biotechnology 10:779-783.
Martin, et al., Generation of the Germline Peripheral B Cell Repertoire: VH81X-λ B Cells Are Unable to Complete All Developmental Programs, J. Immunol., 1998, vol. 160, pp. 3748-3758.
Martinez, et al., Characterization of a novel modification on IgG2 light chain: Evidence for the presence of O-linked mannosylation, J. Chromatogr. A, 2007, vol. 1156 pp. 183-187.
Marvin, Bispecific antibodies for dual-modality cancer therapy: killing two signaling cascades with one stone, Curr Opin Drug Discov Devel, 2006, vol. 9(2), pp. 184-193.
Marvin, et al., Recombinant approaches to IgG-like bispecific antibodies, Acta Pharmacologica Sinica, 2005, vol. 26 (6), pp. 649-658.
Mateo et al, Humanization of a mouse nonoclonal antibody that blocks the epidermal growth factor receptor: recovery of antagonistic activity, 1997, Immunotechnology, 3(1):71-81.
McPhee, Engineering human immunodeficiency virus 1 protease heterodimers as macromolecular inhibitors of viral maturation, Proc. Natl. Acad. Sci. USA, 1996, vol. 93, pp. 11477-11481.
Meijer, et al., Isolation of Human Antibody Repertoires with Preservation of the Natural Heavy and Light Chain Pairing, J. Mol. Biol., 2006, vol. 358, pp. 764-772.
Merchant, et al., An efficient route to human bispecific IgG, Nature Biotechnology, 1998, vol. 16, pp. 677-681.
Mertens, Nico, "Tribodies: Fab-scFv fusion proteins as a platform to create multi-functional pharmaceuticals.", SpringerLink 2011, 135-149.
Metz, et al., Bispecific antibody derivatives with restricted binding functionalities that are activated by proteolytic processing, Protein Engineering, Design & Selection, 2012, vol. 25, No. 10, pp. 571-580.
Metz, et al., Bispecific digoxigenin-binding antibodies for targeted payload delivery, PNAS, 2011, vol. 108, No. 20, pp. 8194-8199.
Michaelson et al., Anti-tumor activity of stability-engineered IgG-like bispecific antibodies targeting TRAIL-R2 and LTbetaR, [mAbs 1:2, 128-141; Mar./Apr. 2009]; Mar. 11, 2009.
Michalk et al., Characterization of a novel single-chain bispecific antibody for retargeting of T cells to tumor cells via the TCR co-receptor CD8., PLoS One. Apr. 21, 2014;9(4):e95517. doi: 10.1371/journal.pone.0095517.
Miller et al., Stability engineering of scFvs for the development of bispecific and multivalent antibodies, PEDS, 2010, vol. 23, No. 7, pp. 549-557 & Supplementary Data.
Miller, biogen idec Stability Engineering and Production of IgG-like Bispecifc Antibodies, AAPS National Biotechnology Conference, Jun. 24 to Jun. 27, 2007.
Milutinovic, et al., Sanford Burnham Medical Research Institute / AACR Poster, #4318, "Development of a novel dual agonist Surrobody™ that simultaneously activates both death receptors DR4 and DR5 and induces cancer cell death with high potency".
Mimoto et al., Engineered antibody Fc variant with selectively enhanced FcγRIIb binding over both FcγRIIa(R131) and FcγRIIa(H131)., Protein Eng Des Sel. Oct. 2013;26(10):589-98. doi: 10.1093/protein/gzt022. Epub Jun. 5, 2013.
Mimoto, et al., Novel asymmetrically engineered antibody Fc variant with superior FcγR binding affinity and specificity compared with afucosylated Fc variant, mAbs, 2013, vol. 5, Issue 2, pp. 229-236.
Modjtahedi et al, Phase I trial and tumour localization of the anti-EGFR monoclonal antibody ICR62 in head and neck or lung cancer, 1996, Br J Cancer, 73(2):228-35.
Modjtahedi et al, Targeting of cells expressing wild-type EGFR and type-III mutant EGFR (EGFRVIII) by anti-EGFR MaB ICR62: a two-pronged attack for tumor therapy, 2003, Int J Cancer, 105(2):273-80.
Modjtahedi et al., Antitumor activity of combinations of antibodies directed against different epitopes on the extracellular domain of the human EGF receptor, 1993, J. Cell Biophys. 1993, 22(1-3):129-46.
Modjtahedi et al., The human EGF receptor as a target for cancer therapy: six new rat mAbs against the receptor on the breast carcinoma MDA-MB 468, 1993, Br J Cancer. 1993, 67(2):247-53.
Mølhøj, et al., CD19-/CD3-bispecific antibody of the BiTE class is far superior to tandem diabody with respect to redirected tumor cell lysis, Molecular Immunology 2007, vol. 44, pp. 1935-1943.
Moore et al., Tuning T Cell Affinity Improves Efficacy and Safety of Anti-CD38 x Anti-CD3 Bispecific Antibodies in Monkeys—a Potential Therapy for Multiple Myeloma., 57th ASH Annual Meeting and Exposition (Dec. 5-8, 2015), American Society of Hematology, Orlando, Florida.
Moore, et al., A novel bispecific antibody format enables simultaneous bivalent and monovalent co-engagement of distinct target antigens., MAbs. Nov.-Dec. 2011; 3(6): 546-557; Published online Nov. 1, 2011. doi: 10.4161/mabs.3.6.18123.

(56) References Cited

OTHER PUBLICATIONS

Moore, et al., Application of dual affinity retargeting molecules to achieve optimal redirected T-cell killing of B-cell lymphoma, Blood, 2011, vol. 117, No. 17, pp. 4542-4551.

Moretti et al., BEAT® the bispecific challenge: a novel and efficient platform for the expression of bispecific IgGs. BMC Proceedings 2013 7(Suppl 6):O9.

Morrison, et al., News and Views: Two heads are better than one, Nature Biotechnology, 2007, vol. 25, No. 11, pp. 1233-1234.

Mosmann, 1983, Rapid colorimetric assay for cellular growth and survival: application to proliferation and cytotoxicity assays, J. Immunol. Methods 65:55-63.

Muda, et al., Therapeutic assessment of SEED: a new engineered antibody platform designed to generate mono and bispecific antibodies, Protein Engineering, Design & Selection, 2011, vol. 24, No. 5, pp. 447-454.

Murthy et al., Binding of an antagonistic monoclonal antibody to an intact and fragmented EGF-receptor polypeptide, 1987, Arch Biochem Biophys. 252(2):549-60.

Nagorsen, et al., Blinatumomab: A historical perspective, Pharmacology & Therapeutics, 2012, vol. 136, pp. 334-342, http://dx.doi.org/10.1016/j.pharmthera.2012.07.013.

Nelson, et al., Point of View: Antibody fragments—Hope and hype, mAbs, 2010, vol. 2, Issue 1, pp. 77-83.

Neville et al., Enhancement of immunotoxin efficacy by acid-cleavable cross-ling agents utilizing diphtheria toxin and toxin mutants, 1989, Biol. Chem. 264:14653-14661.

Nielsen, et al., Human T cells resistant to complement lysis by bivalent antibody can be efficiently lysed by dimers of monovalent antibody, Blood, 2002, vol. 100, No. 12, pp. 4067-4073.

Nisonoff, et al., Letters to the Editors: Recombination of a Mixture of Univalent Antibody Fragments of Different Specificity, Arch. Biochem. Biophys., 1961, pp. 460-462.

Nisonoff, et al., Quantitative Estimation of the Hybridization of Rabbit Antibodies, Nature, 1962, vol. 194, No. 4826, pp. 355-359.

North, et al., A New Clustering of Antibody CDR Loop Conformations, J. Mol. Biol., 2011, vol. 406, pp. 228-256, doi:10.1016/j.jmb.2010.10.030.

O'Connor et al., Humanization of an antibody against human protein C and calcium-dependence involving framework residues, 1998, Protein Eng 11:321-8.

Olafsen, et al., Covalent disulfide-linked anti-CEA diabody allows site-specific conjugation and radiolabeling for tumor targeting applications, Protein Engineering, Design & Selection, 2004, vol. 17, No. 1, pp. 21-27.

Page et al., 1993, Intermantional. Journal of Oncology 3:473-476.

Panke, et al., Quantification of cell surface proteins with bispecific antibodies, Protein Engineering, Design & Selection, 2013, vol. 26, No. 10, pp. 645-654.

Pessano, et al., The T3/T cell receptor complex: antigenic distinction between the two 20-kd T3 (T3-δ and T3-ε) subunits, The EMBO Journal, 1985, vol. 4, No. 2, pp. 337-344.

Pettit et al., Antineoplastic agents 365. Dolastatin 10 SAR probes, 1998, Anti-Cancer Drug Design 13:243-277.

Pettit et al., Dolastatins 24. Synthesis of (−)-dolastatin 10.I X-ray molecular structure of N,N-dimethylvalyl-valyl-dolaisoleuine tert-butyl ester, 1996, J. Chem. Soc. Perkin Trans. 1 5:859-863.

Pettit et al., Specific activities of dolastatin 10 and peptide derivatives against Cryptococcus neoformans, 1998, Antimicrob. Agents Chemother. 42(11):2961-2965.

Pettit et al., Structure-activity studies with chiral isomers and with segments of the antimitotic marine peptide dolastation 10, 1989, J. Am. Chem. Soc. 111:5463-5465.

Pettit, et al., The dolastatins; 18: Sterospecific synthesis of dolaproine1, 1996, Synthesis 719-725.

Pichler et al., Differences of T-Cell Activation by the Anti-CD3 Antibodies Leu4 and BMA030, Mar. 30, 1987.

Potapov et al., Protein-Protein Recognition: Juxtaposition of Domain and Interface Cores in Immunoglobulins and Other Sandwich-like Proteins, J. Mol. Biol., 2004, vol. 342, pp. 665-679.

Presta et al., Humanization of an anti-vascular endothelial growth factor monoclonal antibody for the therapy of solid tumors and other disorders, 1997, Cancer Res.57(20):4593-9.

Queen et al., A humanized antibody that binds to the interleukin 2 receptor, 1989, Proc Natl Acad Sci, USA 86:10029-33.

Rader et al., A phage display approach for rapid antibody humanization: designed combinatorial V gene libraries, 1998, Proc. Natl. Acad. Sci. USA 95:8910-8915.

Raghavan et al., Fc receptors and their interactios with immunoglobulins, 1996, Annu Rev Cell Dev Biol 12:181-220.

Rattel, et al., AACR Poster, "Validation of Cynomolgus Monkeys as Relevant Species for Safety Assessment of a Novel Human BiTE Antibody Platform for Cancer Therapy," 2010.

Reddy et al., Elimination of Fc receptor-dependent effector functions of a modified IgG4 monoclonal antibody to human CD4., *J Immunol.* Feb. 15, 2000;164(4):1925-33.

Reiter et al., Disulfide stabilization of antibody Fv: computer predictions and experimental evaluation, Protein Eng., 1995, vol. 8(12), pp. 1323-1331.

Reiter et al., Engineering interchain disulfide bonds into conserved framework regions of Fv fragments: improved biochemical characteristics of recombinant immunotoxins containing disulfide-stabilized Fv, Protein Eng., 1994, vol. 7(5), pp. 697-704.

Remington's Pharmaceutical Sciences 16th edition, Osol, A. Ed. (1980) (Book Abstract).

Repp, et al., Combined Fc-protein- and Fc-glyco-engineering of scFv-Fc fusion proteins synergistically enhances CD16a binding but does not further enhance NK-cell mediated ADCC, Journal of Immunological Methods, 2011, vol. 373, Issues 1-2, pp. 67-78.

Ridgeway, et al., 'Knobs-into-holes' engineering of antibody CH3 domains for heavy chain heterodimerization, Protein Engineering,1996, vol. 9, No. 7, pp. 617-621.

Riechmann et al., Reshaping human antibodies for therapy, 1988, Nature 332:323-329.

Riethmüller, Symmetry breaking: bispecific antibodies, the beginnings, and 50 years on, Cancer Immunity, 2012, vol. 12, p. 12, pp. 1-7.

Rodeck et al., Interactions between growth factor receptors and corresponding monoclonal antibodies in human tumors, 1987, J Cell Biochem. 35(4):315-20.

Roguska et al., Humanization of murine monoclonal antibodies through variable domain resurfacing, 1994, Proc. Natl. Acad. Sci. USA 91:969-973.

Roosnek, et al., Triggering T Cells by Otherwise Inert Hybrid Anti-CD3/Antitumor Antibodies Requires Encounter with the Specific Target Cell, J. Exp. Med., 1989, vol. 170, pp. 297-302.

Roque et al., Antibodies and genetically engineered related molecules: production and purification, 2004, Biotechnol. Prog. 20:639-654.

Rose, et al., Mutation of Y407 in the CH3 domain dramatically alters glycosylation and structure of human IgG, mAbs, 2013, vol. 5, Issue 2, pp. 219-228.

Rose, et al., Quantitative Analysis of the Interaction Strength and Dynamics of Human IgG4 Half Molecules by Native Mass Spectrometry, Structure , 2011, vol. 19, pp. 1274-1282.

Rosok et al., A combinatorial library strategy for the rapid humanization of anticarcinoma BR 96 Fab, 1996, J. Biol. Chem. 271(37): 22611-22618.

Rossi, et al. A new class of bispecific antibodies to redirect T cells for cancer immunotherapy, mAbs 2014, vol. 6, Issue 2, pp. 381-391.

Roux, et al., Structural analysis of the nurse shark (new) antigen receptor (NAR): Molecular convergence of NAR and unusual mammalian immunoglobulins, Proc. Natl. Acad. Sci. USA, 1998, vol. 95, pp. 11804-11809.

Rudnick, et al., Affinity and Avidity in Antibody-Based Tumor Targeting, Cancer Biotherapy and Radiopharmaceuticals, 2009, vol. 24, No. 2, pp. 155-161, doi: 10.1089/cbr.2009.0627.

Röthlisberger, et al., Domain Interactions in the Fab Fragment: A Comparative Evaluation of the Single-chain Fv and Fab Format Engineered with Variable Domains of Different Stability, J. Mol. Biol. , 2005, vol. 347, pp. 773-789.

(56) References Cited

OTHER PUBLICATIONS

Salmeron et al., A conformational epitope expressed upon association of CD3-epsilon with either CD3-delta or CD3-gamma is the main target for recognition by anti-CD3 monoclonal antibodies, Nov. 1, 1991.
Sancho et al., CD3-Surface Expression Is Required for CD4-p56ick-mediated Up-regulation of T Cell Antigen Receptor-CD3 Signaling in T Cells, Apr. 16, 1992.
Schaefer, et al., A Two-in-One Antibody against HER3 and EGFR Has Superior Inhibitory Activity Compared with Monospecific Antibodies, Cancer Cell, 2011, vol. 20, pp. 472-486 & Supplemental Information, pp. 1-21.
Schaefer, et al., Immunoglobulin domain crossover as a generic approach for the production of bispecific IgG antibodies, PNAS, 2011, vol. 108, No. 27, pp. 11187-11192.
Schlapschy, et al., Functional humanization of an anti-CD16 Fab fragment: obstacles of switching from murine λ to human λ or κ light chains, Protein Engineering, Design & Selection, 2009, vol. 22, No. 3, pp. 175-188, doi:10.1093/protein/gzn066.
Schlereth, et al., Eradication of Tumors from a Human Colon Cancer Cell Line and from Ovarian Cancer Metastases in Immunodeficient Mice by a Single-Chain EP-CAM-/CD3-Bispecific Antibody Construct, Cancer Res 2005, vol. 65(7), pp. 2882-2889.
Schlereth, et al., T-cell activation and B-cell depletion in chimpanzees treated with a bispecific anti-CD19/anti-CD3 single-chain antibody construct, Cancer Immunol Immunother, 2006, vol. 55, pp. 503-514, doi:10.1007/s00262-005-0001-1.
Schoonjans, et al., Fab Chains As an Efficient Heterodimerization Scaffold for the Production of Recombinant Bispecific and Trispecific Antibody Derivatives, The Journal of Immunology, 2000, vol. 165, pp. 7050-7057.
Schroder et al., The Peptides, vol. pp. 76-136, 1965, Academic Press.
Senter et al, Proceedings of the American Association for Cancer Research, 2004, vol. 45, Abstract No. 623.
Senter, Potent antibody drug conjugates for cancer therapy, 2009, Current Opin. Chem. Biol. 13:235.
Shalaby, et al., Development of Humanized Bispecific Antibodies Reactive with Cytotoxic Lymphocytes and Tumor Cells Overexpressing the HER2 Protooncogene, J.Exp.Med., 1992, vol. 175, pp. 217-225.
Shan, et al., Characterization of scFv-Ig Constructs Generated from the Anti-CD20 mAb 1F5 Using Linker Peptides of Varying Lengths, J Immunol, 1999, vol. 162, pp. 6589-6595.
Shearman, et al., Construction, Expression and Characterization of Humanized Antibodies Directed Against the Human α/β T Cell Receptor, The Journal of Immunology, 1991, vol. 147, No. 12, pp. 4366-4373.
Shen, et al., Catumaxomab, a rat/murine hybrid trifunctional bispecific monoclonal antibody for the treatment of cancer, Curr Opin Mol Ther, 2008, vol. 10(3), pp. 273-284.
Shen, et al., Single Variable Domain-IgG Fusion: A Novel Recombinant Approach to Fc Domain-Containing Bispecific Antibodies, The Journal of Biological Chemistry, 2006, vol. 281, No. 16, pp. 10706-10714.
Shields et al., Lack of fucose on human IgG1 N-linked oligosaccharide improves binding to human FcγRIII and antibody-dependent cellular toxicity, 2002, J Biol Chem 277:26733-26740.
Shier et al., Identification of functional and structural amino-acid residues by parsimonious mutagenesis, 1995, Gene 169:147-155.
Shinkawa et al., The absence of fucose but not the presence of galactose or bisecting N-acetylglucosamine of human IgG1 complex-type oligosaccharides shows the critical role of enhancing antibody-dependent cellular cytotoxicity, 2003, J Biol Chem 278:3466-3473.
Skehan et al., Identification of functional and structural amino-acid residues by parsimonious mutagenesis, 1990, J. Natl. Cancer Inst. 82(13):1107-12.
Soumyarani et al, Oxidatively modified high density lipoprotein promotes inflammatory response in human monocytes-macrophages by enhanced production of ROS, TNF-α, MMP-9, and MMP-2., Mol Cell Biochem. Jul. 2012;366(1-2):277-85. doi: 10.1007/s11010-012-1306-y. Epub Apr. 17, 2012.
Spies et al., Alternative molecular formats and therapeutic applications for bispecific antibodies., Mol Immunol. Jan. 27, 2015. pii: S0161-5890(15)00005-X. doi: 10.1016/j.molimm.2015.01.003.
Spiess, et al., Bispecific antibodies with natural architecture produced by co-culture of bacteria expressing two distinct half-antibodies, Nature Biotechnology, 2013, doi:10.1038/nbt.2621 & Supplemental Information.
Stamova, Unexpected recombinations in single chain bispecific anti-CD3-anti-CD33 antibodies can be avoided by a novel linker module, Oct. 29, 2011.
Stanfield, et al., Maturation of Shark Single-domain (IgNAR) Antibodies: Evidence for Induced-fit Binding, J. Mol. Biol., 2007, vol. 367, pp. 358-372.
Stewart, et al., Recombinant CD36 inhibits oxLDL-induced ICAM-1-dependent monocyte adhesion., Mol Immunol. Feb. 2006;43(3):255-67.
Strop, P. et al., Generating Bispecific Human IgG1 and IgG2 Antibodies from Any Antibody Pair, J. Mol. Biol., 2012, doi:10.1016/j.jmb.2012.04.020.
Tan et al., "Superhumanized" antibodies: reduction of immunogenic potential by complementarity-determining region grafting with human germline sequences: application to an anti-CD28, 2002, J. Immunol. 169:1119-1125.
Tan, Philip, Presentation at PepTalk, Jan. 25, 2013, "Bi-specific ADAPTIR Molecule Targeting CD86 and Delivering Monomeric IL10 to Inhibit Antigen Presenting Cells".
Tarcsa et al, Chapter 10 Dual-Variable Domain Immunoglobulin (DVD-Ig™) Technology: A Versatile, Novel Format for the Next Generation of Dual-Targeting Biologics, Bispecific Antibodies 2011, pp. 171-185, 2011.
Teachey, et al., Cytokine release syndrome after blinatumomab treatment related to abnormal macrophage activation and ameliorated with cytokine-directed therapy, Blood, 2013, vol. 121, No. 26, pp. 5154-5157.
Tedgui, et al., Cytokines in atherosclerosis: pathogenic and regulatory pathways., Physiol Rev. Apr. 2006;86(2):515-81.
Thompson, et al., An Anti-CD3 Single-chain Immunotoxin with a Truncated Diphtheria Toxin Avoids Inhibition by Pre-existing Antibodies in Human Blood, J.Biol.Chem., 1995, vol. 270, No. 47, pp. 28037-28041.
Thompson, et al., Improved binding of a bivalent single-chain immunotoxin results in increased efficacy for in vivo T-cell depletion, Protein Engineering, 2001, vol. 14, No. 12, pp. 1035-1041.
Thorne, et al., CD36 is a receptor for oxidized high density lipoprotein: implications for the development of atherosclerosis., FEBS Lett. Mar. 20, 2007;581(6):1227-32. Epub Feb. 28, 2007.
Thorpe et al., New coupling agents for the synthesis of immunotoxins containing a hindered disulfide bond with improved stability in Vivo, 1987, Cancer Res. 47:5924-5931.
Thotakura et al., Enzymatic deglycosylating of glycoproteins, 1987, Meth. Enzymol. 138:350.
Thurman et al., Detection of complement activation using monoclonal antibodies against C3d., J Clin Invest. May 2013;123(5):2218-30. doi: 10.1172/JCI65861. Epub Apr. 24, 2013.
Tomlinson et. al., Methods for generating multivalent and bispecific antibody fragments, 2000, Methods Enzymol. 326:461-479.
Topp, et al., Targeted Therapy With the T-Cell-Engaging Antibody Blinatumomab of Chemotherapy-Refractory Minimal Residual Disease in B-Lineage Acute Lymphoblastic Leukemia Patients Results in High Response Rate and Prolonged Leukemia-Free Survival, J Clin Oncol vol. 29, No. 18, pp. 2493-2498.
Traunecker, et al., Bispecific single chain molecules (Janusins) target cytotoxic lymphocytes on HIV infected cells, The EMBO Journal, 1991, vol. 1, No. 12, pp. 3655-3659.
Tsurushita et al., Humanization of monoclonal antibodies, 2004, Molecular Biology of B Cells 533-545.
Umaña et al., Engineered glycoforms of an antineuro-blastoma IgG1 with optimized antibody-dependent cellular cytotoxic activity, 1999, Nat Biotechnol 17:176-180.

(56) References Cited

OTHER PUBLICATIONS

Valliere-Douglass, et al., O-Fucosylation of an antibody light chain: Characterization of a modification occurring on an IgG1 molecule, Glycobiology, 2009, vol. 19, No. 2, pp. 144-152, doi:10.1093/glycob/cwn116.

Van Boxel, et al., Some lessons from the systematic production and structural analysis of soluble αβ T-cell receptors, Journal of Immunological Methods, 2009, vol. 350, pp. 14-21.

Van Wauwe, et al., OKT3: A Monoclonal Anti-Human T Lymphoctye Antibody with Potent Mitogenic Properties, The Journal of Immunology, 1980, vol. 124, No. 6, pp. 2708-2713.

Verdier, et al., Determination of lymphocyte subsets and cytokine levels in Cynomolgus monkeys, Toxicology, 1995, vol. 105, pp. 81-90.

Verhoeyen et al., Reshaping human antibodies: grafting an antilysozyme activity, 1988, Science, 239:1534-1536.

Veri, et al., Therapeutic Control of B Cell Activation via Recruitment of Fcγ Receptor IIb (CD32B) Inhibitory Function With a Novel Bispecific Antibody Scaffold, Arthritis & Rheumatism, 2010, vol. 62, No. 7, pp. 1933-1943.

Vettermann, et al., Powered by pairing: The surrogate light chain amplifies immunoglobulin heavy chain signaling and pre-selects the antibody repertoire, Seminars in Immunology 18, 2006, pp. 44-55.

Von Kreudenstein, et al., Improving biophysical properties of a bispecific antibody scaffold to aid developability: Quality by molecular design, mAbs, 2013, vol. 5, Issue 5, pp. 1-9, http://dx.doi.org/10.4161/mabs.25632 & Supplemental Material.

Wang et al., Conserved amino acid networks involved in antibody variable domain interactions, Proteins, 2009, vol. 76, pp. 99-114.

Wang et al., Expression and characterization of recombinant soluble monkey CD3 molecules: mapping the FN18 polymorphic epitope, Molecular Immunology, 2004, vol. 40, pp. 1179-1188.

Wang, et al., A block in both early T lymphocyte and natural killer cell development in transgenic mice with high-copy numbers of the human CD3E gene, Proc. Natl. Acad. Sci. USA, 1994, vol. 91, pp. 9402-9406.

Ward, et al., Protein Engineering of Homodimeric Tyrosyl-tRNA Synthetase to Produce Active Heterodimers, The Journal of Biological Chemistry, 1986, vol. 261, No. 21, pp. 9576-9578.

Wawrzynczak et al., Methods for preparing immunotoxins: Effect of the linkage on activity and stability. In Immunoconjugates. Antibody Conjugates in Radio imaging and Therapy of Cancer. (C.-W. Vogel, editor). New York, Oxford University Press, pp. 28-55.

Weatherill, et al., Towards a universal disulphide stabilised single chain Fv format: importance of interchain disulphide bond location and vL-vH orientation, Protein Engineering, Design & Selection, 2012, vol. 25, No. 7, pp. 321-329.

Weiner, et al., The Role of T Cell Activation Bispecific Antibody Therapy in Anti-CD3 X Antitumor, Journal of Immunology, 1994, vol. 152, pp. 2385-2392.

Wesolowski, et al., Single domain antibodies: promising experimental and therapeutic tools in infection and immunity, Med Microbiol Immunol, 2009, vol. 198, pp. 157-174.

Whitlow, et al., An improved linker for single-chain Fv with reduced aggregation and enhanced proteolytic stability, Protein Engineering, 1993, vol. 6 , No. 8, pp. 989-995.

Wong, et al., The Mechanism of Anti-CD3 Monoclonal Antibodies, Transplantation, 1990, vol. 50, No. 4, pp. 683-689.

Woods, et al., LC-MS characterization and purity assessment of a prototype bispecific antibody, mAbs, 2013, vol. 5, Issue 5, pp. 711-722, http://dx.doi.org/10.4161/mabs.25488.

Woyke et al., In vitro activities and postantifungal effects of the potent dolastation 10 derivative auristatin PHE, 2001, Antimicrob. Agents and Chemother. 45(12):3580-3584.

Wu et al, Molecular construction and optimization of anti-human IL-11α/β dual variable domain immunoglobulin (DVD-Ig™) molecules, [mAbs 1:4, 339-347; Jul./Aug. 2009]; Landes Bioscience, Apr. 10, 2009.

Wu et al, Simultaneous targeting of multiple disease mediators by a dual-variable-domain immunoglobulin, (DVD-Ig™) molecules, Jul.-Aug. 2009; 339-347, Oct. 14, 2007.

Wu et al., Humanization of a murine monoclonal antibody by simultaneous optimization of framework and CDR residues, 1999, J. Mol. Biol. 294:151-162.

Wu, et al., Multimerization of a chimeric anti-CD20 single-chain Fv-Fc fusion protein is mediated through variable domain exchange, Protein Engineering, 2001, vol. 14, No. 12, pp. 1025-1033.

Wucherpfennig, et al., Structural Biology of the T-cell Receptor: Insights into Receptor Assembly, Ligand Recognition, and Initiation of Signaling, Cold Spring Harb Perspect Biol 2010;2:a005140.

Xie, et al., A new format of bispecific antibody: highly efficient heterodimerization, expression and tumor cell lysis, Journal of Immunological Methods, 2005, vol. 296 , pp. 95-101, doi:10.1016/j.jim.2004.11.005.

Xu, et al., Combinatorial surrobody libraries, PNAS, 2008, vol. 105, No. 31, pp. 10756-10761.

Xu, et al., Rapid optimization and prototyping for therapeutic antibody-like molecules, mAbs, 2013, vol. 5, Issue 2, pp. 237-254.

Xu, et al. Surrobodies with Functional Tails, J. Mol. Biol., 2010, vol. 397, pp. 352-360.

Yang et al., Differential in vitro activation of CD8-CD4+ and CD4-CD8+ T lymphocytes by combinations of anti-CD2 and anti-CD3 antibodies, Apr. 1, 1988.

Yelton et al., Affinity maturation of the BR96 anti-carcinoma antibody by codon-based mutagenesis, 1995, J. Immunol. 155:1994-2004.

Yeung, et al., Engineering human IgG1 affinity to human neonatal Fc receptor: impact of affinity improvement on pharmacokinetics in primates, J Immunol. Jun. 15, 2009;182(12):7663-71. doi: 10.4049/jimmunol.0804182.

Yoshino et al., Upgrading of flow cytometric analysis for absolute counts, cytokines and other antigenic molecules of cynomolgus monkeys (*Macaca fascicularis*) by using anti-human cross-reactive antibodies, Exp. Anim., 2000, vol. 49(2), pp. 97-100.

Yu et al., The biosynthetic gene cluster of the maytansinoids antitumor agent ansamitocin from actinosynnema pretiosum, 2002, PNAS 99:7968-7973.

Zeidler, et al., The Fc-region of a new class of intact bispecific antibody mediates activation of accessory cells and NK cells and induces direct phagocytosis of tumour cells, Br J Cancer, 2000, vol. 83(2), pp. 261-266.

Zhu, et al., Identification of Heavy Chain Residues in a Humanized Anti-CD3 Antibody Important for Efficient Antigen Binding and T Cell Activation, The Journal of Immunology, 1995, vol. 155, pp. 1903-1910.

Zhu, et al., Remodeling domain interfaces to enhance heterodimer formation, Protein Science, 1997, vol. 6, pp. 781-788.

Zuo, et al., An efficient route to the production of an IgG-like bispecific antibody, Protein Engineering, 2000, vol. 13, No. 5, pp. 361-367.

Kharmate et al., Inhibition of tumor promoting signals by activation of SSTR2 and opioid receptors in human breast cancer cells., Cancer Cell Int. Sep. 23, 2013;13(1):93. doi: 10.1186/1475-2867-13-93.

Ott et al., CTLA-4 and PD-1/PD-L1 blockade: new immunotherapeutic modalities with durable clinical benefit in melanoma patients., Clin Cancer Res. Oct. 1, 2013;19(19):5300-9. doi: 10.1158/1078-0432.CCR-13-0143.

Spranger et al., Mechanism of tumor rejection with doublets of CTLA-4, PD-1/Pd-L1, or IDO blockade involves restored IL-2 production and proliferation of CD8(+) T cells directly within the tumor microenvironment., J Immunother Cancer. Feb. 18, 2014;2:3. doi: 10.1186/2051-1426-2-3. eCollection 2014.

Bernett et al., Multiple Bispecific Checkpoint Combinations Promote T cell activation., Nov. 11, 2016, retrieved from the internet: http://files.shareholder.com/downloads/AMDA-2B2V8N/0x0x916283/67AE1A8B-40E8-4316-9F79-384D06B2C395/XNCR_SITC_2016_PD1xCTLA4_Poster126_12Nov2016.pdf.

Hedvat et al., Dual Blockade of PD-1 and CTLA-4 with Bispecific Antibodies Promotes Human T cell Activation and Proliferation., Nov. 11, 2016, retrieved from the internet: http://files.shareholder.

(56) References Cited

OTHER PUBLICATIONS com/downloads/AMDA-2B2V8N/0x0x916284/D8084990-61EC-4DFE-8B76-60CF58B8C06F/CPI_bispecifics.pdf.

Chichili et al., Co-targeting of PD-1 and CTLA-4 Inhibitory Pathways with Bispecific DART® and TRIDENT™ Molecules., Apr. 4, 2017, retrieved from the internet: http://files.shareholder.com/downloads/AMDA-278VRP/0x0x935572/8CC86417-40BA-41C0-935D-EF1B7DBOB5BB/AACR_2017_-_Co-targeting_PD-1_and_CTLA-4_Inhibitory_Pathways_with_DART_and_TRIDENT_Molecules.pdf.

Jin et al. The Design and Engineering of IgG-Like Bispecific Antibodies., Chapter 9, Bispecific Antibodies, pp. 151-169.

Zamyatnin AA., Amino Acid, Peptide, and Protein Volume in Solution., Annu Rev Biophys Bioeng. 1984;13:145-65.

Zalevsky et al. "Enhanced antibody half-life improves in vivo activity." Nature Biotechnology, vol. 28, No. 2, Feb. 1, 2010, pp. 157-159.

Ziebig et al., Effect of the oxLDL Binding Protein Fc-CD68 on Plaque Extension and Vulnerability in Atherosclerosis., Circulation Research 108: 695-703, 2011.

Ishigaki et al., Impact of Plasma Oxidized Low-Density Lipoprotein Removal on Atherosclerosis., Circulation 118: 75-83, 2008.

Wigginton et al., An immunoglobulin E-reactive chimeric human immunoglobulin G1 anti-idiotype inhibits basophil degranulation through cross-linking of FcεRI with FcγRIIb., Clinical & Experimental Allergy, 38:313-319. doi:10.1111/j.1365-2222.2007.02896.x.

Chu et al., Inhibition of B cell receptor-mediated activation of primary human B cells by coengagement of CD19 and FcgammaRIIb with Fc-engineered antibodies., Mol Immunol. Sep. 2008;45(15):3926-33. doi: 10.1016/j.molimm.2008.06.027. Epub Aug. 8, 2008.

Smith et al., Mouse model recapitulating human Fcγ receptor structural and functional diversity., Proc Natl Acad Sci U S A. Apr. 17, 2012;109(16):6181-6. doi: 10.1073/pnas.1203954109. Epub Apr. 2, 2012.

Tabrizi et al., Biodistribution mechanisms of therapeutic monoclonal antibodies in health and disease., AAPS J. Mar. 2010;12(1):33-43. doi: 10.1208/s12248-009-9157-5. Epub Nov. 19, 2009.

DiGiandomenico et al., A multifunctional bispecific antibody protects against Pseudomonas aeruginosa., Sci Transl Med. Nov. 12, 2014;6(262):262ra155. doi: 10.1126/scitranslmed.3009655.

Scott et al., Antibody therapy of cancer., Nat Rev Cancer. Mar. 22, 2012;12(4):278-87. doi: 10.1038/nrc3236.

Clynes et al., Redirected T Cell Cytotoxicity in Cancer Therapy., Annu Rev Med. Jan. 27, 2019;70:437-450. doi: 10.1146/annurev-med-062617-035821. Epub Oct. 31, 2018.

Merchant et al., Monovalent antibody design and mechanism of action of onartuzumab, a MET antagonist with anti-tumor activity as a therapeutic agent., Proc Natl Acad Sci U S A. Aug. 6, 2013;110(32):E2987-96. doi: 10.1073/pnas.1302725110. Epub Jul. 23, 2013.

Fos et al., ICOS ligation recruits the p50alpha PI3K regulatory subunit to the immunological synapse., J Immunol. Aug. 1, 2008;181(3):1969-77.

Sanmamed et al., Agonists of Co-stimulation in Cancer Immunotherapy Directed Against CD137, OX40, GITR, CD27, CD28, and ICOS., Semin Oncol. Aug. 2015;42(4):640-55. doi: 10.1053/j.seminoncol.2015.05.014. Epub Jun. 11, 2015.

Vieira et al., ICOS-mediated signaling regulates cytokine production by human T cells and provides a unique signal to selectively control the clonal expansion of Th2 helper cells., Eur J Immunol. May 2004;34(5):1282-90.

Madrenas et al., Conversion of CTLA-4 from inhibitor to activator of T cells with a bispecific tandem single-chain Fv ligand., J Immunol. May 15, 2004;172(10):5948-56.

Yokosuka et al., Spatiotemporal basis of CTLA-4 costimulatory molecule-mediated negative regulation of T cell activation., Immunity. Sep. 24, 2010;33(3):326-39. doi: 10.1016/j.immuni.2010.09.006.

Carpenter et al., Activation of human B cells by the agonist CD40 antibody CP-870,893 and augmentation with simultaneous toll-like receptor 9 stimulation., J Transl Med. Nov. 11, 2009;7:93. doi: 10.1186/1479-5876-7-93.

Fan et al., Engagement of the ICOS pathway markedly enhances efficacy of CTLA-4 blockade in cancer immunotherapy., J Exp Med. Apr. 7, 2014;211(4):715-25. doi: 10.1084/jem.20130590. Epub Mar. 31, 2014.

Gilboa et al., Use of oligonucleotide aptamer ligands to modulate the function of immune receptors., Clin Cancer Res. Mar. 1, 2013;19(5):1054-62. doi: 10.1158/1078-0432.CCR-12-2067.

Uy et al., Preliminary Results of a Phase 1 Study of Flotetuzumab, a CD123 x CD3 Bispecific Dart® Protein, in Patients with Relapsed/Refractory Acute Myeloid Leukemia and Myelodysplastic Syndrome., Blood 2017 130:637.

Vey et al., Interim Results from a Phase 1 First-in-Human study of flotetuzumab, a CD123 x CD3 bispecific Dart molecule, in AML/MDS., Annals of Oncology (2017) 28 (suppl_5): v355-v371. 10.1093/annonc/mdx373.

Ravandi et al., Complete Responses in Relapsed/Refractory Acute Myeloid Leukemia (AML) Patients on a Weekly Dosing Schedule of XmAb14045, a CD123 x CD3 T Cell-Engaging Bispecific Antibody: Initial Results of a Phase 1 Study., Blood 2018 132:763; doi: https://doi.org/10.1182/blood-2018-99-119786.

Bacac et al., A Novel Carcinoembryonic Antigen T-Cell Bispecific Antibody (CEA TCB) for the Treatment of Solid Tumors., Clin Cancer Res. Jul. 1, 2016;22(13):3286-97.

Schuster et al., Immunotherapy with the trifunctional anti-CD20 x anti-CD3 antibody FBTA05 (Lymphomun) in paediatric high-risk patients with recurrent CD20-positive B cell malignancies., Br J Haematol. Apr. 2015;169(1):90-102. doi: 10.1111/bjh.13242. Epub Dec. 11, 2014.

\* cited by examiner

Figure 2A antigen sequences

Human PD-1 sequence

>sp|Q15116  SEQ ID NO: 1
MQIPQAPWPVVWAVLQLGWRPGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVPTAHPSPSPRPAGQFQTLVVG
VVGGLLGSLVLLVWVLAVICSRAARGTIGARRTGQPLKEDPSAVPVFSVDYGELDFQWREKTPEPPVPCVPEQTEYATIVFPSGMG
TSSPARRGSADGPRSAQPLRPEDGHCSWPL

Human PD-1 sequence, extracellular domain

>sp|Q15116|21-170  SEQ ID NO: 2
PGWFLDSPDRPWNPPTFSPALLVVTEGDNATFTCSFSNTSESFVLNWYRMSPSNQTDKLAAFPEDRSQPGQDCRFRVTQLPNGRDF
HMSVVRARRNDSGTYLCGAISLAPKAQIKESLRAELRVTERRAEVPTAHPSPSPRPAGQFQTLV

Macaca fascicularis PD-1 sequence

>tr|B0LAJ3  SEQ ID NO: 3
MQIPQAPWPVVWAVLQLGWRPGWFLESPDRPWNAPTFSPALLLVTEGDNATFTCSFSNASESFVLNWYRMSPSNQTDKLAAFPEDR
SQPGQDCRFRVTRLPNGRDFHMSVVRARRNDSGTYLCGAISLAPKAQIKESLRAELRVTERRAEVPTAHPSPSPRPAGQFQALVVG
VVGGLLGSLVLLVWVLAVICSRAAQGTIEARRTGQPLKEDPSAVPVFSVDYGELDFQWREKTPEPPAPCVPEQTEYATIVFPSGLG
TSSPARRGSADGPRSPRPLRPEDGHCSWPL

Macaca fascicularis PD-1 sequence, extracellular domain (predicted)

>tr|B0LAJ3|21-170  SEQ ID NO: 4
PGWFLESPDRPWNAPTFSPALLLVTEGDNATFTCSFSNASESFVLNWYRMSPSNQTDKLAAFPEDRSQPGQDCRFRVTRLPNGRDF
HMSVVRARRNDSGTYLCGAISLAPKAQIKESLRAELRVTERRAEVPTAHPSPSPRPAGQFQALV

Human CTLA-4 sequence

>sp|P16410  SEQ ID NO: 5
MACLGFQRHKAQLNLATRTWPCTLLFFLLFIPVFCKAMHVAQPAVVLASSRGIASFVCEYASPGKATEVRVTVLRQADSQVTEVCA
ATYMMGNELTFLDDSICTGTSSGNQVNLTIQGLRAMDTGLYICKVELMYPPPYYLGIGNGTQIYVIDPEPCPDSDFLLWILAAVSS
GLFFYSFLLTAVSLSKMLKKRSPLTTGVYVKMPPTEPECEKQFQPYFIPIN

Human CTLA-4 sequence, extracellular domain

>sp|P16410|36-161  SEQ ID NO: 6
KAMHVAQPAVVLASSRGIASFVCEYASPGKATEVRVTVLRQADSQVTEVCAATYMMGNELTFLDDSICTGTSSGNQVNLTIQGLRA
MDTGLYICKVELMYPPPYYLGIGNGTQIYVIDPEPCPDSD

Figure 2B

Macaca fascicularis CTLA-4 sequence

>tr|G7PL88 SEQ ID NO: 7
MACLGFQRHKARLNLATRTRPYTLLFSLLFIPVFSKAMHVAQPAVVLANSRGIASFVCEYASPGKATEVRVTVLRQADSQVTEVCA
ATYMMGNELTFLDDSICTGTSSGNQVNLTIQGLRAMDTGLYICKVELMYPPPYYMGIGNGTQIYVIDPEPCPDSDFLLWILAAVSS
GLFFYSFLLTAVSLSKMLKKRSPLTTGVYVKMPPTEPECEKQFQPYFIPIN

Macaca fascicularis CTLA-4 sequence, extracellular domain (predicted)

>tr|G7PL88 SEQ ID NO: 8
KAMHVAQPAVVLANSRGIASFVCEYASPGKATEVRVTVLRQADSQVTEVCAATYMMGNELTFLDDSICTGTSSGNQVNLTIQGLRA
MDTGLYICKVELMYPPPYYMGIGNGTQIYVIDPEPCPDSD

Human LAG-3 sequence

>sp|P18627 SEQ ID NO: 9
MWEAQFLGLLFLQPLWVAPVKPLQPGAEVPVVWAQEGAPAQLPCSPTIPLQDLSLLRRAGVTWQHQPDSGPPAAAPGHPLAPGPHP
AAPSSWGPRPRRYTVLSVGPGGLRSGRLPLQPRVQLDERGRQRGDFSLWLRPARRADAGEYRAAVHLRDRALSCRLRLRLGQASMT
ASPPGSLRASDWVILNCSFSRPDRPASVHWFRNRGQGRVPVRESPHHHLAESFLFLPQVSPMDSGPWGCILTYRDGFNVSIMYNLT
VLGLEPPTPLTVYAGAGSRVGLPCRLPAGVGTRSFLTAKWTPPGGGPDLLVTGDNGDFTLRLEDVSQAQAGTYTCHIHLQEQQLNA
TVTLAIITVTPKSFGSPGSLGKLLCEVTPVSGQERFVWSSLDTPSQRSFSGPWLEAQEAQLLSQPWQCQLYQGERLLGAAVYFTEL
SSPGAQRSGRAPGALPAGHLLLFLILGVLSLLLLVTGAFGFHLWRRQWRPRRFSALEQGIHPPQAQSKIEELEQEPEPEPEPEPEP
EPEPEPEQL

Human LAG-3 sequence, extracellular domain

>sp|P18627|29-450 SEQ ID NO: 10
VPVVWAQEGAPAQLPCSPTIPLQDLSLLRRAGVTWQHQPDSGPPAAAPGHPLAPGPHPAAPSSWGPRPRRYTVLSVGPGGLRSGRL
PLQPRVQLDERGRQRGDFSLWLRPARRADAGEYRAAVHLRDRALSCRLRLRLGQASMTASPPGSLRASDWVILNCSFSRPDRPASV
HWFRNRGQGRVPVRESPHHHLAESFLFLPQVSPMDSGPWGCILTYRDGFNVSIMYNLTVLGLEPPTPLTVYAGAGSRVGLPCRLPA
GVGTRSFLTAKWTPPGGGPDLLVTGDNGDFTLRLEDVSQAQAGTYTCHIHLQEQQLNATVTLAIITVTPKSFGSPGSLGKLLCEVT
PVSGQERFVWSSLDTPSQRSFSGPWLEAQEAQLLSQPWQCQLYQGERLLGAAVYFTELSSPGAQRSGRAPGALPAGHL

Macaca fascicularis LAG-3 sequence (predicted)

>gi|544467815|ref|XP_005570011.1 SEQ ID NO: 11
MWEAQFLGLLFLQPLWVAPVKPPQPGAEISVVWAQEGAPAQLPCSPTIPLQDLSLLRRAGVTWQHQPDSGPPAXAPGHPPVPGHRP
AAPYSWGPRPRRYTVLSVGPGGLRSGRLPLQPRVQLDERGRQRGDFSLWLRPARRADAGEYRATVHLRDRALSCRLRLRVGQASMT
ASPPGSLRTSDWVILNCSFSRPDRPASVHWFRSRGQGRVPVQGSPHHHLAESFLFLPHVGPMDSGLWGCILTYRDGFNVSIMYNLT
VLGLEPATPLTVYAGAGSRVELPCRLPPAVGTQSFLTAKWAPPGGGPDLLVAGDNGDFTLRLEDVSQAQAGTYICHIRLQGQQLNA
TVTLAIITVTPKSFGSPGSLGKLLCEVTPASGQEHFVWSPLNTPSQRSFSGPWLEAQEAQLLSQPWQCQLHQGERLLGAAVYFTEL
SSPGAQRSGRAPGALRAGHLPLFLILGVLFLLLLVTGAFGFHLWRRQWRPRRFSALEQGIHPPQAQSKIEELEQEPELEPEPELER
ELGPEPEPGPEPEPEQL

Figure 2C

Macaca fascicularis LAG-3 sequence, extracellular domain (predicted)

```
>gi|544467815|ref|XP_005570011.1|29-450 SEQ ID NO: 12
ISVVWAQEGAPAQLPCSPTIPLQDLSLLRRAGVTWQHQPDSGPPAXAPGHPPVPGHRPAAPYSWGPRPRRYTVLSVGPGGLRSGRL
PLQPRVQLDERGRQRGDFSLWLRPARRADAGEYRATVHLRDRALSCRLRLRVGQASMTASPPGSLRTSDWVILNCSFSRPDRPASV
HWFRSRGQGRVPVQGSPHHHLAESFLFLPHVGPMDSGLWGCILTYRDGFNVSIMYNLTVLGLEPATPLTVYAGAGSRVELPCRLPP
AVGTQSFLTAKWAPPGGGPDLLVAGDNGDFTLRLEDVSQAQAGTYICHIRLQGQQLNATVTLAIITVTPKSFGSPGSLGKLLCEVT
PASGQEHFVWSPLNTPSQRSFSGPWLEAQEAQLLSQPWQCQLHQGERLLGAAVYFTELSSPGAQRSGRAPGALRAGHL
```

Human BTLA sequence

```
>sp|Q7Z6A9 SEQ ID NO: 13
MKTLPAMLGTGKLFWVFFLIPYLDIWNIHGKESCDVQLYIKRQSEHSILAGDPFELECPVKYCANRPHVTWCKLNGTTCVKLEDRQ
TSWKEEKNISFFILHFEPVLPNDNGSYRCSANFQSNLIESHSTTLYVTDVKSASERPSKDEMASRPWLLYRLLPLGGLPLLITTCF
CLFCCLRRHQGKQNELSDTAGREINLVDAHLKSEQTEASTRQNSQVLLSETGIYDNDPDLCFRMQEGSEVYSNPCLEENKPGIVYA
SLNHSVIGPNSRLARNVKEAPTEYASICVRS
```

Human BTLA sequence, extracellular domain

```
>sp|Q7Z6A9|31-157 SEQ ID NO: 14
KESCDVQLYIKRQSEHSILAGDPFELECPVKYCANRPHVTWCKLNGTTCVKLEDRQTSWKEEKNISFFILHFEPVLPNDNGSYRCS
ANFQSNLIESHSTTLYVTDVKSASERPSKDEMASRPWLLYR
```

Macaca fascicularis BTLA sequence (predicted)

```
>gi|355746406|gb|EHH51020.1 SEQ ID NO: 15
MKTLPAMLGSGRLFWVVFLIPYLDIWNIHGKESCDVQLYIKRQSYHSIFAGDRFKLECPVKYCAHRPQVTWCKLNGTTCVKLEGRH
TSWKQEKNLSFFILHFEPVLPSDNGSYRCSANFLSAIIESHSTTLYVTDVKSASERPSKDEMASRPWLLYSLLPLGGLPLLITTCF
CLFCFLRRHQGKQNELSDTTRREITLVDVPFKSEQTEASTRQNSQVLLSETGIYDNEPDFCFRMQEGSEVYSNPCLEENKPGIIYA
SLNHSIIGLNARQARNVKEAPTEYASICVRS
```

Macaca fascicularis BTLA sequence, extracellular domain (predicted)

```
>gi|355746406|gb|EHH51020.1|31-157 SEQ ID NO: 16
KESCDVQLYIKRQSYHSIFAGDRFKLECPVKYCAHRPQVTWCKLNGTTCVKLEGRHTSWKQEKNLSFFILHFEPVLPSDNGSYRCS
ANFLSAIIESHSTTLYVTDVKSASERPSKDEMASRPWLLYS
```

Human TIM-3 sequence

```
>sp|Q8TDQ0 SEQ ID NO: 17
MFSHLPFDCVLLLLLLLTRSSEVEYRAEVGQNAYLPCFYTPAAPGNLVPVCWGKGACPVFECGNVVLRTDERDVNYWTSRYWLNG
DFRKGDVSLTIENVTLADSGIYCCRIQIPGIMNDEKFNLKLVIKPAKVTPAPTRQRDFTAAFPRMLTTRGHGPAETQTLGSLPDIN
LTQISTLANELRDSRLANDLRDSGATIRIGIYIGAGICAGLALALIFGALIFKWYSHSKEKIQNLSLISLANLPPSGLANAVAEGI
RSEENIYTIEENVYEVEEPNEYYCYVSSRQQPSQPLGCRFAM
```

Figure 2D

Human TIM-3 sequence, extracellular domain

>sp|Q8TDQ0|22-202  SEQ ID NO: 18
SEVEYRAEVGQNAYLPCFYTPAAPGNLVPVCWGKGACPVFECGNVVLRTDERDVNYWTSRYWLNGDFRKGDVSLTIENVTLADSGI
YCCRIQIPGIMNDEKFNLKLVIKPAKVTPAPTRQRDFTAAFPRMLTTRGHGPAETQTLGSLPDINLTQISTLANELRDSRLANDLR
DSGATIRIG

Macaca fascicularis TIM-3 sequence (predicted)

>gi|355750365|gb|EHH54703.1  SEQ ID NO: 19
MFSHLPFDCVLLLLLLLTRSSEVEYIAEVGQNAYLPCSYTPAPPGNLVPVCWGKGACPVFDCSNVVLRTDNRDVNDRTSGRYWLK
GDFHKGDVSLTIENVTLADSGVYCCRIQIPGIMNDEKHNVKLVVIKPAKVTPAPTLQRDLTSAFPRMLTTGEHGPAETQTPGSLPD
VNLTVSNFFCELQIFTLTNELRDSGATIRTAIYIAAGISAGLALALIFGALIFKWYSHSKEKTQNLSLISLANIPPSGLANAVAEG
IRSEENIYTIEEDVYEVEEPNEYYCYVSSGQQPSQPLGCRVAMP

Macaca fascicularis TIM-3 sequence, extracellular domain (predicted)

>gi|355750365|gb|EHH54703.1|22-203  SEQ ID NO: 20
SEVEYIAEVGQNAYLPCSYTPAPPGNLVPVCWGKGACPVFDCSNVVLRTDNRDVNDRTSGRYWLKGDFHKGDVSLTIENVTLADSG
VYCCRIQIPGIMNDEKHNVKLVVIKPAKVTPAPTLQRDLTSAFPRMLTTGEHGPAETQTPGSLPDVNLTVSNFFCELQIFTLTNEL
RDSGATIRTA

II. Figure 3A skew variants

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

Figure 3B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

Figure 3C

| Monomer 1 | Monomer 2 |
|---|---|
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| N208D Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

Figure 3D

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

Figure 3E

| Monomer 1 | Monomer 2 |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |

Figure 3F

| Monomer 1 | Monomer 2 |
|---|---|
| T366S/L368A/Y407V/Y349C | T366W/S354C |
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| Q295E N384D Q418E N421D | |
| N208D Q295E Q418E N421D | |
| Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

III.  Figure 4  pI variants

| Variant constant region | Substitutions |
|---|---|
| pI_ISO(-) | I199T N203D K274Q R355Q N384S K392N V397M Q419E DEL447 |
| pI_(-)_isosteric_A | N208D Q295E N384D Q418E N421D |
| pI_(-)_isosteric A-Fc only | Q295E N384D Q418E N421D |
| pI_(-)_isosteric_B | N208D Q295E Q418E N421D |
| pI_(-)_isosteric_B-Fc only | Q295E Q418E N421D |
| pI_ISO(+RR) | Q196K I199T P217R P228R N276K |
| pI_ISO(+) | Q196K I199T N276K |
| pI_(+)_isosteric_A | E269Q E272Q E283Q E357Q |
| pI_(+)_isosteric_B | E269Q E272Q E283Q |
| pI_(+)_isosteric_E269Q/E272Q | E269Q E272Q |
| pI_(+)_isosteric_E269Q/E283Q | E269Q E283Q |
| pI_(+)_

IV. Figure 5: Ablation variants

| Variant | Variant(s), cont. |
|---|---|
| G236R | P329K |
| S239G | A330L |
| S239K | A330S/P331S |
| S239Q | I332K |
| S239R | I332R |
| V266D | V266D/A327Q |
| S267K | V266D/P329K |
| S267R | S267R/A327Q |
| H268K | S267R/P329K |
| E269R | G236R/L328R |
| 299R | E233P/L234V/L235A/G236del/S239K |
| 299K | E233P/L234V/L235A/G236del/S267K |
| K322A | E233P/L234V/L235A/G236del/S239K/A327G |
| A327G | E233P/L234V/L235A/G236del/S267K/A327G |
| A327L | E233P/L234V/L235A/G236del |
| A327N | S239K/S267K |
| A327Q | 267K/P329K |
| L328E | |
| L328R | |
| P329A | |
| P329H | |

Figure 6A useful combinations

| scFv monomer (+) | Fab monomer (-) |
|---|---|
| Heterodimer pI variants S364K/E357Q | Heterodimerization pI variants L368D/K370S |
| Optional scFv charged linker including but not limited to (GKPGS)$_4$ (SEQ ID NO: 37755) | Isosteric pI substitutions N208D/Q295E/N384D/Q418E/N421D |
| FcKO E233P/L234V/L235A/G236del/S267K | FcKO E233P/L234V/L235A/G236del/S267K |
| ± 428L/434S for FcRn | ± 428L/434S for FcRn |
| scFv of ABD of either ICOS or a checkpoint inhibitor | Fv/Fab of the other of ABD of either ICOS or a checkpoint inhibitor |

Figure 6B

| scFv monomer | Fab monomer |
|---|---|
| Heterodimer pI variants S364K/E357Q | Heterodimerization pI variants L368D/K370S |
| Optional scFv charged linker including, but not limited to (GKPGS)$_4$ (SEQ ID NO: 37755) | pI substitutions I199T N203D K274Q R355Q Q419E K447del |
| FcKO E233P/L234V/L235A/G236del/S267K | FcKO E233P/L234V/L235A/G236del/S267K |
| ± 428L/434S for FcRn (optional) | ± 428L/434S for FcRn (optional) |
| scFv of either ICOS or a checkpoint inhibitor | Fv/Fab of the other of ABD of either ICOS or a checkpoint inhibitor |

Figure 7A Linkers

Positive charged scFv linkers

| Name | Sequence | Length | Charge | SEQ ID NO: |
|---|---|---|---|---|
| Gly-Ser 15 | GGGGSGGGGSGGGGS | 15 | 0 | 37699 |
| Whitlow linker | GSTSGSGKPGSGEGSTKG | 18 | +1 | 37700 |
| 6paxA_1 (+A) | IRPRAIGGSKPRVA | 14 | +4 | 37701 |
| +B | GKGGSGKGGSGKGGS | 15 | +3 | 37702 |
| +C | GGKGSGGKGSGGKGS | 15 | +3 | 37703 |
| +D | GGGKSGGGKSGGGKS | 15 | +3 | 37704 |
| +E | GKGKSGKGKSGKGKS | 15 | +6 | 37705 |
| +F | GGGKSGGKGSGKGGS | 15 | +3 | 37706 |
| +G | GKPGSGKPGSGKPGS | 15 | +3 | 37707 |
| +H | GKPGSGKPGSGKPGSGKPGS | 20 | +4 | 37708 |
| +I | GKGKSGKGKSGKGKSGKGKS | 20 | +8 | 37709 |

Negative charged scFv linkers

| Name | Sequence | Length | Charge | SEQ ID NO: |
|---|---|---|---|---|
| Gly-Ser 15 | GGGGSGGGGSGGGGSGGGGS | 20 | 0 | 37710 |
| 3hsc_2 (-A) | STAGDTHLGGEDFD | 14 | -4 | 37711 |
| -B | GEGGSGEGGSGEGGS | 15 | -3 | 37712 |
| -C | GGEGSGGEGSGGEGS | 15 | -3 | 37713 |
| -D | GGGESGGGESGGGES | 15 | -3 | 37714 |
| -E | GEGESGEGESGEGES | 15 | -6 | 37715 |
| -F | GGGESGGEGSGEGGS | 15 | -3 | 37716 |
| -G | GEGESGEGESGEGESGEGES | 20 | -8 | 37717 |

Figure 7B scFv linkers

| | |
|---|---|
| GGGGSGGGGSGGGGS | (SEQ ID NO: 37718) |
| GGGGSGGGGSGGGGSGGGGS | (SEQ ID NO: 37719) |
| GSTSGSGKPGSGEGSTKG | (SEQ ID NO: 37720) |
| PRGASKSGSASQTGSAPGS | (SEQ ID NO: 37721) |
| GTAAAGAGAAGGAAAGAAG | (SEQ ID NO: 37722) |
| GTSGSSGSGSGGSGSGGGG | (SEQ ID NO: 37723) |
| GKPGSGKPGSGKPGSGKPGS | (SEQ ID NO: 37724) |

VII. Figure 8 Tms of skews

| XENP | Heterodimer-skewing variant, Chain 1 | Heterodimer-skewing variant, Chain 2 | Heterodimer Yield (%) | CH3 Tm (°C) |
|---|---|---|---|---|
| 12757 | none | none | 52.7 | 83.1 |
| 12758 | L368D/K370S | S364K | 94.4 | 76.6 |
| 12759 | L368D/K370S | S364K/E357L | 90.2 | 77.2 |
| 12760 | L368D/K370S | S364K/E357Q | 95.2 | 77.5 |
| 12761 | T411E/K360E/Q362E | D401K | 85.6 | 80.6 |
| 12496 | L368E/K370S | S364K | 91.5 | n.d. |
| 12511 | K370S | S364K | 59.9 | n.d. |
| 12840 | L368E/K370S | S364K/E357Q | 59.5 | n.d. |
| 12841 | K370S | S364K/E357Q | 90.4 | n.d. |
| 12894 | L368E/K370S | S364K | 41.0 | n.d. |
| 12895 | K370S | S364K | 49.3 | n.d. |
| 12896 | L368E/K370S | S364K/E357Q | 73.9 | n.d. |
| 12901 | K370S | S364K/E357Q | 87.9 | n.d. |

Figure 9A   XENP19690 1G6_H1.279_L1.194 anti-PD-1 Fv sequences

| What | sequence | SEQ ID NO: |
|---|---|---|
| Vh domain | EVQLVESGGGLVKPGGSLRLSCVASGFTFSNYWMNWVRQAPGKGLEWVAEIRLYSNNYATHYAESVKGRFTISRDDSKSTLYLQMN NLKTEDTGVYYCTRYYGNYGGYFDVWGRGTLVTVSS | 37759 |
| vhCDR1 | NYWMN | 37760 |
| vhCDR2 | EIRLYSNNYATHYAESVKG | 37761 |
| vhCDR3 | YYGNYGGYFDV | 37762 |
| scFv linker | GKPGSGKPGSGKPGSGKPGS | 37708 |
| Vl domain | EIVLTQSPATLSASPGERVTLTCRASQSVGNLVAWYQQKPGQAPRLLINYASHRYTGVPDRFTGSGYGTEFTLTISSVQSEDFGVY YCQQDFSSPRTFGGGTKVEIK | 37763 |
| vlCDR1 | RASQSVGNDVA | 37764 |
| vlCDR2 | YASHRYT | 37765 |
| vlCDR3 | QQDFSSPRT | 37766 |
| scFv | EVQLVESGGGLVKPGGSLRLSCVASGFTFSNYWMNWVRQAPGKGLEWVAEIRLYSNNYATHYAESVKGRFTISRDDSKSTLYLQMN NLKTEDTGVYYCTRYYGNYGGYFDVWGRGTLVTVSS/GKPGSGKPGSGKPGSGKPGS/EIVLTQSPATLSASPGERVTLTCRASQS VGNLVAWYQQKPGQAPRLLINYASHRYTGVPDRFTGSGYGTEFTLTISSVQSEDFGVYYCQQDFSSPRTFGGGTKVEIK/ | 37767 |

Figure 9B   1G6_H1.280_L1.224 anti-PD-1 Fv sequences

| What | sequence | SEQ ID NO: |
|---|---|---|
| Variable heavy (vh) domain | EVQLVESGGGLVKPGGSLRLTCVASGFTFSNYWMNWVRQAPGKGLEWVAEIRLYSNNYATHYAESVKGRFTISRDDSKSTLYLQMN NLKTEDTGVYYCTRYYGNYGGYFDVWGRGTLVTVSS | 37768 |
| vhCDR1 | NYWMN | 37769 |
| vhCDR2 | EIRLYSNNYATHYAESVKG | 37770 |
| vhCDR3 | YYGNYGGYFDV | 37771 |
| scFv linker | GKPGSGKPGSGKPGSGKPGS | 37708 |
| Variable light (vl) domain | EIVLTQSPATLSVSPGERVTLTCRASQSVGNEVAWYQQKPGQAPRLLINYASHRYTSVPDRFTGSGYGTEFTLTISSVQSEDFAVY YCQQDWSSPRTFGGGTKVEIK | 37772 |
| vlCDR1 | RASQSVGNDVA | 37773 |
| vlCDR2 | YASHRYT | 37774 |
| vlCDR3 | QQDWSSPRT | 37775 |
| scFv | EVQLVESGGGLVKPGGSLRLTCVASGFTFSNYWMNWVRQAPGKGLEWVAEIRLYSNNYATHYAESVKGRFTISRDDSKSTLYLQMN NLKTEDTGVYYCTRYYGNYGGYFDVWGRGTLVTVSS/GKPGSGKPGSGKPGSGKPGS/EIVLTQSPATLSVSPGERVTLTCRASQS VGNEVAWYQQKPGQAPRLLINYASHRYTSVPDRFTGSGYGTEFTLTISSVQSEDFAVYYCQQDWSSPRTFGGGTKVEIK | 37776 |

Figure 9C XENP19692 1G6_L1.194_H1.279 anti-PD-1 Fv sequences

| What | sequence | SEQ ID NO: |
|---|---|---|
| Variable light (vl) domain | EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGGGTKVEIK | 37777 |
| vlCDR1 | RASQSVGNDVA | 37778 |
| vlCDR2 | YASHRYT | 37779 |
| vlCDR3 | QQDFSSPRT | 37780 |
| scFv linker | GKPGSGKPGSGKPGSGKPGS | 37708 |
| Variable heavy (vh) domain | EVQLVESGGGLVKPGGSLRLSCVASGFTFSNYWMNWVRQAPGKGLEWVAEIRLYSNNYATHYAESVKGRFTISRDDSKSTLYLQMNNLKTEDTGVYYCTRYYGNYGGYFDVWGRGTLVTVSS | 37781 |
| vhCDR1 | NYWMN | 37782 |
| vhCDR2 | EIRLYSNNYATHYAESVKG | 37783 |
| vhCDR3 | YYGNYGGYFDV | 37784 |
| scFv | EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGGGTKVEIK/GKPGSGKPGSGKPGSGKPGS/EVQLVESGGGLVKPGGSLRLSCVASGFTFSNYWMNWVRQAPGKGLEWVAEIRLYSNNYATHYAESVKGRFTISRDDSKSTLYLQMNNLKTEDTGVYYCTRYYGNYGGYFDVWGRGTLVTVSS | 37785 |

Figure 9D XENP19669 1G6_L1.210_H1.288 anti-PD-1 Fv sequences

| What | sequence | SEQ ID NO: |
|---|---|---|
| Variable heavy (vh) domain | EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGCGTKVEIK | 37786 |
| vhCDR1 | RASQSVGNDVA | 37787 |
| vhCDR2 | YASHRYT | 37789 |
| vhCDR3 | QQDFSSPRT | 37790 |
| scFv linker | GKPGSGKPGSGKPGSGKPGS | 37708 |
| Variable light (vl) domain | EVQLVESGGGLVKPGGSLRLSCVASGFTFSNYWMNWVRQAPGKCLEWVAEIRLYSNNYATHYAESVKGRFTISRDDSKSTLYLQMNNLKTEDTGVYYCTRYYGNYGGYFDVWGRGTLVTVSS | 37790 |
| vlCDR1 | NYWMN | 37791 |
| vlCDR2 | EIRLYSNNYATHYAESVKG | 37792 |
| vlCDR3 | YYGNYGGYFDV | 37793 |
| scFv | EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGCGTKVEIK/GKPGSGKPGSGKPGSGKPGS/EVQLVESGGGLVKPGGSLRLSCVASGFTFSNYWMNWVRQAPGKCLEWVAEIRLYSNNYATHYAESVKGRFTISRDDSKSTLYLQMNNLKTEDTGVYYCTRYYGNYGGYFDVWGRGTLVTVSS | 37794 |

Figure 9E XENP20162 2E9_H1L1 anti-PD-1 Fv sequences

| What | sequence | SEQ ID NO: |
|---|---|---|
| Variable heavy (vh) domain | QVQLVQSGAEVKKPGASVKVSCKASGYAFTNYWLGWVRQAPGQGLEWMGNFYPGSSNTYYNEKFQGRVTMTADKSI STAYMELSRLRSDDTAVYFCARHYGTNYRYFDVWGAGTLVTVSS | 37795 |
| vhCDR1 | NYWLG | 37796 |
| vhCDR2 | NFYPGSSNTYYNEKFQG | 37797 |
| vhCDR3 | HYGTNYRYFDV | 37798 |
| scFv linker | GKPGSGKPGSGKPGS | 37708 |
| Variable light (vl) domain | DIVLTQSPGTLSLSPGERATLSCRASQSVSNDVAWYQQKPGQSPRLLIYYASNRYTGVPDRFTGSGYGTDFTLTIS RLEPEDFAVYFCQQDYSSPYTFGGGTKVEIK | 37799 |
| vlCDR1 | RASQSVSNDVA | 37800 |
| vlCDR2 | YASNRYT | 37801 |
| vlCDR3 | QQDYSSPYT | 37802 |
| scFv | QVQLVQSGAEVKKPGASVKVSCKASGYAFTNYWLGWVRQAPGQGLEWMGNFYPGSSNTYYNEKFQGRVTMTADKSI STAYMELSRLRSDDTAVYFCARHYGTNYRYFDVWGAGTLVTVSS/GKPGSGKPGSGKPGS/DIVLTQSPGT LSLSPGERATLSCRASQSVSNDVAWYQQKPGQSPRLLIYYASNRYTGVPDRFTGSGYGTDFTLTISRLEPEDFAVY FCQQDYSSPYTFGGGTKVEIK | 37803 |

Figure 10A [CTLA-4]_H0.25_L0 Anti-CTLA-4 Fv sequences (XENP19235 Fab, XENP19769 scFv)

| What | sequence | SEQ ID NO: |
|---|---|---|
| Variable heavy (vh) domain | QVQLVESGGGVVQPGRSLRLSCAASGFTFSSYAMHWVRQAPGKGLEWVTFISYDGNNKYYADSVKGRFTISRDNSKNTLYLQMNSLRAEDTAIYYCARTGWLGPFDYWGQGTLVTVSS | 37804 |
| vhCDR1 | SYAMH | 37805 |
| vhCDR2 | FISYDGNNKYYADSVKG | 37806 |
| vhCDR3 | TGWLGPFDY | 37807 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37808 |
| vlCDR1 | RASQSVGSSYLA | 37809 |
| vlCDR2 | GAFSRAT | 37810 |
| vlCDR3 | QQYGSSPWT | 37811 |
| scFv | QVQLVESGGGVVQPGRSLRLSCAASGFTFSSYAMHWVRQAPGKGLEWVTFISYDGNNKYYADSVKGRFTISRDNSKNTLYLQMNSLRAEDTAIYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK/ | 37812 |

Figure 10B [CTLA-4]_H0.26_L0 Anti-CTLA-4 Fv sequences (XENP19236 Fab, XENP19770 scFv)

| What | sequence | SEQ ID NO: |
|---|---|---|
| Variable heavy (vh) domain | QVQLVESGGGVVQPGRSLRLSCAASGFTFSSYGMHWVRQAPGKGLEWVTFISYDGNNKYYADSVKGRFTISRDNSKNTLYLQMNSLRAEDTAIYYCARTGWLGPFDYWGQGTLVTVSS | 37813 |
| vhCDR1 | SYGMH | 37814 |
| vhCDR2 | FISYDGNNKYYADSVKG | 37815 |
| vhCDR3 | TGWLGPFDY | 37816 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37817 |
| vlCDR1 | RASQSVGSSYLA | 37818 |
| vlCDR2 | GAFSRAT | 37819 |
| vlCDR3 | QQYGSSPWT | 37820 |
| scFv | QVQLVESGGGVVQPGRSLRLSCAASGFTFSSYGMHWVRQAPGKGLEWVTFISYDGNNKYYADSVKGRFTISRDNSKNTLYLQMNSLRAEDTAIYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37821 |

Figure 10C [CTLA-4]_H0.27_L0 Anti-CTLA-4 Fv sequences (XENP19237 Fab, XENP19771 scFv)

| What | sequence | SEQ ID NO: |
|---|---|---|
| Variable heavy (vh) domain | QVQLVESGGGVVQPGRSLRLSCAASGFTFSSYSMHWVRQAPGKGLEWVTFISYDGNNKYYADSVKGRFTISRDNSKNT LYLQMNSLRAEDTAIYYCARTGWLGPFDYWGQGTLVTVSS | 37822 |
| vhCDR1 | SYSMH | 37823 |
| vhCDR2 | FISYDGNNKYYADSVKG | 37824 |
| vhCDR3 | TGWLGPFDY | 37825 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISR LEPEDFAVYYCQQYGSSPWTFGQGTKVEIK | 37826 |
| vlCDR1 | RASQSVGSSYLA | 37827 |
| vlCDR2 | GAFSRAT | 37828 |
| vlCDR3 | QQYGSSPWT | 37829 |
| scFv | QVQLVESGGGVVQPGRSLRLSCAASGFTFSSYSMHWVRQAPGKGLEWVTFISYDGNNKYYADSVKGRFTISRDNSKNT LYLQMNSLRAEDTAIYYCARTGWLGPFDYWGQGTLVTVSS/GKPGSGKPGSGKPGSGKPGS/EIVLTQSPGTLSLSPG ERATLSCRASQSVGSSYLAWYQQKPGQAPRLLIYGAFSRATGIPDRFSGSGSGTDFTLTISRLEPEDFAVYYCQQYGS SPWTFGQGTKVEIK | 37830 |

Figure 10D [CTLA-4]_H0.29_L0 Fab XENP19773, scFv XENP19239

| What | sequence | SEQ ID NO: |
|---|---|---|
| Variable heavy (vh) domain | | |
| vhCDR1 | | |
| vhCDR2 | | |
| vhCDR3 | | |
| scFv linker | GKPGSGKPGSGKPGSGKPGS | 37708 |
| Variable light (vl) domain | | |
| vlCDR1 | | |
| vlCDR2 | | |
| vlCDR3 | | |
| scFv | QVQLVESGGGVVQPGRSLRLSCAASGFTFSSYSMHWVRQAPGKGLEWVTFISYDGNNKYYADSVKGRFTISRDNSKNT LYLQMNSLRAEDTAIYYCARTGWLGPFDYWGQGTLVTVSS/GKPGSGKPGSGKPGSGKPGS/EIVLTQSPGTLSLSPG ERATLSCRASQSVGSSYLAWYQQKPGQAPRLLIYGAFSRATGIPDRFSGSGSGTDFTLTISRLEPEDFAVYYCQQYGS SPWTFGQGTKVEIK | 37831 |

Figure 10E [CTLA-4]_H0.38_L0 (Fab XENP19248, scFv XENP19782)

| What | sequence | SEQ ID NO: |
|---|---|---|
| Variable heavy (vh) domain | QVQLVESGGGVVQPGRSLRLSCAASGFTFSSYTMHWVRQAPGKGLEWVAFISYDGNNKYYADSVKGRFTISRDNSKNTLYLQMNSLRAEDTAIYYCARTGWLGFFDYWGQGTLVTVSS | 37832 |
| vhCDR1 | SYTMH | 37833 |
| vhCDR2 | FISYDGNNKYYADSVKG | 37834 |
| vhCDR3 | TGWLGFFDY | 37835 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37836 |
| vlCDR1 | RASQSVGSSYLA | 37837 |
| vlCDR2 | GAFSRAT | 37838 |
| vlCDR3 | QQYGSSPWT | 37839 |
| scFv | QVQLVESGGGVVQPGRSLRLSCAASGFTFSSYTMHWVRQAPGKGLEWVAFISYDGNNKYYADSVKGRFTISRDNSKNTLYLQMNSLRAEDTAIYYCARTGWLGFFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK/ | 37840 |

Figure 10F [CTLA-4]_H0.39_L0 (Fab XENP19249, scFv XENP19783)

| What | sequence | SEQ ID NO: |
|---|---|---|
| Variable heavy (vh) domain | QVQLVESGGGVVQPGRSLRLSCAASGFTFSSYTMHWVRQAPGKGLEWVGFISYDGNNKYYADSVKGRFTISRDNSKNTLYLQMNSLRAEDTAIYYCARTGWLGFFDYWGQGTLVTVSS | 37841 |
| vhCDR1 | SYTMH | 37842 |
| vhCDR2 | FISYDGNNKYYADSVKG | 37843 |
| vhCDR3 | TGWLGFFDY | 37844 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37845 |
| vlCDR1 | RASQSVGSSYLA | 37846 |
| vlCDR2 | GAFSRAT | 37847 |
| vlCDR3 | QQYGSSPWT | 37848 |
| scFv | QVQLVESGGGVVQPGRSLRLSCAASGFTFSSYTMHWVRQAPGKGLEWVGFISYDGNNKYYADSVKGRFTISRDNSKNTLYLQMNSLRAEDTAIYYCARTGWLGFFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37849 |

Figure 10G [CTLA-4]_H0.40_L0 (Fab XENP19250, scFv XENP19784)

| What | sequence | SEQ ID NO: |
|---|---|---|
| Variable heavy (vh) domain | QVQLVESGGGVVQPGRSLRLSCAASGFTFSSYTMHWVRQAPGKGLEWVSFISYDGNNKYYADSVKGRFTISRDNSKNTL YLQMNSLRAEDTAIYYCARTGWLGFFDYWGQGTLVTVSS | 37850 |
| vhCDR1 | SYTMH | 37851 |
| vhCDR2 | FISYDGNNKYYADSVKG | 37852 |
| vhCDR3 | TGWLGFFDY | 37853 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISRL EPEDFAVYYCQQYGSSPWTFGQGTKVEIK | 37854 |
| vlCDR1 | RASQSVGSSYLA | 37855 |
| vlCDR2 | GAFSRAT | 37856 |
| vlCDR3 | QQYGSSPWT | 37857 |
| scFv | QVQLVESGGGVVQPGRSLRLSCAASGFTFSSYTMHWVRQAPGKGLEWVSFISYDGNNKYYADSVKGRFTISRDNSKNTL YLQMNSLRAEDTAIYYCARTGWLGFFDYWGQGTLVTVSS/GKPGSGKPGSGKPGSGKPGS/EIVLTQSPGTLSLSPGER ATLSCRASQSVGSSYLAWYQQKPGQAPRLLIYGAFSRATGIPDRFSGSGSGTDFTLTISRLEPEDFAVYYCQQYGSSPW TFGQGTKVEIK | 37858 |

Figure 10H [CTLA-4]_H0.70_L0 (Fab XENP19280, scFv XENP19818)

| What | sequence | SEQ ID NO: |
|---|---|---|
| Variable heavy (vh) domain | QVQLVESGGGVVQPGRSLRLSCAASGFTFSSYTMHWVRQAPGKGLEWVTFISYDGSNKYYADSVKGRFTISRDNSKNT LYLQMNSLRAEDTAIYYCARTGWLGFFDYWGQGTLVTVSS | 37859 |
| vhCDR1 | SYTMH | 37860 |
| vhCDR2 | FISYDGSNKYYADSVKG | 37861 |
| vhCDR3 | TGWLGFFDY | 37862 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISR LEPEDFAVYYCQQYGSSPWTFGQGTKVEIK | 37863 |
| vlCDR1 | RASQSVGSSYLA | 37864 |
| vlCDR2 | GAFSRAT | 37865 |
| vlCDR3 | QQYGSSPWT | 37866 |
| scFv | QVQLVESGGGVVQPGRSLRLSCAASGFTFSSYTMHWVRQAPGKGLEWVTFISYDGSNKYYADSVKGRFTISRDNSKNT LYLQMNSLRAEDTAIYYCARTGWLGFFDYWGQGTLVTVSS/GKPGSGKPGSGKPGSGKPGS/EIVLTQSPGTLSLSPG ERATLSCRASQSVGSSYLAWYQQKPGQAPRLLIYGAFSRATGIPDRFSGSGSGTDFTLTISRLEPEDFAVYYCQQYGS SPWTFGQGTKVEIK | 37867 |

Figure 10I [CTLA-4]_H0_L0.22 (Fab XENP19437, scFv XENP19910)

| What | sequence | SEQ ID NO: |
|---|---|---|
| Variable heavy (vh) domain | QVQLVESGGGVVQPGRSLRLSCAASGFTFSSYTMHWVRQAPGKGLEWVTFISYDGNNKYYADSVKGRFTISRDNSKNT LYLQMNSLRAEDTAIYYCARTGWLGPFDYWGQGTLVTVSS | 37868 |
| vhCDR1 | SYTMH | 37869 |
| vhCDR2 | FISYDGNNKYYADSVKG | 37870 |
| vhCDR3 | TGWLGPFDY | 37871 |
| scFv linker | GKPGSGKPGSGKPGSGKPGS | 37708 |
| Variable light (vl) domain | EIVLTQSPGTLSLSPGERATLSCRASQSVSSSYLAWYQQKPGQAPRLLIYGAFSRATGIPDRFSGSGSGTDFTLTISR LEPEDFAVYYCQQYGSSPWTFGQGTKVEIK | 37872 |
| vlCDR1 | RASQSVSSSYLA | 37873 |
| vlCDR2 | GAFSRAT | 37874 |
| vlCDR3 | QQYGSSPWT | 37875 |
| scFv | QVQLVESGGGVVQPGRSLRLSCAASGFTFSSYTMHWVRQAPGKGLEWVTFISYDGNNKYYADSVKGRFTISRDNSKNT LYLQMNSLRAEDTAIYYCARTGWLGPFDYWGQGTLVTVSS/GKPGSGKPGSGKPGSGKPGS/EIVLTQSPGTLSLSPG ERATLSCRASQSVSSSYLAWYQQKPGQAPRLLIYGAFSRATGIPDRFSGSGSGTDFTLTISRLEPEDFAVYYCQQYGS SPWTFGQGTKVEIK | 37876 |

Figure 10J [CTLA-4]_H2_L0 (Fab XENP,19545 scFv XENP19552)

| What | sequence | SEQ ID NO: |
|---|---|---|
| Variable heavy (vh) domain | EVQLVESGGGLVQPGGSLRLSCAASGFTFSSYTMHWVRQAPGKGLEWVTFISYDGNNKYYPGSVKGRFTISRENAKNS LYLQMNSLRAGDTAVYYCARTGWLGPFDYWGQGTLVTVSS | 37877 |
| vhCDR1 | SYTMH | 37878 |
| vhCDR2 | FISYDGNNKYYPGSVKG | 37879 |
| vhCDR3 | TGWLGPFDY | 37880 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISR LEPEDFAVYYCQQYGSSPWTFGQGTKVEIK | 37881 |
| vlCDR1 | RASQSVGSSYLA | 37882 |
| vlCDR2 | GAFSRAT | 37883 |
| vlCDR3 | QQYGSSPWT | 37884 |
| scFv | EVQLVESGGGLVQPGGSLRLSCAASGFTFSSYTMHWVRQAPGKGLEWVTFISYDGNNKYYPGSVKGRFTISRENAKNS LYLQMNSLRAGDTAVYYCARTGWLGPFDYWGQGTLVTVSS/GKPGSGKPGSGKPGSGKPGS/EIVLTQSPGTLSLSPG ERATLSCRASQSVGSSYLAWYQQKPGQAPRLLIYGAFSRATGIPDRFSGSGSGTDFTLTISRLEPEDFAVYYCQQYGS SPWTFGQGTKVEIK | 37885 |

Figure 10K [CTLA-4]_H3.21_L0.124 (Fab XENP20422, scFv XENP20431)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNS LYLQMNSLRAEDTAVYYCARGGLLGPFDLWGQGTMVTVSS | 37886 |
| vhCDR1 | SYTMH | 37887 |
| vhCDR2 | FISYDGNTKYYADSVKG | 37888 |
| vhCDR3 | GGLLGPFDL | 37889 |
| scFv linker | GKPGSGKPGSGKPGSGKPGS | 37708 |
| Variable light (vl) domain | EIVLTQSPATLSVSPGERATLSCRASQSVGSSYLAWYQQKPGQAPRLLIYGASSRATGIPDRFSGSGSGTDFTLTISR LEPEDFAVYYCQQYGSSPWTFGQGTKVEIK | 37890 |
| vlCDR1 | RASQSVGSSYLA | 37891 |
| vlCDR2 | GASSRAT | 37892 |
| vlCDR3 | QQYGSSPWT | 37893 |
| scFv | EVQLVESGGGLVKPGGSLRLSCAASGFTFSSYTMHWVRQAPGKGLEWVSFISYDGNTKYYADSVKGRFTISRDNAKNS LYLQMNSLRAEDTAVYYCARGGLLGPFDLWGQGTMVTVSS/GKPGSGKPGSGKPGSGKPGS/EIVLTQSPATLSVSPG ERATLSCRASQSVGSSYLAWYQQKPGQAPRLLIYGASSRATGIPDRFSGSGSGTDFTLTISRLEPEDFAVYYCQQYGS SPWTFGQGTKVEIK | 37894 |

Figure 10L [CTLA-4]_H3.21_L0.129 (Fab XENP20423, scFv XENP20432)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNS LYLQMNSLRAEDTAVYYCARGGLLGPFDLWGQGTMVTVSS | 37895 |
| vhCDR1 | SYTMH | 37896 |
| vhCDR2 | FISYDGNTKYYADSVKG | 37897 |
| vhCDR3 | GGLLGPFDL | 37898 |
| scFv linker | GKPGSGKPGSGKPGSGKPGS | 37708 |
| Variable light (vl) domain | EIVLTQSPATLSLSPGERATLSCRASQSVGSSYLAWYQQKPGQAPRLLIYGASSRATGIPDRFSGSGSGTDFTLTISR LEPEDFAVYYCQQYGSSPWTFGQGTKVEIK | 37899 |
| vlCDR1 | RASQSVGSSYLA | 37900 |
| vlCDR2 | GASSRAT | 37901 |
| vlCDR3 | QQYGSSPWT | 37902 |
| scFv | EVQLVESGGGLVKPGGSLRLSCAASGFTFSSYTMHWVRQAPGKGLEWVSFISYDGNTKYYADSVKGRFTISRDNAKNS LYLQMNSLRAEDTAVYYCARGGLLGPFDLWGQGTMVTVSS/GKPGSGKPGSGKPGSGKPGS/EIVLTQSPATLSLSPG ERATLSCRASQSVGSSYLAWYQQKPGQAPRLLIYGASSRATGIPDRFSGSGSGTDFTLTISRLEPEDFAVYYCQQYGS SPWTFGQGTKVEIK | 37903 |

Figure 10M [CTLA-4]_H3.21_L0.132 (Fab XENP20424, scFv XENP20433)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGPFDLWGQGTMVTVSS | 37904 |
| vhCDR1 | SYTMH | 37905 |
| vhCDR2 | FISYDGNTKYYADSVKG | 37906 |
| vhCDR3 | GGLLGPFDL | 37907 |
| scFv linker | GKPGSGKPGSGKPGSGKPGS | 37708 |
| Variable light (vl) domain | EIVLTQSPATLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 37908 |
| vlCDR1 | RASQSVSSSYLA | 37909 |
| vlCDR2 | GASSRAT | 37910 |
| vlCDR3 | QQYGSSPWT | 37911 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGPFDLWGQGTMVTVSS/GKPGSGKPGSGKPGSGKPGS/EIVLTQSPATLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 37912 |

Figure 10N [CTLA-4]_H3.23_L0.124 (Fab XENP20425, scFv XENP20434)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGHLGPFDLWGQGTMVTVSS | 37913 |
| vhCDR1 | SYTMH | 37914 |
| vhCDR2 | FISYDGNYKYYADSVKG | 37915 |
| vhCDR3 | GGHLGPFDL | 37916 |
| scFv linker | GKPGSGKPGSGKPGSGKPGS | 37708 |
| Variable light (vl) domain | EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 37917 |
| vlCDR1 | RASQSVGSSYLA | 37918 |
| vlCDR2 | GASSRAT | 37919 |
| vlCDR3 | QQYGSSPWT | 37920 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS/GKPGSGKPGSGKPGSGKPGS/EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 37921 |

Figure 10O [CTLA-4]_H3.23_L0.129 (Fab XENP20426, scFv XENP20435)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGFFDLWGQGTMVTVSS | 37922 |
| vhCDR1 | SYTMH | 37923 |
| vhCDR2 | FISYDGNYKYYADSVKG | 37924 |
| vhCDR3 | GGHLGFFDL | 37925 |
| scFv linker | GKPGSGKPGSGKPGSGKPGS | 37708 |
| Variable light (vl) domain | EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 37926 |
| vlCDR1 | RASQSVGSSYLA | 37927 |
| vlCDR2 | GASSRAT | 37928 |
| vlCDR3 | QQYGSSPWT | 37929 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGFFDLWGQGTMVTVSS/GKPGSGKPGSGKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 37930 |

Figure 10P [CTLA-4]_H3.23_L0.132 (Fab XENP20427, scFv XENP20436)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGFFDLWGQGTMVTVSS | 37931 |
| vhCDR1 | SYTMH | 37932 |
| vhCDR2 | FISYDGNYKYYADSVKG | 37933 |
| vhCDR3 | GGHLGFFDL | 37934 |
| scFv linker | GKPGSGKPGSGKPGSGKPGS | 37708 |
| Variable light (vl) domain | EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 37935 |
| vlCDR1 | RASQSVGSSYLA | 37936 |
| vlCDR2 | GASSRAT | 37937 |
| vlCDR3 | QQYGSSPWT | 37938 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGFFDLWGQGTMVTVSS/GKPGSGKPGSGKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 37939 |

Figure 10Q [CTLA-4] H3.25_L0.124 (Fab XENP20428, scFv XENP20437)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNS LYLQMNSLRAEDTAVYYCARGGLLGPFDLWGQGTMVTVSS | 37940 |
| vhCDR1 | SYTMH | 37941 |
| vhCDR2 | FISYDGNYKYYADSVKG | 37942 |
| vhCDR3 | GGLLGPFDL | 37943 |
| scFv linker | GKPGSGKPGSGKPGSGKPGS | 37708 |
| Variable light (vl) domain | EIVLTQSPATLSVSPGERATLSCRASQSVGSSYLAWYQQKPGQAPRLLIYGASSRATGIPDRFSGSGSGTDFTLTISR LEPEDFAVYYCQQYGSSPWTFGQGTKVEIK | 37944 |
| vlCDR1 | RASQSVGSSYLA | 37945 |
| vlCDR2 | GASSRAT | 37946 |
| vlCDR3 | QQYGSSPWT | 37947 |
| scFv | EVQLVESGGGLVKPGGSLRLSCAASGFTFSSYTMHWVRQAPGKGLEWVSFISYDGNYKYYADSVKGRFTISRDNAKNS LYLQMNSLRAEDTAVYYCARGGLLGPFDLWGQGTMVTVSS/GKPGSGKPGSGKPGSGKPGS/EIVLTQSPATLSVSPG ERATLSCRASQSVGSSYLAWYQQKPGQAPRLLIYGASSRATGIPDRFSGSGSGTDFTLTISRLEPEDFAVYYCQQYGS SPWTFGQGTKVEIK | 37948 |

Figure 10R [CTLA-4] H3.25_L0.129 (Fab XENP20429, scFv XENP20438)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNS LYLQMNSLRAEDTAVYYCARGGLLGPFDLWGQGTMVTVSS | 37949 |
| vhCDR1 | SYTMH | 37950 |
| vhCDR2 | FISYDGNYKYYADSVKG | 37951 |
| vhCDR3 | GGLLGPFDL | 37952 |
| scFv linker | GKPGSGKPGSGKPGSGKPGS | 37708 |
| Variable light (vl) domain | EIVLTQSPATLSLSPGERATLSCRASQSVGSSYLAWYQQKPGQAPRLLIYGASSRATGIPDRFSGSGSGTDFTLTISR LEPEDFAVYYCQQYGSSPWTFGQGTKVEIK | 37953 |
| vlCDR1 | RASQSVGSSYLA | 37954 |
| vlCDR2 | GASSRAT | 37955 |
| vlCDR3 | QQYGSSPWT | 37956 |
| scFv | EVQLVESGGGLVKPGGSLRLSCAASGFTFSSYTMHWVRQAPGKGLEWVSFISYDGNYKYYADSVKGRFTISRDNAKNS LYLQMNSLRAEDTAVYYCARGGLLGPFDLWGQGTMVTVSS/GKPGSGKPGSGKPGSGKPGS/EIVLTQSPATLSLSPG ERATLSCRASQSVGSSYLAWYQQKPGQAPRLLIYGASSRATGIPDRFSGSGSGTDFTLTISRLEPEDFAVYYCQQYGS SPWTFGQGTKVEIK | 37957 |

Figure 10S [CTLA-4]_H3.25_L0.132 (Fab XENP20430, scFv XENP20439)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGLLGFFDLWGQGTMVTVSS | 37958 |
| vhCDR1 | SYTMH | 37959 |
| vhCDR2 | FISYDGNYKYYADSVKG | 37960 |
| vhCDR3 | GGLLGFFDL | 37961 |
| scFv linker | GKPGSGKPGSGKPGSGKPGS | 37708 |
| Variable light (vl) domain | EIVLTQSPATLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 37962 |
| vlCDR1 | RASQSVSSSYLA | 37963 |
| vlCDR2 | GASSRAT | 37964 |
| vlCDR3 | QQYGSSPWT | 37965 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGLLGFFDLWGQGTMVTVSS/GKPGSGKPGSGKPGSGKPGS/EIVLTQSPATLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 37966 |

Figure 10T [CTLA-4]_H3.4_L0.118 (Fab XENP20341, scFv XENP20378)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDENHKYYADSVKGRFTISRDNAKNSLYLQMNSLRAEDTAVYYCARTGHLGFFDLWGQGTMVTVSS | 37967 |
| vhCDR1 | SSYTMH | 37968 |
| vhCDR2 | FISYDGNHKYYADSVKG | 37969 |
| vhCDR3 | TGHLGFFDL | 37970 |
| scFv linker | GKPGSGKPGSGKPGSGKPGS | 37708 |
| Variable light (vl) domain | EIVLTQSPATLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37971 |
| vlCDR1 | RASQSVGSSYLA | 37972 |
| vlCDR2 | GAFSRAT | 37973 |
| vlCDR3 | QQYGSSPWT | 37974 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGFFDLWGQGTMVTVSS/GKPGSGKPGSGKPGSGKPGS/EIVLTQSPATLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37975 |

Figure 10U [CTLA-4]_H3.4_L0.119 (Fab XENP20342, scFv XENP20379)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 37976 |
| vhCDR1 | SYTMH | 37977 |
| vhCDR2 | FISYDGNHKYYADSVKG | 37978 |
| vhCDR3 | TGHLGPFDL | 37979 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37980 |
| vlCDR1 | RASQSVGSSYLA | 37981 |
| vlCDR2 | GAFSRAT | 37982 |
| vlCDR3 | QQYGSSPWT | 37983 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37984 |

Figure 10V [CTLA-4]_H3.4_L0.12 (Fab XENP20071, scFv XENP20078)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 37985 |
| vhCDR1 | SYTMH | 37986 |
| vhCDR2 | FISYDGNHKYYADSVKG | 37987 |
| vhCDR3 | TGHLGPFDL | 37988 |
| scFv linker | GKPGSGKPGSGKPGSGKPGS | 37708 |
| Variable light (vl) domain | EIVLTQSPGTLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37989 |
| vlCDR1 | RASQSVGSSYLA | 37990 |
| vlCDR2 | GAFSRAT | 37991 |
| vlCDR3 | QQYGSSPWT | 37992 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPGTLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 37993 |

Figure 10W [CTLA-4]_H3.4_L0.121 (Fab XENP20344, scFv XENP20381)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 37994 |
| vhCDR1 | SYTMH | 37995 |
| vhCDR2 | FISYDGNHKYYADSVKG | 37996 |
| vhCDR3 | TGHLGPFDL | 37997 |
| scFv linker | GKPGSGKPGSGKPGSGKPGS | 37708 |
| Variable light (vl) domain | EIVLTQSPGTLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 37998 |
| vlCDR1 | RASQSVGSSYLA | 37999 |
| vlCDR2 | GASSRAT | 38000 |
| vlCDR3 | QQYGSSPWT | 38001 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPGTLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 38002 |

Figure 10X [CTLA-4]_H3.4_L0.122 (Fab XENP20345, scFv XENP20382)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 38003 |
| vhCDR1 | SYTMH | 38004 |
| vhCDR2 | FISYDGNHKYYADSVKG | 38005 |
| vhCDR3 | TGHLGPFDL | 38006 |
| scFv linker | GKPGSGKPGSGKPGSGKPGS | 37708 |
| Variable light (vl) domain | EIVLTQSPATLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 38007 |
| vlCDR1 | RASQSVGSSYLA | 38008 |
| vlCDR2 | GAFSRAT | 38009 |
| vlCDR3 | QQYGSSPWT | 38010 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 38011 |

Figure 10Y [CTLA-4]_H3.4_L0.123 (Fab XENP20346, scFv XENP20383)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 38012 |
| vhCDR1 | SYTMH | 38013 |
| vhCDR2 | FISYDGNHKYYADSVKG | 38014 |
| vhCDR3 | TGHLGPFDL | 38015 |
| scFv linker | GKPGSGKPGSGKPGSGKPGS | 37708 |
| Variable light (vl) domain | EIVLTQSPATLSVSPGERATLSCRASQSVGSSSYLAWYQQKPGQAPRLLIYGAFSRATGIPDRFSGSGSGTDFTLTISRLEPEDFAVYYCQQYGSSPWTFGQGTKVEIK | 38016 |
| vlCDR1 | RASQSVGSSSYLA | 38017 |
| vlCDR2 | GAFSRAT | 38018 |
| vlCDR3 | QQYGSSPWT | 38019 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSVSPGERATLSCRASQSVGSSSYLAWYQQKPGQAPRLLIYGAFSRATGIPDRFSGSGSGTDFTLTISRLEPEDFAVYYCQQYGSSPWTFGQGTKVEIK | 38020 |

Figure 10Z [CTLA-4]_H3.4_L0.124 (Fab XENP20347, scFv XENP20384)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 38021 |
| vhCDR1 | SYTMH | 38022 |
| vhCDR2 | FISYDGNHKYYADSVKG | 38023 |
| vhCDR3 | TGHLGPFDL | 38024 |
| scFv linker | GKPGSGKPGSGKPGSGKPGS | 37708 |
| Variable light (vl) domain | EIVLTQSPATLSVSPGERATLSCRASQSVGSSSYLAWYQQKPGQAPRLLIYGASSRATGIPDRFSGSGSGTDFTLTISRLEPEDFAVYYCQQYGSSPWTFGQGTKVEIK | 38025 |
| vlCDR1 | RASQSVGSSSYLA | 38026 |
| vlCDR2 | GASSRAT | 38027 |
| vlCDR3 | QQYGSSPWT | 38028 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSVSPGERATLSCRASQSVGSSSYLAWYQQKPGQAPRLLIYGASSRATGIPDRFSGSGSGTDFTLTISRLEPEDFAVYYCQQYGSSPWTFGQGTKVEIK | 38029 |

Figure 10AA [CTLA-4]_H3.4_L0.125 (Fab XENP20348, scFv XENP20385)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS | 38030 |
| vhCDR1 | SYTMH | 38031 |
| vhCDR2 | FISYDGNHKYYADSVKG | 38032 |
| vhCDR3 | TGHLGPFDL | 38033 |
| scFv linker | GKPGSGKPGSGKPGSGKPGS | 37708 |
| Variable light (vl) domain | EIVLTQSPGTLSLSPGERATLSCRASQSVGSSSYLAWYQQKPGQAPRLLIYGAFSRATGIPDRFSGSGSGTDFTLTISRLEPEDF AVYYCQQYGSSPWTFGQGTKVEIK | 38034 |
| vlCDR1 | RASQSVSSSYLA | 38035 |
| vlCDR2 | GAFSRAT | 38036 |
| vlCDR3 | QQYGSSPWT | 38037 |
| scFv | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS/GKPGSGKPGSGKPGSGKPGS/EIVLTQSPGTLSLSPGERATLSCRASQS VGSSSYLAWYQQKPGQAPRLLIYGAFSRATGIPDRFSGSGSGTDFTLTISRLEPEDFAVYYCQQYGSSPWTFGQGTKVEIK | 38038 |

Figure 10BB [CTLA-4]_H3.4_L0.126 (Fab XENP20349, scFv XENP20386)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS | 38039 |
| vhCDR1 | SYTMH | 38040 |
| vhCDR2 | FISYDGNHKYYADSVKG | 38041 |
| vhCDR3 | TGHLGPFDL | 38042 |
| scFv linker | GKPGSGKPGSGKPGSGKPGS | 37708 |
| Variable light (vl) domain | EIVLTQSPGTLSLSPGERATLSCRASQSVGSSSYLAWYQQKPGQAPRLLIYGASSRATGIPDRFSGSGSGTDFTLTISRLEPEDF AVYYCQQYGSSPWTFGQGTKVEIK | 38043 |
| vlCDR1 | RASQSVGSSSYLA | 38044 |
| vlCDR2 | GASSRAT | 38045 |
| vlCDR3 | QQYGSSPWT | 38046 |
| scFv | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS/GKPGSGKPGSGKPGSGKPGS/EIVLTQSPGTLSLSPGERATLSCRASQS VGSSSYLAWYQQKPGQAPRLLIYGASSRATGIPDRFSGSGSGTDFTLTISRLEPEDFAVYYCQQYGSSPWTFGQGTKVEIK | 38047 |

Figure 10CC [CTLA-4]_H3.4_L0.127 (Fab XENP20350, scFv XENP20387)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 38048 |
| vhCDR1 | SYTMH | 38049 |
| vhCDR2 | FISYDGNHKYYADSVKG | 38050 |
| vhCDR3 | TGHLGPFDL | 38051 |
| scFv linker | GKPGSGKPGSGKPGSGKPGS | 37708 |
| Variable light (vl) domain | EIVLTQSPGTLSVSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 38052 |
| vlCDR1 | RASQSVSSSYLA | 38053 |
| vlCDR2 | GASSRAT | 38054 |
| vlCDR3 | QQYGSSPWT | 38055 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPGTLSVSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 38056 |

Figure 10DD [CTLA-4]_H3.4_L0.128 (Fab XENP20351, scFv XENP20388)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 38057 |
| vhCDR1 | SYTMH | 38058 |
| vhCDR2 | FISYDGNHKYYADSVKG | 38059 |
| vhCDR3 | TGHLGPFDL | 38060 |
| scFv linker | GKPGSGKPGSGKPGSGKPGS | 37708 |
| Variable light (vl) domain | EIVLTQSPATLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 38061 |
| vlCDR1 | RASQSVSSSYLA | 38062 |
| vlCDR2 | GAFSRAT | 38063 |
| vlCDR3 | QQYGSSPWT | 38064 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 38065 |

Figure 10EE [CTLA-4]_H3.4_L0.129 (Fab XENP20352, scFv XENP20389)

| What | sequence | SEQ ID NO: |
|---|---|---|
| Variable heavy (vh) domain | | |
| vhCDR1 | | |
| vhCDR2 | | |
| vhCDR3 | | |
| scFv linker | GKPGSGKPGSGKPGSGKPGS | 37708 |
| Variable light (vl) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 38066 |
| vlCDR1 | SYTMH | 38067 |
| vlCDR2 | FISYDGNHKYYADSVKG | 38068 |
| vlCDR3 | TGHLGPFDL | 38069 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 38070 |

Figure 10FF [CTLA-4]_H3.4_L0.130 (Fab XENP20353, scFv XENP20390)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 38071 |
| vhCDR1 | SYTMH | 38072 |
| vhCDR2 | FISYDGNHKYYADSVKG | 38073 |
| vhCDR3 | TGHLGPFDL | 38074 |
| scFv linker | GKPGSGKPGSGKPGSGKPGS | 37708 |
| Variable light (vl) domain | EIVLTQSPATLSVSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 38075 |
| vlCDR1 | RASQSVSSSYLA | 38076 |
| vlCDR2 | GASSRAT | 38077 |
| vlCDR3 | QQYGSSPWT | 38078 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSVSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 38079 |

Figure 10GG [CTLA-4]_H3.4_L0.131 (Fab XENP20354, scFv XENP20391)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS | 38080 |
| vhCDR1 | SYTMH | 38081 |
| vhCDR2 | FISYDGNHKYYADSVKG | 38082 |
| vhCDR3 | TGHLGPFDL | 38083 |
| scFv linker | GKPGSGKPGSGKPGSGKPGS | 37708 |
| Variable light (vl) domain | EIVLTQSPGTLSLSPGERATLSCRASQSVSSSYLAWYQQKPGQAPRLLIYGASSRATGIPDRFSGSGSGTDFTLTISRLEPED FAVYYCQQYGSSPWTFGQGTKVEIK | 38084 |
| vlCDR1 | RASQSVSSSYLA | 38085 |
| vlCDR2 | GASSRAT | 38086 |
| vlCDR3 | QQYGSSPWT | 38087 |
| scFv | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS/GKPGSGKPGSGKPGSGKPGS/EIVLTQSPGTLSLSPGERATLSCRAS QSVSSSYLAWYQQKPGQAPRLLIYGASSRATGIPDRFSGSGSGTDFTLTISRLEPEDFAVYYCQQYGSSPWTFGQGTKVEIK | 38088 |

Figure 10HH [CTLA-4]_H3.4_L0.132 (Fab XENP20355, scFv XENP20392)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS | 38089 |
| vhCDR1 | SYTMH | 38090 |
| vhCDR2 | FISYDGNHKYYADSVKG | 38091 |
| vhCDR3 | TGHLGPFDL | 38092 |
| scFv linker | GKPGSGKPGSGKPGSGKPGS | 37708 |
| Variable light (vl) domain | EIVLTQSPATLSLSPGERATLSCRASQSVSSSYLAWYQQKPGQAPRLLIYGASSRATGIPDRFSGSGSGTDFTLTISRLEPED FAVYYCQQYGSSPWTFGQGTKVEIK | 38093 |
| vlCDR1 | RASQSVSSSYLA | 38094 |
| vlCDR2 | GASSRAT | 38095 |
| vlCDR3 | QQYGSSPWT | 38096 |
| scFv | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS/GKPGSGKPGSGKPGSGKPGS/EIVLTQSPATLSLSPGERATLSCRAS QSVSSSYLAWYQQKPGQAPRLLIYGASSRATGIPDRFSGSGSGTDFTLTISRLEPEDFAVYYCQQYGSSPWTFGQGTKVEIK | 38097 |

Figure 10II [CTLA-4]_H3.5_L2.1 (Fab XENP20357, scFv XENP20394)

| What | sequence | SEQ ID NO: |
|---|---|---|
| Variable heavy (vh) domain | EVQLVESGGGLVKPGGSLRLSCAASGFTFSSSYTMHWVRQAPGKGLEWVSFISYDGNTKYYADSVKGRFTISRDNAKNSLYLQMNSLRAEDTAVYYCARTGHLGPFDLWGQGTMVTVSS | 38098 |
| vhCDR1 | SYTMH | 38099 |
| vhCDR2 | FISYDGNTKYYADSVKG | 38100 |
| vhCDR3 | TGHLGPFDL | 38101 |
| scFv linker | GKPGSGKPGSGKPGSGKPGS | 37708 |
| Variable light (vl) domain | EIVMTQSPATLSVSPGERATLSCRASQSVSSSYLAWYQQKPGQAPRLLIYGAFSRATGIPARFSGSGSGTEFTLTISSLQSEDFAVYYCQQYGSSPWTFGQGTKVEIK | 38102 |
| vlCDR1 | RASQSVSSSYLA | 38103 |
| vlCDR2 | GAFSRAT | 38104 |
| vlCDR3 | QQYGSSPWT | 38105 |
| scFv | EVQLVESGGGLVKPGGSLRLSCAASGFTFSSSYTMHWVRQAPGKGLEWVSFISYDGNTKYYADSVKGRFTISRDNAKNSLYLQMNSLRAEDTAVYYCARTGHLGPFDLWGQGTMVTVSS/GKPGSGKPGSGKPGSGKPGS/EIVMTQSPATLSVSPGERATLSCRASQSVSSSYLAWYQQKPGQAPRLLIYGAFSRATGIPARFSGSGSGTEFTLTISSLQSEDFAVYYCQQYGSSPWTFGQGTKVEIK | 38106 |

Figure 10JJ [CTLA-4]_H3.5_L2.2 (Fab XENP20358, scFv XENP20395)

| What | sequence | SEQ ID NO: |
|---|---|---|
| Variable heavy (vh) domain | EVQLVESGGGLVKPGGSLRLSCAASGFTFSSSYTMHWVRQAPGKGLEWVSFISYDGNTKYYADSVKGRFTISRDNAKNSLYLQMNSLRAEDTAVYYCARTGHLGPFDLWGQGTMVTVSS | 38107 |
| vhCDR1 | SYTMH | 38108 |
| vhCDR2 | FISYDGNTKYYADSVKG | 38109 |
| vhCDR3 | TGHLGPFDL | 38110 |
| scFv linker | GKPGSGKPGSGKPGSGKPGS | 37708 |
| Variable light (vl) domain | EIVMTQSPATLSVSPGERATLSCRASQSVSSSYLAWYQQKPGQAPRLLIYGASSRATGIPARFSGSGSGTEFTLTISSLQSEDFAVYYCQQYGSSPWTFGQGTKVEIK | 38111 |
| vlCDR1 | RASQSVSSSYLA | 38112 |
| vlCDR2 | GASSRAT | 38113 |
| vlCDR3 | QQYGSSPWT | 38114 |
| scFv | EVQLVESGGGLVKPGGSLRLSCAASGFTFSSSYTMHWVRQAPGKGLEWVSFISYDGNTKYYADSVKGRFTISRDNAKNSLYLQMNSLRAEDTAVYYCARTGHLGPFDLWGQGTMVTVSS/GKPGSGKPGSGKPGSGKPGS/EIVMTQSPATLSVSPGERATLSCRASQSVSSSYLAWYQQKPGQAPRLLIYGASSRATGIPARFSGSGSGTEFTLTISSLQSEDFAVYYCQQYGSSPWTFGQGTKVEIK | 38115 |

Figure 10KK [CTLA-4]_H3.5_L2.3 (Fab XENP20359, scFv XENP20396)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS | 38116 |
| vhCDR1 | SYTMH | 38117 |
| vhCDR2 | FISYDGNTKYYADSVKG | 38118 |
| vhCDR3 | TGHLGPFDL | 38119 |
| scFv linker | GKPGSGKPGSGKPGSGKPGS | 37708 |
| Variable light (vl) domain | EIVMTQSPATLSVSPGERATLSCRASQSVSSSYLAWYQQKPGQAPRLLIYGASSRATGIPARFSGSGSGTEFTLTISSLQSEDFAVYYCQQYGSSPWTFGQGTKVEIK | 38120 |
| vlCDR1 | RASQSVSSSYLA | 38121 |
| vlCDR2 | GASSRAT | 38122 |
| vlCDR3 | QQYGSSPWT | 38123 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS/GKPGSGKPGSGKPGSGKPGS/EIVMTQSPATLSVSPGERATLSCRASQSVSSSYLAWYQQKPGQAPRLLIYGASSRATGIPARFSGSGSGTEFTLTISSLQSEDFAVYYCQQYGSSPWTFGQGTKVEIK | 38124 |

Figure 10LL [CTLA-4]_H3_L0 (Fab XENP19546, scFv XENP19553)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGFFDYWGQGTLVTVSS | 38125 |
| vhCDR1 | SYTMH | 38126 |
| vhCDR2 | FISYDGNNKYYADSVKG | 38127 |
| vhCDR3 | TGWLGPFDY | 38128 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 38129 |
| vlCDR1 | RASQSVGSSYLA | 38130 |
| vlCDR2 | GAFSRAT | 38131 |
| vlCDR3 | QQYGSSPWT | 38132 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 38133 |

Figure 10MM [CTLA-4]_H3_L0.22 (Fab XENP20011)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGFFDYWGQGTLVTVSS | 38134 |
| vhCDR1 | SYTMH | 38135 |
| vhCDR2 | FISYDGNNKYYADSVKG | 38136 |
| vhCDR3 | TGWLGFFDY | 38137 |
| scFv linker | GKPGSGKPGSGKPGSGKPGS | 37708 |
| Variable light (vl) domain | EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 38138 |
| vlCDR1 | RASQSVSSSYLA | 38139 |
| vlCDR2 | GAFSRAT | 38140 |
| vlCDR3 | QQYGSSPWT | 38141 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGFFDYWGQGTLVTVSS/GKPGSGKPGSGKPGSGKPGS/EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 38142 |

Figure 10NN [CTLA-4]_H3_L0.44 (Fab XENP20052)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGFFDYWGQGTLVTVSS | 38143 |
| vhCDR1 | SYTMH | 38144 |
| vhCDR2 | FISYDGNNKYYADSVKG | 38145 |
| vhCDR3 | TGWLGFFDY | 38146 |
| scFv linker | GKPGSGKPGSGKPGSGKPGS | 37708 |
| Variable light (vl) domain | EIVLTQSPGTLSLSPGERATLSCRASQSVGSSYLSWYQQKPGQAPRLLIYGAFSRATGIPDRFSGSGSGTDFTLTISRLEPEDFAVYYCQQYGSSPWTFGQGTKVEIK | 38147 |
| vlCDR1 | RASQSVGSSYLS | 38148 |
| vlCDR2 | GAFSRAT | 38149 |
| vlCDR3 | QQYGSSPWT | 38150 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGFFDYWGQGTLVTVSS/GKPGSGKPGSGKPGSGKPGS/EIVLTQSPGTLSLSPGERATLSCRASQSVGSSYLSWYQQKPGQAPRLLIYGAFSRATGIPDRFSGSGSGTDFTLTISRLEPEDFAVYYCQQYGSSPWTFGQGTKVEIK | 38151 |

Figure 10OO [CTLA-4]_H3_L0.67 (Fab XENP20018)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS | 38152 |
| vhCDR1 | SYTMH | 38153 |
| vhCDR2 | FISYDGNNKYYADSVKG | 38154 |
| vhCDR3 | TGWLGPFDY | 38155 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYDAFSRATGIPDRFSGSGSGTDFTLTISRLEPEDFAVYYCQQYGSSPWTFGQGTKVEIK | 38156 |
| vlCDR1 | RASQSVGSSYLA | 38157 |
| vlCDR2 | DAFSRAT | 38158 |
| vlCDR3 | QQYGSSPWT | 38159 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYDAFSRATGIPDRFSGSGSGTDFTLTISRLEPEDFAVYYCQQYGSSPWTFGQGTKVEIK | 38160 |

Figure 10PP [CTLA-4]_H3_L0.74 (Fab XENP20020)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS | 38161 |
| vhCDR1 | SYTMH | 38162 |
| vhCDR2 | FISYDGNNKYYADSVKG | 38163 |
| vhCDR3 | TGWLGPFDY | 38164 |
| scFv linker | GKPGSGKPGSGKPGSGKPGS | 37708 |
| Variable light (vl) domain | EIVLTQSPGTLSLSPGERATLSCRASQSVGSSYLAWYQQKPGQAPRLLIYGAYSRATGIPDRFSGSGSGTDFTLTISRLEPEDFAVYYCQQYGSSPWTFGQGTKVEIK | 38165 |
| vlCDR1 | RASQSVGSSYLA | 38166 |
| vlCDR2 | GAYSRAT | 38167 |
| vlCDR3 | QQYGSSPWT | 38168 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAYSRATGIPDRFSGSGSGTDFTLTISRLEPEDFAVYYCQQYGSSPWTFGQGTKVEIK | 38169 |

Figure 11A
7G8_H3.30_L1.34 (Fab XENP22594)

| What | sequence | SEQ ID NO: |
|---|---|---|
| Variable heavy (vh) domain | EVQLVESGGGLVQPGGSLRLSCAASGFTFDDAWMSWVRQAPGKGLEWVAEISTKANNHATYYAESVK GRFTISRDDSKSSVYLQMNSLRAEDTAVYYCTRLATWDWYFDVWGQGTTVTVSS | 38170 |
| vhCDR1 | DAWMS | 38171 |
| vhCDR2 | EISTKANNHATYYAESVKG | 38172 |
| vhCDR3 | LATWDWYFDV | 38173 |
| Variable light (vl) domain | DIVLTQSPSSLSASVGDRVTITCRASQSVDYDGDSYMNWYQQKPGKPPKLLIYAASELESGIPARFS GSGSGTDFTLTISSLQPEDFATYYCQQSNEDPFTFGSGTKLEIK | 38174 |
| vlCDR1 | RASQSVDYDGDSYMN | 38175 |
| vlCDR2 | AASELES | 38176 |
| vlCDR3 | QQSNEDPFT | 38177 |

Figure 11B
2A11_H1.144_L2.142 (Fab XENP22656)

| What | sequence | SEQ ID NO: |
|---|---|---|
| Variable heavy (vh) domain | EVQLVQSGAEVKKPGATVKISCKASGFNIKDYFMHWVQQAPGKGLEWMGWIDPELGDTEYAPKFQGR VTITADTSTNTAYMELSSLRSEDTAVYYCYARGVYQALDYWGQGTLVTVSS | 38178 |
| vhCDR1 | DYFMH | 38179 |
| vhCDR2 | WIDPELGDTEYAPKFQG | 38180 |
| vhCDR3 | RGVYQALDY | 38181 |
| Variable light (vl) domain | DIQMTQSPAFLSVTPGEKVTITCQASQDIGNYLNWFQQKPGQTVKLLIYFTSYLHSGVPSRFSGSGS GTDYTFTISSLEAEDAATYFCQQGNTLPYTFGGGTKVEIK | 38182 |
| vlCDR1 | QASQDIGNYLN | 38183 |
| vlCDR2 | FTSYLHS | 38184 |
| vlCDR3 | QQGNTLPYT | 38185 |

Figure 11C
7G8_H3.18_L1.11 (Fab XENP21670)

| What | sequence | SEQ ID NO: |
|---|---|---|
| Variable heavy (vh) domain | EVQLVESGGGLVQPGGSLRLSCAASGFTFDLAWMDWVRQAPGKGLEWVAEISTKANNHATYYAESVKGRFTISRDDSKSSVYLQMNSLRAEDTAVYYCTRLATWDWYFDVWGQGTTVTVSS | 38186 |
| vhCDR1 | DAWMD | 38187 |
| vhCDR2 | EISTKANNHATYYAESVKG | 38188 |
| vhCDR3 | LATWDWYFDV | 38189 |
| Variable light (vl) domain | DTVLTQSPSSLSASVGDRVTITCRASQSVDYDGDSYMNWYQQKPGKPPKLLIYAASELESGIPARLSGSGSGTDFTLTISSLQPEDFATYYCQQSNEDPFTFGSGTKLEIK | 38190 |
| vlCDR1 | RASQSVDYDGDSYMN | 38191 |
| vlCDR2 | AASELES | 38192 |
| vlCDR3 | QQSNEDPFT | 38193 |

Figure 11D
2A11_H0L0 (Fab XENP20930)

| What | sequence | SEQ ID NO: |
|---|---|---|
| Variable heavy (vh) domain | EVKLEESGGGLVQPGGSMKLSCAASGFTFSDAWMDWVRQSPEKGLEWVAEIRTKANNHATYYAESVKGRFTISRDDSKSSVYLQMNSLRAEDTGIYYCTRLANWDWYFDVWGAGTTVTVSS | 38194 |
| vhCDR1 | DAWMD | 38195 |
| vhCDR2 | EIRTKANNHATYYAESVKG | 38196 |
| vhCDR3 | LANWDWYFDV | 38197 |
| Variable light (vl) domain | DTVLTQSPASLAVSLGQRATISCKASQSVDYDGDSYMNWYQQKPGQPPKLLIYAASNLESGIPARLSGSGSGTDFTLNIHPVEEEDAATYYCQQSNEDPFTFGSGTKLEVK | 38198 |
| vlCDR1 | KASQSVDYDGDSYMN | 38199 |
| vlCDR2 | AASNLES | 38200 |
| vlCDR3 | QQSNEDPFT | 38201 |

Figure 11E
2A11_H1.125_L2.113 (Fab XENP21921)

| What | sequence | SEQ ID NO: |
|---|---|---|
| Variable heavy (vh) domain | EVQLVQSGAEVKKPGATVKISCKASGFNIKHYEMHWVQQAPGKGLEWMGWIDPYLGDTEYAPKFQGR VTITADTSTNTAYMELSSLRSEDTAVYYCYARGVYQALDYWGQGTLVTVSS | 38202 |
| vhCDR1 | HYFMH | 38203 |
| vhCDR2 | WIDPYLGDTEYAPKFQG | 38204 |
| vhCDR3 | RGVYQALDY | 38205 |
| Variable light (vl) domain | DIQMTQSPAFLSVTPGEKVTITCQASQDIGNYLNWFQQKPDQTVKLLIYFTSYLHSGVPSRFSGSGS GTDYTFTISSLEAEDAATYFCQQGNTLPYTFGGGTKVEIK | 38206 |
| vlCDR1 | QASQDIGNYLN | 38207 |
| vlCDR2 | FTSYLHS | 38208 |
| vlCDR3 | QQGNTLPYT | 38209 |

Figure 11F
2A11_H1L2 (Fab XENP20847)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 38210 |
| vhCDR1 | DYYMH | 38211 |
| vhCDR2 | WIDPENGDTEYAPKFQG | 38212 |
| vhCDR3 | RGVRQALDY | 38213 |
| Variable light (vl) domain | DIQMTQSPAFLSVTPGEKVTITCQASQDIGNYLNWFQQKPDQTVKLLIYYTSRLHSGVPSRFSGSGS GTDYTFTISSLEAEDAATYFCQQGNTLPYTFGGGTKVEIK | 38214 |
| vlCDR1 | QASQDIGNYLN | 38215 |
| vlCDR2 | YTSRLHS | 38216 |
| vlCDR3 | QQGNTLPYT | 38217 |

Figure 11G
2A11_H1_L2.25 (Fab XENP21372)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 38218 |
| vhCDR1 | DYYMH | 38219 |
| vhCDR2 | WIDPENGDTEYAPKFQG | 38220 |
| vhCDR3 | RGVRQALDY | 38221 |
| Variable light (vl) domain | DIQMTQSPAFLSVTPGEKVTITCQASQDIGNHLNWFQQKPDQTVKLLIYYTSRLHSGVPSRFSGSGS GTDYTFTISSLEAEDAATYFCQQGNTLPYTFGGGTKVEIK | 38222 |
| vlCDR1 | QASQDIGNHLN | 38223 |
| vlCDR2 | YTSRLHS | 38224 |
| vlCDR3 | QQGNTLPYT | 38225 |

Figure 11H
2A11_H1_L2.47 (Fab XENP21394)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 38226 |
| vhCDR1 | DYYMH | 38227 |
| vhCDR2 | WIDPENGDTEYAPKFQG | 38228 |
| vhCDR3 | RGVRQALDY | 38229 |
| Variable light (vl) domain | DIQMTQSPAFLSVTPGEKVTITCQASQDIGNYLNWFQQKPDQTVKLLIYYTSRLHSGVPSRFSGSGS GTDYTFTISSLEAEDAATYFCQQGNTLPYTFGGGTKVEIK | 38230 |
| vlCDR1 | QASQDIGNYLN | 38231 |
| vlCDR2 | YTSRLHS | 38232 |
| vlCDR3 | QQGNTLPYT | 38233 |

Figure 11I
2A11_H1_L2.50 (Fab XENP21401)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 38234 |
| vhCDR1 | DYYMH | 38235 |
| vhCDR2 | WIDPENGDTEYAPKFQG | 38236 |
| vhCDR3 | RGVRQALDY | 38237 |
| Variable light (vl) domain | DIQMTQSPAFLSVTPGEKVTITCQASQDIGNYLNWFQQKPDQTVKLLIYYTSYLHSGVPSRFSGSGS GTDYTFTISSLEAEDAATYFCQQGNTLPYTFGGGTKVEIK | 38238 |
| vlCDR1 | QASQDIGNYLN | 38239 |
| vlCDR2 | YTSYLHS | 38240 |
| vlCDR3 | QQGNTLPYT | 38241 |

Figure 11J
2A11_H1L2 (Fab XENP20847)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 38242 |
| vhCDR1 | DYYMH | 38243 |
| vhCDR2 | WIDPENGDTEYAPKFQG | 38244 |
| vhCDR3 | RGVRQALDY | 38245 |
| Variable light (vl) domain | DIQMTQSPAFLSVTPGEKVTITCQASQDIGNYLNWFQQKPDQTVKLLIYYTSRLHSGVPSRFSGSGS GTDYTFTISSLEAEDAATYFCQQGNTLPYTFGGGTKVEIK | 38246 |
| vlCDR1 | QASQDIGNYLN | 38247 |
| vlCDR2 | YTSRLHS | 38248 |
| vlCDR3 | QQGNTLPYT | 38249 |

Figure 11K
7G8_H3.23_L1.11 (fab XENP21670)

| What | sequence | SEQ ID NO: |
|---|---|---|
| Variable heavy (vh) domain | EVQLVESGGGLVQPGGSLRLSCAASGFTFDDAWMDWVRQAPGKGLEWVAEISTKANNHATYYAESVK GRFTISRDDSKSSVYLQMNSLRAEDTAVYYCTRLATWDWYFDVWGQGTTVTVSS | 38250 |
| vhCDR1 | DAWMD | 38251 |
| vhCDR2 | EISTKANNHATYYAESVKG | 38252 |
| vhCDR3 | LATWDWYFDV | 38253 |
| Variable light (vl) domain | DTVLTQSPSSLSASVGDRVTITCRASQSVDYDGDSYMNWYQQKPGKPPKLLIYAASELESGIPARLS GSGSGTDFTLTISSLQPEDFATYYCQQSNEDPFTFGSGTKLEIK | 38254 |
| vlCDR1 | RASQSVDYDGDSYMN | 38255 |
| vlCDR2 | AASELES | 38256 |
| vlCDR3 | QQSNEDPFT | 38257 |

Figure 11L
7G8_H3.28_L1 (Fab XENP21892)

| What | sequence | SEQ ID NO: |
|---|---|---|
| Variable heavy (vh) domain | EVQLVESGGGLVQPGGSLRLSCAASGFTFDDAWMDWVRQAPGKGLEWVAEISTKAYNHATYYAESVK GRFTISRDDSKSSVYLQMNSLRAEDTAVYYCTRLATWDWYFDVWGQGTTVTVSS | 38258 |
| vhCDR1 | DAWMD | 38259 |
| vhCDR2 | EISTKAYNHATYYAESVKG | 38260 |
| vhCDR3 | LATWDWYFDV | 38261 |
| Variable light (vl) domain | DTVLTQSPSSLSASVGDRVTITCRASQSVDYDGDSYMNWYQQKPGKPPKLLIYAASNLESGIPARLS GSGSGTDFTLTISSLQPEDFATYYCQQSNEDPFTFGSGTKLEIK | 38262 |
| vlCDR1 | RASQSVDYDGDSYMN | 38263 |
| vlCDR2 | AASNLES | 38264 |
| vlCDR3 | QQSNEDPFT | 38265 |

Figure 11M
7G8_H3.28_L1.11 (Fab XENP21893)

| What | sequence | SEQ ID NO: |
|---|---|---|
| Variable heavy (vh) domain | EVQLVESGGGLVQPGGSLRLSCAASGFTFDDAWMDWVRQAPGKGLEWVAEISTKAYNHATYYAESVKGRFTISRDDSKSSVYLQMNSLRAEDTAVYYCTRLATWDWYFDVWGQGTTVTVSS | 38266 |
| vhCDR1 | DAWMD | 38267 |
| vhCDR2 | EISTKAYNHATYYAESVKG | 38268 |
| vhCDR3 | LATWDWYFDV | 38269 |
| Variable light (vl) domain | DTVLTQSPSSLSASVGDRVTITCRASQSVDYDGDSYMNWYQQKPGKPPKLLIYAASELESGIPARLSGSGSGTDFTLTISSLQPEDFATYYCQQSNEDPFTFGSGTKLEIK | 38270 |
| vlCDR1 | RASQSVDYDGDSYMN | 38271 |
| vlCDR2 | AASELES | 38272 |
| vlCDR3 | QQSNEDPFT | 38273 |

Figure 11N
7G8_H3.28_L1.13 (Fab XENP21894)

| What | sequence | SEQ ID NO: |
|---|---|---|
| Variable heavy (vh) domain | EVQLVESGGGLVQPGGSLRLSCAASGFTFDDAWMDWVRQAPGKGLEWVAEISTKAYNHATYYAESVKGRFTISRDDSKSSVYLQMNSLRAEDTAVYYCTRLATWDWYFDVWGQGTTVTVSS | 38274 |
| vhCDR1 | DAWMD | 38275 |
| vhCDR2 | EISTKAYNHATYYAESVKG | 38276 |
| vhCDR3 | LATWDWYFDV | 38277 |
| Variable light (vl) domain | DTVLTQSPSSLSASVGDRVTITCRASQSVDHDGDSYMNWYQQKPGKPPKLLIYAASELESGIPARLSGSGSGTDFTLTISSLQPEDFATYYCQQSNEDPFTFGSGTKLEIK | 38278 |
| vlCDR1 | RASQSVDHDGDSYMN | 38279 |
| vlCDR2 | AASELES | 38280 |
| vlCDR3 | QQSNEDPFT | 38281 |

Figure 12A (anti BTLA4 variable heavy and light chains + CDRs)

| What: anti-BTLA XENP20269 9C6_H0L0 | sequence | SEQ ID NO: |
|---|---|---|
| Variable heavy (vh) domain | QVQLKESGPGLVAPSQSLSITCTVSGFSLTGYGVNWVRQPPGKGLEWLGMIWIDGSTDYNSALKSRLSIN KDNSKSQVFLKMNSLQTDDTARYYCARDRPDGRAMDYWGQGTSVTVSS | 38282 |
| vhCDR1 | GYGVN | 38283 |
| vhCDR2 | MIWIDGSTDYNSALKS | 38284 |
| vhCDR3 | DRPDGRAMDY | 38285 |
| Variable light (vl) domain | SIVMTQTPKFLLVSAGDRVTITCKASQSVSNDVAWYQQKPGQSPKLLIYYASNRYTGVPDRFTGSGYGTD FTFTISTVQAEDLAVYFCQQDYSSPTFGGGTKLEIK | 38286 |
| vlCDR1 | KASQSVSNDVA | 38287 |
| vlCDR2 | YASNRYT | 38288 |
| vlCDR3 | QQDYSSPT | 38289 |

Figure 12B

| What: anti-BTLA XENP20872 9C6_H1.1L1 | sequence | SEQ ID NO: |
|---|---|---|
| Variable heavy (vh) domain | QVQLKESGAEVKKPGASVKVSCKVSGFSLTGYGVNWVRQAPGQGLEWMGMIWIDGSTDYNSKFQGRVTMT KDNSKSTVYMELSSLRSEDTAVYYCARDRPDGRAMDYWGQGTMVTVSS | 38290 |
| vhCDR1 | GYGVN | 38291 |
| vhCDR2 | MIWIDGSTDYNSKFQG | 38292 |
| vhCDR3 | DRPDGRAMDY | 38293 |
| Variable light (vl) domain | SIVMTQSPDSLAVSLGERATINCKASQSVSNDVAWYQQKPGQSPKLLIYYASNRYTGVPDRFTGSGYGTD FTLTISSLQAEDVAVYFCQQDYSSPTFGGGTKLEIK | 38294 |
| vlCDR1 | KASQSVSNDVA | 38295 |
| vlCDR2 | YASNRYT | 38296 |
| vlCDR3 | QQDYSSPT | 38297 |

Figure 12C (anti BTLA4 variable heavy and light chains + CDRs)

| What: anti-BTLA XENP020882 9C6_H1.1IL1 | sequence | SEQ ID NO: |
|---|---|---|
| Variable heavy (vh) domain | QVQLVQSGAEVKKPGASVKVSCKVSGFSLT<ins>GYGVN</ins>WVRQAPGQGLEWMGM<ins>IWIDGSTDYNSKFQG</ins>RLSIN KDNSKSTVYMELSSLRSEDTAVYYCARD<ins>RPDGRAMDY</ins>WGQGTMVTVSS | 38298 |
| vhCDR1 | GYGVN | 38299 |
| vhCDR2 | MIWIDGSTDYNSKFQG | 38300 |
| vhCDR3 | DRPDGRAMDY | 38301 |
| Variable light (vl) domain | SIVMTQSPDSLAVSLGERATINCKAS<ins>QSVSNDVA</ins>WYQQKPGQSPKLLIY<ins>YASNRYT</ins>GVPDRFTGSGYGTD FTLTISSLQAEDVAVYFC<ins>QQDYSSPT</ins>FGGGTKLEIK | 38302 |
| vlCDR1 | KASQSVSNDVA | 38303 |
| vlCDR2 | YASNRYT | 38304 |
| vlCDR3 | QQDYSSPT | 38305 |

Figure 13A (anti-TIM3 variable heavy and light chains + CDRs)

| What: anti-TIM3 XENP21503 1D10_H0L0 | sequence | SEQ ID NO: |
|---|---|---|
| Variable heavy (vh) domain | EVQLVESGGGLVKPGGSLKFSCAASGFAFSSFIMSWVRQTPEKRLEWVAYISSDGASTFYPDTMKGRFTI SRDNAKNTLYLQMSSLKSEDTAMYYCTRLGAYWGQGTLVTVSA | 38306 |
| vhCDR1 | SFDM | 38307 |
| vhCDR2 | YISSDGASTFYPDTMKG | 38308 |
| vhCDR3 | LGAY | 38309 |
| Variable light (vl) domain | DVVMTQTPLTLSVTIGQPASISCKSSQSLLDSDGKTYLNWLLQRPGQSPKRLIYLVSKLDSGVPDRFTGS GSGTDFTLKISRVEAEDLGVYYCWQGTHFPYTFGGGTKLEIK | 38310 |
| vlCDR1 | KSSQSLLDSDGKTYLN | 38311 |
| vlCDR2 | VSKLDS | 38312 |
| vlCDR3 | WQGTHFPYT | 38313 |

Figure 13B

| What: anti-TIM3 XENP21492 1D12_H0L0 | sequence | SEQ ID NO: |
|---|---|---|
| Variable heavy (vh) domain | EVQLVESGGGLVKPGGSLKFSCAASGFAFSSFIMSWVRQTPEKRLEWVAYISSDGASTFYPDTMKGRFTI SRDNAKNTLYLQMSSLKSEDTAMYYCTRLGAYWGQGTLVTVSA | 38314 |
| vhCDR1 | SFDMS | 38315 |
| vhCDR2 | YISSDGASTFYPDTMKG | 38316 |
| vhCDR3 | LGAY | 38317 |
| Variable light (vl) domain | DIVLTQSPASLAVSLGQRATISCRASESVEYYGTSLMQWYQQKPGQPPKLLIYAASNVESGVPARFSGSG SGTDFSLNIHPVEEDDIAMYFCQQSRKVPWTFGGGTKLEIK | 38318 |
| vlCDR1 | RASESVEYYGTSLQ | 38319 |
| vlCDR2 | AASNVES | 38320 |
| vlCDR3 | QQSRKVPWT | 38321 |

Figure 13C (anti-TIM3 variable heavy and light chains + CDRs)

| What: anti-TIM3 XENP21189 3H3_H1L2.1 | sequence | SEQ ID NO: |
|---|---|---|
| Variable heavy (vh) domain | QVTLKESGPVLVKPTETLTLTCTVSGFSLNGYGVNWVRQPPGKGLEWLAMIWGDGSTDYNSALKSRLTIS KDNSKSQVVLTMTNMDPVDTATYYCARSYYTSDEDYWGQGTLVTVSS | 38322 |
| vhCDR1 | GYGVN | 38323 |
| vhCDR2 | MIWGDGSTDYNSALKS | 38324 |
| vhCDR3 | SYYTSDEDY | 38325 |
| Variable light (vl) domain | DIVMTQSPDSLAVSLGERATINCKSSQSLLNSRTRKNYLAWYQQKPGQSPKLLIYWASTRESGVPDRFTG SGSGTDFTLTISSLQAEDVAVYYCKQSYSLRTFGGGTKVEIK | 38326 |
| vlCDR1 | KSSQSLLNSRTRKNYLA | 38327 |
| vlCDR2 | WASTRES | 38328 |
| vlCDR3 | KQSYSLRT | 38329 |

Figure 13D

| What: anti-TIM3 XENP21493 6C8_H0L0 | sequence | SEQ ID NO: |
|---|---|---|
| Variable heavy (vh) domain | QVQLKESGPGLVAPSQSLSITCTVSGFSLNGYGVNWVRQPPGKGLEWLGMIWGDGSTDYNSALKSRLSIS KDNSKSQVFLKMNSLQTDDTARYYCARSYYTSDEDYWGQGTLVTVSA | 38330 |
| vhCDR1 | GYGVN | 38331 |
| vhCDR2 | MIWGDGSTDYNSALKS | 38332 |
| vhCDR3 | SYYTSDEDY | 38333 |
| Variable light (vl) domain | DIVMTQSQKFMSTSVGDRVSVTCKASQNVGSNVAWCQQKPGQSPKALIYSASFRYSGVPDRFTGSGSGTD FTLTISNVQSEDLAEYFCQQYNSYPYTFGGGTKLEIK | 38334 |
| vlCDR1 | KASQNVGSNVA | 38335 |
| vlCDR2 | SASFRYS | 38336 |
| vlCDR3 | QQYNSYPYT | 38337 |

Figure 13E (anti-TIM3 variable heavy and light chains + CDRs)

| What: anti-TIM3 XENP21494 6D9H0_1D12_0 | sequence | SEQ ID NO: |
|---|---|---|
| Variable heavy (vh) domain | QVQLKQSGPGLVQPSQSLSITCTVSGFSLTSYGVHWVRQSPGKGLEWLGVIWSGGSTEYNAAFISRLSIS KDNSKSQVFFKMNSLQADDTAIYYCARGGLLSPFDYWGQGTTLTVSS | 38338 |
| vhCDR1 | SYGVH | 38339 |
| vhCDR2 | VIWSGGSTEYNAAFIS | 38340 |
| vhCDR3 | GGLLSPFDY | 38341 |
| Variable light (vl) domain | DIVLTQSPASLAVSLGQRATISCRASESVEYYGTSLMQWYQQKPGQPPKLLIYAASNVESGVPARFSGSG SGTDFSLNIHPVEEDDIAMYFCQQSRKVPWTFGGGTKLEIK | 38342 |
| vlCDR1 | RASESVEYYGTSLMQ | 38343 |
| vlCDR2 | AASNVES | 38344 |
| vlCDR3 | QQSRKVPWT | 38345 |

Figure 13F

| What: anti-TIM3 XENP21495 7A9_H0L0 | sequence | SEQ ID NO: |
|---|---|---|
| Variable heavy (vh) domain | EVKLLESGGGLVQPGGSLKLSCAASGFDFSRYWMSWVRQAPGKGLEWIGEINPDSSTINYTPSLKDKFLI SRDNAKNTLYLQMSKVRSEDTALYYCARPNGYYVGTIFPFAYWGQGTLVTVSA | 38346 |
| vhCDR1 | RYWMS | 38347 |
| vhCDR2 | EINPDSSTINYTPSLKD | 38348 |
| vhCDR3 | PNGYYVGTIFPFAY | 38349 |
| Variable light (vl) domain | QAVVTQESALTTSPGETVTLTCRSSTGAVTTSNYANWVQEKPDHLFTGLIGGTNNRAPGVPARFSGSLIG DKAALTITGAQTEDEAIYFCALWYSNHWVFGGGTKLTVLG | 38350 |
| vlCDR1 | RSSTGAVTTSNYAN | 38351 |
| vlCDR2 | GTNNRAP | 38352 |
| vlCDR3 | ALWYSNHWV | 38353 |

Figure 13G (anti-TIM3 variable heavy and light chains + CDRs)

| What: anti-TIM3 XENP21496 7B11_H0L0 | sequence | SEQ ID NO: |
|---|---|---|
| Variable heavy (vh) domain | QVQLKQSGPGLVQPSQSLSITCTVSGFSLTSYAVNWVRQSPGKGLEWLGVIWSGGSTDYNAAFISRLSIS KDNSKSQVFFKMNSLQANDTAIYYCVSLYYRYDGFDYWGQGTLVTVSA | 38354 |
| vhCDR1 | SYAVN | 38355 |
| vhCDR2 | VIWSGGSTDYNAAFIS | 38356 |
| vhCDR3 | LYYRYDGFDY | 38357 |
| Variable light (vl) domain | DIVLTQSQKFLSTSVGDRVSVTCKASQNVGTHVARYQQKPGQSPKALVYSASYRYSGVPDRFTGSGSGTD FTLTISNVQSEDLAEYFCQQYNSYPLTFGGGTKLEIK | 38358 |
| vlCDR1 | KASQNVGTHVA | 38359 |
| vlCDR2 | SASYRYS | 38360 |
| vlCDR3 | QQYNSYPLT | 38361 |

Figure 13H

| What: anti-TIM3 XENP21501 B11var_H0L0 | sequence | SEQ ID NO: |
|---|---|---|
| Variable heavy (vh) domain | QVQLKQSGPGLVQPSQSLSITCTVSGFSLTSYAVNWVRQSPGKGLEWLGVIWSGGSTDYNAAFISRLSIS KDNSKSQVFFKMNSLQADDTAIYYCVSLYYRYDGFDYWGQGTLVTVSA | 38362 |
| vhCDR1 | SYAVN | 38363 |
| vhCDR2 | VIWSGGSTDYNAAFIS | 38364 |
| vhCDR3 | LYYRYDGFDY | 38365 |
| Variable light (vl) domain | DIVLTQSQKFLSTSVGDRVSVTCKASQNVGTHVARYQQKPGQSPKALVYSASYRYSGVPDRFTGSGSGTD FTLTISNVQSEDLAEYFCQQYNSYPLTFGGGTKLEIK | 38366 |
| vlCDR1 | KASQNVGTHVA | 38367 |
| vlCDR2 | SASYRYS | 38368 |
| vlCDR3 | QQYNSYPLT | 38369 |

Figure 13I (anti-TIM3 variable heavy and light chains + CDRs)

| What: anti-TIM3 XENP21502 7C2_H0L0 | sequence | SEQ ID NO: |
|---|---|---|
| Variable heavy (vh) domain | EVKVVESGGGLVKPGGSLKLSCAASGFTFSRYAMSWVRQTPEKRLEWVASISSGGSTYYPDSVQGRFTIS RDNARNILYLQMSSLRSEDTAMYYCARGDYEGYFDYWGQGTSLTVSS | 38370 |
| vhCDR1 | RYAMS | 38371 |
| vhCDR2 | SISSGGSTYYPDSVQG | 38372 |
| vhCDR3 | GDYEGYFDY | 38373 |
| Variable light (vl) domain | DIVMTQSPSSLAMSVGQKVTMSCKSSQSLLNSINQKNYLAWYQQKPGQSPKLLVYFASTRESGVPDRFIG SGSGTDFTLTISSVQAEDLADYFCQQHYSTPLTFGAGTKLELK | 38374 |
| vlCDR1 | KSSQSLLNSINQKNYLA | 38375 |
| vlCDR2 | FASTRES | 38376 |
| vlCDR3 | QQHYSTPLT | 38377 |

Figure 14A (CTLA-4 X PD-1)

XENP19738

XENP019738_ipilimumab_H3L0-1G6_L1.210_H1.288 Fab-Fc Heavy Chain (SEQ ID NOS 38378-38382)
EVQLVESGGGLVKPGGSLRLSCAASGFTFSSYYMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWEQGDVFSCSVMHEALHNHYTQKSLSLSPGK XENP019738_ipilimumab_H3L0-1G6_L1.210_H1.288 scFv-Fc Heavy Chain (SEQ ID NOS 38383-38392, linker disclosed as SEQ ID NO: 37708)
EIVLTQSPATLSASPGERVTLTCRASQSVGRDVAWYQQKPGQAPRLLINYASHRYTGVPDRFTGSGYGTEFTLTISSVQSEDFGVYYCQQEFSSPRTFGCGTKVEIK/GKPGSGKPGSGKPGS/
EVQLVESGGGLVKPGGSLRLSCVASGFTFSNYWMNWVRQAPGKCLEWVAEIRLYSNNYATHYAESVKGRFTISRDDSKSTLYLQMNLKTEDTGVYYCTRYYGNYGGYFDYWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLITVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLITVDKSRWQQGNVFSCSVMHEALHNHYTQKSLSLSPGK XENP019738_ipilimumab_H3L0-1G6_L1.210_H1.288 Light Chain (SEQ ID NOS 38393-38397)
EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC

Figure 14B

XENP19739

XENP019739_ipilimumab_H3L0-1G6_H1.279_L1.194 Fab-Fc Heavy Chain (SEQ ID NOS 38398-38402)
EVQLVESGGGLVKPGGSLRLSCAASGFTFSSYYMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWEQGDVFSCSVMHEALHNHYTQKSLSLSPGK XENP019739_ipilimumab_H3L0-1G6_H1.279_L1.194 scFv-Fc Heavy Chain (SEQ ID NOS 38403-38412, linker disclosed as SEQ ID NO: 37708)
EVQLVESGGGLVKPGGSLRLSCVASGFTFSNYWMNWVRQAPGKGLEWVAEIRLYSNNYATHYAESVKGRFTISRDDSKSTLYLQMNLKTEDTGVYYCTRYYGNYGGYFDYWGRGTLVTVSS/GKPGSG
KPGSGKPGS/EIVLTQSPATLSASPGERVTLTCRASQSVGRDVAWYQQKPGQAPRLLINYASHRYTGVPDRFTGSGYGTEFTLTISSVQSEDFGVYYCQQDFSSPRTFGGGTKVEIK/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLITVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLITVDKSRWQQGNVFSCSVMHEALHNHYTQKSLSLSPGK XENP019739_ipilimumab_H3L0-1G6_H1.279_L1.194 Light Chain (SEQ ID NOS 38413-38417)
EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC Figure 14C (CTLA-4 X PD-1)

XENP19741

XENP019741_ipilimumab_H3L0-1G6_L1.194_H1.279 Fab-Fc Heavy Chain (SEQ ID NOS 38418-38422)
EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP019741_ipilimumab_H3L0-1G6_L1.194_H1.279 scFv-Fc Heavy Chain (SEQ ID NOS 38423-38432, linker disclosed as SEQ ID NO: 37708)
EIVLTQSPATLSASPGERVTLTCRASQSVGNDYAWYQQKPGQAPRLLINYASHRYTGVPDRFTGSSGYGTEFTLTISSVQSEDFGVYYCQQDFSSPRTFGGGTKVEIK/GKPGSGKPGSGKPGS/
EVQLVESGGGLVKPGGSLRLSCVASGFTFSNYWMSWVRQAPGKGLEWVAEIRLYSNTAFHYAESVKGRFTISRDDSKSTLYLQMNLKTEDTGVYYCTRYIGNYGSFFDYWGRGTLVTVSS/EPKSSD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP019741_ipilimumab_H3L0-1G6_L1.194_H1.279 Light Chain (SEQ ID NOS 38433-38437)
EIVLTQSPGTLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC

Figure 14D

XENP20053

XENP020053_ipilimumab_H3L0.22-1G6_L1.194_H1.279 Fab-Fc Heavy Chain (SEQ ID NOS 38438-38442)
EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP020053_ipilimumab_H3L0.22-1G6_L1.194_H1.279 scFv-Fc Heavy Chain (SEQ ID NOS 38443-38452, linker disclosed as SEQ ID NO: 37708)
EIVLTQSPATLSASPGERVTLTCRASQSVGNDYAWYQQKPGQAPRLLINYASHRYTGVPDRFTGSSGYGTEFTLTISSVQSEDFGVYYCQQDFSSPRTFGGGTKVEIK/GKPGSGKPGSGKPGS/
EVQLVESGGGLVKPGGSLRLSCVASGFTFSNYWMSWVRQAPGKGLEWVAEIRLYSNTAFHYAESVKGRFTISRDDSKSTLYLQMNLKTEDTGVYYCTRYIGNYGSFFDYWGRGTLVTVSS/EPKSSD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP020053_ipilimumab_H3L0.22-1G6_L1.194_H1.279 Light Chain (SEQ ID NOS 38453-38457)
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC Figure 14E (CTLA-4 X PD-1)

XENP20066

XENP020066 ipilimumab_H3_L0.22-1G6_H1.279_L1.194 Fab-Fc Heavy Chain (SEQ ID NOS 38458-38462)
EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGNVFSCSVMHEALHNHYTQKSLSLSPGK XENP020066 ipilimumab_H3_L0.22-1G6_H1.279_L1.194 scFv-Fc Heavy Chain (SEQ ID NOS 38463-38472, linker disclosed as SEQ ID NO: 37708)
EVQLVESGGGLVKPGGSLRLSCVASGFTFSNYWMNWVRQAPGKGLEWVAEIRLYSNNYATHYAESVKGRFTISRDDSKSTLYLQMNLKTEDTGVYYCTRYYGNYGGYFDVWGRGTLVTVSS/GKPGSSG
KPGSGKPGSGKPGS/EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGGGTKVEIK/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP020066 ipilimumab_H3_L0.22-1G6_H1.279_L1.194 Light Chain (SEQ ID NOS 38473-38477)
EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSFWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC

Figure 14F

XENP20130

XENP020130 ipilimumab_H3_L0.22-1G6_H1.210_H1.288 Fab-Fc Heavy Chain (SEQ ID NOS 38478-38482)
EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGNVFSCSVMHEALHNHYTQKSLSLSPGK XENP020130 ipilimumab_H3_L0.22-1G6_H1.210_H1.288 scFv-Fc Heavy Chain (SEQ ID NOS 38483-38492, linker disclosed as SEQ ID NO: 37708)
EIVLTQSPGTLSLSPGERATLSCRASQSVSSSYLAWYQQKPGQAPRLLINYASHRYTSNNYATHYAESVKGRFTISRDDSKSTLYLQMNLKTEDTGVYYCQQEFSSPRTFGCGTKVEIK/GKPGSGKPGSGKPGS/
EVQLVESGGGLVKPGGSLRLSCVASGFTFSNYWMNWVRQAPGKCLEWVAEIRLYSNNYATHYAESVKGRFTISRDDSKSTLYLQMNLKTEDTGVYYCTRYYGNYGGYFDVWGRGTKVEIK/GKPGSSGKPGSGKPGS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP020130 ipilimumab_H3_L0.22-1G6_H1.210_H1.288 Light Chain (SEQ ID NOS 38493-38497)
EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSFWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC Figure 14G (CTLA-4 X PD-1)

XENP020146

XENP020146 ipilimumab_H3_L0.22-1G6_H1.280_L1.224 Fab-Fc Heavy Chain (SEQ ID NOS 38498-38502)
EVQLVESGGGLVKPGGSLRLSCAASGFTFSSYEMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP020146 ipilimumab_H3_L0.22-1G6_H1.280_L1.224 scFv-Fc Heavy Chain (SEQ ID NOS 38503-38512, linker disclosed as SEQ ID NO: 37708)
EVQLVESGGGLVKPGGSLRLTCVASGFTFSNYWMHWVRQAPGKGLEWVAEIRLYSNNYATHYAESVKGRFTISRDDSKSTLYLQMNNLKTEDTGVYYCTRXYGNYGGYFDVWGRGTLVTVSS/GKPGSG
KPGSGKPGSGKPGS/EIVLTQSPATLSVSPGERVTLTCRASQSVGNDYAWYQQKPGQAPRLLINYASHRYTSVPDRFTGSGYGTEFTLTISSVQSEDFAVYYCQQDWSSPRTFGGGTKVEIK/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP020146 ipilimumab_H3_L0.22-1G6_H1.280_L1.224 Light Chain (SEQ ID NOS 38513-38517)
EIVLTQSPGTLSLSPGERATLSCRASQSVSSYLAWYQQKPGQAPRLLIYGAFSRATGIPDRFSGSGSGTDFTLTISRLEPEDFAVYYCQQYGSSPWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC

Figure 14H

XENP20717

XENP020717 ipilimumab_H3_L0.22-1G6_L1.194_H1.279_M428L/N434S Fab-Fc Heavy Chain (SEQ ID NOS 38518-38522)
EVQLVESGGGLVKPGGSLRLSCAASGFTFSSYEMHWVRQAPGKGLEWVSFISYDGNNKYYADSVKGRFTISRDNAKNSLYLQMNSLRAEDTAVYYCARTGWLGPFDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP020717 ipilimumab_H3_L0.22-1G6_L1.194_H1.279_M428L/N434S scFv-Fc Heavy Chain (SEQ ID NOS 38523-38532, linker disclosed as SEQ ID NO: 37708)
EVQLVESGGGLVKPGGSLRLTCVASGFTFSNYWMHWVRQAPGKGLEWVAEIRLYSNNYATHYAESVKGRFTISRDDSKSTLYLQMNNLKTEDTGVYYCQQDFSSPRTFGGGTKVEIK/GKPGSGKPGSGKPGS/
EIVLTQSPATLSASPGERVTLTCRASQSVGNDYAWYQQKPGQAPRLLINYASHRYTGVPDRFTGSGYGTEFTLTISSVQSEDFGVYYCQQDFSSPRTFGGGTKVEIK/GKPGSGKPGSGKPGS/
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK XENP020717 ipilimumab_H3_L0.22-1G6_L1.194_H1.279_M428L/N434S Light Chain (SEQ ID NOS 38533-38537)
EIVLTQSPGTLSLSPGERATLSCRASQSVSSYLAWYQQKPGQAPRLLIYGAFSRATGIPDRFSGSGSGTDFTLTISRLEPEDFAVYYCQQYGSSEWTFGQGTKVEIK/RTVAAPSVFIFPPSDEQLKS
GTASVVCLLNNFYPREAKVQWKVDNALQSGNSQESVTEQDSKDSTYSLSSTLTLSKADYEKHKVYACEVTHQGLSSPVTKSFNRGEC Figure 14I (CTLA-4 X PD-1)

XENP22836

XENP022836 2E9_H1L1_Fab-[CTLA-4]_H3.23_L0.129_scFv HC-Fab (SEQ ID NOS 38538-38542)
QVQLVQSGAEVKKPGASVKVSCKASGYAFTNYWLGWVRQAPGQGLEWMGNFYPGSSNTYNEKFQGRVTMTADKSISTAYMELSRLRSDDTAVYFCARHYGTNYRYFDVWGAGTLVTVSS/ASTKGPSV
FPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWQEGDVFSCSVMHEALHNHYTQKSLSLSPGK

XENP022836 2E9_H1L1_Fab-[CTLA-4]_H3.23_L0.129_scFv HC-scFV (SEQ ID NOS 38543-38552, linker disclosed as SEQ ID NO: 37708)
EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP022836 2E9_H1L1_Fab-[CTLA-4]_H3.23_L0.129_scFv Light Chain (SEQ ID NOS 38553-38557)
DIVLTQSPGTLSLSPGERATLSCRASQSVSNDVAWYQQKPGQSPRLLIYYASNRYTGVPDRFTGSGYGTDFTLTISRLEPEDFAVYFCQQDYSSPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC Figure 15A (LAG-3 X PD-1)

XENP20206

XENP020206_2A11_H1L2-1G6_L1.194_H1.279 Fab-Fc Heavy Chain (SEQ ID NOS 38558-38562)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQQGDVFSCSVMHEALHNHYTQKSLSLSPGK XENP020206_2A11_H1L2-1G6_L1.194_H1.279 scFv-Fc Heavy Chain (SEQ ID NOS 38563-38572, linker disclosed as SEQ ID NO: 37708)
EIVLTQSPATLSASPGERVTLTCRASQSVGNEVAWYQQKPGQAPRLLINYASHRYTGVPDRFTGSGYGTEFTLTISSVQSEDFGVYYCQQEFSSPRTFGGGTKVEIK/GKPGSGKPGSGKPGS/
EVQLVESGGGLVKPGGSLRLSCVASGFTFSNYWMNWVRQAPGKGLEWVAEIRLYSNYATHYAESVKGRFTISRDDSKSTLYLQMNLKTEDTGVYYCTRYYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP020206_2A11_H1L2-1G6_L1.194_H1.279 Light Chain (SEQ ID NOS 38573-38577)
DIQMTQSPAFLSVTPGEKVTITCQASQDIGNYLNWFQQKPDQTVKLLIYYTSRLHSGVPSRFSGSGSGTDYTFTISSLEAEDAATYFCQQGNTLPYTFGGGTKVEIKRTVAAPSVFIFPPSDEQLKSGT
ASVVCLLNNFYPREAKVQWKVDNALQSGNSQESVTEQDSKDSTYSLSSTLTLSKADYEKHKVYACEVTHQGLSSPVTKSFNRGEC

Figure 15B

XENP21582

XENP021582_2A11_H1_L2.91_Fab-1G6_L1.194_H1.279 Fab-Fc Heavy Chain (SEQ ID NOS 38578-38582)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQQGDVFSCSVMHEALHNHYTQKSLSLSPGK XENP021582_2A11_H1_L2.91_Fab-1G6_L1.194_H1.279 scFv-Fc Heavy Chain (SEQ ID NOS 38583-38592, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQEFSSPRTFGGGTKVEIK/GKPGSGKPGSGKPGS/
EVQLVESGGGLVKPGGSLRLSCVASGFTFSNYWMNWVRQAPGKGLEWVAEIRLYSNYATHYAESVKGRFTISRDDSKSTLYLQMNLKTEDTGVYYCTRYYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP021582_2A11_H1_L2.91_Fab-1G6_L1.194_H1.279 Light Chain (SEQ ID NOS 38593-38597)
DIQMTQSPAFLSVTPGEKVTITCQASQDIGNYLNWFQQKPGQTVKLLIYYTSRLHSGVPSRFSGSGSGTDYTFTISSLEAEDAATYFCQQGNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC Figure 15C (LAG-3 X PD-1)

XENP21584

XENP021584_2A11_H1_L2.93_Fab-1G6_L1.194_H1.279 Fab-Fc Heavy Chain (SEQ ID NOS 38598-38602)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWEQGDVFSCSVMHEALHNHYTQKSLSLSPGK XENP021584_2A11_H1_L2.93_Fab-1G6_L1.194_H1.279 scFv-Fc Heavy Chain (SEQ ID NOS 38603-38612, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQEFSSPRTFGGGTKVEIK/GKPGSGKPGSGKPGS/
EVQLVESGGGLVKPGGSLRLSCVASGFTFSNYWMNWVRQAPGKGLEWVAEIRLYSNNYATHYAESVKGRFTISRDDSKSTLYLQMNLKTEDTGVYCTRXYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPEVLDSDGSFFLYSKLTVDKSRWQQGNVFSCSVMHEALHNHYTQKSLSLSPGK XENP021584_2A11_H1_L2.93_Fab-1G6_L1.194_H1.279 Light Chain (SEQ ID NOS 38613-38617)
DIQMTQSPAFLSVTPGEKVTITCQASQDIGNYLRWFQQKPDQTPKLLIYYTSRLESGVPSRFSGSGSGTDYTFTISSLEAEDAATYFCQQGNILPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 15D

XENP21588

XENP021588_2A11_H1_L2.97_Fab-1G6_L1.194_H1.279 Fab-Fc Heavy Chain (SEQ ID NOS 38618-38622)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWEQGDVFSCSVMHEALHNHYTQKSLSLSPGK >XENP021588_2A11_H1_L2.97_Fab-1G6_L1.194_H1.279 scFv-Fc Heavy Chain (SEQ ID NOS 38623-38632, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQEFSSPRTFGGGTKVEIK/GKPGSGKPGSGKPGS/
EVQLVESGGGLVKPGGSLRLSCVASGFTFSNYWMNWVRQAPGKGLEWVAEIRLYSNNYATHYAESVKGRFTISRDDSKSTLYLQMNLKTEDTGVYYCTRXYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPEVLDSDGSFFLYSKLTVDKSRWQQGNVFSCSVMHEALHNHYTQKSLSLSPGK XENP021588_2A11_H1_L2.97_Fab-1G6_L1.194_H1.279 Light Chain (SEQ ID NOS 38633-38637)
DIQMTQSPAFLSVTPGEKVTITCQASQDIGNYLRWFQQKPDQTPKLLIYYTSRLESGVPSRFSGSGSGTDYTFTISSLEAEDAATYYCQQGNILPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC Figure 15E (LAG-3 X PD-1)

XENP22123

XENP022123_2A11_H1_L2.122_Fab-1G6_L1.194_H1.279 Fab-Fc Heavy Chain (SEQ ID NOS 38638-38642)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP022123_2A11_H1_L2.122_Fab-1G6_L1.194_H1.279 scFv-Fc Heavy Chain (SEQ ID NOS 38643-38652, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQFSSSPRTFGGGTKVEIK/GKPGSGKPGSGKPGS/
EVQLVESGGGLVKPGGSLRLSCVASGFTFSNYWMNWVRQAPGKGLEWVAEIRLYSNYATHYAESVKGRFTISRDDSKSTLYLQMNLKTEDTGVYYCTRYYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP022123_2A11_H1_L2.122_Fab-1G6_L1.194_H1.279 Light Chain (SEQ ID NOS 38653-38657)
DIQMTQSPAFLSVTPGEKVTITCQASQDIGNYLNWFQQKPGQTPKLLIYYTSRLHSGVPSRFSGSGSGTDYTFTISSLEAEDAATYFCQQGNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 15F

XENP22124

XENP022124_2A11_H1_L2.123_Fab-1G6_L1.194_H1.279 Fab-Fc Heavy Chain (SEQ ID NOS 38658-38662)
EVQLVQSGAEVKKPGATVKISCKASGFNIKDYYMHWVQQAPGKGLEWMGWIDEENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP022124_2A11_H1_L2.123_Fab-1G6_L1.194_H1.279 scFv-Fc Heavy Chain (SEQ ID NOS 38663-38672, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQFSSSPRIFGGGTKVEIK/GKPGSGKPGSGKPGS/
EVQLVESGGGLVKPGGSLRLSCVASGFTFSNMNRWVRQAPGKGLEWVAEIRLYSNNYATHYAESVKGRFTISRDDSKSTLYLQMNLKTEDTGVYYCTRYYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP022124_2A11_H1_L2.123_Fab-1G6_L1.194_H1.279 Light Chain (SEQ ID NOS 38673-38677)
DIQMTQSPAFLSVTPGEKVTITCQASQDIGNYLNWFQQKPGQSPKLLIYYTSRLHSGVPSRFSGSGSGTDYTFTISSLEAEDAATYFCQQGNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC Figure 15G (LAG-3 X PD-1)

XENP22125

XENP022125_2A11_H1_L2.124_Fab-1G6_L1.194_H1.279 Fab-Fc Heavy Chain (SEQ ID NOS 38678-38682)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYAREVRQALDHWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWEEQGDVFSCSVMHEALHNHYTQKSLSLSPGK XENP022125_2A11_H1_L2.124_Fab-1G6_L1.194_H1.279 scFv-Fc Heavy Chain (SEQ ID NOS 38683-38692, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQEFSSERTFGGGTKVEIK/GKPGSGKPGSGKPGSGKPGS/
EVQLVESGGGLVKPGGSLRLSCVASGFTFSNYWMNWVRQAPGKGLEWVAEIRLYSNNYATHYAESVKGRFTISRDDSKSTLYLQMNLKTEDTGVYYCTRYYGNYGGYFDWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP022125_2A11_H1_L2.124_Fab-1G6_L1.194_H1.279 Light Chain (SEQ ID NOS 38693-38697)
DIQMTQSPAFLSVTPGEKVTITCQASQDIGNYLNWFQQKPGKVPKLLIYYTSRLHSGVPSRFSGSGSGTDYTFTISSLEAEDAATYFCQQENTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 15H

XENP22604

XENP022604_7G8_H3.30_L1.34-1G6_L1.194_H1.279 Fab-Fc Heavy Chain (SEQ ID NOS 38698-38702)
EVQLVESGGGLVQPGGSLRLSCAASGFTFDDAWMSWVRQAPGKGLEWVAEISTKANNHAIYYAESVKGRFTISRDDSKSSVYLQMNSLRAEDTAVYYCTRLATWNWYFDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK XENP022604_7G8_H3.30_L1.34-1G6_L1.194_H1.279 scFv-Fc Heavy Chain (SEQ ID NOS 38703-38712, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQDFSSERTFGGGTKVEIK/GKPGSGKPGSGKPGSGKPGS/
EVQLVESGGGLVKPGGSLRLSCVASGFTFSNYWMNWVRQAPGKGLEWVAEIRLYSNNYATHYAESVKGRFTISRDDSKSTLYLQMNLKTEDTGVYYCTRYYGNYGGYFDWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP022604_7G8_H3.30_L1.34-1G6_L1.194_H1.279 Light Chain (SEQ ID NOS 38713-38717)
DIVLTQSPSSLSASVGDRVTITCRASQSVDYDGDSYMNWYQQKPGKPPKLLIYAASELESGIPARFSGSGSGTDFTLTISSLQPEDFATYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 15I (LAG-3 X PD-1)

XENP022672

XENP022672_2A11_H1.144_L2.142_Fab-1G6_L1.194_H1.279 Fab-Fc Heavy Chain (SEQ ID NOS 38718-38722)
EVQLVQSGAEVKKPGATVKISCKASGFNIKDYFMHWVQQAPGKGLEWMGWIDPELGETEYAPKFQGRVTITADTSTNTAYMELSSLRSEDTAVYYCYARGVYQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQQGDVFSCSVMHEALHNHYTQKSLSLSPGK XENP022672_2A11_H1.144_L2.142_Fab-1G6_L1.194_H1.279 scFv-Fc Heavy Chain (SEQ ID NOS 38723-38732, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQEFSSPRTFGGGTKVEIK/GKPGSGKPGSGKPGSGKPGS/
EVQLVESGGGLVKPGGSLRLSCVASGFTFSNYWMNWVRQAPGKGLEWVAEIRLYSNNYATHYAESVKGRFTISRDDSKSTLYLQMNNLKTEDTGVYCTRYYGNYGGYFDWGRGTLVTVSS/EPKSSD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLITVDKSRWQQGNVFSCSVMHEALHNHYTQKSLSLSPGK XENP022672_2A11_H1.144_L2.142_Fab-1G6_L1.194_H1.279 Light Chain (SEQ ID NOS 38733-38737)
DIQMTQSPAFLSVTPGEKVTITCQASQDIGNYLNWFQQKPGQTVKLLIYETSYLHSGVPSRFSGSGSGTDYTFTISSLEAEDAATYFCQQGNILPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 15J

XENP22847

XENP022847_7G8_H3.30_L1.34_Fab-1G6_L1.194_H1.279_scFv M428L/N434S Fab-Fc Heavy Chain (SEQ ID NOS 38738-38742)
EVQLVESGGGLVQPGGSLRLSCAASGFTFDDAWMSWVRQAPGKGLEWVAEISFKANGHATVYAESVKGRFTISRDDSKSSVYLQMNSLRAEDTAVYYCTRLATWDNVFDVWGQGTTVTVSS/ASTKGPSVFPLAPSSKSTSGGTA
ALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTPEVTCVVVDVKHEDPEVKFNWYVDGVEVHN
AKTKPREEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVLHEA
LHSHYTQKSLSLSPGK XENP022847_7G8_H3.30_L1.34_Fab-1G6_L1.194_H1.279_scFv M428L/N434S scFv-Fc Heavy Chain (SEQ ID NOS 38743-38752, linker disclosed as SEQ ID NO: 37708)
EIVLTQSPATLSASPGERVTLTCRASQSVGNDVAWYQQKPGQAPRLLINYASHRYTGVPDRFTGSGYGTEFTLTISSVQSEDFGVYYCQQEFSSPRTFGGGTKVEIK/GKPGSGKPGSGKPGSGKPGS/EVQLVESGGGLVKPGG
SLRLSCVASGFTFSNYWMNWVRQAPGKGLEWVAEIRLYSNNYATHYAESVKGRFTISRDDSKSTLYLQMNNLKTEDTGVYCTRYYGNYGGYFDWGRGTLVTVSS/EPKSSDKTHTCPPCPAPPVAGPSVFLFPPKPKDTLMIS
RTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLD
SDGSFFLYSKLITVDKSRWQQGNVFSCSVMHEALHSHYTQKSLSLSPGK XENP022847_7G8_H3.30_L1.34_Fab-1G6_L1.194_H1.279_scFv M428L/N434S Light Chain (SEQ ID NOS 38753-38757)
DIVLTQSPSSLSASVGDRVTITCRASQSVYDYQDSKMQWYQQKPGKPPKLLIYAASNLESGIPARFSGSGSGTDFTLTISSLQPEDFATYYCQQSNEDPFTFGSGTKLEIK/RTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRGEC Figure 15K (LAG-3 X PD-1)

XENP22849

XENP022849_2A11_H1.144_L2.142_Fab-1G6_L1.194_H1.279_scFv_M428L/N434S Fab-Fc Heavy Chain (SEQ ID NOS 38758-38762)
EVQLVQSGAEVKKPGATVKISCKASGFNIKDYFMHWVQQAPGKGLEWMGWIDPENGDTEYAPKFQGRVTITADTSTNTAYMELSSLRSEDTAVYYCYARGVYQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVLHEALHSHYTQKSLSLSPGK XENP022849_2A11_H1.144_L2.142_Fab-1G6_L1.194_H1.279_scFv_M428L/N434S scFv-Fc Heavy Chain (SEQ ID NOS 38763-38772, linker disclosed as SEQ ID NO: 37708)
EIVLTQSPATLSASPGERVLTCRASQSVGNEVAWYQQKPGQAPRLLINYASHRYTGVPDRFTGSGYGTEFTLTISSVQSEDFGVYYCQQEFSSPRTFGGGTKVEIK/GKPGSGKPGSGKPGSGKPGS/
EVQLVESGGGLVKPGGSLRLSCVASGFTFSNYWMNWVRQAPGKGLEWVAEIRLKSNNYATHYAESVKGRFTISRDDSKSTLYLQMNLKTEDIGVYYCTRYYGNYGGYFDYWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK >XENP022849_2A11_H1.144_L2.142_Fab-1G6_L1.194_H1.279_scFv_M428L/N434S Light Chain (SEQ ID NOS 38773-38777)
DIQMTQSPAFLSVTPGEKVTITCQASQDIGNILNWFQQKPGQTVKLLIYETSYLHSGVPSRFSGSGSGTDYTFTISSLEAEDAATYFCQQGNTLFYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC Figure 16A (BTLA X PD-1)

XENP20895

XENP020895_9C6_H0L0-1G6_L1.194_H1.279 Fab-Fc Heavy Chain (SEQ ID NOS 38778-38782)
QVQLKESGPGLVAPSQSLSITCTVSGFSLTGYGVNWVRQPPGKGLEWLGMIWGDGSTDYNSALKRSLSINKDNSKSQVFLKMNSLQTDDTARYYCARDRDGRAMDYWGQTSVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP020895_9C6_H0L0-1G6_L1.194_H1.279 scFv-Fc Heavy Chain (SEQ ID NOS 38783-38792, linker disclosed as SEQ ID NO: 37708)
EIVLTQSPATLSASPGERVTLTCRASQSVGNDVAWYQQKPGQAPRLLINYASHRYTGVPDRFTGSSYGTEFTLTISSVQSEDFGVYYCQQDFSSPRTFGGGTKVEIK/GKPGSGKPGSGKPGS/
EVQLVESGGGLVKPGGSLRLSCVASGFTFSNYWMNWVRQAPKGLEWVAEIRLYSNNYATHYAESVKGRFTISRDDSKSTLYLQMNNLKTEDTGVYYCTRYYGNYGGYFDVWGRGTLVTVSS/EPKSSD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP020895_9C6_H0L0-1G6_L1.194_H1.279 Light Chain (SEQ ID NOS 38793-38797)
SIVMTQTPKFLIVSAGDRVTITCKASQSVSNDVAWYQQKPGQSPKLLIYYASNRYTGVPDRFTGSGYGTDFTFTISTVQAEDLAVYFCQQDNSSPTFGGGTKLEIK/RTVAAPSVFIFPPSDEQLKSGT
ASVVCLLNNFYPREAKVQWKVDNALQSGNSQESVTEQDSKDSTYSLSSTLTLSKADYEKHKVYACEVTHQGLSSPVTKSFNRGEC

Figure 16B

XENP21220

XENP021220_9C6_H1.1_L1-1G6_L1.194_H1.279 Fab-Fc Heavy Chain (SEQ ID NOS 38798-38802)
QVQLKESGAEVKKPGASVKVSCKVSGFSLTGYGVNWVRQAPGQGLEWMGMIWGDGSTDYNSKFQGRVTMTKDNSKSTVYMELSSLRSEDTAVYYCARDRDGRAMDYWGQGTMVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK XENP021220_9C6_H1.1_L1-1G6_L1.194_H1.279 scFv-Fc Heavy Chain (SEQ ID NOS 38803-38812, linker disclosed as SEQ ID NO: 37708)
EIVLTQSPATLSASPGERVTLTCRASQSVGNDVAWYQQKPGQAPRLLINYASHRYTGVPDRFTGSSYGTEFTLTISSVQSEDFGVYYCQQDFSSPRTFGGGTKVEIK/GKPGSGKPGSGKPGS/
EVQLVESGGGLVKPGGSLRLSCVASGFTFSNYWMNWVRQAPKGLEWVAEIRLYSNNYATHYAESVKGRFTISRDDSKSTLYLQMNNLKTEDTGVYYCTRYYGNYGGYFDVWGRGTLVTVSS/EPKSSD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP021220_9C6_H1.1_L1-1G6_L1.194_H1.279 Light Chain (SEQ ID NOS 38813-38817)
SIVMTQSPDSLAVSLGERATINCKASQSVSNDVAWYQQKPGQSPKLLIYYASNRYTGVPDRFTGSGYGTDFTLTISSLQAEDVAVYFCQQDNSSPTFGGGTKLEIK/RTVAAPSVFIFPPSDEQLKSGT
ASVVCLLNNFYPREAKVQWKVDNALQSGNSQESVTEQDSKDSTYSLSSTLTLSKADYEKHKVYACEVTHQGLSSPVTKSFNRGEC Figure 16C (BTLA x PD-1)

XENP21221

XENP021221_9C6_H1.11_L1.194_H1-1G6_L1.194_H1.279 Fab-Fc Heavy Chain (SEQ ID NOS 38818-38822)
QVQLVQSGAEVKKPGASVKVSCKVSGGTAALGCLVKDYFPEPVTVSWNSGALTSGVHTFPAVLQSSGLYSLSSVVTVPSSLGTQTYICNVNHKPSDTKVDKKVEPKSCDKTHTCPPCPAPPVAGPSVFLFPPKPKDTLMISRTP
LAPSSKSTSGGTAALGCLVKDYFPEPVTVSWNSGALTSGVHTFPAVLQSSGLYSLSSVVTVPSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESDGQ
PENNYKTTPPVLDSDGSFFLYSKLTVDKSRWQEGNVFSCSVMHEALHNHYTQKSLSLSPGK XENP021221_9C6_H1.11_L1.194_H1-1G6_L1.194_H1.279 scFv-Fc Heavy Chain (SEQ ID NOS 38823-38832, linker disclosed as SEQ ID NO: 37708)
EIVLTQSPATLSASPGERVTLTCRASQSVRNDVAWYQQKPGQAPRLLINYASHRYTGVPDRFTGSGYGTEFTLTISSVQSEDFGVYYCQQFSSRTFGGGTKVEIK/GKPGSGKPGSGKPGS/
EVQLVESGGGLVKPGGSLRLSCVASGFTFSNYWMNWVRQAPGKGLEWVAEIRLYSNYATHYAESVKGRFTISRDDSKSTLYLQMNNLKTEDTGVYYCTRYGNYGGYFDVWGRGTLVTVSS/EPKSSD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK XENP021221_9C6_H1.11_L1.194_H1-1G6_L1.194_H1.279 Light Chain (SEQ ID NOS 38833-38837)
SIVMTQSPDSLAVSLGERATINCKASQSVSNDVAWYQQKPGQSPKLLIYYASNRYTGVPDRFTGSGYGTDFTLTISSLQAEDVAVYFCQQDYSSPTFGGGTKLEIK/RTVAAPSVFIFPPSDEQLKSGT
ASVVCLLNNFYPREAKVQWKVDNALQSGNSQESVTEQDSKDSTYSLSSTLTLSKADYEKHKVYACEVTHQGLSSPVTKSFNRGEC

Figure 16D

XENP22858

XENP022858_9C6_H1.1_L1_Fab-1G6_L1.194_H1.279 scFv M428L/N434S Fab-Fc Heavy Chain (SEQ ID NOS 38838-38842)
QVQLKESGAEVKKPGASVKVSCKVSGYTFTGYVMNWVRQAPGQGLEWMGMIWLDGSTDYNSKFQGRVTMTKDNSKSTVYMELSSLRSEDTAVYYCARRRDGRAMDYWGQGTMVTVSS/ASTKGPSVFP
LAPSSKSTSGGTAALGCLVKDYFPEPVTVSWNSGALTSGVHTFPAVLQSSGLYSLSSVVTVPSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESDGQ
PENNYKTTPPVLDSDGSFFLYSKLTVDKSRWQEGNVFSCSVMHEALHNHYTQKSLSLSPGK XENP022858_9C6_H1.1_L1_Fab-1G6_L1.194_H1.279 scFv M428L/N434S scFv-Fc Heavy Chain (SEQ ID NOS 38843-38852, linker disclosed as
SEQ ID NO: 37708)
EIVLTQSPATLSASPGERVTLTCRASQSVRNDVAWYQQKPGQAPRLLINYASHRYTGVPDRFTGSGYGTEFTLTISSVQSEDFGVYYCQQFSSRTFGGGTKVEIK/GKPGSGKPGSGKPGS/
EVQLVESGGGLVKPGGSLRLSCVASGFTFSNYWMNWVRQAPGKGLEWVAEIRLYSNYATHYAEVKGRFTISRDDSKSTLYLQMNNLKTEDTGVYYCTRYGNYGGYFDVWGRGTLVTVSS/EPKSSD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTL
PPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK XENP022858_9C6_H1.1_L1_Fab-1G6_L1.194_H1.279 scFv M428L/N434S Light Chain (SEQ ID NOS 38853-38857)
SIVMTQSPDSLAVSLGERATINCKASQSVSNDVAWYQQKPGQSPKLLIYYASNRYTGVPDRFTGSGYGTDFTLTISSLQAEDVAVYFCQQDYSSPTFGGGTKLEIK/RTVAAPSVFIFPPSDEQLKSGT
ASVVCLLNNFYPREAKVQWKVDNALQSGNSQESVTEQDSKDSTYSLSSTLTLSKADYEKHKVYACEVTHQGLSSPVTKSFNRGEC

Figure 17A

XENP20153

>XENP020153 2A11_H1L2-[CTLA-4]_H3.4_L0.12 Fab-Fc Heavy Chain (SEQ ID NOS 38858-38862)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK >XENP020153 2A11_H1L2-[CTLA-4]_H3.4_L0.12 scFv-Fc Heavy Chain (SEQ ID NOS 38863-38872, linker disclosed as SEQ ID NO: 37708)
EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGS
GKPGSGKPGS/EIVLTQSPGTLSVSPGERATLSCRASQSVGSSYLAWYQQKPGQAPRLLIYGAFSRATGIPDRFSGSGSGTDFLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP020153 2A11_H1L2-[CTLA-4]_H3.4_L0.12 Light Chain (SEQ ID NOS 38873-38877)
DIQMTQSPAFLSVTPGEKVTITCQASQDIGNYLNWFQQKPDQTVKLLIYTTSPLHSGVPSRFSGSGSGTDYTFTISSLEAEDAATYFCQQGNNLPYTFGGGTKVEIK/RTVAAPSVFIFPPSDEQLSG
TASVVCLLNNFYPREAKVQWKVDNALQSGNSQESVTEQDSKDSTYSLSSTLTLSKADYEKHKVYACEVTHQGLSSPVTKSFNRGEC

Figure 17B

XENP20833

>XENP020833 7G8_H3L1 Fab-[CTLA-4]_H3.23_L0.129 Fab-Fc Heavy Chain (SEQ ID NOS 38878-38882)
EVQLVESGGGLVQPGGSLRLSCAASGFTFSDAWMEWVRQAPGKGLEWVAEIRTKAANHATTYAESVKGRFTISRDDSKSSVYLQMNSLRAEDTAVYYCTRLANWDWYFDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK >XENP020833 7G8_H3L1 Fab-[CTLA-4]_H3.23_L0.129 scFv-Fc Heavy Chain (SEQ ID NOS 38883-38892, linker disclosed as SEQ ID NO: 37708)
EVQLVESGGGLVQPGGSLRLSCAASGFTFSSYEMHWVRQAPGKGLEWVSFISYDGNYKYYADSVKGRFTISRDNAKNSLYLQMNSLRAEDTAVYYCARGEHLGPFDLWGQGTMVTVSS/GKPGSGKPGS
GKPGSGKPGS/EIVLTQSPGTLSVSPATLSLSPGERATLSCRASQSVGSSYLAWYQQKPGQAPRLLIYGASSRATGIPDRFSGSGSGTDFLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP020833 7G8_H3L1 Fab-[CTLA-4]_H3.23_L0.129 Light Chain (SEQ ID NOS 38893-38897)
DTVLTQSPSSLSASVGDRVTITCRASQSVEYDCDSYMHWYQQKPGKPPKLLIYAASNLESGIPARLSGSGSGTDFLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17C

XENP21859

>XENP021859_2A11_H1_L2.47_Fab-[CTLA-4]_H3.23_L0.129 Fab-Fc Heavy Chain (SEQ ID NOS 38898-38902)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK >XENP021859_2A11_H1_L2.47_Fab-[CTLA-4]_H3.23_L0.129 scFv-Fc Heavy Chain (SEQ ID NOS 38903-38912, linker disclosed as SEQ ID NO: 37708)
EVQLVESGGGLVKPGGSLRLSCAASGFTFSSYTMHWVRQAPGKGLEWVSFISTDGNYKYYADSVKGRFTISRDNAKNSLYLQMNSLRAEDTAVYYCARGGHLGFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021859_2A11_H1_L2.47_Fab-[CTLA-4]_H3.23_L0.129 Light Chain (SEQ ID NOS 38913-38917)
DIQMTQSPAFLSVTPGEKVTITCQASQDIGNYLNWFQQKPDQTVKLLIYYTSHLRSGVPSRFSGSGSGTDYTFTISSLEAEDAATYFCQQGNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 17D

XENP21860

>XENP021860_2A11_H1_L2.50_Fab-[CTLA-4]_H3.23_L0.129 Fab-Fc Heavy Chain (SEQ ID NOS 38918-38922)
EVQLVQSGAEVKKPGATVKISCKASGFNIKDYYMHWVQQAPGKGLEWMGWIDPENGDTEYAPKFQGRVTITADTSTNTAYMELSSLRSEDTAVYYCYARGVRQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQEGDVFSCSVMHEALHNHYTQKSLSLSPGK >XENP021860_2A11_H1_L2.50_Fab-[CTLA-4]_H3.23_L0.129 scFv-Fc Heavy Chain (SEQ ID NOS 38923-38932, linker disclosed as SEQ ID NO: 37708)
EVQLVESGGGLVKPGGSLRLSCAASGFTFSSYTMHWVRQAPGKGLEWVSFISTDGNYKYYADSVKGRFTISRDNAKNSLYLQMNSLRAEDTAVYYCARGGHLGFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021860_2A11_H1_L2.50_Fab-[CTLA-4]_H3.23_L0.129 Light Chain (SEQ ID NOS 38933-38937)
DIQMTQSPAFLSVTPGEKVTITCQASQDIGNYLNWFQQKPDQTVKLLIYYTSYLESGVPSRFSGSGSGTDYTFTISSLEAEDAATYFCQQNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 17E

XENP21895

>XENP021895_7G8_H3.18_L1-[CTLA-4]_H3.23_L0.129 Fab-Fc Heavy Chain   (SEQ ID NOS 38938-38942)
EVQLVESGGGLVQPGGSLRLSCAASGFTFDDAWMDWVRQAPGKGLEWVAEISTKANHATYAESVKGRFTISRDDSKSSVYLQMNSLRAEDTAVYYCTRLATWDWYFDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWQEGDVFSCSVMHEALHNHYTQKSLSLSPGK >XENP021895_7G8_H3.18_L1-[CTLA-4]_H3.23_L0.129 scFv-Fc Heavy Chain   (SEQ ID NOS 38943-38952, linker disclosed as SEQ ID NO:
37708)
EVQLVESGGGLVKPGGSLRLSCAASGFTFSSYMHWVRQAPGKGLEWVSFISVDGNYKYYADSVKGRFTISRDNAKNSLYLQMNSLRAEDTAVYCARGGHLGFDLWGQGTMTVSS/GKPGSGKPGS
GKPGSGKPGS/EIVLTQSPATLSLSPGERATLSCRASQSVYGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021895_7G8_H3.18_L1-[CTLA-4]_H3.23_L0.129 Light Chain   (SEQ ID NOS 38953-38957)
DIVLTQSPSSLSASVGDRVTITCRASQSVLRDGSYMNWYQQKPGKPPKLLIYAASNLESGIPARLSGSGSGTDFTLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17F

XENP21896

>XENP021896_7G8_H3.18_L1.11-[CTLA-4]_H3.23_L0.129 Fab-Fc Heavy Chain   (SEQ ID NOS 38958-38962)
EVQLVESGGGLVQPGGSLRLSCAASGFTFDDAWMDWVRQAPGKGLEWVAEISTKANHATYAESVKGRFTISRDDSKSSVYLQMNSLRAEDTAVYYCTRLATWDWYFDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWQEGDVFSCSVMHEALHNHYTQKSLSLSPGK >XENP021896_7G8_H3.18_L1.11-[CTLA-4]_H3.23_L0.129 scFv-Fc Heavy Chain   (SEQ ID NOS 38963-38972, linker disclosed as SEQ ID NO:
37708)
EVQLVESGGGLVKPGGSLRLSCAASGFTFSSYMHWVRQAPGKGLEWVSFISVDGNYKYYADSVKGRFTISRDNAKNSLYLQMNSLRAEDTAVYCARGGHLGFDLWGQGTMTVSS/GKPGSGKPGS
GKPGSGKPGS/EIVLTQSPATLSLSPGERATLSCRASQSVYGSSYLAWYQQKPGQAPRLLIYGASSRAHGIPDRFSGSGSGTDFTLTISRLEPEDFAVYYCQQYGSSRWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021896_7G8_H3.18_L1.11-[CTLA-4]_H3.23_L0.129 Light Chain   (SEQ ID NOS 38973-38977)
DIVLTQSPSSLSASVGDRVTITCRASQSVLRDGSYMNWYQQKPGKPPKLLIYAASELESGIPARLSGSGSGTDFTLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17G

XENP21902

>XENP021902_7G8_H3.23_L1.11-[CTLA-4]_H3.23_L0.129 Fab-Fc Heavy Chain  (SEQ ID NOS 38978-38982)
EVQLVESGGGLVQPGGSLRLSCAASGFTFSDAWMEWVRQAPGKGLEWVAEISTKAXNHATYYAESVKGRFTISRDDSKSSVYLQMNSLRAEDTAVYYCTRLATWDWYEDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVSHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK >XENP021902_7G8_H3.23_L1.11-[CTLA-4]_H3.23_L0.129 scFv-Fc Heavy Chain  (SEQ ID NOS 38983-38992, linker disclosed as SEQ ID NO:
37708)
EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPEDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021902_7G8_H3.23_L1.11-[CTLA-4]_H3.23_L0.129 Light Chain  (SEQ ID NOS 38993-38997)
DIVLTQSPSSLSASVGDRVTITCRASQSVYDGDSYMNWYQQKPGKPPKLLIYAASELESGIPARLSGSGSGTDFTLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17H

XENP21904

>XENP021904_7G8_H3.28_L1-[CTLA-4]_H3.23_L0.129 Fab-Fc Heavy Chain  (SEQ ID NOS 38998-39002)
EVQLVESGGGLVQPGGSLRLSCAASGFTFDDAWMEWVRQAPGKGLEWVAEISTKAXNHATYYAESVKGRFTISRDDSKSSVYLQMNSLRAEDTAVYYCTRLATWDWYEDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVSHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK >XENP021904_7G8_H3.28_L1-[CTLA-4]_H3.23_L0.129 scFv-Fc Heavy Chain  (SEQ ID NOS 39003-39012, linker disclosed as SEQ ID NO:
37708)
EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPEDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021904_7G8_H3.28_L1-[CTLA-4]_H3.23_L0.129 Light Chain  (SEQ ID NOS 39013-39017)
DIVLTQSPSSLSASVGDRVTITCRASQSVYDGDSYMNWYQQKPGKPPKLLIYAASNLESGIPARLSGSGSGTDFTLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17I

XENP21905

>XENP021905_7G8_H3.28_L1.11-[CTLA-4]_H3.23_L0.129 Fab-Fc Heavy Chain  (SEQ ID NOS 39018-39022)
EVQLVESGGGLVQPGGSLRLSCAASGFTFDDAWMDWVRQAPGKGLEWVAEISTKAYNHATYYAESVKGRFTISRDDSKSSVYLQMNSLRAEDTAVYYCTRLATWDWYFDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK >XENP021905_7G8_H3.28_L1.11-[CTLA-4]_H3.23_L0.129 scFv-Fc Heavy Chain  (SEQ ID NOS 39023-39032, linker disclosed as SEQ ID NO:
37708)
EVQLVESGGGLVKPGGSLRLSCAASGFTFSSYTMHWVRQAPGKGLEWVSEISYDGNYKYYADSVKGRFTISRDNAKNSLYLQMNSLRAEDTAVYYCARGGHLGFFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021905_7G8_H3.28_L1.11-[CTLA-4]_H3.23_L0.129 Light Chain  (SEQ ID NOS 39033-39037)
DIVLTQSPSSLSASVGDRVTITCRASQSVEDGDSYMNWYQQKPGKPPKLLIYAASELESGIPARLSGSGSGTDFTLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17J

XENP21906

>XENP021906_7G8_H3.28_L1.13-[CTLA-4]_H3.23_L0.129 Fab-Fc Heavy Chain  (SEQ ID NOS 39038-39042)
EVQLVESGGGLVQPGGSLRLSCAASGFTFDDAWMDWVRQAPGKGLEWVAEISTKAYNRATYYAESVKGRFTISRDDSKSSVYLQMNSLRAEDTAVYYCTRLATWDWYFDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK >XENP021906_7G8_H3.28_L1.13-[CTLA-4]_H3.23_L0.129 scFv-Fc Heavy Chain  (SEQ ID NOS 39043-39052, linker disclosed as SEQ ID NO:
37708)
EVQLVESGGGLVKPGGSLRLSCAASGFTFSSYTMHWVRQAPGKGLEWVSEISYDGNYKYYADSVKGRFTISRDNAKNSLYLQMNSLRAEDTAVYYCARGGHLGFFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP021906_7G8_H3.28_L1.13-[CTLA-4]_H3.23_L0.129 Light Chain  (SEQ ID NOS 39053-39057)
DIVLTQSPSSLSASVGDRVTITCRASQSVEHDGDSYMNWYQQKPGKPPKLLIYAASELESGIPARLSGSGSGTDFTLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17K

XENP22505

>XENP022505_2A11_H1.125_L2.113_Fab-[CTLA-4]_H3.23_L0.129 Fab-Fc Heavy Chain (SEQ ID NOS 39058-39062)
EVQLVQSGAEVKKPGATVKISCKASGFNIKHYFMHWVQQAPGKGLEWMGWIDPYLGETEYARKFQGRVTITADTSTNTAYMELSSLRSEDTAVYYCYARGVYQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWEQGDVFSCSVMHEALHNHYTQKSLSLSPGK >XENP022505_2A11_H1.125_L2.113_Fab-[CTLA-4]_H3.23_L0.129 scFv-Fc Heavy Chain (SEQ ID NOS 39063-39072, linker disclosed as SEQ ID NO: 37708)
EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPS
REQMKNQVKLTCLVKGFYPSDIAVEWESNGQPENNYKTTPPVLDSDGSFFLYSKLTVDKSRWQQGNVFSCSVMHEALHNHYTQKSLSLSPGK >XENP022505_2A11_H1.125_L2.113_Fab-[CTLA-4]_H3.23_L0.129 Light Chain (SEQ ID NOS 39073-39077)
DIQMTQSPAFLSVTPGEKVTITCQASQDIGNYLNWFQQKPDQTVKLLIYETSYLHSGVPSRFSGSGSGTDYTFTISSLEAEDAATYFCQQGNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 17L

XENP22510

>XENP022510_2A11_H1_L2.25_Fab-[CTLA-4]_H3.23_L0.129 Fab-Fc Heavy Chain (SEQ ID NOS 39078-39082)
EVQLVQSGAEVKKPGATVKISCKASGFNIKDYYMHWVQQAPGKGLEWMGWIDPENGETEYARKFQGRVTITADTSTNTAYMELSSLRSEDTAVYYCYARGVYQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWEQGDVFSCSVMHEALHNHYTQKSLSLSPGK >XENP022510_2A11_H1_L2.25_Fab-[CTLA-4]_H3.23_L0.129 scFv-Fc Heavy Chain (SEQ ID NOS 39083-39092, linker disclosed as SEQ ID NO: 37708)
EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPS
REQMKNQVKLTCLVKGFYPSDIAVEWESNGQPENNYKTTPPVLDSDGSFFLYSKLTVDKSRWQQGNVFSCSVMHEALHNHYTQKSLSLSPGK >XENP022510_2A11_H1_L2.25_Fab-[CTLA-4]_H3.23_L0.129 Light Chain (SEQ ID NOS 39093-39097)
DIQMTQSPAFLSVTPGEKVTITCQASQDIGNHLNWFQQKPDQTVKLLIYYTSRLHSGVPSRFSGSGSGTDYTFTISSLEAEDAATYFCQQGNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 17M

XENP22602

>XENP022602_7G8_H3.30_L1.34-[CTLA-4]_H3.23_L0.129 Fab-Fc Heavy Chain (SEQ ID NOS 39098-39102)
EVQLVESGGGLVQPGGSLRLSCAASGFTFDDAWMSWVRQAPGKGLEWVAEISRANNEATYYAESVKGRFTISRDDSKSSVYLQMNSLRAEDTAVYYCTRLATWDWYEDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWQQGNVFSCSVMHEALHNHYTQKSLSLSPGK >XENP022602_7G8_H3.30_L1.34-[CTLA-4]_H3.23_L0.129 scFv-Fc Heavy Chain (SEQ ID NOS 39103-39112, linker disclosed as SEQ ID NO: 37708)
EVQLVESGGGLVKPGGSLRLSCAASGFTFSSYTMHWVRQAPGKGLEWVSEISYDGNYKYYADSVKGRFTISRDNAKNSLYLQMNSLRAEDTAVYYCARGGHLGEFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP022602_7G8_H3.30_L1.34-[CTLA-4]_H3.23_L0.129 Light Chain (SEQ ID NOS 39113-39117)
DIVLTQSPSSLSASVGDRVTITCRASQSVYDGDSYMRWYQQKPGKPPKLLIYAASELESGIPARFSGSGSGTDFTLTISSLQPEDFATYYCQQSNEDPFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

Figure 17N

XENP22675

>XENP022675_2A11_H1.144_L2.142_Fab-[CTLA-4]_H3.23_L0.129 Fab-Fc Heavy Chain (SEQ ID NOS 39118-39122)
EVQLVQSGAEVKKPGATVKISCKASGFNIKDYFMHWVQQAPGKGLEWMGWIDPELGDTEYAPKFQGRVTITADTSTNTAYMELSSLRSEDTAVYYCYARGVYQALDYWGQGTLVTVSS/ASTKGPSVFP
LAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCDVSGFYPSDIAVEWESDGQ
PENNYKTTPPVLDSDGSFFLYSKLTVDKSRWQQGNVFSCSVMHEALHNHYTQKSLSLSPGK >XENP022675_2A11_H1.144_L2.142_Fab-[CTLA-4]_H3.23_L0.129 scFv-Fc Heavy Chain (SEQ ID NOS 39123-39132, linker disclosed as SEQ ID NO: 37708)
EVQLVESGGGLVKPGGSLRLSCAASGFTFSSYTMHWVRQAPGKGLEWVSEISYDGNYKYYADSVKGRFTISRDNAKNSLYLQMNSLRAEDTAVYYCARGGHLGEFDLWGQGTMVTVSS/GKPGSGKPGS
GKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVKLTCLVKGFYPSDIAVEWESNGQPENNYKTTPPVLDSDGSFFLYSKLTVDKSRWQQGNVFSCSVMHEALHNHYTQKSLSLSPGK >XENP022675_2A11_H1.144_L2.142_Light Chain (SEQ ID NOS 39133-39137)
DIQMTQSPAFLSVTPGEKVTITCQASQDIGNYLNWFQQKPGQTVKLLIYETSYLHSGVPSRFSGSGSGTDYTFTISSLEAEDAATYFCQQGNTLPYTFGGGTKVEIK/RTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPVTKSFNRGEC

Figure 17O

XENP22841

>XENP022841_7G8_H3.30_L1.34_Fab-[CTLA-4]_H3.23_L0.129_scFv_M428L/N434S Fab-Fc Heavy Chain (SEQ ID NOS 39138-39142)
EVQLVESGGGLVQPGGSLRLSCAASGFTFDDAWMSWVRQAPGKGLEWVAKISWANWHATYYAESYKGRFTISRDDSKSSVYLQMNSLRAEDTAVYYCTRLATWDWYFDVWGQGTTVTVSS/ASTKGPS
VFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVSHEDPEVKFNWYVDGVEVHNAKTKPREEYNSTYRVVSVLTVLHQDWLNGKEYKCKVSNKALPAPIEKTISKAKGQPREPQVYTLPPSREEMTKNQVSLTCLVKGFYPSDIAVEWES
DGQPENNYKTTPPVLDSDGSFFLYSKLTVDKSRWEQGDVFSCSVLHEALHSHYTQKSLSLSPGK >XENP022841_7G8_H3.30_L1.34_Fab-[CTLA-4]_H3.23_L0.129_scFv_M428L/N434S scFv-Fc Heavy Chain (SEQ ID NOS 39143-39152, linker disclosed as SEQ ID NO: 37708)
EVQLVESGGGLVKPGGSLRLSCAASGFTFSSYEMHWVRQAPGKGLEWVSFISYDGNYKYYADSVKGRFTISRDNAKNSLYLQMNSLRAEDTAVYYCARGGHLGPDLWGQGTMVTVSS/<u>GKPGSGKPGS</u>
<u>GKPGSGKPGS</u>/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK/EPKSSDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPS
REQMTKNQVSLTCLVKGFYPSDIAVEWESNGQPENNYKTTPPVLDSDGSFFLYSKLTVDKSRWQQGNVFSCSVLHEALHSHYTQKSLSLSPGK >XENP022841_7G8_H3.30_L1.34_Fab-[CTLA-4]_H3.23_L0.129_scFv_M428L/N434S Light Chain (SEQ ID NOS 39153-39157)
DIVLTQSPSSLSASVGDRVTITCRASQSVDYDGDSYMNWYQQKPGKPPKLLIYAASELESGIPARFSGSGSGTDFLTISSLQPEDFATYYCQQSNEDFTFGSGTKLEIK/RTVAAPSVFIFPPSDEQ
LKSGTASVVCLLNNFYPREAKVQWKVDNALQSGNSQESVTEQDSKDSTYSLSSTLTLSKADYEKHKVYACEVTHQGLSSPVTKSFNRGEC

XENP22843

Figure 19A depict cytokine release assay (A: IL-2, G: IFNγ) after SEB stimulation of human PBMCs and treatment with an anti-PD-1 x anti-CTLA-4 bispecific antibody.

Figure 20A-C depicts CD45+ events, CD4+ events and CD8+ events on Day 14 after human PBMCs were engrafted into NSG mice on Day 0 followed by dosing with the indicated test articles on Day 1.

Figure 22

| XENP | Clone | VH | VL | KD (M) | ka (1/Ms) | kd (1/s) |
|---|---|---|---|---|---|---|
| Experiment #1 | | | | | | |
| 16275 | mAb8213 | H0 | L0 | 4.94E-09; 5.93E-09 | 7.34E04; 8.63E04 | 3.63E-04; 5.12E-04 |
| 17973 | ABTIM3 | H0 | L0 | 1.74E-09; 2.75E-09 | 1.45E05; 1.97E05 | 2.52E-04; 5.42E-04 |
| 20850 | 1D12 | H1 | L1 | 9.07E-09 | 2.45E05 | 2.22E-03 |
| 20851 | 1D12 | H1 | L2 | 2.84E-08 | 1.72E05 | 4.87E-03 |
| 20853 | 3H3 | H1 | L1 | 4.49E-09 | 1.04E05 | 4.66E-04 |
| 20854 | 3H3 | H1 | L2 | 7.64E-09 | 7.07E04 | 5.40E-04 |
| 20855 | 3H3 | H2 | L1 | 5.16E-09 | 1.97E05 | 1.02E-03 |
| 20856 | 3H3 | H2 | L2 | 1.30E-08 | 1.11E05 | 1.44E-03 |
| 20857 | 3H3 | H3 | L1 | 7.11E-09 | 1.04E05 | 7.39E-04 |
| 20858 | 3H3 | H3 | L2 | 1.57E-08 | 8.16E04 | 1.28E-03 |
| 20859 | 3H3 | H4 | L1 | 4.50E-09 | 1.53E05 | 6.88E-04 |
| 20860 | 3H3 | H4 | L2 | 8.20E-09 | 9.15E04 | 7.50E-04 |
| 20861 | 7B11 | H1 | L1 | 1.07E-08 | 2.86E05 | 3.06E-03 |
| 20862 | 7B11 | H1 | L2 | 1.24E-08 | 1.37E05 | 1.70E-03 |
| 20863 | 7B11 | H2 | L1 | 9.24E-09 | 2.77E05 | 2.56E-03 |
| 20864 | 7B11 | H2 | L2 | 1.85E-08 | 1.34E05 | 2.48E-03 |
| 20865 | 7C2 | H1 | L1 | 5.90E-09 | 3.01E05 | 1.78E-03 |
| Experiment #2 | | | | | | |
| 16275 | mAb8213 | H0 | L0 | 8.37E-10 | 1.84E05 | 1.54E-04 |
| 21188 | 3H3 | H1 | L1.1 | 5.34E-09 | 1.38E05 | 7.35E-04 |
| 21189 | 3H3 | H1 | L2.1 | 2.61E-09 | 1.54E05 | 4.00E-04 |
| 21190 | 3H3 | H2 | L1.1 | 8.61E-09 | 2.93E05 | 2.52E-03 |
| 21191 | 3H3 | H2 | L2.1 | 6.90E-09 | 2.52E05 | 1.74E-03 |
| 21192 | 3H3 | H3 | L1.1 | 1.25E-08 | 1.14E05 | 1.42E-03 |
| 21193 | 3H3 | H3 | L2.1 | 6.32E-09 | 1.56E05 | 9.87E-04 |
| 21194 | 3H3 | H4 | L1.1 | 4.60E-09 | 1.80E05 | 8.26E-04 |
| 21195 | 3H3 | H4 | L2.1 | 2.50E-09 | 1.78E05 | 4.45E-04 |
| 21196 | 7B11 | H1 | L1.1 | 3.11E-08 | 4.32E05 | 1.34E-02 |
| 21201 | 7B11 | H1 | L2.1 | 3.76E-08 | 3.87E05 | 1.45E-02 |
| 21202 | 7B11 | H2.1 | L1.1 | 3.25E-08 | 5.00E05 | 1.63E-02 |
| 21203 | 7B11 | H2.1 | L2.1 | 2.66E-08 | 4.80E05 | 1.28E-02 |
| 21204 | 7C2 | H1.1 | L1.1 | 9.41E-10 | 1.56E06 | 1.47E-03 |
| Experiment #3 | | | | | | |
| 16275 | mAb8213 | H0 | L0 | 8.50E-11 | 1.86E05 | 1.58E-05 |
| 21492 | 1D12 | H0 | L0 | 1.07E-07 | 1.97E05 | 2.11E-02 |
| 21495 | 7A9 | H0 | L0 | 3.06E-08 | 2.03E05 | 6.21E-03 |
| 21496 | 7B11 | H0 | L0 | 2.24E-08 | 2.61E05 | 5.84E-03 |
| 21501 | 7B11var | H0 | L0 | 2.02E-08 | 2.90E05 | 5.84E-03 |
| 21502 | 7C2 | H0 | L0 | 6.43E-09 | 2.68E06 | 1.72E-02 |

Figure 23A

| Full-length mAb XENP | scFv XENP | VH | VL | scFv orientation | Human PD-1 mAb $K_D$ (M) | scFv $T_m$ (°C) |
|---|---|---|---|---|---|---|
| 17906 | 17922 | H1 | L1 | VH-VL | 1.49E-07 | 56.5 |
| 18094 | 18493 | H1.1 | L1 | VH-VL | 1.62E-07 | 56.5 |
| 18095 | 18494 | H1.2 | L1 | VH-VL | 1.59E-07 | 57.0 |
| 18096 | 18495 | H1.3 | L1 | VH-VL | 1.86E-07 | 55.0 |
| 18101 | 18496 | H1.4 | L1 | VH-VL | 1.66E-07 | 56.5 |
| 18102 | 18501 | H1.5 | L1 | VH-VL | 1.79E-07 | 56.0 |
| 18103 | 18502 | H1.6 | L1 | VH-VL | 1.43E-07 | 56.0 |
| 18104 | 18503 | H1.7 | L1 | VH-VL | 1.18E-07 | 56.0 |
| 18105 | 18504 | H1.8 | L1 | VH-VL | 1.21E-07 | 57.0 |
| 18106 | 18505 | H1.9 | L1 | VH-VL | 1.91E-07 | 54.5 |
| 18107 | 18506 | H1.10 | L1 | VH-VL | 2.80E-07 | |
| 18108 | 18507 | H1.11 | L1 | VH-VL | 1.22E-07 | 56.5 |
| 18109 | 18508 | H1.12 | L1 | VH-VL | 1.48E-07 | 56.0 |
| 18110 | 18509 | H1.13 | L1 | VH-VL | 1.65E-07 | 55.5 |
| 18111 | 18510 | H1.14 | L1 | VH-VL | 1.59E-07 | 55.5 |
| 18112 | 18511 | H1.15 | L1 | VH-VL | 1.30E-07 | 55.5 |
| 18113 | 18512 | H1.16 | L1 | VH-VL | 1.39E-07 | 55.0 |
| 18114 | 18513 | H1.17 | L1 | VH-VL | 5.15E-07 | |
| 18115 | 18514 | H1.18 | L1 | VH-VL | 1.20E-07 | 55.5 |
| 18116 | 18515 | H1.19 | L1 | VH-VL | 1.70E-07 | 56.0 |
| 18117 | 18516 | H1.20 | L1 | VH-VL | 1.47E-07 | |
| 18118 | 18517 | H1.21 | L1 | VH-VL | 2.04E-07 | |
| 18119 | 18518 | H1.22 | L1 | VH-VL | 1.24E-07 | 55.5 |
| 18120 | 18519 | H1.23 | L1 | VH-VL | 1.39E-06 | |
| 18121 | 18520 | H1.24 | L1 | VH-VL | 1.84E-07 | |
| 18122 | 18521 | H1.25 | L1 | VH-VL | 1.71E-07 | |
| 18123 | 18522 | H1.26 | L1 | VH-VL | 1.20E-07 | 54.5 |
| 18124 | 18523 | H1.27 | L1 | VH-VL | 2.02E-07 | 55.0 |
| 18125 | 18524 | H1.28 | L1 | VH-VL | 9.64E-08 | 56.0 |
| 18126 | 18525 | H1.29 | L1 | VH-VL | 1.51E-07 | |
| 18127 | 18526 | H1.30 | L1 | VH-VL | 2.01E-07 | |
| 18128 | 18527 | H1.31 | L1 | VH-VL | 1.83E-07 | |
| 18129 | 18528 | H1.32 | L1 | VH-VL | 2.53E-07 | |
| 18130 | 18529 | H1.33 | L1 | VH-VL | 1.87E-07 | |
| 18131 | 18530 | H1.34 | L1 | VH-VL | 1.45E-07 | |
| 18132 | 18531 | H1.35 | L1 | VH-VL | 2.19E-07 | |
| 18133 | 18532 | H1.36 | L1 | VH-VL | 2.18E-07 | |
| 18134 | 18533 | H1.37 | L1 | VH-VL | 2.63E-07 | |
| 18135 | 18534 | H1.38 | L1 | VH-VL | 2.12E-07 | |
| 18136 | 18535 | H1.39 | L1 | VH-VL | 1.90E-07 | |
| 18137 | 18536 | H1.40 | L1 | VH-VL | 3.78E-07 | |
| 18138 | 18537 | H1.41 | L1 | VH-VL | 1.60E-07 | |
| 18139 | 18538 | H1.42 | L1 | VH-VL | 1.74E-07 | |
| 18140 | 18539 | H1.43 | L1 | VH-VL | 1.64E-07 | |

Figure 23B

| Full-length mAb XENP | scFv XENP | VH | VL | scFv orientation | Human PD-1 mAb $K_D$ (M) | scFv $T_m$ (°C) |
|---|---|---|---|---|---|---|
| 18141 | 18540 | H1.44 | L1 | VH-VL | Weak | 55.0 |
| 18142 | 18541 | H1.45 | L1 | VH-VL | 1.34E-07 | 51.0 |
| 18143 | 18542 | H1.46 | L1 | VH-VL | 1.10E-07 | 56.5 |
| 18144 | 18543 | H1.47 | L1 | VH-VL | 1.11E-07 | |
| 18145 | 18544 | H1.48 | L1 | VH-VL | 9.01E-08 | |
| 18146 | 18545 | H1.49 | L1 | VH-VL | 1.33E-07 | 56.0 |
| 18147 | 18546 | H1.50 | L1 | VH-VL | 1.44E-07 | 56.5 |
| 18148 | 18547 | H1.51 | L1 | VH-VL | 1.17E-07 | 51.0 |
| 18149 | 18548 | H1.52 | L1 | VH-VL | 9.92E-08 | 57.0 |
| 18150 | 18549 | H1.53 | L1 | VH-VL | 1.36E-07 | 55.5 |
| 18151 | 18550 | H1.54 | L1 | VH-VL | 1.70E-07 | |
| 18152 | 18551 | H1.55 | L1 | VH-VL | 1.31E-07 | |
| 18153 | 18552 | H1.56 | L1 | VH-VL | Weak | |
| 18154 | 18553 | H1.57 | L1 | VH-VL | 3.66E-07 | |
| 18155 | 18554 | H1.58 | L1 | VH-VL | Weak | |
| 18156 | 18555 | H1.59 | L1 | VH-VL | 1.65E-06 | |
| 18157 | 18556 | H1.60 | L1 | VH-VL | 1.84E-07 | |
| 18158 | 18557 | H1.61 | L1 | VH-VL | Weak | |
| 18159 | 18558 | H1.62 | L1 | VH-VL | 1.37E-07 | |
| 18160 | 18559 | H1.63 | L1 | VH-VL | 1.00E-07 | 56.0 |
| 18161 | 18560 | H1.64 | L1 | VH-VL | 1.75E-07 | |
| 18162 | 18561 | H1.65 | L1 | VH-VL | 2.76E-07 | |
| 18163 | 18562 | H1.66 | L1 | VH-VL | 2.02E-07 | |
| 18164 | 18563 | H1.67 | L1 | VH-VL | 8.12E-07 | |
| 18165 | 18564 | H1.68 | L1 | VH-VL | 2.23E-07 | |
| 18166 | 18565 | H1.69 | L1 | VH-VL | 1.82E-07 | |
| 18167 | 18566 | H1.70 | L1 | VH-VL | 1.97E-07 | |
| 18168 | 18567 | H1.71 | L1 | VH-VL | 4.53E-07 | |
| 18169 | 18568 | H1.72 | L1 | VH-VL | 4.29E-07 | |
| 18170 | 18569 | H1.73 | L1 | VH-VL | 1.79E-07 | 54.5 |
| 18171 | 18570 | H1.74 | L1 | VH-VL | 1.45E-07 | 55.5 |
| 18172 | 18571 | H1.75 | L1 | VH-VL | 1.65E-07 | 53.0 |
| 18173 | 18572 | H1.76 | L1 | VH-VL | 1.41E-07 | 55.5 |
| 18174 | 18573 | H1.77 | L1 | VH-VL | 1.25E-07 | 54.0 |
| 18175 | 18574 | H1.78 | L1 | VH-VL | 1.09E-07 | 53.5 |
| 18176 | 18575 | H1.79 | L1 | VH-VL | 2.52E-07 | |
| 18177 | 18576 | H1.80 | L1 | VH-VL | 1.91E-07 | |
| 18178 | 18577 | H1.81 | L1 | VH-VL | 2.13E-07 | |
| 18179 | 18578 | H1.82 | L1 | VH-VL | 2.40E-07 | |
| 18180 | 18579 | H1.83 | L1 | VH-VL | Weak | |
| 18181 | 18580 | H1.84 | L1 | VH-VL | 1.03E-07 | 55.5 |
| 18182 | 18581 | H1.85 | L1 | VH-VL | 8.62E-08 | 55.0 |
| 18183 | 18582 | H1.86 | L1 | VH-VL | 8.39E-08 | 55.5 |
| 18184 | 18583 | H1.87 | L1 | VH-VL | 9.43E-08 | 54.0 |

Figure 23C

| Full-length mAb XENP | scFv XENP | VH | VL | scFv orientation | Human PD-1 mAb $K_D$ (M) | scFv $T_m$ (°C) |
|---|---|---|---|---|---|---|
| 18185 | 18584 | H1.88 | L1 | VH-VL | 8.51E-08 | 56.0 |
| 18186 | 18585 | H1.89 | L1 | VH-VL | 8.09E-08 | 54.5 |
| 18187 | 18586 | H1.90 | L1 | VH-VL | 7.54E-08 | 55.0 |
| 18188 | 18587 | H1.91 | L1 | VH-VL | 1.04E-07 | 54.5 |
| 18189 | 18588 | H1.92 | L1 | VH-VL | 1.07E-07 | |
| 18190 | 18589 | H1.93 | L1 | VH-VL | 1.21E-07 | |
| 18191 | 18590 | H1.94 | L1 | VH-VL | 8.46E-08 | |
| 18192 | 18591 | H1.95 | L1 | VH-VL | 9.15E-08 | |
| 18193 | 18592 | H1.96 | L1 | VH-VL | 6.42E-08 | |
| 18194 | 18593 | H1.97 | L1 | VH-VL | 8.23E-08 | |
| 18195 | 18594 | H1.98 | L1 | VH-VL | 2.41E-07 | 56.0 |
| 18196 | 18595 | H1.99 | L1 | VH-VL | 2.10E-07 | 56.5 |
| 18201 | 18596 | H1.100 | L1 | VH-VL | 2.51E-07 | 55.0 |
| 18202 | 18601 | H1.101 | L1 | VH-VL | 2.32E-07 | 58.0 |
| 18203 | 18602 | H1.102 | L1 | VH-VL | 2.15E-07 | 56.0 |
| 18204 | 18603 | H1.103 | L1 | VH-VL | 2.89E-07 | |
| 18205 | 18604 | H1.104 | L1 | VH-VL | 1.98E-07 | 56.0 |
| 18206 | 18605 | H1.105 | L1 | VH-VL | 2.57E-07 | 53.5 |
| 18207 | 18606 | H1.106 | L1 | VH-VL | 1.85E-07 | 54.5 |
| 18208 | 18607 | H1.107 | L1 | VH-VL | 2.33E-07 | 55.5 |
| 18209 | 18608 | H1.108 | L1 | VH-VL | 2.07E-07 | 55.0 |
| 18210 | 18609 | H1.109 | L1 | VH-VL | 2.38E-07 | 54.5 |
| 18211 | 18610 | H1.110 | L1 | VH-VL | 1.78E-07 | 56.0 |
| 18212 | 18611 | H1.111 | L1 | VH-VL | 1.56E-07 | 55.5 |
| 18213 | 18612 | H1.112 | L1 | VH-VL | 1.60E-07 | 55.0 |
| 18214 | 18613 | H1.113 | L1 | VH-VL | 1.65E-07 | 55.0 |
| 18215 | 18614 | H1.114 | L1 | VH-VL | 2.79E-07 | 55.0 |
| 18216 | 18615 | H1.115 | L1 | VH-VL | 1.93E-07 | 55.0 |
| 18217 | 18616 | H1.116 | L1 | VH-VL | 1.80E-07 | 54.0 |
| 18218 | 18617 | H1.117 | L1 | VH-VL | 1.80E-07 | 56.0 |
| 18219 | 18618 | H1.118 | L1 | VH-VL | 2.51E-07 | 55.0 |
| 18220 | 18619 | H1.119 | L1 | VH-VL | 1.57E-07 | 55.5 |
| 18221 | 18620 | H1.120 | L1 | VH-VL | 1.64E-07 | 54.0 |
| 18222 | 18621 | H1.121 | L1 | VH-VL | 1.53E-07 | 53.5 |
| 18223 | 18622 | H1.122 | L1 | VH-VL | 1.67E-07 | 54.5 |
| 18224 | 18623 | H1.123 | L1 | VH-VL | 1.71E-07 | 52.5 |
| 18225 | 18624 | H1.124 | L1 | VH-VL | 1.51E-07 | 53.0 |
| 18226 | 18625 | H1.125 | L1 | VH-VL | 1.88E-07 | 53.0 |
| 18227 | 18626 | H1.126 | L1 | VH-VL | 1.45E-07 | 53.5 |
| 18228 | 18627 | H1.127 | L1 | VH-VL | 1.60E-07 | 52.5 |
| 18229 | 18628 | H1.128 | L1 | VH-VL | 1.51E-07 | 55.0 |
| 18230 | 18629 | H1.129 | L1 | VH-VL | 1.81E-07 | |
| 18231 | 18630 | H1.130 | L1 | VH-VL | 1.41E-07 | 56.0 |
| 18232 | 18631 | H1.131 | L1 | VH-VL | 1.34E-07 | 55.5 |

Figure 23D

| Full-length mAb XENP | scFv XENP | VH | VL | scFv orientation | Human PD-1 mAb $K_D$ (M) | scFv $T_m$ (°C) |
|---|---|---|---|---|---|---|
| 18233 | 18632 | H1.132 | L1 | VH-VL | 1.92E-07 | |
| 18234 | 18633 | H1.133 | L1 | VH-VL | 1.97E-07 | 55.5 |
| 18235 | 18634 | H1.134 | L1 | VH-VL | 2.20E-07 | |
| 18236 | 18635 | H1.135 | L1 | VH-VL | 1.53E-07 | 54.5 |
| 18237 | 18636 | H1.136 | L1 | VH-VL | 2.00E-07 | |
| 18238 | 18637 | H1.137 | L1 | VH-VL | 1.16E-07 | 57.0 |
| 18239 | 18638 | H1.138 | L1 | VH-VL | 1.42E-07 | 55.5 |
| 18240 | 18639 | H1.139 | L1 | VH-VL | 1.62E-07 | 56.5 |
| 18241 | 18640 | H1.140 | L1 | VH-VL | 1.18E-07 | 57.0 |
| 18242 | 18641 | H1.141 | L1 | VH-VL | 1.53E-07 | 55.5 |
| 18243 | 18642 | H1.142 | L1 | VH-VL | 1.70E-07 | 56.5 |
| 18244 | 18643 | H1.143 | L1 | VH-VL | 1.34E-07 | |
| 18245 | 18644 | H1.144 | L1 | VH-VL | 1.50E-07 | 55.0 |
| 18246 | 18645 | H1.145 | L1 | VH-VL | 1.42E-07 | 57.0 |
| 18247 | 18646 | H1.146 | L1 | VH-VL | 1.44E-07 | 54.0 |
| 18248 | 18647 | H1.147 | L1 | VH-VL | 1.28E-07 | 55.0 |
| 18249 | 18648 | H1.148 | L1 | VH-VL | 1.32E-07 | 56.0 |
| 18250 | 18649 | H1.149 | L1 | VH-VL | 1.27E-07 | 54.5 |
| 18251 | 18650 | H1.150 | L1 | VH-VL | 1.23E-07 | 55.5 |
| 18252 | 18651 | H1.151 | L1 | VH-VL | 1.12E-07 | 57.0 |
| 18253 | 18652 | H1.152 | L1 | VH-VL | 8.58E-08 | 56.5 |
| 18254 | 18653 | H1.153 | L1 | VH-VL | 1.66E-07 | 55.5 |
| 18255 | 18654 | H1.154 | L1 | VH-VL | 1.37E-07 | 56.5 |
| 18256 | 18655 | H1.155 | L1 | VH-VL | 9.70E-08 | 56.5 |
| 18257 | 18656 | H1.156 | L1 | VH-VL | 2.80E-07 | |
| 18258 | 18657 | H1.157 | L1 | VH-VL | 1.51E-07 | 57.0 |
| 18259 | 18658 | H1.158 | L1 | VH-VL | 1.32E-07 | 56.5 |
| 18260 | 18659 | H1.159 | L1 | VH-VL | 1.39E-07 | 56.0 |
| 18261 | 18660 | H1.160 | L1 | VH-VL | 1.28E-07 | 57.0 |
| 18262 | 18661 | H1.161 | L1 | VH-VL | 1.53E-07 | 56.5 |
| 18263 | 18662 | H1.162 | L1 | VH-VL | 2.78E-07 | |
| 18264 | 18663 | H1.163 | L1 | VH-VL | 1.07E-07 | 55.5 |
| 18265 | 18664 | H1.164 | L1 | VH-VL | 2.16E-07 | |
| 18266 | 18665 | H1.165 | L1 | VH-VL | Weak | |
| 18267 | 18666 | H1.166 | L1 | VH-VL | 2.43E-07 | |
| 18268 | 18667 | H1.167 | L1 | VH-VL | Weak | |
| 18269 | 18668 | H1.168 | L1 | VH-VL | Weak | |
| 18270 | 18669 | H1.169 | L1 | VH-VL | 7.90E-06 | |
| 18271 | 18670 | H1.170 | L1 | VH-VL | Weak | |
| 18272 | 18671 | H1.171 | L1 | VH-VL | Weak | |
| 18273 | 18672 | H1.172 | L1 | VH-VL | Weak | |
| 18274 | 18673 | H1.173 | L1 | VH-VL | Weak | |
| 18275 | 18674 | H1.174 | L1 | VH-VL | Weak | |
| 18276 | 18675 | H1.175 | L1 | VH-VL | Weak | |

Figure 23E

| Full-length mAb XENP | scFv XENP | VH | VL | scFv orientation | Human PD-1 mAb $K_D$ (M) | scFv $T_m$ (°C) |
|---|---|---|---|---|---|---|
| 18277 | 18676 | H1.176 | L1 | VH-VL | 1.32E-07 | 56.0 |
| 18278 | 18677 | H1.177 | L1 | VH-VL | Weak | |
| 18279 | 18678 | H1.178 | L1 | VH-VL | Weak | |
| 18280 | 18679 | H1.179 | L1 | VH-VL | 3.40E-07 | |
| 18281 | 18680 | H1.180 | L1 | VH-VL | Weak | |
| 18282 | 18681 | H1.181 | L1 | VH-VL | Weak | |
| 18283 | 18682 | H1.182 | L1 | VH-VL | Weak | |
| 18284 | 18683 | H1.183 | L1 | VH-VL | Weak | |
| 18285 | 18684 | H1.184 | L1 | VH-VL | Weak | |
| 18286 | 18685 | H1.185 | L1 | VH-VL | Weak | |
| 18287 | 18686 | H1.186 | L1 | VH-VL | Weak | |
| 18288 | 18687 | H1.187 | L1 | VH-VL | Weak | |
| 18289 | 18688 | H1.188 | L1 | VH-VL | 1.61E-07 | 56.5 |
| 18290 | 18689 | H1.189 | L1 | VH-VL | Weak | |
| 18291 | 18690 | H1.190 | L1 | VH-VL | Weak | |
| 18292 | 18691 | H1.191 | L1 | VH-VL | Weak | |
| 18293 | 18692 | H1.192 | L1 | VH-VL | Weak | |
| 18294 | 18693 | H1.193 | L1 | VH-VL | Weak | |
| 18295 | 18694 | H1.194 | L1 | VH-VL | Weak | |
| 18296 | 18695 | H1.195 | L1 | VH-VL | 5.81E-07 | |
| 18301 | 18696 | H1.196 | L1 | VH-VL | Weak | |
| 18302 | 18701 | H1.197 | L1 | VH-VL | 6.15E-07 | |
| 18303 | 18702 | H1.198 | L1 | VH-VL | Weak | |
| 18304 | 18703 | H1.199 | L1 | VH-VL | Weak | |
| 18305 | 18704 | H1.200 | L1 | VH-VL | 1.77E-07 | |
| 18306 | 18705 | H1.201 | L1 | VH-VL | Weak | |
| 18307 | 18706 | H1.202 | L1 | VH-VL | Weak | |
| 18308 | 18707 | H1.203 | L1 | VH-VL | 3.95E-07 | |
| 18309 | 18708 | H1.204 | L1 | VH-VL | Weak | |
| 18310 | 18709 | H1.205 | L1 | VH-VL | Weak | |
| 18311 | 18710 | H1.206 | L1 | VH-VL | Weak | |
| 18312 | 18711 | H1.207 | L1 | VH-VL | Weak | |
| 18313 | 18712 | H1.208 | L1 | VH-VL | Weak | |
| 18314 | 18713 | H1.209 | L1 | VH-VL | Weak | |
| 18315 | 18714 | H1.210 | L1 | VH-VL | Weak | |
| 18316 | 18715 | H1.211 | L1 | VH-VL | 1.40E-07 | 58.5 |
| 18317 | 18716 | H1.212 | L1 | VH-VL | 1.24E-07 | |
| 18318 | 18717 | H1.213 | L1 | VH-VL | Weak | |
| 18319 | 18718 | H1.214 | L1 | VH-VL | Weak | |
| 18320 | 18719 | H1.215 | L1 | VH-VL | Weak | |
| 18321 | 18720 | H1.216 | L1 | VH-VL | Weak | |
| 18322 | 18721 | H1.217 | L1 | VH-VL | Weak | |
| 18323 | 18722 | H1.218 | L1 | VH-VL | Weak | |
| 18324 | 18723 | H1.219 | L1 | VH-VL | Weak | |

Figure 23F

| Full-length mAb XENP | scFv XENP | VH | VL | scFv orientation | Human PD-1 mAb $K_D$ (M) | scFv $T_m$ (°C) |
|---|---|---|---|---|---|---|
| 18325 | 18724 | H1.220 | L1 | VH-VL | Weak | |
| 18326 | 18725 | H1.221 | L1 | VH-VL | Weak | |
| 18327 | 18726 | H1.222 | L1 | VH-VL | Weak | |
| 18328 | 18727 | H1.223 | L1 | VH-VL | Weak | |
| 18329 | 18728 | H1.224 | L1 | VH-VL | Weak | |
| 18330 | 18729 | H1.225 | L1 | VH-VL | Weak | |
| 18331 | 18730 | H1.226 | L1 | VH-VL | Weak | |
| 18332 | 18731 | H1.227 | L1 | VH-VL | Weak | |
| 18333 | 18732 | H1.228 | L1 | VH-VL | Weak | |
| 18334 | 18733 | H1.229 | L1 | VH-VL | Weak | |
| 18335 | 18734 | H1.230 | L1 | VH-VL | Weak | |
| 18336 | 18735 | H1.231 | L1 | VH-VL | Weak | |
| 18337 | 18736 | H1.232 | L1 | VH-VL | Weak | |
| 18338 | 18737 | H1.233 | L1 | VH-VL | Weak | |
| 18339 | 18738 | H1.234 | L1 | VH-VL | Weak | |
| 18340 | 18739 | H1.235 | L1 | VH-VL | Weak | |
| 18341 | 18740 | H1.236 | L1 | VH-VL | Weak | |
| 18342 | 18741 | H1.237 | L1 | VH-VL | 1.95E-07 | |
| 18343 | 18742 | H1.238 | L1 | VH-VL | 1.16E-07 | 57.0 |
| 18344 | 18743 | H1 | L1.1 | VH-VL | 1.11E-07 | 56.5 |
| 18345 | 18744 | H1 | L1.2 | VH-VL | 1.20E-07 | 54.5 |
| 18346 | 18745 | H1 | L1.3 | VH-VL | 1.07E-07 | 55.0 |
| 18347 | 18746 | H1 | L1.4 | VH-VL | 8.73E-08 | 57.0 |
| 18348 | 18747 | H1 | L1.5 | VH-VL | 1.02E-07 | 56.5 |
| 18349 | 18748 | H1 | L1.6 | VH-VL | 1.12E-07 | 57.0 |
| 18350 | 18749 | H1 | L1.7 | VH-VL | 1.40E-07 | 55.5 |
| 18351 | 18750 | H1 | L1.8 | VH-VL | 1.40E-07 | 56.0 |
| 18352 | 18751 | H1 | L1.9 | VH-VL | 1.24E-07 | 57.0 |
| 18353 | 18752 | H1 | L1.10 | VH-VL | 1.44E-07 | 54.5 |
| 18354 | 18753 | H1 | L1.11 | VH-VL | 1.46E-07 | 56.0 |
| 18355 | 18754 | H1 | L1.12 | VH-VL | 1.39E-07 | 58.0 |
| 18356 | 18755 | H1 | L1.13 | VH-VL | 1.46E-07 | |
| 18357 | 18756 | H1 | L1.14 | VH-VL | 9.95E-08 | 57.5 |
| 18358 | 18757 | H1 | L1.15 | VH-VL | 1.21E-07 | 56.5 |
| 18359 | 18758 | H1 | L1.16 | VH-VL | 2.86E-07 | |
| 18360 | 18759 | H1 | L1.17 | VH-VL | 1.13E-07 | 54.5 |
| 18361 | 18760 | H1 | L1.18 | VH-VL | 2.71E-07 | |
| 18362 | 18761 | H1 | L1.19 | VH-VL | 2.84E-07 | |
| 18363 | 18762 | H1 | L1.20 | VH-VL | 1.75E-07 | |
| 18364 | 18763 | H1 | L1.21 | VH-VL | 1.22E-07 | 58.0 |
| 18365 | 18764 | H1 | L1.22 | VH-VL | 3.33E-07 | |
| 18366 | 18765 | H1 | L1.23 | VH-VL | 8.20E-08 | 59.0 |
| 18367 | 18766 | H1 | L1.24 | VH-VL | 4.46E-07 | |
| 18368 | 18767 | H1 | L1.25 | VH-VL | 4.09E-07 | |

Figure 23G

| Full-length mAb XENP | scFv XENP | VH | VL | scFv orientation | Human PD-1 mAb $K_D$ (M) | scFv $T_m$ (°C) |
|---|---|---|---|---|---|---|
| 18369 | 18768 | H1 | L1.26 | VH-VL | Weak | |
| 18370 | 18769 | H1 | L1.27 | VH-VL | 3.73E-07 | |
| 18371 | 18770 | H1 | L1.28 | VH-VL | 1.22E-07 | |
| 18372 | 18771 | H1 | L1.29 | VH-VL | Weak | |
| 18373 | 18772 | H1 | L1.30 | VH-VL | Weak | |
| 18374 | 18773 | H1 | L1.31 | VH-VL | Weak | |
| 18375 | 18774 | H1 | L1.32 | VH-VL | 7.36E-07 | |
| 18376 | 18775 | H1 | L1.33 | VH-VL | Weak | |
| 18377 | 18776 | H1 | L1.34 | VH-VL | 1.45E-06 | |
| 18378 | 18777 | H1 | L1.35 | VH-VL | 4.28E-07 | |
| 18379 | 18778 | H1 | L1.36 | VH-VL | Weak | |
| 18380 | 18779 | H1 | L1.37 | VH-VL | Weak | |
| 18381 | 18780 | H1 | L1.38 | VH-VL | Weak | |
| 18382 | 18781 | H1 | L1.39 | VH-VL | 5.45E-07 | |
| 18383 | 18782 | H1 | L1.40 | VH-VL | Weak | |
| 18384 | 18783 | H1 | L1.41 | VH-VL | Weak | |
| 18385 | 18784 | H1 | L1.42 | VH-VL | Weak | |
| 18386 | 18785 | H1 | L1.43 | VH-VL | Weak | |
| 18387 | 18786 | H1 | L1.44 | VH-VL | Weak | |
| 18388 | 18787 | H1 | L1.45 | VH-VL | Weak | |
| 18389 | 18788 | H1 | L1.46 | VH-VL | 2.19E-07 | |
| 18390 | 18789 | H1 | L1.47 | VH-VL | 1.06E-07 | 55.0 |
| 18391 | 18790 | H1 | L1.48 | VH-VL | 1.35E-07 | |
| 18392 | 18791 | H1 | L1.49 | VH-VL | 1.49E-07 | |
| 18393 | 18792 | H1 | L1.50 | VH-VL | 1.17E-07 | 57.0 |
| 18394 | 18793 | H1 | L1.51 | VH-VL | 1.09E-07 | 55.5 |
| 18395 | 18794 | H1 | L1.52 | VH-VL | 9.28E-08 | 54.0 |
| 18396 | 18795 | H1 | L1.53 | VH-VL | 1.46E-07 | |
| 18401 | 18796 | H1 | L1.54 | VH-VL | 4.49E-07 | |
| 18402 | 18801 | H1 | L1.55 | VH-VL | Weak | |
| 18403 | 18802 | H1 | L1.56 | VH-VL | Weak | |
| 18404 | 18803 | H1 | L1.57 | VH-VL | Weak | |
| 18405 | 18804 | H1 | L1.58 | VH-VL | Weak | |
| 18406 | 18805 | H1 | L1.59 | VH-VL | Weak | |
| 18407 | 18806 | H1 | L1.60 | VH-VL | Weak | |
| 18408 | 18807 | H1 | L1.61 | VH-VL | Weak | |
| 18409 | 18808 | H1 | L1.62 | VH-VL | Weak | |
| 18410 | 18809 | H1 | L1.63 | VH-VL | Weak | |
| 18411 | 18810 | H1 | L1.64 | VH-VL | 1.79E-07 | |
| 18412 | 18811 | H1 | L1.65 | VH-VL | 2.91E-07 | |
| 18413 | 18812 | H1 | L1.66 | VH-VL | 3.29E-07 | |
| 18414 | 18813 | H1 | L1.67 | VH-VL | 1.46E-07 | 54.0 |
| 18415 | 18814 | H1 | L1.68 | VH-VL | 1.60E-07 | |
| 18416 | 18815 | H1 | L1.69 | VH-VL | Weak | |

Figure 23H

| Full-length mAb XENP | scFv XENP | VH | VL | scFv orientation | Human PD-1 mAb $K_D$ (M) | scFv $T_m$ (°C) |
|---|---|---|---|---|---|---|
| 18417 | 18816 | H1 | L1.70 | VH-VL | 1.34E-07 | |
| 18418 | 18817 | H1 | L1.71 | VH-VL | 3.71E-07 | |
| 18419 | 18818 | H1 | L1.72 | VH-VL | 6.40E-07 | |
| 18420 | 18819 | H1 | L1.73 | VH-VL | 1.52E-07 | |
| 18421 | 18820 | H1 | L1.74 | VH-VL | 1.75E-07 | |
| 18422 | 18821 | H1 | L1.75 | VH-VL | 1.78E-07 | |
| 18423 | 18822 | H1 | L1.76 | VH-VL | 1.33E-07 | 56.5 |
| 18424 | 18823 | H1 | L1.77 | VH-VL | 3.78E-07 | |
| 18425 | 18824 | H1 | L1.78 | VH-VL | Weak | |
| 18426 | 18825 | H1 | L1.79 | VH-VL | Weak | |
| 18427 | 18826 | H1 | L1.80 | VH-VL | Weak | |
| 18428 | 18827 | H1 | L1.81 | VH-VL | 2.54E-07 | |
| 18429 | 18828 | H1 | L1.82 | VH-VL | 7.67E-08 | |
| 18430 | 18829 | H1 | L1.83 | VH-VL | 1.07E-05 | |
| 18431 | 18830 | H1 | L1.84 | VH-VL | 5.39E-07 | |
| 18432 | 18831 | H1 | L1.85 | VH-VL | 1.56E-07 | |
| 18433 | 18832 | H1 | L1.86 | VH-VL | 1.24E-07 | 55.5 |
| 18434 | 18833 | H1 | L1.87 | VH-VL | 2.51E-07 | |
| 18435 | 18834 | H1 | L1.88 | VH-VL | 1.40E-07 | 56.0 |
| 18436 | 18835 | H1 | L1.89 | VH-VL | 6.50E-07 | |
| 18437 | 18836 | H1 | L1.90 | VH-VL | 1.22E-06 | |
| 18438 | 18837 | H1 | L1.91 | VH-VL | 1.79E-07 | |
| 18439 | 18838 | H1 | L1.92 | VH-VL | 4.04E-07 | |
| 18440 | 18839 | H1 | L1.93 | VH-VL | 7.76E-07 | |
| 18441 | 18840 | H1 | L1.94 | VH-VL | 8.48E-08 | 53.0 |
| 18442 | 18841 | H1 | L1.95 | VH-VL | 1.23E-07 | 54.5 |
| 18443 | 18842 | H1 | L1.96 | VH-VL | 1.30E-07 | 55.5 |
| 18444 | 18843 | H1 | L1.97 | VH-VL | 1.06E-07 | 56.5 |
| 18445 | 18844 | H1 | L1.98 | VH-VL | 1.84E-07 | |
| 18446 | 18845 | H1 | L1.99 | VH-VL | 1.48E-06 | |
| 18447 | 18846 | H1 | L1.100 | VH-VL | 9.17E-08 | 55.5 |
| 18448 | 18847 | H1 | L1.101 | VH-VL | 1.35E-07 | |
| 18449 | 18848 | H1 | L1.102 | VH-VL | 1.06E-07 | 55.0 |
| 18450 | 18849 | H1 | L1.103 | VH-VL | 9.46E-08 | 60.0 |
| 18451 | 18850 | H1 | L1.104 | VH-VL | 1.08E-07 | 57.0 |
| 18452 | 18851 | H1 | L1.105 | VH-VL | 1.02E-07 | 55.0 |
| 18453 | 18852 | H1 | L1.106 | VH-VL | 1.01E-07 | 57.5 |
| 18454 | 18853 | H1 | L1.107 | VH-VL | Weak | |
| 18455 | 18854 | H1 | L1.108 | VH-VL | Weak | |
| 18456 | 18855 | H1 | L1.109 | VH-VL | Weak | |
| 18457 | 18856 | H1 | L1.110 | VH-VL | Weak | |
| 18458 | 18857 | H1 | L1.111 | VH-VL | Weak | |
| 18459 | 18858 | H1 | L1.112 | VH-VL | 1.92E-07 | |
| 18460 | 18859 | H1 | L1.113 | VH-VL | Weak | |

Figure 23I

| Full-length mAb XENP | scFv XENP | VH | VL | scFv orientation | Human PD-1 mAb $K_D$ (M) | scFv $T_m$ (°C) |
|---|---|---|---|---|---|---|
| 18461 | 18860 | H1 | L1.114 | VH-VL | 2.87E-07 | |
| 18462 | 18861 | H1 | L1.115 | VH-VL | Weak | |
| 18463 | 18862 | H1 | L1.116 | VH-VL | 5.60E-08 | 55.5 |
| 18464 | 18863 | H1 | L1.117 | VH-VL | 1.58E-07 | 58.0 |
| 18465 | 18864 | H1 | L1.118 | VH-VL | 7.90E-08 | 51.00, 58.00 |
| 18466 | 18865 | H1 | L1.119 | VH-VL | 4.88E-08 | 54.0 |
| 18467 | 18866 | H1 | L1.120 | VH-VL | 7.74E-08 | 50.50, 57.00 |
| 18468 | 18867 | H1 | L1.121 | VH-VL | 1.08E-07 | 54.5 |
| 18469 | 18868 | H1 | L1.122 | VH-VL | 9.36E-08 | 51.0 |
| 18470 | 18869 | H1 | L1.123 | VH-VL | 1.32E-07 | 49.00, 59.00 |
| 18471 | 18870 | H1 | L1.124 | VH-VL | 8.70E-08 | 53.5 |
| 18472 | 18871 | H1 | L1.125 | VH-VL | 1.06E-07 | 53.0 |
| 18473 | 18872 | H1 | L1.126 | VH-VL | 7.34E-08 | 51.0 |
| 18474 | 18873 | H1 | L1.127 | VH-VL | 1.10E-07 | 55.5 |
| 18475 | 18874 | H1 | L1.128 | VH-VL | 1.07E-07 | 57.0 |
| 18476 | 18875 | H1 | L1.129 | VH-VL | 1.00E-07 | 57.0 |
| 18477 | 18876 | H1 | L1.130 | VH-VL | 1.18E-07 | 54.5 |
| 18478 | 18877 | H1 | L1.131 | VH-VL | 1.96E-07 | 55.5 |
| 18479 | 18878 | H1 | L1.132 | VH-VL | 1.51E-07 | 55.0 |
| 18480 | 18879 | H1 | L1.133 | VH-VL | 1.32E-07 | 54.0 |
| 18481 | 18880 | H1 | L1.134 | VH-VL | 1.97E-07 | 57.0 |
| 18482 | 18881 | H1 | L1.135 | VH-VL | 1.56E-07 | 54.5 |
| 18483 | 18882 | H1 | L1.136 | VH-VL | 2.41E-07 | 56.5 |
| 18484 | 18883 | H1 | L1.137 | VH-VL | 1.87E-07 | 56.0 |
| 18485 | 18884 | H1 | L1.138 | VH-VL | 2.05E-07 | 56.0 |
| 18486 | 18885 | H1 | L1.139 | VH-VL | 1.76E-07 | 54.0 |
| 18487 | 18886 | H1 | L1.140 | VH-VL | 2.52E-07 | |
| 18488 | 18887 | H1 | L1.141 | VH-VL | 2.05E-07 | 57.0 |
| 18489 | 18888 | H1 | L1.142 | VH-VL | 1.09E-07 | 54.0 |
| 18490 | 18889 | H1 | L1.143 | VH-VL | 2.36E-07 | |
| 18491 | 18890 | H1 | L1.144 | VH-VL | 1.83E-07 | 57.0 |
| 18492 | 18891 | H1 | L1.145 | VH-VL | 1.63E-07 | 54.0 |
| 18892 | 18895 | H0 | L0 | VH-VL | 1.24E-07 | 62.0 |
| N/A | 18896 (rvs scFv) | H1 | L1 | VL-VH | | 58.5 |
| N/A | 18921 | H1 | L3 | VH-VL | | 55.0 |
| N/A | 18922 | H1 | L4 | VH-VL | | 57.0 |
| N/A | 18923 | H1 | L5 | VH-VL | | 60.0 |
| N/A | 18924 | H2 | L1 | VH-VL | | |
| N/A | 18925 | H2 | L2 | VH-VL | | |
| N/A | 18926 | H2 | L3 | VH-VL | | |
| N/A | 18927 | H2 | L4 | VH-VL | | |
| N/A | 18928 | H2 | L5 | VH-VL | | |
| N/A | 18929 | H3 | L1 | VH-VL | | |
| N/A | 18930 | H3 | L2 | VH-VL | | |

Figure 23J

| Full-length mAb XENP | scFv XENP | VH | VL | scFv orientation | Human PD-1 mAb K$_D$ (M) | scFv T$_m$ (°C) |
|---|---|---|---|---|---|---|
| N/A | 18931 | H3 | L3 | VH-VL | | |
| N/A | 18932 | H3 | L4 | VH-VL | | |
| N/A | 18933 | H3 | L5 | VH-VL | | |
| N/A | 18934 | H4 | L1 | VH-VL | | |
| N/A | 18935 | H4 | L2 | VH-VL | | |
| N/A | 18936 | H4 | L3 | VH-VL | | |
| N/A | 18937 | H4 | L4 | VH-VL | | |
| N/A | 18938 | H4 | L5 | VH-VL | | |
| 18910 | N/A | H1.90 | L1.119 | VH-VL | 1.254E-08 | |
| 18911 | N/A | H1.90 | L1.23 | VH-VL | 2.278E-08 | |
| 18912 | N/A | H1.90 | L1.67 | VH-VL | 3.224E-08 | |
| 18913 | N/A | H1.90 | L1.94 | VH-VL | 2.27E-08 | |
| 18914 | N/A | H1.90 | L1.116 | VH-VL | 1.634E-08 | |
| 18915 | N/A | H1.155 | L1.119 | VH-VL | 1.971E-08 | |
| 18980 | 19064 | H1.239 | L1 | VH-VL | | 56.5 |
| 18981 | 19065 | H1.240 | L1 | VH-VL | | 56.5 |
| 18982 | 19066 | H1.241 | L1 | VH-VL | | 57.0 |
| 18983 | 19067 | H1.242 | L1 | VH-VL | | 56.5 |
| 18984 | 19068 | H1.243 | L1 | VH-VL | | 55.0 |
| 18985 | 19069 | H1.244 | L1 | VH-VL | | 55.5 |
| 18986 | 19070 | H1.245 | L1 | VH-VL | | 56.0 |
| 18987 | 19071 | H1.246 | L1 | VH-VL | | 54.0 |
| 18988 | 19072 | H1.247 | L1 | VH-VL | | 56.5 |
| 18989 | 19073 | H1.248 | L1 | VH-VL | | 55.0 |
| 18990 | 19074 | H1.249 | L1 | VH-VL | | 54.0 |
| 18991 | 19075 | H1.250 | L1 | VH-VL | | 56.0 |
| 18992 | 19076 | H1.251 | L1 | VH-VL | 6.054E-08 | 57.0 |
| 18993 | 19077 | H1.252 | L1 | VH-VL | | 56.5 |
| 18994 | 19078 | H1.253 | L1 | VH-VL | | 55.0 |
| 18995 | 19079 | H1.254 | L1 | VH-VL | | 56.5 |
| 18996 | 19080 | H1.255 | L1 | VH-VL | | |
| 19001 | 19081 | H1.256 | L1 | VH-VL | | 56.0 |
| 19002 | 19082 | H1.257 | L1 | VH-VL | 5.607E-08 | 58.0 |
| 19003 | 19083 | H1.258 | L1 | VH-VL | | 56.0 |
| 19004 | 19084 | H1.259 | L1 | VH-VL | | |
| 19005 | 19085 | H1.260 | L1 | VH-VL | | |
| 19006 | 19086 | H1.261 | L1 | VH-VL | 7.064E-08 | 57.0 |
| 19007 | 19087 | H1.262 | L1 | VH-VL | 6.263E-08 | 57.0 |
| 19008 | 19088 | H1.263 | L1 | VH-VL | | 50.0 |
| 19009 | 19089 | H1.264 | L1 | VH-VL | | 52.0 |
| 19010 | 19090 | H1.265 | L1 | VH-VL | | 56.0 |
| 19011 | 19091 | H1.266 | L1 | VH-VL | | 55.0 |
| 19012 | 19092 | H1.267 | L1 | VH-VL | | |
| 19013 | 19093 | H1.268 | L1 | VH-VL | | 56.5 |

Figure 23K

| Full-length mAb XENP | scFv XENP | VH | VL | scFv orientation | Human PD-1 mAb K$_D$ (M) | scFv T$_m$ (°C) |
|---|---|---|---|---|---|---|
| 19014 | 19094 | H1.269 | L1 | VH-VL | | 54.5 |
| 19015 | 19095 | H1.270 | L1 | VH-VL | | 52.0 |
| 19016 | 19096 | H1.271 | L1 | VH-VL | 2.267E-08 | 55.5 |
| 19017 | 19101 | H1.272 | L1 | VH-VL | | 55.5 |
| 19018 | 19102 | H1.273 | L1 | VH-VL | | 52.0 |
| 19019 | 19103 | H1.274 | L1 | VH-VL | | 56.5 |
| 19020 | 19104 | H1.275 | L1 | VH-VL | | 50.0 |
| 19021 | 19105 | H1.276 | L1 | VH-VL | | |
| 19022 | 19106 | H1.277 | L1 | VH-VL | | 58.0 |
| 19023 | 19107 | H1 | L1.146 | VH-VL | 6.46E-08 | 57.0 |
| 19024 | 19108 | H1 | L1.147 | VH-VL | | 54.5 |
| 19025 | 19109 | H1 | L1.148 | VH-VL | 6.665E-08 | 58.0 |
| 19026 | 19110 | H1 | L1.149 | VH-VL | | 55.5 |
| 19027 | 19111 | H1 | L1.150 | VH-VL | 7.238E-08 | 57.5 |
| 19028 | 19112 | H1 | L1.151 | VH-VL | | |
| 19029 | 19113 | H1 | L1.152 | VH-VL | | 56.0 |
| 19030 | 19114 | H1 | L1.153 | VH-VL | | 55.0 |
| 19031 | 19115 | H1 | L1.154 | VH-VL | | 54.5 |
| 19032 | 19116 | H1 | L1.155 | VH-VL | | 55.5 |
| 19033 | 19117 | H1 | L1.156 | VH-VL | | 56.5 |
| 19034 | 19118 | H1 | L1.157 | VH-VL | | 56.0 |
| 19035 | 19119 | H1 | L1.158 | VH-VL | 9.671E-08 | 58.0 |
| 19036 | 19120 | H1 | L1.159 | VH-VL | | 52.0 |
| 19037 | 19121 | H1 | L1.160 | VH-VL | | |
| 19038 | 19122 | H1 | L1.161 | VH-VL | | 47.5 |
| 19039 | 19123 | H1 | L1.162 | VH-VL | | |
| 19040 | 19124 | H1 | L1.163 | VH-VL | | 55.5 |
| 19041 | 19125 | H1 | L1.164 | VH-VL | | 56.0 |
| 19042 | 19126 | H1 | L1.165 | VH-VL | | 58.5 |
| 19043 | 19127 | H1 | L1.166 | VH-VL | | 49.0 |
| 19044 | 19128 | H1 | L1.167 | VH-VL | | 53.0 |
| 19045 | 19129 | H1 | L1.168 | VH-VL | | 54.0 |
| 19046 | 19130 | H1 | L1.169 | VH-VL | | 67.0 |
| 19047 | 19131 | H1 | L1.170 | VH-VL | | 65.5 |
| 19048 | 19132 | H1 | L1.171 | VH-VL | | 51.5 |
| 19049 | 19133 | H1 | L1.172 | VH-VL | | 53.0 |
| 19050 | 19134 | H1 | L1.173 | VH-VL | | 54.5 |
| 19051 | 19135 | H1 | L1.174 | VH-VL | | 53.5 |
| 19052 | 19136 | H1 | L1.175 | VH-VL | | 54.0 |
| 19053 | 19137 | H1 | L1.176 | VH-VL | | 54.0 |
| 19054 | 19138 | H1 | L1.177 | VH-VL | | 56.0 |
| 19055 | 19139 | H1 | L1.178 | VH-VL | | 52.5 |
| 19056 | 19140 | H1 | L1.179 | VH-VL | | |
| 19057 | 19141 | H1 | L1.180 | VH-VL | | |

Figure 23L

| Full-length mAb XENP | scFv XENP | VH | VL | scFv orientation | Human PD-1 mAb K_D (M) | scFv T_m (°C) |
|---|---|---|---|---|---|---|
| 19058 | 19142 | H1 | L1.181 | VH-VL | | |
| 19059 | 19143 | H1 | L1.182 | VH-VL | | 52.0 |
| 19060 | 19144 | H1 | L1.183 | VH-VL | | 53.5 |
| 19061 | 19145 | H1 | L1.184 | VH-VL | | |
| 19062 | 19146 | H1 | L1.185 | VH-VL | | 55.5 |
| 19063 | 19147 | H1 | L1.186 | VH-VL | | 54.0 |
| N/A | 19148 | H1.257 | L1.152 | VH-VL | | 57.5 |
| N/A | 19149 | H1.257 | L1.151 | VH-VL | | 55.5 |
| N/A | 19150 | H1.139 | L1.134 | VH-VL | | 57.5 |
| N/A | 19151 | H1.48 | L1.187 | VH-VL | | 53.5 |
| N/A | 19152 | H1.48 | L1.151 | VH-VL | | 52.5 |
| N/A | 19153 | H1.43 | L1.159 | VH-VL | | 50.0 |
| N/A | 19154 | H1.90 | L1.119 | VH-VL | | 53.0 |
| N/A | 19155 | H1.90 | L1.23 | VH-VL | | 57.5 |
| N/A | 19156 | H1.90 | L1.67 | VH-VL | | 53.0 |
| N/A | 19157 | H1.90 | L1.94 | VH-VL | | 52.0 |
| N/A | 19158 | H1.90 | L1.116 | VH-VL | | 54.5 |
| N/A | 19159 | H1.155 | L1.119 | VH-VL | | 54.5 |
| 19160 | N/A | H1.269 | L1.116 | VH-VL | | |
| 19161 | N/A | H1.271 | L1.116 | VH-VL | 1.233E-08 | |
| 19162 | N/A | H1.272 | L1.116 | VH-VL | | |
| 19163 | N/A | H1.90 | L1.177 | VH-VL | | |
| 19164 | N/A | H1.269 | L1.177 | VH-VL | | |
| 19165 | N/A | H1.271 | L1.177 | VH-VL | 4.682E-09 | |
| 19166 | N/A | H1.272 | L1.177 | VH-VL | 6.386E-09 | |
| 19167 | N/A | H1.90 | L1.175 | VH-VL | | |
| 19168 | N/A | H1.269 | L1.175 | VH-VL | | |
| 19169 | N/A | H1.271 | L1.175 | VH-VL | | |
| 19170 | N/A | H1.272 | L1.175 | VH-VL | | |
| 19172 | 19182 | H1 | L1.190 | VH-VL | 2.577E-08 | 58.5 |
| 19173 | 19183 | H1 | L1.191 | VH-VL | | 57.0 |
| 19174 | N/A | H1.90 | L1.190 | VH-VL | 1.103E-08 | |
| 19175 | N/A | H1.90 | L1.191 | VH-VL | | |
| 19176 | N/A | H1.269 | L1.190 | VH-VL | | |
| 19177 | N/A | H1.271 | L1.190 | VH-VL | 8.287E-09 | |
| 19178 | N/A | H1.272 | L1.190 | VH-VL | 7.09E-09 | |
| 19179 | N/A | H1.269 | L1.191 | VH-VL | | |
| 19180 | N/A | H1.271 | L1.191 | VH-VL | | |
| 19181 | N/A | H1.272 | L1.191 | VH-VL | | |
| 19193 | 19203 | H1 | L1.188 | VH-VL | 2.596E-08 | |
| 19194 | 19204 | H1 | L1.189 | VH-VL | 1.366E-08 | 64.0 |
| 19195 | 19205 | H1.278 | L1.188 | VH-VL | 6.689E-09 | 66.0 |
| 19196 | 19206 | H1.278 | L1.189 | VH-VL | 4.683E-09 | 67.5 |
| 19201 | 19202 | H1.278 | L1 | VH-VL | 1.861E-08 | 60.0 |

Figure 23M

| Full-length mAb XENP | scFv XENP | VH | VL | scFv orientation | Human PD-1 mAb K$_D$ (M) | scFv T$_m$ (°C) |
|---|---|---|---|---|---|---|
| N/A | 19207 | H1.278 | L1.188 | VH-VL | | 68.0 |
| N/A | 19208 | H1.278 | L1.189 | VH-VL | | 69.5 |
| 19589 | 19618 | H1.279 | L1.189 | VH-VL | 1.254E-08 | 68.5 |
| 19590 | 19619 | H1.280 | L1.189 | VH-VL | 5.393E-09 | 69.0 |
| 19591 | 19620 | H1.281 | L1.189 | VH-VL | | 68.0 |
| 19592 | 19621 | H1.282 | L1.189 | VH-VL | 1.291E-08 | 68.5 |
| 19593 | 19622 | H1.283 | L1.189 | VH-VL | 7.859E-09 | 69.0 |
| 19594 | 19623 | H1.284 | L1.189 | VH-VL | | 70.5 |
| 19595 | 19624 | H1.285 | L1.189 | VH-VL | | 70.0 |
| 19596 | 19625 | H1.286 | L1.189 | VH-VL | 1.41E-08 | 69.5 |
| 19601 | 19626 | H1.278 | L1.192 | VH-VL | 6.268E-09 | 67.5 |
| 19602 | 19627 | H1.278 | L1.193 | VH-VL | 1.37E-08 | 69.5 |
| 19603 | 19628 | H1.278 | L1.194 | VH-VL | 7.5E-09 | 69.0 |
| 19604 | 19629 | H1.278 | L1.195 | VH-VL | | 69.5 |
| 19605 | 19630 | H1.278 | L1.196 | VH-VL | 4.443E-08 | 71.0 |
| 19606 | 19631 | H1.278 | L1.197 | VH-VL | 2.079E-08 | 69.5 |
| 19607 | 19632 | H1.278 | L1.198 | VH-VL | | 67.5 |
| 19608 | 19633 | H1.278 | L1.199 | VH-VL | | 67.5 |
| 19609 | 19634 | H1.278 | L1.200 | VH-VL | | 67.5 |
| 19610 | 19635 | H1.278 | L1.201 | VH-VL | | 67.5 |
| 19611 | 19636 | H1.278 | L1.202 | VH-VL | | 67.5 |
| 19612 | 19637 | H1.278 | L1.203 | VH-VL | | 67.5 |
| 19613 | 19638 | H1.278 | L1.204 | VH-VL | | 67.0 |
| 19614 | 19639 | H1.278 | L1.205 | VH-VL | 1.266E-08 | 68.0 |
| 19615 | 19640 | H1.278 | L1.206 | VH-VL | | 69.0 |
| 19616 | 19641 | H1.278 | L1.207 | VH-VL | | 68.5 |
| 19617 | 19642 | H1.278 | L1.208 | VH-VL | | 68.5 |
| N/A | 19643 | H1.279 | L1.189 | VL-VH | | 71.5 |
| N/A | 19644 | H1.280 | L1.189 | VL-VH | | 70.5 |
| N/A | 19645 | H1.281 | L1.189 | VL-VH | | 69.5 |
| N/A | 19646 | H1.282 | L1.189 | VL-VH | | 70.0 |
| N/A | 19647 | H1.283 | L1.189 | VL-VH | | 70.5 |
| N/A | 19648 | H1.284 | L1.189 | VL-VH | | 70.5 |
| N/A | 19649 | H1.285 | L1.189 | VL-VH | | 71.5 |
| N/A | 19650 | H1.278 | L1.192 | VL-VH | | 69.0 |
| N/A | 19651 | H1.278 | L1.193 | VL-VH | | 71.5 |
| N/A | 19652 | H1.278 | L1.194 | VL-VH | | 71.5 |
| N/A | 19653 | H1.278 | L1.195 | VL-VH | | 71.5 |
| N/A | 19654 | H1.278 | L1.196 | VL-VH | | 64.0 |
| N/A | 19655 | H1.278 | L1.197 | VL-VH | | 72.0 |
| N/A | 19664 | H1.287 | L1.209 | VH-VL | | 70.5 |
| N/A | 19665 | H1.287 | L1.209 | VL-VH | | 72.0 |
| N/A | 19666 | H1.284 | L1.194 | VH-VL | | 70.5 |
| N/A | 19667 | H1.284 | L1.194 | VL-VH | | 72.5 |

Figure 23N

| Full-length mAb XENP | scFv XENP | VH | VL | scFv orientation | Human PD-1 mAb $K_D$ (M) | scFv $T_m$ (°C) |
|---|---|---|---|---|---|---|
| N/A | 19668 | H1.288 | L1.210 | VH-VL | | 72.5 |
| N/A | 19669 | H1.288 | L1.210 | VL-VH | | 72.0 |
| 19678 | N/A | H1.279 | L1.192 | VH-VL | | |
| 19679 | N/A | H1.280 | L1.192 | VH-VL | | |
| 19680 | N/A | H1.281 | L1.192 | VH-VL | | |
| 19681 | N/A | H1.282 | L1.192 | VH-VL | | |
| 19682 | N/A | H1.279 | L1.193 | VH-VL | | |
| 19683 | N/A | H1.280 | L1.193 | VH-VL | | |
| 19684 | N/A | H1.281 | L1.193 | VH-VL | | |
| 19685 | N/A | H1.282 | L1.193 | VH-VL | | |
| 19686 | 19690 | H1.279 | L1.194 | VH-VL | 7.268E-09 | 70.0 |
| 19687 | N/A | H1.280 | L1.194 | VH-VL | | |
| 19688 | N/A | H1.281 | L1.194 | VH-VL | | |
| 19689 | 19691 | H1.282 | L1.194 | VH-VL | 1.212E-08 | 70.5 |
| N/A | 19692 | H1.279 | L1.194 | VL-VH | | 71.5 |
| N/A | 19693 | H1.282 | L1.194 | VL-VH | | 71.5 |
| N/A | 21215 | H1.280 | L1.224 | VH-VL | | 65.0 |
| N/A | 21216 | H1.280 | L1.224 | VL-VH | | 66.5 |

Figure 24A

| Fab XENP | scFv XENP | VH | VL | Human CTLA-4 Fab K$_D$ (M) | Cyno CTLA-4 Fab K$_D$ (M) | Fab T$_m$ (°C) | scFv T$_m$ (°C) | VH 9-mers | Δ VH 9-mers | VL 9-mers | Δ VL 9-mers |
|---|---|---|---|---|---|---|---|---|---|---|---|
| 9950 | 19533 | H0 | L0 | 5.61E-09 | 3.29E-08 | 75.8 | 63.9 | 65 | 0 | 82 | 0 |
| 19211 | 19745 | H0.1 | L0 | 6.33E-09 | n.t. | 75.5 | 64 | 65 | 0 | 82 | 0 |
| 19212 | 19746 | H0.2 | L0 | 5.60E-09 | n.t. | 74.8 | 63 | 61 | -4 | 82 | 0 |
| 19213 | 19747 | H0.3 | L0 | 6.39E-09 | n.t. | 75 | 63.5 | 65 | 0 | 82 | 0 |
| 19214 | 19748 | H0.4 | L0 | 6.49E-09 | n.t. | 71.5 | 58 | 56 | -9 | 82 | 0 |
| 19215 | 19749 | H0.5 | L0 | 1.09E-08 | n.t. | 74.5 | n.t. | 52 | -13 | 82 | 0 |
| 19216 | 19750 | H0.6 | L0 | 6.60E-09 | n.t. | 76 | 63.5 | 56 | -9 | 82 | 0 |
| 19217 | 19751 | H0.7 | L0 | 1.55E-08 | n.t. | 75.5 | n.t. | 56 | -9 | 82 | 0 |
| 19218 | 19752 | H0.8 | L0 | 6.94E-09 | n.t. | 78 | 66 | 65 | 0 | 82 | 0 |
| 19219 | 19753 | H0.9 | L0 | 6.20E-09 | n.t. | 75.5 | 65.5 | 56 | -9 | 82 | 0 |
| 19220 | 19754 | H0.10 | L0 | 3.25E-08 | n.t. | n.t. | n.t. | 59 | -6 | 82 | 0 |
| 19221 | 19755 | H0.11 | L0 | 4.12E-08 | n.t. | n.t. | n.t. | 64 | -1 | 82 | 0 |
| 19222 | 19756 | H0.12 | L0 | 1.08E-08 | n.t. | 76 | 64.5 | 63 | -2 | 82 | 0 |
| 19223 | 19757 | H0.13 | L0 | 7.05E-08 | n.t. | n.t. | n.t. | 65 | 0 | 82 | 0 |
| 19224 | 19758 | H0.14 | L0 | 4.24E-08 | n.t. | n.t. | n.t. | 64 | -1 | 82 | 0 |
| 19225 | 19759 | H0.15 | L0 | 5.00E-07 | n.t. | n.t. | n.t. | 64 | -1 | 82 | 0 |
| 19226 | 19760 | H0.16 | L0 | 1.29E-08 | n.t. | 76.5 | 65 | 63 | -2 | 82 | 0 |
| 19227 | 19761 | H0.17 | L0 | 6.59E-08 | n.t. | n.t. | n.t. | 63 | -2 | 82 | 0 |
| 19228 | 19762 | H0.18 | L0 | 5.00E-07 | n.t. | n.t. | n.t. | 64 | -1 | 82 | 0 |
| 19229 | 19763 | H0.19 | L0 | 7.02E-09 | n.t. | 74 | 61.5 | 64 | -1 | 82 | 0 |
| 19230 | 19764 | H0.20 | L0 | 1.19E-08 | n.t. | 75.5 | n.t. | 64 | -1 | 82 | 0 |
| 19231 | 19765 | H0.21 | L0 | 5.00E-07 | n.t. | n.t. | n.t. | 64 | -1 | 82 | 0 |
| 19232 | 19766 | H0.22 | L0 | 4.09E-08 | n.t. | n.t. | n.t. | 64 | -1 | 82 | 0 |
| 19233 | 19767 | H0.23 | L0 | 5.00E-07 | n.t. | n.t. | n.t. | 64 | -1 | 82 | 0 |
| 19234 | 19768 | H0.24 | L0 | 1.13E-07 | n.t. | n.t. | n.t. | 64 | -1 | 82 | 0 |
| 19235 | 19769 | H0.25 | L0 | 5.97E-08 | n.t. | n.t. | n.t. | 74 | 9 | 82 | 0 |
| 19236 | 19770 | H0.26 | L0 | 5.70E-08 | n.t. | n.t. | n.t. | 74 | 9 | 82 | 0 |
| 19237 | 19771 | H0.27 | L0 | 6.54E-08 | n.t. | n.t. | n.t. | 68 | 3 | 82 | 0 |
| 19238 | 19772 | H0.28 | L0 | 4.33E-08 | n.t. | n.t. | n.t. | 65 | 0 | 82 | 0 |
| 19239 | 19773 | H0.29 | L0 | 5.00E-07 | n.t. | n.t. | n.t. | 68 | 3 | 82 | 0 |
| 19240 | 19774 | H0.30 | L0 | 5.00E-07 | n.t. | n.t. | n.t. | 65 | 0 | 82 | 0 |
| 19241 | 19775 | H0.31 | L0 | 5.00E-07 | n.t. | n.t. | n.t. | 63 | -2 | 82 | 0 |
| 19242 | 19776 | H0.32 | L0 | 2.87E-08 | n.t. | n.t. | n.t. | 65 | 0 | 82 | 0 |
| 19243 | 19777 | H0.33 | L0 | 5.00E-07 | n.t. | n.t. | n.t. | 65 | 0 | 82 | 0 |
| 19244 | 19778 | H0.34 | L0 | 5.00E-07 | n.t. | n.t. | n.t. | 63 | -2 | 82 | 0 |
| 19245 | 19779 | H0.35 | L0 | 2.31E-08 | n.t. | n.t. | n.t. | 63 | -2 | 82 | 0 |
| 19246 | 19780 | H0.36 | L0 | 4.92E-09 | n.t. | 74 | 62.5 | 61 | -4 | 82 | 0 |
| 19247 | 19781 | H0.37 | L0 | 5.53E-08 | n.t. | n.t. | n.t. | 60 | -5 | 82 | 0 |
| 19248 | 19782 | H0.38 | L0 | 3.63E-08 | n.t. | n.t. | n.t. | 66 | 1 | 82 | 0 |
| 19249 | 19783 | H0.39 | L0 | 2.64E-08 | n.t. | n.t. | n.t. | 68 | 3 | 82 | 0 |
| 19250 | 19784 | H0.40 | L0 | 2.80E-09 | n.t. | 61.5 | 66.5 | 66 | 1 | 82 | 0 |
| 19251 | 19785 | H0.41 | L0 | 1.55E-08 | n.t. | 63 | n.t. | 65 | 0 | 82 | 0 |
| 19252 | 19786 | H0.42 | L0 | 4.66E-08 | n.t. | n.t. | n.t. | 65 | 0 | 82 | 0 |
| 19253 | 19787 | H0.43 | L0 | 4.42E-08 | n.t. | n.t. | n.t. | 65 | 0 | 82 | 0 |
| 19254 | 19788 | H0.44 | L0 | 5.00E-07 | n.t. | n.t. | n.t. | 65 | 0 | 82 | 0 |
| 19255 | 19789 | H0.45 | L0 | 1.40E-08 | n.t. | 71 | n.t. | 65 | 0 | 82 | 0 |
| 19256 | 19790 | H0.46 | L0 | 5.00E-07 | n.t. | n.t. | n.t. | 65 | 0 | 82 | 0 |
| 19257 | 19791 | H0.47 | L0 | 5.00E-07 | n.t. | n.t. | n.t. | 65 | 0 | 82 | 0 |
| 19258 | 19792 | H0.48 | L0 | 5.01E-08 | n.t. | n.t. | n.t. | 65 | 0 | 82 | 0 |

Figure 24B

| Fab XENP | scFv XENP | VH | VL | Human CTLA-4 Fab K$_D$ (M) | Cyno CTLA-4 Fab K$_D$ (M) | Fab T$_m$ (°C) | scFv T$_m$ (°C) | VH 9-mers | Δ VH 9-mers | VL 9-mers | Δ VL 9-mers |
|---|---|---|---|---|---|---|---|---|---|---|---|
| 19259 | 19793 | H0.49 | L0 | 5.00E-07 | n.t. | n.t. | n.t. | 65 | 0 | 82 | 0 |
| 19260 | 19794 | H0.50 | L0 | 1.41E-09 | n.t. | n.t. | 66.5 | 65 | 0 | 82 | 0 |
| 19261 | 19795 | H0.51 | L0 | 8.43E-09 | n.t. | n.t. | 57.5 | 65 | 0 | 82 | 0 |
| 19262 | 19796 | H0.52 | L0 | 1.13E-08 | 3.69E-08 | 74.5 | n.t. | 65 | 0 | 82 | 0 |
| 19263 | 19801 | H0.53 | L0 | 1.27E-08 | n.t. | n.t. | n.t. | 65 | 0 | 82 | 0 |
| 19264 | 19802 | H0.54 | L0 | 5.00E-07 | n.t. | n.t. | n.t. | 65 | 0 | 82 | 0 |
| 19265 | 19803 | H0.55 | L0 | 3.43E-08 | n.t. | n.t. | n.t. | 65 | 0 | 82 | 0 |
| 19266 | 19804 | H0.56 | L0 | 5.95E-08 | n.t. | n.t. | n.t. | 65 | 0 | 82 | 0 |
| 19267 | 19805 | H0.57 | L0 | 9.15E-09 | n.t. | 62.5 | 62 | 65 | 0 | 82 | 0 |
| 19268 | 19806 | H0.58 | L0 | 3.93E-09 | n.t. | 58.5 | 59 | 65 | 0 | 82 | 0 |
| 19269 | 19807 | H0.59 | L0 | 1.91E-09 | n.t. | 73 | 60 | 65 | 0 | 82 | 0 |
| 19270 | 19808 | H0.60 | L0 | 7.46E-09 | n.t. | 63.5 | 59.5 | 65 | 0 | 82 | 0 |
| 19271 | 19809 | H0.61 | L0 | n.t. | n.t. | n.t. | n.t. | 65 | 0 | 82 | 0 |
| 19272 | 19810 | H0.62 | L0 | 5.48E-08 | n.t. | n.t. | n.t. | 56 | -9 | 82 | 0 |
| 19273 | 19811 | H0.63 | L0 | 3.66E-09 | n.t. | 58 | 59 | 65 | 0 | 82 | 0 |
| 19274 | 19812 | H0.64 | L0 | 2.04E-08 | n.t. | n.t. | n.t. | 65 | 0 | 82 | 0 |
| 19275 | 19813 | H0.65 | L0 | 5.00E-07 | n.t. | n.t. | n.t. | 56 | -9 | 82 | 0 |
| 19276 | 19814 | H0.66 | L0 | 2.08E-08 | n.t. | 59.5 | n.t. | 65 | 0 | 82 | 0 |
| 19277 | 19815 | H0.67 | L0 | 1.10E-08 | n.t. | 58.5 | n.t. | 65 | 0 | 82 | 0 |
| 19278 | 19816 | H0.68 | L0 | 7.32E-09 | n.t. | 62 | 63.5 | 65 | 0 | 82 | 0 |
| 19279 | 19817 | H0.69 | L0 | 1.79E-08 | n.t. | 58 | n.t. | 65 | 0 | 82 | 0 |
| 19280 | 19818 | H0.70 | L0 | 1.42E-08 | n.t. | 56.5 | n.t. | 71 | 6 | 82 | 0 |
| 19281 | 19819 | H0.71 | L0 | 3.00E-08 | n.t. | n.t. | n.t. | 64 | -1 | 82 | 0 |
| 19282 | 19820 | H0.72 | L0 | 5.00E-07 | n.t. | n.t. | n.t. | 64 | -1 | 82 | 0 |
| 19283 | 19821 | H0.73 | L0 | 2.07E-09 | n.t. | 76 | 64.5 | 64 | -1 | 82 | 0 |
| 19284 | 19822 | H0.74 | L0 | 1.24E-08 | n.t. | 59 | n.t. | 64 | -1 | 82 | 0 |
| 19285 | 19823 | H0.75 | L0 | 3.55E-09 | n.t. | 76 | 65 | 64 | -1 | 82 | 0 |
| 19286 | 19824 | H0.76 | L0 | 1.08E-08 | n.t. | 76.5 | 65 | 64 | -1 | 82 | 0 |
| 19287 | 19825 | H0.77 | L0 | 3.42E-08 | n.t. | n.t. | n.t. | 64 | -1 | 82 | 0 |
| 19288 | 19826 | H0.78 | L0 | 2.10E-08 | n.t. | 75.5 | n.t. | 64 | -1 | 82 | 0 |
| 19289 | 19827 | H0.79 | L0 | 3.79E-08 | n.t. | n.t. | n.t. | 62 | -3 | 82 | 0 |
| 19290 | 19828 | H0.80 | L0 | 1.24E-08 | n.t. | 75.5 | n.t. | 62 | -3 | 82 | 0 |
| 19291 | 19829 | H0.81 | L0 | 5.65E-09 | n.t. | 74.5 | 63 | 59 | -6 | 82 | 0 |
| 19292 | 19830 | H0.82 | L0 | 5.13E-09 | n.t. | 73.5 | 62.5 | 56 | -9 | 82 | 0 |
| 19293 | 19831 | H0.83 | L0 | 5.33E-09 | n.t. | 72.5 | 61.5 | 56 | -9 | 82 | 0 |
| 19294 | 19832 | H0.84 | L0 | 7.94E-09 | n.t. | 67.5 | n.t. | 56 | -9 | 82 | 0 |
| 19295 | 19833 | H0.85 | L0 | 2.10E-09 | n.t. | 70 | 55.5 | 56 | -9 | 82 | 0 |
| 19296 | 19834 | H0.86 | L0 | 6.78E-09 | n.t. | 75.8 | 65 | 56 | -9 | 82 | 0 |
| 19301 | 19835 | H0.87 | L0 | 5.15E-08 | n.t. | n.t. | n.t. | 56 | -9 | 82 | 0 |
| 19302 | 19836 | H0.88 | L0 | 9.63E-09 | n.t. | 73.5 | n.t. | 58 | -7 | 82 | 0 |
| 19303 | 19837 | H0.89 | L0 | 2.12E-08 | n.t. | n.t. | n.t. | 65 | 0 | 82 | 0 |
| 19304 | 19838 | H0.90 | L0 | 7.82E-09 | n.t. | 75.5 | 55.5 | 65 | 0 | 82 | 0 |
| 19305 | 19839 | H0.91 | L0 | 6.11E-09 | n.t. | 75.5 | 65 | 61 | -4 | 82 | 0 |
| 19306 | 19840 | H0.92 | L0 | 5.72E-09 | n.t. | 73.5 | 61 | 65 | 0 | 82 | 0 |
| 19307 | 19841 | H0.93 | L0 | 5.13E-09 | n.t. | 74.5 | 63.5 | 56 | -9 | 82 | 0 |
| 19308 | 19842 | H0.94 | L0 | 5.90E-09 | n.t. | 75.5 | 64 | 56 | -9 | 82 | 0 |
| 19309 | 19843 | H0.95 | L0 | 1.02E-08 | n.t. | 76 | 64 | 56 | -9 | 82 | 0 |
| 19310 | 19844 | H0.96 | L0 | 1.53E-08 | n.t. | 77 | 65.5 | 57 | -8 | 82 | 0 |
| 19311 | 19845 | H0.97 | L0 | 6.30E-09 | 3.17E-08 | 76 | 64 | 65 | 0 | 82 | 0 |

Figure 24C

| Fab XENP | scFv XENP | VH | VL | Human CTLA-4 Fab $K_D$ (M) | Cyno CTLA-4 Fab $K_D$ (M) | Fab $T_m$ (°C) | scFv $T_m$ (°C) | VH 9-mers | Δ VH 9-mers | VL 9-mers | Δ VL 9-mers |
|---|---|---|---|---|---|---|---|---|---|---|---|
| 19312 | 19846 | H0.98 | L0 | 7.36E-09 | 3.38E-08 | 74.5 | 61.5 | 70 | 5 | 82 | 0 |
| 19313 | 19847 | H0.99 | L0 | 7.01E-09 | 3.53E-08 | 76 | 63.5 | 71 | 6 | 82 | 0 |
| 19314 | 19848 | H0.100 | L0 | 1.10E-08 | 3.14E-08 | 75.5 | n.t. | 65 | 0 | 82 | 0 |
| 19315 | 19849 | H0.101 | L0 | 2.90E-08 | 5.00E-07 | 72 | n.t. | 65 | 0 | 82 | 0 |
| 19316 | 19850 | H0.102 | L0 | 3.48E-08 | 5.00E-07 | 79 | n.t. | 65 | 0 | 82 | 0 |
| 19317 | 19851 | H0.103 | L0 | 1.02E-08 | 3.68E-08 | 77.5 | 65.5 | 65 | 0 | 82 | 0 |
| 19318 | 19852 | H0.104 | L0 | 5.00E-07 | 5.00E-07 | 72.5 | n.t. | 65 | 0 | 82 | 0 |
| 19319 | 19853 | H0.105 | L0 | 5.00E-07 | 5.00E-07 | 78.5 | n.t. | 65 | 0 | 82 | 0 |
| 19320 | 19854 | H0.106 | L0 | 2.37E-08 | 5.00E-07 | 74 | n.t. | 65 | 0 | 82 | 0 |
| 19321 | 19855 | H0.107 | L0 | 5.00E-07 | 5.00E-07 | 70 | n.t. | 65 | 0 | 82 | 0 |
| 19322 | 19856 | H0.108 | L0 | 1.67E-08 | 2.17E-08 | 76.5 | 64.5 | 65 | 0 | 82 | 0 |
| 19323 | 19857 | H0.109 | L0 | 1.51E-08 | 4.39E-08 | 77 | 65 | 65 | 0 | 82 | 0 |
| 19324 | 19858 | H0.110 | L0 | 5.00E-07 | 5.00E-07 | 76.5 | n.t. | 65 | 0 | 82 | 0 |
| 19325 | 19859 | H0.111 | L0 | 6.52E-09 | 3.30E-08 | 76 | 64 | 65 | 0 | 82 | 0 |
| 19326 | 19860 | H0.112 | L0 | 5.00E-07 | 5.00E-07 | 77 | n.t. | 65 | 0 | 82 | 0 |
| 19327 | 19861 | H0.113 | L0 | 1.12E-08 | 3.64E-08 | 76.5 | 65 | 65 | .0 | 82 | 0 |
| 19328 | 19862 | H0.114 | L0 | 3.64E-09 | 2.28E-08 | 76.5 | 64.5 | 65 | 0 | 82 | 0 |
| 19329 | 19863 | H0.115 | L0 | 1.19E-08 | 4.10E-08 | 76 | n.t. | 65 | 0 | 82 | 0 |
| 19330 | 19864 | H0.116 | L0 | 3.45E-08 | 5.00E-07 | 76 | n.t. | 65 | 0 | 82 | 0 |
| 19331 | 19865 | H0.117 | L0 | 5.00E-07 | 5.00E-07 | 76.5 | n.t. | 65 | 0 | 82 | 0 |
| 19332 | 19866 | H0.118 | L0 | 1.65E-08 | 5.00E-07 | 76 | n.t. | 65 | 0 | 82 | 0 |
| 19333 | 19867 | H0.119 | L0 | 5.00E-07 | 5.00E-07 | 73.5 | n.t. | 65 | 0 | 82 | 0 |
| 19334 | 19868 | H0.120 | L0 | 5.00E-07 | 5.00E-07 | 73.5 | n.t. | 65 | 0 | 82 | 0 |
| 19335 | 19869 | H0.121 | L0 | 5.00E-07 | 5.00E-07 | 74 | n.t. | 65 | 0 | 82 | 0 |
| 19336 | 19870 | H0.122 | L0 | 2.20E-08 | 5.00E-07 | 75.5 | n.t. | 64 | -1 | 82 | 0 |
| 19337 | 19871 | H0.123 | L0 | 2.25E-08 | 5.00E-07 | 75.5 | n.t. | 64 | -1 | 82 | 0 |
| 19338 | 19872 | H0.124 | L0 | 5.00E-07 | 5.00E-07 | 71 | n.t. | 63 | -2 | 82 | 0 |
| 19339 | 19873 | H0.125 | L0 | 3.08E-08 | 5.00E-07 | 75 | n.t. | 63 | -2 | 82 | 0 |
| 19340 | 19874 | H0.126 | L0 | 5.00E-07 | 5.00E-07 | 70.5 | n.t. | 63 | -2 | 82 | 0 |
| 19341 | 19875 | H0.127 | L0 | 3.20E-08 | 5.00E-07 | 70.5 | n.t. | 63 | -2 | 82 | 0 |
| 19342 | 19876 | H0.128 | L0 | 1.84E-08 | 5.00E-07 | 71 | n.t. | 63 | -2 | 82 | 0 |
| 19343 | 19877 | H0.129 | L0 | 5.00E-07 | 5.00E-07 | 72 | n.t. | 63 | -2 | 82 | 0 |
| 19344 | 19878 | H0.130 | L0 | 6.51E-09 | 3.93E-08 | 76 | 64 | 63 | -2 | 82 | 0 |
| 19345 | 19879 | H0.131 | L0 | 5.82E-09 | 3.40E-08 | 78 | 66.5 | 62 | -3 | 82 | 0 |
| 19346 | 19880 | H0.132 | L0 | 6.46E-09 | 3.82E-08 | 74.5 | 62.5 | 65 | 0 | 82 | 0 |
| 19347 | 19881 | H0.133 | L0 | 2.03E-08 | 4.95E-08 | 77.5 | n.t. | 62 | -3 | 82 | 0 |
| 19348 | 19882 | H0.134 | L0 | 1.58E-07 | 5.00E-07 | low signal | 64.5 | 62 | -3 | 82 | 0 |
| 19349 | 19883 | H0.135 | L0 | 6.69E-09 | 4.03E-08 | 76.5 | 64.5 | 62 | -3 | 82 | 0 |
| 19350 | 19884 | H0.136 | L0 | 7.41E-09 | 4.21E-08 | 75.5 | 63 | 62 | -3 | 82 | 0 |
| 19416 | 19885 | H0 | L0.1 | 1.14E-08 | 4.63E-08 | n.t. | n.t. | 65 | 0 | 81 | -1 |
| 19417 | 19886 | H0 | L0.2 | 6.94E-09 | 3.77E-08 | 75.5 | 62 | 65 | 0 | 81 | -1 |
| 19418 | 19887 | H0 | L0.3 | 9.31E-09 | 4.19E-08 | 75.5 | low signal | 65 | 0 | 81 | -1 |
| 19419 | 19888 | H0 | L0.4 | 1.95E-07 | 5.00E-07 | n.t. | n.t. | 65 | 0 | 81 | -1 |
| 19420 | 19889 | H0 | L0.5 | 8.28E-09 | 3.95E-08 | 76 | low signal | 65 | 0 | 79 | -3 |
| 19421 | 19890 | H0 | L0.6 | 5.00E-07 | 5.16E-08 | n.t. | n.t. | 65 | 0 | 71 | -11 |
| 19422 | 19891 | H0 | L0.7 | 1.36E-08 | 7.79E-08 | n.t. | n.t. | 65 | 0 | 78 | -4 |
| 19423 | 19892 | H0 | L0.8 | 1.07E-08 | 5.50E-08 | n.t. | n.t. | 65 | 0 | 82 | 0 |
| 19424 | 19893 | H0 | L0.9 | 8.18E-09 | 4.70E-08 | 76.5 | 64.5 | 65 | 0 | 78 | -4 |
| 19425 | 19894 | H0 | L0.10 | 8.97E-09 | 4.60E-08 | 76.5 | 64.5 | 65 | 0 | 73 | -9 |

Figure 24D

| Fab XENP | scFv XENP | VH | VL | Human CTLA-4 Fab $K_D$ (M) | Cyno CTLA-4 Fab $K_D$ (M) | Fab $T_m$ (°C) | scFv $T_m$ (°C) | VH 9-mers | Δ VH 9-mers | VL 9-mers | Δ VL 9-mers |
|---|---|---|---|---|---|---|---|---|---|---|---|
| 19426 | 19895 | H0 | L0.11 | 5.00E-07 | 5.00E-07 | n.t. | n.t. | 65 | 0 | 73 | -9 |
| 19427 | 19896 | H0 | L0.12 | 7.59E-09 | 4.14E-08 | 77 | 63.5 | 65 | 0 | 77 | -5 |
| 19428 | 19901 | H0 | L0.13 | 9.71E-09 | 5.19E-08 | 75.5 | 63 | 65 | 0 | 73 | -9 |
| 19429 | 19902 | H0 | L0.14 | 8.04E-09 | 4.90E-08 | 76 | 63.5 | 65 | 0 | 73 | -9 |
| 19430 | 19903 | H0 | L0.15 | 9.79E-09 | 5.37E-08 | 73.5 | 61 | 65 | 0 | 82 | 0 |
| 19431 | 19904 | H0 | L0.16 | 1.43E-08 | 5.23E-08 | n.t. | n.t. | 65 | 0 | 73 | -9 |
| 19432 | 19905 | H0 | L0.17 | 2.17E-08 | 4.96E-08 | n.t. | n.t. | 65 | 0 | 73 | -9 |
| 19433 | 19906 | H0 | L0.18 | 8.28E-09 | 4.59E-08 | 75.5 | 62.5 | 65 | 0 | 77 | -5 |
| 19434 | 19907 | H0 | L0.19 | 2.86E-09 | 1.64E-08 | 72 | 57.5 | 65 | 0 | 81 | -1 |
| 19435 | 19908 | H0 | L0.20 | 5.00E-07 | 9.64E-07 | n.t. | n.t. | 65 | 0 | 81 | -1 |
| 19436 | 19909 | H0 | L0.21 | 1.79E-08 | 5.00E-07 | n.t. | n.t. | 65 | 0 | 82 | 0 |
| 19437 | 19910 | H0 | L0.22 | 1.46E-08 | 5.28E-08 | n.t. | 64.5 | 65 | 0 | 91 | 9 |
| 19438 | 19911 | H0 | L0.23 | 2.02E-08 | 5.47E-08 | n.t. | n.t. | 65 | 0 | 82 | 0 |
| 19439 | 19912 | H0 | L0.24 | 1.26E-08 | 5.36E-08 | n.t. | n.t. | 65 | 0 | 81 | -1 |
| 19440 | 19913 | H0 | L0.25 | 4.60E-09 | 2.85E-08 | 76 | 64 | 65 | 0 | 81 | -1 |
| 19441 | 19914 | H0 | L0.26 | 9.55E-09 | 4.17E-08 | 76 | 64 | 65 | 0 | 81 | -1 |
| 19442 | 19915 | H0 | L0.27 | 1.20E-08 | 5.58E-08 | n.t. | n.t. | 65 | 0 | 81 | -1 |
| 19443 | 19916 | H0 | L0.28 | 5.00E-07 | 5.00E-07 | n.t. | n.t. | 65 | 0 | 81 | -1 |
| 19444 | 19917 | H0 | L0.29 | 2.09E-08 | 5.16E-08 | n.t. | n.t. | 65 | 0 | 80 | -2 |
| 19445 | 19918 | H0 | L0.30 | 1.10E-08 | 5.42E-08 | n.t. | n.t. | 65 | 0 | 80 | -2 |
| 19446 | 19919 | H0 | L0.31 | 8.90E-09 | 4.62E-08 | 76.5 | 65 | 65 | 0 | 81 | -1 |
| 19447 | 19920 | H0 | L0.32 | 8.69E-09 | 5.14E-08 | 76 | 64.5 | 65 | 0 | 80 | -2 |
| 19448 | 19921 | H0 | L0.33 | 1.37E-07 | 5.00E-07 | n.t. | n.t. | 65 | 0 | 80 | -2 |
| 19449 | 19922 | H0 | L0.34 | 4.27E-08 | 5.00E-07 | n.t. | n.t. | 65 | 0 | 81 | -1 |
| 19450 | 19923 | H0 | L0.35 | 5.00E-07 | 5.00E-07 | n.t. | n.t. | 65 | 0 | 79 | -3 |
| 19451 | 19924 | H0 | L0.36 | 1.60E-08 | 5.00E-07 | n.t. | 63.5 | 65 | 0 | 79 | -3 |
| 19452 | 19925 | H0 | L0.37 | 7.60E-09 | 3.37E-08 | 75 | 63 | 65 | 0 | 79 | -3 |
| 19453 | 19926 | H0 | L0.38 | 5.73E-08 | 5.00E-07 | n.t. | n.t. | 65 | 0 | 81 | -1 |
| 19454 | 19927 | H0 | L0.39 | 2.39E-08 | 5.00E-07 | n.t. | n.t. | 65 | 0 | 79 | -3 |
| 19455 | 19928 | H0 | L0.40 | 1.15E-08 | 3.66E-08 | 73.5 | 60.5 | 65 | 0 | 79 | -3 |
| 19456 | 19929 | H0 | L0.41 | 7.20E-09 | 3.96E-08 | 76 | 64 | 65 | 0 | 78 | -4 |
| 19457 | 19930 | H0 | L0.42 | 5.00E-07 | 5.00E-07 | n.t. | n.t. | 65 | 0 | 77 | -5 |
| 19458 | 19931 | H0 | L0.43 | 5.00E-07 | 5.00E-07 | n.t. | n.t. | 65 | 0 | 68 | -14 |
| 19459 | 19932 | H0 | L0.44 | 3.85E-08 | 5.00E-07 | n.t. | 60 | 65 | 0 | 82 | 0 |
| 19460 | 19933 | H0 | L0.45 | 7.16E-08 | 5.00E-07 | n.t. | n.t. | 65 | 0 | 82 | 0 |
| 19461 | 19934 | H0 | L0.46 | 9.56E-09 | 5.16E-08 | 72 | low signal | 65 | 0 | 74 | -8 |
| 19462 | 19935 | H0 | L0.47 | 1.91E-08 | 4.75E-08 | n.t. | n.t. | 65 | 0 | 75 | -7 |
| 19463 | 19936 | H0 | L0.48 | 9.34E-09 | 4.70E-08 | 75 | 61.5 | 65 | 0 | 74 | -8 |
| 19464 | 19937 | H0 | L0.49 | 1.10E-08 | 4.42E-08 | n.t. | n.t. | 65 | 0 | 68 | -14 |
| 19465 | 19938 | H0 | L0.50 | 9.39E-09 | 4.63E-08 | 71.5 | 58 | 65 | 0 | 73 | -9 |
| 19466 | 19939 | H0 | L0.51 | 7.20E-09 | 4.05E-08 | 75 | 62.5 | 65 | 0 | 75 | -7 |
| 19467 | 19940 | H0 | L0.52 | 7.50E-09 | 3.91E-08 | 75 | 62.5 | 65 | 0 | 74 | -8 |
| 19468 | 19941 | H0 | L0.53 | 1.87E-07 | 5.00E-07 | n.t. | n.t. | 65 | 0 | 74 | -8 |
| 19469 | 19942 | H0 | L0.54 | 2.15E-08 | 4.66E-08 | n.t. | n.t. | 65 | 0 | 76 | -6 |
| 19470 | 19943 | H0 | L0.55 | 5.00E-07 | 5.00E-07 | n.t. | n.t. | 65 | 0 | 73 | -9 |
| 19471 | 19944 | H0 | L0.56 | 5.75E-09 | 3.57E-08 | 76 | 64 | 65 | 0 | 73 | -9 |
| 19472 | 19945 | H0 | L0.57 | 7.61E-09 | 3.87E-08 | 73 | 60 | 65 | 0 | 75 | -7 |
| 19473 | 19946 | H0 | L0.58 | 7.85E-09 | 4.46E-08 | n.t. | n.t. | 65 | 0 | 66 | -16 |
| 19474 | 19947 | H0 | L0.59 | 7.36E-09 | 4.29E-08 | 75.5 | 63.5 | 65 | 0 | 75 | -7 |

Figure 24E

| Fab XENP | scFv XENP | VH | VL | Human CTLA-4 Fab K$_D$ (M) | Cyno CTLA-4 Fab K$_D$ (M) | Fab T$_m$ (°C) | scFv T$_m$ (°C) | VH 9-mers | Δ VH 9-mers | VL 9-mers | Δ VL 9-mers |
|---|---|---|---|---|---|---|---|---|---|---|---|
| 19475 | 19948 | H0 | L0.60 | 6.52E-08 | 5.00E-07 | n.t. | n.t. | 65 | 0 | 76 | -6 |
| 19476 | 19949 | H0 | L0.61 | 5.00E-07 | 5.00E-07 | n.t. | n.t. | 65 | 0 | 73 | -9 |
| 19477 | 19950 | H0 | L0.62 | 2.36E-08 | 5.40E-08 | n.t. | n.t. | 65 | 0 | 79 | -3 |
| 19478 | 19951 | H0 | L0.63 | 8.66E-09 | 5.13E-08 | 75 | 62.5 | 65 | 0 | 79 | -3 |
| 19479 | 19952 | H0 | L0.64 | 2.65E-08 | 5.00E-07 | n.t. | n.t. | 65 | 0 | 79 | -3 |
| 19480 | 19953 | H0 | L0.65 | 1.23E-08 | 4.90E-08 | n.t. | n.t. | 65 | 0 | 79 | -3 |
| 19481 | 19954 | H0 | L0.66 | 1.55E-08 | 5.53E-08 | n.t. | n.t. | 65 | 0 | 79 | -3 |
| 19482 | 19955 | H0 | L0.67 | 5.00E-08 | 5.00E-07 | n.t. | n.t. | 65 | 0 | 82 | 0 |
| 19483 | 19956 | H0 | L0.68 | 6.98E-09 | 4.30E-08 | 75.5 | 63 | 65 | 0 | 80 | -2 |
| 19484 | 19957 | H0 | L0.69 | 1.62E-08 | 4.75E-08 | n.t. | n.t. | 65 | 0 | 81 | -1 |
| 19485 | 19958 | H0 | L0.70 | 6.58E-09 | 4.02E-08 | 76 | 64.5 | 65 | 0 | 82 | 0 |
| 19486 | 19959 | H0 | L0.71 | 8.41E-09 | 4.21E-08 | 76 | 64.5 | 65 | 0 | 82 | 0 |
| 19487 | 19960 | H0 | L0.72 | 9.76E-09 | 4.90E-08 | 75 | 63 | 65 | 0 | 82 | 0 |
| 19488 | 19961 | H0 | L0.73 | 4.75E-09 | n.t. | 76.5 | 65 | 65 | 0 | 91 | 9 |
| 19489 | 19962 | H0 | L0.74 | 9.11E-09 | n.t. | 76 | 64.5 | 65 | 0 | 82 | 0 |
| 19490 | 19963 | H0 | L0.75 | 3.53E-08 | n.t. | n.t. | n.t. | 65 | 0 | 81 | -1 |
| 19491 | 19964 | H0 | L0.76 | 4.95E-08 | n.t. | n.t. | n.t. | 65 | 0 | 81 | -1 |
| 19492 | 19965 | H0 | L0.77 | 6.63E-09 | n.t. | 76.5 | 65.5 | 65 | 0 | 81 | -1 |
| 19493 | 19966 | H0 | L0.78 | 4.18E-09 | n.t. | 76.5 | 65 | 65 | 0 | 81 | -1 |
| 19494 | 19967 | H0 | L0.79 | 5.13E-09 | 3.81E-08 | 76 | 64 | 65 | 0 | 81 | -1 |
| 19495 | 19968 | H0 | L0.80 | 4.44E-09 | 2.91E-08 | 72.5 | 59.5 | 65 | 0 | 79 | -3 |
| 19496 | 19969 | H0 | L0.81 | 6.03E-09 | 3.61E-08 | 75.5 | 64 | 65 | 0 | 78 | -4 |
| 19501 | 19970 | H0 | L0.82 | 5.34E-09 | 3.25E-08 | 76 | 64 | 65 | 0 | 78 | -4 |
| 19502 | 19971 | H0 | L0.83 | 5.18E-09 | 3.14E-08 | 75.5 | 63.5 | 65 | 0 | 81 | -1 |
| 19503 | 19972 | H0 | L0.84 | 5.22E-09 | 3.20E-08 | 74 | 61.5 | 65 | 0 | 73 | -9 |
| 19504 | 19973 | H0 | L0.85 | 4.90E-09 | 3.00E-08 | 76 | 64.5 | 65 | 0 | 80 | -2 |
| 19505 | 19974 | H0 | L0.86 | 3.51E-09 | 2.65E-08 | 74.5 | 61.5 | 65 | 0 | 77 | -5 |
| 19506 | 19975 | H0 | L0.87 | 7.35E-09 | 4.11E-08 | 75.5 | 63.5 | 65 | 0 | 82 | 0 |
| 19507 | 19976 | H0 | L0.88 | 6.06E-09 | 3.73E-08 | n.t. | n.t. | 65 | 0 | 82 | 0 |
| 19508 | 19977 | H0 | L0.89 | 6.40E-09 | 3.95E-08 | 75.5 | 64.5 | 65 | 0 | 73 | -9 |
| 19509 | 19978 | H0 | L0.90 | 7.22E-09 | 3.74E-08 | 75.5 | 63 | 65 | 0 | 75 | -7 |
| 19510 | 19979 | H0 | L0.91 | 4.69E-09 | 3.06E-08 | 75 | 62.5 | 65 | 0 | 74 | -8 |
| 19511 | 19980 | H0 | L0.92 | 7.82E-09 | 4.24E-08 | 75 | 62.5 | 65 | 0 | 73 | -9 |
| 19512 | 19981 | H0 | L0.93 | 7.70E-08 | 5.00E-07 | n.t. | n.t. | 65 | 0 | 73 | -9 |
| 19513 | 19982 | H0 | L0.94 | 5.40E-07 | 5.00E-07 | n.t. | n.t. | 65 | 0 | 73 | -9 |
| 19514 | 19983 | H0 | L0.95 | 1.71E-07 | 5.00E-07 | n.t. | n.t. | 65 | 0 | 73 | -9 |
| 19515 | 19984 | H0 | L0.96 | 1.80E-09 | 1.06E-08 | 72.5 | 59.5 | 65 | 0 | 73 | -9 |
| 19516 | 19985 | H0 | L0.97 | 8.41E-08 | 5.00E-07 | n.t. | n.t. | 65 | 0 | 73 | -9 |
| 19517 | 19986 | H0 | L0.98 | 5.00E-07 | 5.00E-07 | n.t. | n.t. | 65 | 0 | 73 | -9 |
| 19518 | 19987 | H0 | L0.99 | 5.00E-07 | 5.00E-07 | n.t. | n.t. | 65 | 0 | 73 | -9 |
| 19519 | 19988 | H0 | L0.100 | 8.03E-08 | 5.00E-07 | n.t. | n.t. | 65 | 0 | 73 | -9 |
| 19520 | 19989 | H0 | L0.101 | 1.84E-08 | 6.21E-08 | n.t. | n.t. | 65 | 0 | 73 | -9 |
| 19521 | 19990 | H0 | L0.102 | 2.02E-09 | 2.20E-08 | 76 | 62 | 65 | 0 | 73 | -9 |
| 19522 | 19991 | H0 | L0.103 | 7.60E-09 | 4.24E-08 | 75.5 | 65 | 65 | 0 | 73 | -9 |
| 19523 | 19992 | H0 | L0.104 | 7.47E-08 | 5.00E-07 | n.t. | n.t. | 65 | 0 | 75 | -7 |
| 19524 | 19993 | H0 | L0.105 | 5.00E-07 | 5.00E-07 | n.t. | n.t. | 65 | 0 | 74 | -8 |
| 19525 | 19994 | H0 | L0.106 | 2.33E-08 | 3.30E-08 | n.t. | n.t. | 65 | 0 | 77 | -5 |
| 19526 | 19995 | H0 | L0.107 | 5.00E-07 | 5.00E-07 | n.t. | n.t. | 65 | 0 | 73 | -9 |
| 19527 | 19996 | H0 | L0.108 | 5.00E-07 | 5.00E-07 | n.t. | n.t. | 65 | 0 | 80 | -2 |

Figure 24F

| Fab XENP | scFv XENP | VH | VL | Human CTLA-4 Fab K$_D$ (M) | Cyno CTLA-4 Fab K$_D$ (M) | Fab T$_m$ (°C) | scFv T$_m$ (°C) | VH 9-mers | Δ VH 9-mers | VL 9-mers | Δ VL 9-mers |
|---|---|---|---|---|---|---|---|---|---|---|---|
| 19528 | 20001 | H0 | L0.109 | 5.00E-07 | 5.00E-07 | n.t. | n.t. | 65 | 0 | 77 | -5 |
| 19529 | 20002 | H0 | L0.110 | 5.00E-07 | 5.00E-07 | n.t. | n.t. | 65 | 0 | 81 | -1 |
| 19530 | 20003 | H0 | L0.111 | 4.58E-09 | 1.68E-08 | 73.5 | 60.5 | 65 | 0 | 73 | -9 |
| 19531 | 20004 | H0 | L0.112 | 6.08E-09 | 2.93E-08 | 75.5 | 63.5 | 65 | 0 | 77 | -5 |
| 19532 | 20005 | H0 | L0.113 | 6.82E-09 | 4.48E-08 | n.t. | 62 | 65 | 0 | 74 | -8 |
|  | 19534 | H0.36 | L0.50 | n.t. | n.t. | n.t. | 62.5 | 61 | -4 | 73 | -9 |
|  | 19535 | H0.36 | L0.51 | n.t. | n.t. | n.t. | 62 | 61 | -4 | 75 | -7 |
|  | 19536 | H0.37 | L0.50 | n.t. | n.t. | n.t. | 59.5 | 60 | -5 | 73 | -9 |
|  | 19537 | H0.37 | L0.113 | n.t. | n.t. | n.t. | 63.5 | 60 | -5 | 74 | -8 |
|  | 19538 | H0.134 | L0.51 | n.t. | n.t. | n.t. | 64 | 62 | -3 | 75 | -7 |
| 20006 | 19539 | H0.134 | L0.53 | 5.02E-09 | 2.00E-08 | 75.5 | 65 | 62 | -3 | 74 | -8 |
|  | 19540 | H0.134 | L0.57 | n.t. | n.t. | n.t. | 61 | 62 | -3 | 75 | -7 |
|  | 19541 | H0.137 | L0.114 | n.t. | n.t. | n.t. | 66 | 60 | -5 | 74 | -8 |
|  | 19542 | H0.138 | L0.115 | n.t. | n.t. | n.t. | 64 | 59 | -6 | 73 | -9 |
|  | 19543 | H0.139 | L0.116 | n.t. | n.t. | n.t. | 62.5 | 59 | -6 | 73 | -9 |
| 19585 | 19587 | H0.140 | L0 | 2.83E-09 | 1.76E-08 | 78.5 | 68 | 56 | -9 | 82 | 0 |
| 19586 | 19588 | H0 | L0.117 | 4.09E-09 | 2.52E-08 | 76.5 | 63.5 | 65 | 0 | 69 | -13 |
| 19544 | 19551 | H1 | L0 | 1.77E-08 | 2.51E-08 | 74.5 | 61.5 | 70 | 5 | 82 | 0 |
| 19545 | 19552 | H2 | L0 | 1.10E-07 | 5.00E-07 | n.t. | 66.5 | 69 | 4 | 82 | 0 |
| 19546 | 19553 | H3 | L0 | 2.87E-09 | 1.92E-08 | 78.3 | 65.9 | 72 | 7 | 82 | 0 |
| 19547 | 19554 | H4 | L0 | 5.00E-07 | 5.00E-07 | 67.5 | 51.8 | 71 | 6 | 82 | 0 |
| 19548 | 19555 | H0 | L1 | 7.42E-09 | 4.37E-08 | 73.5 | 59.8 | 65 | 0 | 81 | -1 |
| 19549 | 19556 | H0 | L2 | 3.15E-09 | 2.32E-08 | 75 | 61 | 65 | 0 | 81 | -1 |
| 9950 | 19550 | H0 | L0 | 5.61E-09 | 3.29E-08 | 75.8 | 63.5 | 65 | 0 | 82 | 0 |
| 20007 |  | H3 | L1 | 3.35E-09 | 1.89E-08 | 75 | n.t. | 72 | 7 | 81 | -1 |
| 20008 |  | H3 | L2 | 1.41E-09 | 1.28E-08 | 77 | n.t. | 72 | 7 | 81 | -1 |
| 20009 |  | H3 | L0.12 | 2.46E-09 | 1.71E-08 | 79 | n.t. | 72 | 7 | 77 | -5 |
| 20010 |  | H3 | L0.18 | 2.17E-09 | 1.57E-08 | 77 | n.t. | 72 | 7 | 77 | -5 |
| 20011 |  | H3 | L0.22 | 4.13E-09 | 2.46E-08 | 78.5 | n.t. | 72 | 7 | 91 | 9 |
| 20012 |  | H3 | L0.27 | 1.31E-09 | 1.04E-08 | 77.5 | n.t. | 72 | 7 | 81 | -1 |
| 20013 |  | H3 | L0.32 | 1.59E-09 | 1.48E-08 | 78.5 | n.t. | 72 | 7 | 80 | -2 |
| 20014 |  | H3 | L0.36 | 3.75E-09 | 2.39E-08 | 77.5 | n.t. | 72 | 7 | 79 | -3 |
| 20015 |  | H3 | L0.37 | 1.44E-09 | 1.06E-08 | 77 | n.t. | 72 | 7 | 79 | -3 |
| 20016 |  | H3 | L0.39 | 1.29E-08 | 3.75E-08 | 77.5 | n.t. | 72 | 7 | 79 | -3 |
| 20017 |  | H3 | L0.41 | 1.84E-09 | 1.65E-08 | 78 | n.t. | 72 | 7 | 78 | -4 |
| 20018 |  | H3 | L0.67 | 3.49E-08 | 5.00E-07 | 77.5 | n.t. | 72 | 7 | 82 | 0 |
| 20019 |  | H3 | L0.69 | 2.64E-09 | n.t. | 77.5 | n.t. | 72 | 7 | 81 | -1 |
| 20020 |  | H3 | L0.74 | 2.68E-09 | n.t. | 78.8 | n.t. | 72 | 7 | 82 | 0 |
| 20021 |  | H3 | L0.75 | 2.81E-09 | n.t. | 78 | n.t. | 72 | 7 | 81 | -1 |
| 20022 |  | H3 | L0.103 | 3.69E-09 | 2.64E-08 | 78 | n.t. | 72 | 7 | 73 | -9 |
| 20052 |  | H3 | L0.44 | 6.78E-09 | 4.20E-08 | 75.8 | n.t. | 72 | 7 | 82 | 0 |
| 20068 | 20075 | H3.1 | L0.12 | 5.37E-10 | 3.64E-09 | 81 | 69 | 68 | 3 | 77 | -5 |
| 20069 | 20076 | H3.2 | L0.12 | 6.24E-10 | 4.10E-09 | 81 | 69.5 | 68 | 3 | 77 | -5 |
| 20070 | 20077 | H3.3 | L0.12 | 2.21E-09 | 1.08E-08 | 81 | 67 | 68 | 3 | 77 | -5 |
| 20071 | 20078 | H3.4 | L0.12 | 1.37E-09 | 6.14E-09 | 81 | 69.5 | 68 | 3 | 77 | -5 |
| 20072 | 20079 | H3.5 | L0.12 | 3.72E-09 | 1.59E-08 | 81.5 | 70 | 68 | 3 | 77 | -5 |
| 20073 | 20080 | H3.6 | L0.12 | 8.14E-09 | 2.59E-08 | 81.5 | 69.5 | 68 | 3 | 77 | -5 |
| 20074 | 20081 | H3.7 | L0.12 | 1.58E-09 | 1.11E-08 | 80 | 67 | 62 | -3 | 77 | -5 |
| 20323 | 20360 | H3.9 | L0.12 | 1.16E-09 | 5.54E-09 | n.t. | 69.5 | 68 | 3 | 77 | -5 |

Figure 24G

| Fab XENP | scFv XENP | VH | VL | Human CTLA-4 Fab K$_D$ (M) | Cyno CTLA-4 Fab K$_D$ (M) | Fab T$_m$ (°C) | scFv T$_m$ (°C) | VH 9-mers | Δ VH 9-mers | VL 9-mers | Δ VL 9-mers |
|---|---|---|---|---|---|---|---|---|---|---|---|
| 20324 | 20361 | H3.10 | L0.12 | 7.08E-10 | 3.34E-09 | n.t. | 68.5 | 68 | 3 | 77 | -5 |
| 20325 | 20362 | H3.11 | L0.12 | 1.65E-09 | 6.52E-09 | n.t. | 71 | 68 | 3 | 77 | -5 |
| 20326 | 20363 | H3.12 | L0.12 | 1.20E-08 | 4.13E-08 | n.t. | 70 | 68 | 3 | 77 | -5 |
| 20327 | 20364 | H3.13 | L0.12 | 8.15E-10 | 4.56E-09 | n.t. | 70 | 68 | 3 | 77 | -5 |
| 20328 | 20365 | H3.14 | L0.12 | 3.46E-09 | 1.95E-08 | n.t. | 69.5 | 68 | 3 | 77 | -5 |
| 20329 | 20366 | H3.15 | L0.12 | 8.65E-09 | 3.62E-08 | n.t. | 71.5 | 68 | 3 | 77 | -5 |
| 20330 | 20367 | H3.16 | L0.12 | 1.56E-08 | 6.23E-08 | n.t. | 70.5 | 68 | 3 | 77 | -5 |
| 20331 | 20368 | H3.17 | L0.12 | 3.93E-09 | 2.51E-08 | n.t. | 70.5 | 68 | 3 | 77 | -5 |
| 20332 | 20369 | H3.18 | L0.12 | 1.71E-08 | 8.46E-08 | n.t. | 69.5 | 68 | 3 | 77 | -5 |
| 20333 | 20370 | H3.19 | L0.12 | 4.09E-09 | 1.60E-08 | n.t. | 71.5 | 68 | 3 | 77 | -5 |
| 20334 | 20371 | H3.20 | L0.12 | 2.59E-08 | 2.54E-06 | n.t. | 70.5 | 68 | 3 | 77 | -5 |
| 20335 | 20372 | H3.21 | L0.12 | 1.55E-09 | 9.54E-09 | n.t. | 71 | 68 | 3 | 77 | -5 |
| 20336 | 20373 | H3.22 | L0.12 | 7.49E-09 | 2.98E-08 | n.t. | 69.5 | 68 | 3 | 77 | -5 |
| 20337 | 20374 | H3.23 | L0.12 | 1.17E-09 | 4.78E-09 | n.t. | 70.5 | 68 | 3 | 77 | -5 |
| 20338 | 20375 | H3.24 | L0.12 | 8.44E-09 | 2.96E-08 | n.t. | 69.5 | 68 | 3 | 77 | -5 |
| 20339 | 20376 | H3.25 | L0.12 | 4.51E-10 | 2.75E-09 | n.t. | 69.5 | 68 | 3 | 77 | -5 |
| 20340 | 20377 | H3.26 | L0.12 | 1.97E-09 | 1.23E-08 | n.t. | 69 | 68 | 3 | 77 | -5 |
| 20341 | 20378 | H3.4 | L0.118 | 1.55E-09 | 6.67E-09 | n.t. | 70.5 | 68 | 3 | 82 | 0 |
| 20342 | 20379 | H3.4 | L0.119 | 1.89E-09 | 8.23E-09 | n.t. | 70 | 68 | 3 | 82 | 0 |
| 20343 | 20380 | H3.4 | L0.120 | 2.70E-09 | 1.06E-08 | n.t. | 70 | 68 | 3 | 86 | 4 |
| 20344 | 20381 | H3.4 | L0.121 | 1.28E-09 | 5.54E-09 | n.t. | 71 | 68 | 3 | 86 | 4 |
| 20345 | 20382 | H3.4 | L0.122 | 1.98E-09 | 8.47E-09 | n.t. | 71 | 68 | 3 | 82 | 0 |
| 20346 | 20383 | H3.4 | L0.123 | 2.74E-09 | 1.14E-08 | n.t. | 71.5 | 68 | 3 | 91 | 9 |
| 20347 | 20384 | H3.4 | L0.124 | 1.41E-09 | 5.67E-09 | n.t. | 72.5 | 68 | 3 | 91 | 9 |
| 20348 | 20385 | H3.4 | L0.125 | 3.20E-09 | 1.37E-08 | n.t. | 70.5 | 68 | 3 | 91 | 9 |
| 20349 | 20386 | H3.4 | L0.126 | 1.68E-09 | 7.52E-09 | n.t. | 71.5 | 68 | 3 | 91 | 9 |
| 20350 | 20387 | H3.4 | L0.127 | 2.46E-09 | 9.53E-09 | n.t. | 72 | 68 | 3 | 95 | 13 |
| 20351 | 20388 | H3.4 | L0.128 | 3.16E-09 | 1.33E-08 | n.t. | 72 | 68 | 3 | 91 | 9 |
| 20352 | 20389 | H3.4 | L0.129 | 1.65E-09 | 7.31E-09 | n.t. | 73 | 68 | 3 | 91 | 9 |
| 20353 | 20390 | H3.4 | L0.130 | 2.77E-09 | 1.09E-08 | n.t. | 73 | 68 | 3 | 100 | 18 |
| 20354 | 20391 | H3.4 | L0.131 | 2.70E-09 | 1.08E-08 | n.t. | 72.5 | 68 | 3 | 100 | 18 |
| 20355 | 20392 | H3.4 | L0.132 | 2.78E-09 | 1.12E-08 | n.t. | 73.5 | 68 | 3 | 100 | 18 |
| 20356 | 20393 | H3.5 | L2 | 2.17E-09 | 1.13E-08 | n.t. | 67 | 68 | 3 | 81 | -1 |
| 20357 | 20394 | H3.5 | L2.1 | 4.52E-09 | 2.41E-08 | n.t. | 67.5 | 68 | 3 | 90 | 8 |
| 20358 | 20395 | H3.5 | L2.2 | 1.90E-09 | 1.04E-08 | n.t. | 68.5 | 68 | 3 | 89 | 7 |
| 20359 | 20396 | H3.5 | L2.3 | 3.90E-09 | 2.05E-08 | n.t. | 69 | 68 | 3 | 98 | 16 |
| 20422 | 20431 | H3.21 | L0.124 | 5.55E-09 | 1.23E-08 | n.t. | 74 | 68 | 3 | 91 | 9 |
| 20423 | 20432 | H3.21 | L0.129 | 5.42E-09 | 1.36E-08 | n.t. | 74.5 | 68 | 3 | 91 | 9 |
| 20424 | 20433 | H3.21 | L0.132 | 5.27E-09 | 1.60E-08 | n.t. | 75 | 68 | 3 | 100 | 18 |
| 20425 | 20434 | H3.23 | L0.124 | 2.63E-09 | 4.99E-09 | n.t. | 73.5 | 68 | 3 | 91 | 9 |
| 20426 | 20435 | H3.23 | L0.129 | 2.97E-09 | 4.99E-09 | n.t. | 74 | 68 | 3 | 91 | 9 |
| 20427 | 20436 | H3.23 | L0.132 | 4.84E-09 | 8.89E-09 | n.t. | 74.5 | 68 | 3 | 100 | 18 |
| 20428 | 20437 | H3.25 | L0.124 | 4.80E-09 | 8.65E-09 | n.t. | 72.5 | 68 | 3 | 91 | 9 |
| 20429 | 20438 | H3.25 | L0.129 | 2.05E-09 | 3.99E-09 | n.t. | 73 | 68 | 3 | 91 | 9 |
| 20430 | 20439 | H3.25 | L0.132 | 1.80E-09 | 3.81E-09 | n.t. | 73.5 | 68 | 3 | 100 | 18 |

Figure 37A

Bottle opener backbone 1

Fab side heavy chain (SEQ ID NO:37725)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEYNSTYRVVSVLTVLHQDWLNGKEYKCKVSNKALPAPI
EKTISKAKGQPREPQVYTLPPSREEMTKNQVSLTCDVSGFYPSDIAVEWESNGQPENNYKTTPPVLDSDGSFFLYSKLTVDKSRWQQGNVFSCSVMHEALHNHYTQK
SLSLSPGK scFv heavy chain (SEQ ID NO:37726)

EPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKV
SNKALPAPIEKTISKADYEKHKVYACEVTHQGLSSPVTKSFNRGEC
ALHNHYTQKSLSLSPGK constant light chain (SEQ ID NO:37727)

RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Bottle opener backbone 2

Fab side heavy chain (SEQ ID NO:37728)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEYNSTYRVVSVLTVLHQDWLNGKEYKCKVSNKALPAPI
EKTISKAKGQPREPQVYTLPPSREEMTKNQVSLTCDVSGFYPSDIAVEWESNGQPENNYKTTPPVLDSDGSFFLYSKLTVDKSRWQQGNVFSCSVMHEALHNHYTQK
SLSLSPGK scFv heavy chain (SEQ ID NO:37729)

EPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVKLTCLVKGFYPSDIAVEWESNGQPENNYKTTPPVLDSDGSFFLYSKLTVDKSRWQQGNVFSCSVMHE
ALHNHYTQKSLSLSPGK

Figure 37B

Bottle opener backbone 3

Fab side heavy chain (SEQ ID NO:37731)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVSHEDPEVKFNWYVDGVEVHNAKTKPREEEYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK scFv heavy chain (SEQ ID NO:37732)

EPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVKLTCLVKGFYPSDIAVEWESNGQPENNYKTTPPVLDSDGSFFLYSKLTVDKSRWQQGNVFSCSVMHE
ALHNHYTQKSLSLSPGK

Bottle opener backbone 4

Fab side heavy chain (SEQ ID NO:37734)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVSHEDPEVKFNWYVDGVEVHNAKTKPREEEYNSTYRVVSVLTVLHQDWLNGKEYKCKVSNKALPAPI
EKTISKAKGQPREPQVYTLPPSREEMTENEVSLTCLVKSGFYPSDIAVEWESDGQPENNYKTTPPVLDSDGSFFLYSKLEVDKSRWEQGDVFSCSVMHEALHNHYTQ
KSLSLSPGK scFv heavy chain (SEQ ID NO:37735)

EPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNGQPENNYKTTPPVLDSKGSFFLYSKLTVDKSRWQQGNVFSCSVMHE
ALHNHYTQKSLSLSPGK

Figure 37C

Bottle opener backbone 5 (356D/358L allotype)

Fab side heavy chain (SEQ ID NO: 39158)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVSHEDPEVKFNWYVDGVEVHNAKTKPREEEYNSTYRVVSVLTVLHQDWLNGKEYKCKVSNKALPAPI
EKTISKAKGQPREPQVYTLPPSRDELTKNQVSLTCDVSGFYPSDIAVEWESDGQPENNYKTTPPVLDSDGSFFLYSKLTVDKSRWEQGDVFSCSVMHEALHNHYTQK
SLSLSPGK scFv heavy chain (SEQ ID NO: 39159)

EPKSSDKTHTCPPCPAPPVAGPSVFLFPPKPKDTLMISRTPEVTCVVVDVKHEDPEVKFNWYDGVEVHNAKTKPREEQYASTYRVVSVLTVLHQDWLNGKEYKCKV
SNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHE
ALHNHYTQKSLSLSPGK

Bottle opener backbone 6

Fab side heavy chain (SEQ ID NO: 39160)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVSHEDPEVKFNWYVDGVEVHNAKTKPREEEYASTYRVVSVLTVLHQDWLNGKEYKCKVSNKALPAPI
EKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQK
SLSLSPGK scFv heavy chain (SEQ ID NO: 39161)

EPKSSDKTHTCPPCPAPPVAGPSVFLFPPKPKDTLMISRTPEVTCVVVDVKHEDPEVKFNWYDGVEVHNAKTKPREEQYASTYRVVSVLTVLHQDWLNGKEYKCKV
SNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHE
ALHNHYTQKSLSLSPGK

Figure 37D

Bottle opener backbone 7

Fab side heavy chain (SEQ ID NO: 39162)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTPREEEYSSTYRVVSVLTVLHQDWLNGKEYKCKVSNKALPAPI
EKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQK
SLSLSPGK scFv heavy chain (SEQ ID NO: 39163)

EPKSSDKTHTCPPCPAPPVAGPSVFLFPPKPKDTLMISRTPEVTCVVVDVKHEDPEVKFNWYVDGVEVHNAKTPREEQYSSTYRVVSVLTVLHQDWLNGKEYKCKV
SNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHE
ALHNHYTQKSLSLSPGK

Bottle opener backbone 8

Fab side heavy chain (SEQ ID NO: 39164)

ASTKGPSVFPLAPCSRSTSESTAALGCLVKDYFPEPVTVSWNSGALTSGVHTFPAVLQSSGLYSLSSVVTVPSSSLGTKTYTCNVDHKPSDTKVDKRVESKYGPPCP
PCPAPEFLGGPSVFLFPPKPKDTLMISRTPEVTCVVVDVKQEDPEVQFNWYVDGVEVHNAKTPREEFNSTYRVVSVLTVLHQDWLNGKEYKCKVSNKGLPSSIEK
TISKAKGQPREPQVYTLPPSQEEMTKNQVSLTCDVSGFYPSDIAVEWESDGQPENNYKTTPPVLDSDGSFFLYSKLTVDKSRWEEGDVFSCSVMHEALHNHYTQKSL
SLSLGK scFv heavy chain (SEQ ID NO: 39165)

ESKYGPPCPPCPAPEFLGGPSVFLFPPKPKDTLMISRTPEVTCVVVDVKQEDPEVQFNWYVDGVEVHNAKTPREEQFNSTYRVVSVLTVLHQDWLNGKEYKCKVSN
KGLPSSIEKTISKAKGQPREPQVYTLPPSQEEMTKNQVKLTCLVKGFYPSDIAVEWESNGQPENNYKTTPPVLDSDGSFFLYSKLTVDKSRWQEGNVFSCSVMHEAL
HNHYTQKSLSLSLGK

Figure 37E

Bottle opener backbone 9

Fab side heavy chain (SEQ ID NO: 39166)

ASTKGPSVFPLAPCSRSTSESTAALGCLVKDYFPEPVTVSWNSGALTSGVHTFPAVLQSSGLYSLSSVVTVPSSNFGTQTYTCNVDHKPSDTKVDKTVERKCCVECP
PCPAPPVAGPSVFLFPPKPKDTLMISRTPEVTCVVVDVSHEDPEVQFNWYVDGVEVHNAKTKPREEEFNSTFRVVSVLTVVHQDWLNGKEYKCKVSNKGLPAPIEKT
ISKTKGQPREPQVYTLPPSREEMTKNQVSLTCDVSGFYPSDIAVEWESDGQPENNYKTTPPMLDSDGSFFLYSKLTVDKSRWQEGDVFSCSVMHEALHNHYTQKSLS
LSPGK scFv heavy chain (SEQ ID NO: 39167)

ERKCSVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNK
GLPAPIEKTISKTKGQPREPQVYTLPPSREQMTKNQVKLTCLVKGFYPSDIAVEWESNGQPENNYKTTPPMLDSDGSFFLYSKLTVDKSRWQQGNVFSCSVMHEALH
NHYTQKSLSLSPGK

Bottle opener backbone 10

Fab side heavy chain (SEQ ID NO: 39168)

ASTKGPSVFPLAPCSRSTSESTAALGCLVKDYFPEPVTVSWNSGALTSGVHTFPAVLQSSGLYSLSSVVTVPSSNFGTQTYTCNVDHKPSDTKVDKTVERKCCVECP
PCPAPPVAGPSVFLFPPKPKDTLMISRTPEVTCVVVDVKHEDPEVQFNWYVDGVEVHNAKTKPREEEFNSTFRVVSVLTVVHQDWLNGKEYKCKVSNKGLPAPIEKT
ISKTKGQPREPQVYTLPPSREEMTKNQVSLTCDVSGFYPSDIAVEWESDGQPENNYKTTPPMLDSDGSFFLYSKLTVDKSRWQEGDVFSCSVMHEALHNHYTQKSLS
LSPGK scFv heavy chain (SEQ ID NO: 39169)

ERKCSVECPPCPAPPVAGPSVFLFPPKPKDTLMISRTPEVTCVVVDVKHEDPEVQFNWYVDGVEVHNAKTKPREEQFNSTFRVVSVLTVVHQDWLNGKEYKCKVSNK
GLPAPIEKTISKTKGQPREPQVYTLPPSREQMTKNQVKLTCLVKGFYPSDIAVEWESNGQPENNYKTTPPMLDSDGSFFLYSKLTVDKSRWQQGNVFSCSVMHEALH
NHYTQKSLSLSPGK

Figure 38A mAb-scFv backbone 1 (356E/358M allotype)

monomer 1 (Fab-scFv side) (SEQ ID NO:37737)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYT
LPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK monomer 2 (Fab side) (SEQ ID NO:37738)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSSDKTHTCPPCPAPP
VAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK constant light chain (SEQ ID NO:37739)

RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 38B mAb-scFv backbone 2

Fab-scFv-Hc - 356D/358L allotype (SEQ ID NO: 39170)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK

>mAb-scFv Fab-Hc - 356D/358L allotype (SEQ ID NO: 39171)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYT
LPPSRDQLTKNQVKLTCLVKGFYPSDIAVEWESNGQPENNYKTTPPVLDSDGSFFLYSKLTVDKSRWQQGNVFSCSVMHEALHNHYTQKSLSLSPGK mAb-scFv backbone 3

>mAb-scFv Fab-scFv-Hc - N297A (SEQ ID NO: 39172)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYASTYRVVSVLTVLHQDWLNGKEYKCKVSNKALPAPIEKTISKAKGQPREPQVYT
LPPSREEMTKNQVSLTCLVKGFYPSDIAVEWESDGQPENNYKTTPPVLDSDGSFFLYSKLTVDKSRWQEGDVFSCSVMHEALHNHYTQKSLSLSPGK

>mAb-scFv Fab-Hc - N297A (SEQ ID NO: 39173)

ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEQYASTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK

Figure 38C mAb-scFv backbone 4

>mAb-scFv Fab-scFv-Hc - N297S (SEQ ID NO: 39174)
ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYSSTYRVVSVLTVLHQDWLNGKEYKCKVSNKALPAPIEKTISKAKGQPREPQVYT
LPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK

>mAb-scFv Fab-Hc - N297S (SEQ ID NO: 39175)
ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSSDKTHTCPPCPAPP
VAGPSVFLFPPKPKDTLMISRTPEVTCVVVDVKHEDPEVKFNWYVDGVEVHNAKTKPREEQYSSTYRVVSVLTVLHQDWLNGKEYKCKVSNKALPAPIEKTISKAKGQPREPQVYT
LPPSREQMTKNQVSLTCLVKGFYPSDIAVEWESNGQPENNYKTTPPVLDSDGSFFLYSKLTVDKSRWQQGNVFSCSVMHEALHNHYTQKSLSLSPGK mAb-scFv backbone 5 mAb-scFv Fab-scFv-IgG4-Hc (SEQ ID NO: 39176)
ASTKGPSVFPLAPCSRSTSESTAALGCLVKDYFPEPVTVSWNSGALTSGVHTFPAVLQSSGLYSLSSVVTVPSSSLGTKTYTCNVDHKPSDTKVDKRVESKYGPPCPPCPAPEFLG
GPSVFLFPPKPKDTLMISRTPEVTCVVVDVSQEDPEVQFNWYVDGVEVHNAKTKPREEEFNSTYRVVSVLTVLHQDWLNGKEYKCKVSNKGLPSSIEKTISKAKGQPREPQVYTLP
PSQEEMTKNQVSLTCLVKGFYPSDIAVEWESDGQPENNYKTTPPVLDSDGSFFLYSKLTVDKSRWEEGDVFSCSVMHEALHNHYTQKSLSLGK

>mAb-scFv Fab-IgG4-Hc (SEQ ID NO: 39177)
ASTKGPSVFPLAPCSRSTSESTAALGCLVKDYFPEPVTVSWNSGALTSGVHTFPAVLQSSGLYSLSSVVTVPSSSLGTKTYTCNVDHKPSDTKVDKRVESKYGPPCPPCPAPEFLG
GPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSKLTVDKSRWQEGNVFSCSVMHEALHNHYTQKSLSLGK

Figure 38D mAb-scFv backbone 6

>mAb-scFv Fab-scFv-IgG2-Hc - without S267K (SEQ ID NO: 39178)

ASTKGPSVFPLAPCSRSTSESTAALGCLVKDYFPEPVTVSWNSGALTSGVHTFPAVLQSSGLYSLSSVVTVPSSNFGTQTYTCNVDHKPSDTKVDKTVERKCCVECPPCPAPPVAG
PSVFLFPPKPKDTLMISRTPEVTCVVVDVSHEDPEVQFNWYVDGVEVHNAKTKPREEEFNSTFRVVSVLTVVHQDWLNGKEYKCKVSNKGLPAPIEKTISKTKGQPREPQVYTLPP
SREEMTKNQVSLTCDVSGFYPSDIAVEWESDGQPENNYKTTPPMLDSDGSFFLYSKLTVDKSRWEQGDVFSCSVMHEALHNHYTQKSLSLSPGK

>mAb-scFv Fab-IgG2-Hc - without S267K (SEQ ID NO: 39179)

ASTKGPSVFPLAPCSRSTSESTAALGCLVKDYFPEPVTVSWNSGALTSGVHTFPAVLQSSGLYSLSSVVTVPSSNFGTQTYTCNVDHKPSDTKVDKTVERKCSVECPPCPAPPVAG
PSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPP
SREQMTKNQVKLTCLVKGFYPSDIAVEWESNGQPENNYKTTPPMLDSDGSFFLYSKLTVDKSRWQQGNVFSCSVMHEALHNHYTQKSLSLSPGK mAb-scFv backbone 7

>mAb-scFv Fab-scFv-IgG2-Hc - with S267K (SEQ ID NO: 39180)

ASTKGPSVFPLAPCSRSTSESTAALGCLVKDYFPEPVTVSWNSGALTSGVHTFPAVLQSSGLYSLSSVVTVPSSNFGTQTYTCNVDHKPSDTKVDKTVERKCCVECPPCPAPPVAG
PSVFLFPPKPKDTLMISRTPEVTCVVVDVKHEDPEVQFNWYVDGVEVHNAKTKPREEEFNSTFRVVSVLTVVHQDWLNGKEYKCKVSNKGLPAPIEKTISKTKGQPREPQVYTLPP
SREEMTKNQVSLTCDVSGFYPSDIAVEWESDGQPENNYKTTPPMLDSDGSFFLYSKLTVDKSRWEQGDVFSCSVMHEALHNHYTQKSLSLSPGK

>mAb-scFv Fab-IgG2-Hc - with S267K (SEQ ID NO: 39181)

ASTKGPSVFPLAPCSRSTSESTAALGCLVKDYFPEPVTVSWNSGALTSGVHTFPAVLQSSGLYSLSSVVTVPSSNFGTQTYTCNVDHKPSDTKVDKTVERKCSVECPPCPAPPVAG
PSVFLFPPKPKDTLMISRTPEVTCVVVDVKHEDPEVQFNWYVDGVEVHNAKTKPREEQFNSTFRVVSVLTVVHQDWLNGKEYKCKVSNKGLPAPIEKTISKTKGQPREPQVYTLPP
SREQMTKNQVKLTCLVKGFYPSDIAVEWESNGQPENNYKTTPPMLDSDGSFFLYSKLTVDKSRWQQGNVFSCSVMHEALHNHYTQKSLSLSPGK

| 1st/2nd antigens | PD-1 | CTLA-4 | TIM-3 | LAG-3 | TIGIT | BTLA |
|---|---|---|---|---|---|---|
| PD-1 | XXX | A, B, C, D, E | A, B, C, D, E | A, B, C, D, E | A, B, C, D, E | A, B, C, D, E |
| CTLA-4 | A, B, C, D, F | XXX | A, B, C, D, F | A, B, C, D, F | A, B, C, D, F | A, B, C, D, F |
| TIM-3 | A, B, C, D, G | A, B, C, D, G | XXX | A, B, C, D, G | A, B, C, D, G | A, B, C, D, G |
| LAG-3 | A, B, C, D, H | A, B, C, D, H | A, B, C, D, H | XXX | A, B, C, D, H | A, B, C, D, H |
| TIGIT | A, B, C, D, I | A, B, C, D, I | A, B, C, D, I | A, B, C, D, I | XXX | A, B, C, D, I |
| BTLA | A, B, C, D, J | A, B, C, D, J | A, B, C, D, J | A, B, C, D, J | A, B, C, D, J | XXX |

| 1st/2nd antigens | PD-1 | CTLA-4 | TIM-3 | LAG-3 | TIGIT | BTLA |
|---|---|---|---|---|---|---|
| PD-1 | XXX | A, B, C, D, E | A, B, C, D, E | A, B, C, D, E | A, B, C, D, E | A, B, C, D, E |
| CTLA-4 | A, B, C, D, F | XXX | A, B, C, D, F | A, B, C, D, F | A, B, C, D, F | A, B, C, D, F |
| TIM-3 | A, B, C, D, G | A, B, C, D, G | XXX | A, B, C, D, G | A, B, C, D, G | A, B, C, D, G |
| LAG-3 | A, B, C, D, H | A, B, C, D, H | A, B, C, D, H | XXX | A, B, C, D, H | A, B, C, D, H |
| TIGIT | A, B, C, D, I | A, B, C, D, I | A, B, C, D, I | A, B, C, D, I | XXX | A, B, C, D, I |
| BTLA | A, B, C, D, J | A, B, C, D, J | A, B, C, D, J | A, B, C, D, J | A, B, C, D, J | XXX |

(doc 3154955)

Figure 40

| 1st/2nd antigens | PD-1 | CTLA-4 | TIM-3 | LAG-3 | TIGIT | BTLA |
|---|---|---|---|---|---|---|
| PD-1 | ------ | Q, R, S | Q, R, S | Q, R, S | Q, R, S | Q, R, S |
| CTLA-4 | Q, R, T | ------ | Q, R, T | Q, R, T | Q, R, T | Q, R, T |
| TIM-3 | Q, R, U | Q, R, U | ------ | Q, R, U | Q, R, U | Q, R, U |
| LAG-3 | Q, R, V | Q, R, V | Q, R, V | ------ | Q, R, V | Q, R, V |
| TIGIT | Q, R, W | Q, R, W | Q, R, W | Q, R, W | ------ | Q, R, W |
| BTLA | Q, R, X | Q, R, X | Q, R, X | Q, R, X | Q, R, X | ------ | e.g. anti-PD1, anti-CTLA4

FIGURE 54

| XENP (bivalent mAb) | Clone | VH | VL | KD (M; human BTLA) |
|---|---|---|---|---|
| 20269 | 9C6 | H0 | L0 | 1.3E-08 |
| 20744 | 9C6 | H0 | L1 | 1.4E-08 |
| 20745 | 9C6 | H0 | L2 | 1.9E-08 |
| 20746 | 9C6 | H1 | L0 | 1.8E-08 |
| 20747 | 9C6 | H1 | L1 | 2.7E-08 |
| 20748 | 9C6 | H1 | L2 | 4.2E-08 |
| 20749 | 9C6 | H2 | L0 | 2.1E-08 |
| 20750 | 9C6 | H2 | L1 | 3.7E-08 |
| 20751 | 9C6 | H2 | L2 | 5.1E-08 |
| 20752 | 9C6 | H3 | L0 | 2.3E-08 |
| 20753 | 9C6 | H3 | L1 | 3.2E-08 |
| 20754 | 9C6 | H3 | L2 | 3.1E-08 |
| 20872 | 9C6 | H1.1 | L1 | 2.4E-08 |
| 20873 | 9C6 | H1.2 | L1 | 3.8E-08 |
| 20874 | 9C6 | H1.3 | L1 | 5.0E-08 |
| 20875 | 9C6 | H1.4 | L1 | 4.5E-08 |
| 20876 | 9C6 | H1.5 | L1 | 4.7E-08 |
| 20877 | 9C6 | H1.6 | L1 | 4.6E-08 |
| 20878 | 9C6 | H1.7 | L1 | 4.5E-08 |
| 20879 | 9C6 | H1.8 | L1 | 4.7E-08 |
| 20880 | 9C6 | H1.9 | L1 | 3.5E-08 |
| 20881 | 9C6 | H1.10 | L1 | 5.1E-08 |
| 20882 | 9C6 | H1.11 | L1 | 2.2E-08 |
| 20883 | 9C6 | H1.12 | L1 | 3.4E-08 |
| 20884 | 9C6 | H1.13 | L1 | 3.0E-08 |
| 20885 | 9C6 | H1.14 | L1 | 3.4E-08 |
| 20886 | 9C6 | H1.15 | L1 | 3.4E-08 |
| 20887 | 9C6 | H1.16 | L1 | 3.7E-08 |
| 20888 | 9C6 | H1 | L1.1 | 3.1E-08 |
| 20889 | 9C6 | H1 | L1.2 | 3.0E-08 |
| 20890 | 9C6 | H1 | L1.3 | 3.2E-08 |
| 20891 | 9C6 | H1 | L1.4 | 3.1E-08 |
| 20892 | 9C6 | H1 | L1.5 | 3.1E-08 |
| 20893 | 9C6 | H1 | L1.6 | 3.4E-08 |
| 20894 | 9C6 | H1 | L1.7 | 6.2E-08 |

FIGURE 55A

| Fab XENP | VH | VL | Human LAG-3 Fab $K_D$ (M) | Fab $T_m$ (°C) |
|---|---|---|---|---|
| 20847 | H1 | L2 | 1.37E-08 | 73.5 |
| 21228 | H1.1 | L2 | 1.43E-08 | 72.5 |
| 21232 | H1.5 | L2 | 1.73E-08 | 73 |
| 21235 | H1.8 | L2 | 1.15E-08 | 72.5 |
| 21236 | H1.9 | L2 | 1.26E-08 | 73 |
| 21239 | H1.12 | L2 | 1.25E-08 | 73.5 |
| 21245 | H1.18 | L2 | 1.27E-08 | 72.5 |
| 21249 | H1.22 | L2 | 9.50E-09 | 72.5 |
| 21256 | H1.29 | L2 | 1.30E-08 | 73.5 |
| 21264 | H1.37 | L2 | 3.60E-09 | 73 |
| 21284 | H1.57 | L2 | 2.36E-08 | 73.5 |
| 21286 | H1.59 | L2 | 3.61E-08 | 73.5 |
| 21291 | H1.64 | L2 | 6.71E-09 | 73 |
| 21292 | H1.65 | L2 | 7.08E-09 | 73 |
| 21295 | H1.68 | L2 | 1.31E-08 | 72.5 |
| 21301 | H1.70 | L2 | 5.47E-09 | 72.5 |
| 21302 | H1.71 | L2 | 1.25E-08 | 74.5 |
| 21304 | H1.73 | L2 | 1.63E-08 | 73.5 |
| 21306 | H1.75 | L2 | 1.69E-08 | 74 |
| 21327 | H1.96 | L2 | 1.93E-08 | 73.5 |
| 21329 | H1.98 | L2 | 1.11E-08 | 73.5 |
| 21332 | H1.101 | L2 | 1.43E-08 | 73.5 |
| 21336 | H1.105 | L2 | 5.41E-09 | 73 |
| 21339 | H1.108 | L2 | 1.29E-08 | 73.5 |
| 21342 | H1.111 | L2 | 1.18E-08 | 73.5 |
| 21344 | H1.113 | L2 | 1.16E-08 | 73 |
| 21351 | H1 | L2.4 | 1.07E-08 | 71.5 |
| 21353 | H1 | L2.6 | 1.68E-08 | 70.5 |
| 21360 | H1 | L2.13 | 1.17E-08 | 74 |
| 21369 | H1 | L2.22 | 1.74E-08 | 71 |
| 21370 | H1 | L2.23 | 9.74E-09 | 73 |
| 21371 | H1 | L2.24 | 1.80E-08 | 73 |
| 21382 | H1 | L2.35 | 5.44E-09 | 73 |
| 21392 | H1 | L2.45 | 5.09E-09 | 72 |
| 21394 | H1 | L2.47 | 3.40E-09 | 73.5 |
| 21395 | H1 | L2.48 | 8.27E-09 | 72 |
| 21401 | H1 | L2.50 | 2.30E-09 | 73.5 |
| 21402 | H1 | L2.51 | 8.47E-09 | 73 |
| 21409 | H1 | L2.58 | 3.11E-09 | 77 |

FIGURE 55B

| Fab XENP | VH | VL | Human LAG-3 Fab $K_D$ (M) | Fab $T_m$ (°C) |
|---|---|---|---|---|
| 21411 | H1 | L2.60 | 1.46E-08 | 75 |
| 21421 | H1 | L2.70 | 6.58E-09 | 74 |
| 21423 | H1 | L2.72 | 1.15E-08 | 73 |
| 21424 | H1 | L2.73 | 7.68E-09 | 74 |
| 21426 | H1 | L2.75 | 1.61E-08 | 74.5 |
| 21609 | H1.64 | L2.35 | 1.16E-08 | |
| 21610 | H1.64 | L2.47 | 3.30E-09 | |
| 21611 | H1.64 | L2.50 | 2.34E-09 | |
| 21612 | H1.70 | L2.35 | 1.30E-08 | |
| 21613 | H1.70 | L2.47 | 6.29E-09 | |
| 21614 | H1.70 | L2.50 | 6.48E-09 | |
| 21615 | H1.105 | L2.35 | 5.82E-09 | |
| 21616 | H1.105 | L2.47 | 3.62E-09 | |
| 21617 | H1.105 | L2.50 | 2.02E-09 | |
| 21705 | H.117 | L2 | 2.90E-09 | |
| 21706 | H.118 | L2 | 4.06E-09 | |
| 21707 | H.119 | L2 | 7.72E-09 | |
| 21708 | H.120 | L2 | 8.48E-09 | |
| 21709 | H.121 | L2 | 3.19E-09 | |
| 21710 | H.122 | L2 | 4.54E-09 | |
| 21711 | H.123 | L2 | 7.63E-09 | |
| 21712 | H.124 | L2 | 1.08E-08 | |
| 21713 | H.126 | L2 | 1.63E-09 | |
| 21714 | H.128 | L2 | 5.70E-09 | |
| 21715 | H.129 | L2 | 1.16E-08 | |
| 21716 | H.130 | L2 | 9.43E-09 | |
| 21717 | H.131 | L2 | 1.63E-08 | |
| 21718 | H.132 | L2 | 2.12E-08 | |
| 21719 | H.133 | L2 | 1.60E-08 | |
| 21720 | H.134 | L2 | 2.45E-08 | |
| 21721 | H.135 | L2 | 5.71E-09 | |
| 21722 | H.136 | L2 | 3.03E-09 | |
| 21723 | H.137 | L2 | 7.26E-09 | |
| 21724 | H.138 | L2 | 8.29E-09 | |
| 21725 | H.139 | L2 | 7.00E-09 | |
| 21726 | H.140 | L2 | 1.03E-08 | |
| 21727 | H.141 | L2 | 4.74E-09 | |
| 21728 | H.142 | L2 | 1.61E-06 | |
| 21729 | H.143 | L2 | 4.70E-09 | |

FIGURE 55C

| Fab XENP | VH | VL | Human LAG-3 Fab $K_D$ (M) | Fab $T_m$ (°C) |
|---|---|---|---|---|
| 21730 | H.144 | L2 | 1.64E-09 | |
| 21731 | H.145 | L2 | 5.19E-09 | |
| 21732 | H.146 | L2 | 2.95E-09 | |
| 21794 | H1.125 | L2 | 8.13E-10 | |
| 21795 | H1.127 | L2 | 2.36E-09 | |
| 21796 | H1 | L2.102 | 1.21E-08 | |
| 21801 | H1 | L2.103 | 3.22E-08 | |
| 21802 | H1 | L2.104 | 2.09E-07 | |
| 21803 | H1 | L2.105 | 8.35E-08 | |
| 21804 | H1 | L2.106 | 1.43E-07 | |
| 21805 | H1 | L2.107 | | |
| 21806 | H1 | L2.108 | | |
| 21807 | H1 | L2.109 | 1.68E-08 | |
| 21808 | H1 | L2.110 | | |
| 21809 | H1 | L2.111 | 2.24E-09 | |
| 21810 | H1 | L2.112 | 3.26E-09 | |
| 21811 | H1 | L2.113 | 1.29E-09 | |
| 21812 | H1 | L2.114 | 2.79E-09 | |
| 21813 | H1 | L2.115 | 6.06E-09 | |
| 21814 | H1 | L2.116 | 1.58E-09 | |
| 21815 | H1 | L2.117 | | |
| 21816 | H1 | L2.118 | 1.13E-08 | |
| 21817 | H1 | L2.119 | 3.99E-09 | |
| 21818 | H1 | L2.120 | 2.90E-09 | |
| 21819 | H1 | L2.121 | 1.12E-08 | |
| 21912 | H1.117 | L2.50 | | |
| 21913 | H1.125 | L2.50 | 1.75E-10 | |
| 21914 | H1.126 | L2.50 | 2.75E-10 | |
| 21915 | H1.144 | L2.50 | 4.63E-10 | |
| 21916 | H1.127 | L2.50 | 5.28E-10 | |
| 21917 | H1.136 | L2.50 | 5.12E-10 | |
| 21918 | H1.154 | L2.50 | 9.22E-10 | |
| 21919 | H1.141 | L2.50 | 1.71E-09 | |
| 21920 | H1.117 | L2.113 | 7.96E-10 | |
| 21921 | H1.125 | L2.113 | 1.38E-10 | |
| 21922 | H1.126 | L2.113 | 3.96E-10 | |
| 21923 | H1.144 | L2.113 | 2.84E-10 | |
| 21924 | H1.127 | L2.113 | 5.20E-10 | |
| 21925 | H1.136 | L2.113 | 3.08E-10 | |

FIGURE 55D

| Fab XENP | VH | VL | Human LAG-3 Fab K$_D$ (M) | Fab T$_m$ (°C) |
|---|---|---|---|---|
| 21926 | H1.154 | L2.113 | 9.08E-10 | |
| 21927 | H1.141 | L2.113 | 5.63E-10 | |
| 21928 | H1.117 | L2.116 | 3.23E-10 | |
| 21929 | H1.125 | L2.116 | 3.64E-10 | |
| 21930 | H1.126 | L2.116 | 9.37E-10 | |
| 21931 | H1.144 | L2.116 | 9.74E-10 | |
| 21932 | H1.127 | L2.116 | 1.66E-09 | |
| 21933 | H1.136 | L2.116 | 1.31E-09 | |
| 21934 | H1.154 | L2.116 | 3.58E-09 | |
| 21935 | H1.141 | L2.116 | 2.16E-09 | |
| 21915 | H1.144 | L2.50 | 7.66E-10 | |
| 21923 | H1.144 | L2.113 | 7.31E-10 | |
| 22138 | H1.158 | L2.126 | 1.58E-07 | |
| 22139 | H1.159 | L2.126 | 2.12E-07 | |
| 22140 | H1.160 | L2.126 | 1.70E-07 | |
| 22141 | H1.161 | L2.126 | 8.77E-08 | |
| 22142 | H1.162 | L2.126 | 1.20E-07 | |
| 22143 | H1.163 | L2.126 | 4.62E-07 | |
| 22144 | H1.164 | L2.126 | 3.46E-07 | |
| 22145 | H1.165 | L2.126 | 2.01E-07 | |
| 22146 | H1.166 | L2.126 | 2.59E-07 | |
| 22147 | H1.167 | L2.126 | 4.12E-08 | |
| 22148 | H1.168 | L2.126 | 3.43E-07 | |
| 22149 | H1.169 | L2.126 | 3.24E-07 | |
| 22453 | H1.144 | L2.131 | 2.00E-09 | |
| 22454 | H1.167 | L2.128 | 3.00E-07 | |
| 22455 | H1.167 | L2.129 | 1.68E-06 | |
| 22456 | H1.167 | L2.130 | 2.64E-07 | |
| 22457 | H1.167 | L2.131 | 3.76E-07 | |
| 22461 | H1.125 | L2.131 | 1.67E-09 | |
| 22450 | H1.144 | L2.128 | 2.55E-09 | 67 |
| 22451 | H1.144 | L2.129 | 4.26E-09 | 67.5 |
| 22452 | H1.144 | L2.130 | 4.95E-09 | 68.5 |
| 22458 | H1.125 | L2.128 | 2.24E-09 | 65 |
| 22459 | H1.125 | L2.129 | 5.64E-09 | 67 |
| 22460 | H1.125 | L2.130 | 3.21E-09 | 67 |
| 22570 | H1.144 | L2.132 | 2.44E-09 | 66.5 |
| 22571 | H1.144 | L2.133 | 4.71E-09 | 67 |
| 22572 | H1.144 | L2.134 | 5.54E-09 | 69 |

FIGURE 55E

| Fab XENP | VH | VL | Human LAG-3 Fab $K_D$ (M) | Fab $T_m$ (°C) |
|---|---|---|---|---|
| 22574 | H1.125 | L2.132 | 1.98E-09 | 65.5 |
| 22575 | H1.125 | L2.133 | 3.19E-09 | 65 |
| 22578 | H1.141 | L2.132 | 2.93E-12 | 66.5 |
| 22579 | H1.141 | L2.133 | 9.21E-09 | 68 |
| 22580 | H1.141 | L2.134 | 4.12E-09 | 69.5 |
| 22609 | H1.144 | L2.136 | 4.60E-09 | 67.5 |
| 22610 | H1.125 | L2.136 | 3.81E-09 | 66 |
| 22611 | H1.141 | L2.136 | 4.30E-09 | 68 |
| 22612 | H1.144 | L2.137 | 2.03E-08 | |
| 22613 | H1.125 | L2.137 | 5.09E-09 | 66 |
| 22614 | H1.141 | L2.137 | 7.35E-09 | 68.5 |
| 22576 | H1.125 | L2.134 | 3.46E-09 | 66.5 |
| 22615 | H1.144 | L2.126 | 2.69E-09 | |
| 22616 | H1.144 | L2.91 | 1.26E-08 | 74 |
| 22617 | H1.144 | L2.93 | 8.31E-09 | 72.5 |
| 22618 | H1.144 | L2.122 | 9.12E-09 | 74.5 |
| 22619 | H1.144 | L2.124 | 1.03E-08 | 73.5 |
| 22620 | H1.125 | L2.126 | 1.20E-09 | 64 |
| 22621 | H1.125 | L2.91 | 5.96E-09 | 73.5 |
| 22622 | H1.125 | L2.93 | 5.81E-09 | 72 |
| 22623 | H1.125 | L2.122 | 6.81E-09 | 73 |
| 22624 | H1.125 | L2.124 | 7.00E-09 | 73 |
| 22652 | H1.144 | L2.138 | 1.32E-09 | 74 |
| 22653 | H1.144 | L2.139 | 2.41E-09 | |
| 22654 | H1.144 | L2.140 | 2.89E-09 | |
| 22655 | H1.144 | L2.141 | 3.65E-09 | |
| 22656 | H1.144 | L2.142 | 1.29E-09 | 74 |
| 22657 | H1.144 | L2.143 | 3.33E-09 | |
| 22658 | H1.144 | L2.144 | 3.04E-09 | |
| 22659 | H1.144 | L2.145 | 3.43E-09 | |
| 22660 | H1.125 | L2.138 | 9.29E-10 | 73.5 |
| 22661 | H1.125 | L2.139 | 2.34E-09 | |
| 22662 | H1.125 | L2.140 | 2.24E-09 | 73.5 |
| 22663 | H1.125 | L2.141 | 2.41E-09 | 73 |
| 22664 | H1.125 | L2.142 | 3.62E-10 | 73.5 |
| 22665 | H1.125 | L2.143 | 2.74E-09 | |
| 22666 | H1.125 | L2.144 | 2.58E-09 | |
| 22667 | H1.125 | L2.145 | 2.70E-09 | |

| XENP | Clone | VH | VL | KD (M) | kdis(1/s) | DSF T$_M$ (°C) |
|---|---|---|---|---|---|---|
| 20844 | 7G8 | H3 | L1 | 4.84E-08 | 3.51E-02 | 59.0 |
| 20911 | 7G8 | H3.1 | L1 | 2.13E-08 | 6.47E-03 | |
| 20912 | 7G8 | H3.2 | L1 | 5.51E-08 | 1.22E-02 | |
| 20913 | 7G8 | H3.3 | L1 | 2.16E-08 | 7.75E-03 | |
| 20914 | 7G8 | H3.4 | L1 | 1.64E-08 | 7.57E-03 | |
| 20915 | 7G8 | H3.5 | L1 | 8.38E-08 | 3.72E-03 | |
| 20916 | 7G8 | H3.6 | L1 | 6.50E-08 | 1.90E-02 | |
| 20917 | 7G8 | H3.8 | L1 | 1.62E-08 | 8.26E-03 | |
| 20918 | 7G8 | H3 | L1.1 | 8.19E-08 | 2.45E-02 | |
| 20919 | 7G8 | H3 | L1.2 | Weak | Weak | |
| 20920 | 7G8 | H3 | L1.3 | Weak | Weak | |
| 20921 | 7G8 | H3 | L1.4 | 8.16E-08 | 2.17E-02 | |
| 20922 | 7G8 | H3 | L1.5 | Weak | Weak | |
| 20923 | 7G8 | H3 | L1.6 | 4.42E-06 | 3.89E-02 | |
| 20924 | 7G8 | H3 | L1.8 | 6.43E-08 | 1.41E-02 | |
| 20925 | 7G8 | H3.1 | L1.1 | 4.31E-08 | 5.78E-03 | |
| 20926 | 7G8 | H3.1 | L1.5 | 5.26E-08 | 5.85E-03 | |
| 20927 | 7G8 | H3.5 | L1.1 | 1.61E-06 | 7.44E-03 | |
| 20928 | 7G8 | H3.5 | L1.5 | 7.31E-08 | 6.77E-03 | |
| 20929 | 7G8 | H3 | L0 | 4.17E-08 | 3.08E-02 | |
| 20930 | 7G8 | H0 | L0 | 6.59E-08 | 6.10E-02 | |
| 20931 | 7G8 | H1 | L0 | 1.09E-07 | 3.18E-02 | |
| 20932 | 7G8 | H2 | L0 | 8.33E-08 | 6.28E-02 | |
| 20933 | 7G8 | H0.1 | L0 | 2.44E-08 | 2.70E-02 | |
| 20934 | 7G8 | H0.2 | L0 | 2.11E-08 | 2.05E-02 | |
| 20935 | 7G8 | H0.3 | L0 | 3.07E-08 | 1.43E-02 | |
| 20936 | 7G8 | H0.4 | L0 | 3.55E-08 | 3.29E-02 | |
| 20937 | 7G8 | H0.5 | L0 | 5.33E-08 | 3.46E-02 | |
| 20938 | 7G8 | H0.6 | L0 | 1.86E-08 | 2.48E-02 | |
| 20939 | 7G8 | H0.7 | L0 | 7.57E-08 | 9.20E-02 | |
| 20940 | 7G8 | H0.8 | L0 | 2.24E-08 | 3.65E-02 | |
| 20941 | 7G8 | H0.9 | L0 | 7.91E-08 | 1.16E-01 | |
| 20942 | 7G8 | H0.10 | L0 | 1.08E-07 | 1.05E-01 | |
| 20943 | 7G8 | H0.11 | L0 | 8.29E-08 | 1.15E-01 | |
| 20944 | 7G8 | H0.12 | L0 | 1.19E-06 | 3.47E-01 | |
| 20945 | 7G8 | H0.13 | L0 | 9.61E-08 | 1.03E-01 | |
| 20946 | 7G8 | H0.14 | L0 | 1.85E-07 | 2.53E-01 | |
| 20947 | 7G8 | H0.15 | L0 | 7.88E-08 | 1.99E-01 | |

FIGURE 56B

| XENP | Clone | VH | VL | KD (M) | kdis(1/s) | DSF $T_M$ (°C) |
|---|---|---|---|---|---|---|
| 20948 | 7G8 | H0.17 | L0 | 4.14E-08 | 5.74E-02 | |
| 20949 | 7G8 | H0.18 | L0 | 3.74E-08 | 4.05E-02 | |
| 20950 | 7G8 | H0.19 | L0 | 3.85E-08 | 3.85E-02 | |
| 20951 | 7G8 | H0.20 | L0 | 7.09E-08 | 9.98E-02 | |
| 20952 | 7G8 | H0.21 | L0 | 6.30E-08 | 3.75E-02 | |
| 20953 | 7G8 | H0.22 | L0 | 9.92E-08 | 5.17E-02 | |
| 20954 | 7G8 | H0.23 | L0 | 4.49E-08 | 2.71E-02 | |
| 20955 | 7G8 | H0.24 | L0 | Weak | Weak | |
| 20956 | 7G8 | H0.25 | L0 | 9.22E-08 | 6.99E-02 | |
| 20957 | 7G8 | H0.26 | L0 | 1.09E-07 | 1.18E-01 | |
| 20958 | 7G8 | H0.27 | L0 | 3.45E-08 | 5.35E-02 | |
| 20959 | 7G8 | H0.28 | L0 | 5.30E-08 | 5.63E-02 | |
| 20960 | 7G8 | H0.29 | L0 | 6.01E-08 | 4.73E-02 | |
| 20961 | 7G8 | H0.30 | L0 | 2.31E-08 | 2.00E-02 | |
| 20962 | 7G8 | H0.31 | L0 | 1.05E-08 | 1.29E-02 | |
| 20963 | 7G8 | H0.32 | L0 | 6.80E-08 | 5.77E-02 | |
| 20964 | 7G8 | H0.33 | L0 | 6.46E-08 | 1.61E-02 | |
| 20965 | 7G8 | H0.34 | L0 | 3.29E-08 | 1.77E-02 | |
| 20966 | 7G8 | H0.35 | L0 | 8.17E-08 | 1.70E-02 | |
| 20967 | 7G8 | H0.36 | L0 | 3.61E-07 | 1.49E-01 | |
| 20968 | 7G8 | H0.37 | L0 | 8.90E-08 | 1.33E-01 | |
| 20969 | 7G8 | H0.38 | L0 | 1.00E-07 | 1.66E-01 | |
| 20970 | 7G8 | H0.39 | L0 | 1.19E-07 | 1.62E-01 | |
| 20971 | 7G8 | H0.40 | L0 | 2.45E-07 | 1.49E-01 | |
| 20972 | 7G8 | H0.41 | L0 | 6.40E-08 | 1.48E-01 | |
| 20973 | 7G8 | H0.42 | L0 | 5.41E-08 | 1.17E-01 | |
| 20974 | 7G8 | H0.43 | L0 | 1.30E-06 | 4.23E-01 | |
| 20975 | 7G8 | H0.44 | L0 | 5.03E-07 | 2.47E-01 | |
| 20976 | 7G8 | H0.45 | L0 | 3.41E-08 | 5.79E-02 | |
| 20977 | 7G8 | H0.46 | L0 | 2.45E-08 | 4.35E-02 | |
| 20978 | 7G8 | H0.47 | L0 | 3.94E-08 | 3.73E-02 | |
| 20979 | 7G8 | H0.48 | L0 | 3.16E-08 | 3.07E-02 | |
| 20980 | 7G8 | H0.49 | L0 | 2.89E-08 | 2.66E-02 | |
| 20981 | 7G8 | H0.50 | L0 | 2.70E-08 | 2.71E-02 | |
| 20982 | 7G8 | H0.51 | L0 | 3.12E-08 | 3.57E-02 | |
| 20983 | 7G8 | H0.52 | L0 | 3.38E-08 | 2.95E-02 | |
| 20984 | 7G8 | H0.53 | L0 | 3.05E-08 | 2.31E-02 | |
| 20985 | 7G8 | H0.54 | L0 | 6.81E-08 | 5.02E-02 | |

FIGURE 56C

| XENP | Clone | VH | VL | KD (M) | kdis(1/s) | DSF $T_M$ (°C) |
|---|---|---|---|---|---|---|
| 20986 | 7G8 | H0.55 | L0 | 4.72E-08 | 4.53E-02 | |
| 20987 | 7G8 | H0.56 | L0 | 1.37E-07 | 1.06E-01 | |
| 20988 | 7G8 | H0.57 | L0 | 5.69E-08 | 4.86E-02 | |
| 20989 | 7G8 | H0.58 | L0 | 6.58E-08 | 6.12E-02 | |
| 20990 | 7G8 | H0.59 | L0 | 3.52E-07 | 8.60E-02 | |
| 20991 | 7G8 | H0.60 | L0 | 7.59E-08 | 6.07E-02 | |
| 20992 | 7G8 | H0.61 | L0 | 1.86E-06 | 2.22E-01 | |
| 20993 | 7G8 | H0.62 | L0 | 3.12E-08 | 3.17E-02 | |
| 20994 | 7G8 | H0.63 | L0 | 2.50E-07 | 1.67E-01 | |
| 20995 | 7G8 | H0.64 | L0 | 9.55E-08 | 6.47E-02 | |
| 20996 | 7G8 | H0.65 | L0 | 1.53E-06 | 2.43E-01 | |
| 21001 | 7G8 | H0.66 | L0 | 3.19E-06 | 1.47E-01 | |
| 21002 | 7G8 | H0.67 | L0 | 1.12E-06 | 3.70E-01 | |
| 21003 | 7G8 | H0.68 | L0 | 7.10E-06 | 3.57E-01 | |
| 21004 | 7G8 | H0.69 | L0 | 1.34E-07 | 1.39E-01 | |
| 21005 | 7G8 | H0.70 | L0 | 1.45E-07 | 8.55E-02 | |
| 21006 | 7G8 | H0.71 | L0 | 2.35E-08 | 2.46E-02 | |
| 21007 | 7G8 | H0.72 | L0 | 4.36E-08 | 4.93E-02 | |
| 21008 | 7G8 | H0.73 | L0 | 1.57E-07 | 8.04E-02 | |
| 21009 | 7G8 | H0.74 | L0 | 6.39E-08 | 5.12E-02 | |
| 21010 | 7G8 | H0.75 | L0 | 9.21E-08 | 8.34E-02 | |
| 21011 | 7G8 | H0.76 | L0 | 5.84E-08 | 8.50E-02 | |
| 21012 | 7G8 | H0.77 | L0 | 1.07E-07 | 6.84E-02 | |
| 21013 | 7G8 | H0.78 | L0 | 1.56E-07 | 9.33E-02 | |
| 21014 | 7G8 | H0.79 | L0 | 5.11E-08 | 5.02E-02 | |
| 21015 | 7G8 | H0.80 | L0 | 1.11E-07 | 6.42E-02 | |
| 21016 | 7G8 | H0.81 | L0 | 6.41E-08 | 7.22E-02 | |
| 21017 | 7G8 | H0.82 | L0 | 1.08E-07 | 1.12E-01 | |
| 21018 | 7G8 | H0.83 | L0 | 3.88E-08 | 5.32E-02 | |
| 21019 | 7G8 | H0.84 | L0 | 1.04E-07 | 1.06E-01 | |
| 21020 | 7G8 | H0.85 | L0 | 5.13E-08 | 5.55E-02 | |
| 21021 | 7G8 | H0.86 | L0 | 8.11E-08 | 8.50E-02 | |
| 21022 | 7G8 | H0.87 | L0 | 1.61E-07 | 1.14E-01 | |
| 21023 | 7G8 | H0.88 | L0 | 8.22E-08 | 9.43E-02 | |
| 21024 | 7G8 | H0.89 | L0 | 6.36E-08 | 9.23E-02 | |
| 21025 | 7G8 | H0.90 | L0 | 6.07E-08 | 6.79E-02 | |
| 21026 | 7G8 | H0.91 | L0 | 8.91E-08 | 9.16E-02 | |
| 21027 | 7G8 | H0.92 | L0 | 7.61E-08 | 7.27E-02 | |

FIGURE 56D

| XENP | Clone | VH | VL | KD (M) | kdis(1/s) | DSF $T_M$ (°C) |
|---|---|---|---|---|---|---|
| 21028 | 7G8 | H0.93 | L0 | 6.69E-08 | 6.88E-02 | |
| 21029 | 7G8 | H0.94 | L0 | 9.67E-08 | 2.04E-01 | |
| 21030 | 7G8 | H0.95 | L0 | 3.11E-08 | 3.15E-02 | |
| 21031 | 7G8 | H0.96 | L0 | 3.74E-08 | 3.89E-02 | |
| 21032 | 7G8 | H0.97 | L0 | 4.45E-08 | 3.44E-02 | |
| 21033 | 7G8 | H0.98 | L0 | 3.64E-08 | 2.58E-02 | |
| 21034 | 7G8 | H0.99 | L0 | 2.23E-08 | 1.77E-02 | |
| 21035 | 7G8 | H0.100 | L0 | 3.37E-08 | 2.26E-02 | |
| 21036 | 7G8 | H0.101 | L0 | 2.27E-08 | 1.79E-02 | |
| 21037 | 7G8 | H0.102 | L0 | 1.64E-08 | 1.84E-02 | |
| 21038 | 7G8 | H0.103 | L0 | 1.09E-08 | 1.03E-02 | |
| 21039 | 7G8 | H0.104 | L0 | 7.96E-08 | 4.16E-01 | |
| 21040 | 7G8 | H0.105 | L0 | 3.54E-08 | 2.87E-02 | |
| 21041 | 7G8 | H0.106 | L0 | 5.76E-08 | 3.36E-01 | |
| 21042 | 7G8 | H0.107 | L0 | 5.06E-08 | 3.82E-02 | |
| 21043 | 7G8 | H0.110 | L0 | 1.16E-07 | 4.05E-02 | |
| 21044 | 7G8 | H0.111 | L0 | 2.33E-07 | 2.48E-01 | |
| 21045 | 7G8 | H0.112 | L0 | 4.31E-07 | 5.82E-01 | |
| 21046 | 7G8 | H0.114 | L0 | 4.20E-08 | 7.45E-02 | |
| 21047 | 7G8 | H0.115 | L0 | 6.98E-08 | 7.11E-02 | |
| 21048 | 7G8 | H0.116 | L0 | 3.52E-08 | 3.42E-02 | |
| 21049 | 7G8 | H0.117 | L0 | 8.34E-07 | 2.83E-01 | |
| 21050 | 7G8 | H0.118 | L0 | 1.50E-07 | 1.23E-01 | |
| 21051 | 7G8 | H0.119 | L0 | 2.71E-08 | 4.85E-02 | |
| 21052 | 7G8 | H0.120 | L0 | 8.60E-08 | 7.91E-02 | |
| 21053 | 7G8 | H0.121 | L0 | 1.92E-07 | 3.86E-01 | |
| 21054 | 7G8 | H0.122 | L0 | 4.63E-08 | 2.90E-02 | |
| 21055 | 7G8 | H0.123 | L0 | 6.45E-07 | 1.88E-01 | |
| 21056 | 7G8 | H0.124 | L0 | 2.15E-07 | 2.02E-01 | |
| 21057 | 7G8 | H0.125 | L0 | 9.51E-07 | 1.77E-01 | |
| 21058 | 7G8 | H0.126 | L0 | 3.12E-07 | 1.44E-01 | |
| 21059 | 7G8 | H0.127 | L0 | 1.35E-07 | 1.43E-01 | |
| 21060 | 7G8 | H0.128 | L0 | 1.34E-07 | 1.68E-01 | |
| 21061 | 7G8 | H0.129 | L0 | 1.17E-08 | 1.53E-02 | |
| 21062 | 7G8 | H0.130 | L0 | 1.24E-07 | 9.49E-02 | |
| 21063 | 7G8 | H0.131 | L0 | 1.44E-07 | 6.58E-01 | |
| 21064 | 7G8 | H0.132 | L0 | 3.56E-05 | 2.33E-02 | |
| 21065 | 7G8 | H0.134 | L0 | <1.0E-12 | <1.0E-07 | |

FIGURE 56E

| XENP | Clone | VH | VL | KD (M) | kdis(1/s) | DSF T$_M$ (°C) |
|---|---|---|---|---|---|---|
| 21066 | 7G8 | H0.141 | L0 | 1.11E-07 | 2.25E-01 | |
| 21067 | 7G8 | H0.142 | L0 | 6.72E-08 | 8.34E-02 | |
| 21068 | 7G8 | H0.143 | L0 | 2.35E-07 | 2.77E-01 | |
| 21069 | 7G8 | H0.145 | L0 | 6.09E-08 | 6.17E-02 | |
| 21070 | 7G8 | H0.146 | L0 | 5.40E-08 | 9.04E-02 | |
| 21071 | 7G8 | H0.147 | L0 | 5.53E-07 | 3.88E-01 | |
| 21072 | 7G8 | H0.148 | L0 | 2.10E-07 | 1.79E-01 | |
| 21074 | 7G8 | H0 | L0.1 | 9.61E-08 | 1.30E-01 | |
| 21075 | 7G8 | H0 | L0.2 | 8.81E-08 | 9.74E-02 | |
| 21076 | 7G8 | H0 | L0.3 | 1.86E-07 | 2.70E-01 | |
| 21077 | 7G8 | H0 | L0.4 | 1.09E-07 | 1.76E-01 | |
| 21078 | 7G8 | H0 | L0.5 | 4.48E-08 | 4.49E-01 | |
| 21079 | 7G8 | H0 | L0.6 | 1.28E-07 | 1.39E-01 | |
| 21080 | 7G8 | H0 | L0.7 | 5.79E-06 | 7.16E-02 | |
| 21081 | 7G8 | H0 | L0.8 | 1.16E-07 | 4.00E-01 | |
| 21082 | 7G8 | H0 | L0.9 | 8.20E-06 | 1.43E-01 | |
| 21083 | 7G8 | H0 | L0.10 | 6.42E-08 | 1.08E-01 | |
| 21084 | 7G8 | H0 | L0.11 | 2.70E-08 | 2.64E-02 | |
| 21085 | 7G8 | H0 | L0.12 | 6.51E-08 | 7.19E-02 | |
| 21086 | 7G8 | H0 | L0.13 | 7.75E-08 | 1.04E-01 | |
| 21087 | 7G8 | H0 | L0.14 | 1.19E-07 | 2.90E-01 | |
| 21088 | 7G8 | H0 | L0.15 | 1.57E-07 | 3.83E-01 | |
| 21089 | 7G8 | H0 | L0.16 | 0.00E+00 | <1.0E-07 | |
| 21090 | 7G8 | H0 | L0.17 | 2.80E-07 | 3.17E-01 | |
| 21091 | 7G8 | H0 | L0.18 | 6.26E-05 | 2.72E+01 | |
| 21092 | 7G8 | H0 | L0.19 | 1.27E-06 | 2.47E-01 | |
| 21093 | 7G8 | H0 | L0.20 | 5.16E-08 | 7.64E-02 | |
| 21094 | 7G8 | H0 | L0.21 | 5.43E-08 | 8.04E-02 | |
| 21095 | 7G8 | H0 | L0.22 | 1.06E-07 | 1.33E-01 | |
| 21096 | 7G8 | H0 | L0.23 | 5.58E-08 | 1.71E-01 | |
| 21101 | 7G8 | H0 | L0.24 | 4.43E-08 | 1.79E-01 | |
| 21102 | 7G8 | H0 | L0.25 | 6.10E-08 | 1.51E-01 | |
| 21103 | 7G8 | H0 | L0.26 | 7.99E-08 | 1.48E-01 | |
| 21104 | 7G8 | H0 | L0.27 | 5.62E-08 | 1.35E-01 | |
| 21105 | 7G8 | H0 | L0.28 | 7.77E-08 | 9.49E-02 | |
| 21106 | 7G8 | H0 | L0.29 | 7.83E-08 | 5.16E-02 | |
| 21107 | 7G8 | H0 | L0.30 | 5.72E-08 | 4.66E-02 | |
| 21108 | 7G8 | H0 | L0.31 | 1.05E-07 | 4.67E-02 | |

FIGURE 56F

| XENP | Clone | VH | VL | KD (M) | kdis(1/s) | DSF $T_M$ (°C) |
|---|---|---|---|---|---|---|
| 21109 | 7G8 | H0 | L0.32 | 4.68E-08 | 4.50E-02 | |
| 21110 | 7G8 | H0 | L0.33 | 6.87E+05 | 4.23E+08 | |
| 21111 | 7G8 | H0 | L0.34 | 2.75E-08 | 2.68E-02 | |
| 21112 | 7G8 | H0 | L0.35 | 9.77E-08 | 8.71E-02 | |
| 21113 | 7G8 | H0 | L0.36 | 1.20E-07 | 6.11E-02 | |
| 21114 | 7G8 | H0 | L0.37 | 3.00E-08 | 3.15E-02 | |
| 21115 | 7G8 | H0 | L0.38 | 1.12E-07 | 7.85E-02 | |
| 21116 | 7G8 | H0 | L0.39 | 3.17E-08 | 5.71E-02 | |
| 21117 | 7G8 | H0 | L0.40 | 2.27E-07 | 7.01E-01 | |
| 21118 | 7G8 | H0 | L0.41 | 8.48E-08 | 1.31E-01 | |
| 21119 | 7G8 | H0 | L0.42 | 2.50E-10 | 4.30E-03 | |
| 21120 | 7G8 | H0 | L0.43 | 2.39E-07 | 2.12E-01 | |
| 21121 | 7G8 | H0 | L0.44 | 2.46E-06 | 1.14E-01 | |
| 21122 | 7G8 | H0 | L0.45 | 1.75E-07 | 5.49E-01 | |
| 21123 | 7G8 | H0 | L0.46 | 2.60E-06 | 3.50E-01 | |
| 21124 | 7G8 | H0 | L0.47 | 6.27E-08 | 5.49E-02 | |
| 21125 | 7G8 | H0 | L0.48 | 3.15E-08 | 3.71E-02 | |
| 21126 | 7G8 | H0 | L0.49 | 5.22E-08 | 5.09E-02 | |
| 21127 | 7G8 | H0 | L0.50 | 4.37E-08 | 3.69E-02 | |
| 21128 | 7G8 | H0 | L0.51 | 2.23E-09 | 1.89E-02 | |
| 21129 | 7G8 | H0 | L0.52 | 5.88E-08 | 9.73E-02 | |
| 21130 | 7G8 | H0 | L0.53 | 3.55E-08 | 3.99E-02 | |
| 21131 | 7G8 | H0 | L0.54 | 8.64E-08 | 1.08E-01 | |
| 21132 | 7G8 | H0 | L0.55 | Weak | Weak | |
| 21133 | 7G8 | H0 | L0.56 | 6.02E-07 | 2.78E-01 | |
| 21134 | 7G8 | H0 | L0.57 | 3.63E-08 | 3.47E-02 | |
| 21135 | 7G8 | H0 | L0.58 | 1.65E-07 | 9.58E-02 | |
| 21136 | 7G8 | H0 | L0.59 | 2.27E-08 | 2.30E-02 | |
| 21137 | 7G8 | H0 | L0.60 | 2.65E-08 | 3.61E-02 | |
| 21138 | 7G8 | H0 | L0.61 | 9.30E-08 | 1.32E-01 | |
| 21139 | 7G8 | H0 | L0.62 | 2.91E-08 | 3.44E-02 | |
| 21140 | 7G8 | H0 | L0.63 | 3.40E-08 | 3.40E-02 | |
| 21141 | 7G8 | H0 | L0.64 | 3.69E-08 | 2.72E-02 | |
| 21142 | 7G8 | H0 | L0.65 | 3.09E-08 | 4.10E-02 | |
| 21143 | 7G8 | H0 | L0.66 | 7.34E-08 | 1.20E-01 | |
| 21144 | 7G8 | H0 | L0.67 | 1.26E-07 | 6.24E-02 | |
| 21145 | 7G8 | H0 | L0.68 | 8.99E-08 | 3.43E-01 | |
| 21146 | 7G8 | H0 | L0.69 | 5.94E-08 | 2.05E-01 | |

FIGURE 56G

| XENP | Clone | VH | VL | KD (M) | kdis(1/s) | DSF $T_M$ (°C) |
|---|---|---|---|---|---|---|
| 21147 | 7G8 | H0 | L0.70 | 4.22E-08 | 8.54E-02 | |
| 21148 | 7G8 | H0 | L0.71 | 1.79E-07 | 2.51E-01 | |
| 21149 | 7G8 | H0 | L0.72 | 1.23E-07 | 2.35E-01 | |
| 21150 | 7G8 | H0 | L0.73 | 7.55E-08 | 1.58E-01 | |
| 21151 | 7G8 | H0 | L0.74 | 1.64E-07 | 1.84E-01 | |
| 21152 | 7G8 | H0 | L0.75 | 9.32E-08 | 1.42E-01 | |
| 21153 | 7G8 | H0 | L0.76 | Weak | Weak | |
| 21154 | 7G8 | H0 | L0.77 | 1.87E-07 | 8.91E-02 | |
| 21155 | 7G8 | H0 | L0.78 | 2.94E-07 | 4.70E-02 | |
| 21156 | 7G8 | H0 | L0.79 | Weak | Weak | |
| 21157 | 7G8 | H0 | L0.80 | Weak | Weak | |
| 21158 | 7G8 | H0 | L0.81 | Weak | Weak | |
| 21159 | 7G8 | H0 | L0.82 | 6.04E-07 | 4.40E-01 | |
| 21160 | 7G8 | H0 | L0.83 | 6.50E-08 | 3.50E-02 | |
| 21161 | 7G8 | H0 | L0.84 | 3.52E-06 | 1.08E-01 | |
| 21162 | 7G8 | H0 | L0.85 | 9.89E-08 | 4.37E-02 | |
| 21163 | 7G8 | H0 | L0.86 | 4.90E-08 | 4.85E-02 | |
| 21164 | 7G8 | H0 | L0.87 | 1.25E-07 | 1.41E-01 | |
| 21165 | 7G8 | H0 | L0.88 | 1.90E-07 | 1.87E-01 | |
| 21166 | 7G8 | H0 | L0.89 | 3.52E-06 | 6.60E-02 | |
| 21167 | 7G8 | H0 | L0.90 | 2.54E-08 | 2.01E-02 | |
| 21168 | 7G8 | H0 | L0.91 | 1.12E-06 | 1.99E-01 | |
| 21169 | 7G8 | H0 | L0.92 | 1.20E-07 | 7.65E-02 | |
| 21170 | 7G8 | H0 | L0.93 | 4.81E-08 | 5.41E-02 | |
| 21171 | 7G8 | H0 | L0.94 | 6.64E-07 | 1.82E-01 | |
| 21172 | 7G8 | H0 | L0.95 | 7.61E-08 | 8.11E-02 | |
| 21173 | 7G8 | H0 | L0.96 | 7.95E-07 | 8.67E-02 | |
| 21174 | 7G8 | H0 | L0.97 | 6.75E-08 | 6.60E-02 | |
| 21175 | 7G8 | H0 | L0.98 | 6.19E-08 | 4.49E-02 | |
| 21176 | 7G8 | H0 | L0.99 | 3.97E-08 | 4.14E-02 | |
| 21177 | 7G8 | H0 | L0.100 | 8.53E-08 | 5.75E-02 | |
| 21178 | 7G8 | H0 | L0.101 | 3.33E-07 | 1.95E+00 | |
| 21179 | 7G8 | H0 | L0.102 | 1.04E-07 | 2.79E-01 | |
| 21180 | 7G8 | H0 | L0.103 | 1.50E-07 | 2.14E+01 | |
| 21181 | 7G8 | H0 | L0.104 | 6.11E+16 | 2.82E+26 | |
| 21182 | 7G8 | H0 | L0.105 | Weak | Weak | |
| 21183 | 7G8 | H0 | L0.106 | 3.27E-06 | 7.92E-02 | |
| 21184 | 7G8 | H0 | L0.107 | Weak | Weak | |

FIGURE 56H

| XENP | Clone | VH | VL | KD (M) | kdis(1/s) | DSF $T_M$ (°C) |
|---|---|---|---|---|---|---|
| 21558 | 7G8 | H3.1 | L0.59 | 7.44E-09 | 4.35E-03 | |
| 21559 | 7G8 | H3.4 | L0.59 | 6.72E-09 | 4.71E-03 | |
| 21560 | 7G8 | H0.129 | L0.59 | 7.05E-09 | 6.94E-03 | |
| 21561 | 7G8 | H0.31 | L0.59 | 6.39E-09 | 6.75E-03 | |
| 21562 | 7G8 | H0.103 | L0.59 | 3.09E-08 | 5.24E-03 | |
| 21563 | 7G8 | H0.71 | L0.59 | 7.04E-09 | 7.48E-03 | |
| 21564 | 7G8 | H3.1 | L0 | 6.73E-09 | 6.58E-03 | |
| 21565 | 7G8 | H3.4 | L0 | 8.47E-09 | 8.54E-03 | |
| 21566 | 7G8 | H3.1 | L0.11 | 4.56E-08 | 3.76E-02 | |
| 21567 | 7G8 | H3.4 | L0.11 | 5.84E-08 | 4.23E-02 | |
| 21568 | 7G8 | H0.129 | L0.11 | 1.26E-07 | 8.67E-02 | |
| 21569 | 7G8 | H3.1 | L0.34 | 1.05E-08 | 7.33E-03 | |
| 21570 | 7G8 | H3.4 | L0.34 | 1.13E-08 | 9.28E-03 | |
| 21571 | 7G8 | H0.129 | L0.34 | 1.33E-08 | 1.29E-02 | |
| 21662 | 7G8 | H3.18 | L1 | 3.04E-09 | 3.04E-03 | |
| 21663 | 7G8 | H3.15 | L1 | 3.50E-09 | 2.64E-03 | |
| 21664 | 7G8 | H3.19 | L1 | 7.41E-09 | 7.68E-03 | |
| 21665 | 7G8 | H3.17 | L1 | 4.07E-09 | 3.47E-03 | |
| 21666 | 7G8 | H3.16 | L1 | 1.63E-08 | 4.73E-03 | |
| 21667 | 7G8 | H3.21 | L1 | 8.57E-09 | 2.33E-03 | |
| 21668 | 7G8 | H3.22 | L1 | | | |
| 21669 | 7G8 | H3.23 | L1 | 4.10E-09 | 3.88E-03 | |
| 21670 | 7G8 | H3.18 | L1.11 | 2.88E-09 | 2.39E-03 | 54.5 |
| 21671 | 7G8 | H3.15 | L1.11 | 2.76E-09 | 2.48E-03 | |
| 21672 | 7G8 | H3.19 | L1.11 | 4.23E-09 | 4.54E-03 | |
| 21673 | 7G8 | H3.17 | L1.11 | 3.75E-09 | 2.73E-03 | |
| 21674 | 7G8 | H3.16 | L1.11 | 1.16E-08 | 3.38E-03 | |
| 21675 | 7G8 | H3.21 | L1.11 | 9.61E-09 | 2.05E-03 | |
| 21676 | 7G8 | H3.22 | L1.11 | | | |
| 21677 | 7G8 | H3.23 | L1.11 | 2.83E-09 | 2.29E-03 | |
| 21678 | 7G8 | H3.18 | L1.13 | 6.65E-09 | 5.02E-03 | |
| 21679 | 7G8 | H3.15 | L1.13 | 8.37E-09 | 4.87E-03 | |
| 21680 | 7G8 | H3.19 | L1.13 | 1.70E-08 | 9.72E-03 | |
| 21681 | 7G8 | H3.17 | L1.13 | 1.19E-08 | 7.68E-03 | |
| 21682 | 7G8 | H3.16 | L1.13 | 2.95E-08 | 1.38E-02 | |
| 21683 | 7G8 | H3.21 | L1.13 | 1.10E-08 | 5.13E-03 | |
| 21684 | 7G8 | H3.22 | L1.13 | | | |
| 21685 | 7G8 | H3.23 | L1.13 | 1.02E-08 | 7.76E-03 | |

FIGURE 56I

| XENP | Clone | VH | VL | KD (M) | kdis(1/s) | DSF $T_M$ (°C) |
|---|---|---|---|---|---|---|
| 21686 | 7G8 | H3.18 | L1.15 | 9.47E-09 | 7.62E-03 | |
| 21687 | 7G8 | H3.15 | L1.15 | 2.04E-08 | 7.79E-03 | |
| 21688 | 7G8 | H3.19 | L1.15 | 1.75E-08 | 1.04E-02 | |
| 21689 | 7G8 | H3.17 | L1.15 | 2.19E-08 | 1.21E-02 | |
| 21690 | 7G8 | H3.16 | L1.15 | 9.19E-08 | 9.61E-03 | |
| 21691 | 7G8 | H3.21 | L1.15 | 2.34E-08 | 8.44E-03 | |
| 21692 | 7G8 | H3.22 | L1.15 | 2.12E-08 | 1.31E-02 | |
| 21693 | 7G8 | H3.23 | L1.15 | 8.80E-09 | 6.46E-03 | |
| 21694 | 7G8 | H3 | L1.9 | 3.14E-07 | 1.16E-01 | |
| 21695 | 7G8 | H3 | L1.10 | 8.99E-08 | 3.06E-02 | |
| 21696 | 7G8 | H3 | L1.11 | 4.10E-08 | 1.48E-02 | |
| 21701 | 7G8 | H3 | L1.12 | 4.12E-06 | 2.07E-01 | |
| 21702 | 7G8 | H3 | L1.13 | 2.91E-07 | 8.61E-02 | |
| 21703 | 7G8 | H3 | L1.14 | 1.34E-07 | 2.39E-02 | |
| 21704 | 7G8 | H3 | L1.15 | 1.08E-06 | 3.49E-01 | |
| 21742 | 7G8 | H3.11 | L1.13 | 1.85E-08 | 1.25E-02 | |
| 21743 | 7G8 | H3.4 | L1.13 | 2.90E-08 | 2.04E-02 | |
| 21744 | 7G8 | H3.1 | L1.13 | 4.92E-08 | 1.89E-02 | |
| 21745 | 7G8 | H3.11 | L1.15 | 1.84E-08 | 1.33E-02 | |
| 21746 | 7G8 | H3.4 | L1.15 | 4.31E-08 | 1.71E-02 | |
| 21747 | 7G8 | H3.1 | L1.15 | 2.69E-07 | 0.0364 | |
| 21889 | 7G8 | H3.27 | L1 | 2.48E-09 | 3.04E-03 | |
| 21890 | 7G8 | H3.27 | L1.11 | 2.20E-09 | 1.81E-03 | |
| 21891 | 7G8 | H3.27 | L1.13 | 5.02E-09 | 5.79E-03 | |
| 21892 | 7G8 | H3.28 | L1 | 3.55E-09 | 4.33E-03 | |
| 21893 | 7G8 | H3.28 | L1.11 | 2.10E-09 | 2.67E-03 | |
| 21894 | 7G8 | H3.28 | L1.13 | 6.83E-09 | 7.95E-03 | |
| 22379 | 7G8 | H3.29 | L1.11 | | | |
| 22380 | 7G8 | H3.30 | L1.11 | 2.07E-09 | 2.11E-03 | 59.5 |
| 22381 | 7G8 | H3.31 | L1.11 | 6.94E-09 | 6.82E-03 | |
| 22382 | 7G8 | H3.32 | L1.11 | | | |
| 22383 | 7G8 | H3.33 | L1.11 | 6.00E-09 | 5.14E-03 | 62.5 |
| 22384 | 7G8 | H3.34 | L1.11 | 9.12E-09 | 2.43E-03 | 55.0 |
| 22385 | 7G8 | H3.35 | L1.11 | 3.18E-09 | 2.66E-03 | 56.0 |
| 22386 | 7G8 | H3.36 | L1.11 | | | |
| 22387 | 7G8 | H3.37 | L1.11 | | | |
| 22388 | 7G8 | H3.38 | L1.11 | | | |
| 22389 | 7G8 | H3.39 | L1.11 | 3.57E-09 | 2.54E-03 | |

FIGURE 56J

| XENP | Clone | VH | VL | KD (M) | kdis(1/s) | DSF $T_M$ (°C) |
|---|---|---|---|---|---|---|
| 22390 | 7G8 | H3.40 | L1.11 | | | |
| 22391 | 7G8 | H3.41 | L1.11 | | | |
| 22392 | 7G8 | H3.42 | L1.11 | | | |
| 22393 | 7G8 | H3.43 | L1.11 | | | |
| 22394 | 7G8 | H3.44 | L1.11 | | | |
| 22395 | 7G8 | H3.45 | L1.11 | | | |
| 22396 | 7G8 | H3.46 | L1.11 | | | |
| 22401 | 7G8 | H3.47 | L1.11 | 3.50E-09 | 2.68E-03 | |
| 22402 | 7G8 | H3.48 | L1.11 | | | |
| 22403 | 7G8 | H3.49 | L1.11 | 2.37E-09 | 2.85E-03 | 55.0 |
| 22404 | 7G8 | H3.50 | L1.11 | | | |
| 22405 | 7G8 | H3.51 | L1.11 | | | |
| 22406 | 7G8 | H3.52 | L1.11 | | | |
| 22407 | 7G8 | H3.53 | L1.11 | | | |
| 22408 | 7G8 | H3.18 | L1.16 | 2.83E-09 | 3.27E-03 | 58.0 |
| 22409 | 7G8 | H3.18 | L1.17 | 3.04E-09 | 3.25E-03 | 56.0 |
| 22410 | 7G8 | H3.18 | L1.18 | | | |
| 22411 | 7G8 | H3.18 | L1.19 | | | |
| 22412 | 7G8 | H3.18 | L1.20 | | | |
| 22413 | 7G8 | H3.18 | L1.21 | | | |
| 22414 | 7G8 | H3.18 | L1.22 | | | |
| 22415 | 7G8 | H3.18 | L1.23 | | | |
| 22416 | 7G8 | H3.18 | L1.24 | | | |
| 22417 | 7G8 | H3.18 | L1.25 | | | |
| 22418 | 7G8 | H3.18 | L1.26 | | | |
| 22419 | 7G8 | H3.18 | L1.27 | | | |
| 22420 | 7G8 | H3.18 | L1.28 | 2.36E-09 | 2.55E-03 | |
| 22421 | 7G8 | H3.18 | L1.29 | | | |
| 22422 | 7G8 | H3.18 | L1.30 | 1.95E-09 | 3.13E-03 | 63.0 |
| 22423 | 7G8 | H3.18 | L1.31 | 2.65E-09 | 2.84E-03 | |
| 22424 | 7G8 | H3.18 | L1.32 | 2.98E-09 | 2.95E-03 | |
| 22425 | 7G8 | H3.18 | L1.33 | | | |
| 22582 | 7G8 | H3.30 | L1.30 | 2.34E-09 | 2.03E-03 | 67.5 |
| 22583 | 7G8 | H3.33 | L1.30 | 4.51E-09 | 3.15E-03 | 68.5 |
| 22588 | 7G8 | H3.54 | L1.30 | 8.45E-10 | 2.18E-03 | 65.5 |
| 22589 | 7G8 | H3.55 | L1.30 | 2.86E-09 | 4.56E-03 | 67.5 |
| 22590 | 7G8 | H3.56 | L1.30 | 4.85E-08 | 1.55E-03 | 66.5 |
| 22591 | 7G8 | H3.57 | L1.30 | 3.24E-09 | 3.45E-03 | 68.5 |

FIGURE 56K

| XENP | Clone | VH | VL | KD (M) | kdis(1/s) | DSF $T_M$ (°C) |
|---|---|---|---|---|---|---|
| 22592 | 7G8 | H3.58 | L1.30 | 1.97E-09 | 2.31E-03 | 67.0 |
| 22593 | 7G8 | H3.59 | L1.30 | 3.54E-09 | 3.88E-03 | 69.0 |
| 22594 | 7G8 | H3.30 | L1.34 | 6.30E-10 | 1.48E-03 | 68.5 |
| 22595 | 7G8 | H3.30 | L1.36 | 2.86E-09 | 2.86E-03 | 69.5 |
| 22596 | 7G8 | H3.33 | L1.34 | 3.45E-09 | 3.02E-03 | 68.5 |
| 22601 | 7G8 | H3.33 | L1.36 | 1.09E-08 | 6.95E-03 | 70.0 |

FIGURE 57A

| XENP | Fab side (Anti-LAG-3) | scFv side (Anti-CTLA-4) | Human LAG-3 KD (M) |
|---|---|---|---|
| 22518 | 2A11_H1.144_L2.133 | [CTLA-4]_H3.23_L0.129 | 1.7E-09 |
| 22506 | 2A11_H1.144_L2.113 | [CTLA-4]_H3.23_L0.129 | 2.0E-10 |
| 22505 | 2A11_H1.125_L2.113 | [CTLA-4]_H3.23_L0.129 | 4.0E-10 |
| 22509 | 2A11_H1_L2.113 | [CTLA-4]_H3.23_L0.129 | 7.8E-10 |
| 20444 | 2A11_H1L2 | [CTLA-4]_H3.23_L0.129 | 3.5E-09 |
| 21859 | 2A11_H1_L2.47 | [CTLA-4]_H3.23_L0.129 | 3.5E-10 |
| 21860 | 2A11_H1_L2.50 | [CTLA-4]_H3.23_L0.129 | 1.2E-09 |
| 22507 | 2A11_H1.117_L2.116 | [CTLA-4]_H3.23_L0.129 | 6.2E-10 |
| 22508 | 2A11_H1.144_L2 | [CTLA-4]_H3.23_L0.129 | 1.2E-09 |
| 22510 | 2A11_H1_L2.25 | [CTLA-4]_H3.23_L0.129 | 2.3E-08 |
| 22630 | 2A11_H1.144_L2.137 | [CTLA-4]_H3.23_L0.129 | 9.4E-10 |

FIGURE 57B

| XENP | Fab side (Anti-LAG-3) | scFv side (Anti-CTLA-4) | human LAG-3 KD (nM) |
|---|---|---|---|
| 20833 | 7G8_H3L1 | [CTLA-4]_H3.23_L0.129 | 9.1 |
| 21895 | 7G8_H3.18_L1 | [CTLA-4]_H3.23_L0.129 | 1.1 |
| 21896 | 7G8_H3.18_L1.11 | [CTLA-4]_H3.23_L0.129 | 1.0 |
| 21901 | 7G8_H3.15_L1.11 | [CTLA-4]_H3.23_L0.129 |  |
| 21902 | 7G8_H3.23_L1.11 | [CTLA-4]_H3.23_L0.129 | 1.1 |
| 21903 | 7G8_H3.18_L1.13 | [CTLA-4]_H3.23_L0.129 | 2.2 |
| 21904 | 7G8_H3.28_L1 | [CTLA-4]_H3.23_L0.129 | 1.7 |
| 21905 | 7G8_H3.28_L1.11 | [CTLA-4]_H3.23_L0.129 | 1.1 |
| 21906 | 7G8_H3.28_L1.13 | [CTLA-4]_H3.23_L0.129 | 2.1 |
| 22555 | 7G8_H3.30_L1.11 | [CTLA-4]_H3.23_L0.129 | 1.2 |
| 22556 | 7G8_H3.33_L1.11 | [CTLA-4]_H3.23_L0.129 | 2.6 |
| 22557 | 7G8_H3.18_L1.30 | [CTLA-4]_H3.23_L0.129 | 0.7 |
| 22558 | 7G8_H3.30_L1.30 | [CTLA-4]_H3.23_L0.129 | 0.3 |
| 22559 | 7G8_H3.33_L1.30 | [CTLA-4]_H3.23_L0.129 | 1.6 |
| 22602 | 7G8_H3.30_L1.34 | [CTLA-4]_H3.23_L0.129 | 0.2 |
| 22603 | 7G8_H3.30_L1.36 | [CTLA-4]_H3.23_L0.129 | 0.4 |

FIGURE 62A

| XENP | Fab side (anti-LAG-3) | scFv side (anti-PD-1) | Human LAG-3 KD (M) |
|---|---|---|---|
| 20206 | 2A11_H1L2 | 1G6 L1.194_H1.279 | 2.2E-09 |
| 21584 | 2A11_H1_L2.93 | 1G6 L1.194_H1.279 | 1.4E-08 |
| 22123 | 2A11_H1_L2.122 | 1G6 L1.194_H1.279 | 1.9E-08 |
| 22125 | 2A11_H1_L2.124 | 1G6 L1.194_H1.279 | 2.0E-08 |
| 21582 | 2A11_H1_L2.91 | 1G6 L1.194_H1.279 | 6.2E-09 |
| 22627 | 2A11_H1.144_L2.133 | 1G6 L1.194_H1.279 | 3.8E-10 |
| 22628 | 2A11_H1.125_L2.113 | 1G6 L1.194_H1.279 | <1.0E-12 |
| 22629 | 2A11_H1.144_L2.113 | 1G6 L1.194_H1.279 | 4.4E-11 |

FIGURE 62B

| XENP | Fab side (anti-LAG-3) | scFv side (anti-PD-1) | Human LAG-3 KD (nM) |
|---|---|---|---|
| 22521 | 7G8_H3.18_L1.11 | 1G6_L1.194_H1.279 | NT |
| 22522 | 7G8_H3.28_L1.13 | 1G6_L1.194_H1.279 | NT |
| 22565 | 7G8_H3.30_L1.11 | 1G6_L1.194_H1.279 | NT |
| 22566 | 7G8_H3.33_L1.11 | 1G6_L1.194_H1.279 | NT |
| 22567 | 7G8_H3.18_L1.30 | 1G6_L1.194_H1.279 | 1.0 |
| 22568 | 7G8_H3.30_L1.30 | 1G6_L1.194_H1.279 | 0.3 |
| 22569 | 7G8_H3.33_L1.30 | 1G6_L1.194_H1.279 | 1.5 |
| 22604 | 7G8_H3.30_L1.34 | 1G6_L1.194_H1.279 | 0.5 |
| 22605 | 7G8_H3.30_L1.36 | 1G6_L1.194_H1.279 | 0.5 |

The results shown are based upon data generated by the TCGA Research Network:
http://cancergenome.nih.gov/

**p ≤ 0.01
*p ≤ 0.05

Study #1

FIGURE 76C      FIGURE 76D
Study #2
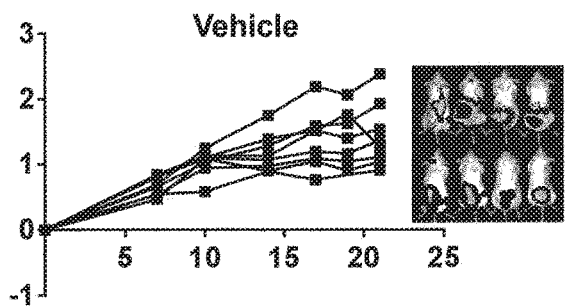
Vehicle
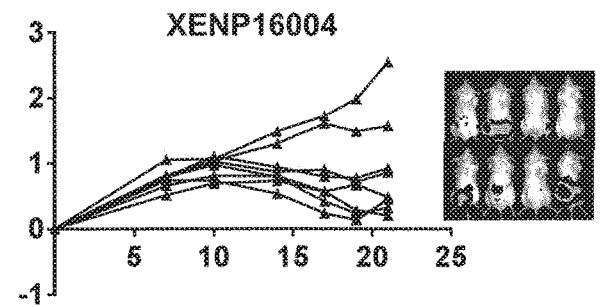
XENP16004
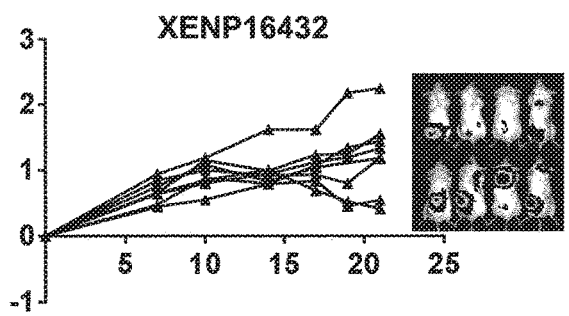
XENP16432
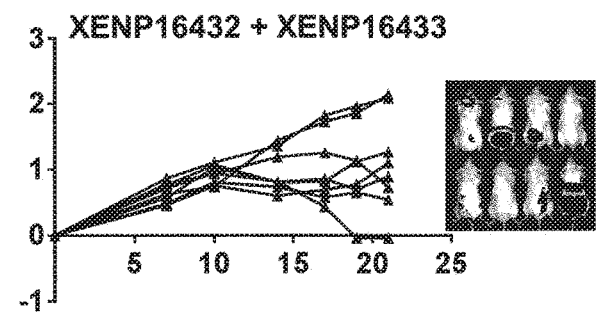
XENP16432 + XENP16433

BISPECIFIC CHECKPOINT INHIBITOR ANTIBODIES

CROSS REFERENCE TO RELATED APPLICATIONS

This application claims priority to U.S. Provisional Patent Application No. 62/350,145, filed Jun. 14, 2016, U.S. Provisional Patent Application No. 62/353,511, filed Jun. 22, 2016 and U.S. Provisional Patent Application No. 62/420,500, filed Nov. 10, 2016, the contents of which are expressly fully incorporated by reference in their entirety.

SEQUENCE LISTING

The instant application contains a Sequence Listing which has been submitted electronically in ASCII format and is hereby incorporated by reference in its entirety. Said ASCII copy, created on Oct. 10, 2017, is named 067461-5191-WO_SUBSTITUTE_SEQUENCE_LISTING.TEXT and is 33,716,785 kilobytes in size.

BACKGROUND OF THE INVENTION

Checkpoint receptors such as CTLA-4, PD-1 (programmed cell death 1), TIM-3 (T cell immunoglobulin and mucin domain 3), LAG-3 (lymphocyte-activation gene 3), TIGIT (T cell immunoreceptor with Ig and ITIM domains), and others, inhibit the activation, proliferation, and/or effector activities of T cells and other cell types. Guided by the hypothesis that checkpoint receptors suppress the endogenous T cell response against tumor cells, preclinical and clinical studies of anti-CTLA4 and anti-PD1 antibodies, including nivolumab, pembrolizumab, ipilimumab, and tremelimumab, have indeed demonstrated that checkpoint blockade results in impressive anti-tumor responses, stimulating endogenous T cells to attack tumor cells, leading to long-term cancer remissions in a fraction of patients with a variety of malignancies. Unfortunately, only a subset of patients responds to these therapies, with response rates generally ranging from 10 to 30% and sometimes higher for each monotherapy, depending on the indication and other factors. Therapeutic combination of these agents, for example ipilimumab plus nivolumab, leads to even higher response rates, approaching 60% in some cases. Preclinical studies have shown additional synergies between anti-PD-1 antibodies and/or anti-CTLA-4 antibodies with blockade of more recently identified checkpoint receptors, including LAG-3, TIM-3, BTLA and TIGIT. While the potential of multiple checkpoint blockade is very promising, combination therapy with such agents is expected to carry a high financial burden. Moreover, autoimmune toxicities of combination therapies, for example nivolumab plus ipilimumab, are significantly elevated compared to monotherapy, causing many patients to halt the therapy.

A number of studies (Ahmadzadeh et al., Blood 114:1537 (2009), Matsuzaki et al., PNAS 107(17):7875-7880 (2010), Fourcade et al., Cancer Res. 72(4):887-896 (2012) and Gros et al., J. Clinical Invest. 124(5):2246 (2014)) examining tumor-infiltrating lymphocytes (TILs) have shown that TILs commonly express multiple checkpoint receptors. Moreover, it is likely that TILs that express multiple checkpoints are in fact the most tumor-reactive. In contrast, non-tumor reactive T cells in the periphery are more likely to express a single checkpoint. Checkpoint blockade with monospecific full-length antibodies is likely nondiscriminatory with regards to de-repression of tumor-reactive TILs versus autoantigen-reactive single expressing T cells that are assumed to contribute to autoimmune toxicities.

Accordingly, the invention is directed to bispecific antibodies that bind to two different checkpoint inhibitor proteins.

I. BRIEF SUMMARY OF THE INVENTION

The present invention provides bispecific heterodimeric antibodies that bind to two different checkpoint cell surface receptors such as human PD-1, human CTLA-4, human TIM-3, human LAG-3 and human TIGIT. Thus, in some aspects, suitable bispecific antibodies bind PD-1 and CTLA-4, PD-1 and TIM-3, PD-1 and LAG-3, PD-1 and TIGIT, PD-1 and BTLA, CTLA-4 and TIM-3, CTLA-4 and LAG-3, CTLA-4 and TIGIT, CTLA-4 and BTLA, TIM-3 and LAG-3, TIM-3 and TIGIT, TIM-3 and BTLA, LAG-3 and TIGIT, LAG-3 and BTLA and TIGIT and BTLA.

In one aspect, the invention provides bottle opener formats that comprise: a) a first monomer (the "scFv monomer", sometimes referred to as the "scFv heavy chain") that comprises a scFv with a variable heavy and variable light domain linked using a charged scFv linker (with the +H sequence of FIG. 7 being preferred in some embodiments), an Fc domain comprising the skew variants S364K/E357Q, the ablation variants E233P/L234V/L235A/G236del/S267K, and an Fv that binds to a checkpoint receptor as outlined herein; b) a second monomer (the "Fab monomer" or "heavy chain") that comprises an Fc domain with the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second checkpoint receptor as outlined herein; and c) a light chain. In this particular embodiment, suitable monomer Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3, LAG-3 and TIGIT, TIGIT and LAG-3, LAG-3 and BTLA, BTLA and LAG-3, BTLA and TIGIT, and TIGIT and BTLA.

Other aspects of the invention are provided herein.

II. BRIEF DESCRIPTION OF THE DRAWINGS

FIG. 1A-1I depict several formats of the present invention. The first is the "bottle opener" format, with a first and a second anti-antigen binding domain. Additionally, mAb-Fv, mAb-scFv, Central-scFv, Central-Fv, one armed central-scFv, one scFv-mAb, scFv-mAb and a dual scFv format are all shown. For all of the scFv domains depicted, they can be either N- to C-terminus variable heavy-(optional linker)-variable light, or the opposite. In addition, for the one armed scFv-mAb, the scFv can be attached either to the N-terminus of a heavy chain monomer or to the N-terminus of the light chain.

FIG. 2A-2D depict the antigen sequences for a number of antigens of use in the invention, including both human and cynomolgus monkey in many cases, to facilitate the development of antigen binding domains that bind to both for ease of clinical development.

FIG. 3A-3F depict useful pairs of heterodimerization variant sets (including skew and pI variants). On FIG. 3E, there are variants for which there are no corresponding "monomer 2" variants; these are pI variants which can be used alone on either monomer, or included on the Fab side of a bottle opener, for example, and an appropriate charged scFv linker can be used on the second monomer that utilizes a scFv as the second antigen binding domain. Suitable charged linkers are shown in FIG. 7.

FIG. 4 depict a list of isosteric variant antibody constant regions and their respective substitutions. pI_(−) indicates lower pI variants, while pI_(+) indicates higher pI variants. These can be optionally and independently combined with other heterodimerization variants of the invention (and other variant types as well, as outlined herein).

FIG. 5 depict useful ablation variants that ablate FcγR binding (sometimes referred to as "knock outs" or "KO" variants). Generally, ablation variants are found on both monomers, although in some cases they may be on only one monomer.

FIG. 6A-6B show two particularly useful embodiments of the invention, that can be used for either the format of FIG. 1A or FIG. 1F. For the FIG. 1A format, the "non-Fv" components of this embodiment are shown in FIG. 37A, although the other formats of can be used as well (and that of FIG. 38 as well).

Figures 1A, 1B, 1C, 1D, 1E:
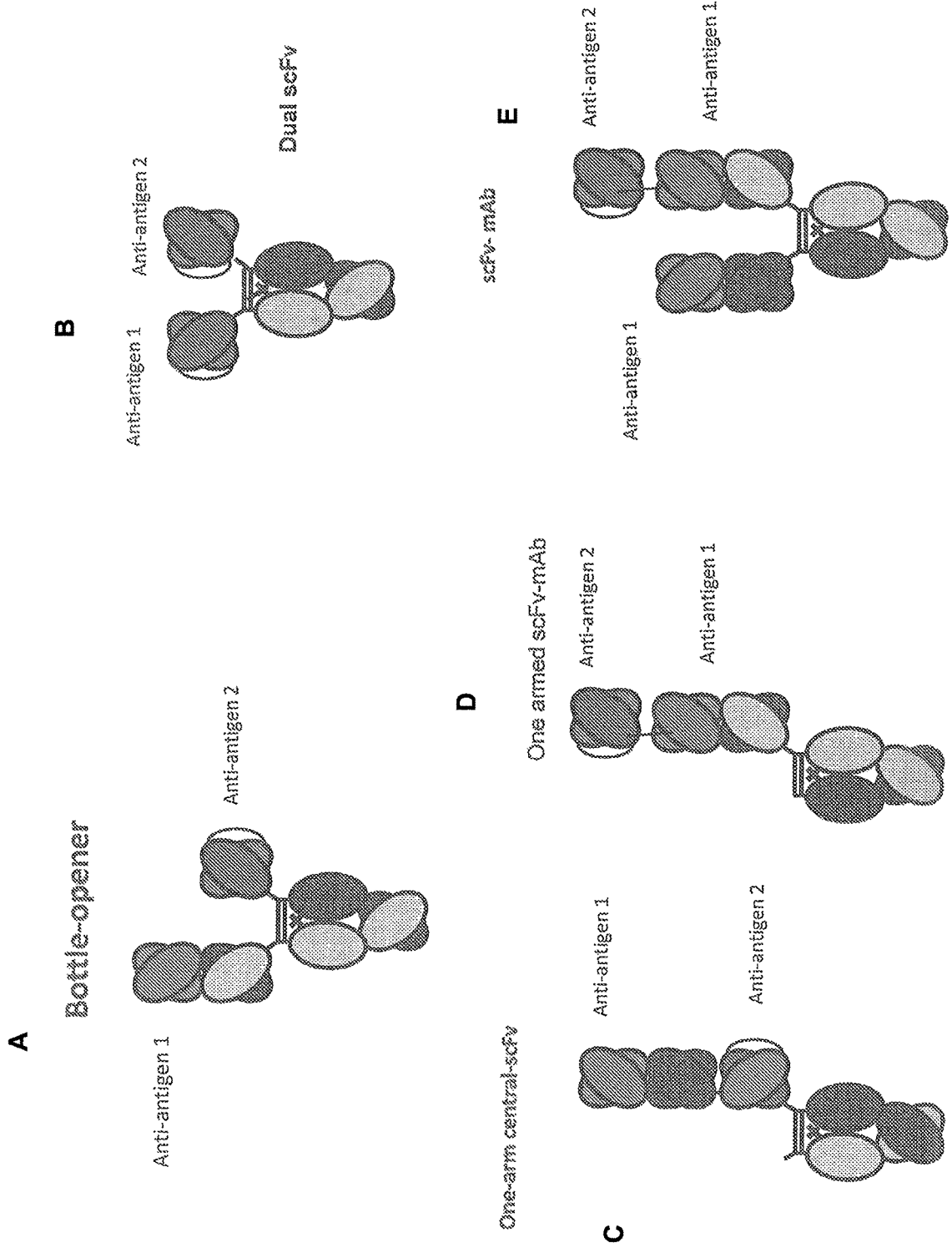

FIG. 7A-7B depicts a number of charged scFv linkers that find use in increasing or decreasing the pI of heterodimeric antibodies that utilize one or more scFv as a component. The (+H) positive linker finds particular use herein, particularly with anti-CD3 vl and vh sequences shown herein. A single prior art scFv linker with a single charge is referenced as "Whitlow", from Whitlow et al., Protein Engineering 6(8): 989-995 (1993). It should be noted that this linker was used for reducing aggregation and enhancing proteolytic stability in scFvs.

FIG. 8 depicts a list of engineered heterodimer-skewing Fc variants with heterodimer yields (determined by HPLC-CIEX) and thermal stabilities (determined by DSC). Not determined thermal stability is denoted by "n.d.".

FIG. 9A-9E depict a select number of PD-1 ABDs, with additional anti-PD-1 ABDs being listed as SEQ ID NOs: 6209-11464, SEQ ID NOs: 11465-17134, SEQ ID NOs: 33003-33072, SEQ ID NOs: 33073-35394 and SEQ ID NOs: 36127-36146. The CDRs are underlined, the scFv linker is double underlined (in the sequences, the scFv linker is a positively charged scFv (GKPGS)$_4$ linker (SEQ ID NO: 37755), although as will be appreciated by those in the art, this linker can be replaced by other linkers, including uncharged or negatively charged linkers, some of which are depicted in FIG. 7), and the slashes indicate the border(s) of the variable domains. In addition, the naming convention illustrates the orientation of the scFv from N- to C-terminus. That is, "H1.279_L1.194" shows that the orientation is vh-scFv linker-vl (from N- to C-terminus, with optional domain linkers on one or both sides, depending on the format used), although these sequences may also be used in the opposite orientation, (from N- to C-terminus) vl-linker-vh. Similarly, "L1.194_H1.279" shows that the orientation is vl-scFv linker-vh (from N- to C-terminus, again with optional domain linkers), with the opposite orientation also included within the invention. As noted herein and is true for every sequence herein containing CDRs, the exact identification of the CDR locations may be slightly different depending on the numbering used as is shown in Table 1, and thus included herein are not only the CDRs that are underlined but also CDRs included within the vh and vl domains using other numbering systems. Furthermore, as for all the sequences in the Figures, these vh and vl sequences can be used either in a scFv format or in a Fab format.

FIG. 10A-10PP depict a number of CTLA-4 ABDs, with additional anti-CTLA-4 ABDs being listed as SEQ ID NOs: 21-2918, SEQ ID NOs: 2919-6208, SEQ ID NOs: 36739-36818 and SEQ ID NOs: 35395-35416. The CDRs are underlined, the scFv linker is double underlined (in the sequences, the scFv linker is a positively charged scFv (GKPGS)$_4$ linker (SEQ ID NO: 37755), although as will be appreciated by those in the art, this linker can be replaced by other linkers, including uncharged or negatively charged linkers, some of which are depicted in FIG. 7), and the slashes indicate the border(s) of the variable domains. As above, the naming convention illustrates the orientation of the scFv from N- to C-terminus; in the sequences listed in this figure, they are all oriented as vh-scFv linker-vl (from N- to C-terminus), although these sequences may also be used in the opposite orientation, (from N- to C-terminus) vl-linker-vh; additionally, some of the sequences in SEQ ID NOs: 21-2918, SEQ ID NOs: 2919-6208, SEQ ID NOs: 36739-36818 and SEQ ID NOs: 35395-35416 are in the opposite orientation. As noted herein and is true for every sequence herein containing CDRs, the exact identification of the CDR locations may be slightly different depending on the numbering used as is shown in Table 1, and thus included herein are not only the CDRs that are underlined but also CDRs included within the vh and vl domains using other numbering systems. Furthermore, as for all the sequences in the Figures, these vh and vl sequences can be used either in a scFv format or in a Fab format. In particular, many of the figures include the XENP identifier for both the scFv format as well as the Fab format; see for example FIG. 10A, that shows that XENP19235 is the molecule using the Fab format and XENP19769 is the scFv molecule.

FIG. 11A-11N depict a number of LAG-3 ABDs, with additional anti-LAG-3 ABDs being listed as SEQ ID NOs: 17135-20764, SEQ ID NOs: 36819-36962, SEQ ID NOs: 35417-35606, SEQ ID NOs: 25194-32793 and SEQ ID NOs: 32794-33002. The CDRs are underlined, the scFv linker is double underlined (in the sequences, the scFv linker is a positively charged scFv (GKPGS)$_4$ linker, although as will be appreciated by those in the art, this linker can be replaced by other linkers, including uncharged or negatively charged linkers, some of which are depicted in FIG. 7), and the slashes indicate the border(s) of the variable domains. As above, the naming convention illustrates the orientation of the scFv from N- to C-terminus; in the sequences listed in this figure, they are all oriented as vh-scFv linker-vl (from N- to C-terminus), although these sequences may also be used in the opposite orientation, (from N- to C-terminus) vl-linker-vh; additionally, some of the sequences in SEQ ID NOs: 17135-20764, SEQ ID NOs: 36819-36962, SEQ ID NOs: 35417-35606, SEQ ID NOs: 25194-32793 and SEQ ID NOs: 32794-33002 are in the opposite orientation. As noted herein and is true for every sequence herein containing CDRs, the exact identification of the CDR locations may be slightly different depending on the numbering used as is shown in Table 1, and thus included herein are not only the CDRs that are underlined but also CDRs included within the vh and vl domains using other numbering systems. Furthermore, as for all the sequences in the Figures, these vh and vl sequences can be used either in a scFv format or in a Fab format.

FIG. 12A-12C depict a number of BTLA ABDs, with additional anti-BTLA ABDs being listed as SEQ ID NOs: 20885-21503 and SEQ ID NOs: 36707-36738. The CDRs are underlined, the scFv linker is double underlined (in the sequences, the scFv linker is a positively charged scFv $(GKPGS)_4$ linker, although as will be appreciated by those in the art, this linker can be replaced by other linkers, including uncharged or negatively charged linkers, some of which are depicted in FIG. 7), and the slashes indicate the border(s) of the variable domains. As above, the naming convention illustrates the orientation of the scFv from N- to C-terminus; in the sequences listed in this figure, they are all oriented as vh-scFv linker-vl (from N- to C-terminus), although these sequences may also be used in the opposite orientation, (from N- to C-terminus) vl-linker-vh; additionally, some of the sequences in SEQ ID NOs: 20885-21503 and SEQ ID NOs: 36707-36738 are in the opposite orientation. As noted herein and is true for every sequence herein containing CDRs, the exact identification of the CDR locations may be slightly different depending on the numbering used as is shown in Table 1, and thus included herein are not only the CDRs that are underlined but also CDRs included within the vh and vl domains using other numbering systems. Furthermore, as for all the sequences in the Figures, these vh and vl sequences can be used either in a scFv format or in a Fab format.

FIG. 13A-13I depict a number of TIM-3 ABDs, with additional anti-TIM-3 ABDs being listed as SEQ ID NOs: 20765-20884, SEQ ID NOs: 37587-37698 and SEQ ID NOs: 36347-36706. The CDRs are underlined, the scFv linker is double underlined (in the sequences, the scFv linker is a positively charged scFv $(GKPGS)_4$ linker, although as will be appreciated by those in the art, this linker can be replaced by other linkers, including uncharged or negatively charged linkers, some of which are depicted in FIG. 7), and the slashes indicate the border(s) of the variable domains. As above, the naming convention illustrates the orientation of the scFv from N- to C-terminus; in the sequences listed in this figure, they are all oriented as vh-scFv linker-vl (from N- to C-terminus), although these sequences may also be used in the opposite orientation, (from N- to C-terminus) vl-linker-vh; additionally, some of the sequences in SEQ ID NOs: 20765-20884, SEQ ID NOs: 37587-37698 and SEQ ID NOs: 36347-36706 are in the opposite orientation. As noted herein and is true for every sequence herein containing CDRs, the exact identification of the CDR locations may be slightly different depending on the numbering used as is shown in Table 1, and thus included herein are not only the CDRs that are underlined but also CDRs included within the vh and vl domains using other numbering systems. Furthermore, as for all the sequences in the Figures, these vh and vl sequences can be used either in a scFv format or in a Fab format.

FIG. 14A-14I depicts the amino acid sequences of specific anti-CTLA-4×anti-PD-1 antibodies in the bottle opener format (Fab-scFv-Fc). The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domain has different orientations (N- to C-terminus) of either vh-linker-vl or vl-linker-vh as indicated, although this can be reversed. In addition, each sequence outlined herein can include or exclude the M428L/N434S variants in one or preferably both Fc domains, which results in longer half-life in serum.

FIG. 15A-15K depicts the amino acid sequences of specific anti-LAG-3×anti-PD-1 Fab-scFv-Fc bispecific antibodies. The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domains have the orientation (N- to C-terminus) vl-linker-vh, although this can be reversed. In addition, each sequence outlined herein can include or exclude the M428L/N434S variants in one or preferably both Fc domains, which results in longer half-life in serum.

FIG. 16A-16D depicts the amino acid sequences of specific anti-BTLA×anti-PD-1 Fab-scFv-Fc bispecific antibodies. The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domains have the orientation (N- to C-terminus) vl-linker-vh, although this can be reversed. In addition, each sequence outlined herein can include or exclude the M428L/N434S variants in one or preferably both Fc domains, which results in longer half-life in serum.

FIG. 17A-17O depicts the amino acid sequences of specific anti-LAG-3×anti-CTLA-4 Fab-scFv-Fc bispecific antibodies. The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domains have the orientation (N- to C-terminus) vh-linker-vl, although this can be reversed. In addition, each sequence outlined herein can include or exclude the M428L/N434S variants in one or preferably both Fc domains, which results in longer half-life in serum.

Figure 18:
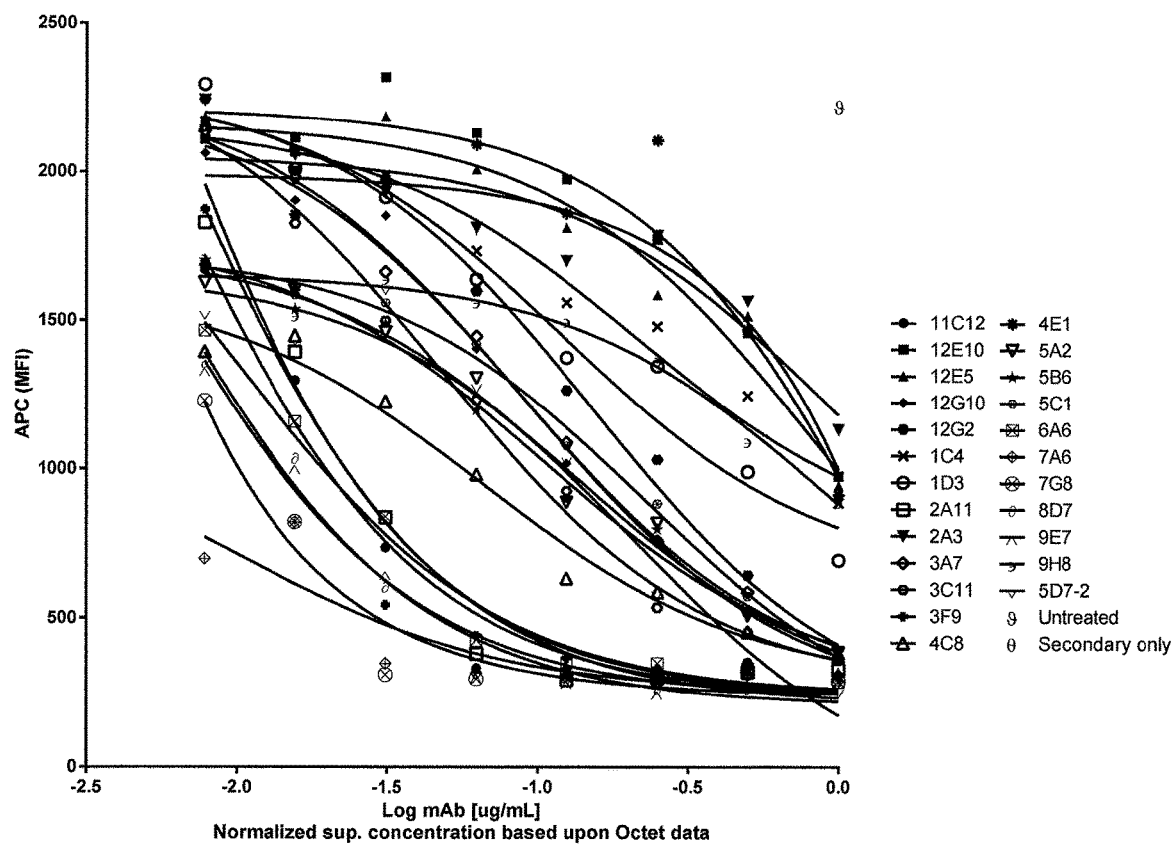

FIG. 18 shows the results of some anti-LAG-3 hybridoma screening. 1 μg of human LAG-3-hIg in 10 μL was mixed with 50 μL of hybridoma supernatant (diluted 2-fold, 8 times in RPMI media with 10% FBS) for 20 minutes at room temperature. 40 μL of Daudi or Ramos cells (which endogenously express MHC-II) were added and incubated at 4° C. for 30 minutes. The cells were then washed and incubated with anti-human-Fc-Alexa647 secondary antibody for 30 minutes. Cells were then washed and analyzed by FACS for Alexa647.

Figures 19, 19A:
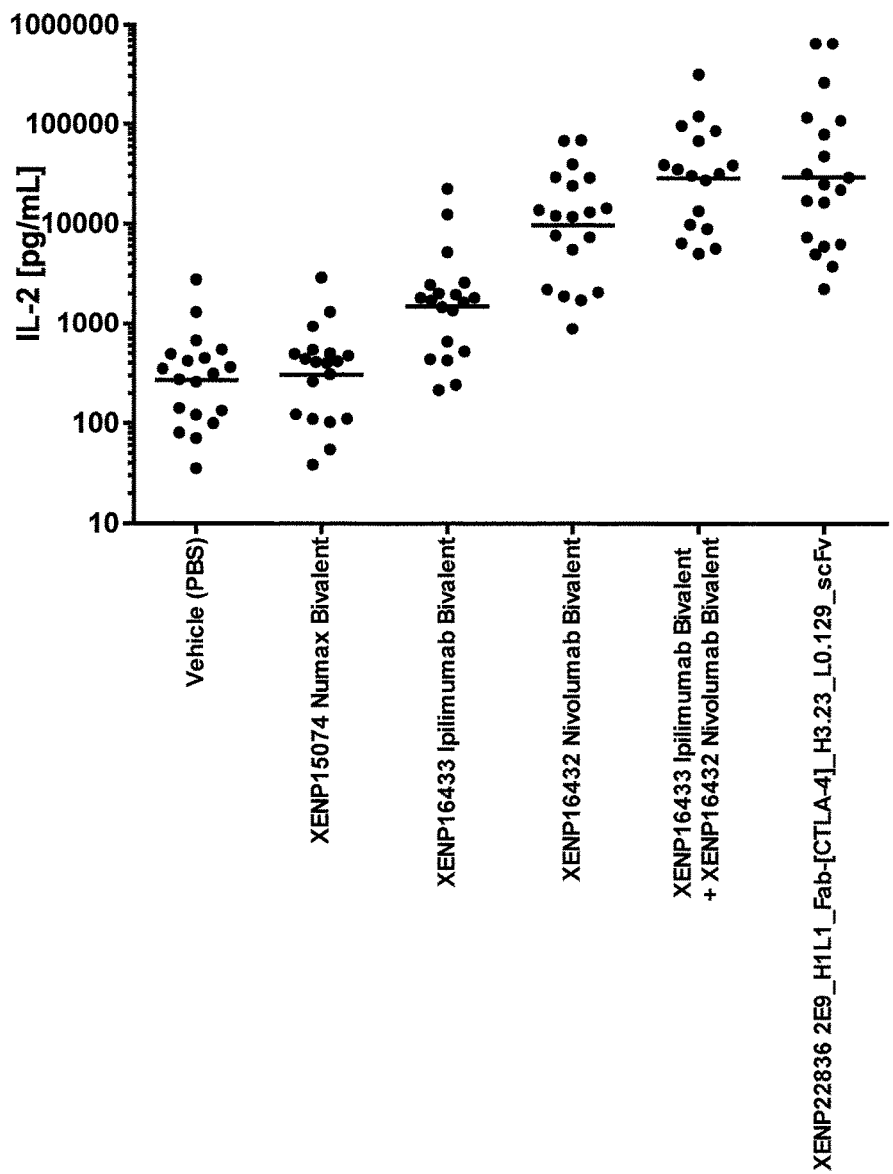
Figure 19B:
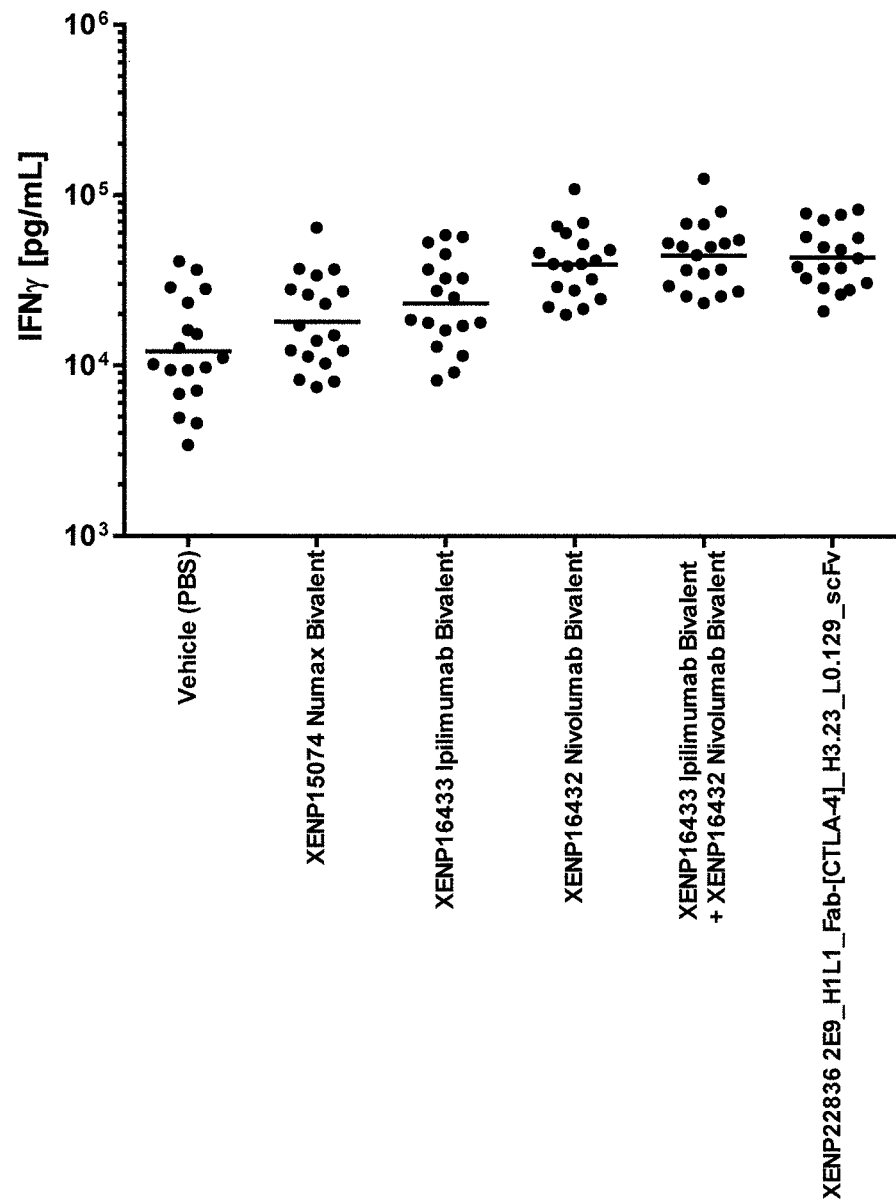

FIG. 19A-19B depict cytokine release assays (A:IL-2, B: IFNγ) after SEB stimulation of human PBMCs and treatment with an anti-CTLA-4×anti-PD-1 bispecific antibody.

Figures 20, 20A:
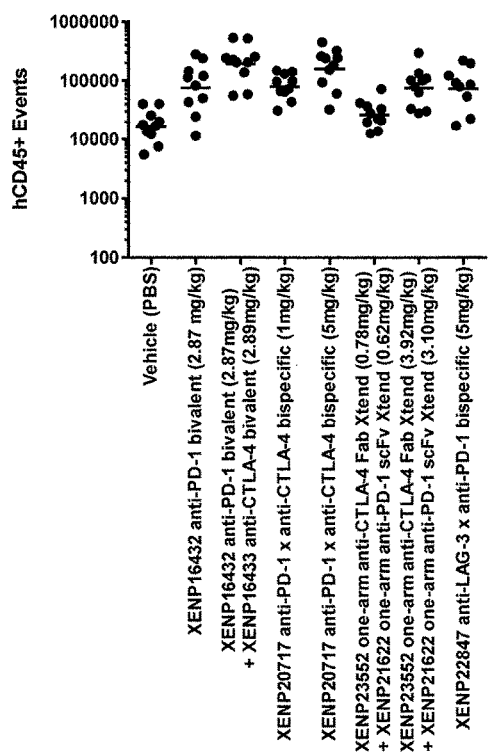
Figure 20B:
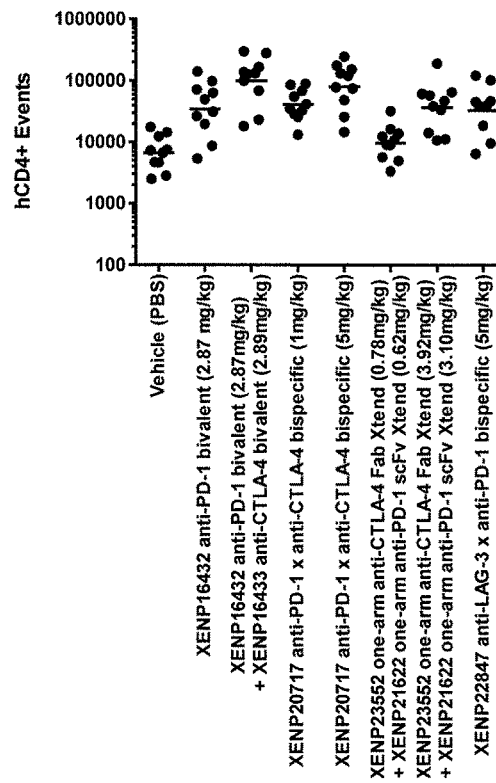
Figure 20C:
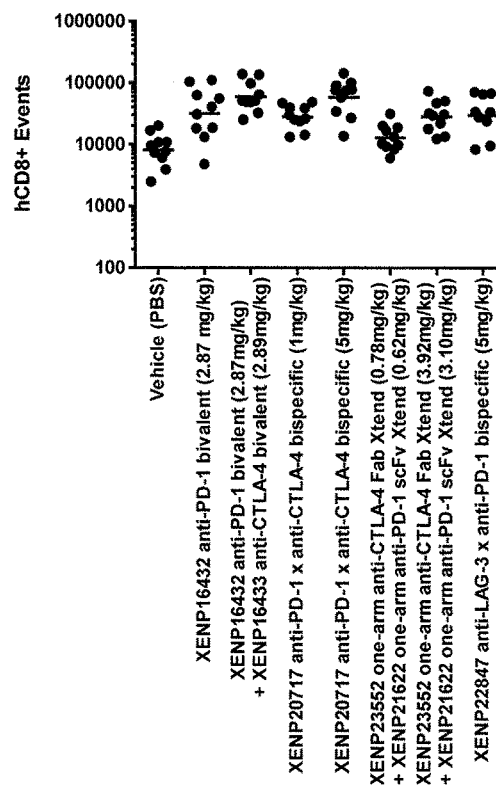

FIG. 20A-20C depict CD45+ events and CD8+ events on Day 14 after human PBMCs were engrafted into NSG mice on Day 0 followed by dosing with the indicated test articles on Day 1.

Figure 21A:
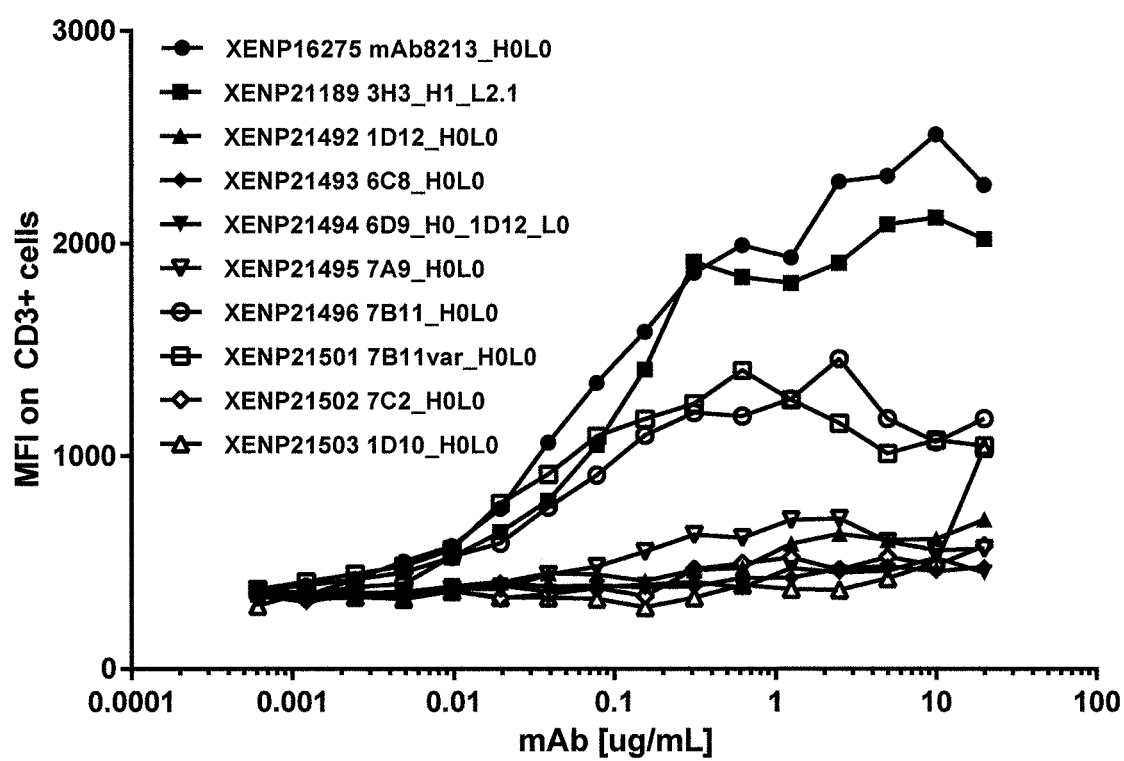
Figure 21B:
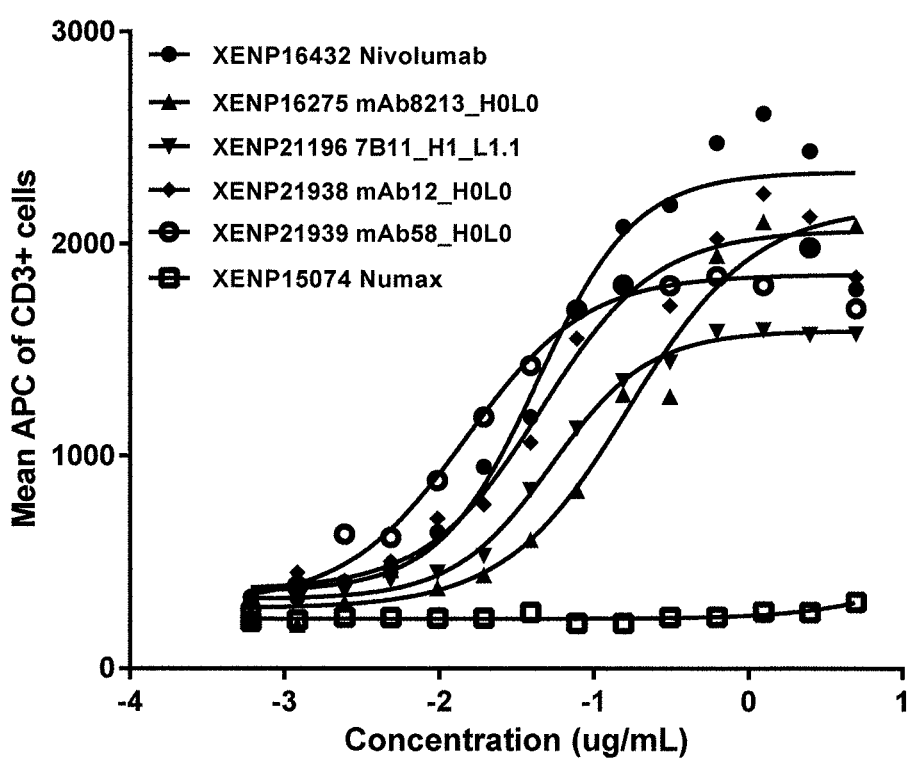

FIG. 21A-21B depicts T cell binding in an SEB-stimulated PBMC assay by chimeric antibodies generated from anti-TIM-3 hybridomas.

FIG. 22 depicts some anti-TIM-3 antigen binding domain engineering data from three experiments. This depicts XENP code for bivalent embodiments, the derivative clone, the designations of the vh and vl engineered domains, the KD binding constant, association constant and dissociation constant against human TIM-3 as measured by OCTET®.

FIG. 23A-23N depicts some anti-PD-1 antigen binding domain engineering data. This depicts the XENP code for the bivalent and scFv embodiments, the designation of the vh and vl engineered domains, the scFv orientation (N- to C-terminal), the KD binding constant against human PD-1 as measured by OCTET®, and the Tm of the scFv.

FIG. 24A-24G depicts the results of some anti-CTLA-4 Fab screening. This depicts the XENP code for the Fab and scFv embodiments, the designation of the vh and vl engineered domains, the KD binding constant against human and cyno CTLA-4 as measured by OCTET®, and the Tm of the scFv and Fab. Additionally, the number of sequence 9-mers that were an exact match to at least one human VH or VL germline are depicted as a measure of humanness for the variable regions of both Fabs and scFvs.

Figure 25:
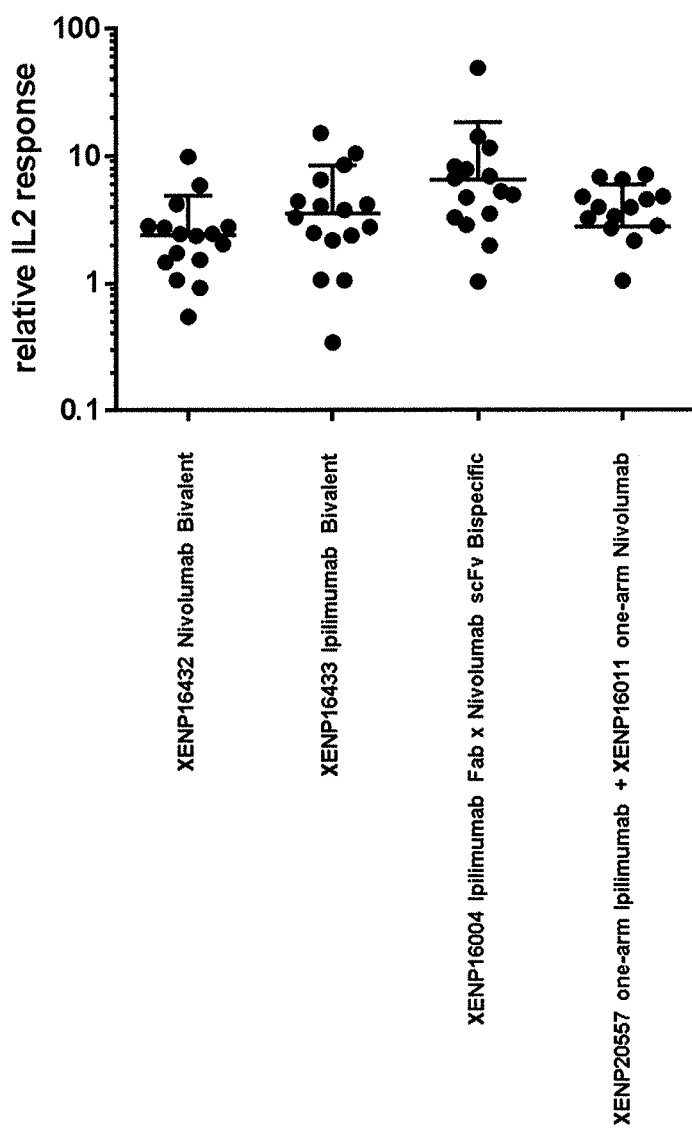

FIG. 25 depicts a mixed lymphocyte reaction looking enhancement of IL-2 release by nivolumab (anti-PD-1 monoclonal antibody, marketed as Opdivo®) alone, ipilimumab alone (anti-CTLA-4 monoclonal antibody, marketed as Yervoy®), a prototype anti-CTLA-4×anti-PD-1 bispecific based on the nivolumab and ipilimumab arms, and a "one-armed" combination control.

Figure 26:
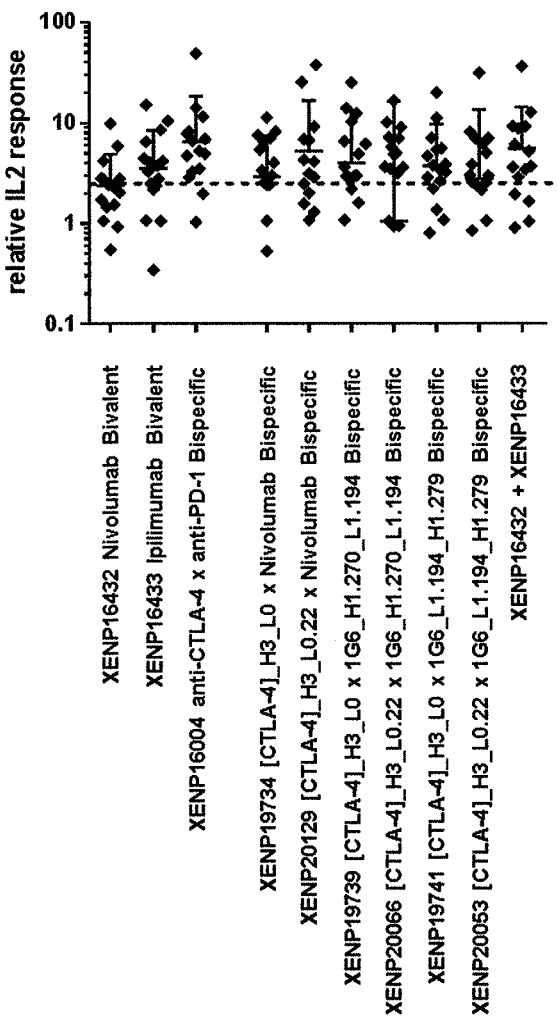

FIG. 26 depicts mixed lymphocyte reaction looking at enhancement of IL-2 release by anti-CTLA-4×anti-PD-1 bispecific antibodies with variant anti-CTLA-4 Fab arms and variant anti-PD-1 scFv arms, as well as nivolumab alone, ipilimumab alone, and a prototype anti-CTLA-4× anti-PD-1 bispecific based on the nivolumab and ipilimumab arms as controls.

Figure 27:
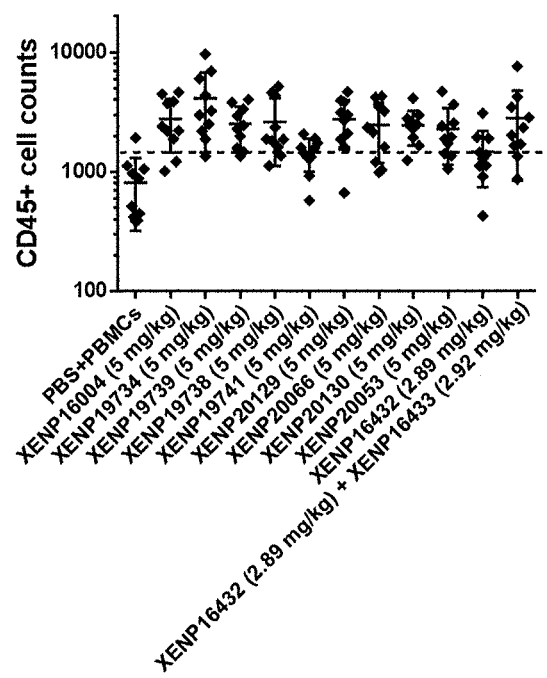

FIG. 27 shows that anti-CTLA-4×anti-PD-1 bispecifics enhance engraftment (as measured by human CD45 counts) in human PBMC-engrafted NSG mice. Enhancement is greater than that seen with nivolumab (XENP16432) alone (dashed line).

Figure 28:
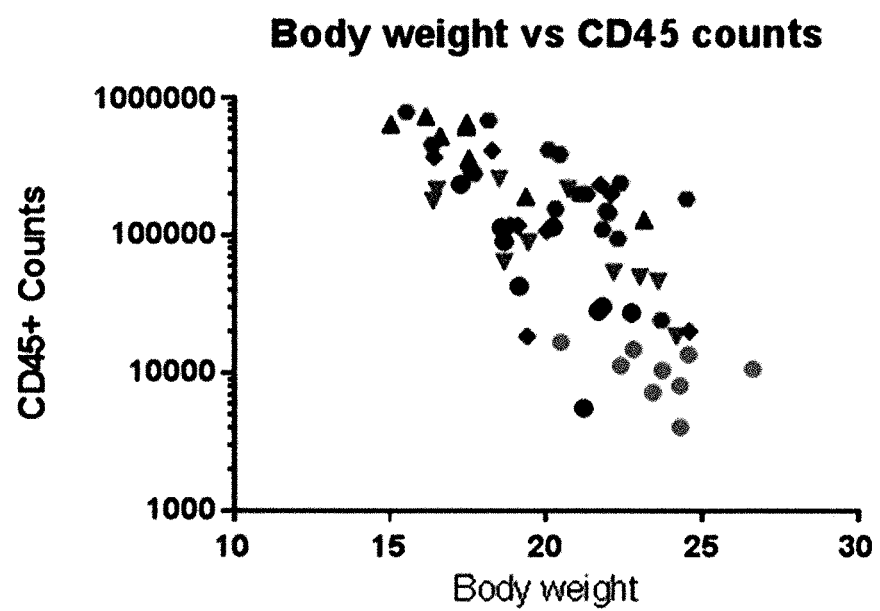

FIG. 28 depicts the correlation between body weight and CD45 cell count in Graft-versus-Host disease, demonstrating that CD45 cell levels are predictive of disease.

Figure 29:
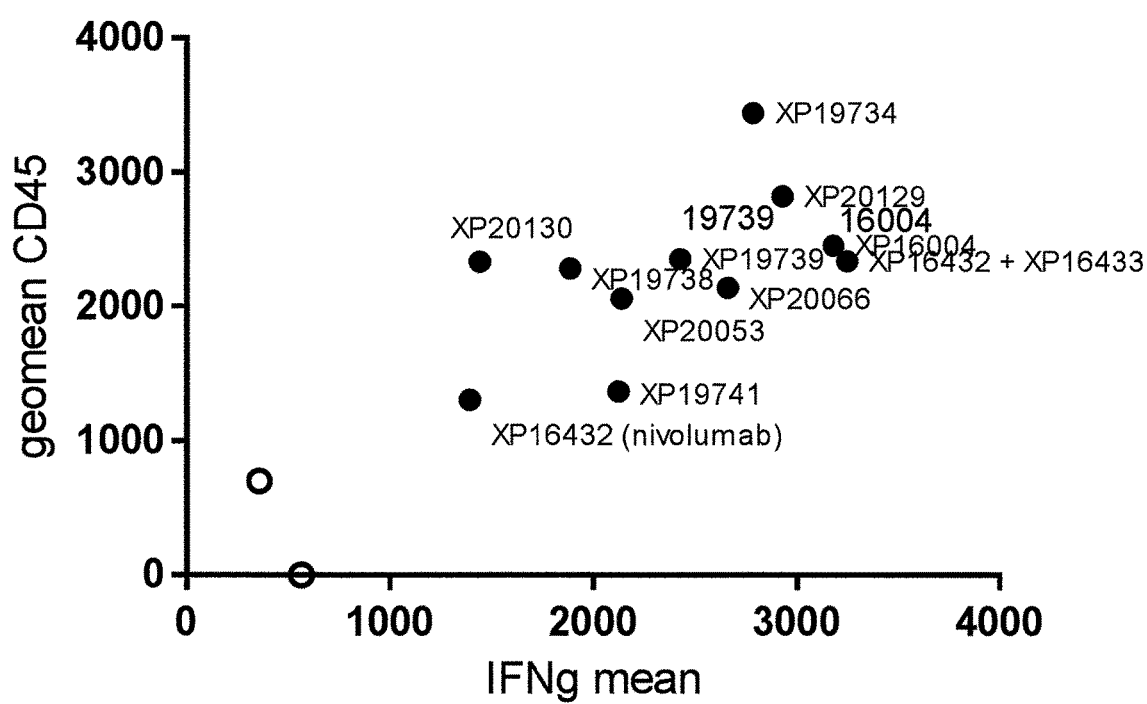

FIG. 29 depicts the correlation between CD45 cell count and IFNγ release in the study depicted in FIG. 27.

Figure 30:
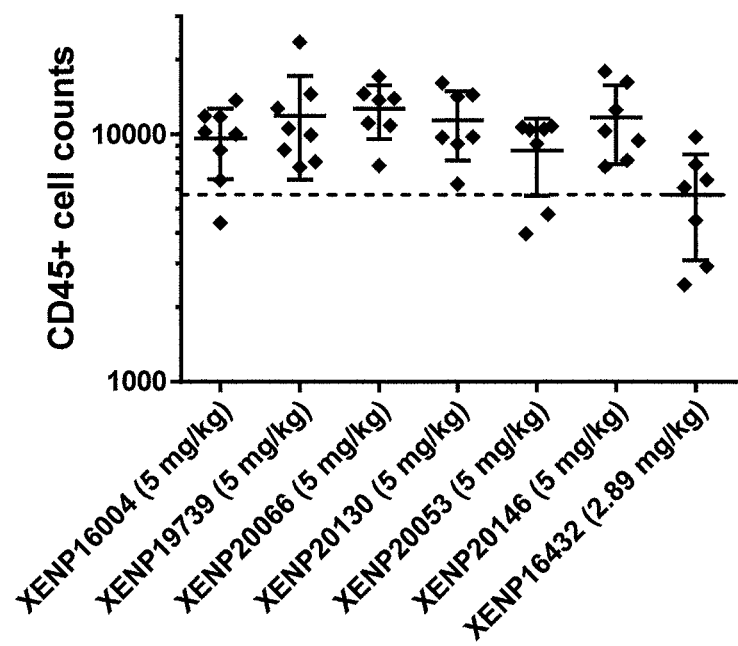

FIG. 30 shows that anti-CTLA-4×anti-PD-1 bispecifics enhance engraftment (as measured by human CD45 counts) in human PBMC-engrafted NSG mice. Enhancement is greater than that seen with nivolumab (XENP16432) alone (dashed line).

Figure 31:
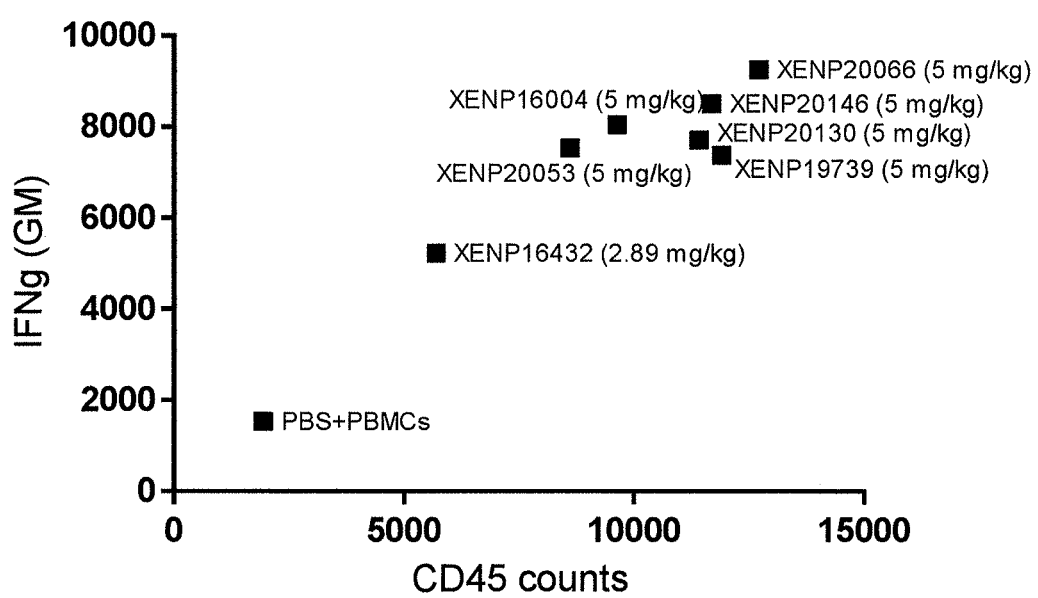

FIG. 31 depicts the correlation between CD45 cell count and IFNγ release in the study depicted in FIG. 30.

Figure 32:
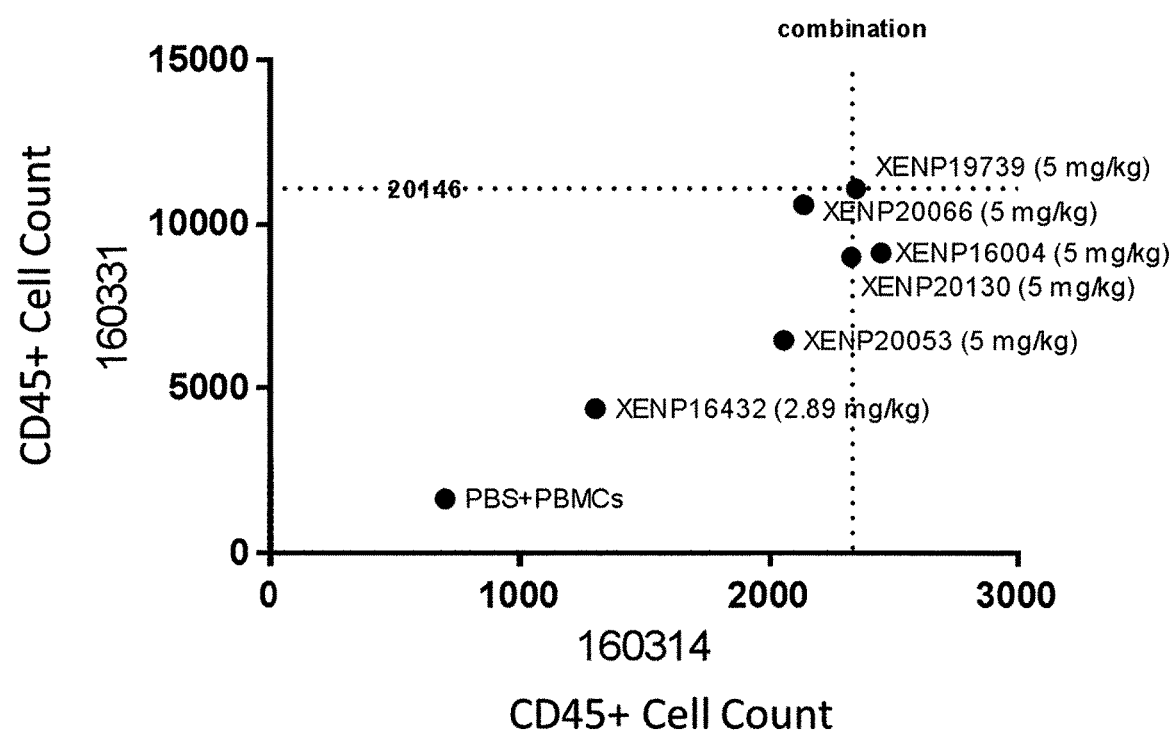

FIG. 32 shows the comparison of test article effects between the studies depicted in FIGS. 27 and 30 demonstrating the consistent superiority of anti-PD-1×anti-CTLA-4 bispecific checkpoint antibodies over nivolumab alone.

Figure 33A:
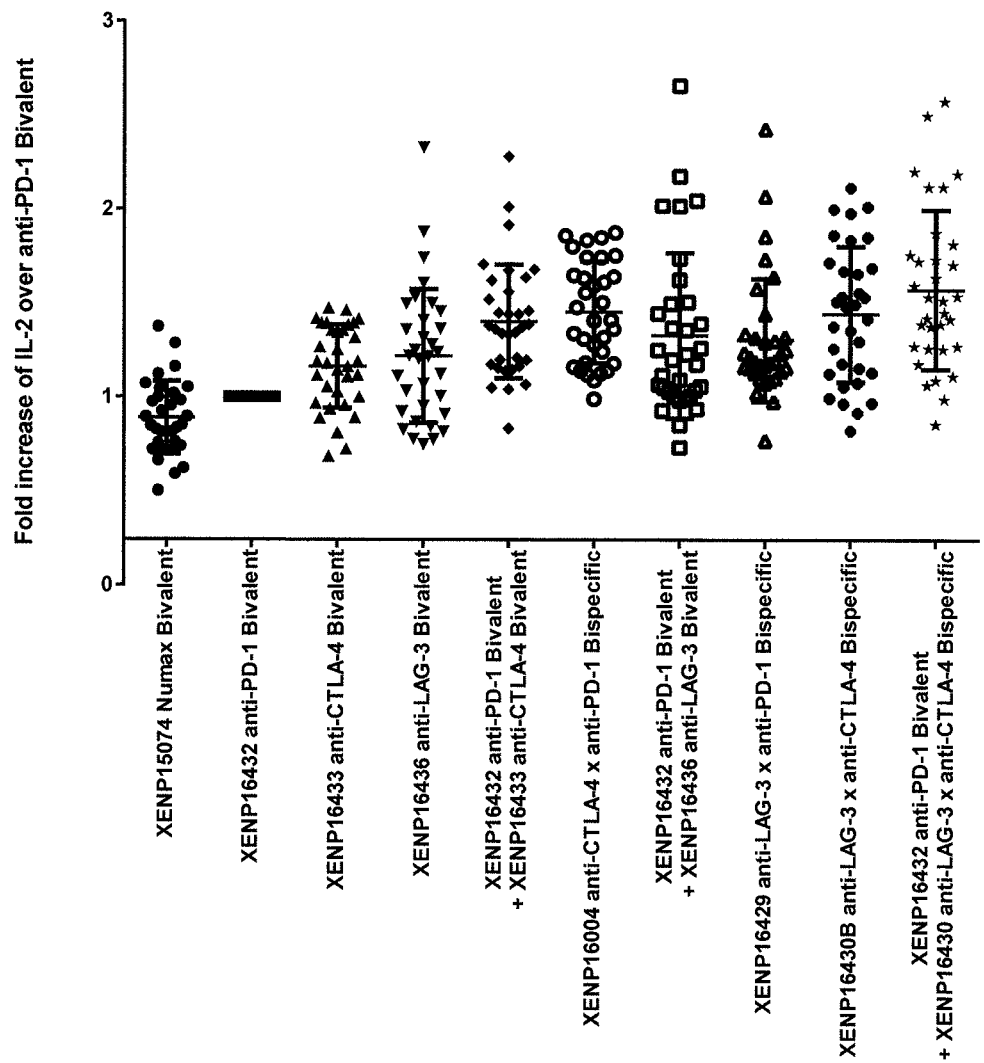
Figure 33B:
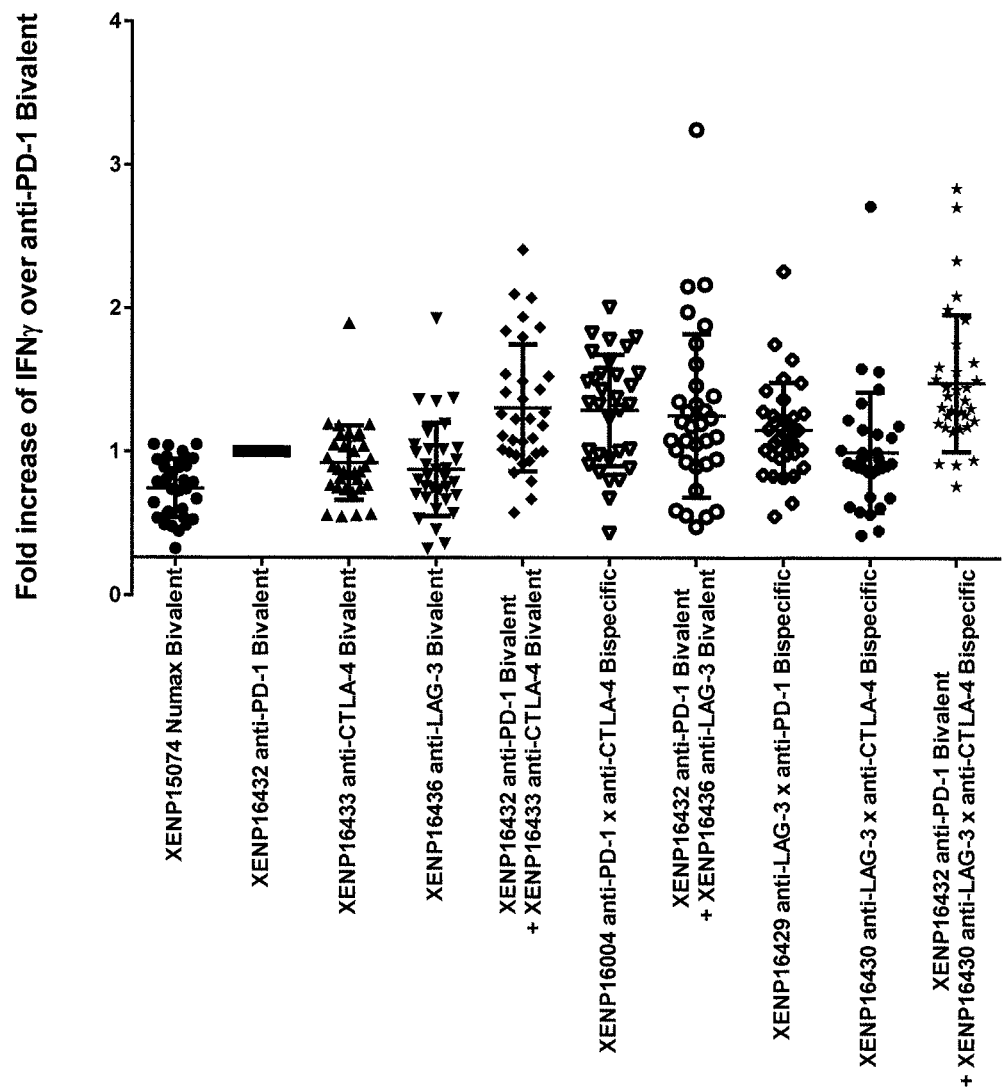

FIG. 33A-33B show the results of mixed lymphocyte reactions to evaluate anti-CTLA-4×anti-PD-1, anti-LAG-3× anti-PD-1, and anti-LAG-3×anti-CTLA-4 bispecifics. Analyte levels were normalized to those induced by nivolumab alone (values greater than one represent an enhancement relative to nivolumab).

Figure 34:
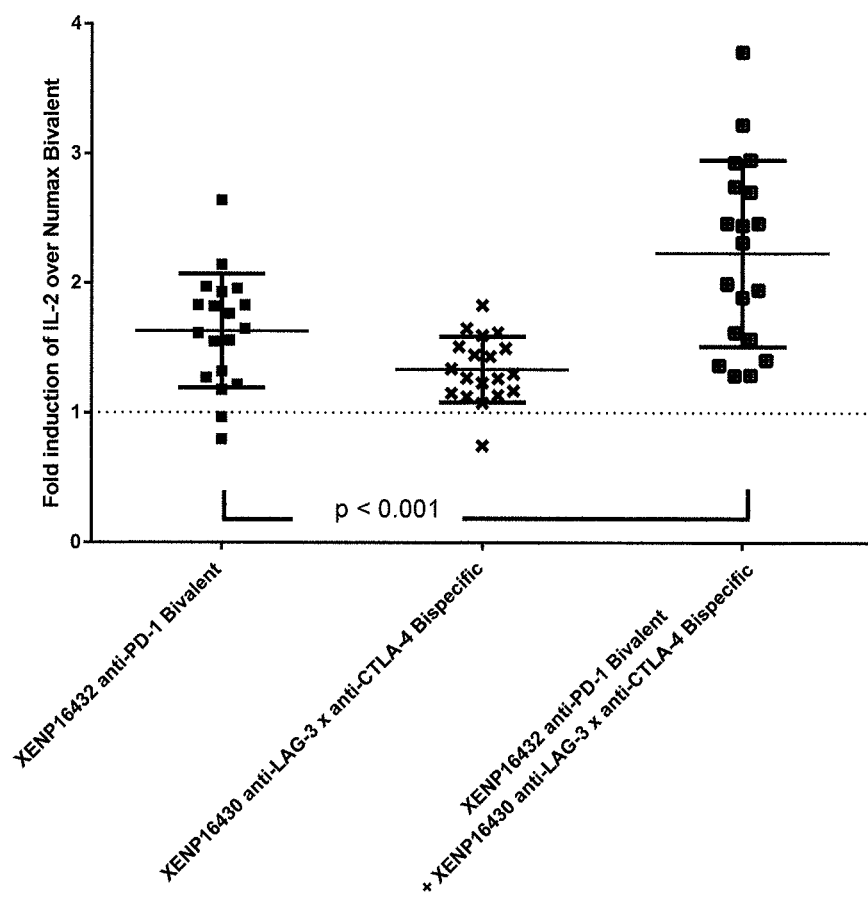

FIG. 34 shows SEB reactions to evaluate anti-LAG-3× anti-CTLA-4 bispecifics. The anti-LAG-3×anti-CTLA-4 bispecific itself enhances the IL-2 response relative to control, although it is inferior to nivolumab alone. However, the anti-LAG-3×anti-CTLA-4 bispecific combined with nivolumab leads to significantly higher IL-2 response than either alone.

Figure 35:
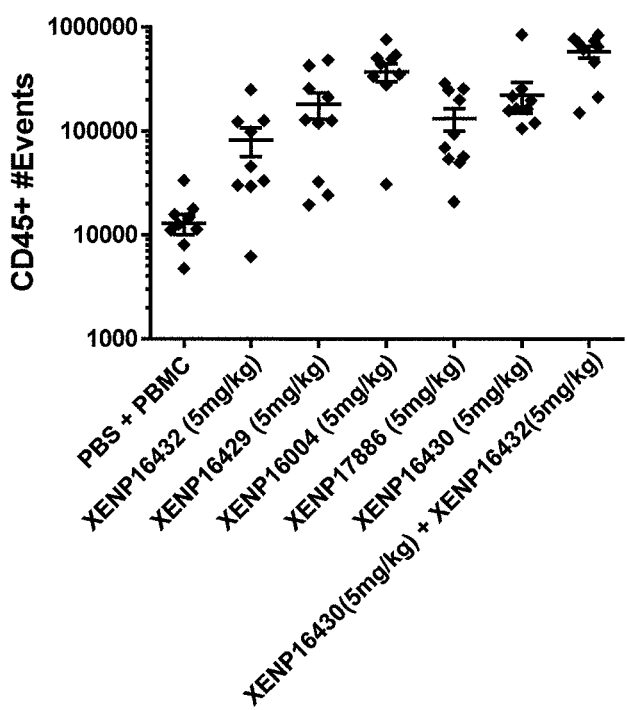

FIG. 35 Anti-CTLA-4×anti-PD-1, anti-LAG-3×anti-PD-1, anti-BTLA×anti-PD-1, and anti-LAG-3×anti-CTLA-4 bispecifics enhance engraftment (as measured by human CD45 counts) in human PBMC-engrafted NSG mice. Enhancement is greater than that seen with nivolumab (XENP 16432) alone. Also, the anti-LAG-3×anti-CTLA-4 bispecific combines with nivolumab to yield the highest engraftment levels.

Figure 36A:
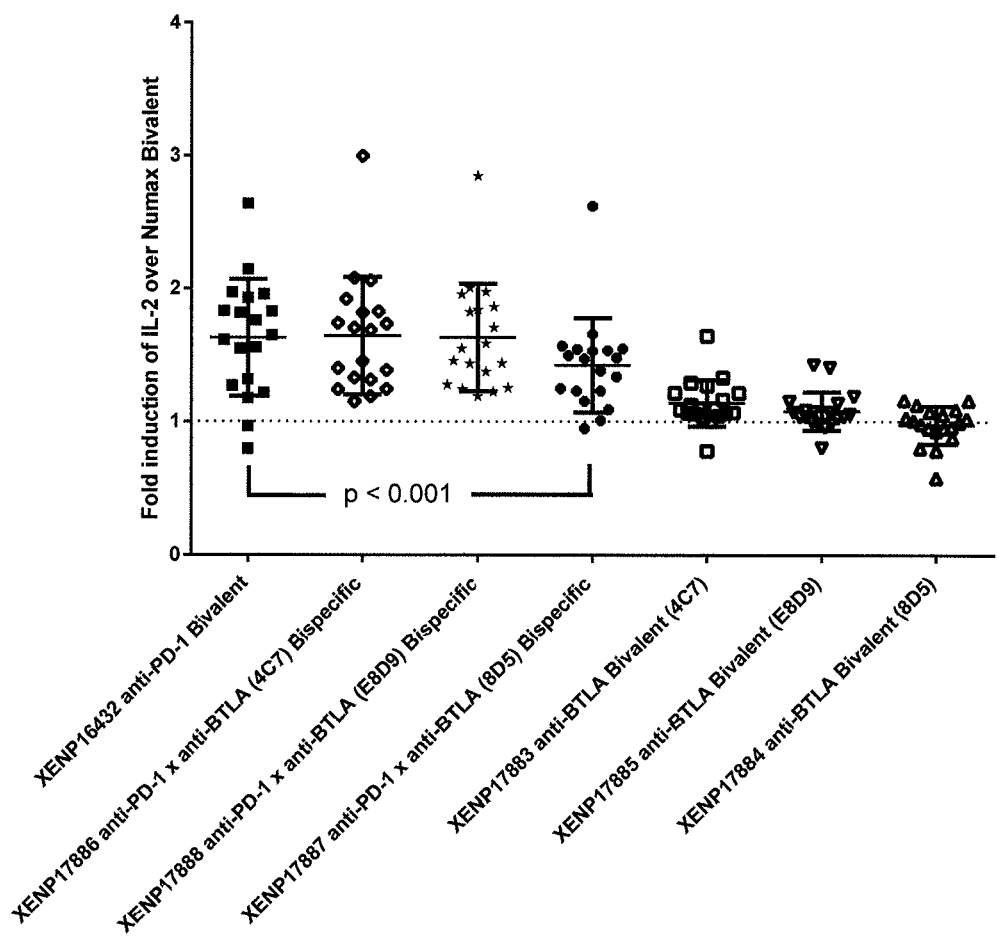
Figure 36B:
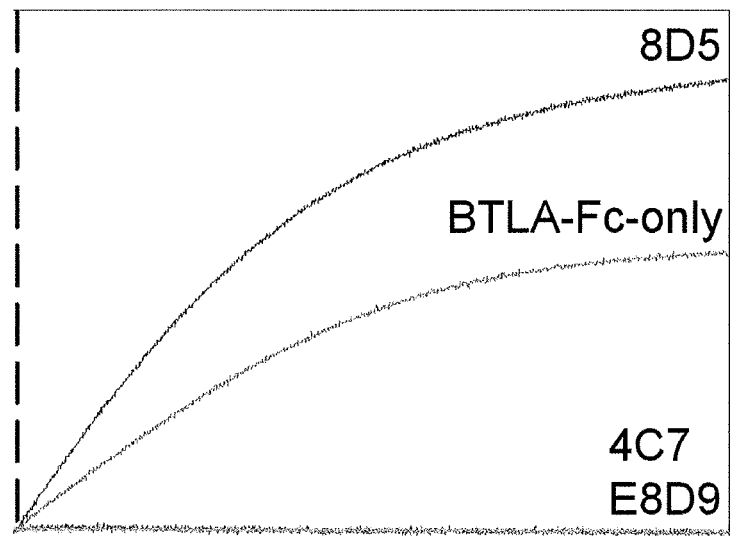

FIG. 36A-36B show that the anti-BTLA×anti-PD-1 bispecifics require disruption of the HVEM/BTLA interaction to possess equivalent de-repressive activity as nivolumab.

FIG. 37A-37E shows the sequences of several useful bottle opener format backbones based on human IgG1, without the Fv sequences (e.g. the scFv and the vh and vl for the Fab side). Bottle opener backbone 1 is based on human IgG1 (356E/358M allotype), and includes the S364K/E357Q:L368D/K370S skew variants, the N208D/Q295E/N384D/Q418E/N421D pI variants on the Fab side and the E233P/L234V/L235A/G236del/S267K ablation variants on both chains. Bottle opener backbone 2 is based on human IgG1 (356E/358M allotype), and includes different skew variants, the N208D/Q295E/N384D/Q418E/N421D pI variants on the Fab side and the E233P/L234V/L235A/G236del/S267K ablation variants on both chains. Bottle opener backbone 3 is based on human IgG1 (356E/358M allotype), and includes different skew variants, the N208D/Q295E/N384D/Q418E/N421D pI variants on the Fab side and the E233P/L234V/L235A/G236del/S267K ablation variants on both chains. Bottle opener backbone 4 is based on human IgG1 (356E/358M allotype), and includes different skew variants, the N208D/Q295E/N384D/Q418E/N421D pI variants on the Fab side and the E233P/L234V/L235A/G236del/S267K ablation variants on both chains. Bottle opener backbone 5 is based on human IgG1 (356D/358L allotype), and includes the S364K/E357Q:L368D/K370S skew variants, the N208D/Q295E/N384D/Q418E/N421D pI variants on the Fab side and the E233P/L234V/L235A/G236del/S267K ablation variants on both chains. Bottle opener backbone 6 is based on human IgG1 (356E/358M allotype), and includes the S364K/E357Q:L368D/K370S skew variants, N208D/Q295E/N384D/Q418E/N421D pI variants on the Fab side and the E233P/L234V/L235A/G236del/S267K ablation variants on both chains, as well as an N297A variant on both chains. Bottle opener backbone 7 is identical to 6 except the mutation is N297S. Alternative formats for bottle opener backbones 6 and 7 can exclude the ablation variants E233P/L234V/L235A/G236del/S267K in both chains. Backbone 8 is based on human IgG4, and includes the S364K/E357Q:L368D/K370S skew variants, the N208D/Q295E/N384D/Q418E/N421D pI variants on the Fab side and the E233P/L234V/L235A/G236del/S267K ablation variants on both chains, as well as a S228P (EU numbering, this is S241P in Kabat) variant on both chains that ablates Fab arm exchange as is known in the art. Alternative formats for bottle opener backbone 8 can exclude the ablation variants E233P/L234V/L235A/G236del/S267K in both chains Backbone 9 is based on human IgG2, and includes the S364K/E357Q:L368D/K370S skew variants, the N208D/Q295E/N384D/Q418E/N421D pI variants on the Fab side. Backbone 10 is based on human IgG2, and includes the S364K/E357Q:L368D/K370S skew variants, the N208D/Q295E/N384D/Q418E/N421D pI variants on the Fab side as well as a S267K variant on both chains.

As will be appreciated by those in the art and outlined below, these sequences can be used with any vh and vl pairs outlined herein, with one monomer including a scFv (optionally including a charged scFv linker) and the other monomer including the Fab sequences (e.g. a vh attached to the "Fab side heavy chain" and a vl attached to the "constant light chain"). That is, any Fv sequences outlined herein for anti-CTLA-4, anti-PD-1, anti-LAG-3, anti-TIM-3, anti-TIGIT and anti-BTLA, whether as scFv (again, optionally with charged scFv linkers) or as Fabs, can be incorporated into these FIG. 37 backbones in any combination. The constant light chain depicted in FIG. 37A can be used for all of the constructs in the figure, although the kappa constant light chain can also be substituted.

Figures 1F, 1G, 1H, 1I:
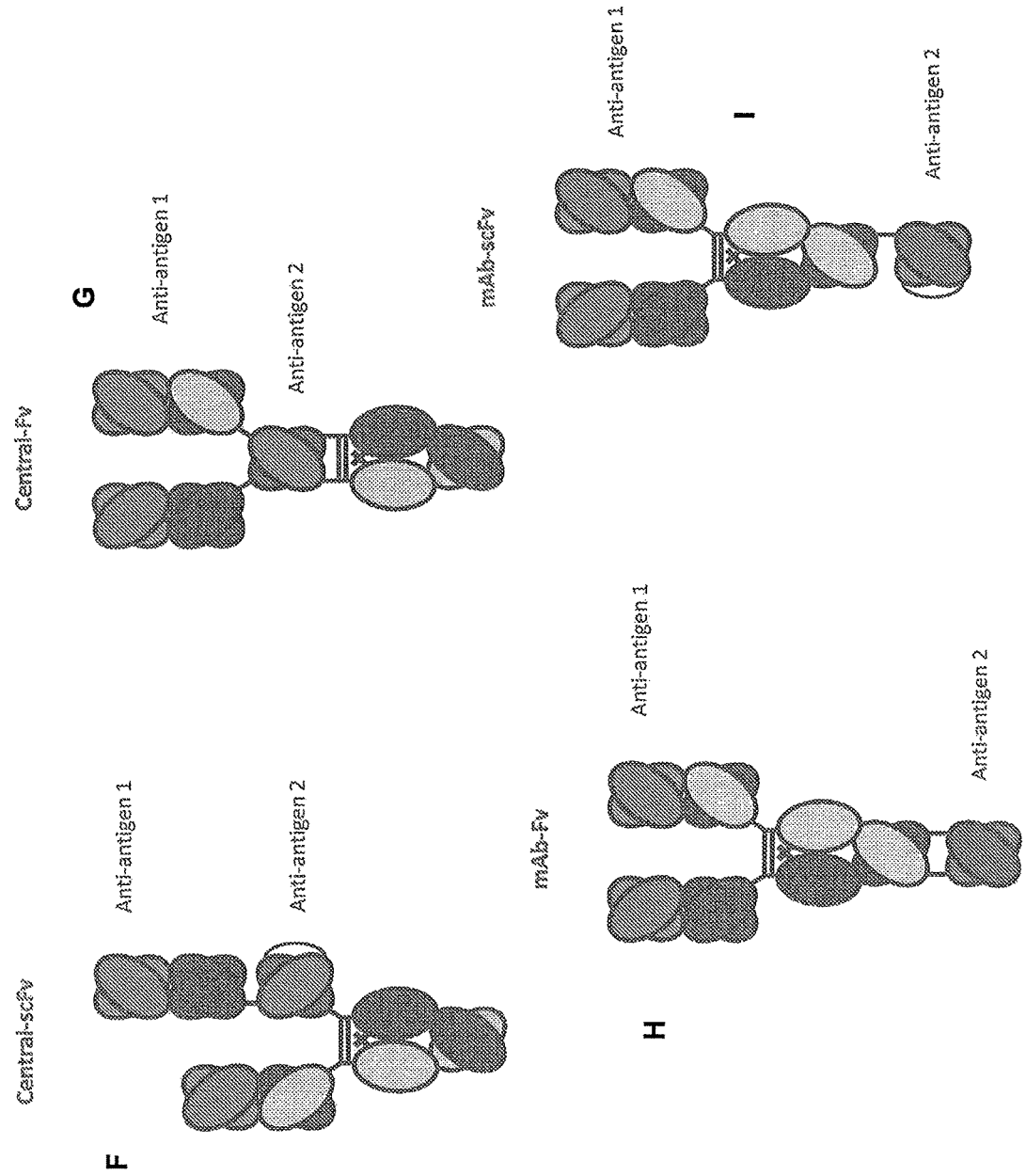

It should be noted that these bottle opener backbones find use in the Central-scFv format of FIG. 1F, where an additional, second Fab (vh-CH1 and vl-constant light) with the same antigen binding as the first Fab is added to the N-terminus of the scFv on the "bottle opener side".

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 38A-38 D shows the sequences of a mAb-scFv backbone of use in the invention, to which the Fv sequences of the invention are added. mAb-scFv backbone 1 is based on human IgG1 (356E/358M allotype), and includes the S364K/E357Q:L368D/K370S skew variants, the N208D/Q295E/N384D/Q418E/N421D pI variants on the Fab side and the E233P/L234V/L235A/G236del/S267K ablation variants on both chains. Backbone 2 is based on human IgG1 (356D/358L allotype), and includes the S364K/E357Q:L368D/K370S skew variants, the N208D/Q295E/N384D/Q418E/N421D pI variants on the Fab side and the E233P/L234V/L235A/G236del/S267K ablation variants on both chains. Backbone 3 is based on human IgG1 (356E/358M allotype), and includes the S364K/E357Q:L368D/K370S skew variants, N208D/Q295E/N384D/Q418E/N421D pI variants on the Fab side and the E233P/L234V/L235A/G236del/S267K ablation variants on both chains, as well as an N297A variant on both chains. Backbone 4 is identical to 3 except the mutation is N297S. Alternative formats for mAb-scFv backbones 3 and 4 can exclude the ablation variants E233P/L234V/L235A/G236del/S267K in both chains. Backbone 5 is based on human IgG4, and includes the S364K/E357Q:L368D/K370S skew variants, the N208D/Q295E/N384D/Q418E/N421D pI variants on the Fab side and the E233P/L234V/L235A/G236del/S267K ablation variants on both chains, as well as a S228P (EU numbering, this is S241P in Kabat) variant on both chains that ablates Fab arm exchange as is known in the art. Backbone 6 is based on human IgG2, and includes the S364K/E357Q:L368D/K370S skew variants, the N208D/Q295E/N384D/Q418E/N421D pI variants on the Fab side. Backbone 7 is based on human IgG2, and includes the S364K/E357Q:L368D/K370S skew variants, the N208D/Q295E/N384D/Q418E/N421D pI variants on the Fab side as well as a S267K variant on both chains.

As will be appreciated by those in the art and outlined below, these sequences can be used with any vh and vl pairs outlined herein, with one monomer including both a Fab and an scFv (optionally including a charged scFv linker) and the other monomer including the Fab sequence (e.g. a vh attached to the "Fab side heavy chain" and a vl attached to the "constant light chain"). That is, any Fv sequences outlined herein for anti-CTLA-4, anti-PD-1, anti-LAG-3, anti-TIM-3, anti-TIGIT and anti-BTLA, whether as scFv (again, optionally with charged scFv linkers) or as Fabs, can be incorporated into this FIG. 38 backbone in any combination. The monomer 1 side is the Fab-scFv pI negative side, and includes the heterodimerization variants L368D/K370S, the isosteric pI variants N208D/Q295E/N384D/Q418E/N421D, the ablation variants E233P/L234V/L235A/G236del/S267K, (all relative to IgG1). The monomer 2 side is the scFv pI positive side, and includes the heterodimerization variants 364K/E357Q. However, other skew variant pairs can be substituted, particularly [S364K/E357Q: L368D/K370S]; [L368D/K370S:S364K]; [L368E/K370S: S364K]; [T411T/E360E/Q362E:D401K]; [L368D/K370S: S364K/E357L], [K370S:S364K/E357Q], [T366S/L368A/Y407V:T366W] and [T366S/L368A/Y407V/Y394C: T366W/S354C].

The constant light chain depicted in FIG. 38A can be used for all of the constructs in the figure, although the kappa constant light chain can also be substituted.

It should be noted that these mAb-scFv backbones find use in the both the mAb-Fv format of FIG. 1H (where one monomer comprises a vl at the C-terminus and the other a vh at the C-terminus) as well as the scFv-mAb format of FIG. 1E (with a scFv domain added to the C-terminus of one of the monomers).

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 39A-39B depicts a matrix of possible combinations for the bispecific checkpoint antibodies of the present invention. In FIG. 39A, the combinations are not bound by format, and any format of FIG. 1 can be used. An "A" in a box means that the CDRs from the first ABD (listed on the X axis) can be combined with the CDRs of the second ABD (listed on Y axis). A "B" in the box means the vh and vl chains from the first ABD can be combined with the vh and vl chains from the second ABD. A "C" in the box means that the CDRs from the first ABD can be combined with the vh and vl chains from the second ABD. A "D" in the box means that the vh and vl chains from the first ABD can be combined with the CDRs from the second ABD. An "E" in the box means that the PD-1 ABD is selected from the group of 1G6_H1.279_L1.194; 1G6_H1.280_L1.224; 1G6_L1.194_H1.279; 1G6_L1.210_H1.288; and 2E9_H1L1. An "F" in the box means that the CTLA-4 ABD is selected from the group of [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; 0[CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44;

[CTLA-4]_H3_L0.67; and [CTLA-4]_H3_L0.74. A "G" in the box means that the TIM-3 ABD is selected from the group of 1D10_H0L0; 1D12_H0L0; 3H3_H1_L2.1; 6C8_H0L0; 6D9_H0_1D12_L0; 7A9_H0L0; 7B11_H0L0; 7B11var_H0L0; and 7C2_H0L0. An "H" in the box means that the LAG-3 ABD is selected from the group of identifiers 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1. An "I" in box means that A "J" in the box means that the BTLA ABD is selected from the group 9C6_H0L0; 9C6_H1.1_L1; and 9C6_H1.11_L1. FIG. 39B is identical to FIG. 39A except that FIG. 39B is specific to the bottle opener format. In B, when the first ABD binds PD-1, the first ABD is the scFv monomer, and the other ABD (CTLA-4, LAG-3, TIGIT, TIM-3 and BTLA) are in the Fab monomer. In B, when the first ABD binds CTLA-4, it is in the scFv monomer (except when combined with PD-1, when it is the Fab side), with the other ABD (CTLA-4, LAG-3, TIGIT, TIM-3 and BTLA) are in the Fab monomer.

FIG. 40 depicts a matrix of possible bottle opener format combinations. A "Q" in the box means that the first ABD domain (again, listed on the X axis) is the scFv and the second ABD (again, listed on the Y axis) is the Fab side. An "R" in the box means that the first ABD is the Fab side and the second ABD is the scFv. An "S" in the box means that the first ABD is anti-PD-1 and is the scFv side. A "T" in the box means that the first ABD is anti-CTLA-4 and is the scFv side. A "U" in the box means that the first ABD is anti-TIM-3 and is the scFv side. A "V" in the box means that the first ABD is anti LAG-3 and is the scFv side. A "W" in the box means that the first ABD is anti TIGIT and is the scFv side. An "X" in the box means that the first ABD is anti-BTLA and is the scFv side. In addition, each combination outlined in FIG. 39 can use the CDRs, scFvs and vh and vl combinations of FIG. 38. In addition, particular embodiments of the bottle opener backbones of FIG. 39 are the sequences of FIG. 36.

Figure 41A:
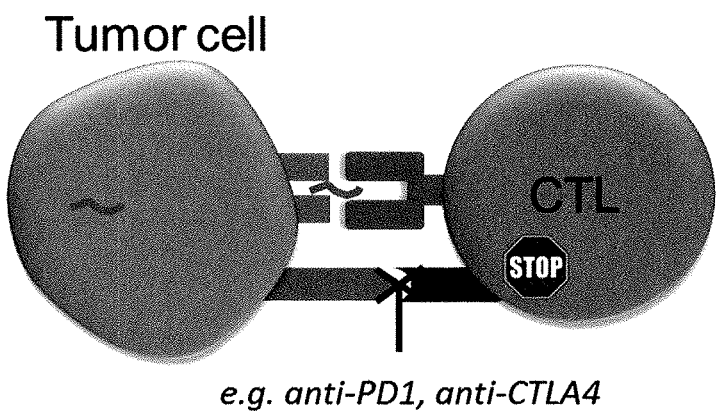
Figure 41B:
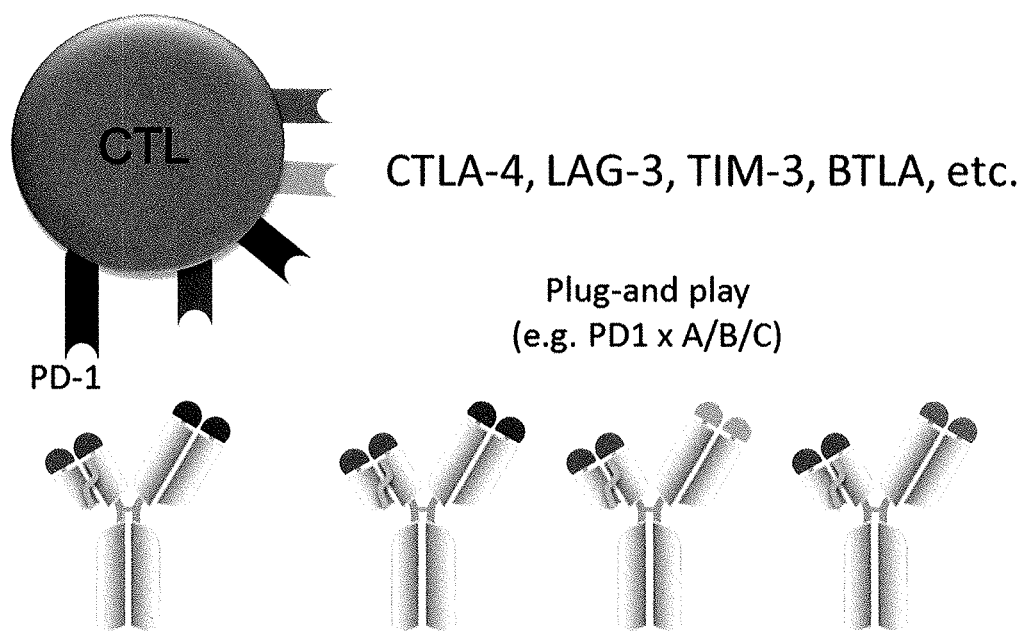

FIG. 41A-41B depicts a schematic associated with the benefit that a bispecific checkpoint antibody can provide over combination therapies using two different antibodies or drugs.

Figure 42:
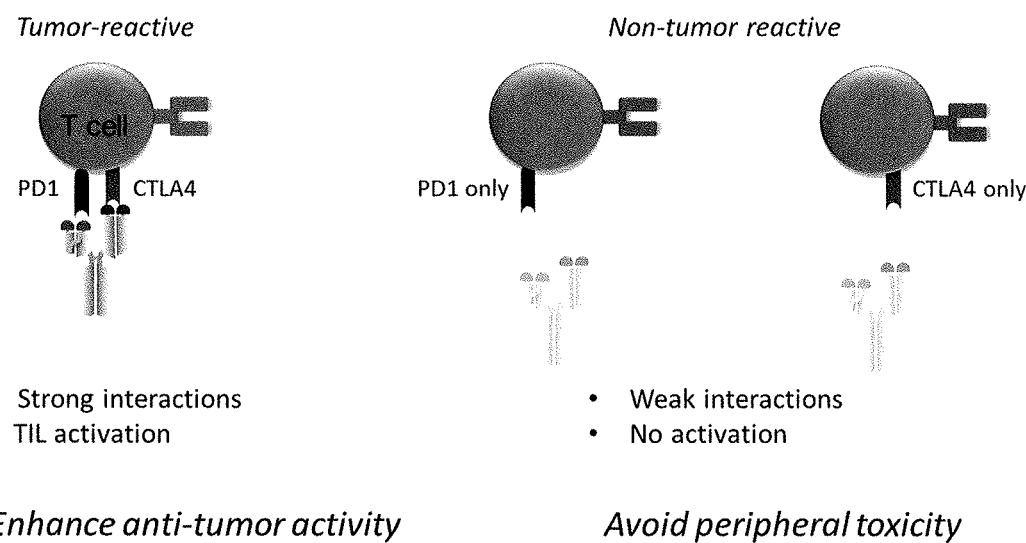

FIG. 42 depicts a similar schematic, showing that because tumor TILs co-express multiple checkpoints, a bivalent binding increases avidity, enhancing anti-tumor activity and avoiding peripheral toxicity.

Figure 43:
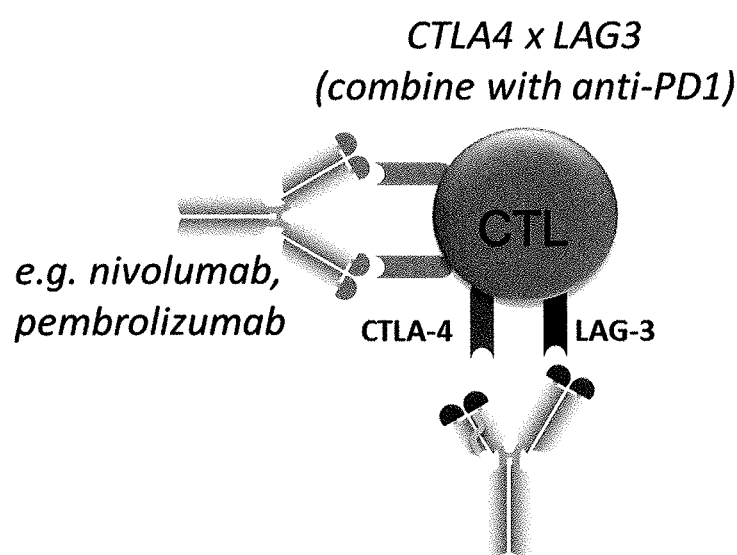

FIG. 43 shows that bispecific checkpoint antibodies of the invention (e.g. anti-LAG-3×anti-CTLA-4) can be combined with other monospecific checkpoint antibodies (e.g. nivolumab, pemobrolizumab).

Figure 44:
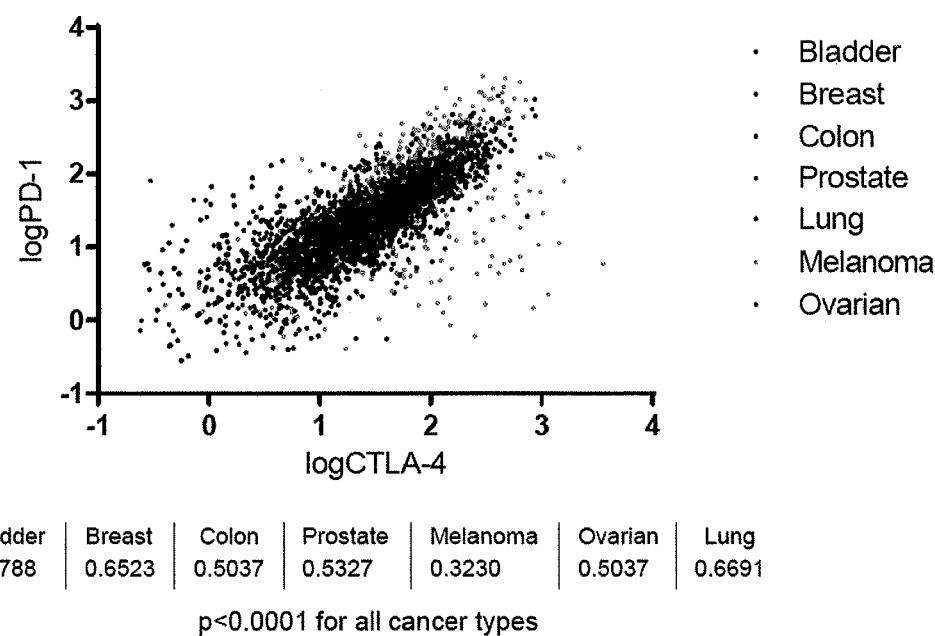

FIG. 44 shows that PD-1 and CTLA-4 are coexpressed in a variety of tumor types, including bladder, breast, colon, prostate, lung, melanoma and ovarian cancer.

Figure 45A:
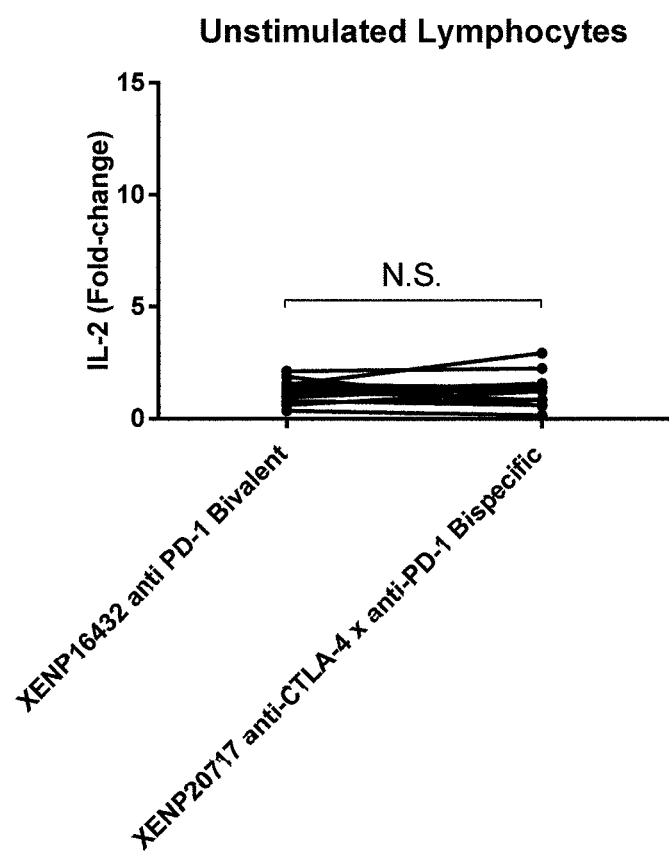
Figure 45B:
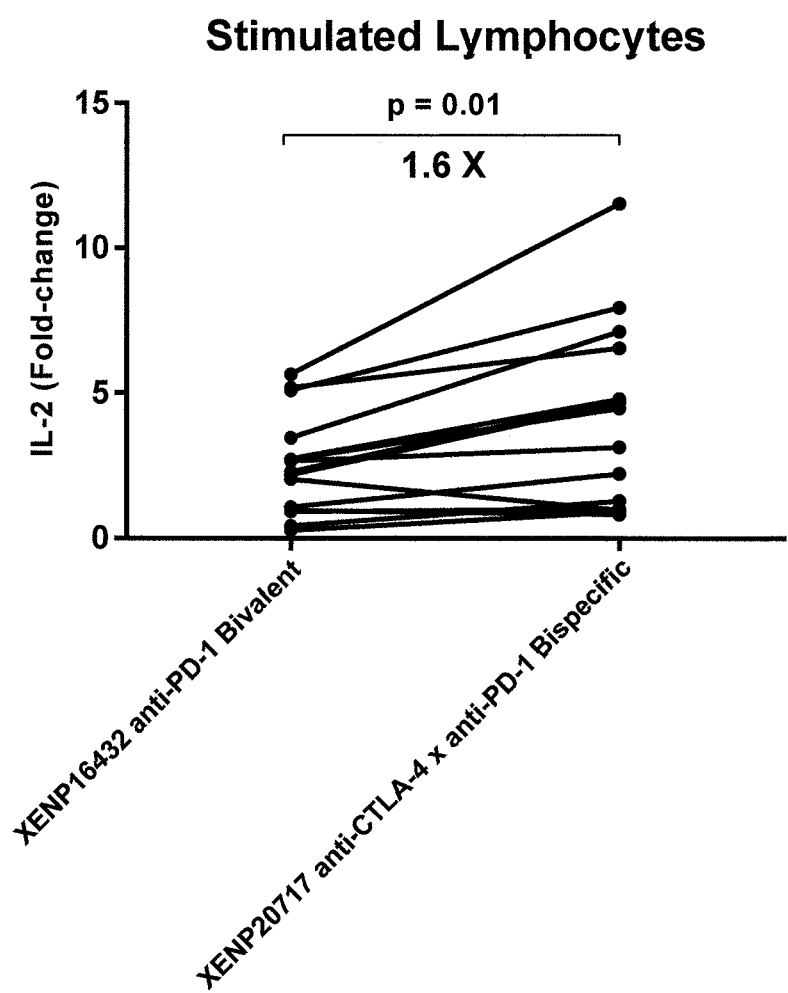
Figure 45C:
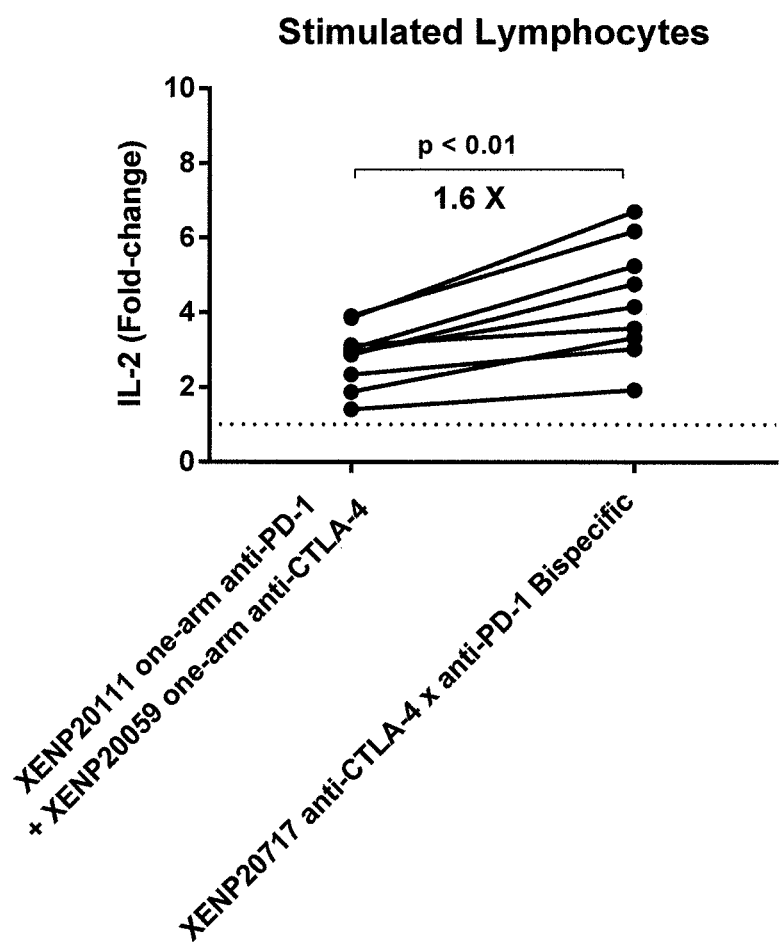

FIG. 45A-45C depicts a comparison of the enhancement of IL-2 B) by anti-PD-1 bivalent and anti-CTLA-4×anti-PD-1 and C) and one-arm anti-PD-1+one-arm anti-CTLA-4 and anti-CTLA-4×anti-PD-1 in an SEB-stimulated PBMC assay as well as C) a control experiment without SEB stimulation.

Figure 46A:
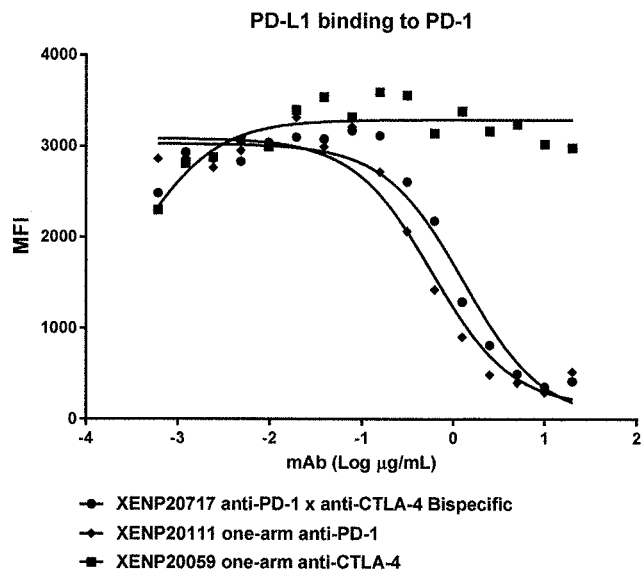
Figure 46B:
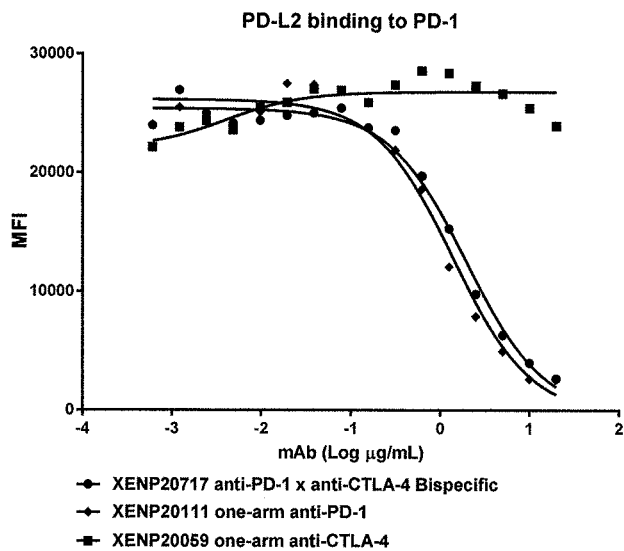

FIG. 46A-46B depicts blocking of PD-1 to ligands PD-L1 and PD-L2 by an exemplary anti-CTLA-4×anti-PD-1 bispecific in comparison to one-arm anti-PD-1 and one-arm anti-CTLA-4 antibodies.

Figure 47:
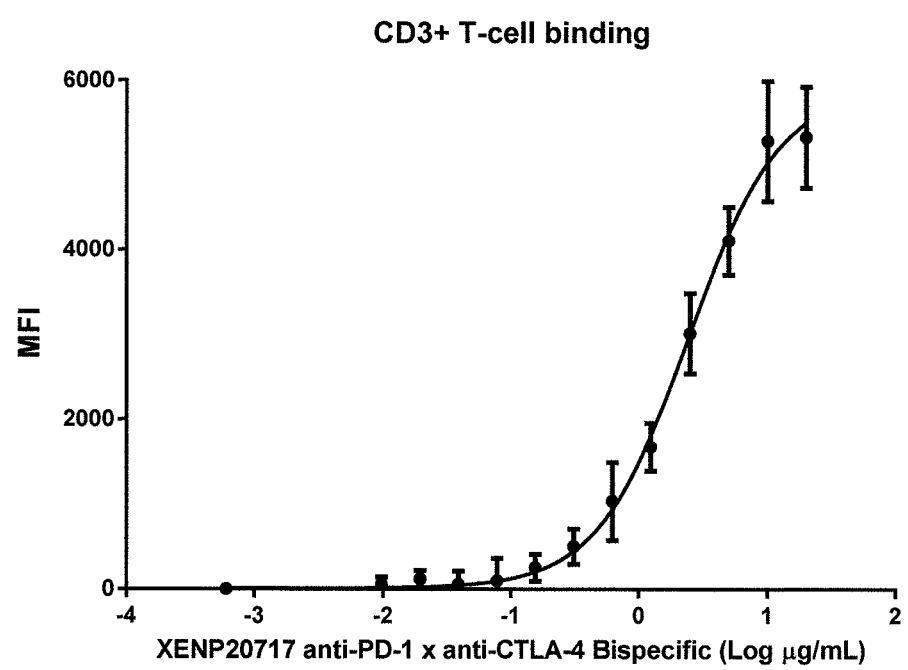

FIG. 47 depicts T cell binding in an SEB-stimulated PBMC assay by an exemplary anti-CTLA-4×anti-PD-1 bispecific antibody.

Figure 48:
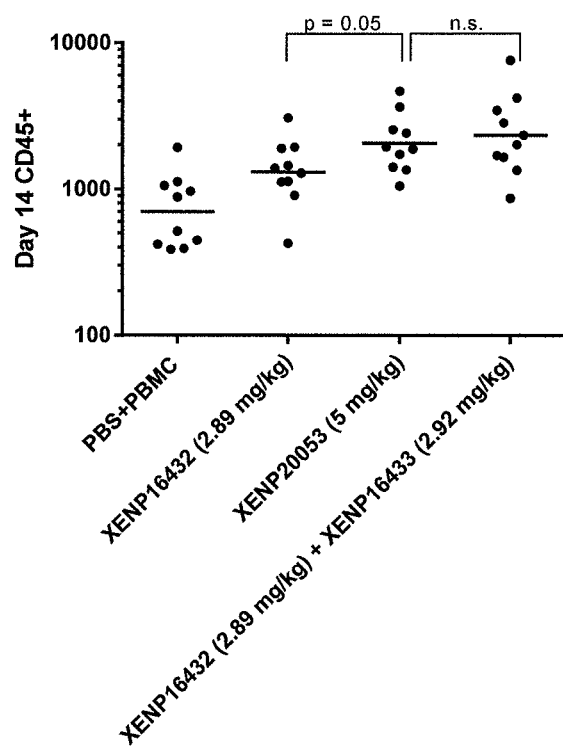

FIG. 48 shows that anti-CTLA-4×anti-PD-1 bispecifics enhance engraftment (as measured by human CD45 counts) in human PBMC-engrafted NSG mice. Enhancement is greater than that seen with nivolumab (XENP16432) alone.

Figure 49:
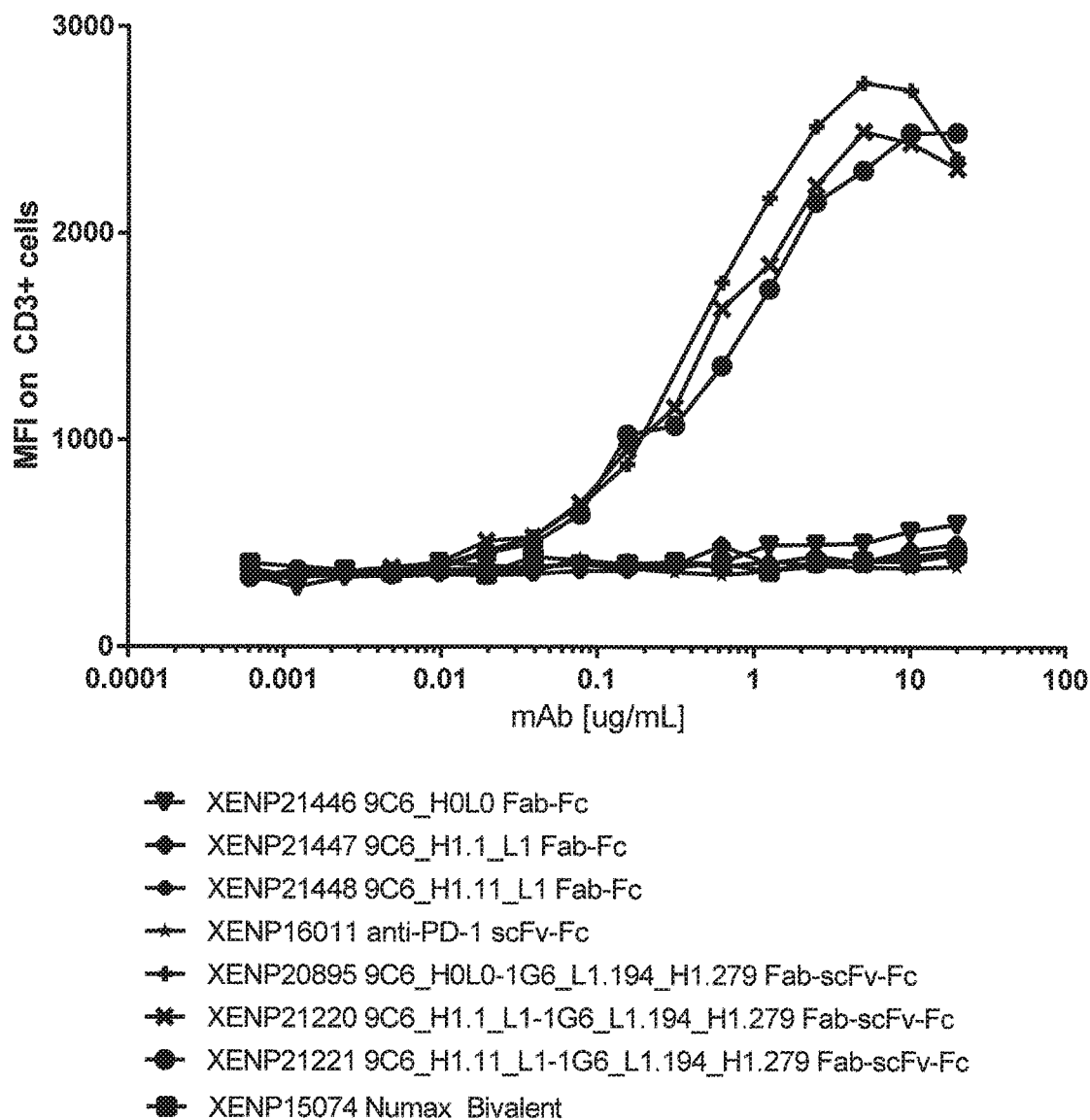

FIG. 49 shows that the anti-BTLA×anti-PD-1 bispecific candidates bind more avidly to T cells compared to "one-armed" controls in an SEB-stimulated PBMC assay.

Figure 50A:
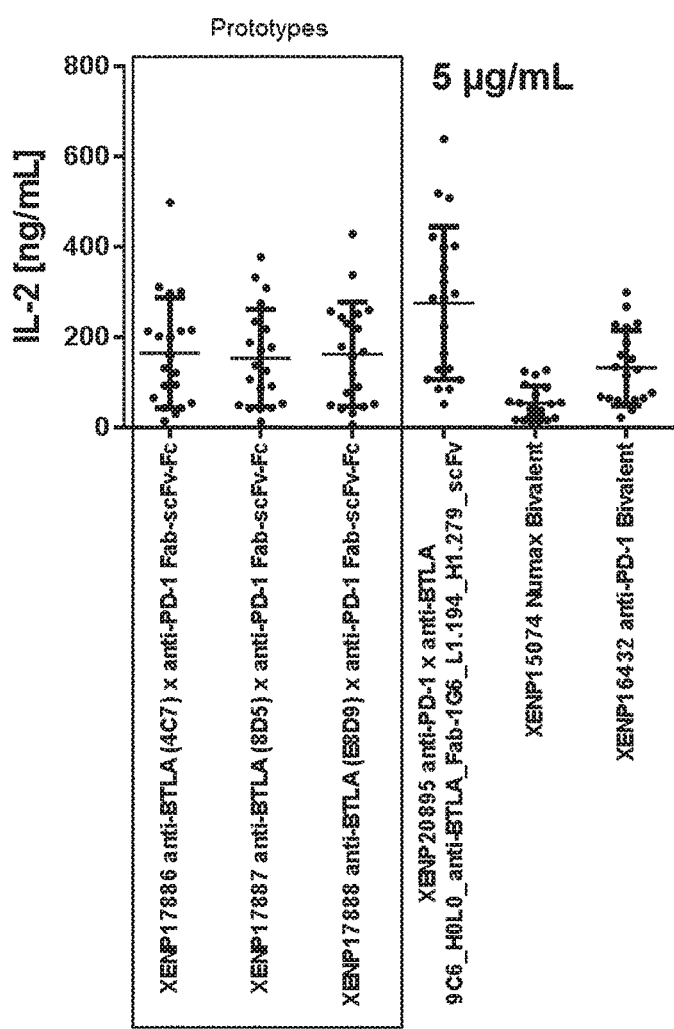
Figure 50B:
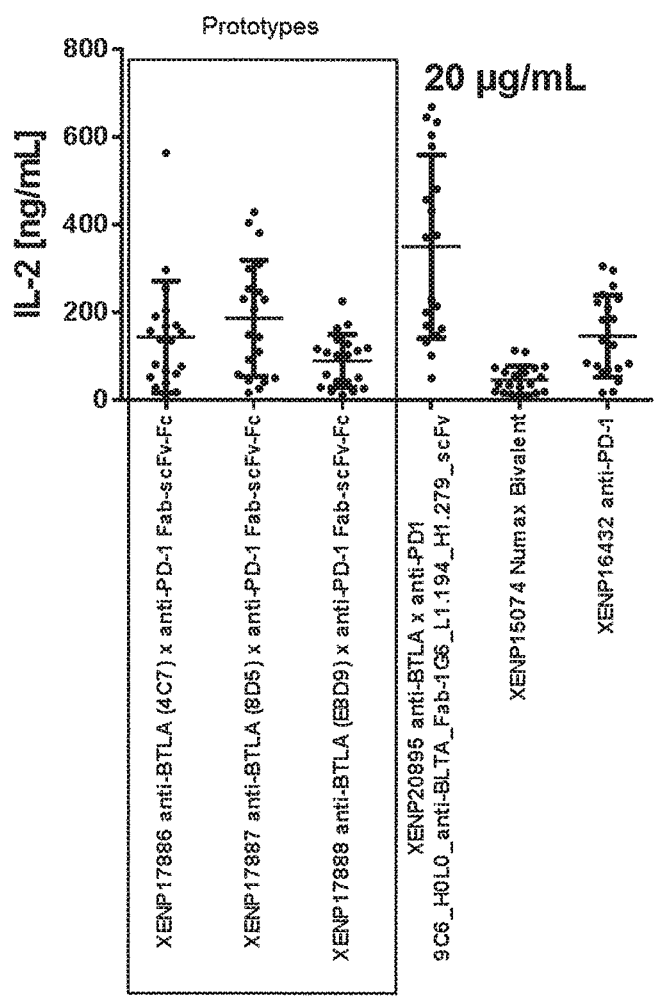

FIG. 50A-50B show that anti-BTLA×anti-PD-1 chimeric bispecific promotes IL-2 secretion from SEB stimulated PBMCs. PBMCs were stimulated with 10 ng/mL SEB for 3 days with indicated test articles. Cell supernatants were collected and assayed with MSD for indicated analyte. A: 20 µg/mL test article; B 5 µg/mL test article.

Figure 51A:
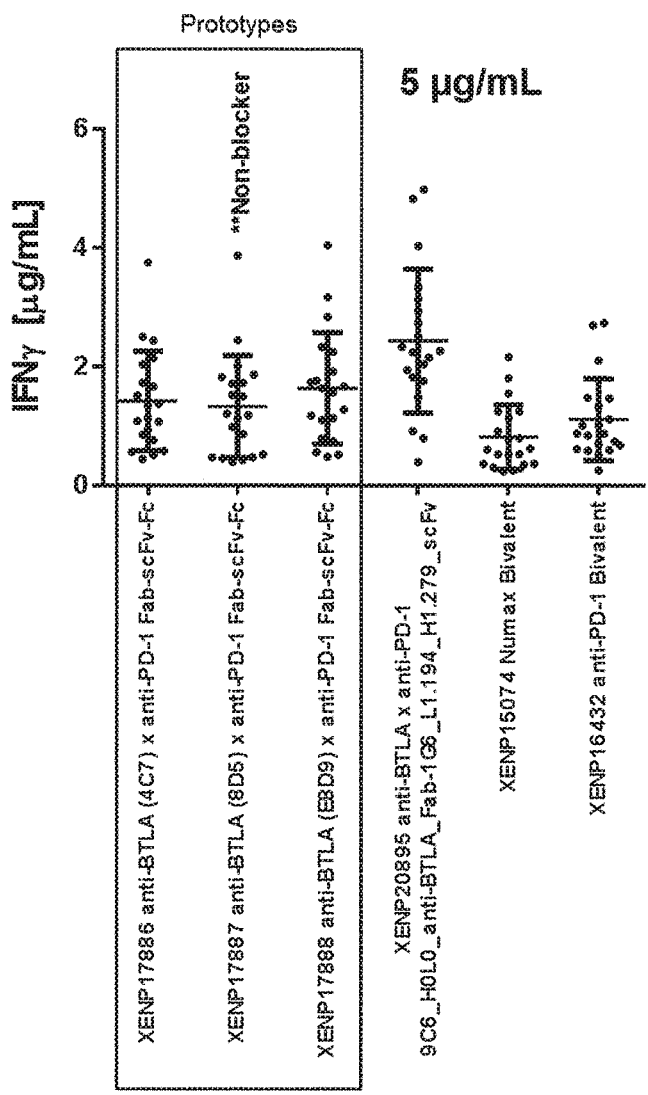
Figure 51B:
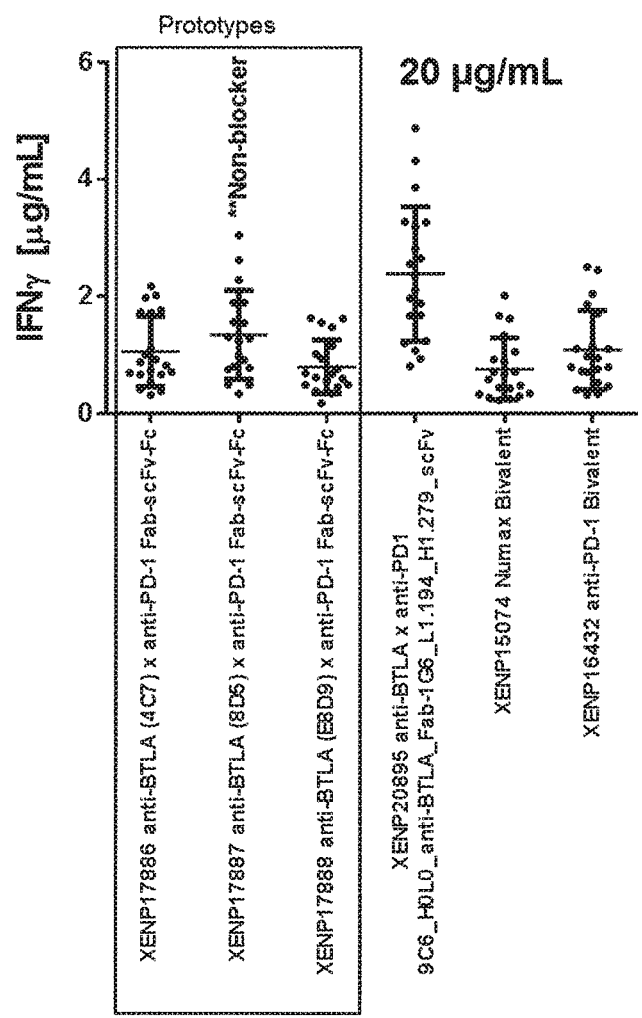

FIG. 51A-51B show that anti-BTLA×anti-PD-1 chimeric bispecific promotes IFNγ secretion from SEB stimulated PBMCs. PBMCs were stimulated with 10 ng/mL SEB for 3 days with indicated test articles. Cell supernatants were collected and assayed with MSD for indicated analyte. A: 20 µg/mL test article; B 5 µg/mL test article.

Figure 52A:
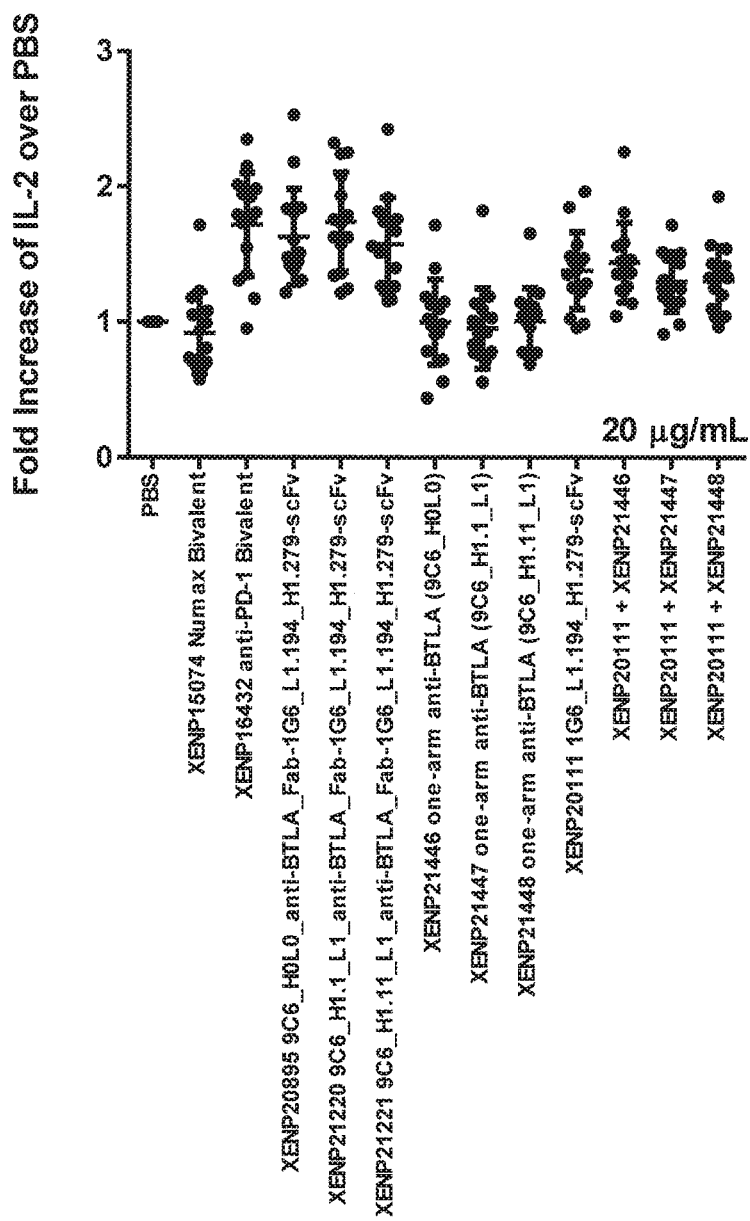
Figure 52B:
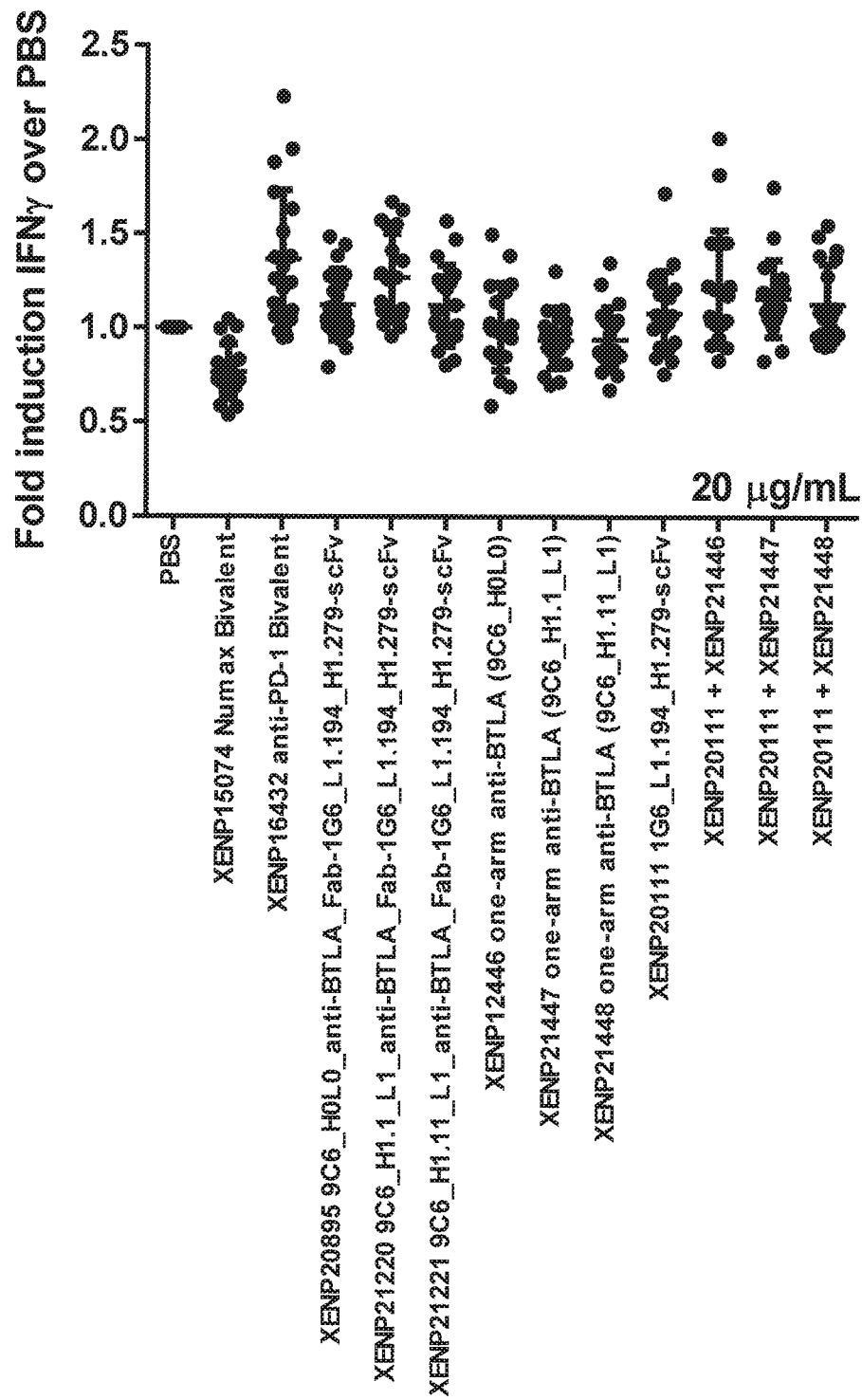
Figure 53A:
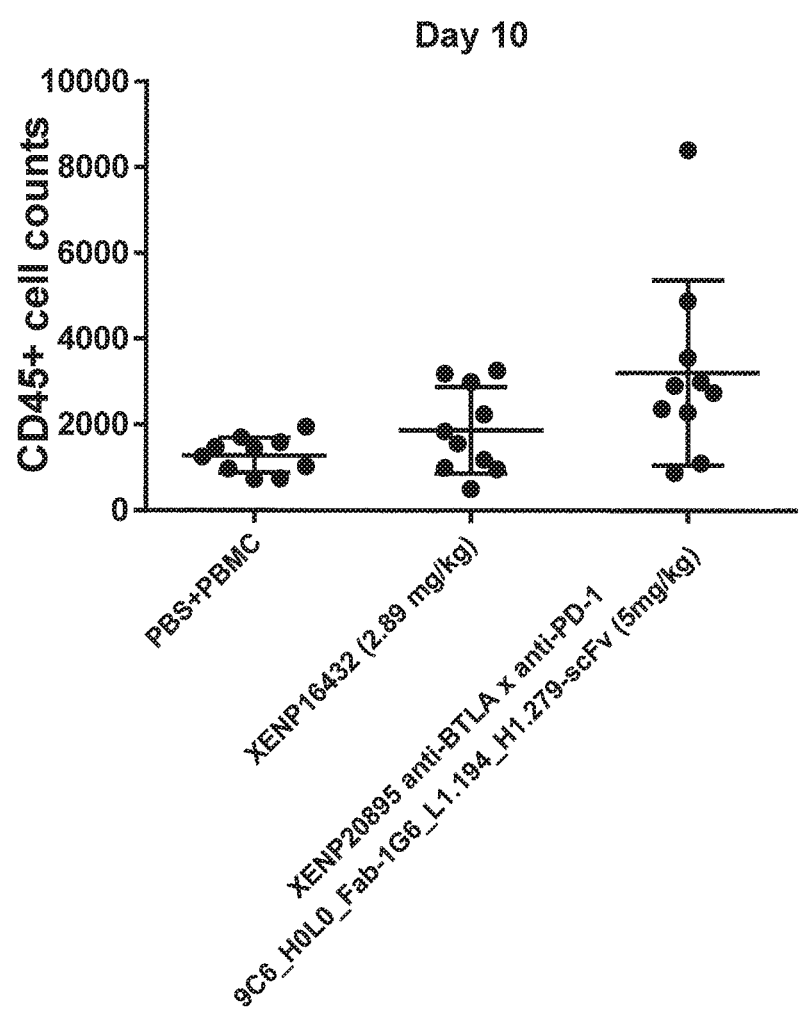
Figure 53B:
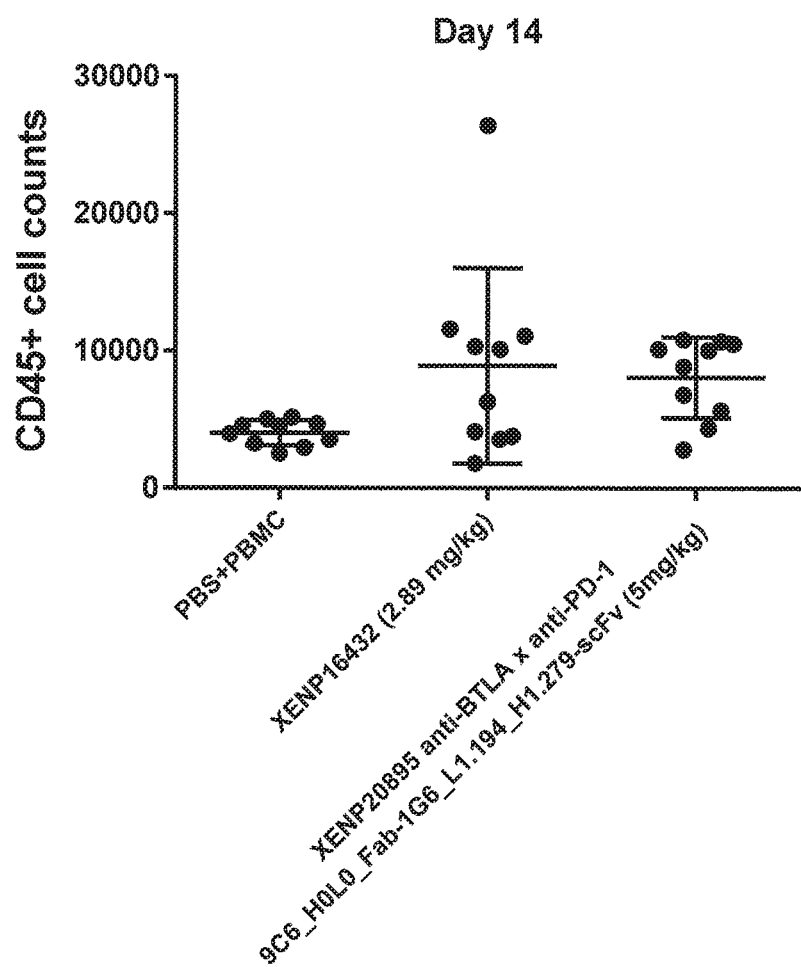
Figure 53C:
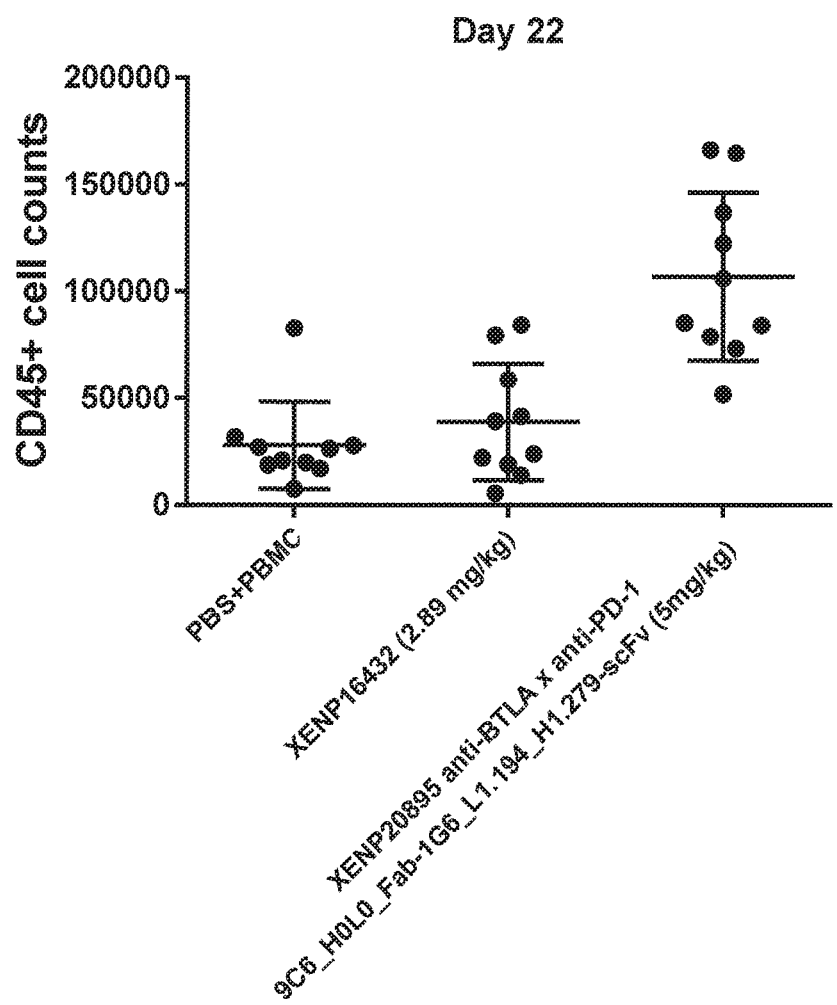
Figure 53D:
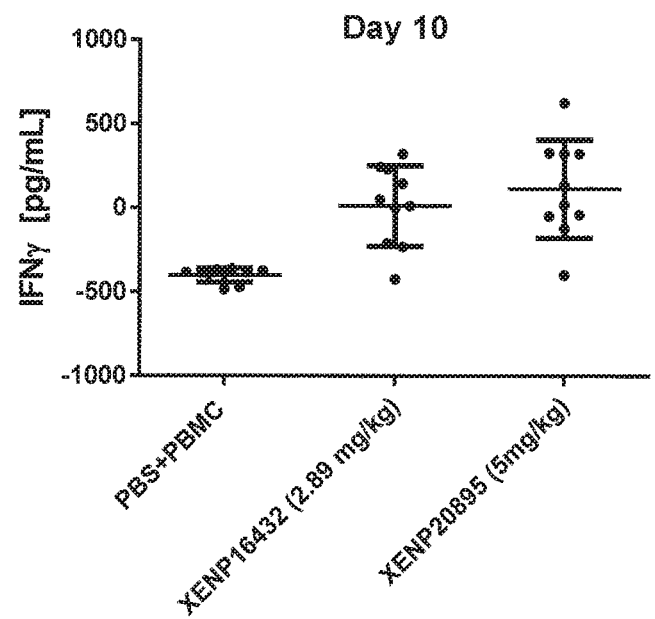
Figure 53E:
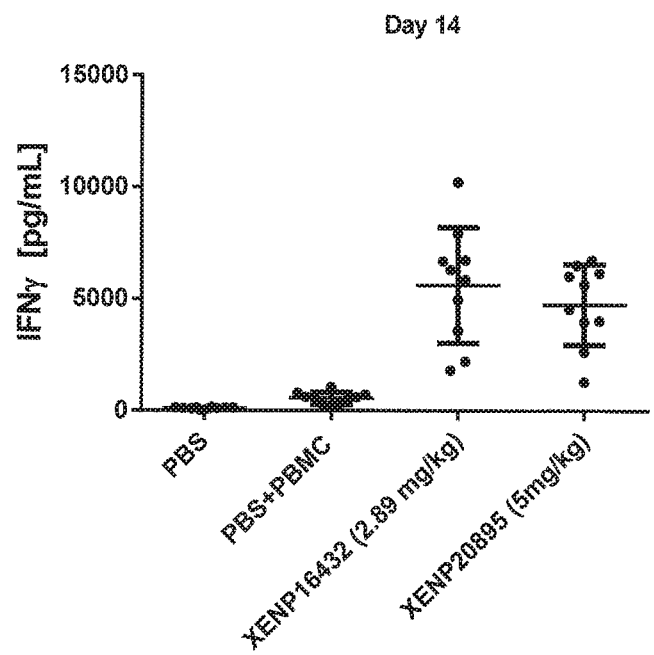
Figure 53F:
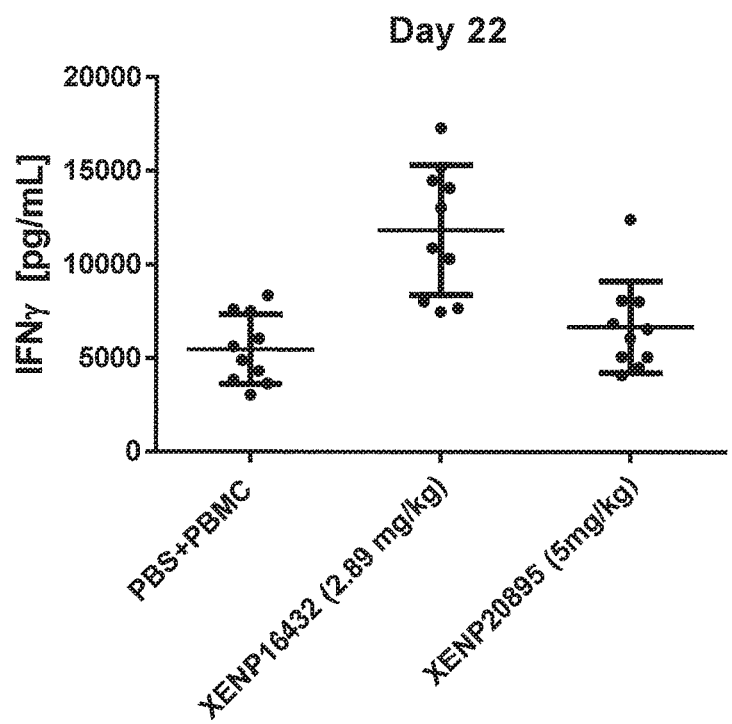

FIG. 52A-52B shows that anti-BTLA×anti-PD-1 bispecific antibodies (chimeric and with humanized/optimized anti-BTLA Fab arms) promotes IL-2 secretion and IFN-γ from SEB stimulated PBMCs. Both panels were PBMCs stimulated with 10 ng/mL SEB for 3 days with indicated 20 µg/mL test articles. Cell supernatants were collected 72 hours later and assayed for indicated analyte.

FIG. 53A-53F shows the time course (Days 10, 14 and 22) enhancement in CD45 cell counts and IFNγ secretion by an exemplary anti-BTLA×anti-PD-1 bispecific antibody in a GVHD study.

FIG. 54 depicts some 9C6 anti-BTLA antigen binding domain engineering data. This depicts XENP code for bivalent embodiments, the designations of the vh and vl engineered domains, and the KD binding constant against human BTLA as measured by OCTET®.

FIG. 55A-55E depicts some 2A11 anti-LAG-3 antigen binding domain engineering data. This depicts XENP code for Fab embodiments, the designations of the vh and vl engineered domains, the KD binding constant against human LAG-3 as measured by OCTET® and the Tm of the Fab.

FIG. 56A-56K depicts some 7G8 anti-LAG-3 antigen binding domain engineering data. This depicts XENP code for Fab embodiments, the designations of the vh and vl engineered domains, the KD binding constant against human LAG-3 as measured by OCTET® and the Tm of the Fab.

FIG. 57A-57B depicts the Kds for anti-LAG-3×anti-CTLA-4 bispecific, heterodimeric bottle opener formats based on either optimized 2A11 or 7G8 anti-LAG-3 Fab arms as measured by OCTET®.

Figure 58:
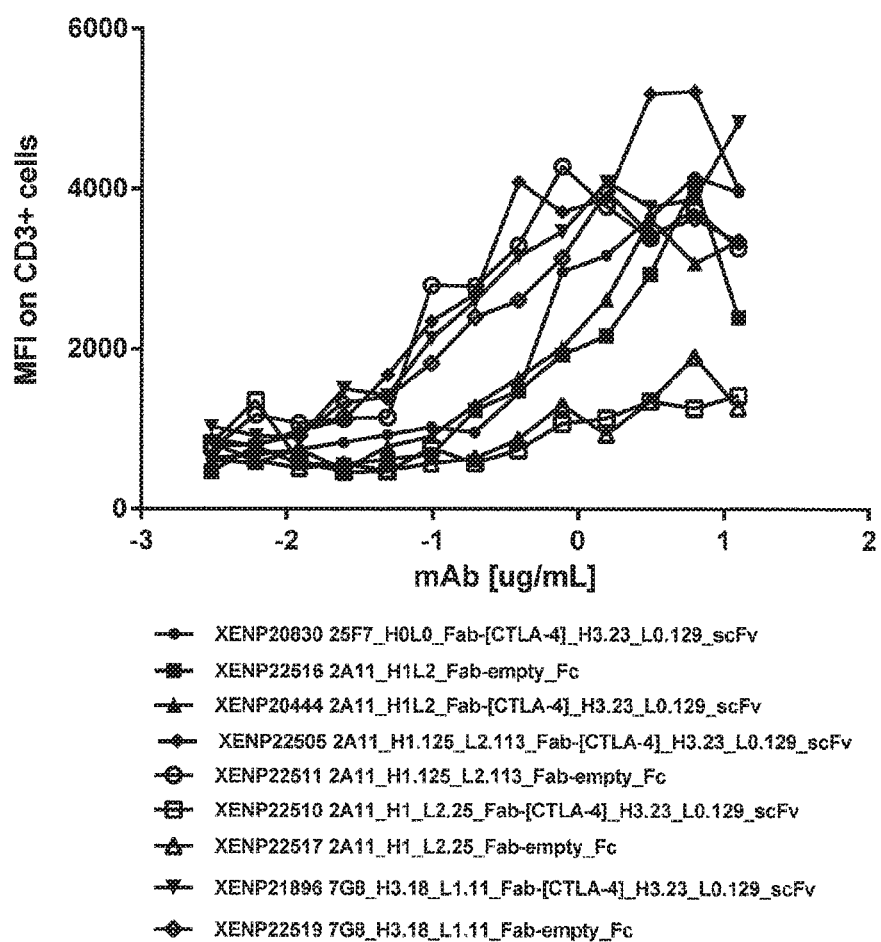

FIG. 58 shows that anti-LAG-3 (7G8)×anti-CTLA-4 and anti-LAG-3 (2A11)×anti-CTLA-4 bispecifics bind more avidly than one-armed anti-LAG-3 controls. PBMCs were stimulated with 100 ng/mL SEB for 3 days. Cells were then treated with the indicated test articles for 30 min at 4C degrees and washed twice. Cells were then treated with an anti-CD3-FITC and anti-human-Fc-APC antibody. Cells were then washed twice and analyzed by flow cytometry.

Figure 59A:
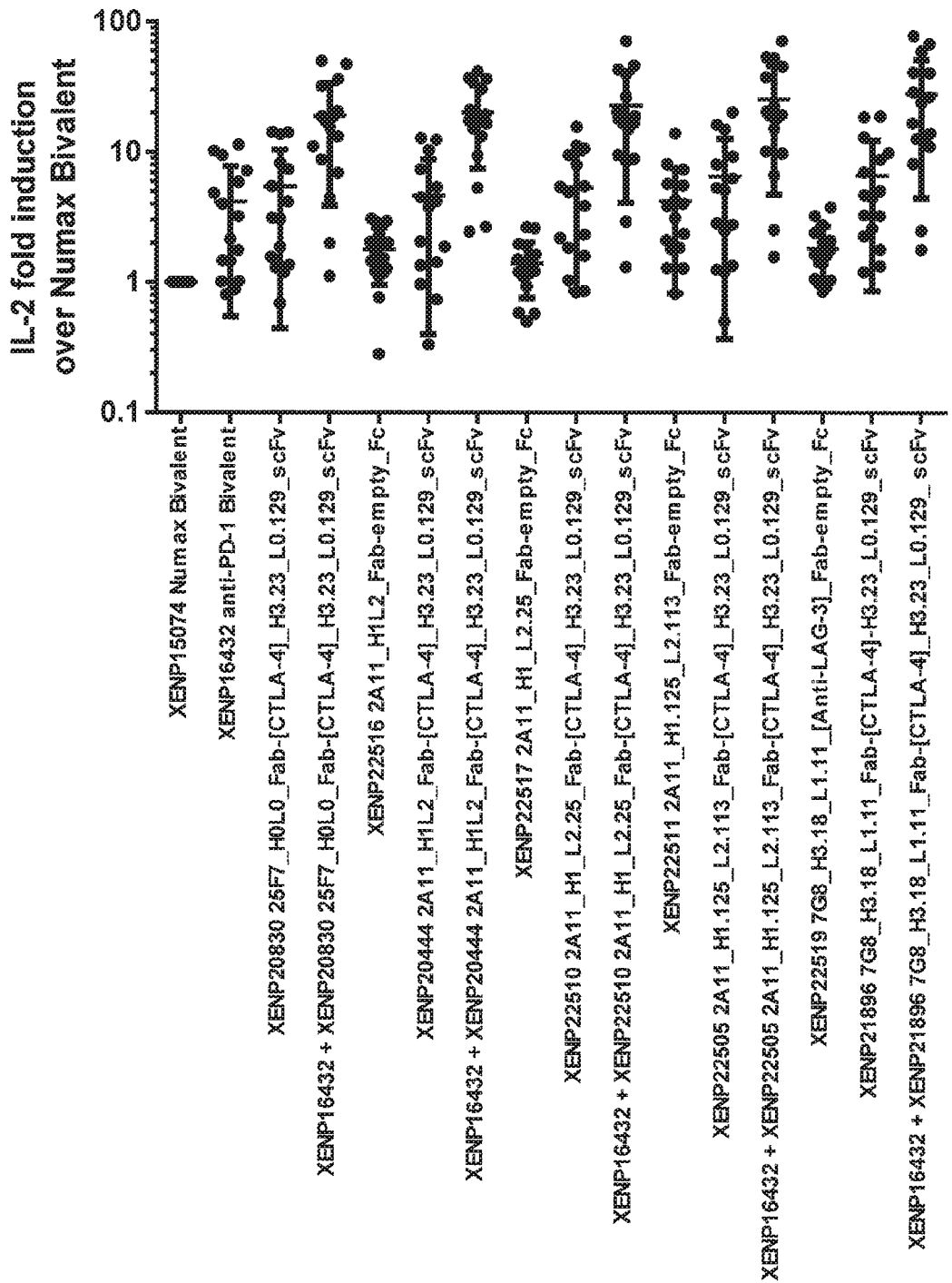
Figure 59B:
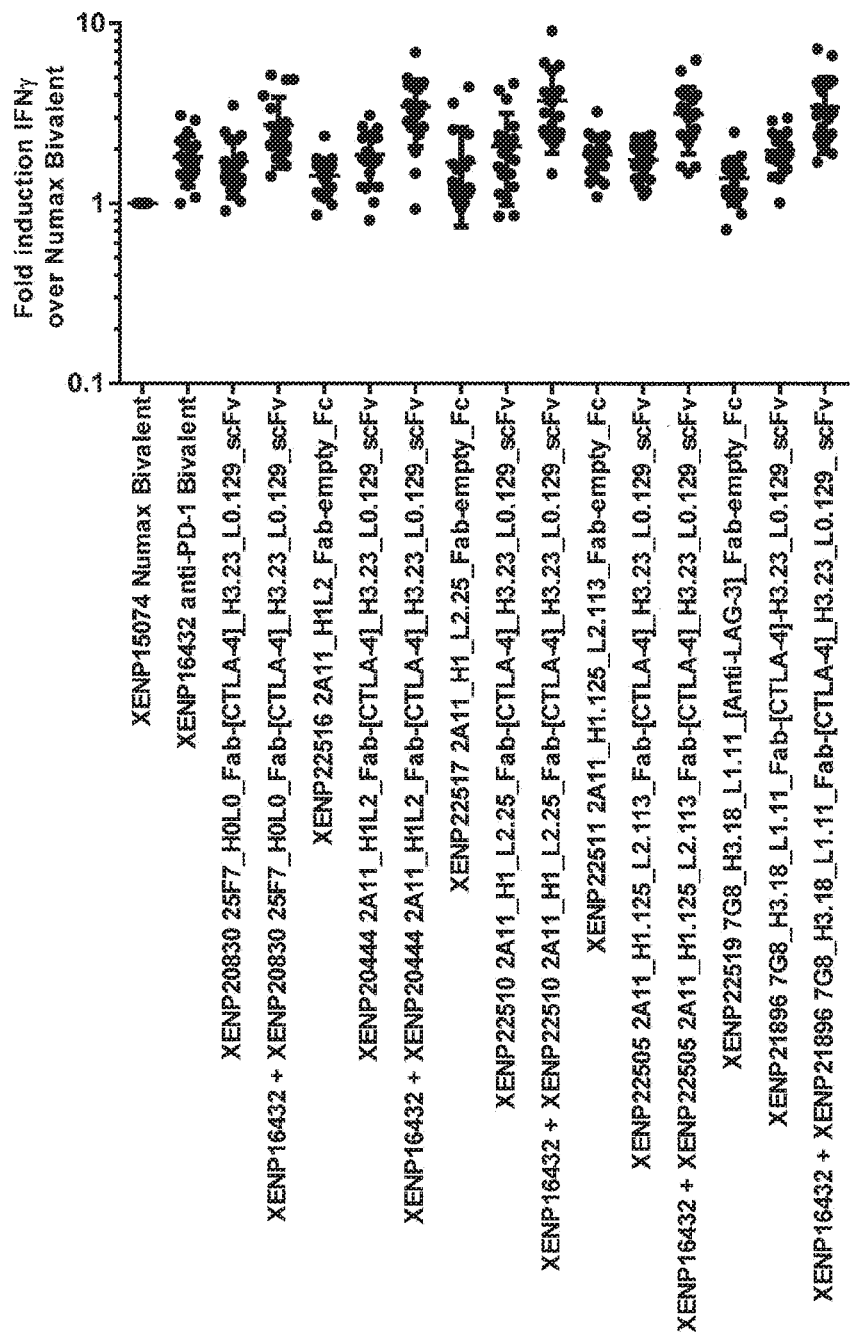

FIG. 59A-59B shows that 7G8 based anti-LAG-3×anti-CTLA-4 bispecifics exhibit more selective function on PBMCs than 2A11 based anti-LAG-3×anti-CTLA-4 bispecifics as indicated by enhancement in IL-2 and IFNγ release. PBMCs were stimulated with 500 ng/mL of SEB for 2 days. Cells were then washed twice in culture medium and stimulated with 500 ng/mL SEB in combination with the indicated amounts of test articles. Cells were assayed for the indicated analyte (either IL-2 or IFN-γ) 24 hours after treatment. Each point represents a unique donor tested in technical singlet.

Figure 60A:
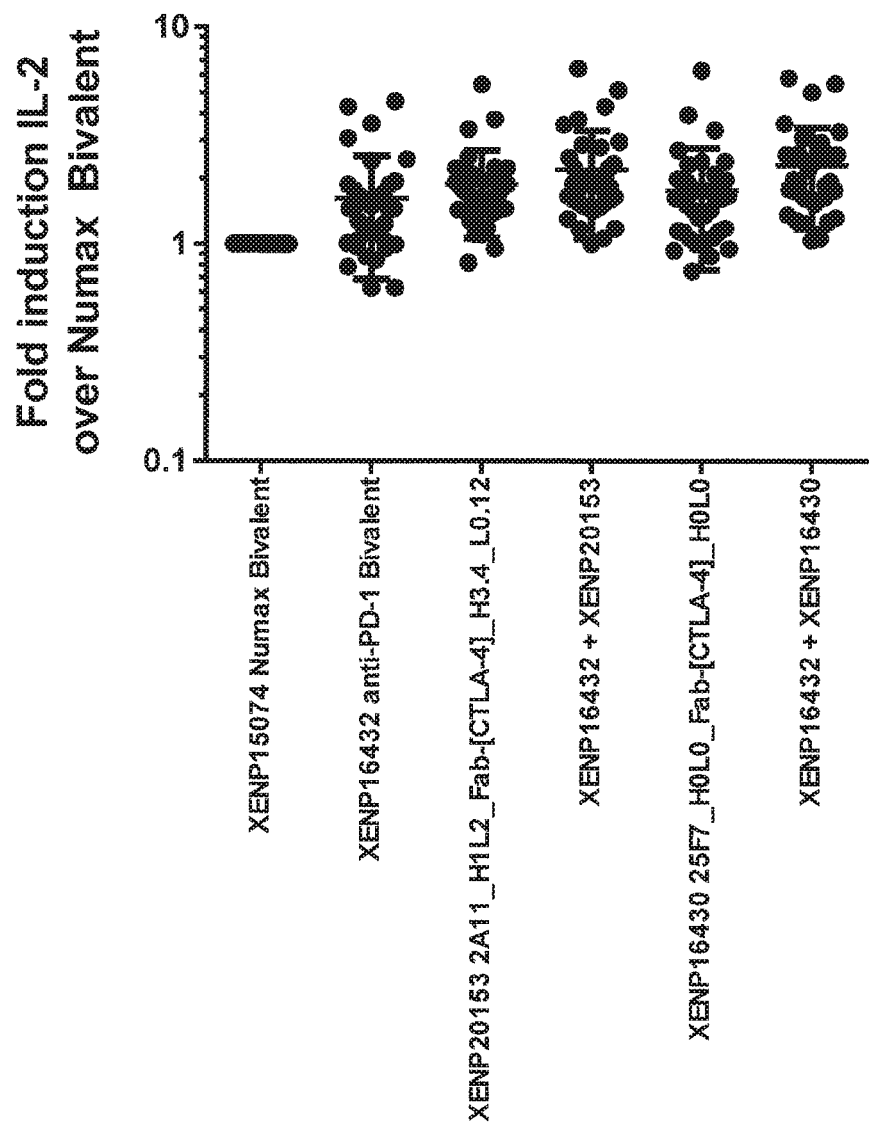
Figure 60B:
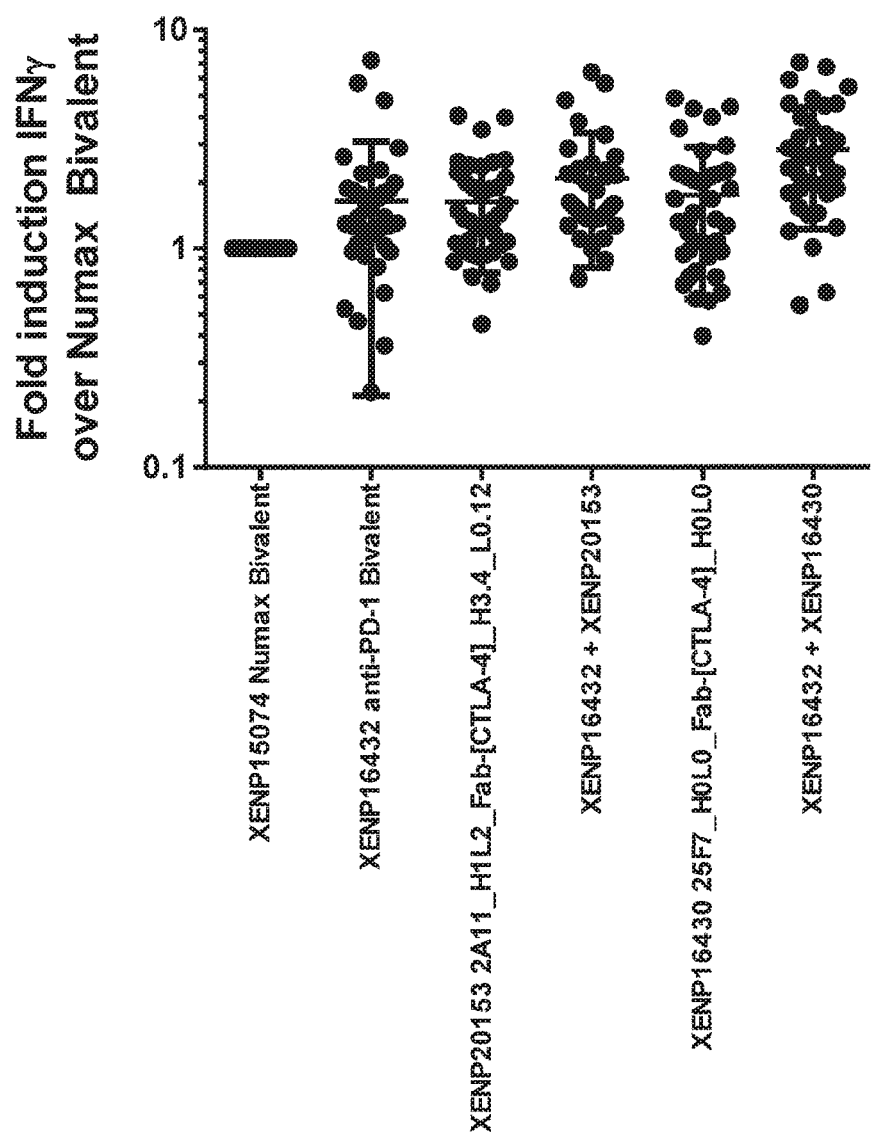

FIG. 60A-60B depicts mixed lymphocyte reactions (MLRs) with anti-LAG-3×anti-CTLA-4 bispecific antibodies. 40 unique MLR reactions were made in the presence of 20 μg/mL of indicated test articles. Cell supernatants were then assayed by MSD 6 days after treatment for A: IL-2 and B: IFNγ.

Figure 61A:
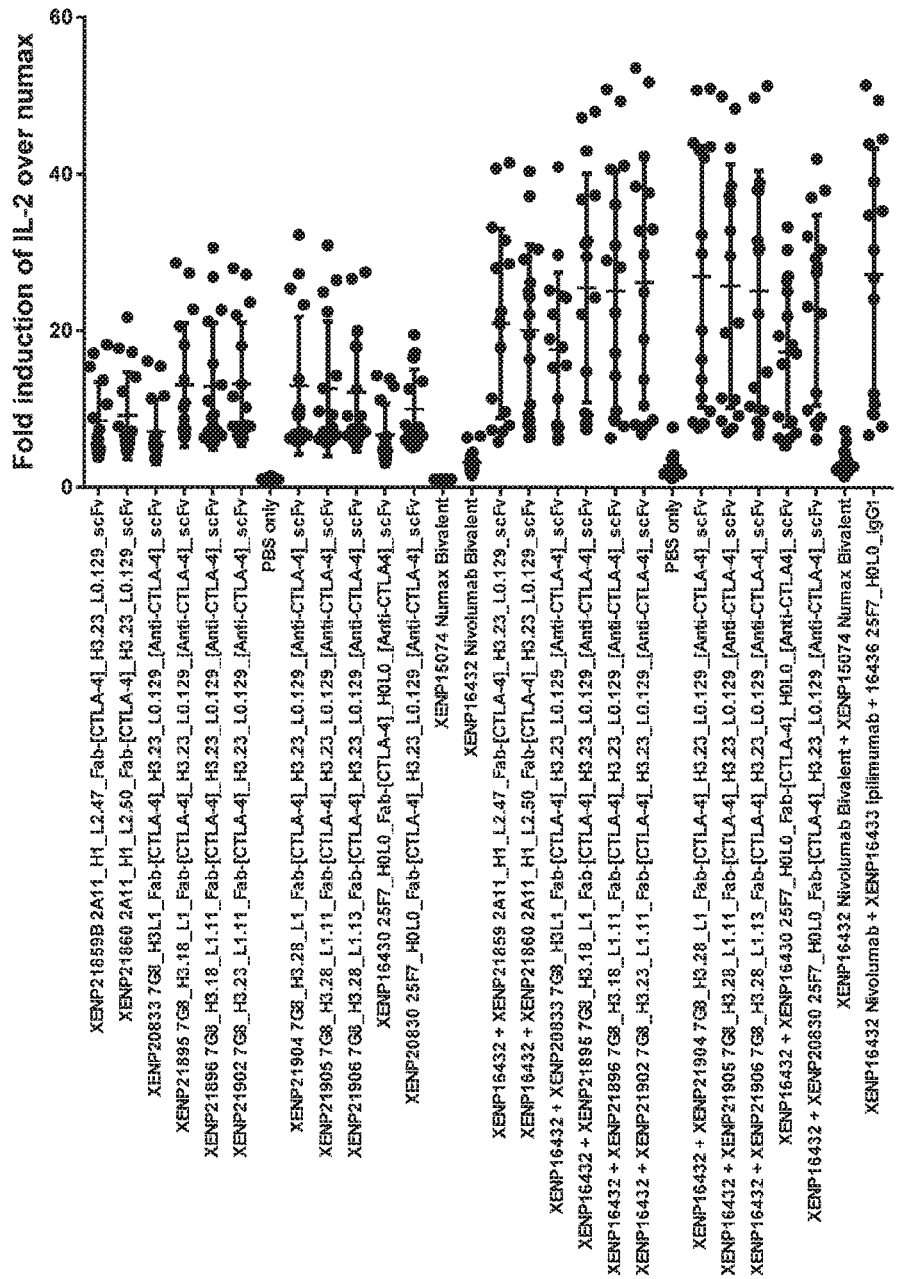
Figure 61B:
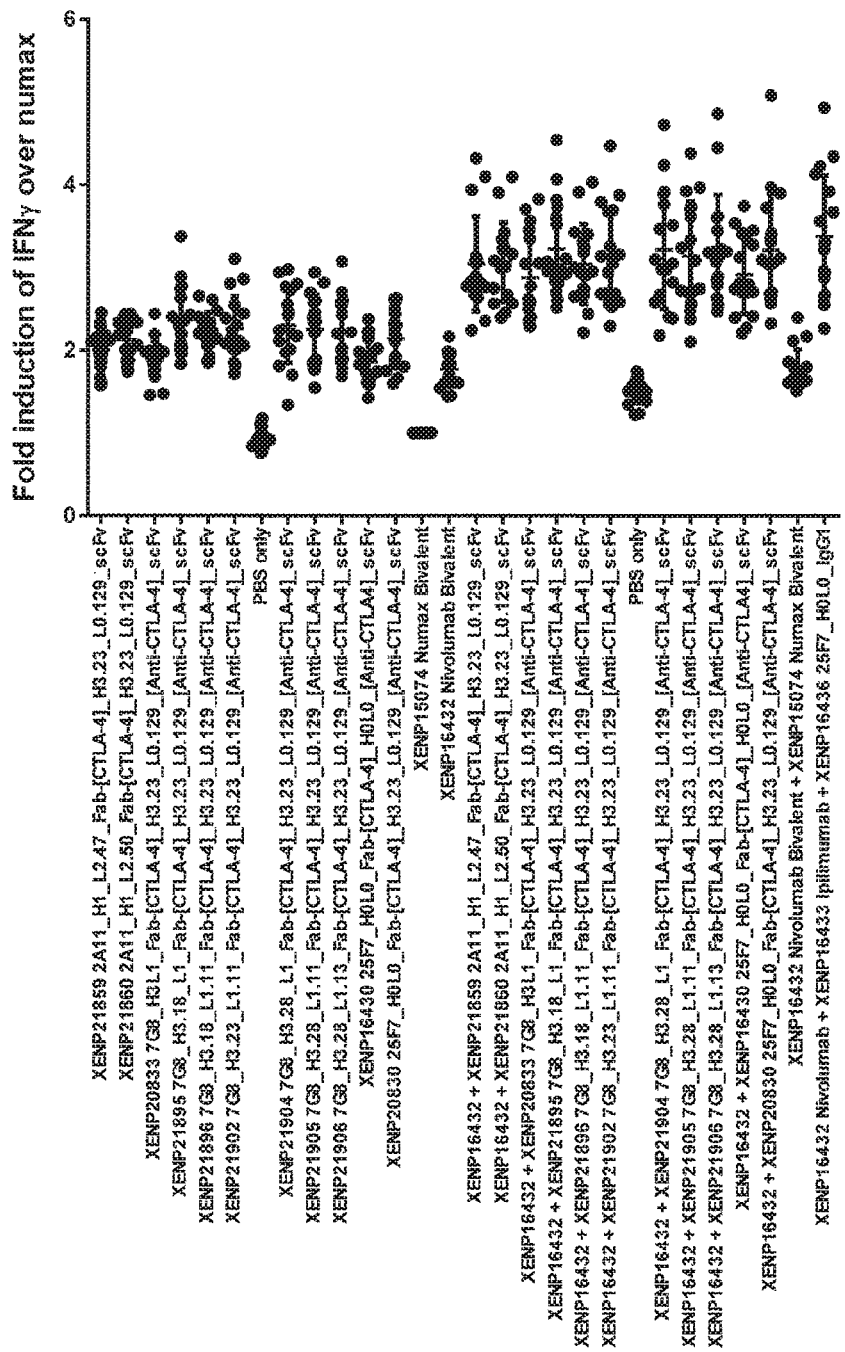

FIG. 61A-61B shows enhancement of IL-2 and IFNγ release by additional anti-LAG-3×anti-CTLA-4 candidates in the SEB assays. PBMCs were stimulated with 500 ng/mL SEB for 2 days. Cells were then washed twice in culture medium and stimulated with 500 ng/mL SEB in combination with indicated amounts of test articles. Cells were assayed for indicated analyte (either IL-2 or IFN-γ) 24 hours after treatment. Each point represents a unique donor tested in technical singlet.

FIG. 62A-62B depicts the Kds for anti-LAG-3×anti-PD-1 bispecific, heterodimeric bottle opener formats based on either optimized 2A11 or 7G8 anti-LAG-3 Fab arms as measured by OCTET®.

Figure 63A:
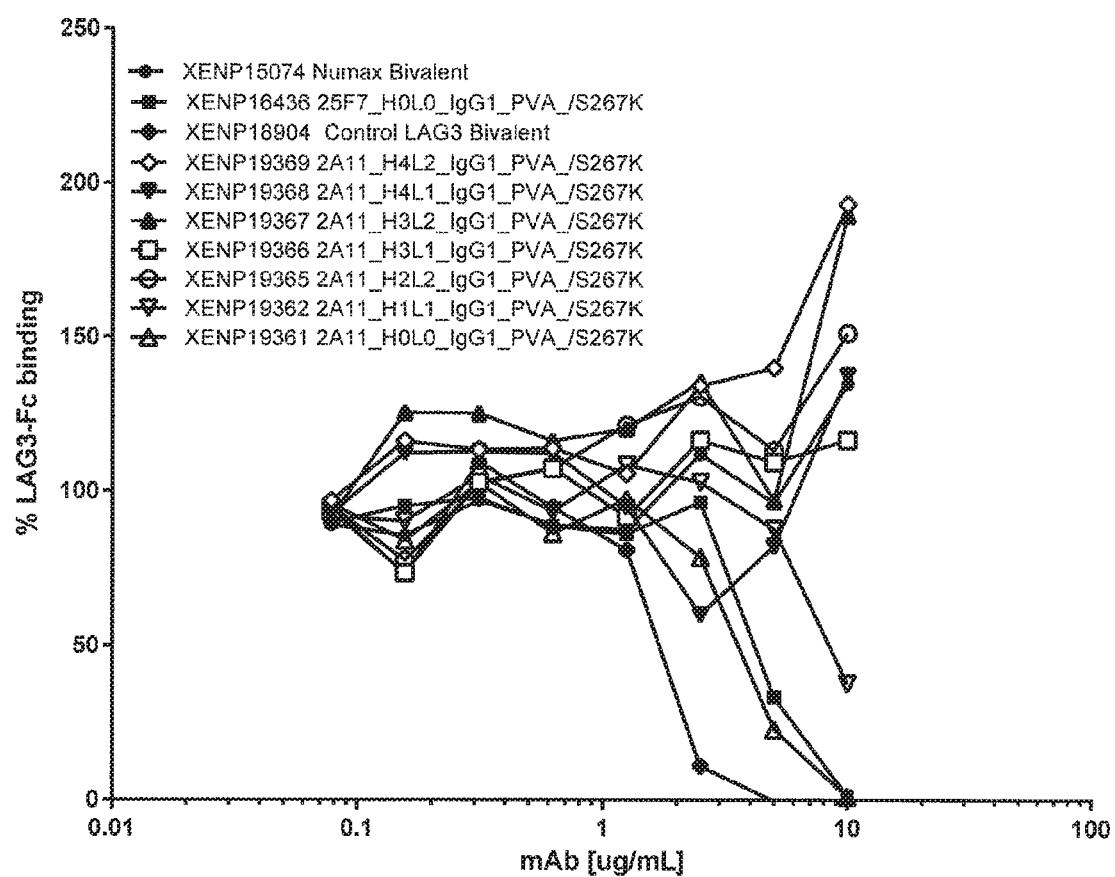
Figure 63B:
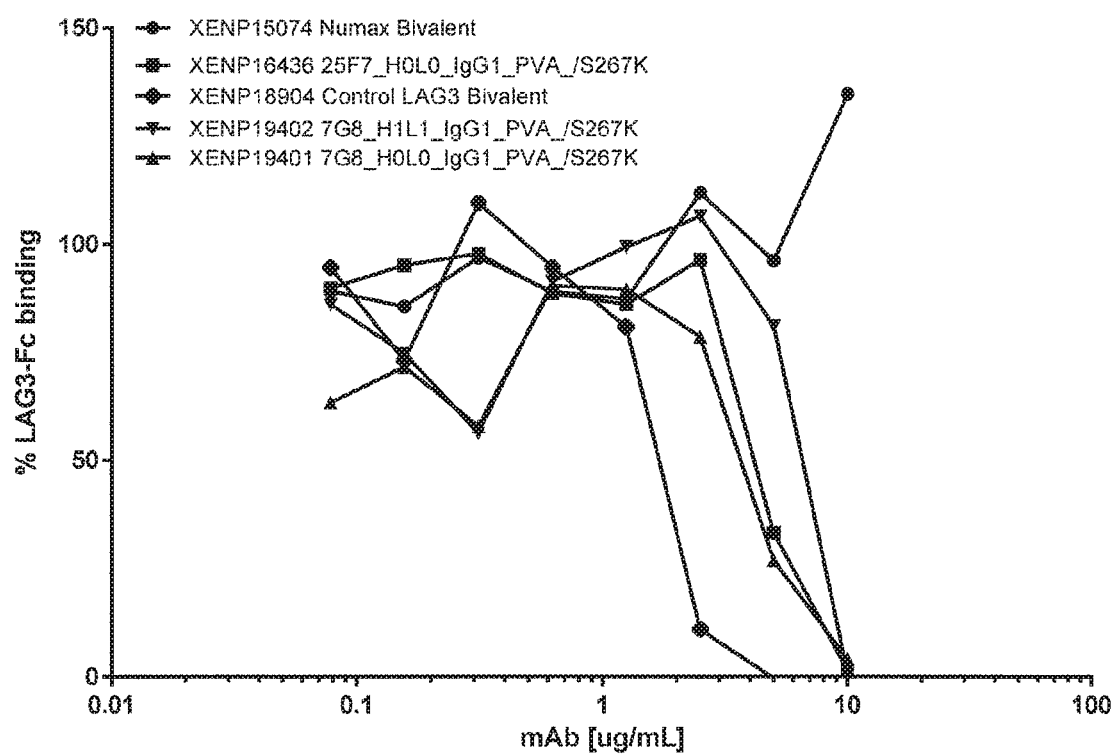

FIG. 63A-63B depicts the ability of humanized/optimized 7G8 and 2A11 anti-LAG-3 clones to block LAG-3 binding to Daudi cells endogenously expressing MHC-II.

Figure 64A:
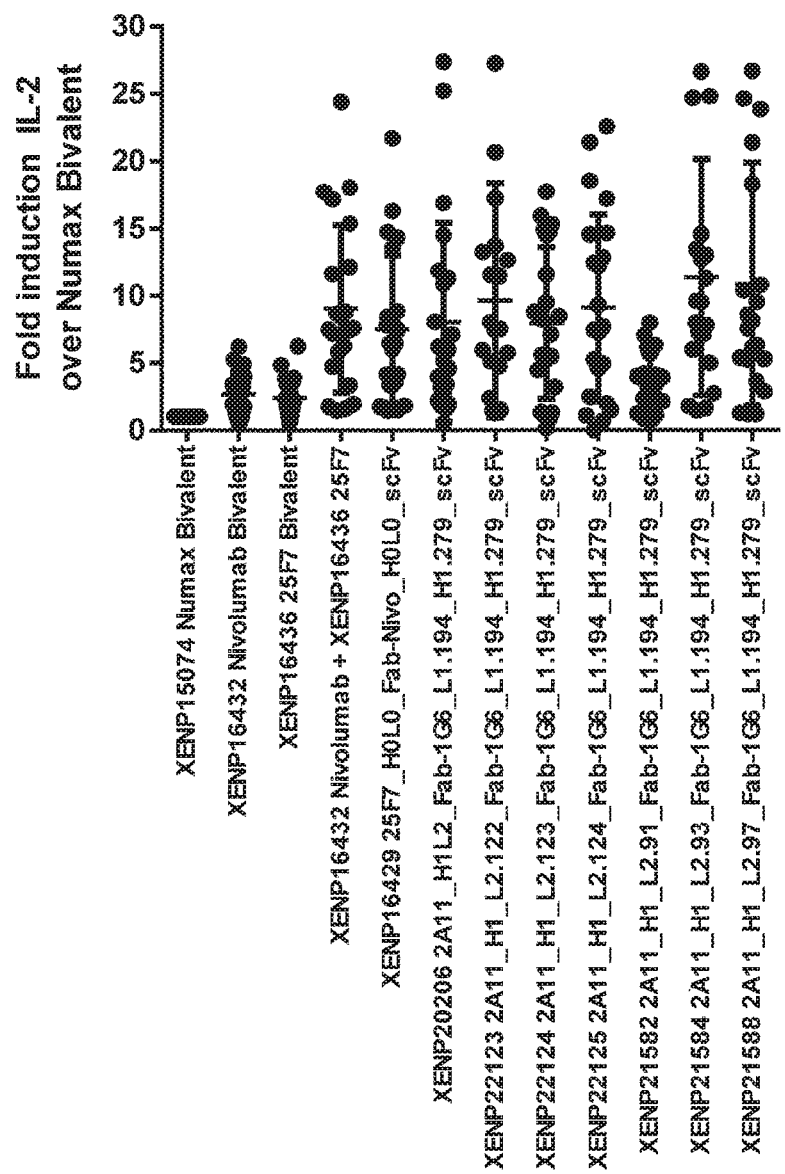
Figure 64B:
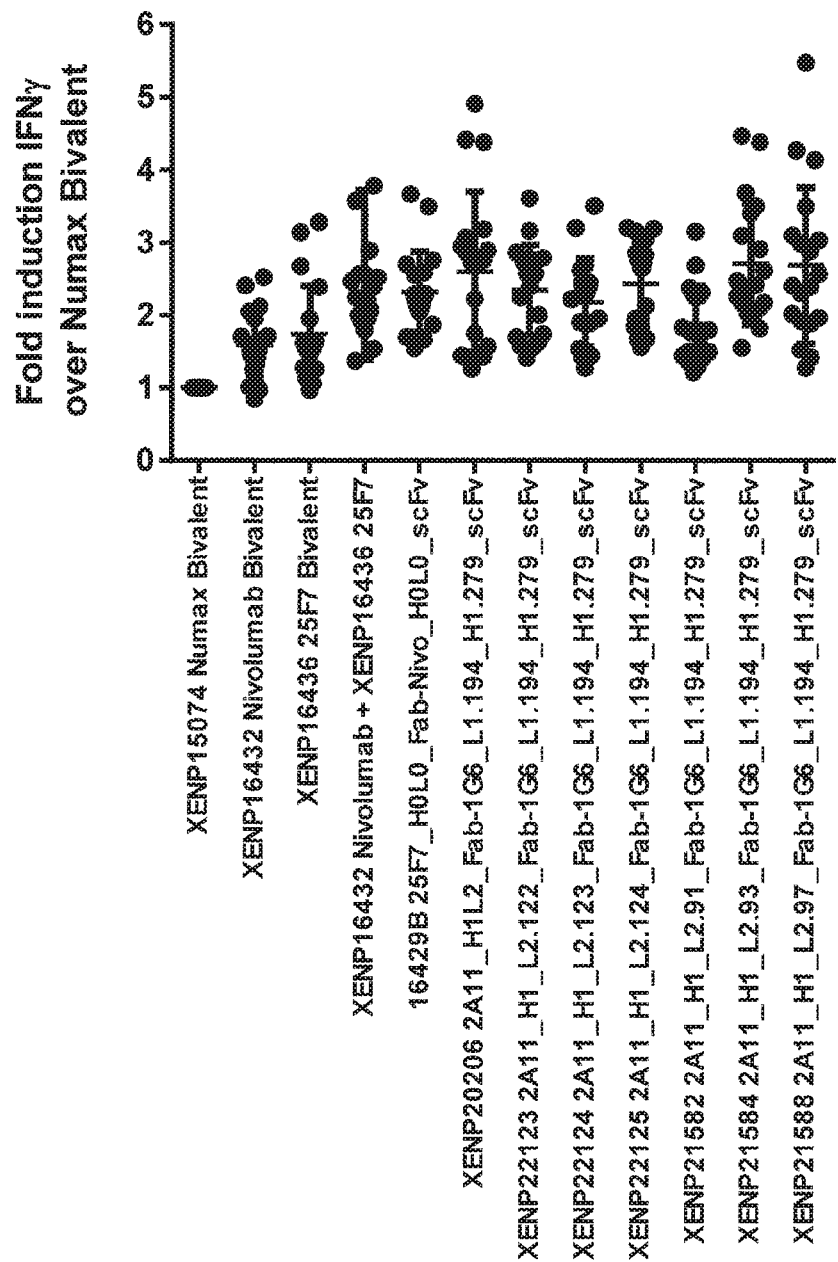

FIG. 64A-64B depicts anti-LAG-3×anti-PD-1 candidate function on SEB stimulated T cells. PBMCs were stimulated with 500 ng/ml SEB for 2 days. Cells were then washed twice in culture medium and stimulated with 500 ng/mL SEB in combination with indicated amounts of test articles. Cells were assayed for indicated analyte 24 h after treatment. Each point represents a unique donor tested in technical singlet.

Figure 65:
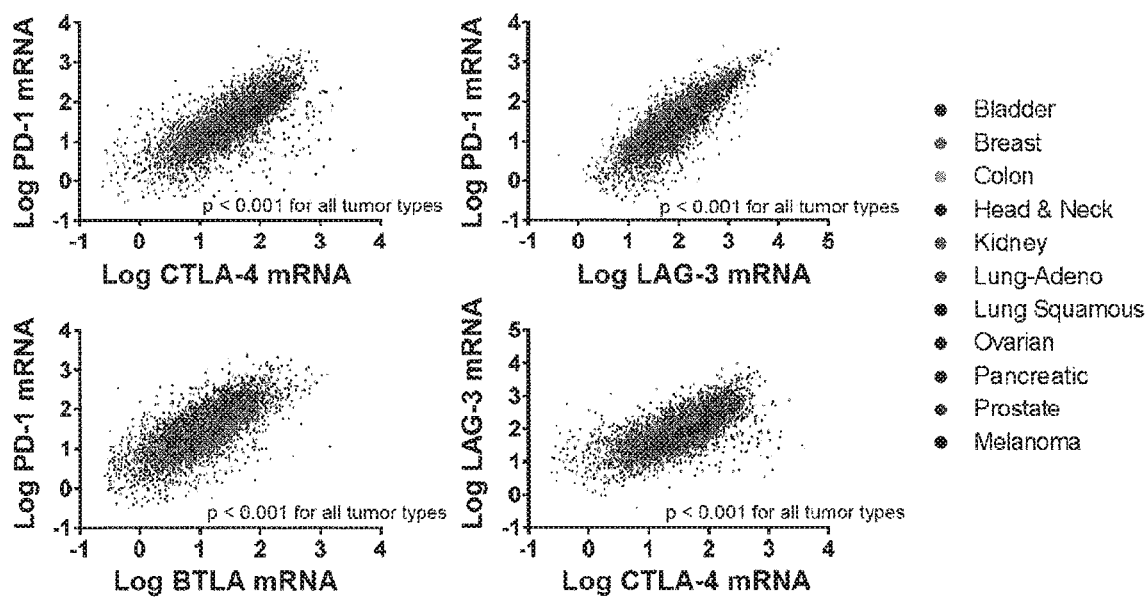

FIG. 65 are graphs, showing that tumor infiltrating lymphocytes (TILs) co-express multiple checkpoint receptors in various tumors. In particular, the graphs show that various tumors coexpress PD-1 and CTLA-4, PD-1 and BTLA, PD-1 and LAG-3; and LAG-3 and CTLA-4. The results shown are based upon data generated by the TCGA Research network: http://cancergenome.nih.gov/

Figure 66:
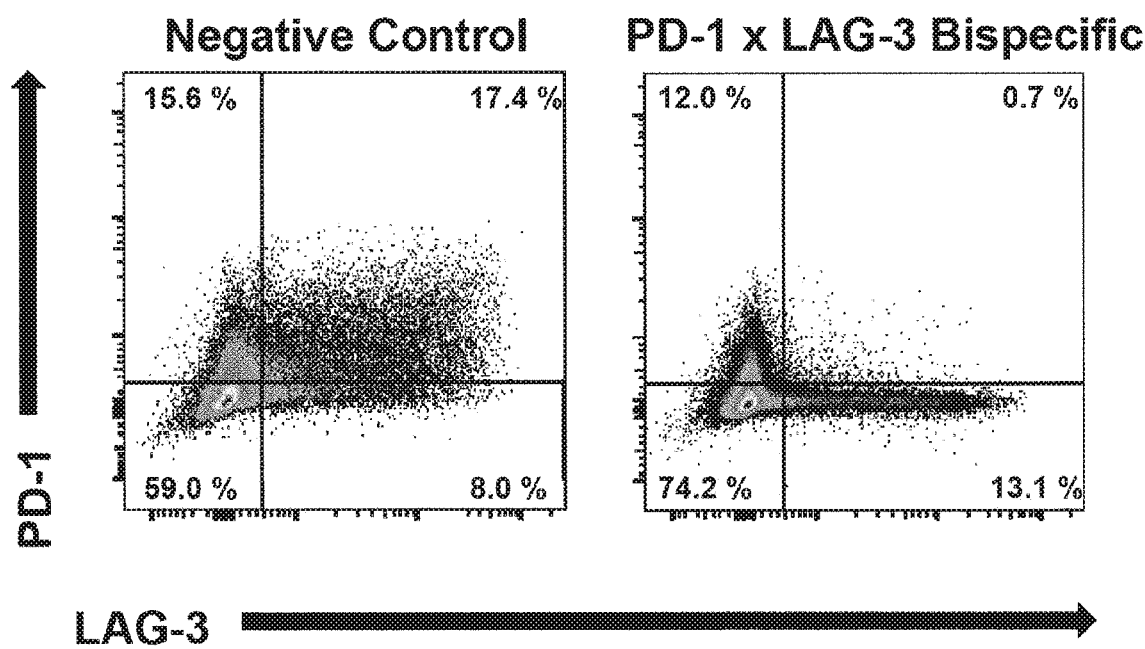
Figure 67A:
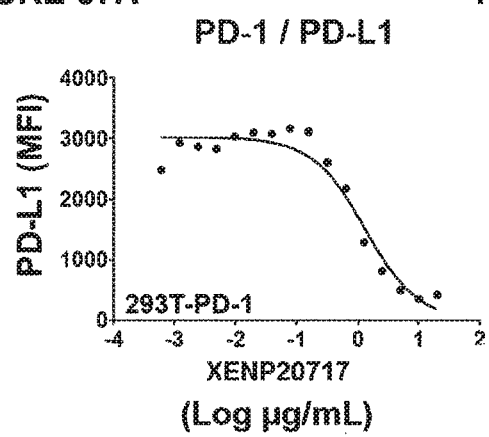
Figure 67B:
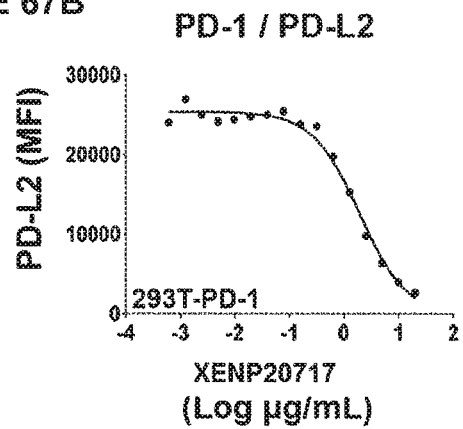
Figure 67C:
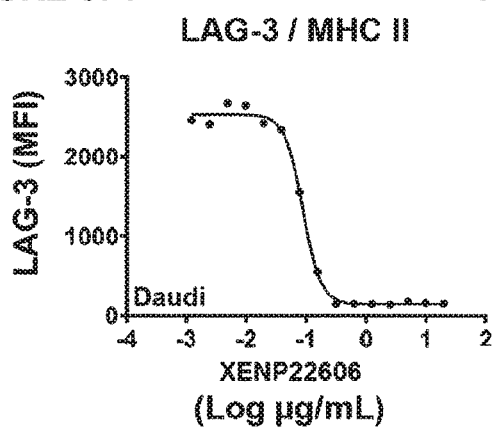
Figure 67D:
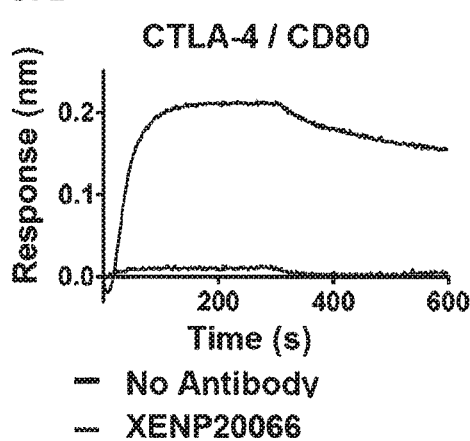
Figure 67E:
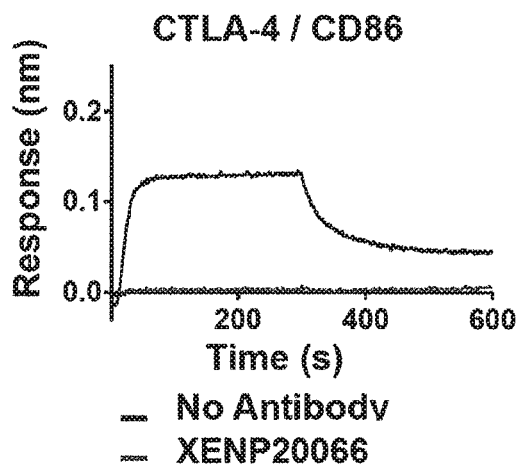
Figure 67F:
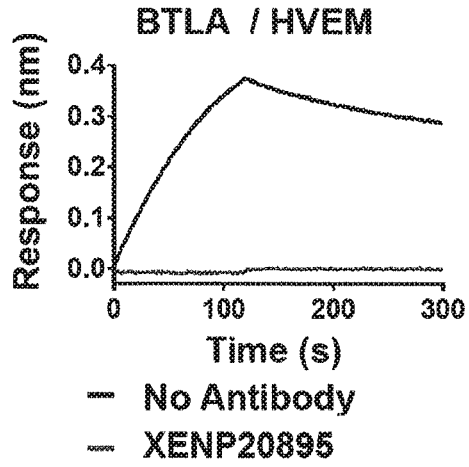

FIG. 66 shows that subject bispecific antibodies provided herein selectively target dual-checkpoint positive T cells. Bispeicifc PD-1×LAG-3 antibodies are used to show PD-1 and LAG-3 receptor occupancy in CD3+ T-cells stimulated with staphylococcal enterotoxin B (SEB) as compared to a negative control.

FIG. 67A-67F are graphs showing that component antibody domains of the subject antibodies provided herein are capable of blocking checkpoint receptor/ligand interactions. In particular, a bispecific antibody comprising a 1G6 anti-PD-1 scFv arm is capable of blocking PD-1/PD-L1 and PD-1/PD-L2 interactions; 7G8 anti-LAG-3 one arm is capable of blocking LAG-3/MHC II interaction; a bispecific antibody comprising an exemplary anti-PD-1 Fab arm is capable of blocking CTLA-4/CD80 and CTLA-4/CD86 interactions; and a bispecific antibody comprising a 9C6 anti-BTLA Fab arm is capable of blocking BTLA/HVEM interaction.

Figure 68:
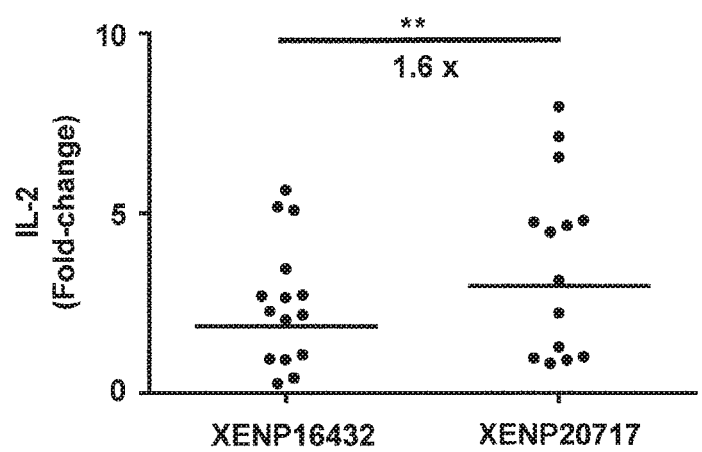

FIG. 68 compares the enhancement of IL-2 release by an exemplary anti-CTLA-4×anti-PD-1 bispecific antibody and nivolumab.

Figure 69:
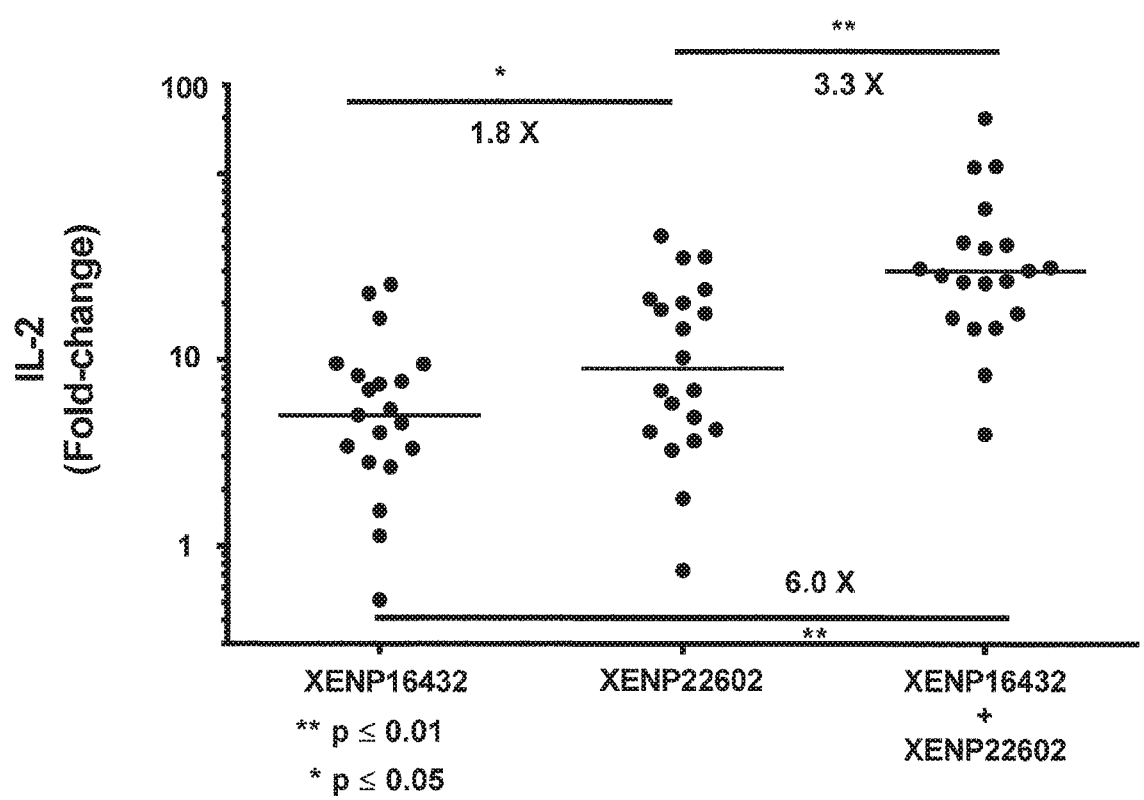

FIG. 69 compares the enhancement of IL-2 release by an exemplary anti-LAG-3×anti-CTLA-4 bispecific antibody, the same bispecific antibody in combination with nivolumab, and nivolumab alone.

Figure 70:
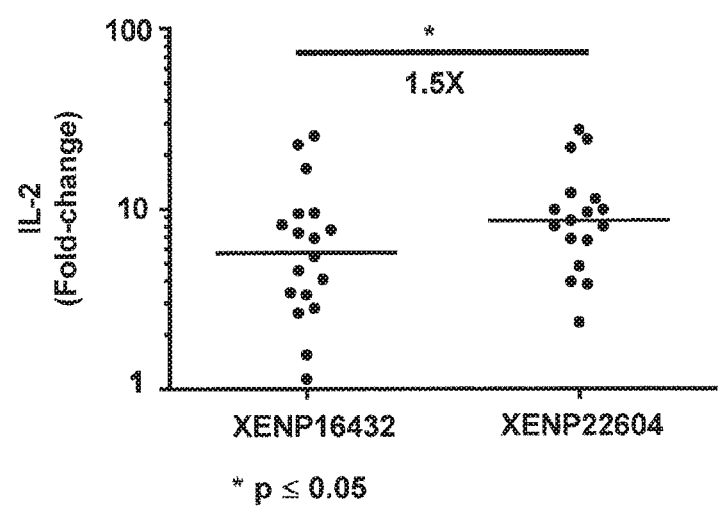

FIG. 70 compares the enhancement of IL-2 release by an exemplary anti-LAG-3×anti-PD-1 bispecific antibody and nivolumab.

Figure 71:
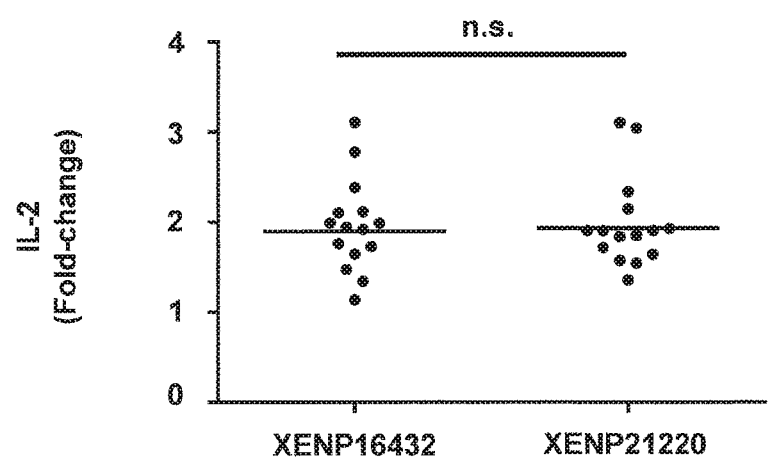

FIG. 71 compares the enhancement of IL-2 release by an exemplary anti-BTLA×anti-PD-1 bispecific antibody and nivolumab.

Figure 72:
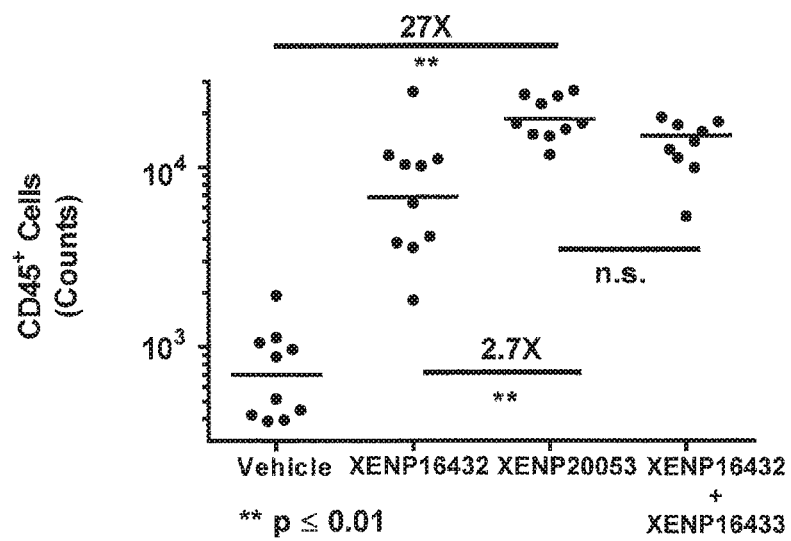

FIG. 72 compares the enhancement of GVHD (as indicated by CD45 cell count) by an exemplary anti-PD-1×anti-CTLA-4 bispecific antibody, nivolumab alone, and nivolumab in combination with ipilimumab.

Figure 73:
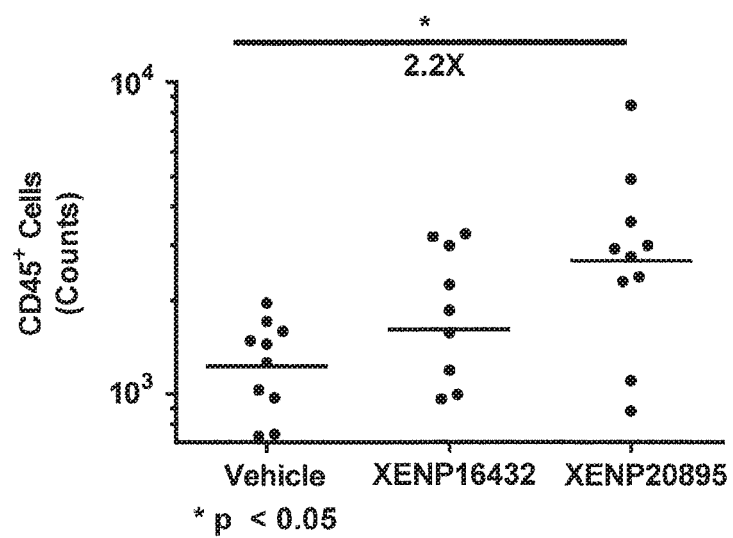

FIG. 73 compares the enhancement of GVHD (as indicated by CD45 cell count) by an exemplary anti-BTLA×anti-PD-1 bispecific antibody and nivolumab.

Figure 74:
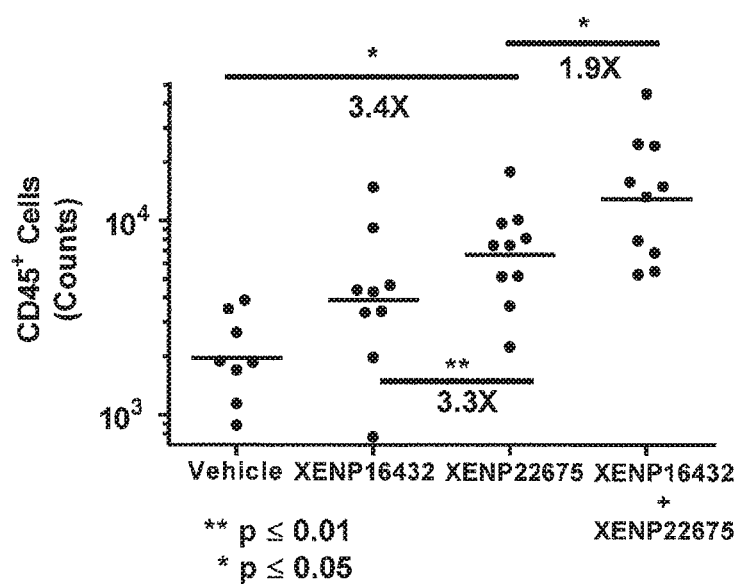

FIG. 74 compares the enhancement of GVHD (as indicated by CD45 cell count) by an exemplary anti-LAG-3×anti-CTLA-4 bispecific antibody, the same bispecific antibody in combination with nivolumab, and nivolumab alone.

Figure 75:
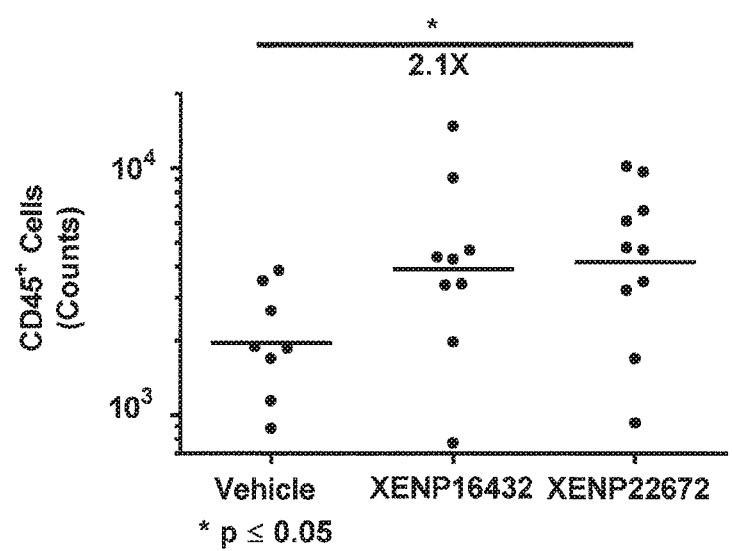
Figure 76A:
Figure 76B:
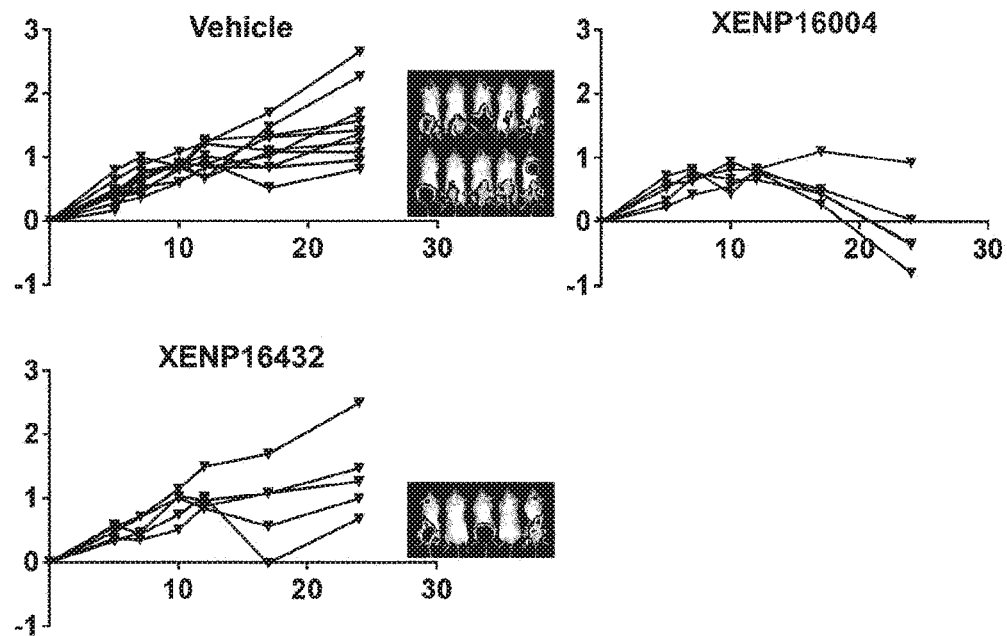

FIG. 75 compares the enhancement of GVHD (as indicated by CD45 cell count) by an exemplary anti-LAG-3×anti-PD-1 bispecific antibody and nivolumab.

FIGS. 76A-76D depicts two studies, showing that anti-CTLA-4×anti-PD-1 bispecific antibodies can promote in vivo T cell mediated anti-tumor efficacy. KG1a-luc cancer cells were engrafted into mice. Twenty-one days later, huPMCs were engrafted into the same mice and weekly antibody treatments (anti-CTLA-4×anti-PD-1 bispecific antibodies; anti-PD-1 bivalent antibodies; or anti-PD-1 bivalent antibody+anti-CTLA-4 bivalent antibody) were administered. IVIS cancer cell imaging was conducted on the mice to assess tumor size, as determined by change in tumor flux.

III. DETAILED DESCRIPTION OF THE INVENTION

A. Incorporation of Materials

1. Figures and Legends

All the figures and accompanying legends of U.S. Ser. Nos. 62/350,145, 62/353,511 and 62/420,500 are expressly and independently incorporated by reference herein in their entirety, particularly for the amino acid sequences depicted therein.

2. Sequences

Reference is made to the accompanying sequence listing as following: anti-PD-1 sequences suitable for use as ABDs include SEQ ID NOs: 6209-11464 (PD-1 scFv sequences, although the Fv sequences therein can be formatted as Fabs), SEQ ID NOs: 11465-17134 (PD-1 Fab sequences, although the Fv sequences therein can be formatted as scFvs), SEQ ID NOs: 33003-33072 (additional PD-1 Fab sequences, although the Fv sequences therein can be formatted as scFvs), SEQ ID NOs: 33073-35394 (additional PD-1 scFv sequences, although the Fv sequences therein can be formatted as Fabs) and SEQ ID NOs: 36127-36146 (PD-1 bivalent constructs, which can be formatted as either scFvs or Fabs). Anti-CTLA-4 sequences suitable for use as ABDs include SEQ ID NOs: 21-2918 (CTLA-4 scFv sequences, although the Fv sequences therein can be formatted as Fabs), SEQ ID NOs: 2919-6208 (CTLA-4 Fab sequences, although the Fv sequences therein can be formatted as scFvs), SEQ ID NOs: 36739-36818 (additional CTLA-4 Fab sequences, although the Fv sequences therein can be formatted as scFvs) and SEQ ID NOs: 35395-35416 (CTLA-4 one armed constructs, which can be formatted as either Fabs or scFvs). Anti-LAG-3 sequences suitable for use as ABDs include SEQ ID NOs: 17135-20764 (LAG-3 Fabs, although the Fv sequences therein can be formatted as scFvs), SEQ ID NOs: 36819-36962 (additional LAG-3 Fabs although the Fv sequences therein can be formatted as scFvs), SEQ ID NOs: 35417-35606 (additional LAG-3 Fabs although the Fv sequences therein can be formatted as scFvs), SEQ ID NOs: 25194-32793 (additional LAG-3 Fabs although the Fv sequences therein can be formatted as scFvs) and SEQ ID NOs: 32794-33002 (one armed LAG-3 constructs which can be formatted as either Fabs or scFvs). Anti-TIM-3 sequences suitable for use as ABDs include SEQ ID NOs: 20765-20884 (TIM-3 Fabs, although the Fv sequences therein can be formatted as scFvs), SEQ ID NOs: 37587-37698 (additional TIM-3 Fabs, the Fv sequences therein can be formatted as scFvs) and SEQ ID NOs: 36347-36706 (bivalent TIM-3 constructs which can be formatted as either Fabs or scFvs). Anti-BTLA sequences suitable for use as ABDs include SEQ ID NOs: 20885-21503 (BTLA Fabs although the Fv sequences therein can be formatted as scFvs) and SEQ ID NOs: 36707-36738 (additional BTLA Fabs although the Fv sequences therein can be formatted as scFvs). Anti-TIGIT sequences suitable for use as ABDs include SEQ ID NOs: 21504-21523 (TIGIT Fab although the Fv sequences therein can be formatted as scFvs) and SEQ ID NOs: 37435-37586 (additional TIGIT Fabs although the Fv sequences therein can be formatted as scFvs).

Bispecific antibodies of the invention include LAG3× CTLA4 constructs of SEQ ID NOs: 35607-35866 and SEQ ID NOs: 21524-22620. PD-1×CTLA4 constructs include those listed as SEQ ID NOs: 36167-36346 and SEQ ID NOs: 23316-23735. PD-1×TIM3 constructs include those listed as SEQ ID NOs: 25174-25193. PD-1×LAG3 constructs include those listed as SEQ ID NOs: 35867-36126 and SEQ ID NOs: 23736-25133. PD-1×TIGIT constructs include those listed as SEQ ID NOs: 25134-25173. PD-1×BTLA constructs include those listed as SEQ ID NOs: 22724-23315 and SEQ ID NOs: 36147-36166. CTLA4×BTLA constructs include those listed as SEQ ID NOs: 22624-22723. Finally, the names for XENP23552, XENP22841, XENP22842, XENP22843, XENP22844, XENP22845, XENP22846, XENP22847, XENP22848, XENP22849, XENP22850, XENP22851, XENP22852, XENP22858, XENP22854, XENP22855 all should have included the "M428L/N434S" notation in the title, which were inadvertently left off.

B. Overview

Therapeutic antibodies directed against immune checkpoint inhibitors such as PD-1 are showing great promise in limited circumstances in the clinic for the treatment of cancer. Cancer can be considered as an inability of the patient to recognize and eliminate cancerous cells. In many instances, these transformed (e.g. cancerous) cells counteract immunosurveillance. There are natural control mechanisms that limit T-cell activation in the body to prevent unrestrained T-cell activity, which can be exploited by cancerous cells to evade or suppress the immune response. Restoring the capacity of immune effector cells-especially T cells—to recognize and eliminate cancer is the goal of immunotherapy. The field of immuno-oncology, sometimes referred to as "immunotherapy" is rapidly evolving, with several recent approvals of T cell checkpoint inhibitory antibodies such as Yervoy, Keytruda and Opdivo. These antibodies are generally referred to as "checkpoint inhibitors" because they block normally negative regulators of T cell immunity. It is generally understood that a variety of immunomodulatory signals, both costimulatory and coinhibitory, can be used to orchestrate an optimal antigen-specific immune response.

Generally, these monoclonal antibodies bind to checkpoint inhibitor proteins such as CTLA-4 and PD-1, which under normal circumstances prevent or suppress activation of cytotoxic T cells (CTLs). By inhibiting the checkpoint protein, for example through the use of antibodies that bind these proteins, an increased T cell response against tumors can be achieved. That is, these cancer checkpoint proteins suppress the immune response; when the proteins are blocked, for example using antibodies to the checkpoint protein, the immune system is activated, leading to immune stimulation, resulting in treatment of conditions such as cancer and infectious disease.

However, as discussed above, studies have shown that TILs commonly express multiple checkpoint receptors; this may suggest that single checkpoint blockade could be insufficient to promote a complete T cell response. Moreover, it is likely that TILs that express multiple checkpoints are in fact the most tumor-reactive, thus suggesting that therapies that engage more than one checkpoint antigen could be very useful.

Accordingly, the present invention provides bispecific checkpoint antibodies, that bind to cells expressing the two antigens and methods of activating T cells and/or NK cells to treat diseases such as cancer and infectious diseases, and other conditions where increased immune activity results in treatment.

Thus, the invention is directed, in some instances, to solving the issue of toxicity and expense of administering multiple antibodies by providing bispecific antibodies that bind to two different checkpoint inhibitor molecules on a single cell and advantageously requiring administration of only one therapeutic substance.

Bispecific antibodies, which can bind two different targets simultaneously, offer the potential to improve the selectivity of targeting TILs vs peripheral T cells, while also reducing cost of therapy. The bivalent interaction of an antibody with two targets on a cell surface should—in some cases—lead to a higher binding avidity relative to a monovalent interaction with one target at a time. Because of this, normal bivalent antibodies tend to have high avidity for their target on a cell surface. With bispecific antibodies, the potential exists to create higher selectivity for cells that simultaneously express two different targets, utilizing the higher avidity afforded by simultaneous binding to both targets.

Accordingly, the present invention is directed to novel constructs to provide heterodimeric antibodies that allow binding to more than one checkpoint antigen or ligand, e.g. to allow for bispecific binding. Hence, for example, an anti-PD1×anti-CTLA4 (PD1×CTLA4) bispecific antibody is expected to be more selective for PD1+CTLA4+ double positive TILs versus single positive PD1-only or CTLA4-only T cells. Selective blockade of double-positive TILs versus single positive T cells is therefore expected to improve the therapeutic index of combined checkpoint blockade. This is similarly true for the other possible combinations as outlined herein. Accordingly, suitable bispecific antibodies of the invention bind PD-1 and CTLA-4, PD-1 and TIM-3, PD-1 and LAG-3, PD-1 and TIGIT, PD-1 and BTLA, CTLA-4 and TIM-3, CTLA-4 and LAG-3, CTLA-4 and TIGIT, CTLA-4 and BTLA, TIM-3 and LAG-3, TIM-3 and TIGIT, TIM-3 and BTLA, LAG-3 and TIGIT, LAG-3 and BTLA and TIGIT and BTLA. Note that generally these bispecific antibodies are named "anti-PD-1×anti-CTLA-4", or generally simplistically or for ease (and thus interchangeably) as "PD-1×CTLA-4", etc. for each pair.

The heterodimeric bispecific checkpoint antibodies of the invention are useful to treat a variety of types of cancers. As will be appreciated by those in the art, in contrast to traditional monoclonal antibodies that bind to tumor antigens, or to the newer classes of bispecific antibodies that bind, for example, CD3 and tumor antigens (such as described in U.S. Ser. No. 15/141,350, for example), checkpoint antibodies are used to increase the immune response but are not generally tumor specific in their action. That is, the bispecific checkpoint antibodies of the invention inhibit the suppression of the immune system, generally leading to T cell activation, which in turn leads to greater immune response to cancerous cells and thus treatment. Such antibodies can therefore be expected to find utility for treatment of a wide variety of tumor types. For example, the FDA recently approved Keytruda®, an anti-PD-1 monospecific antibody on the basis of a genetic feature, rather than a tumor type.

As discussed below, there are a variety of ways that T cell activation can be measured. Functional effects of the bispecific checkpoint antibodies on NK and T-cells can be assessed in vitro (and in some cases in vivo, as described more fully below) by measuring changes in the following parameters: proliferation, cytokine release and cell-surface makers. For NK cells, increases in cell proliferation, cytotoxicity (ability to kill target cells as measured by increases in CD107a, granzyme, and perforin expression, or by directly measuring target cells killing), cytokine production (e.g. IFN-γ and TNF), and cell surface receptor expression (e.g. CD25) is indicative of immune modulation, e.g. enhanced killing of cancer cells. For T-cells, increases in proliferation, increases in expression of cell surface markers of activation (e.g. CD25, CD69, CD137, and PD1), cytotoxicity (ability to kill target cells), and cytokine production (e.g. IL-2, IL-4, IL-6, IFN-γ, TNF-α, IL-10, IL-17A) are indicative of immune modulation, e.g. enhanced killing of cancer cells. Accordingly, assessment of treatment can be done using assays that evaluate one or more of the following: (i) increases in immune response, (ii) increases in activation of αβ and/or γδ T cells, (iii) increases in cytotoxic T cell activity, (iv) increases in NK and/or NKT cell activity, (v) alleviation of αβ and/or γδ T-cell suppression, (vi) increases in pro-inflammatory cytokine secretion, (vii) increases in IL-2 secretion; (viii) increases in interferon-γ production, (ix) increases in Th1 response, (x) decreases in Th2 response, (xi) decreases in cell number and/or activity of at least one of regulatory T cells and cells (xii) increases of tumor immune infiltrates.

Thus, in some embodiments the invention provides the use of bispecific checkpoint antibodies to perform one or more of the following in a subject in need thereof: (a) upregulating pro-inflammatory cytokines; (b) increasing T-cell proliferation, expansion or tumor infiltration; (c) increasing interferon-γ, TNF-α and other cytokine production by T-cells; (d) increasing IL-2 secretion; (e) stimulating antibody responses; (0 inhibiting cancer cell growth; (g) promoting antigenic specific T cell immunity; (h) promoting CD4+ and/or CD8+ T cell activation; (i) alleviating T-cell suppression; (j) promoting NK cell activity; (k) promoting apoptosis or lysis of cancer cells; and/or (l) cytotoxic or cytostatic effect on cancer cells.

Accordingly, the present invention provides bispecific, heterodimeric checkpoint antibodies. The heterodimeric antibody constructs are based on the self-assembling nature of the two Fc domains of the heavy chains of antibodies, e.g. two "monomers" that assemble into a "dimer". Heterodimeric antibodies are made by altering the amino acid sequence of each monomer as more fully discussed below. Thus, the present invention is generally directed to the creation of heterodimeric antibodies, which can co-engage checkpoint antigens in several ways, relying on amino acid variants in the constant regions that are different on each chain to promote heterodimeric formation and/or allow for ease of purification of heterodimers over the homodimers.

Thus, the present invention provides bispecific checkpoint antibodies. An ongoing problem in antibody technologies is the desire for "bispecific" antibodies that bind to two (or more) different antigens simultaneously, in general thus allowing the different antigens to be brought into proximity and resulting in new functionalities and new therapies. In general, these antibodies are made by including genes for each heavy and light chain into the host cells (generally, in the present invention, genes for two heavy chain monomers and a light chain as outlined herein). This generally results in the formation of the desired heterodimer (A-B), as well as the two homodimers (A-A and B-B). However, a major obstacle in the formation of bispecific antibodies is the difficulty in purifying the heterodimeric antibodies away from the homodimeric antibodies and/or biasing the formation of the heterodimer over the formation of the homodimers.

To solve this issue, there are a number of mechanisms that can be used to generate the heterodimers of the present invention. In addition, as will be appreciated by those in the art, these mechanisms can be combined to ensure high heterodimerization. Thus, amino acid variants that lead to the production of heterodimeric antibodies are referred to as "heterodimerization variants". As discussed below, heterodimerization variants can include steric variants (e.g. the "knobs and holes" or "skew" variants described below and the "charge pairs" variants described below) as well as "pI variants", which allows purification of homodimers away from heterodimers.

One mechanism, generally referred to in the art as "knobs and holes" ("KIH") or sometimes herein as "skew" variants, referring to amino acid engineering that creates steric and/or electrostatic influences to favor heterodimeric formation and disfavor homodimeric formation can also optionally be used, as described in Ridgway et al., Protein Engineering 9(7):617 (1996); Atwell et al., J. Mol. Biol. 1997 270:26; U.S. Pat. No. 8,216,805, US 2012/0149876, all of which are hereby incorporated by reference in their entirety. The Figures identify a number of "monomer A-monomer B" pairs that include "knobs and holes" amino acid substitutions. In addition, as described in Merchant et al., Nature Biotech. 16:677 (1998), these "knobs and hole" mutations can be combined with disulfide bonds to skew formation to heterodimerization. Of use in the present invention are T366S/L368A/Y407V paired with T366W, as well as this variant with a bridging disulfide, T366S/L368A/Y407V/Y349C paired with T366W/S354C, particularly in combination with other heterodimerization variants including pI variants as outlined below.

An additional mechanism that finds use in the generation of heterodimeric antibodies is sometimes referred to as "electrostatic steering" or "charge pairs" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R and others shown in the Figures.

In the present invention, in some embodiments, pI variants are used to alter the pI of one or both of the monomers and thus allowing the isoelectric separation of A-A, A-B and B-B dimeric proteins.

In the present invention, there are several basic mechanisms that can lead to ease of purifying heterodimeric proteins; one relies on the use of pI variants, such that each monomer has a different pI, thus allowing the isoelectric purification of A-A, A-B and B-B dimeric proteins. Alternatively, some scaffold formats, such as the "triple F" format, also allows separation on the basis of size. As is further outlined below, it is also possible to "skew" the formation of heterodimers over homodimers. Thus, a combination of steric heterodimerization variants and pI or charge pair variants find particular use in the invention. Additionally, as more fully outlined below, scaffolds that utilize scFv(s) such as the Triple F format can include charged scFv linkers (either positive or negative), that give a further pI boost for purification purposes. As will be appreciated by those in the art, some Triple F formats are useful with just charged scFv linkers and no additional pI adjustments, although the invention does provide the use of skew variants with charged scFv linkers as well (and combinations of Fc, FcRn and KO variants discussed herein).

In the present invention that utilizes pI as a separation mechanism to allow the purification of heterodimeric proteins, amino acid variants can be introduced into one or both of the monomer polypeptides; that is, the pI of one of the monomers (referred to herein for simplicity as "monomer A") can be engineered away from monomer B, or both monomer A and B can be changed, with the pI of monomer A increasing and the pI of monomer B decreasing. As is outlined more fully below, the pI changes of either or both monomers can be done by removing or adding a charged residue (e.g. a neutral amino acid is replaced by a positively or negatively charged amino acid residue, e.g. glycine to glutamic acid), changing a charged residue from positive or negative to the opposite charge (e.g. aspartic acid to lysine) or changing a charged residue to a neutral residue (e.g. loss of a charge; lysine to serine). A number of these variants are shown in the Figures. In addition, suitable pI variants for use in the creation of heterodimeric antibodies herein are those that are isotypic, e.g. importing pI variants from different IgG isotypes such that pI is changed without introducing significant immunogenicity; see FIG. 29 from US Publication No. 20140288275, hereby incorporated by reference in its entirety.

Accordingly, in this embodiment of the present invention provides for creating a sufficient change in pI in at least one of the monomers such that heterodimers can be separated from homodimers. As will be appreciated by those in the art, and as discussed further below, this can be done by using a "wild type" heavy chain constant region and a variant region that has been engineered to either increase or decrease it's pI_(wt A-+B or wt A--B), or by increasing one region and decreasing the other region (A+-B- or A-B+).

Thus, in general, a component of some embodiments of the present invention are amino acid variants in the constant regions of antibodies that are directed to altering the isoelectric point (pI) of at least one, if not both, of the monomers of a dimeric protein to form "pI heterodimers" (when the protein is an antibody, these are referred to as "pI antibodies") by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) to get good separation will depend in part on the starting pI of the scFv and Fab of interest. That is, to determine which monomer to engineer or in which "direction" (e.g. more positive or more negative), the Fv sequences of the two target antigens are calculated and a decision is made from there. As is known in the art, different Fvs will have different starting pIs which are exploited in the present invention. In general, as outlined herein, the pIs are engineered to result in a total pI difference of each monomer of at least about 0.1 logs, with 0.2 to 0.5 being preferred as outlined herein.

Furthermore, as will be appreciated by those in the art and outlined herein, in some cases (depending on the format) heterodimers can be separated from homodimers on the basis of size (e.g. molecular weight). For example, as shown in some embodiments of FIG. 1, some formats result in homodimers and heterodimers with different sizes (e.g. for bottle openers, one homodimer is a "dual scFv" format, one homodimer is a standard antibody, and the heterodimer has one Fab and one scFv.

In addition, as depicted in FIG. 1, it will be recognized that it is possible that some antigens are bound bivalently (e.g. two antigen binding sites to a single antigen). As will be appreciated, any combination of Fab and scFvs can be utilized to achieve the desired result and combinations.

In the case where pI variants are used to achieve purified heterodimers over homodimers, by using the constant region(s) of the heavy chain(s), a more modular approach to designing and purifying multispecific proteins, including antibodies, is provided. Thus, in some embodiments, heterodimerization variants (including skew and purification heterodimerization variants) are not included in the variable regions, such that each individual antibody must be engineered. In addition, in some embodiments, the possibility of immunogenicity resulting from the pI variants is significantly reduced by importing pI variants from different IgG isotypes such that pI is changed without introducing significant immunogenicity. Thus, an additional problem to be solved is the elucidation of low pI constant domains with high human sequence content, e.g. the minimization or avoidance of non-human residues at any particular position.

A side benefit that can occur with this pI engineering is also the extension of serum half-life and increased FcRn binding. That is, as described in U.S. Ser. No. 13/194,904 (incorporated by reference in its entirety), lowering the pI of antibody constant domains (including those found in antibodies and Fc fusions) can lead to longer serum retention in vivo. These pI variants for increased serum half life also facilitate pI changes for purification.

In addition, it should be noted that the pI variants of the heterodimerization variants give an additional benefit for the analytics and quality control process of bispecific antibodies, as the ability to either eliminate, minimize and distinguish when homodimers are present is significant. Similarly, the ability to reliably test the reproducibility of the heterodimeric protein production is important.

As will be appreciated by those in the art and discussed more fully below, the heterodimeric fusion proteins of the present invention can take on a wide variety of configurations, as are generally depicted in FIG. 1. Some figures depict "single ended" configurations, where there is one type of specificity on one "arm" of the molecule and a different specificity on the other "arm". Other figures depict "dual ended" configurations, where there is at least one type of specificity at the "top" of the molecule and one or more different specificities at the "bottom" of the molecule. Thus, the present invention is directed to novel immunoglobulin compositions that co-engage a first and a second antigen. First and second antigens of the invention are herein referred to as antigen-1 and antigen-2 respectively (or "checkpoint-1" and "checkpoint-2").

One heterodimeric scaffold that finds particular use in the present invention is the "triple F" or "bottle opener" scaffold format as depicted in FIG. 1A. In this embodiment, one heavy chain of the antibody contains an single chain Fv ("scFv", as defined below) and the other heavy chain is a "regular" FAb format, comprising a variable heavy chain and a light chain. This structure is sometimes referred to herein as "triple F" format (scFv-FAb-Fc) or the "bottle-opener" format, due to a rough visual similarity to a bottle-opener (see FIG. 1A). The two chains are brought together by the use of amino acid variants in the constant regions (e.g. the Fc domain and/or the hinge region) that promote the formation of heterodimeric antibodies as is described more fully below.

There are several distinct advantages to the present "triple F" format. As is known in the art, antibody analogs relying on two scFv constructs often have stability and aggregation problems, which can be alleviated in the present invention by the addition of a "regular" heavy and light chain pairing. In addition, as opposed to formats that rely on two heavy chains and two light chains, there is no issue with the incorrect pairing of heavy and light chains (e.g. heavy 1 pairing with light 2, etc.)

Furthermore, as outlined herein, additional amino acid variants may be introduced into the bispecific antibodies of the invention, to add additional functionalities. For example, amino acid changes within the Fc region can be added (either to one monomer or both) to facilitate increased ADCC or CDC (e.g. altered binding to Fcγ receptors) as well as to increase binding to FcRn and/or increase serum half-life of the resulting molecules. As is further described herein and as will be appreciated by those in the art, any and all of the variants outlined herein can be optionally and independently combined with other variants.

Similarly, another category of functional variants are "Fcγ ablation variants" or "Fc knock out (FcKO or KO) variants. In these embodiments, for some therapeutic applications, it is desirable to reduce or remove the normal binding of the Fc domain to one or more or all of the Fcγ receptors (e.g. FcγR1, FcγRIIa, FcγRIIb, FcγRIIIa, etc.) to avoid additional mechanisms of action. That is, for example, it is generally desirable to ablate FcγRIIIa binding to eliminate or significantly reduce ADCC activity. Suitable ablation variants are shown in FIG. 5.

C. Nomenclature

The bispecific antibodies of the invention are listed in several different formats. Each polypeptide is given a unique "XENP" number, although as will be appreciated in the art, a longer sequence might contain a shorter one. For example, the heavy chain of the scFv side monomer of a bottle opener format for a given sequence will have a first XENP number, while the scFv domain will have a different XENP number. Some molecules have three polypeptides, so the XENP number, with the components, is used as a name. Thus, the molecule XENP20717, which is in bottle opener format, comprises three sequences, generally referred to as "XENP20717 HC-Fab", XENP20717 HC-scFv" and "XENP20717 LC" or equivalents, although one of skill in the art would be able to identify these easily through sequence alignment. These XENP numbers are in the sequence listing as well as identifiers, and used in the Figures. In addition, one molecule, comprising the three components, gives rise to multiple sequence identifiers. For example, the listing of the Fab monomer has the full length sequence, the variable heavy sequence and the three CDRs of the variable heavy sequence; the light chain has a full length sequence, a variable light sequence and the three CDRs of the variable light sequence; and the scFv-Fc domain has a full length sequence, an scFv sequence, a variable light sequence, 3 light CDRs, a scFv linker, a variable heavy sequence and 3 heavy CDRs; note that all molecules herein with a scFv domain use a single charged scFv linker (+H), although others can be used. In addition, the naming nomenclature of particular variable domains uses a "Hx.xx_Ly.yy" type of format, with the numbers being unique identifiers to particular variable chain sequences. Thus, the variable domain of the Fab side of XENP22841 is "7G8_H3.30_L1.34", which indicates that the variable heavy domain H3.30 was combined with the light domain L1.34. In the case that these sequences are used as scFvs, the designation "7G8_H3.30_L1.34", indicates that the variable heavy domain H3.30 was combined with the light domain L1.34 and is in vh-linker-vl orientation, from N- to C-terminus. This molecule with the identical sequences of the heavy and light variable domains but in the reverse order would be named "7G8_L1.34_H3.30". Similarly, different constructs may "mix and match" the heavy and light chains as will be evident from the sequence listing and the Figures.

D. Definitions

In order that the application may be more completely understood, several definitions are set forth below. Such definitions are meant to encompass grammatical equivalents.

By "ablation" herein is meant a decrease or removal of activity. Thus for example, "ablating FcγR binding" means the Fc region amino acid variant has less than 50% starting binding as compared to an Fc region not containing the specific variant, with more than 70-80-90-95-98% loss of activity being preferred, and in general, with the activity being below the level of detectable binding in a BIA-CORE®, SPR or BLI assay. Of particular use in the ablation of FcγR binding are those shown in FIG. 5, which generally are added to both monomers.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis as used herein is meant the cell-mediated reaction wherein nonspecific phagocytic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, a "checkpoint antigen binding domain" binds a target checkpoint antigen as outlined herein. As is known in the art, these CDRs are generally present as a first set of variable heavy CDRs (vhCDRs or VHCDRs) and a second set of variable light CDRs (vhCDRs or VLCDRs), each comprising three CDRs: vhCDR1, vhCDR2, vhCDR3 for the heavy chain and vlCDR1, vlCDR2 and vlCDR3 for the light. The CDRs are present in the variable heavy and variable light domains, respectively, and together form an Fv region. (See Table 1 and related discussion above for CDR numbering schemes). Thus, in some cases, the six CDRs of the antigen binding domain are contributed by a variable heavy and a variable light domain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker (a "scFv linker") as outlined herein, into a single polypeptide sequence, which can be either (starting from the N-terminus) vh-linker-vl or vl-linker-vh, with the former being generally preferred (including optional domain linkers on each side, depending on the format used (e.g. from FIG. 1). In general, the C-terminus of the scFv domain is attached to the N-terminus of the hinge in the second monomer.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233– or E233#, E233( ) or E233del designates a deletion of glutamic acid at position 233. Additionally, EDA233– or EDA233# designates a deletion of the sequence GluAspAla that begins at position 233.

By "variant protein" or "protein variant", or "variant" as used herein is meant a protein that differs from that of a parent protein by virtue of at least one amino acid modification. The protein variant has at least one amino acid modification compared to the parent protein, yet not so many that the variant protein will not align with the parental protein using an alignment program such as that described below. In general, variant proteins (such as variant Fc domains, etc., outlined herein, are generally at least 75, 80, 85, 90, 91, 92, 93, 94, 95, 96, 97, 98 or 99% identical to the parent protein, using the alignment programs described below, such as BLAST.

As described below, in some embodiments the parent polypeptide, for example an Fc parent polypeptide, is a human wild type sequence, such as the heavy constant domain or Fc region from IgG1, IgG2, IgG3 or IgG4, although human sequences with variants can also serve as "parent polypeptides", for example the IgG1/2 hybrid of US Publication 2006/0134105 can be included. The protein variant sequence herein will preferably possess at least about 80% identity with a parent protein sequence, and most preferably at least about 90% identity, more preferably at least about 95-98-99% identity. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain as compared to an Fc domain of human IgG1, IgG2 or IgG4.

The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, N434S/M428L is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference). See also Edelman et al., 1969, Proc Natl Acad Sci USA 63:78-85, hereby entirely incorporated by reference. The modification can be an addition, deletion, or substitution.

By "protein" herein is meant at least two covalently attached amino acids, which includes proteins, polypeptides, oligopeptides and peptides. In addition, polypeptides that make up the antibodies of the invention may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains, generally on two different polypeptide chains (e.g. VH-CH1 on one chain and VL-CL on the other). Fab may refer to this region in isolation, or this region in the context of a bispecific antibody of the invention. In the context of a Fab, the Fab comprises an Fv region in addition to the CH1 and CL domains.

By "Fv" or "Fv fragment" or "Fv region" as used herein is meant a polypeptide that comprises the VL and VH domains of an ABD. Fv regions can be formatted as both Fabs (as discussed above, generally two different polypeptides that also include the constant regions as outlined above) and scFvs, where the vl and vh domains are combined (generally with a linker as discussed herein) to form an scFv.

By "single chain Fv" or "scFv" herein is meant a variable heavy domain covalently attached to a variable light domain, generally using a scFv linker as discussed herein, to form a scFv or scFv domain. A scFv domain can be in either orientation from N- to C-terminus (vh-linker-vl or vl-linker-vh). In the sequences depicted in the sequence listing and in the figures, the order of the vh and vl domain is indicated in the name, e.g. H.X_L.Y means N- to C-terminal is vh-linker-vl, and L.Y_H.X is vl-linker-vh.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the human IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants used to increase binding to the FcRn receptor, and in some cases, to increase serum half-life. An "FcRn variant" is one that increases binding to the FcRn receptor, and suitable FcRn variants are shown below.

By "parent polypeptide" as used herein is meant a starting polypeptide that is subsequently modified to generate a variant. The parent polypeptide may be a naturally occurring polypeptide, or a variant or engineered version of a naturally occurring polypeptide. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below. In this context, a "parent Fc domain" will be relative to the recited variant; thus, a "variant human IgG1 Fc domain" is compared to the parent Fc domain of human IgG1, a "variant human IgG4 Fc domain" is compared to the parent Fc domain human IgG4, etc.

By "Fc" or "Fc region" or "Fc domain" as used herein is meant the polypeptide comprising the CH2-CH3 domains of an IgG molecule, and in some cases, inclusive of the hinge. In EU numbering for human IgG1, the CH2-CH3 domain comprises amino acids 231 to 447, and the hinge is 216 to 230. Thus the definition of "Fc domain" includes both amino acids 231-447 (CH2-CH3) or 216-447 (hinge-CH2-CH3), or fragments thereof. An "Fc fragment" in this context may contain fewer amino acids from either or both of the N- and C-termini but still retains the ability to form a dimer with another Fc domain or Fc fragment as can be detected using standard methods, generally based on size (e.g. non-denaturing chromatography, size exclusion chromatography, etc.) Human IgG Fc domains are of particular use in the present invention, and can be the Fc domain from human IgG1, IgG2 or IgG4.

A "variant Fc domain" contains amino acid modifications as compared to a parental Fc domain. Thus, a "variant human IgG1 Fc domain" is one that contains amino acid modifications (generally amino acid substitutions, although in the case of ablation variants, amino acid deletions are included) as compared to the human IgG1 Fc domain. In general, variant Fc domains have at least about 80, 85, 90, 95, 97, 98 or 99 percent identity to the corresponding parental human IgG Fc domain (using the identity algorithms discussed below, with one embodiment utilizing the BLAST algorithm as is known in the art, using default parameters). Alternatively, the variant Fc domains can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Additionally, as discussed herein, the variant Fc domains herein still retain the ability to form a dimer with another Fc domain as measured using known techniques as described herein, such as non-denaturing gel electrophoresis.

By "heavy chain constant region" herein is meant the CH1-hinge-CH2-CH3 portion of an antibody (or fragments thereof), excluding the variable heavy domain; in EU numbering of human IgG1 this is amino acids 118-447 By "heavy chain constant region fragment" herein is meant a heavy chain constant region that contains fewer amino acids from either or both of the N- and C-termini but still retains the ability to form a dimer with another heavy chain constant region.

By "position" as used herein is meant a location in the sequence of a protein. Positions may be numbered sequentially, or according to an established format, for example the EU index for antibody numbering.

By "target antigen" as used herein is meant the molecule that is bound specifically by the antigen binding domain comprising the variable regions of a given antibody. As discussed below, in the present case the target antigens are checkpoint inhibitor proteins.

By "strandedness" in the context of the monomers of the heterodimeric antibodies of the invention herein is meant that, similar to the two strands of DNA that "match", heterodimerization variants are incorporated into each monomer so as to preserve the ability to "match" to form heterodimers. For example, if some pI variants are engineered into monomer A (e.g. making the pI higher) then steric variants that are "charge pairs" that can be utilized as well do not interfere with the pI variants, e.g. the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer one set of the pair will go, such that pI separation is maximized using the pI of the skews as well.

By "target cell" as used herein is meant a cell that expresses a target antigen.

By "host cell" in the context of producing a bispecific antibody according to the invention herein is meant a cell that contains the exogeneous nucleic acids encoding the components of the bispecific antibody and is capable of expressing the bispecific antibody under suitable conditions. Suitable host cells are discussed below.

By "variable region" or "variable domain" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively, and contains the CDRs that confer antigen specificity. Thus, a "variable heavy domain" pairs with a "variable light domain" to form an antigen binding domain ("ABD"). In addition, each variable domain comprises three hypervariable regions ("complementary determining regions," "CDRs") (vhCDR1, vhCDR2 and vhCDR3 for the variable heavy domain and vlCDR1, vlCDR2 and vlCDR3 for the variable light domain) and four framework (FR) regions, arranged from amino-terminus to carboxy-terminus in the following order: FR1-CDR1-FR2-CDR2-FR3-CDR3-FR4.

By "wild type or WT" herein is meant an amino acid sequence or a nucleotide sequence that is found in nature, including allelic variations. A WT protein has an amino acid sequence or a nucleotide sequence that has not been intentionally modified.

The invention provides a number of antibody domains that have sequence identity to human antibody domains. Sequence identity between two similar sequences (e.g., antibody variable domains) can be measured by algorithms such as that of Smith, T. F. & Waterman, M. S. (1981) "Comparison Of Biosequences," Adv. Appl. Math. 2:482 [local homology algorithm]; Needleman, S. B. & Wunsch, CD. (1970) "A General Method Applicable To The Search For Similarities In The Amino Acid Sequence Of Two Proteins," J. Mol. Biol. 48:443 [homology alignment algorithm], Pearson, W. R. & Lipman, D. J. (1988) "Improved Tools For Biological Sequence Comparison," Proc. Natl. Acad. Sci. (U.S.A.) 85:2444 [search for similarity method]; or Altschul, S. F. et al, (1990) "Basic Local Alignment Search Tool," J. Mol. Biol. 215:403-10, the "BLAST" algorithm, see https://blast.ncbi.nlm.nih.gov/Blast.cgi. When using any of the aforementioned algorithms, the default parameters (for Window length, gap penally, etc) are used. In one embodiment, sequence identity is done using the BLAST algorithm, using default parameters The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogenous host cells, and they can be isolated as well.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a BIACORE®, SPR or BLI assay.

E. Antibodies

The present invention relates to the generation of bispecific checkpoint antibodies that bind two different checkpoint antigens as discussed herein. As is discussed below, the term "antibody" is used generally. Antibodies that find use in the present invention can take on a number of formats as described herein, including traditional antibodies as well as antibody derivatives, fragments and mimetics, described herein and depicted in the figures.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to bispecific antibodies that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356E/358M allotype, however the other allotype is included herein. That is, any sequence inclusive of an IgG1 Fc domain included herein can have 356D/358L replacing the 356E/358M allotype.

In addition, many of the antibodies herein have at least one of the cysteines at position 220 replaced by a serine; generally this is the on the "scFv monomer" side for most of the sequences depicted herein, although it can also be on the "Fab monomer" side, or both, to reduce disulfide formation. Specifically included within the sequences herein are one or both of these cysteines replaced (C220S).

Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown in US Publication 2009/0163699, incorporated by reference, the present invention the use of human IgG1/G2 hybrids.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vhCDRs (e.g. vlCDR1, vlCDR2 and vlCDR3). A useful comparison of CDR numbering is as below, see Lafranc et al., Dev. Comp. Immunol. 27(1):55-77 (2003):

TABLE 1

| | Kabat + Chothia | IMGT | Kabat | AbM | Chothia | Contact | Xencor |
|---|---|---|---|---|---|---|---|
| vhCDR1 | 26-35 | 27-38 | 31-35 | 26-35 | 26-32 | 30-35 | 27-35 |
| vhCDR2 | 50-65 | 56-65 | 50-65 | 50-58 | 52-56 | 47-58 | 54-61 |
| vhCDR3 | 95-102 | 105-117 | 95-102 | 95-102 | 95-102 | 93-101 | 103-116 |
| vlCDR1 | 24-34 | 27-38 | 24-34 | 24-34 | 24-34 | 30-36 | 27-38 |
| vlCDR2 | 50-56 | 56-65 | 50-56 | 50-56 | 50-56 | 46-55 | 56-62 |
| vlCDR3 | 89-97 | 105-117 | 89-97 | 89-97 | 89-97 | 89-96 | 97-105 |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

Another type of Ig domain of the heavy chain is the hinge region. By "hinge" or "hinge region" or "antibody hinge region" or "hinge domain" herein is meant the flexible polypeptide comprising the amino acids between the first and second constant domains of an antibody. Structurally, the IgG CH1 domain ends at EU position 215, and the IgG CH2 domain begins at residue EU position 231. Thus for IgG the antibody hinge is herein defined to include positions 216 (E216 in IgG1) to 230 (p230 in IgG1), wherein the numbering is according to the EU index as in Kabat. In some cases, a "hinge fragment" is used, which contains fewer amino acids at either or both of the N- and C-termini of the hinge domain. As noted herein, pI variants can be made in the hinge region as well.

The light chain generally comprises two domains, the variable light domain (containing the light chain CDRs and together with the variable heavy domains forming the Fv region), and a constant light chain region (often referred to as CL or ClO.

Another region of interest for additional substitutions, outlined below, is the Fc region.

The present invention provides a large number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

Thus, the present invention provides different antibody domains. As described herein and known in the art, the heterodimeric antibodies of the invention comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

Thus, the "Fc domain" includes the —CH2-CH3 domain, and optionally a hinge domain (—H-CH2-CH3). In the embodiments herein, when a scFv is attached to an Fc domain, it is the C-terminus of the scFv construct that is attached to all or part of the hinge of the Fc domain; for example, it is generally attached to the sequence EPKS which is the beginning of the hinge. The heavy chain comprises a variable heavy domain and a constant domain, which includes a CH1-optional hinge-Fc domain comprising a CH2-CH3. The light chain comprises a variable light chain and the light constant domain. A scFv comprises a variable heavy chain, an scFv linker, and a variable light domain. In most of the constructs and sequences outlined herein, the C-terminus of the variable heavy chain is attached to the N-terminus of the scFv linker, the C-terminus of which is attached to the N-terminus of a variable light chain (N-vh-linker-vl-C) although that can be switched (N-vl-linker-vh-C).

Some embodiments of the invention comprise at least one scFv domain, which, while not naturally occurring, generally includes a variable heavy domain and a variable light domain, linked together by a scFv linker. As outlined herein, while the scFv domain is generally from N- to C-terminus oriented as vh-scFv linker-vl, this can be reversed for any of the scFv domains (or those constructed using vh and vl sequences from Fabs), to vl-scFv linker-vh, with optional linkers at one or both ends depending on the format (see generally FIG. 1).

As shown herein, there are a number of suitable linkers (for use as either domain linkers or scFv linkers) that can be used to covalently attach the recited domains, including traditional peptide bonds, generated by recombinant techniques. In some embodiments, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n (SEQ ID NO: 37756), (GGGGS)n (SEQ ID NO: 37757), and (GGGS)n (SEQ ID NO: 37758), where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g. TCR, FcR, KIR), hinge region-derived sequences, and other natural sequences from other proteins.

In some embodiments, the linker is a "domain linker", used to link any two domains as outlined herein together. For example, in FIG. 1F, there may be a domain linker that attaches the C-terminus of the CH1 domain of the Fab to the N-terminus of the scFv, with another optional domain linker attaching the C-terminus of the scFv to the CH2 domain (although in many embodiments the hinge is used as this domain linker). While any suitable linker can be used, many embodiments utilize a glycine-serine polymer as the domain linker, including for example (GS)n, (GSGGS)n (SEQ ID NO: 37756), (GGGGS)n (SEQ ID NO: 37757), and (GGGS)n (SEQ ID NO: 37758), where n is an integer of at least one (and generally from 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers, as used in some embodiments of scFv linkers can be used.

In some embodiments, the linker is a scFv linker, used to covalently attach the vh and vl domains as discussed herein. In many cases, the scFv linker is a charged scFv linker, a number of which are shown in FIG. 7. Accordingly, the present invention further provides charged scFv linkers, to facilitate the separation in pI between a first and a second monomer. That is, by incorporating a charged scFv linker, either positive or negative (or both, in the case of scaffolds that use scFvs on different monomers), this allows the monomer comprising the charged linker to alter the pI without making further changes in the Fc domains. These charged linkers can be substituted into any scFv containing standard linkers. Again, as will be appreciated by those in the art, charged scFv linkers are used on the correct "strand" or monomer, according to the desired changes in pI. For example, as discussed herein, to make triple F format heterodimeric antibody, the original pI of the Fv region for each of the desired antigen binding domains are calculated, and one is chosen to make an scFv, and depending on the pI, either positive or negative linkers are chosen.

Charged domain linkers can also be used to increase the pI separation of the monomers of the invention as well, and thus those included in FIG. 7 can be used in any embodiment herein where a linker is utilized.

In particular, the formats depicted in FIG. 1 are antibodies, usually referred to as "heterodimeric antibodies", meaning that the protein has at least two associated Fc sequences self-assembled into a heterodimeric Fc domain and at least two Fv regions, whether as Fabs or as scFvs.

F. Chimeric and Humanized Antibodies

In certain embodiments, the antibodies of the invention comprise a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody (using the methods outlined herein). A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized antibody may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention).

In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

IV. HETERODIMERIC ANTIBODIES

Accordingly, in some embodiments the present invention provides heterodimeric checkpoint antibodies that rely on the use of two different heavy chain variant Fc sequences, that will self-assemble to form heterodimeric Fc domains and heterodimeric antibodies.

The present invention is directed to novel constructs to provide heterodimeric antibodies that allow binding to more than one checkpoint antigen or ligand, e.g. to allow for bispecific binding. The heterodimeric antibody constructs are based on the self-assembling nature of the two Fc domains of the heavy chains of antibodies, e.g. two "monomers" that assemble into a "dimer". Heterodimeric antibodies are made by altering the amino acid sequence of each monomer as more fully discussed below. Thus, the present invention is generally directed to the creation of heterodimeric checkpoint antibodies which can co-engage antigens in several ways, relying on amino acid variants in the constant regions that are different on each chain to promote heterodimeric formation and/or allow for ease of purification of heterodimers over the homodimers.

Thus, the present invention provides bispecific antibodies. An ongoing problem in antibody technologies is the desire for "bispecific" antibodies that bind to two different antigens simultaneously, in general thus allowing the different antigens to be brought into proximity and resulting in new functionalities and new therapies. In general, these antibodies are made by including genes for each heavy and light chain into the host cells. This generally results in the formation of the desired heterodimer (A-B), as well as the two homodimers (A-A and B-B (not including the light chain heterodimeric issues)). However, a major obstacle in the formation of bispecific antibodies is the difficulty in purifying the heterodimeric antibodies away from the homodimeric antibodies and/or biasing the formation of the heterodimer over the formation of the homodimers.

There are a number of mechanisms that can be used to generate the heterodimers of the present invention. In addition, as will be appreciated by those in the art, these mechanisms can be combined to ensure high heterodimerization. Thus, amino acid variants that lead to the production of heterodimers are referred to as "heterodimerization variants". As discussed below, heterodimerization variants can include steric variants (e.g. the "knobs and holes" or "skew" variants described below and the "charge pairs" variants described below) as well as "pI variants", which allows purification of homodimers away from heterodimers. As is generally described in WO2014/145806, hereby incorporated by reference in its entirety and specifically as below for the discussion of "heterodimerization variants", useful mechanisms for heterodimerization include "knobs and holes" ("KIH"; sometimes herein as "skew" variants (see discussion in WO2014/145806), "electrostatic steering" or "charge pairs" as described in WO2014/145806, pI variants as described in WO2014/145806, and general additional Fc variants as outlined in WO2014/145806 and below.

In the present invention, there are several basic mechanisms that can lead to ease of purifying heterodimeric antibodies; one relies on the use of pI variants, such that each monomer has a different pI, thus allowing the isoelectric purification of A-A, A-B and B-B dimeric proteins. Alternatively, some scaffold formats, such as the "triple F" format, also allows separation on the basis of size. As is further outlined below, it is also possible to "skew" the formation of heterodimers over homodimers. Thus, a combination of steric heterodimerization variants and pI or charge pair variants find particular use in the invention.

In general, embodiments of particular use in the present invention rely on sets of variants that include skew variants, which encourage heterodimerization formation over homodimerization formation, coupled with pI variants, which increase the pI difference between the two monomers to facilitate purification of heterodimers away from homodimers.

Additionally, as more fully outlined below, depending on the format of the heterodimer antibody, pI variants can be either contained within the constant and/or Fc domains of a monomer, or charged linkers, either domain linkers or scFv linkers, can be used. That is, scaffolds that utilize scFv(s) such as the Triple F format can include charged scFv linkers (either positive or negative), that give a further pI boost for purification purposes. As will be appreciated by those in the art, some Triple F formats are useful with just charged scFv linkers and no additional pI adjustments, although the invention does provide pI variants that are on one or both of the monomers, and/or charged domain linkers as well. In addition, additional amino acid engineering for alternative functionalities may also confer pI changes, such as Fc, FcRn and KO variants.

In the present invention that utilizes pI as a separation mechanism to allow the purification of heterodimeric proteins, amino acid variants can be introduced into one or both of the monomer polypeptides; that is, the pI of one of the monomers (referred to herein for simplicity as "monomer A") can be engineered away from monomer B, or both monomer A and B change be changed, with the pI of monomer A increasing and the pI of monomer B decreasing. As discussed, the pI changes of either or both monomers can be done by removing or adding a charged residue (e.g. a neutral amino acid is replaced by a positively or negatively charged amino acid residue, e.g. glycine to glutamic acid), changing a charged residue from positive or negative to the opposite charge (e.g. aspartic acid to lysine) or changing a charged residue to a neutral residue (e.g. loss of a charge; lysine to serine). A number of these variants are shown in the Figures.

Accordingly, this embodiment of the present invention provides for creating a sufficient change in pI in at least one of the monomers such that heterodimers can be separated from homodimers. As will be appreciated by those in the art, and as discussed further below, this can be done by using a "wild type" heavy chain constant region and a variant region that has been engineered to either increase or decrease its pI_(wt A−+B or wt A−−B), or by increasing one region and decreasing the other region (A+−B− or A−B+).

Thus, in general, a component of some embodiments of the present invention are amino acid variants in the constant regions of antibodies that are directed to altering the isoelectric point (pI) of at least one, if not both, of the monomers of a dimeric protein to form "pI antibodies" by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) to get good separation will depend in part on the starting pI of the components, for example in the triple F format, the starting pI of the scFv and Fab of interest. That is, to determine which monomer to engineer or in which "direction" (e.g. more positive or more negative), the Fv sequences of the two target antigens are calculated and a decision is made from there. As is known in the art, different Fvs will have different starting pIs which are exploited in the present invention. In general, as outlined herein, the pIs are engineered to result in a total pI difference of each monomer of at least about 0.1 logs, with 0.2 to 0.5 being preferred as outlined herein.

Furthermore, as will be appreciated by those in the art and outlined herein, in some embodiments, heterodimers can be separated from homodimers on the basis of size. As shown in FIG. 1 for example, several of the formats allow separation of heterodimers and homodimers on the basis of size.

A. Heterodimerization Variants

The present invention provides heterodimeric proteins, including heterodimeric antibodies in a variety of formats, which utilize heterodimeric variants to allow for heterodimeric formation and/or purification away from homodimers.

There are a number of suitable pairs of sets of heterodimerization skew variants. These variants come in "pairs" of "sets". That is, one set of the pair is incorporated into the first monomer and the other set of the pair is incorporated into the second monomer. It should be noted that these sets do not necessarily behave as "knobs in holes" variants, with a one-to-one correspondence between a residue on one monomer and a residue on the other; that is, these pairs of sets form an interface between the two monomers that encourages heterodimer formation and discourages homodimer formation, allowing the percentage of heterodimers that spontaneously form under biological conditions to be over 90%, rather than the expected 50% (25% homodimer A/A: 50% heterodimer A/B:25% homodimer B/B).

B. Steric Variants

In some embodiments, the formation of heterodimers can be facilitated by the addition of steric variants. That is, by changing amino acids in each heavy chain, different heavy chains are more likely to associate to form the heterodimeric structure than to form homodimers with the same Fc amino acid sequences. Suitable steric variants are included in in the Figures.

One mechanism is generally referred to in the art as "knobs and holes", referring to amino acid engineering that creates steric influences to favor heterodimeric formation and disfavor homodimeric formation can also optionally be used; this is sometimes referred to as "knobs and holes", as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety. The Figures identify a number of "monomer A-monomer B" pairs that rely on "knobs and holes". In addition, as described in Merchant et al., Nature Biotech. 16:677 (1998), these "knobs and hole" mutations can be combined with disulfide bonds to skew formation to heterodimerization.

An additional mechanism that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R.

Additional monomer A and monomer B variants that can be combined with other variants, optionally and independently in any amount, such as pI variants outlined herein or other steric variants that are shown in FIG. 37 of US 2012/0149876, the figure and legend and SEQ ID NOs of which are incorporated expressly by reference herein.

In some embodiments, the steric variants outlined herein can be optionally and independently incorporated with any pI variant (or other variants such as Fc variants, FcRn variants, etc.) into one or both monomers, and can be independently and optionally included or excluded from the proteins of the invention.

A list of suitable skew variants is found in FIG. 3 and FIG. 8 showing some pairs of particular utility in many embodiments. Of particular use in many embodiments are the pairs of sets including, but not limited to, S364K/E357Q:L368D/K370S; L368D/K370S:S364K; L368E/K370S:S364K; T411T/E360E/Q362E:D401K; L368D/K370S:S364K/E357L, K370S:S364K/E357Q and T366S/L368A/Y407V:T366W (optionally including a bridging disulfide, T366S/L368A/Y407V/Y349C:T366W/S354C). In terms of nomenclature, the pair "S364K/E357Q:L368D/K370S" means that one of the monomers has the double variant set S364K/E357Q and the other has the double variant set L368D/K370S; as above, the "strandedness" of these pairs depends on the starting pI.

C. pI (Isoelectric Point) Variants for Heterodimers

In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

Preferred combinations of pI variants are shown in FIG. 4. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In one embodiment, for example in the FIGS. 1A, E, F, G, H and I formats, a preferred combination of pI variants has one monomer (the negative Fab side) comprising 208D/295E/384D/418E/421D variants (N208D/Q295E/N384D/Q418E/N421D when relative to human IgG1) and a second monomer (the positive scFv side) comprising a positively charged scFv linker, including (GKPGS)$_4$ (SEQ ID NO: 37755). However, as will be appreciated by those in the art, the first monomer includes a CH1 domain, including position 208. Accordingly, in constructs that do not include a CH1 domain (for example for antibodies that do not utilize a CH1 domain on one of the domains, for example in a dual scFv format or a "one armed" format such as those depicted in FIG. 1B, C or D), a preferred negative pI variant Fc set includes 295E/384D/418E/421D variants (Q295E/N384D/Q418E/N421D when relative to human IgG1).

Accordingly, in some embodiments, one monomer has a set of substitutions from FIG. 4 and the other monomer has a charged linker (either in the form of a charged scFv linker because that monomer comprises an scFv or a charged domain linker, as the format dictates, which can be selected from those depicted in FIG. 7).

1. Isotypic Variants

In addition, many embodiments of the invention rely on the "importation" of pI amino acids at particular positions from one IgG isotype into another, thus reducing or eliminating the possibility of unwanted immunogenicity being introduced into the variants. A number of these are shown in FIG. 21 of US Publ. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significant affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g. by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation by ion exchange chromatography or isoelectric focusing, or other methods sensitive to isoelectric point.

D. Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the FIG. 19 of US Pub. 2014/0370013. As discussed herein, which monomer to engineer is generally decided by the inherent pI of the Fv and scaffold regions. Alternatively, the pI of each monomer can be compared.

E. pI Variants that Also Confer Better FcRn In Vivo Binding

In the case where the pI variant decreases the pI of the monomer, they can have the added benefit of improving serum retention in vivo.

Although still under examination, Fc regions are believed to have longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. In mice, Dall'Acqua et al. showed that Fc mutants with increased FcRn binding at pH 6 and pH 7.4 actually had reduced serum concentrations and the same half life as wild-type Fc (Dall'Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

Recently it has been suggested that antibodies with variable regions that have lower isoelectric points may also have longer serum half-lives (Igawa et al., 2010 PEDS. 23(5): 385-392, entirely incorporated by reference). However, the mechanism of this is still poorly understood. Moreover, variable regions differ from antibody to antibody. Constant region variants with reduced pI and extended half-life would provide a more modular approach to improving the pharmacokinetic properties of antibodies, as described herein.

F. Additional Fc Variants for Additional Functionality

In addition to pI amino acid variants, there are a number of useful Fc amino acid modification that can be made for a variety of reasons, including, but not limited to, altering binding to one or more FcγR receptors, altered binding to FcRn receptors, etc.

Accordingly, the proteins of the invention can include amino acid modifications, including the heterodimerization variants outlined herein, which includes the pI variants and steric variants. Each set of variants can be independently and optionally included or excluded from any particular heterodimeric protein.

G. FcγR Variants

Accordingly, there are a number of useful Fc substitutions that can be made to alter binding to one or more of the FcγR receptors. Substitutions that result in increased binding as well as decreased binding can be useful. For example, it is known that increased binding to FcγRIIIa results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present invention include those listed in U.S. Ser. No. 11/124,620 (particularly FIG. 41), Ser. Nos. 11/174,287, 11/396,495, 11/538,406, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T.

In addition, there are additional Fc substitutions that find use in increased binding to the FcRn receptor and increased serum half life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L and 259I/308F/428L.

H. Ablation Variants

Similarly, another category of functional variants are "FcγR ablation variants" or "Fc knock out (FcKO or KO)" variants. In these embodiments, for some therapeutic applications, it is desirable to reduce or remove the normal binding of the Fc domain to one or more or all of the Fcγ receptors (e.g. FcγR1, FcγRIIa, FcγRIIb, FcγRIIIa, etc.) to avoid additional mechanisms of action. That is, for example, in many embodiments, particularly in the use of bispecific checkpoint antibodies desirable to ablate FcγRIIIa binding to eliminate or significantly reduce ADCC activity such that one of the Fc domains comprises one or more Fcγ receptor ablation variants. These ablation variants are depicted in FIG. 5, and each can be independently and optionally included or excluded, with preferred aspects utilizing ablation variants selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del. It should be noted that the ablation variants referenced herein ablate FcγR binding but generally not FcRn binding.

As is known in the art, the Fc domain of human IgG1 has the highest binding to the Fcγ receptors, and thus ablation variants can be used when the constant domain (or Fc domain) in the backbone of the heterodimeric antibody is IgG1. Alternatively, or in addition to ablation variants in an IgG1 background, mutations at the glycosylation position 297 (generally to A or S) can significantly ablate binding to FcγRIIIa, for example. Human IgG2 and IgG4 have naturally reduced binding to the Fcγ receptors, and thus those backbones can be used with or without the ablation variants.

I. Combination of Heterodimeric and Fc Variants

As will be appreciated by those in the art, all of the recited heterodimerization variants (including skew and/or pI variants) can be optionally and independently combined in any way, as long as they retain their "strandedness" or "monomer partition". In addition, all of these variants can be combined into any of the heterodimerization formats.

In the case of pI variants, while embodiments finding particular use are shown in the Figures, other combinations can be generated, following the basic rule of altering the pI difference between two monomers to facilitate purification.

In addition, any of the heterodimerization variants, skew and pI, are also independently and optionally combined with Fc ablation variants, Fc variants, FcRn variants, as generally outlined herein.

V. Useful Formats of the Invention

As will be appreciated by those in the art and discussed more fully below, the bispecific heterodimeric antibodies of the present invention can take on a wide variety of configurations, as are generally depicted in FIG. 1. Some figures depict "single ended" configurations, where there is one type of specificity on one "arm" of the molecule and a different specificity on the other "arm". Other figures depict "dual ended" configurations, where there is at least one type of specificity at the "top" of the molecule and one or more different specificities at the "bottom" of the molecule. Thus, the present invention is directed to novel immunoglobulin compositions that co-engage a different first and a second antigen.

As will be appreciated by those in the art, the heterodimeric formats of the invention can have different valencies as well as be bispecific. That is, heterodimeric antibodies of the invention can be bivalent and bispecific, wherein one checkpoint target is bound by one ABD and the other checkpoint target is bound by a second ABD. The heterodimeric antibodies can also be trivalent and bispecific, wherein the first antigen is bound by two ABDs and the second antigen by a second ABD.

A. Bottle Opener Format

One heterodimeric scaffold that finds particular use in the present invention is the "triple F" or "bottle opener" scaffold format as shown in FIG. 1A. In this embodiment, one heavy chain of the antibody contains a single chain Fv ("scFv", as defined below) and the other heavy chain is a "regular" Fab format, comprising a variable heavy chain and a light chain. This structure is sometimes referred to herein as "triple F" format (scFv-Fab-Fc) or the "bottle-opener" format, due to a rough visual similarity to a bottle-opener (see FIG. 1A). The two chains are brought together by the use of amino acid variants in the constant regions (e.g. the Fc domain, the CH1 domain and/or the hinge region) that promote the formation of heterodimeric antibodies as is described more fully below.

There are several distinct advantages to the present "triple F" format. As is known in the art, antibody analogs relying on two scFv constructs often have stability and aggregation problems, which can be alleviated in the present invention by the addition of a "regular" heavy and light chain pairing. In addition, as opposed to formats that rely on two heavy chains and two light chains, there is no issue with the incorrect pairing of heavy and light chains (e.g. heavy 1 pairing with light 2, etc.).

Many of the embodiments outlined herein rely in general on the bottle opener format that comprises a first monomer comprising an scFv, comprising a variable heavy and a variable light domain, covalently attached using an scFv linker (charged, in many but not all instances), where the scFv is covalently attached to the N-terminus of a first Fc domain usually through a domain linker (which, as outlined herein can either be un-charged or charged and can be exogeneous or endogeneous (e.g. all or part of the native hinge domain). The second monomer of the bottle opener format is a heavy chain, and the composition further comprises a light chain.

In addition, the Fc domains of the bottle opener format generally comprise skew variants (e.g. a set of amino acid substitutions as shown in FIG. 3 and FIG. 8, with particularly useful skew variants being selected from the group consisting of S364K/E357Q:L368D/K370S; L368D/K370S: S364K; L368E/K370S:S364K; T411T/E360E/Q362E: D401K; L368D/K370S:S364K/E357L, K370S:S364K/ E357Q, T366S/L368A/Y407V:T366W and T366S/L368A/ Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the bottle opener format includes skew variants, pI variants, and ablation variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/ L235A/G236del/S267K, and an Fv that binds to a checkpoint receptor as outlined herein; b) a second monomer (the "Fab monomer") that comprises the skew variants L368D/ K370S, the pI variants N208D/Q295E/N384D/Q418E/ N421D, the ablation variants E233P/L234V/L235A/ G236del/S267K, and a variable heavy domain that, with the variable light domain, makes up an Fv that binds to a second checkpoint receptor as outlined herein; and c) a light chain. In this particular embodiment, suitable monomer Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA. In this particular embodiment, a bottle opener with these variants have the scFv side comprising the ABD 1G6_L1.194_H1.279 that binds to PD-1 finds particular use. In this particular embodiment, a bottle opener with these variants have the scFv side comprising the [CTLA-4]_H3.23_L0.129 ABD that binds to CTLA-4 finds particular use.

Of particular use in some embodiments, particularly in the bottle opener format, are CTLA-4×PD-1, LAG-3×PD-1, BTLA×PD-1, TIM-3×PD-1 and LAG-3×CTLA-4.

The ABD sequences for these combinations can be as disclosed in the sequence listing or as shown in FIGS. 9 to 13, and in any combination as shown in FIG. 39 and FIG. 40.

In some embodiments, the bottle opener format includes skew variants, pI variants, ablation variants and FcRn variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, the FcRn variants M428L/N434S and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to a second checkpoint inhibitor as outlined herein; and c) a light chain. In this particular embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA. In this particular embodiment, a bottle opener with these variants have the scFv side comprising the ABD 1G6_L1.194_H1.279 that binds to PD-1 finds particular use. In this particular embodiment, a bottle opener with these variants have the scFv side comprising the [CTLA-4]_H3.23_L0.129 ABD that binds to CTLA-4 finds particular use.

Of particular use in some embodiments, particularly in the bottle opener format, are CTLA-4×PD-1, LAG-3×PD-1, BTLA×PD-1, TIM-3×PD-1 and LAG-3×CTLA-4.

Specifically, FIG. 37 shows some bottle opener "backbone" sequences that are missing the Fv sequences that can be used in the present invention. That is, Fv sequences for the scFv portion and the Fab portion can be used from any combination of PD-1 and CTLA-4, PD-1 and TIM-3, PD-1 and LAG-3, PD-1 and TIGIT, PD-1 and BTLA, CTLA-4 and TIM-3, CTLA-4 and LAG-3, CTLA-4 and TIGIT, CTLA-4 and BTLA, TIM-3 and LAG-3, TIM-3 and TIGIT, TIM-3 and BTLA, LAG-3 and TIGIT, LAG-3 and BTLA and TIGIT and BTLA. The sequences can be any of those disclosed herein in the sequence listing and/or in FIGS. 9 to 13.

For bottle opener backbone 1 from FIG. 37, specific Fv combinations of use in the present invention include PD-1 and CTLA-4, PD-1 and TIM-3, PD-1 and LAG-3, PD-1 and TIGIT, PD-1 and BTLA, CTLA-4 and TIM-3, CTLA-4 and LAG-3, CTLA-4 and TIGIT, CTLA-4 and BTLA, TIM-3 and LAG-3, TIM-3 and TIGIT, TIM-3 and BTLA, LAG-3 and TIGIT, LAG-3 and BTLA and TIGIT and BTLA. The sequences can be any of those disclosed herein in the sequence listing and/or in FIGS. 9 to 13.

For bottle opener backbone 1 from FIG. 37, specific Fv combinations of use in the present invention include CTLA-4 (Fab)×PD-1 (scFv), PD-1 (Fab)×CTLA-4 (scFv), LAG-3 (Fab)×PD-1 (scFv), BTLA (Fab)×PD-1 (scFv) and LAG-3 (Fab)×CTLA-4 (scFv).

For bottle opener backbone 1 from FIG. 37 (optionally including the 428L/434S variants), specific ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

For bottle opener backbone 1 from FIG. 37 (optionally including the 428L/434S variants), specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

For bottle opener backbone 1 from FIG. 37 (optionally including the 428L/434S variants), specific ABDs that bind human LAG-3 include, but are not limited to, 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

For bottle opener backbone 1 from FIG. 37 (optionally including the 428L/434S variants), specific ABDs that bind human BTLA include, but are not limited to, 9C6_H0L0; 9C6_H1.1_L1; and 9C6_H1.11_L1, as well as those listed in SEQ ID SEQ ID NOs: 20885-21503 and SEQ ID NOs: 36707-36738.

For bottle opener backbone 1 from FIG. 37 (optionally including the 428L/434S variants), specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

Specific bottle opener embodiments are outlined below.

B. mAb-Fv Format

One heterodimeric scaffold that finds particular use in the present invention is the mAb-Fv format shown in FIG. 1H. In this embodiment, the format relies on the use of a C-terminal attachment of an "extra" variable heavy domain to one monomer and the C-terminal attachment of an "extra" variable light domain to the other monomer, thus forming a third antigen binding domain, wherein the Fab portions of the two monomers bind one checkpoint target and the "extra" scFv domain binds a different checkpoint target.

In this embodiment, the first monomer comprises a first heavy chain, comprising a first variable heavy domain and a first constant heavy domain comprising a first Fc domain, with a first variable light domain covalently attached to the C-terminus of the first Fc domain using a domain linker (vh1-CH1-hinge-CH2-CH3-[optional linker]-vl2). The second monomer comprises a second variable heavy domain of the second constant heavy domain comprising a second Fc domain, and a third variable heavy domain covalently attached to the C-terminus of the second Fc domain using a domain linker (vh1-CH1-hinge-CH2-CH3-[optional linker]-vh2. The two C-terminally attached variable domains make up a scFv. This embodiment further utilizes a common light chain comprising a variable light domain and a constant light domain, which associates with the heavy chains to form two identical Fabs. As for many of the embodiments herein, these constructs include skew variants, pI variants, ablation variants, additional Fc variants, etc. as desired and described herein. In this embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA.

The ABD sequences for these combinations can be as disclosed in the sequence listing or as shown in FIGS. 9 to 13, and in any combination as shown in FIG. 39 and FIG. 40.

In addition, the Fc domains of the mAb-Fv format comprise skew variants (e.g. a set of amino acid substitutions as shown in FIG. 3 and FIG. 8, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the mAb-Fv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) CTLA-4×PD-1, LAG-3×PD-1, BTLA×PD-1, and LAG-3×CTLA-4.

In some embodiments, the mAb-Fv format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) CTLA-4×PD-1, LAG-3×PD-1, BTLA×PD-1, and LAG-3×CTLA-4.

For mAb-Fv sequences that are similar to the mAb-scFv backbone 1 (optionally including M428L/N434S) from FIG. 38, specific ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

For mAb-Fv sequences that are similar to the mAb-scFv backbone 1 (optionally including M428L/N434S) from FIG. 38, specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

For mAb-Fv sequences that are similar to the mAb-scFv backbone 1 (optionally including M428L/N434S) from FIG. 38, specific ABDs that bind human LAG-3 include, but are not limited to, 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

For mAb-Fv sequences that are similar to the mAb-scFv backbone 1 (optionally including M428L/N434S) from FIG. 38, specific ABDs that bind human BTLA include, but are not limited to, 9C6_H0L0; 9C6_H1.1_L1; and 9C6_H1.11_L1, as well as those listed in SEQ ID NOs: 20885-21503 and SEQ ID NOs: 36707-36738.

For mAb-Fv sequences that are similar to the mAb-scFv backbone 1 (optionally including M428L/N434S) from FIG. 38, specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

C. mAb-scFv

One heterodimeric scaffold that finds particular use in the present invention is the mAb-scFv format shown in FIG. 11. In this embodiment, the format relies on the use of a C-terminal attachment of an scFv to one of the monomers, thus forming a third antigen binding domain, wherein the Fab portions of the two monomers bind one checkpoint target and the "extra" scFv domain binds a different checkpoint target.

In this embodiment, the first monomer comprises a first heavy chain (comprising a variable heavy domain and a constant domain), with a C-terminally covalently attached scFv comprising a scFv variable light domain, an scFv linker and a scFv variable heavy domain in either orientation (vh1-CH1-hinge-CH2-CH3-[optional linker]-vh2-scFv linker-vl2 or vh1-CH1-hinge-CH2-CH3-[optional linker]-vl2-scFv linker-vh2). This embodiment further utilizes a common light chain comprising a variable light domain and a constant light domain, which associates with the heavy chains to form two identical Fabs that bind one of the target antigens. As for many of the embodiments herein, these constructs include skew variants, pI variants, ablation variants, additional Fc variants, etc. as desired and described herein. In this embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA.

The ABD sequences for these combinations can be as disclosed in the sequence listing or as shown in FIGS. 9 to 13, and in any combination as shown in FIG. 39 and FIG. 40.

In addition, the Fc domains of the mAb-scFv format generally comprise skew variants (e.g. a set of amino acid substitutions as shown in FIG. 3 and FIG. 8, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the mAb-scFv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) CTLA-4×PD-1, LAG-3×PD-1, BTLA×PD-1, and LAG-3×CTLA-4.

In some embodiments, the mAb-scFv format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In mAb-scFv formats, specific Fv combinations of use in the present invention include CTLA-4 (Fab)×PD-1 (scFv), PD-1 (Fab)×CTLA-4 (scFv), LAG-3 (Fab)×PD-1 (scFv), BTLA (Fab)×PD-1 (scFv) and LAG-3 (Fab)×CTLA-4 (scFv).

In mAb-scFv backbone 1 (optionally including M428L/N434S) from FIG. 38, specific ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

In mAb-scFv backbone 1 (optionally including M428L/N434S) from FIG. 38, specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

In mAb-scFv backbone 1 (optionally including M428L/N434S) from FIG. 38, specific ABDs that bind human LAG-3 include, but are not limited to, 2A11_H0L0;

2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11 H1L1 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

In mAb-scFv backbone 1 (optionally including M428L/ N434S) from FIG. 38, specific ABDs that bind human BTLA include, but are not limited to, 9C6_H0L0; 9C6_H1.1_L1; and 9C6_H1.11_L1, as well as those listed in SEQ ID NOs: 20885-21503 and SEQ ID NOs: 36707-36738.

In mAb-scFv backbone 1 (optionally including M428L/ N434S) from FIG. 38, specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

D. Central scFv

One heterodimeric scaffold that finds particular use in the present invention is the Central-scFv format shown in FIG. 1F. In this embodiment, the format relies on the use of an inserted scFv domain thus forming a third antigen binding domain, wherein the Fab portions of the two monomers bind one checkpoint target and the "extra" scFv domain binds another. The scFv domain is inserted between the Fc domain and the CH1-Fv region of one of the monomers, thus providing a third antigen binding domain.

In this embodiment, one monomer comprises a first heavy chain comprising a first variable heavy domain, a CH1 domain (and optional hinge) and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using optional domain linkers (vh1-CH1-[optional linker]-vh2-scFv linker-vl2-[optional linker including the hinge]-CH2-CH3, or the opposite orientation for the scFv, vh1-CH1-[optional linker]-vl2-scFv linker-vh2-[optional linker including the hinge]-CH2-CH3). The other monomer is a standard Fab side. This embodiment further utilizes a common light chain comprising a variable light domain and a constant light domain, which associates with the heavy chains to form two identical Fabs that bind a checkpoint inhibitor. As for many of the embodiments herein, these constructs include skew variants, pI variants, ablation variants, additional Fc variants, etc. as desired and described herein. In this embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA.

The ABD sequences for these combinations can be as disclosed in the sequence listing or as shown in FIGS. 9 to 13, and in any combination as shown in FIG. 39 and FIG. 40.

In addition, the Fc domains of the central scFv format generally comprise skew variants (e.g. a set of amino acid substitutions as shown in FIG. 3 and FIG. 8, with particularly useful skew variants being selected from the group consisting of S364K/E357Q:L368D/K370S; L368D/K370S: S364K; L368E/K370S:S364K; T411T/E360E/Q362E: D401K; L368D/K370S:S364K/E357L, K370S:S364K/ E357Q, T366S/L368A/Y407V:T366W and T366S/L368A/ Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the central scFv format includes skew variants, pI variants, and ablation variants. Accordingly, some embodiments include bottle opener formats that comprise: a) a first monomer that comprises the skew variants S364K/E357Q, the ablation variants E233P/ L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In this embodiment, suitable Fv pairs include (Fabs listed first, scFvs second) CTLA-4×PD-1, PD-1×CTLA-4, LAG-3×PD-1, BTLA×PD-1, and LAG-3× CTLA-4.

In some embodiments, the central scFv format includes skew variants, pI variants, ablation variants and FcRn variants. Accordingly, some embodiments include bottle opener formats that comprise: a) a first monomer that comprises the skew variants S364K/E357Q, the ablation variants E233P/ L234V/L235A/G236del/S267K, the FcRn variants M428L/ N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/ Q295E/N384D/Q418E/N421D, the ablation variants E233P/ L234V/L235A/G236del/S267K, the FcRn variants M428L/ N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In this embodiment, suitable Fv pairs include (Fabs listed first, scFvs second) CTLA-4×PD-1, PD-1×CTLA-4, LAG-3×PD-1, BTLA×PD-1, and LAG-3×CTLA-4.

For central-scFv sequences that are similar to/utilize the bottle opener backbone 1 of FIG. 37 (optionally including M428L/N434S), specific Fv combinations of use in the present invention include CTLA-4 (Fab)×PD-1 (scFv), PD-1 (Fab)×CTLA-4 (scFv), LAG-3 (Fab)×PD-1 (scFv), BTLA (Fab)×PD-1 (scFv) and LAG-3 (Fab)×CTLA-4 (scFv).

For central-scFv sequences that are similar to/utilize the bottle opener backbone 1 of FIG. 37, (optionally including M428L/N434S), specific ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

For central-scFv sequences that are similar to/utilize the bottle opener backbone 1 of FIG. 37 (optionally including M428L/N434S), specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

For central-scFv sequences that are similar to/utilize the bottle opener backbone 1 of FIG. 37 (optionally including M428L/N434S), specific ABDs that bind human LAG-3 include, but are not limited to, 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

For central-scFv sequences that are similar to/utilize the bottle opener backbone 1 of FIG. 37 (optionally including M428L/N434S), specific ABDs that bind human BTLA include, but are not limited to, 9C6_H0L0; 9C6_H1.1_L1; and 9C6_H1.11_L1, as well as those listed in SEQ ID NOs: 20885-21503 and SEQ ID NOs: 36707-36738.

For central-scFv sequences that are similar to/utilize the bottle opener backbone 1 of FIG. 37 (optionally including M428L/N434S), specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

E. Central-Fv Format

One heterodimeric scaffold that finds particular use in the present invention is the Central-Fv format shown in FIG. 1G. In this embodiment, the format relies on the use of an inserted scFv domain thus forming a third antigen binding domain, wherein the Fab portions of the two monomers bind one checkpoint target and the "extra" scFv domain binds another. The scFv domain is inserted between the Fc domain and the CH1-Fv region of the monomers, thus providing a third antigen binding domain, wherein each monomer contains a component of the scFv (e.g. one monomer comprises a variable heavy domain and the other a variable light domain).

In this embodiment, one monomer comprises a first heavy chain comprising a first variable heavy domain, a CH1 domain, and Fc domain and an additional variable light domain. The light domain is covalently attached between the C-terminus of the CH1 domain of the heavy constant domain and the N-terminus of the first Fc domain using domain linkers (vh1-CH1-[optional linker]-vl2-hinge-CH2-CH3). The other monomer comprises a first heavy chain comprising a first variable heavy domain, a CH1 domain and Fc domain and an additional variable heavy domain (vh1-CH1-[optional linker]-vh2-hinge-CH2-CH3). The light domain is covalently attached between the C-terminus of the CH1 domain of the heavy constant domain and the N-terminus of the first Fc domain using domain linkers. This embodiment further utilizes a common light chain comprising a variable light domain and a constant light domain, that associates with the heavy chains to form two identical Fabs that bind a TTA. As for many of the embodiments herein, these constructs include skew variants, pI variants, ablation variants, additional Fc variants, etc. as desired and described herein. In this embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA.

The ABD sequences for these combinations can be as disclosed in the sequence listing or as shown in FIGS. 9 to 13, and in any combination as shown in FIG. 39 and FIG. 40.

In central-scFv formats, specific Fv combinations of use in the present invention include CTLA-4 (Fab)×PD-1 (scFv), PD-1 (Fab)×CTLA-4 (scFv), LAG-3 (Fab)×PD-1 (scFv), BTLA (Fab)×PD-1 (scFv) and LAG-3 (Fab)×CTLA-4 (scFv).

In central-scFv formats, specific ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

In central-scFv formats, specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0;

[CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

In central-scFv formats, specific ABDs that bind human LAG-3 include, but are not limited to, 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

In central-scFv formats, specific ABDs that bind human BTLA include, but are not limited to, 9C6_H0L0; 9C6_H1.1_L1; and 9C6_H1.11_L1, as well as those listed in SEQ ID NOs: 20885-21503 and SEQ ID NOs: 36707-36738.

In central-scFv formats, specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

F. One Armed Central-scFv

One heterodimeric scaffold that finds particular use in the present invention is the one armed central-scFv format shown in FIG. 1C. In this embodiment, one monomer comprises just an Fc domain, while the other monomer uses an inserted scFv domain thus forming the second antigen binding domain. In this format, either the Fab portion binds one checkpoint target and the scFv binds another. The scFv domain is inserted between the Fc domain and the CH1-Fv region of one of the monomers.

In this embodiment, one monomer comprises a first heavy chain comprising a first variable heavy domain, a CH1 domain and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using domain linkers. The second monomer comprises an Fc domain. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein. In this embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA.

The ABD sequences for these combinations can be as disclosed in the sequence listing or as shown in FIGS. 9 to 13, and in any combination as shown in FIG. 39 and FIG. 40.

In addition, the Fc domains of the one armed central-scFv format generally comprise skew variants (e.g. a set of amino acid substitutions as shown in FIG. 3 and FIG. 8, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the one armed central-scFv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In this embodiment, suitable Fv pairs include (Fabs listed first, scFvs second) CTLA-4×PD-1, PD-1×CTLA-4, LAG-3×PD-1, BTLA×PD-1, and LAG-3×CTLA-4.

In some embodiments, the one armed central-scFv format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In this embodiment, suitable Fv pairs include (Fabs listed first, scFvs second) CTLA-4×PD-1, PD-1×CTLA-4, LAG-3×PD-1, BTLA×PD-1, and LAG-3×CTLA-4.

In one armed central-scFv formats, specific ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

In one armed central-scFv formats, specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

In one armed central-scFv formats, specific ABDs that bind human LAG-3 include, but are not limited to, 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

In one armed central-scFv formats, specific ABDs that bind human BTLA include, but are not limited to, 9C6_H0L0; 9C6_H1.1_L1; and 9C6_H1.11_L1, as well as those listed in SEQ ID NOs: 20885-21503 and SEQ ID NOs: 36707-36738.

In one armed central-scFv formats, specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

G. One Armed scFv-mAb

One heterodimeric scaffold that finds particular use in the present invention is the one armed scFv-mAb format shown in FIG. 1D. In this embodiment, one monomer comprises just an Fc domain, while the other monomer uses a scFv domain attached at the N-terminus of the heavy chain, generally through the use of a linker: vh-scFv linker-vl-[optional domain linker]-CH1-hinge-CH2-CH3 or (in the opposite orientation) vl-scFv linker-vh-[optional domain linker]-CH1-hinge-CH2-CH3. In this format, either the Fab portion binds one checkpoint target and the scFv binds another. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein. In this embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3× PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA.

The ABD sequences for these combinations can be as disclosed in the sequence listing or as shown in FIGS. 9 to 13, and in any combination as shown in FIG. 39 and FIG. 40.

In addition, the Fc domains of the comprise skew variants (e.g. a set of amino acid substitutions as shown in FIG. 3 and FIG. 8, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the one armed scFv-mAb format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In this embodiment, suitable Fv pairs include (Fabs listed first, scFvs second) CTLA-4×PD-1, PD-1×CTLA-4, LAG-3×PD-1, BTLA×PD-1, and LAG-3×CTLA-4.

In some embodiments, the one armed scFv-mAb format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In this embodiment, suitable Fv pairs include (Fabs listed first, scFvs second) CTLA-4×PD-1, PD-1×CTLA-4, LAG-3×PD-1, BTLA×PD-1, and LAG-3×CTLA-4.

In one armed scFv-mAb formats, specific ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

In one armed scFv-mAb formats, specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

In one armed scFv-mAb formats, specific ABDs that bind human LAG-3 include, but are not limited to, 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

In one armed scFv-mAb formats, specific ABDs that bind human BTLA include, but are not limited to, 9C6_H0L0; 9C6_H1.1_L1; and 9C6_H1.11_L1, as well as those listed in SEQ ID NOs: 20885-21503 and SEQ ID NOs: 36707-36738.

In one armed scFv-mAb formats, specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

H. scFv-mAb Format

One heterodimeric scaffold that finds particular use in the present invention is the mAb-scFv format shown in FIG. 1E. In this embodiment, the format relies on the use of a N-terminal attachment of a scFv to one of the monomers, thus forming a third antigen binding domain, wherein the Fab portions of the two monomers bind one checkpoint target and the "extra" scFv domain binds a different checkpoint target.

In this embodiment, the first monomer comprises a first heavy chain (comprising a variable heavy domain and a constant domain), with a N-terminally covalently attached scFv comprising a scFv variable light domain, an scFv linker and a scFv variable heavy domain in either orientation ((vh1-scFv linker-vl1-[optional domain linker]-vh2-CH1-hinge-CH2-CH3) or (with the scFv in the opposite orientation) ((vl1-scFv linker-vh1-[optional domain linker]-vh2-CH1-hinge-CH2-CH3)). This embodiment further utilizes a common light chain comprising a variable light domain and a constant light domain, that associates with the heavy chains to form two identical Fabs that bind one of the target antigens. As for many of the embodiments herein, these constructs include skew variants, pI variants, ablation variants, additional Fc variants, etc. as desired and described herein. In this embodiment, suitable Fv pairs include (Fabs listed first, scFvs second) PD-1 and CTLA-4, CTLA-4 and PD-1, PD-1 and TIM-3, TIM-3 and PD-1, PD-1 and LAG-3, LAG-3×PD1, PD-1 and TIGIT, TIGIT and PD-1, PD-1 and BTLA, BTLA and PD-1, CTLA-4 and TIM-3, TIM-3 and CTLA-4, CTLA-4 and LAG-3, LAG-3 and CTLA-4, CTLA-4 and TIGIT, TIGIT and CTLA-4, CTLA-4 and BTLA, BTLA and CTLA-4, TIM-3 and LAG-3, LAG-3 and TIM-3, TIM-3 and TIGIT, TIGIT and TIM-3, TIM-3 and BTLA, BTLA and TIM-3. LAG-3 and TIGIT, TIGIT and LAG-3, LAG-3 and BTLA, BTLA and LAG-3, BTLA and TIGIT, and TIGIT and BTLA.

The ABD sequences for these combinations can be as disclosed in the sequence listing or as shown in FIGS. 9 to 13, and in any combination as shown in FIG. 39 and FIG. 40.

In addition, the Fc domains of the scFv-mAb format comprise skew variants (e.g. a set of amino acid substitutions as shown in FIG. 3 and FIG. 8, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the mAb-scFv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) CTLA-4×PD-1, LAG-3×PD-1, BTLA×PD-1, and LAG-3×CTLA-4.

In some embodiments, the mAb-scFv format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) CTLA-4×PD-1, LAG-3×PD-1, BTLA×PD-1, and LAG-3×CTLA-4.

For the mAb-scFv format backbone 1 (optionally including M428L/N434S) from FIG. 38, specific ABDs that bind human PD-1 include, but are not limited to, 1G6_H1.279_L1.194; 1G6_H1.280_L1.224; 1G6_L1.194_H1.279, 1G6_L1.210_H1.288 and 2E9_H1L1, as well as those listed in SEQ ID NOs: 6209-11464, SEQ ID NOs: 11465-17134, SEQ ID NOs: 33003-33072, SEQ ID NOs: 33073-35394 and SEQ ID NOs: 36127-36146.

For the mAb-scFv format backbone 1 (optionally including M428L/N434S) from FIG. 38, specific ABDs that bind human CTLA-4 include, but are not limited to, [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67 and [CTLA-4]_H3_L0.74, as well as those listed in SEQ ID NOs: 21-2918, SEQ ID NOs: 2919-6208, SEQ ID NOs: 36739-36818 and SEQ ID NOs: 35395-35416.

For the mAb-scFv format backbone 1 (optionally including M428L/N434S) from FIG. 38, specific ABDs that bind human LAG-3 include, but are not limited to, 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1, as well as those listed in SEQ ID NOs: 17135-20764, SEQ ID NOs: 36819-36962, SEQ ID NOs: 35417-35606, SEQ ID NOs: 25194-32793 and SEQ ID NOs: 32794-33002.

For the mAb-scFv format backbone 1 (optionally including M428L/N434S) from FIG. 38, specific ABDs that bind human BTLA include, but are not limited to, 9C6_H0L0; 9C6_H1.1_L1; and 9C6_H1.11_L1, as well as those listed in SEQ ID NOs: 20885-21503 and SEQ ID NOs: 36707-36738.

For the mAb-scFv format backbone 1 (optionally including M428L/N434S) from FIG. 38, specific ABDs that bind human TIM-3 include, but are not limited to, 1D10_H0L0; 1D12_H0L0; 3H3_H1_L2.1; 6C8_H0L0; 6D9_H0_1D12_L0; 7A9_H0L0; 7B11_H0L0; 7B11var_H0L0 and 7C2_H0L0, as well as those listed in SEQ ID NOs: 20765-20884, SEQ ID NOs: 37587-37698 and SEQ ID NOs: 36347-36706.

I. Dual scFv Formats

The present invention also provides dual scFv formats as are known in the art and shown in FIG. 1B. In this embodiment, the heterodimeric bispecific antibody is made up of two scFv-Fc monomers (both in either (vh-scFv linker-vl-[optional domain linker]-CH2-CH3) format or (vl-scFv linker-vh-[optional domain linker]-CH2-CH3) format, or with one monomer in one orientation and the other in the other orientation.

In this case, all ABDs are in the scFv format, with any combination of PD-1 and CTLA-4, PD-1 and TIM-3, PD-1 and LAG-3, PD-1 and TIGIT, PD-1 and BTLA, CTLA-4 and TIM-3, CTLA-4 and LAG-3, CTLA-4 and TIGIT, CTLA-4 and BTLA, TIM-3 and LAG-3, TIM-3 and TIGIT, TIM-3 and BTLA, LAG-3 and TIGIT, LAG-3 and BTLA and TIGIT and BTLA being useful. The ABD sequences for these combinations can be as disclosed in the sequence listing or as shown in FIGS. 9 to 13, and in any combination as shown in FIG. 39 and FIG. 40.

In addition, the Fc domains of the dual scFv format comprise skew variants (e.g. a set of amino acid substitutions as shown in FIG. 3 and FIG. 8, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C), optionally ablation variants (including those shown in FIG. 5), optionally charged scFv linkers (including those shown in FIG. 7) and the heavy chain comprises pI variants (including those shown in FIG. 4).

In some embodiments, the dual scFv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) CTLA-4×PD-1, LAG-3×PD-1, BTLA×PD-1, and LAG-3×CTLA-4.

In some embodiments, the dual scFv format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) CTLA-4×PD-1, LAG-3×PD-1, BTLA×PD-1, and LAG-3×CTLA-4.

J. Non-Heterodimeric Bispecific Antibodies

As will be appreciated by those in the art, the Fv sequences outlined herein can also be used in both monospecific antibodies (e.g. "traditional monoclonal antibodies") or non-heterodimeric bispecific formats.

Suitable non-heterodimeric bispecific formats are known in the art, and include a number of different formats as generally depicted in Spiess et al., Molecular Immunology (67):95-106 (2015) and Kontermann, mAbs 4:2, 182-197 (2012), both of which are expressly incorporated by reference and in particular for the figures, legends and citations to the formats therein.

K. Monospecific, Monoclonal Antibodies

As will be appreciated by those in the art, the novel Fv sequences outlined herein can also be used in both monospecific antibodies (e.g. "traditional monoclonal antibodies") or non-heterodimeric bispecific formats. Accordingly, the present invention provides monoclonal (monospecific) antibodies comprising the 6 CDRs and/or the vh and vl sequences from the figures, generally with IgG1, IgG2, IgG3 or IgG4 constant regions, with IgG1, IgG2 and IgG4 (including IgG4 constant regions comprising a S228P amino acid substitution) finding particular use in some embodiments. That is, any sequence herein with a "H_L" designation can be linked to the constant region of a human IgG1 antibody.

VI. ANTIGEN BINDING DOMAINS TO TARGET ANTIGENS

The bispecific antibodies of the invention have two different antigen binding domains (ABDs) that bind to two different target checkpoint antigens ("target pairs"), in either bivalent, bispecific formats or trivalent, bispecific formats as generally shown in FIG. 1. Suitable target checkpoint antigens include human (and sometimes cyno) PD-1, CTLA-4, TIM-3, LAG-3, TIGIT and BTLA, the sequences of which are shown in FIG. 2. Accordingly, suitable bispecific antibodies bind PD-1 and CTLA-4, PD-1 and TIM-3, PD-1 and LAG-3, PD-1 and TIGIT, PD-1 and BTLA, CTLA-4 and TIM-3, CTLA-4 and LAG-3, CTLA-4 and TIGIT, CTLA-4 and BTLA, TIM-3 and LAG-3, TIM-3 and TIGIT, TIM-3 and BTLA, LAG-3 and TIGIT, LAG-3 and BTLA and TIGIT and BTLA. Note that generally these bispecific antibodies are named "anti-PD-1×anti-CTLA-4", or generally simplistically or for ease (and thus interchangeably) as "PD-1×CTLA-4", etc. for each pair. Note that unless specified herein, the order of the antigen list in the name does not confer structure; that is a PD-1×CTLA-4 bottle opener antibody can have the scFv bind to PD-1 or CTLA-4, although in some cases, the order specifies structure as indicated.

As is more fully outlined herein, these combinations of ABDs can be in a variety of formats, as outlined below, generally in combinations where one ABD is in a Fab format and the other is in an scFv format. As discussed herein and shown in FIG. 1, some formats use a single Fab and a single scFv (FIGS. 1A, C and D), and some formats use two Fabs and a single scFv (FIGS. 1E, F, G, H and I).

A. Antigen Binding Domains

As discussed herein, the bispecific checkpoint heterodimeric antibodies of the invention include two antigen binding domains (ABDs), each of which bind to a different checkpoint protein. As outlined herein, these heterodimeric antibodies can be bispecific and bivalent (each antigen is bound by a single ABD, for example, in the format depicted in FIG. 1A), or bispecific and trivalent (one antigen is bound by a single ABD and the other is bound by two ABDs, for example as depicted in FIG. 1F).

In addition, in general, one of the ABDs comprises a scFv as outlined herein, in an orientation from N- to C-terminus of vh-scFv linker-vl or vl-scFv linker-vh. One or both of the other ABDs, according to the format, generally is a Fab, comprising a vh domain on one protein chain (generally as a component of a heavy chain) and a vl on another protein chain (generally as a component of a light chain).

The invention provides a number of ABDs that bind to a number of different checkpoint proteins, as outlined below. As will be appreciated by those in the art, any set of 6 CDRs or vh and vl domains can be in the scFv format or in the Fab format, which is then added to the heavy and light constant domains, where the heavy constant domains comprise variants (including within the CH1 domain as well as the Fc domain). The scFv sequences contained in the sequence listing utilize a particular charged linker, but as outlined herein, uncharged or other charged linkers can be used, including those depicted in FIG. 7.

In addition, as discussed above, the numbering used in the Sequence Listing for the identification of the CDRs is Kabat, however, different numbering can be used, which will change the amino acid sequences of the CDRs as shown in Table 1.

For all of the variable heavy and light domains listed herein, further variants can be made. As outlined herein, in some embodiments the set of 6 CDRs can have from 0, 1, 2, 3, 4 or 5 amino acid modifications (with amino acid substitutions finding particular use), as well as changes in the framework regions of the variable heavy and light domains, as long as the frameworks (excluding the CDRs) retain at least about 80, 85 or 90% identity to a human germline sequence selected from those listed in FIG. 1 of U.S. Pat. No. 7,657,380, which Figure and Legend is incorporated by reference in its entirety herein. Thus, for example, the identical CDRs as described herein can be combined with different framework sequences from human germline sequences, as long as the framework regions retain at least 80, 85 or 90% identity to a human germline sequence selected from those listed in FIG. 1 of U.S. Pat. No. 7,657,380. Alternatively, the CDRs can have amino acid modifications (e.g. from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g. there may be one change in vlCDR1, two in vhCDR2, none in vhCDR3, etc.)), as well as having framework region changes, as long as the framework regions retain at least 80, 85 or 90% identity to a human germline sequence selected from those listed in FIG. 1 of U.S. Pat. No. 7,657,380.

B. PD-1 Antigen Binding Domains

In some embodiments, one of the ABDs binds PD-1. Suitable sets of 6 CDRs and/or vh and vl domains, as well as scFv sequences, are depicted in SEQ ID NOs: 6209-11464, SEQ ID NOs: 11465-17134, SEQ ID NOs: 33003-33072, SEQ ID NOs: 33073-35394 and SEQ ID NOs: 36127-36146. ABD sequences of particular interest in some embodiments are shown in FIG. 9 and include those sequences in the sequence listing with the identifiers 1G6_H1.279_L1.194; 1G6_H1.280_L1.224; 1G6_L1.194_H1.279; 1G6_L1.210_H1.288; and 2E9_H1L1.

As will be appreciated by those in the art, suitable anti-PD-1 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of SEQ ID NOs: 6209-11464, SEQ ID NOs: 11465-17134, SEQ ID NOs: 33003-33072, SEQ ID NOs: 33073-35394 and SEQ ID NOs: 36127-36146. Suitable ABDs can also include the entire vh and vl sequences as depicted in these sequences and Figures, used as scFvs or as Fabs. In many of the embodiments herein that contain an Fv to PD-1, it is the scFv monomer that binds PD-1. As discussed herein, the other of the target pair when PD-1 is one of the antigens is selected from CTLA-4 (suitable sequences are depicted in SEQ ID NOs: 21-2918, SEQ ID NOs: 2919-6208, SEQ ID NOs: 36739-36818 and SEQ ID NOs: 35395-35416 (which can be scFv sequences, CDR sequence sets or vh and vl sequences)), TIM-3 (suitable sequences are depicted in SEQ ID NOs: 20765-20884, SEQ ID NOs: 37587-37698 and SEQ ID NOs: 36347-36706 (which can be scFv sequences, CDR sequence sets or vh and vl sequences)), LAG-3 (suitable sequences are depicted in SEQ ID NOs: 17135-20764, SEQ ID NOs: 36819-36962, SEQ ID NOs: 35417-35606, SEQ ID NOs: 25194-32793 and SEQ ID NOs: 32794-33002 (which can be scFv sequences, CDR sequence sets or vh and vl sequences)), BTLA (suitable sequences are depicted in SEQ ID NOs: 20885-21503 and SEQ ID NOs: 36707-36738 (which can be scFv sequences, CDR sequence sets or vh and vl sequences)), and TIGIT (suitable sequences are depicted in SEQ ID NOs: 21504-21523 and SEQ ID NOs: 37435-37586 (which can be scFv sequences, CDR sequence sets or vh and vl sequences)).

Particularly useful ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1.

In addition to the parental CDR sets disclosed in the sequence listing that form an ABD to PD-1, the invention provides variant CDR sets. In one embodiment, a set of 6 CDRs can have 1, 2, 3, 4 or 5 amino acid changes from the parental CDRs, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

In addition to the parental variable heavy and variable light domains disclosed herein that form an ABD to PD-1, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured at least one of a BIACORE®, surface plasmon resonance (SPR) and/or BLI (biolayer interferometry, e.g. OCTET® assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

Specific preferred embodiments include the 1G6_L1.194_H1.279 anti-PD-1 Fv, in a scFv format, included within any of the bottle opener format backbones of FIG. 37.

Specific preferred embodiments include the 1G6_L1.194_H1.279 anti-PD-1 Fv, in a scFv format, included within any of the mAb-scFv format backbones of FIG. 38.

C. CTLA-4 Antigen Binding Domains

In some embodiments, one of the ABDs binds CTLA-4. Suitable sets of 6 CDRs and/or vh and vl domains, as well as scFv sequences, are depicted in SEQ ID NOs: 21-2918, SEQ ID NOs: 2919-6208, SEQ ID NOs: 36739-36818 and SEQ ID NOs: 35395-35416. ABD sequences of particular interest in some embodiments are shown in FIG. 10 and also include those sequences in the sequence listing with the identifiers [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; 0[CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118;

[CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67; and [CTLA-4]_H3_L0.74.

As will be appreciated by those in the art, suitable anti-CTLA-4 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of SEQ ID NOs: 21-2918, SEQ ID NOs: 2919-6208, SEQ ID NOs: 36739-36818 and SEQ ID NOs: 35395-35416. Suitable ABDs can also include the entire vh and vl sequences as depicted in these sequences and Figures, used as scFvs or as Fabs. In many of the embodiments herein that contain an Fv to CTLA-4, it is the scFv monomer that binds CTLA-4. As discussed herein, the other of the target pair when CTLA-4 is one of the antigens is selected from PD-1 (suitable sequences are depicted in SEQ ID NOs: 6209-11464, SEQ ID NOs: 11465-17134, SEQ ID NOs: 33003-33072, SEQ ID NOs: 33073-35394 and SEQ ID NOs: 36127-36146 (which can be scFv sequences, CDR sequence sets or vh and vl sequences)), TIM-3 (suitable sequences are depicted in SEQ ID NOs: 20765-20884, SEQ ID NOs: 37587-37698 and SEQ ID NOs: 36347-36706 (which can be scFv sequences, CDR sequence sets or vh and vl sequences)), LAG-3 (suitable sequences are depicted in SEQ ID NOs: 17135-20764, SEQ ID NOs: 36819-36962, SEQ ID NOs: 35417-35606, SEQ ID NOs: 25194-32793 and SEQ ID NOs: 32794-33002 (which can be scFv sequences, CDR sequence sets or vh and vl sequences)), BTLA (suitable sequences are depicted in SEQ ID NOs: 20885-21503 and SEQ ID NOs: 36707-36738 (which can be scFv sequences, CDR sequence sets or vh and vl sequences)), and TIGIT (suitable sequences are depicted in SEQ ID NOs: 21504-21523 and SEQ ID NOs: 37435-37586 (which can be scFv sequences, CDR sequence sets or vh and vl sequences)).

In addition to the parental CDR sets disclosed in the sequence listing that form an ABD to CTLA-4, the invention provides variant CDR sets. In one embodiment, a set of 6 CDRs can have 1, 2, 3, 4 or 5 amino acid changes from the parental CDRs, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

In addition to the parental variable heavy and variable light domains disclosed herein that form an ABD to CTLA-4, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

Specific preferred embodiments include the [CTLA-4]_H3_L0.22 anti-CTLA-4 Fv, in a Fab format, included within any of the bottle opener format backbones of FIG. 37.

Specific preferred embodiments include the [CTLA-4]_H3_L0.22 anti-CTLA-4 Fv, in a scFv format, included within any of the bottle opener format backbones of FIG. 37.

Specific preferred embodiments include the [CTLA-4]_H3_L0.22 anti-CTLA-4 Fv, in a scFv format, included within any of the mAb-scFv format backbones of FIG. 38.

Specific preferred embodiments include the [CTLA-4]_H3_L0.22 anti-CTLA-4 Fv, in a Fab format, included within any of the mAb-scFv format backbones of FIG. 38.

D. TIM-3 Antigen Binding Domains

In some embodiments, one of the ABDs binds TIM-3. Suitable sets of 6 CDRs and/or vh and vl domains, as well as scFv sequences, are depicted SEQ ID NOs: 20765-20884, SEQ ID NOs: 37587-37698 and SEQ ID NOs: 36347-36706. ABD sequences of particular interest in some embodiments include those sequences in the sequence listing with the identifiers 1D10_H0L0; 1D12_H0L0; 3H3_H1_L2.1; 6C8_H0L0; 6D9_H0_1D12_L0; 7A9_H0L0; 7B11_H0L0; 7B11var_H0L0; and 7C2_H0L0.

As will be appreciated by those in the art, suitable anti-TIM-3 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of SEQ ID NOs: 20765-20884, SEQ ID NOs: 37587-37698 and SEQ ID NOs: 36347-36706. Suitable ABDs can also include the entire vh and vl sequences as depicted in these sequences and Figures, used as scFvs or as Fabs. In many of the embodiments herein that contain an Fv to TIM-3, it is the Fab monomer that binds TIM-3. As discussed herein, the other of the target pair when TIM-3 is one of the antigens is selected from PD-1 (suitable sequences are depicted in SEQ ID NOs: 6209-11464, SEQ ID NOs: 11465-17134, SEQ ID NOs: 33003-33072, SEQ ID NOs: 33073-35394 and SEQ ID NOs: 36127-36146 (which can be scFv sequences, CDR sequence sets or vh and vl sequences)), CTLA-4 (suitable sequences are depicted in SEQ ID NOs: 21-2918, SEQ ID NOs: 2919-6208, SEQ ID NOs: 36739-36818 and SEQ ID NOs: 35395-35416 (which can be scFv sequences, CDR sequence sets or vh and vl sequences)), LAG-3 (suitable sequences are depicted in SEQ ID NOs: 17135-20764, SEQ ID NOs: 36819-36962, SEQ ID NOs: 35417-35606, SEQ ID NOs: 25194-32793 and SEQ ID NOs: 32794-33002 (which can be scFv sequences, CDR sequence sets or vh and vl sequences)), BTLA (suitable sequences are depicted in SEQ ID NOs: 20885-21503 and SEQ ID NOs: 36707-36738 (which can be scFv sequences, CDR sequence sets or vh and vl sequences)), and TIGIT (suitable sequences are depicted in SEQ ID NOs: 21504-21523 and SEQ ID NOs: 37435-37586 (which can be scFv sequences, CDR sequence sets or vh and vl sequences)).

In addition to the parental CDR sets disclosed in the sequence listing that form an ABD to TIM-3, the invention provides variant CDR sets. In one embodiment, a set of 6

CDRs can have 1, 2, 3, 4 or 5 amino acid changes from the parental CDRs, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

In addition to the parental variable heavy and variable light domains disclosed herein that form an ABD to TIM-3, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured at least one of a BIACORE®, surface plasmon resonance (SPR) and/or BLI (biolayer interferometry, e.g. OCTET® assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

LAG-3 Antigen Binding Domains

In some embodiments, one of the ABDs binds LAG-3. Suitable sets of 6 CDRs and/or vh and vl domains, as well as scFv sequences, are depicted SEQ ID NOs: 17135-20764, SEQ ID NOs: 36819-36962, SEQ ID NOs: 35417-35606, SEQ ID NOs: 25194-32793 and SEQ ID NOs: 32794-33002. ABD sequences of particular interest in some embodiments are shown in FIG. 11 and also include those sequences in the sequence listing with the identifiers 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1.

As will be appreciated by those in the art, suitable anti-LAG-3 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of SEQ ID NOs: 17135-20764, SEQ ID NOs: 36819-36962, SEQ ID NOs: 35417-35606, SEQ ID NOs: 25194-32793 and SEQ ID NOs: 32794-33002. Suitable ABDs can also include the entire vh and vl sequences as depicted in these sequences and Figures, used as scFvs or as Fabs. In many of the embodiments herein that contain an Fv to LAG-3, it is the Fab monomer that binds LAG-3. As discussed herein, the other of the target pair when LAG-3 is one of the antigens is selected from PD-1 (suitable sequences are depicted in SEQ ID NOs: 6209-11464, SEQ ID NOs: 11465-17134, SEQ ID NOs: 33003-33072, SEQ ID NOs: 33073-35394 and SEQ ID NOs: 36127-36146 (which can be scFv sequences, CDR sequence sets or vh and vl sequences)), CTLA-4 (suitable sequences are depicted in SEQ ID NOs: 21-2918, SEQ ID NOs: 2919-6208, SEQ ID NOs: 36739-36818 and SEQ ID NOs: 35395-35416 (which can be scFv sequences, CDR sequence sets or vh and vl sequences)), TIM-3 (suitable sequences are depicted in SEQ ID NOs: 20765-20884, SEQ ID NOs: 37587-37698 and SEQ ID NOs: 36347-36706 (which can be scFv sequences, CDR sequence sets or vh and vl sequences)), BTLA (suitable sequences are depicted in SEQ ID NOs: 20885-21503 and SEQ ID NOs: 36707-36738 (which can be scFv sequences, CDR sequence sets or vh and vl sequences)), and TIGIT (suitable sequences are depicted in SEQ ID NOs: 21504-21523 and SEQ ID NOs: 37435-37586 (which can be scFv sequences, CDR sequence sets or vh and vl sequences).

In addition to the parental CDR sets disclosed in the sequence listing that form an ABD to LAG-3, the invention provides variant CDR sets. In one embodiment, a set of 6 CDRs can have 1, 2, 3, 4 or 5 amino acid changes from the parental CDRs, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

In addition to the parental variable heavy and variable light domains disclosed herein that form an ABD to LAG-3, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

Specific preferred embodiments include the 7G8_H3.30_L1.34 anti-LAG-3 Fv, in a Fab format, included within any of the bottle opener format backbones of FIG. 37.

Specific preferred embodiments include the 7G8_H3.30_L1.34 anti-LAG-3 Fv, in a scFv format, included within any of the bottle opener format backbones of FIG. 37.

E. BTLA Antigen Binding Domains

In some embodiments, one of the ABDs binds BTLA. Suitable sets of 6 CDRs and/or vh and vl domains, as well as scFv sequences, are depicted in SEQ ID NOs: 20885-21503 and SEQ ID NOs: 36707-36738. ABD sequences of particular interest in some embodiments are shown in FIG. 12 and also include those sequences in the sequence listing with the identifiers 9C6_H0L0; 9C6_H1.1_L1; and 9C6_H1.11_L1.

As will be appreciated by those in the art, suitable anti-BTLA ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences SEQ ID NOs: 20885-21503 and SEQ ID NOs: 36707-36738. Suitable ABDs can also include the entire vh and vl sequences as depicted in these sequences and Figures, used as scFvs or as Fabs. In many of the embodiments herein that contain an Fv to BTLA, it is the Fab monomer that binds BTLA. As discussed herein, the other of the target pair when LAG-3 is one of the antigens is selected from PD-1 (suitable sequences are depicted in SEQ ID NOs: 6209-11464, SEQ ID NOs: 11465-17134, SEQ ID NOs: 33003-33072, SEQ ID NOs: 33073-35394 and SEQ ID NOs: 36127-36146 (which can be scFv sequences, CDR sequence sets or vh and vl sequences)), CTLA-4 (suitable sequences are depicted in SEQ ID NOs: 21-2918, SEQ ID NOs: 2919-6208, SEQ ID NOs: 36739-36818 and SEQ ID NOs: 35395-35416 (which can be scFv sequences, CDR sequence sets or vh and vl sequences)), TIM-3 (suitable sequences are depicted in SEQ ID NOs: 20765-20884, SEQ ID NOs: 37587-37698 and SEQ ID NOs: 36347-36706 (which can be scFv sequences, CDR sequence sets or vh and vl sequences)), LAG-3 (suitable sequences are depicted in SEQ ID NOs: 17135-20764, SEQ ID NOs: 36819-36962, SEQ ID NOs: 35417-35606, SEQ ID NOs: 25194-32793 and SEQ ID NOs: 32794-33002 (which can be scFv sequences, CDR sequence sets or vh and vl sequences)), and TIGIT (suitable sequences are depicted in SEQ ID NOs: 21504-21523 and SEQ ID NOs: 37435-37586 (which can be scFv sequences, CDR sequence sets or vh and vl sequences)).

In addition to the parental CDR sets disclosed in the sequence listing that form an ABD to BTLA, the invention provides variant CDR sets. In one embodiment, a set of 6 CDRs can have 1, 2, 3, 4 or 5 amino acid changes from the parental CDRs, as long as the ABD is still able to bind to the target antigen, as measured at least one of a BIACORE®, surface plasmon resonance (SPR) and/or BLI (biolayer interferometry, e.g. OCTET® assay) assay, with the latter finding particular use in many embodiments.

In addition to the parental variable heavy and variable light domains disclosed herein that form an ABD to BTLA, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a BIACORE®, surface plasmon resonance (SPR) and/or BLI (biolayer interferometry, e.g. OCTET® assay) assay, with the latter finding particular use in many embodiments.

Specific preferred embodiments include the 9C6_H1.1_L1 anti-LAG-3 Fv, in a Fab format, included within any of the bottle opener format backbones of FIG. 37.

Specific preferred embodiments include the 7G8_H3.30_L1.34 anti-LAG-3 Fv, in a scFv format, included within any of the bottle opener format backbones of FIG. 37.

F. TIGIT Antigen Binding Domains

In some embodiments, one of the ABDs binds TIGIT. Suitable sets of 6 CDRs and/or vh and vl domains, as well as scFv sequences, are depicted in SEQ ID NOs: 21504-21523 and SEQ ID NOs: 37435-37586.

As will be appreciated by those in the art, suitable anti-TIGIT ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of SEQ ID NOs: 21504-21523 and SEQ ID NOs: 37435-37586. Suitable ABDs can also include the entire vh and vl sequences as depicted in these sequences and Figures, used as scFvs or as Fabs. In many of the embodiments herein that contain an Fv to TIGIT, it is the Fab monomer that binds TIGIT. As discussed herein, the other of the target pair when LAG-3 is one of the antigens is selected from PD-1 (suitable sequences are depicted in SEQ ID NOs: 6209-11464, SEQ ID NOs: 11465-17134, SEQ ID NOs: 33003-33072, SEQ ID NOs: 33073-35394 and SEQ ID NOs: 36127-36146 (which can be scFv sequences, CDR sequence sets or vh and vl sequences)), CTLA-4 (suitable sequences are depicted in SEQ ID NOs: 21-2918, SEQ ID NOs: 2919-6208, SEQ ID NOs: 36739-36818 and SEQ ID NOs: 35395-35416 (which can be scFv sequences, CDR sequence sets or vh and vl sequences)), TIM-3 (suitable sequences are depicted in SEQ ID NOs: 20765-20884, SEQ ID NOs: 37587-37698 and SEQ ID NOs: 36347-36706 (which can be scFv sequences, CDR sequence sets or vh and vl sequences)), LAG-3 (suitable sequences are depicted in SEQ ID NOs: 17135-20764, SEQ ID NOs: 36819-36962, SEQ ID NOs: 35417-35606, SEQ ID NOs: 25194-32793 and SEQ ID NOs: 32794-33002 (which can be scFv sequences, CDR sequence sets or vh and vl sequences)), and BTLA (suitable sequences are depicted in SEQ ID NOs: 20885-21503 and SEQ ID NOs: 36707-36738 (which can be scFv sequences, CDR sequence sets or vh and vl sequences)).

G. Specific Bispecific Embodiments

The invention provides a number of particular bispecific antibodies as outlined below.

1. LAG-3×CTLA-4

In some embodiments, the invention provides bispecific heterodimeric antibodies comprising a first ABD that binds human LAG-3 and a second ABD that binds human CTLA-4, and can be in any format shown in FIG. 1. Most of the disclosure refers to a bottle opener format with the Fab being the LAG-3 side and the CLTA-4 side being the scFv side, but this can be reversed for all of the embodiments herein.

In one embodiment, the LAG-3×CTLA-4 bispecific antibody is in the bottle opener format of FIG. 1A, wherein the CTLA-4 ABD is the scFv. In another embodiment, the LAG-3×CTLA-4 bispecific antibody is in the central-scFv format of FIG. 1F, with the LAG-3 ABD being the Fab components. In another embodiment, the LAG-3×CTLA-4 bispecific antibody is in the central-scFv format of FIG. 1F, with the CTLA-4 ABD being the scFv.

The LAG-3×CTLA-4 bispecific antibodies (in either the bottle opener format or the central-scFv format) generally include skew variants, pI variants and ablation variants as outlined herein. That is, in either format, the Fc domains of the two monomers can comprise skew variants (e.g. a set of amino acid substitutions as shown in FIG. 3 and FIG. 8), optionally ablation variants (including those shown in FIG. 5), and the monomer comprising the Fab side (e.g. the heavy chain constant domain) comprises pI variants (including those shown in FIG. 4).

In some embodiments, the LAG-3×CTLA-4 bispecific antibody comprises Fc domains with skew variants, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C.

In some embodiments, the LAG-3×CTLA-4 antibody includes skew variants, pI variants, and ablation variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second checkpoint inhibitor as outlined herein; and c) a light chain. A specific example of this embodiment utilizes the LAG-3 Fab 7G8_H3.30_L1.34 and the CTLA-4 scFv [CTLA-4]_H3.23_L0.129, although any of the CTLA-4 or LAG-3 Fvs in the sequence listing can be paired in any combination and used.

In some embodiments, the LAG-3×CTLA-4 antibody includes skew variants, pI variants, ablation variants and FcRn variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, the FcRn variants M428L/N434S and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to a second checkpoint inhibitor as outlined herein; and c) a light chain. A specific example of this embodiment utilizes the LAG-3 Fab 7G8_H3.30_L1.34 and the CTLA-4 scFv [CTLA-4]_H3.23_L0.129, although any of the CTLA-4 or LAG-3 Fvs in the sequence listing can be paired in any combination and used.

Additional embodiments include any of the backbones from FIG. 37 with the LAG-3 Fab 7G8_H3.30_L1.34 and the CTLA-4 scFv [CTLA-4]_H3.23_L0.129.

Additional embodiments include any of the backbones from FIG. 38 with the LAG-3 Fab 7G8_H3.30_L1.34 and the CTLA-4 scFv [CTLA-4]_H3.23_L0.129.

In some embodiments, for LAG-3×CLTA-4 bispecific antibodies, the Fv for the LAG-3 Fab side is selected from those sequences in the sequence listing with the identifiers 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1. The Fv for the CTLA-4 scFv side is selected from those sequences in the sequence listing with the identifiers [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; 0[CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67; and [CTLA-4]_H3_L0.74.

In some embodiments, the LAG-3×CTLA-4 bispecific antibody is selected from those constructs listed in SEQ ID NOs: 35607-35866 and SEQ ID NOs: 21524-22620.

In some embodiments, the LAG-3×CTLA-4 bispecific antibody is selected from XENP20206, XENP21582, XENP21584, XENP21588, XENP22123, XENP22124, XENP22125, XENP22604, XENP22672, XENP22847, XENP22847, XENP22841 and XENP22849.

2. BTLA×PD-1

In some embodiments, the invention provides bispecific heterodimeric antibodies comprising a first ABD that binds human BTLA and a second ABD that binds human PD-1, and can be in any format shown in FIG. 1. Most of the disclosure refers to a bottle opener format with the Fab being the BTLA side and the PD-1 side being the scFv side, but this can be reversed for all of the embodiments herein.

In one embodiment, the BTLA×PD-1 bispecific antibody is in the bottle opener format of FIG. 1A, wherein the PD-1 ABD is the scFv. In another embodiment, the BTLA×PD-1 bispecific antibody is in the central-scFv format of FIG. 1F, with the BTLA ABD being the Fab components. In another embodiment, the BTLA×PD-1 bispecific antibody is in the central-scFv format of FIG. 1F, with the PD-1 ABD being the scFv.

The BTLA×PD-1 bispecific antibodies (in either the bottle opener format or the central-scFv format) generally include skew variants, pI variants and ablation variants as outlined herein. That is, in either format, the Fc domains of the two monomers can comprise skew variants (e.g. a set of amino acid substitutions as shown in FIG. 3 and FIG. 8), optionally ablation variants (including those shown in FIG. 5), and the monomer comprising the Fab side (e.g. the heavy chain constant domain) comprises pI variants (including those shown in FIG. 4).

In some embodiments, the BTLA×PD-1 bispecific antibody comprises Fc domains with skew variants, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C.

In some embodiments, the BTLA×PD-1 antibody includes skew variants, pI variants, and ablation variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second checkpoint inhibitor as outlined herein; and c) a light chain. A specific example of this embodiment utilizes the BTLA Fab 9C6_H1.1_L1 and the PD-1 scFv 1G6_L1.194_H1.279 although any of the BTLA or PD-1 Fvs in the sequence listing can be paired in any combination and used.

In some embodiments, the BTLAxPD-1 antibody includes skew variants, pI variants, ablation variants and FcRn variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, the FcRn variants M428L/N434S and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to a second checkpoint inhibitor as outlined herein; and c) a light chain. A specific example of this embodiment utilizes the BTLA Fab 9C6_H1.1_L1 and the PD-1 scFv 1G6_L1.194_H1.279 although any of the BTLA or PD-1 Fvs in the sequence listing can be paired in any combination and used.

Additional embodiments include any of the backbones from FIG. 37 with the BTLA Fab 9C6_H1.1_L1 and the PD-1 scFv 1G6_L1.194_H1.279.

Additional embodiments include any of the backbones from FIG. 38 with the BTLA Fab 9C6_H1.1_L1 and the PD-1 scFv 1G6_L1.194_H1.279.

In some embodiments, for BTLAxPD-1 bispecific antibodies, the Fv for the BTLA Fab side is selected from those sequences in the sequence listing with the identifiers 9C6_H0L0, 9C6_H1.1_L1, 9C6_H1.11_L1. The Fv for the PD-1 scFv side is selected from those sequences in the sequence listing with the identifiers 1G6_H1.279_L1.194; 1G6_H1.280_L1.224; 1G6_L1.194_H1.279; 1G6_L1.210_H1.288; and 2E9_H1L1.

In some embodiments, the BTLAxPD-1 bispecific antibody is selected from constructs include those listed as SEQ ID NOs: 22724-23315 and SEQ ID NOs: 36147-36166.

In some embodiments, the BTLAxPD-1 bispecific antibody is selected from XENP20895, XENP21220, XENP21221 and XENP22858.

3. CTLA-4xPD-1

In some embodiments, the invention provides bispecific heterodimeric antibodies comprising a first ABD that binds human CTLA-4 and a second ABD that binds human PD-1, and can be in any format shown in FIG. 1. Most of the disclosure refers to a bottle opener format with the Fab being the CTLA-4 side and the PD-1 side being the scFv side, but this can be reversed for all of the embodiments herein.

In one embodiment, the CTLA-4xPD-1 bispecific antibody is in the bottle opener format of FIG. 1A, wherein the PD-1 ABD is the scFv. In another embodiment, the CTLA-4xPD-1 bispecific antibody is in the central-scFv format of FIG. 1F, with the CTLA-4 ABD being the Fab components. In another embodiment, the CTLA-4xPD-1 bispecific antibody is in the central-scFv format of FIG. 1F, with the PD-1 ABD being the scFv.

The CTLA-4xPD-1 bispecific antibodies (in either the bottle opener format or the central-scFv format) generally include skew variants, pI variants and ablation variants as outlined herein. That is, in either format, the Fc domains of the two monomers can comprise skew variants (e.g. a set of amino acid substitutions as shown in FIG. 3 and FIG. 8), optionally ablation variants (including those shown in FIG. 5), and the monomer comprising the Fab side (e.g. the heavy chain constant domain) comprises pI variants (including those shown in FIG. 4).

In some embodiments, the CTLA-4xPD-1 bispecific antibody comprises Fc domains with skew variants, with particularly useful skew variants being selected from the group consisting of S364K/E357Q:L368D/K370S; L368D/K370S: S364K; L368E/K370S:S364K; T411T/E360E/Q362E: D401K; L368D/K370S:S364K/E357L, K370S:S364K/ E357Q, T366S/L368A/Y407V:T366W and T366S/L368A/ Y407V/Y349C: T366W/S354C.

In some embodiments, the CTLA-4xPD-1 antibody includes skew variants, pI variants, and ablation variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second checkpoint inhibitor as outlined herein; and c) a light chain. A specific example of this embodiment utilizes the CTLA-4 Fab [CTLA-4]_H3_L0.22 and the PD-1 scFv 1G6_L1.194_H1.279 although any of the CTLA-4 or PD-1 Fvs in the sequence listing can be paired in any combination and used.

In some embodiments, the CTLA-4xPD-1 antibody includes skew variants, pI variants, ablation variants and FcRn variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, the FcRn variants M428L/N434S and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to a second checkpoint inhibitor as outlined herein; and c) a light chain. A specific example of this embodiment utilizes the CTLA-4 Fab [CTLA-4]_H3_L0.22 and the PD-1 scFv 1G6_L1.194_H1.279 although any of the CTLA-4 or PD-1 Fvs in the sequence listing can be paired in any combination and used.

Additional embodiments include any of the backbones from FIG. 37 with the CTLA-4 Fab [CTLA-4]_H3_L0.22 and the PD-1 scFv 1G6_L1.194_H1.279.

Additional embodiments include any of the backbones from FIG. 38 with the CTLA-4 Fab [CTLA-4]_H3_L0.22 and the PD-1 scFv 1G6_L1.194_H1.279.

In some embodiments, for CTLA-4xPD-1 bispecific antibodies, the Fv for the CTLA-4 Fab side is selected from those sequences in the sequence listing with the identifiers with the identifiers [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; 0[CTLA-4]_H0.40_L0; [CTLA-4]_H0.70_L0; [CTLA-4]_H0_L0.22; [CTLA-4]_H2_L0;

[CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67; and [CTLA-4]_H3_L0.74. The Fv for the PD-1 scFv side is selected from those sequences in the sequence listing with the identifiers identifiers 1G6_H1.279_L1.194; 1G6_H1.280_L1.224; 1G6_L1.194_H1.279; 1G6_L1.210_H1.288; and 2E9_H1L1.

In some embodiments, the CTLA-4×PD-1 bispecific antibody is selected from those listed as SEQ ID NOs: 36167-36346 and SEQ ID NOs: 23316-23735.

In some embodiments, the CTLA-4×PD-1 bispecific antibody is selected from XENP19738, XENP19739, XENP19741, XENP20053, XENP20066, XENP20130, XENP20146, XENP20717 and XENP22836.

4. LAG-3×PD-1

In some embodiments, the invention provides bispecific heterodimeric antibodies comprising a first ABD that binds human LAG-3 and a second ABD that binds human PD-1, and can be in any format shown in FIG. 1. Most of the disclosure refers to a bottle opener format with the Fab being the LAG-3 side and the PD-1 side being the scFv side, but this can be reversed for all of the embodiments herein.

In one embodiment, the LAG-3×PD-1 bispecific antibody is in the bottle opener format of FIG. 1A, wherein the PD-1 ABD is the scFv. In another embodiment, the LAG-3×PD-1 bispecific antibody is in the central-scFv format of FIG. 1F, with the LAG-3 ABD being the Fab components. In another embodiment, the LAG-3×PD-1 bispecific antibody is in the central-scFv format of FIG. 1F, with the PD-1 ABD being the scFv.

The LAG-3×PD-1 bispecific antibodies (in either the bottle opener format or the central-scFv format) generally include skew variants, pI variants and ablation variants as outlined herein. That is, in either format, the Fc domains of the two monomers can comprise skew variants (e.g. a set of amino acid substitutions as shown in FIG. 3 and FIG. 8), optionally ablation variants (including those shown in FIG. 5), and the monomer comprising the Fab side (e.g. the heavy chain constant domain) comprises pI variants (including those shown in FIG. 4).

In some embodiments, the LAG-3×PD-1 bispecific antibody comprises Fc domains with skew variants, with particularly useful skew variants being selected from the group consisting of S364K/E357Q:L368D/K370S; L368D/K370S: S364K; L368E/K370S:S364K; T411T/E360E/Q362E: D401K; L368D/K370S:S364K/E357L, K370S:S364K/ E357Q, T366S/L368A/Y407V:T366W and T366S/L368A/ Y407V/Y349C: T366W/S354C.

In some embodiments, the LAG-3×PD-1 antibody includes skew variants, pI variants, and ablation variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second checkpoint inhibitor as outlined herein; and c) a light chain. A specific example of this embodiment utilizes the LAG-3 Fab 7G8_H3.30_L1.34 and the PD-1 scFv 1G6_L1.194_H1.279 although any of the LAG-3 or PD-1 Fvs in the sequence listing can be paired in any combination and used.

In some embodiments, the LAG-3×PD-1 antibody includes skew variants, pI variants, ablation variants and FcRn variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, the FcRn variants M428L/N434S and an Fv that binds to a checkpoint inhibitor as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to a second checkpoint inhibitor as outlined herein; and c) a light chain. A specific example of this embodiment utilizes the LAG-3 Fab 7G8_H3.30_L1.34 and the PD-1 scFv 1G6_L1.194_H1.279 although any of the LAG-3 or PD-1 Fvs in the sequence listing can be paired in any combination and used.

Additional embodiments include any of the backbones from FIG. 37 with the LAG-3 Fab 7G8_H3.30_L1.34 and the PD-1 scFv 1G6_L1.194_H1.279.

Additional embodiments include any of the backbones from FIG. 38 with the LAG-3 Fab 7G8_H3.30_L1.34 and the PD-1 scFv 1G6_L1.194_H1.279.

In some embodiments, for LAG-3×PD-1 bispecific antibodies, the Fv for the LAG-3 Fab side is selected from those sequences in the sequence listing with the identifiers 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1; 7G8_H3.18_L1.11; 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1. The Fv for the PD-1 scFv side is selected from those sequences in the sequence listing with the identifiers identifiers 1G6_H1.279_L1.194; 1G6_H1.280_L1.224; 1G6_L1.194_H1.279; 1G6_L1.210_H1.288; and 2E9_H1L1.

In some embodiments, the LAG-3×PD-1 bispecific antibody is selected from constructs include those listed as SEQ ID NOs: 35867-36126 and SEQ ID NOs: 23736-25133.

In some embodiments, the LAG-3×PD-1 bispecific antibody is selected from XENP20206, XENP21582, XENP21584, XENP21588, XENP22123, XENP22124, XENP22125, XENP22604, XENP22672, XENP22847, XENP22847 and XENP22849

5. TIGITxPD-1

In some embodiments, the TIGITxPD-1 bispecific antibody is selected from those constructs listed in SEQ ID NOs: 25134-25173.

6. TIM-3xPD-1

In some embodiments, the invention provides bispecific heterodimeric antibodies comprising a first ABD that binds human TIM-3 and a second ABD that binds human PD-1, and can be in any format shown in FIG. 1. Most of the disclosure refers to a bottle opener format with the Fab being the TIM-3 side and the PD-1 side being the scFv side, but this can be reversed for all of the embodiments herein.

In one embodiment, the TIM-3xPD-1 bispecific antibody is in the bottle opener format of FIG. 1A, wherein the PD-1 ABD is the scFv. In another embodiment, the TIM-3xPD-1 bispecific antibody is in the central-scFv format of FIG. 1F, with the TIM-3 ABD being the Fab components. In another embodiment, the TIM-3xPD-1 bispecific antibody is in the central-scFv format of FIG. 1F, with the PD-1 ABD being the scFv.

The TIM-3xPD-1 bispecific antibodies (in either the bottle opener format or the central-scFv format) generally include skew variants, pI variants and ablation variants as outlined herein. That is, in either format, the Fc domains of the two monomers can comprise skew variants (e.g. a set of amino acid substitutions as shown in FIG. 3 and FIG. 8), optionally ablation variants (including those shown in FIG. 5), and the monomer comprising the Fab side (e.g. the heavy chain constant domain) comprises pI variants (including those shown in FIG. 4).

In some embodiments, the TIM-3xPD-1 bispecific antibody comprises Fc domains with skew variants, with particularly useful skew variants being selected from the group consisting of S364K/E357Q:L368D/K370S; L368D/K370S: S364K; L368E/K370S:S364K; T411T/E360E/Q362E: D401K; L368D/K370S:S364K/E357L, K370S:S364K/ E357Q, T366S/L368A/Y407V:T366W and T366S/L368A/ Y407V/Y349C:T366W/S354C.

In some embodiments, the TIM-3xPD-1 antibody includes skew variants, pI variants, and ablation variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, and an Fv that binds to a checkpoint inhibitor as outlined herein; b) a second monomer (the "Fab monomer") that comprises the skew variants L368D/K370S, the pI variants N208D/ Q295E/N384D/Q418E/N421D, the ablation variants E233P/ L234V/L235A/G236del/S267K, and a variable heavy domain that, with the variable light domain, makes up an Fv that binds to a second checkpoint inhibitor as outlined herein; and c) a light chain. A specific example of this embodiment utilizes the PD-1 scFv 1G6_L1.194_H1.279 although any of the TIM-3 or PD-1 Fvs in the sequence listing can be paired in any combination and used.

In some embodiments, the TIM-3xPD-1 antibody includes skew variants, pI variants, ablation variants and FcRn variants. Accordingly, some embodiments include bottle opener formats that comprise: a) a first monomer (the "scFv monomer") that comprises a charged scFv linker (with the +H sequence of FIG. 7 being preferred in some embodiments), the skew variants S364K/E357Q, the ablation variants E233P/L234V/L235A/G236del/S267K, the FcRn variants M428L/N434S and an Fv that binds to a checkpoint inhibitor as outlined herein; b) a second monomer (the "Fab monomer") that comprises the skew variants L368D/K370S, the pI variants N208D/Q295E/N384D/ Q418E/N421D, the ablation variants E233P/L234V/L235A/ G236del/S267K, the FcRn variants M428L/N434S and a variable heavy domain that, with the variable light domain, makes up an Fv that binds to a second checkpoint inhibitor as outlined herein; and c) a light chain. A specific example of this embodiment utilizes the PD-1 scFv 1G6_L1.194_H1.279 although any of the TIM-3 or PD-1 Fvs in the sequence listing can be paired in any combination and used.

Additional embodiments include any of the backbones from FIG. 37 with a TIM-3 Fab side and the PD-1 scFv 1G6_L1.194_H1.279.

Additional embodiments include any of the backbones from FIG. 38 with TIM-3 Fab side and the PD-1 scFv 1G6_L1.194_H1.279.

In some embodiments, for TIM-3 Fab sidexPD-1 bispecific antibodies, the Fv for the TIM-3 Fab side Fab side is selected from those sequences in the sequence listing with the identifiers 1D10_H0L0; 1D12_H0L0; 3H3_H1_L2.1; 6C8_H0L0; 6D9_H0_1D12_L0; 7A9_H0L0; 7B11_H0L0; 7B11var_H0L0; and 7C2_H0L0. The Fv for the PD-1 scFv side is selected from those sequences in the sequence listing with the identifiers identifiers 1G6_H1.279_L1.194; 1G6_H1.280_L1.224; 1G6_L1.194_H1.279; 1G6_L1.210_H1.288; and 2E9_H1L1.

In addition, the antibodies of the invention include those that bind to either the same epitope as the antigen binding domains outlined herein, or compete for binding with the antigen binding domains outlined herein. In some embodiments, the bispecific checkpoint antibody can contain one of the ABDs outlined herein and a second ABD that competes for binding with one of the ABDs outlined herein. In some embodiments both ABDs compete for binding with the corresponding ABD outlined herein. Binding competition is generally determined using at least one of a BIACORE®, surface plasmon resonance (SPR) and/or BLI (biolayer interferometry, e.g. OCTET® assay) assay, with the latter finding particular use in many embodiments.

VII. USEFUL EMBODIMENTS

In one embodiment, a particular combination of skew and pI variants that finds use in the present invention is T366S/ L368A/Y407V:T366W (optionally including a bridging disulfide, T366S/L368A/Y407V/Y349C:T366W/S354C) with one monomer comprises Q295E/N384D/Q418E/N481D and the other a positively charged scFv linker (when the format includes an scFv domain). As will be appreciated in the art, the "knobs in holes" variants do not change pI, and thus can be used on either monomer.

VIII. NUCLEIC ACIDS OF THE INVENTION

The invention further provides nucleic acid compositions encoding the bispecific antibodies of the invention (or, in the case of "monospecific" antibodies, nucleic acids encoding those as well).

As will be appreciated by those in the art, the nucleic acid compositions will depend on the format and scaffold of the heterodimeric protein. Thus, for example, when the format requires three amino acid sequences, such as for all the formats depicted in FIG. 1 except for the dual scFv format, three nucleic acid sequences can be incorporated into one or more expression vectors for expression. Similarly, some formats (e.g. dual scFv formats such as disclosed in FIG. 1)

only two nucleic acids are needed; again, they can be put into one or two expression vectors.

As is known in the art, the nucleic acids encoding the components of the invention can be incorporated into expression vectors as is known in the art, and depending on the host cells used to produce the heterodimeric antibodies of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

In some embodiments, nucleic acids encoding each monomer and the optional nucleic acid encoding a light chain, as applicable depending on the format, are each contained within a single expression vector, generally under different or the same promoter controls. In embodiments of particular use in the present invention, each of these two or three nucleic acids are contained on a different expression vector. As shown herein and in 62/025,931, hereby incorporated by reference, different vector ratios can be used to drive heterodimer formation. That is, surprisingly, while the proteins comprise first monomer:second monomer:light chains (in the case of many of the embodiments herein that have three polypeptides comprising the heterodimeric antibody) in a 1:1:2 ratio, these are not the ratios that give the best results.

The heterodimeric antibodies of the invention are made by culturing host cells comprising the expression vector(s) as is well known in the art. Once produced, traditional antibody purification steps are done, including an ion exchange chromotography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the "triple F" heterodimer (e.g., anionic exchange columns, cationic exchange columns). These substitutions also aid in the determination and monitoring of any contaminating dual scFv-Fc and mAb homodimers post-purification (e.g., IEF gels, cIEF, and analytical IEX columns).

IX. BIOLOGICAL AND BIOCHEMICAL FUNCTIONALITY OF THE HETERODIMERIC CHECKPOINT ANTIBODIES

Generally the bispecific checkpoint antibodies of the invention are administered to patients with cancer, and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays. For example, evaluation of changes in immune status (e.g. presence of ICOS+CD4+ T cells following ipi treatment) along with "old fashioned" measurements such as tumor burden, size, invasiveness, LN involvement, metastasis, etc. can be done. Thus, any or all of the following can be evaluated: the inhibitory effects of the checkpoints on CD4+ T cell activation or proliferation, CD8+T (CTL) cell activation or proliferation, CD8+ T cell-mediated cytotoxic activity and/or CTL mediated cell depletion, NK cell activity and NK mediated cell depletion, the potentiating effects of the checkpoints on Treg cell differentiation and proliferation and Treg- or myeloid derived suppressor cell (MDSC)-mediated immunosuppression or immune tolerance, and/or the effects of the checkpoints on proinflammatory cytokine production by immune cells, e.g., IL-2, IFN-γ or TNF-α production by T or other immune cells.

In some embodiments, assessment of treatment is done by evaluating immune cell proliferation, using for example, CFSE dilution method, Ki67 intracellular staining of immune effector cells, and 3H-Thymidine incorporation method, In some embodiments, assessment of treatment is done by evaluating the increase in gene expression or increased protein levels of activation-associated markers, including one or more of: CD25, CD69, CD137, ICOS, PD1, GITR, OX40, and cell degranulation measured by surface expression of CD107A.

In general, gene expression assays are done as is known in the art.

In general, protein expression measurements are also similarly done as is known in the art.

In some embodiments, assessment of treatment is done by assessing cytotoxic activity measured by target cell viability detection via estimating numerous cell parameters such as enzyme activity (including protease activity), cell membrane permeability, cell adherence, ATP production, co-enzyme production, and nucleotide uptake activity. Specific examples of these assays include, but are not limited to, Trypan Blue or PI staining, 51Cr or 35S release method, LDH activity, MTT and/or WST assays, Calcein-AM assay, Luminescent based assay, and others.

In some embodiments, assessment of treatment is done by assessing T cell activity measured by cytokine production, measure either intracellularly in culture supernatant using cytokines including, but not limited to, IFNγ, TNFα, GM-CSF, IL2, IL6, IL4, IL5, IL10, IL13 using well known techniques.

Accordingly, assessment of treatment can be done using assays that evaluate one or more of the following: (i) increases in immune response, (ii) increases in activation of αβ and/or γδ T cells, (iii) increases in cytotoxic T cell activity, (iv) increases in NK and/or NKT cell activity, (v) alleviation of αβ and/or γδ T-cell suppression, (vi) increases in pro-inflammatory cytokine secretion, (vii) increases in IL-2 secretion; (viii) increases in interferon-γ production, (ix) increases in Th1 response, (x) decreases in Th2 response, (xi) decreases or eliminates cell number and/or activity of at least one of regulatory T cells (Tregs.

Assays to Measure Efficacy

In some embodiments, T cell activation is assessed using a Mixed Lymphocyte Reaction (MLR) assay as is known in the art. An increase in activity indicates immunostimulatory activity. Appropriate increases in activity are outlined below.

In one embodiment, the signaling pathway assay measures increases or decreases in immune response as measured for an example by phosphorylation or de-phosphorylation of different factors, or by measuring other post translational modifications. An increase in activity indicates immunostimulatory activity. Appropriate increases in activity are outlined below.

In one embodiment, the signaling pathway assay measures increases or decreases in activation of αβ and/or γδ T cells as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in cytotoxic T cell activity as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in NK and/or NKT cell activity as measured for an example by direct killing of target cells like for an example cancer cells or by cytokine secretion or by changes in expression of activation markers like for an example CD107a, etc. An increase in activity indicates immunostimulatory activity. Appropriate increases in activity are outlined below.

In one embodiment, the signaling pathway assay measures increases or decreases in αβ and/or γδ T-cell suppression, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in pro-inflammatory cytokine secretion as measured for example by ELISA or by LUMINEX®® or by multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in IL-2 secretion as measured for example by ELISA or by LUMINEX® or by multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in interferon-γ production as measured for example by ELISA or by LUMINEX® or by multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in Th1 response as measured for an example by cytokine secretion or by changes in expression of activation markers. An increase in activity indicates immunostimulatory activity. Appropriate increases in activity are outlined below.

In one embodiment, the signaling pathway assay measures increases or decreases in Th2 response as measured for an example by cytokine secretion or by changes in expression of activation markers. An increase in activity indicates immunostimulatory activity. Appropriate increases in activity are outlined below.

In one embodiment, the signaling pathway assay measures increases or decreases cell number and/or activity of at least one of regulatory T cells (Tregs), as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophages cell numbers, as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophage pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in N2 neutrophils increase, as measured for example by flow cytometry or by IHC. A decrease in response indicates immunostimulatory activity. Appropriate decreases are the same as for increases, outlined below.

In one embodiment, the signaling pathway assay measures increases or decreases in N2 neutrophils pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in inhibition of T cell activation, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in inhibition of CTL activation as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in αβ and/or γδ T cell exhaustion as measured for an example by changes in expression of activation markers. A decrease in response indicates immunostimulatory activity. Appropriate decreases are the same as for increases, outlined below.

In one embodiment, the signaling pathway assay measures increases or decreases αβ and/or γδ T cell response as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in stimulation of antigen-specific memory responses as measured for an example by cytokine secretion or by proliferation or by changes in expression of activation markers like for an example CD45RA, CCR7 etc. An increase in activity indicates immunostimulatory activity. Appropriate increases in activity are outlined below.

In one embodiment, the signaling pathway assay measures increases or decreases in apoptosis or lysis of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases in stimulation of cytotoxic or cytostatic effect on cancer cells. as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases direct killing of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases Th17 activity as measured for an example by cytokine secretion or by proliferation or by changes in expression of activation markers. An increase in activity indicates immunostimulatory activity. Appropriate increases in activity are outlined below.

In one embodiment, the signaling pathway assay measures increases or decreases in induction of complement dependent cytotoxicity and/or antibody dependent cell-mediated cytotoxicity, as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, T cell activation is measured for an example by direct killing of target cells like for an example cancer cells or by cytokine secretion or by proliferation or by changes in expression of activation markers like for an example CD137, CD107a, PD1, etc. For T-cells, increases in proliferation, cell surface markers of activation (e.g. CD25, CD69, CD137, PD1), cytotoxicity (ability to kill target cells), and cytokine production (e.g. IL-2, IL-4, IL-6, IFNγ, TNF-α, IL-10, IL-17A) would be indicative of immune modulation that would be consistent with enhanced killing of cancer cells.

In one embodiment, NK cell activation is measured for example by direct killing of target cells like for an example cancer cells or by cytokine secretion or by changes in expression of activation markers like for an example CD107a, etc. For NK cells, increases in proliferation, cytotoxicity (ability to kill target cells and increases CD107a, granzyme, and perforin expression), cytokine production (e.g. IFNγ and TNF), and cell surface receptor expression (e.g. CD25) would be indicative of immune modulation that would be consistent with enhanced killing of cancer cells.

In one embodiment, γδ T cell activation is measured for example by cytokine secretion or by proliferation or by changes in expression of activation markers.

In one embodiment, Th1 cell activation is measured for example by cytokine secretion or by changes in expression of activation markers.

Appropriate increases in activity or response (or decreases, as appropriate as outlined above), are increases of 10%, 20%, 30%, 40%, 50%, 60%, 70%, 80%, 90%, 95% or 98 to 99% percent over the signal in either a reference sample or in control samples, for example test samples that do not contain an antibody of the invention. Similarly, increases of at least one-, two-, three-, four- or five-fold as compared to reference or control samples show efficacy.

X. TREATMENTS

Once made, the compositions of the invention find use in a number of oncology applications, by treating cancer, generally by inhibiting the suppression of T cell activation (e.g. T cells are no longer suppressed) with the binding of the bispecific checkpoint antibodies of the invention.

Accordingly, the heterodimeric compositions of the invention find use in the treatment of these cancers.

XI. COMBINATION THERAPIES

In some embodiments, when the bispecific checkpoint does not include an anti-PD-1 antigen binding domain, the bispecific antibody can be co-administered with a separate anti-PD-1 antibody such as pembrolizumab (Keytruda®) or nivolumab (Opdivo®). Co-administration can be done simultaneously or sequentially, as will be appreciated by those in the art.

That is, a CTLA-4×LAG-3 bispecific checkpoint antibody disclosed herein, or such as any of those that incorporate anti-LAG-3 sequences and anti-CTLA-4 sequences from the sequence listing, and in particular XENP22602, XENP 22675, XENP22841 or XENP 22843, can be co-administered with an anti-PD-1 antibody.

Similarly, a BTLA×CTLA-4 bispecific checkpoint disclosed herein, or such as any of those that incorporate anti-BTLA sequences and anti-CTLA-4 sequences from the sequence listing, can be co-administered with an anti-PD-1 antibody.

A CTLA-4×TIM-3 bispecific checkpoint antibody such as any of those that incorporate anti-TIM-3 sequences and anti-CTLA-4 sequences from the sequence listing, can be co-administered with an anti-PD-1 antibody.

A CTLA-4 and TIGIT bispecific checkpoint antibody such as any of those that incorporate anti-CTLA-4 and anti-TIGIT sequences from the sequence listing, can be co-administered with an anti-PD-1 antibody.

A TIM-3 and LAG-3 bispecific checkpoint antibody such as any of those that incorporate anti-TIM-3 sequences and anti-LAG-3 sequences from the sequence listing, can be co-administered with an anti-PD-1 antibody.

A TIM-3 and TIGIT bispecific checkpoint antibody such as any of those that incorporate anti-TIM-3 sequences and anti-TIGIT sequences from the sequence listing, can be co-administered with an anti-PD-1 antibody.

A TIM-3 and BTLA bispecific checkpoint antibody such as any of those that incorporate anti-TIM-3 and anti-BTLA sequences from the sequence listing, can be co-administered with an anti-PD-1 antibody.

A LAG-3 and TIGIT bispecific checkpoint antibody such as any of those that incorporate anti-LAG-3 sequences and anti-TIGIT sequences from the sequence listing, can be co-administered with an anti-PD-1 antibody.

A LAG-3 and BTLA bispecific checkpoint antibody such as any of those that incorporate anti-LAG-3 sequences and anti-BTLA sequences from the sequence listing, can be co-administered with an anti-PD-1 antibody.

A TIGIT and BTLA bispecific checkpoint antibody such as any of those that incorporate anti-TIGIT sequences and anti-BTLA sequences from the sequence listing, can be co-administered with an anti-PD-1 antibody.

XII. ANTIBODY COMPOSITIONS FOR IN VIVO ADMINISTRATION

Formulations of the antibodies used in accordance with the present invention are prepared for storage by mixing an antibody having the desired degree of purity with optional pharmaceutically acceptable carriers, excipients or stabilizers (as generally outlined in Remington's Pharmaceutical Sciences 16th edition, Osol, A. Ed. [1980]), in the form of lyophilized formulations or aqueous solutions. Acceptable carriers, buffers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Administrative Modalities

The antibodies and chemotherapeutic agents of the invention are administered to a subject, in accord with known methods, such as intravenous administration as a bolus or by continuous infusion over a period of time.

Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the bispecific antibodies used in the present invention depend on the disease or condition to be treated and may be determined by the persons skilled in the art.

An exemplary, non-limiting range for a therapeutically effective amount of an bispecific antibody used in the present invention is about 0.1-100 mg/kg.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

EXAMPLES

Examples are provided below to illustrate the present invention. These examples are not meant to constrain the present invention to any particular application or theory of operation. For all constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in US Publications 2015/0307629, 2014/0288275 and WO2014/145806, all of which are expressly incorporated by reference in their entirety and particularly for the techniques outlined therein.

A. Example 1: TILs from Multiple Cancer Types Co-Express Immune Checkpoint Receptors To investigate potential associations between PD-1, CTLA-4, LAG-3, and BTLA, RNA sequencing data from The Cancer Genome Atlas project (TCGA) were used for analysis. V2 RSEM data were downloaded from FireBrowse (http://firebrowse.org/). Analysis was performed using R with custom routines. The correlation between PD-1 and CTLA-4 expression is depicted in FIG. 66, along with calculated R2 values (FIG. 1; square of the Pearson correlation coefficient). FIG. 66 further shows the correlation between PD-1 and LAG-3 expression, PD-1 and BTLA expression, and LAG-3 and CTLA-4 expression.

FIG. 44 shows that PD-1 and CTLA-4 were co-expressed in cancers including bladder, breast, colon, prostate, melanoma, ovarian and lung cancer. shows that the sets PD-1 and CTLA-4, PD-1 and LAG-3, PD-1 and BTLA, and LAG-3 and CTLA-4 were co-expressed in cancers including bladder, breast, colon, head & neck, kidney, lung-adeno, lung squamous, ovarian, pancreatic, prostate, and melanoma cancer.

B. Example 2: Bispecific Immune Checkpoint Antibodies are Superior to Monospecific Immune Checkpoint Antibodies Prototype immune checkpoint antibodies (e.g. nivolumab and ipilimumab) and bispecific immune checkpoint antibodies based on the prototype antibodies were produced to demonstrate the effect of dual checkpoint blockades. Unless otherwise stated, bispecifics are named herein using the Fab variable region first and the scFv variable region second. Amino acid sequences for the prototype antibodies are listed in the sequence listing. DNA encoding the heavy and light chains were generated by gene synthesis (BLUE HERON BIOTECHNOLOGY, Bothell, Wash.), subcloned using standard molecular biology techniques into the expression vector pTT5 containing bivalent or bispecific constant regions and transiently transfected in HEK293E cells. Antibodies were purified by Protein A chromatography (and cation exchange chromatography for bispecific antibodies). Purity was assessed by size exclusion chromatography, analytical cation exchange chromatography and capillary isoelectric focusing.

1. Double-Positive Cells are Selectively Occupied by Bispecific Immune Checkpoint Antibodies Selective targeting of tumor-reactive TILs expressing multiple immune checkpoint receptors (as shown in Example 1) over non-tumor reactive T cells expressing single immune checkpoint receptors could enhance anti-tumor activity while avoiding peripheral toxicity (as depicted in FIG. 42).

An SEB-stimulated PBMC assay was used to investigate binding of bispecific immune checkpoint antibodies to T cells. The SEB-stimulated PBMC assay is an in vitro method for assaying T helper (TH) cell proliferation and for generating a population of cytotoxic T lymphocytes (CTLs). When PBMCs are stimulated with staphylococcal enterotoxin B (SEB), TH cell populations expand, followed by expansion of a CTL population. PBMCs were stimulated with 100 ng/mL SEB for 3 days and then treated with a prototype anti-LAG-3×anti-PD-1 bispecific antibody and a negative control (NUMAX® bivalent) for 30 minutes at 4° C. Following treatment, cells were incubated with APC-labelled one-arm anti-LAG-3 antibody, FITC-labelled one-arm anti-PD-1 antibody and BV605-labelled anti-CD3 antibody for 30 minutes at 4° C. Scatter plots of the CD3$^+$ T cells are depicted in FIG. 67. The data show that double-positive cells expressing both PD-1 and LAG-3 are selectively occupied by the anti-LAG-3×anti-PD-1 bispecific demonstrating that bispecific immune checkpoint antibodies selectively target T cells expressing multiple checkpoint receptors.

2. Anti-CTLA-4× Anti-PD-1 Bispecific Enhances IL-2 Response in a Mixed Lymphocyte Reaction Prototype immune checkpoint antibodies XENP16432 (nivolumab) and XENP16433 (ipilimumab), bispecific immune checkpoint antibody XENP16004 based on nivolumab and ipilimumab, and a one-arm (monospecific, monovalent) combination control were tested in a mixed-lymphocyte reaction (also known as a mixed-leukocyte reaction or MLR). The MLR is another in vitro method for assaying T helper (TH) cell proliferation and for generating a population of cytotoxic T lymphocytes (CTLs). When allogeneic (different MHC haplotype) lymphocytes are cultured together, TH cell populations expand, followed by expansion of a CTL population. Interleukin-2 (IL-2) secretion was used to monitor T cell activation.

Different sets of human PBMCs were purified from leukapheresis of different anonymous healthy volunteers (HemaCare, VanNuys, Calif.) using Ficoll-Paque™ Plus density gradients. PBMCs from two donors were mixed and then treated with 20 μg/mL of the indicated test articles. Supernatant was collected and concentration of IL-2 was measured using an IL-2 ELISA and data are shown in depicts the results of some anti-CTLA-4 Fab screening. This depicts the XENP code for the Fab and scFv embodiments, the designation of the vh and vl engineered domains, the KD binding constant against human and cyno CTLA-4 as measured by OCTET®, and the Tm of the scFv and Fab. Additionally, the number of sequence 9-mers that were an exact match to at least one human VH or VL germline are depicted as a measure of humanness for the variable regions of both Fabs and scFvs.

FIG. 25A. For each column, each data point is a separate reaction with a different donor-donor combination.

The data show that the prototype anti-PD-1×anti-CTLA-4 bispecific antibody enhanced IL-2 response to a greater extent than nivolumab and ipilimumab alone. Notably, the one-arm combination (each monovalent arm of the bispecific added separately) is inferior to the anti-PD-1×anti-CTLA-4 bispecific, suggesting more avid binding of the bispecific to double-positive PD-1+CTLA-4+ cells which is consistent with the finding depicted in FIG. 67 for an anti-LAG-3×anti-PD-1 bispecific antibody.

3. Additional Bispecific Immune Checkpoint Antibodies Enhance IL-2 Response in a Mixed Lymphocyte Reaction Additional prototype immune checkpoint antibodies and bispecific immune checkpoint antibodies directed towards additional immune checkpoint receptors were tested in a MLR assay as described above. Two sets of MLRs were created where 20 donors were targeting 1 recipient donor and another set of 20 donors targeting another 1 recipient donor totaling 40 MLR reactions. Reactions were incubated with 20 µg/mL of indicated test articles for 6 days. Data depicting fold increase of IL-2 and IFNγ (as assayed by ELISA) following treatment with the indicated test articles over treatment with anti-PD-1 bivalent (XENP16432) are shown in FIG. 32. The data show that additional bispecific immune checkpoint antibodies were also superior to nivolumab alone in activating T cells.

4. Triple Immune Checkpoint Blockade—Anti-PD-1 Bivalent and Anti-LAG-3× Anti-CTLA-4 Bispecific Antibodies are Synergistic in Enhancing IL-2 Response in an SEB-Stimulated PBMC Assay It was hypothesized that a triple immune checkpoint blockade such as with an anti-PD-1 bivalent and an anti-LAG-3×anti-CTLA-4 bispecific as depicted in FIG. 43 would provide additional benefit in enhancing T cell activation. To test the hypothesis, prototype immune checkpoint antibodies XENP16432 (nivolumab), prototype bispecific anti-LAG-3×anti-CTLA-4 immune checkpoint antibody XENP16430 based on 25F7 and ipilimumab, and a combination of XENP16432 and XENP16430 were tested in a SEB-stimulated PBMC assay.

Human PBMCs from multiple donors were stimulated with 10 ng/ml of SEB for 72 h with 20 µg/mL of indicated test articles. Following treatment, cell supernatants were assayed for IL-2 by ELISA. Data are shown in FIG. 33 for fold increase in IL-2 over NUMAX® ® bivalent. Each point indicates a donor represented in technical singlet.

The data show that the anti-LAG-3×anti-CTLA-4 bispecific checkpoint antibody (XENP16430) alone enhanced the IL-2 response relative to control (NUMAX® ® bivalent), although enhancement is lower than nivolumab (XENP16432) alone. However, the anti-CTLA-4×anti-LAG-3 bispecific in combination with nivolumab leads to significantly higher IL-2 response than either alone.

5. Blocking of Checkpoint Receptor/Ligand Interaction is Necessary for T Cell Activation Prototype anti-BTLA antibodies 4A7, E8D9 and 8D5 were screened for their ability to block BTLA interaction with its ligand HVEM using OCTET®, a BioLayer Interferometry (BLI)-based method. Experimental steps for OCTET® generally included the following: Immobilization (capture of ligand or test article onto a biosensor); Association (dipping of ligand- or test article-coated biosensors into wells containing serial dilutions of the corresponding test article or ligand); and Dissociation (returning of biosensors to well containing buffer) in order to determine the monovalent affinity of the test articles. A reference well containing buffer alone was also included in the method for background correction during data processing. 500 nM of each anti-BTLA antibody and 100 nM BTLA-Fc were incubated for over an hour. Anti-Penta-HIS (HIS1K) biosensors were used to capture HVEM-Fc-His and then dipped into antibody/BTLA mixture to measure residual BTLA/HVEM binding. As depicted in FIG. 35B, 8D5 did not block BTLA/HVEM interaction while 4A7 and E8D9 blocked BTLA/HVEM interaction.

The prototype anti-BTLA antibodies and anti-BTLA× anti-PD-1 bispecific antibodies with anti-BTLA Fab arms based on the prototype antibodies were tested in an SEB-stimulated PBMC assay. Specifically, human PBMCs were stimulated with 20 ng/mL of SEB for 72 hours with 20 µg/mL of indicated test articles. Following treatment, cell supernatant were assayed for IL-2 by ELISA. Data are shown in FIG. 35A for fold increase of IL-2 over NUMAX® bivalent (each point represents an individual PBMC donor tested in singlet). The data show that bispecific antibody with the non-blocking 8D5 anti-BTLA Fab arm induced IL-2 significantly less than nivolumab indicating that blocking the BTLA/HVEM interaction is necessary for enhancing T cell activation.

6. Bispecific Immune Checkpoint Antibodies Enhance Engraftment and Disease Activity in Human PBMC-Engrafted NSG Mice Bispecific checkpoint antibodies were evaluated in a Graft-versus-Host Disease (GVHD) model conducted in NSG (NOD-SCID-gamma) immunodeficient mice. When the NSG mice were injected with human PBMCs, the human PBMCs developed an autoimmune response against mouse cells. Treatment of NSG mice injected with human PBMCs followed by treatment with immune checkpoint inhibitors de-repress the engrafted T cells and enhances engraftment.

10 million human PBMCs were engrafted into NSG mice via IV-OSP on Day 0 followed by dosing with the indicated test articles (5 mg/kg or as indicated) on Day 1. CD45+ events were measured on Day 14 (FIG. 34). While the GVHD can be measured directly, increased CD45+ cell levels correlate with decreased body weight (depict a mixed lymphocyte reaction looking enhancement of IL-2 release by nivolumab (anti-PD-1 monoclonal antibody, marketed as Opdivo®) alone, ipilimumab alone (anti-CTLA-4 monoclonal antibody, marketed as Yervoy®), a prototype anti-CTLA-4×anti-PD-1 bispecific based on the nivolumab and ipilimumab arms, and a "one-armed" combination control. FIG. 26B) and are Predictive of Disease.

The data show that the bispecific checkpoint antibodies of the invention enhance proliferation of CD45+ cells in human PBMC-engrafted NSG mice as compared to control (PBS+PBMC). Further, enhancement is greater using antibodies of the invention than that seen with nivolumab (XENP16432) alone. Furthermore, the anti-CTLA-4×anti-LAG-3 bispecific (XENP16430) in combination with nivolumab yielded the highest engraftment levels consistent with the data in Example 2D.

C. Example 3: Hybridomas

1. Hybridoma Generation

To develop PD-1, LAG-3 and BTLA targeting arms for bispecific immune checkpoint antibodies of the invention, monoclonal antibodies were first generated by hybridoma technology through IMMUNOPRECISE®, either through their STANDARD METHOD or RAPID PRIME® METHOD.

For the Standard Method, antigen(s) was injected into 3 BALB/c mice. 7-10 days before being sacrificed for hybridoma generation, the immunized mice received an antigen boost. Antibody titre is evaluated by ELISA on the antigen and the best responding mice are chosen for fusion. A final antigen boost is given 4 days prior to fusion. Lymphocytes from the mice are pooled, purified then fused with SP2/0 myeloma cells. Fused cells are grown on HAT selective Single-Step cloning media for 10-12 days at which point the hybridomas were ready for screening.

For the RAPID PRIME® method, antigen(s) was injected into 3 BALB/c mice. After 19 days, lymphocytes from all the mice are pooled, purified then fused with SP2/0 myeloma cells. Fused cells are grown on HAT selective Single-Step cloning media for 10-12 days at which point the hybridomas were ready for screening.

For generation of anti-PD-1 hybridomas, the STANDARD and RAPID PRIME® methods were used and the antigen(s) used were mouse Fc fusion of human PD-1 (huPD-1-mFc), mouse Fc fusion of cyno PD-1 (cynoPD-1-mFc), His-tagged human PD-1 (huPD-1-His), His-tagged cyno PD-1 (cynoPD-1-His) or mixtures thereof For generation of anti-BTLA hybridomas, the Standard and RAPID PRIME® methods were used and antigen used were mouse Fc fusion of human BTLA (huBTLA-mFc), mouse Fc fusion of cyno BTLA (cynoBTLA-mFc), His-tagged human BTLA (huBTLA-His), or mixture of huBTLA-mFc and cynoBTLA-mFc.

For generation of anti-LAG-3 hybridomas, the RAPID PRIME® method was used and antigen used were mouse Fc fusion of human LAG-3 (huLAG-3-mFc), mouse Fc fusion of cyno LAG-3 (cynoLAG-3-mFc), His-tagged human LAG-3 (huLAG-3-His), mixture of huLAG-3-mFc and cynoLAG-3-mFc, or mixture huLAG-3-His and cynoLAG-3-His.

For generation of anti-TIM-3 hybridomas, the Standard and RAPID PRIME® methods were used and antigen(s) used were mouse Fc fusion of human TIM-3 (huTIM-3-mFc), mouse Fc fusion of cyno TIM-3 (cynoTIM-3-mFc), His-tagged human TIM-3 (huTIM-3-His), His-tagged cyno TIM-3 (cynoTIM-3-His) or mixtures thereof.

2. Screening Anti-PD-1 Hybridoma Clones

Anti-PD-1 hybridoma clones generated as described above were subject to two rounds of screening using OCTET®®. For the first round, anti-mouse Fc (AMC) biosensors were used to capture the clones with dips into 500 nM of bivalent human and cyno PD-1-Fc-His. For the second round, clones identified in the first round that were positive for both human and cyno PD-1 were captured onto AMC biosensors and dipped into 500 nM monovalent human and cyno PD-1-His. Sequences for exemplary anti-PD-1 antibodies are in the sequence listing.

3. Screening Anti-BTLA Hybridoma Clones

Anti-BTLA hybridoma clones generated as described above were subject to two rounds of screening using OCTET®. For the first round, AMC biosensors were used to capture the clones with dips into multiple concentrations of human and cyno BTLA-His to determine KD. For the second round, a blocking assay was used to identify clones which blocked BTLA/HVEM interaction. Anti-Penta-HIS (HIS1K) biosensors were used to capture HVEM-Fc-His and dipped into 25 nM BTLA-Fc alone or 25 nM BTLA-Fc+1:1 dilution of hybridoma samples to measure residual BTLA/HVEM binding. Sequences for exemplary anti-BTLA antibodies are in the sequence listing.

4. Screening Anti-LAG-3 Hybridoma Clones

Anti-LAG-3 hybridoma clones generated as described above were subject to several rounds of screening to identify clones with high affinity, which block LAG-3 binding to Ramos cells endogenously expressing MHC-II, and which bind a different epitope than 25F7 mAb.

Affinity was determined using OCTET®. AMC biosensors were used to capture clones with dips into single concentration of human LAG-3-Fc and cyno LAG-3-Fc. To identify clones which block LAG-3/MHC-II interaction, 1 μg of human LAG-3-hIg in 10 μL was mixed with 50 μL of hybridoma supernatant (diluted 2-fold, 8 times in RPMI media with 10% FBS) for 20 minutes at room temperature. 40 μL of Daudi or Ramos cells (which endogenously express MHC-II) were added and incubated at 4° C. for 30 minutes. The cells were then washed and incubated with anti-human-Fc-Alexa647 secondary antibody for 30 minutes. Cells were then washed and analyzed by FACS for Alexa647. The data is depicted in FIG. 62. To identify clones which bind a different epitope than 25F7 mAb, AMC biosensors were used to capture clones with dips into 100 nM human LAG-3-hFc or 100 nM LAG-3-hFc with 500 nM 25F7 to measure residual binding. Sequences for exemplary anti-LAG-3 antibodies are in the sequence listing.

5. Screening Anti-TIM-3 Hybridoma Clones

Anti-TIM-3 hybridoma clones generated as described above were subject to two rounds of screening. The first round was divided into screens for IgG samples and IgM clones. For IgG clones, AMC biosensors were used to capture the clones and were dipped into multiple concentrations of human and cyno TIM-3-His. For IgM clones, anti-IgM mAbs were coupled using AR2G onto biosensors which were dipped into multiple concentrations of human and cyno TIM-3-His. None of the IgM samples produced binding signals higher than baseline. Following the first round of screening, IgG clones which bound both human and cyno TIM-3 were rescreened with bivalent versions of bivalent human and cyno TIM-3-Fc. Sequences for exemplary anti-TIM-3 antibodies are in the sequence listing.

Several of the clones were chimerized and assessed for T cell binding in an SEB-stimulated PBMC assay. Human PBMCs were stimulated with 100 ng/mL SEB for 3 days. Following stimulation, cells were treated with indicated test articles for 30 minutes at 4 degrees. Binding on $CD3^+$ cells was detected with an anti-human-Fc secondary antibody and depicted in FIG. 21.

6. Component Antibody Domains Derived from Hybridomas Block Checkpoint Receptor/Ligand Interactions As described in Example 2E, blocking of checkpoint receptor/ligand interaction is necessary for T cell activation. The blocking ability of exemplary antibodies comprising domains derived from hybridomas were investigated using either cell binding assays or OCTET® as depicted in are graphs showing that component antibody domains of the subject antibodies provided herein are capable of blocking checkpoint receptor/ligand interactions. In particular, a bispecific antibody comprising a 1G6 anti-PD-1 scFv arm is capable of blocking PD-1/PD-L1 and PD-1/PD-L2 interactions; 7G8 anti-LAG-3 one arm is capable of blocking LAG-3/MHC II interaction; a bispecific antibody comprising an exemplary anti-PD-1 Fab arm is capable of blocking CTLA-4/CD80 and CTLA-4/CD86 interactions; and a bispecific antibody comprising a 9C6 anti-BTLA Fab arm is capable of blocking BTLA/HVEM interaction.

FIG. 68.

Incubation of HEK293T exogenously expressing PD-1 with XENP20717 prevented binding by PD-L1 and PD-L2 to PD-1 in a dose dependent manner. Incubation of LAG-3 with XENP22606 prevented its binding to Daudi cells endogenously expressing MHC-II. Incubation of CTLA-4 with XENP20066 prevented residual binding to CD80 and CD86. Incubation of BTLA with XENP20895 prevented residual binding to HVEM.

D. Example 4: Affinity and Stability Optimization

1. Anti-PD-1 mAbs 1G6 and 2E9

The anti-PD-1 hybridoma clones 1G6 and 2E9 generated in Example 3 were engineered to have optimal affinity and stability in the context of scFv or Fab for use in a bispecific immune checkpoint inhibitor. The clones were first humanized using string content optimization (see, e.g., U.S. Pat. No. 7,657,380, issued Feb. 2, 2010). DNA encoding the heavy and light chains were generated by gene synthesis (Blue Heron Biotechnology, Bothell, Wash.) and subcloned using standard molecular biology techniques into the expression vector pTT5. The C-terminus of the scFv included a polyhistidine tag. A library of Fv variants was constructed by standard mutagenesis (QUIKCHANGE®, STRATAGENE®, Cedar Creek, Tx®) in the full-length bivalent, Fab-His and/or scFv-His formats. Bivalent mAbs were purified by standard protein A chromatography and Fab-His and scFv-His were purified by Ni-NTA chromatography. Sequences for exemplary 1G6 and 2E9 bivalent antibodies, Fabs and scFvs of the invention are listed in the sequence listing (although the polyhistidine tags have been removed for Fabs and scFvs). After the initial screen, combinations were made of variants of interest, and these were expressed, purified, and re-examined for affinity and stability.

Affinity screens of bivalent antibodies were performed using OCTET®. Anti-human Fc (AHC) biosensors were used to capture the test articles and dipped in multiple concentrations of PD-1-His for KD determination. Stability of scFv-His were evaluated using Differential Scanning Fluorimetry (DSF). DSF experiments were performed using a BIO-RAD® CFX® CONNECT REAL-TIME PCR DETECTION SYSTEM. Proteins were mixed with SYPRO® Orange fluorescent dye and diluted to 0.2 mg/mL in PBS. The final concentration of SYPRO® Orange was 10×. After an initial 10 minute incubation period of 25° C., proteins were heated from 25 to 95° C. using a heating rate of 1° C./min. A fluorescence measurement was taken every 30 sec. Melting temperatures (Tm) were calculated using the instrument software. The affinity and stability results are shown in FIG. 23.

2. Anti-CTLA-4 mAb

The parental variable region of an anti-CTLA-4 antibody was engineered for use as a component of various bispecifics. Two approaches were taken to attempt to identify variants with improved properties: (1) single, double, and triple amino acids substitutions were made via QUIKCHANGE® (STRATAGENE®, Cedar Creek, Tx®) mutagenesis, and (2) re-grafted sequences with their framework exchanged with alternative human germlines (IGHV3-7, IGHV3-13, IGHV3-21, IGHV3-64, IGKV3D-20, IGKV3-15) were constructed by DNA synthesis and subcloning. Variant Fabs and scFvs were designed, expressed, and purified. Affinities for human and cyno CTLA-4 were measured for Fabs using OCTET®. AHC biosensors were used to capture Fc fusions of human or cyno CTLA-4 and dipped into multiple concentrations of Fab test articles for KD determination. Thermal stabilities were measured for both Fabs and scFvs using DSF. Additionally, the number of sequence 9-mers that were an exact match to at least one human VH or VL germline were counted as a measure of humanness (see, e.g., U.S. Pat. No. 7,657,380, issued Feb. 2, 2010) for the variable regions of both Fabs and scFvs. After the initial screen, combinations were made of variants of interest, and these were expressed, purified, and re-examined for affinity and stability. Results are summarized in FIG. 24. Several variants possessed increased thermal stability over that of the parental variable region while retaining a similar affinity for both human and cyno CTLA-4. Additionally, increases in sequence humanness as measured by the number of human germline matching sequence 9-mers were identified for several variants. Preferred variants include: H0.25_L0, H0.26_L0, H0.27_L0, H0.29_L0, H0.38_L0, H0.39_L0, H0.40_L0, H0.70_L0, H0_L0.22, H2_L0, H3_L0, H3_L0.22, H3_L0.67, H3_L0.74, H3_L0.44, H3.4_L0.118, H3.4_L0.119, H3.4_L0.120, H3.4_L0.121, H3.4_L0.122, H3.4_L0.123, H3.4_L0.124, H3.4_L0.125, H3.4_L0.126, H3.4_L0.127, H3.4_L0.128, H3.4_L0.129, H3.4_L0.130, H3.4_L0.131, H3.4_L0.132, H3.5_L2.1, H3.5_L2.2, H3.5_L2.3, H3.21_L0.124, H3.21_L0.129, H3.21_L0.132, H3.23_L0.124, H3.23_L0.129, H3.23_L0.132, H3.25_L0.124, H3.25_L0.129, and H3.25_L0.132.

3. Anti-BTLA mAb 9C6

The anti-BTLA hybridoma clone 9C6 generated in Example 3 was humanized and engineered to have optimal affinity and stability in bivalent antibody format as generally described above in Example 4A. Sequences for exemplary anti-BTLA bivalent antibodies of the invention are listed in the sequence listing.

Affinity screens for the variant bivalent antibodies were performed using OCTET®. AHC biosensors were used to capture the test articles and dipped into wells with multiple concentrations of BTLA-His for KD determination (shown in A and B show that anti-BTLA×anti-PD-1 chimeric bispecific promotes IFNγ secretion from SEB stimulated PBMCs. PBMCs were stimulated with 10 ng/mL SEB for 3 days with indicated test articles. Cell supernatants were collected and assayed with MSD for indicated analyte. A: 20 µg/mL test article; B 5 µg/mL test article.

FIG. 52).

4. Anti-LAG-3 mAbs 7G8 and 2A11

The anti-LAG-3 hybridoma clones 7G8 and 2A11 generated in Example 3 were humanized and engineered to have optimal affinity and stability in the context of a Fab for use in a bispecific immune checkpoint inhibitor as generally described above in Example 4A. Sequences for exemplary anti-LAG-3 bivalent antibodies and Fabs of the invention are listed in the sequence listing.

Affinity and stability for variant anti-LAG-3 Fabs were determined as generally described above in Example 4A. AMC biosensors were used to capture mouse Fc fusions of human LAG-3 and dipped into wells containing multiple concentrations of the test articles to determine KD. The results are shown in FIG. 53 for 2A11 variants and FIG. 54 for 7G8 variants.

Exemplary variant 2A11 and 7G8 anti-LAG-3 bivalent antibodies were further screened for their ability to block LAG-3 binding to Daudi cells endogenously expressing MHC-II. 1 µg of LAG-3-mFc was mixed with indicated concentrations of mAb for 30 minutes at room temperature. Daudi cells were then added and incubated for 30 minutes at 4° C. LAG-3-mFc binding was detected with an anti-murine-Fc secondary antibody. The data is depicted in FIG. 63.

5. Anti-TIM-3 mAbs

Anti-TIM-3 hybridoma clones generated in Example 3 were humanized and engineered to have optimal affinity and stability in bivalent antibody format as generally described above in Example 4A. Sequences for exemplary anti-TIM-3 bivalent antibodies of the invention are listed in the sequence listing.

Affinity screens for the variant bivalent antibodies were performed using OCTET®. AHC biosensors were used to capture the test articles and dipped into wells with multiple concentrations of TIM-3-His for KD determination (shown in FIG. 22).

Optimized variants were also tested for T cell binding in an SEB-stimulated PBMC assay. Human PBMCs were stimulated with 100 ng/mL SEB for 72 hours. Following stimulation, cells were treated with the indicated test articles. Binding of 3H3_H1_L2.1 (XENP21189) on CD3+ cells was detected with an anti-human-Fc secondary antibody and depicted in FIG. 21. Binding of 7B11_HJ1_L1.1 (XENP21196) on CD3+ cells was detected with an anti-human-IgG-APC secondary antibody and depicted in FIG. 21.

6. Affinity Screens of Variant Anti-LAG-3× Anti-CTLA-4 Fab-scFv Bispecific Antibodies Bispecific antibodies comprising anti-LAG-3 Fabs derived from the optimized anti-LAG-3 bivalent antibodies described in Example 4D and an exemplary anti-CTLA-4 scFv described in Example 4B were screened for affinity using OCTET® as generally described above. Specifically, AMC or HIS1K biosensors were used to capture mouse Fc fusion of human LAG-3 or His-Avi tagged TEV-Fc fusion of human LAG-3 and dipped into well containing the test articles to determine KD. Results are shown in FIG. 55.

7. Affinity Screens of Variant Anti-LAG-3× Anti-PD-1 Fab-scFv Bispecific Antibodies.

Bispecific antibodies comprising anti-LAG-3 Fabs derived from the optimized anti-LAG-3 bivalent antibodies described in Example 4D and an exemplary anti-PD-1 scFv described in Example 4A were screened for affinity using OCTET® as generally described above. Specifically, AMC or HIS1K biosensors were used to capture mouse Fc fusion of human LAG-3 or His-Avi tagged TEV-Fc fusion of human LAG-3 and dipped into well containing the test articles to determine KD. Results are shown in FIG. 61.

E. Example 5: In Vitro Assessment of Bispecific Immune Checkpoint Antibodies with Affinity and Stability Optimized Arms 1. Anti-PD-1× Anti-CTLA-4 Bispecific Antibodies a. Bispecific Anti-PD-1× Anti-CTLA-4 Bispecific Antibody Blocks PD-1 Interaction with PD-L1 and PD-L2

HEK293T cells expressing PD-1 were incubated with incubated with XENP20717 (anti-PD-1×anti-CTLA-4) and one-arm anti-PD-1 and anti-CTLA-4 controls (respectively XENP20111 and XENP20059) for 30 minutes at 4° C. Following incubation, PD-L1-mFc or PD-L2-mFc was added and allowed to further incubate for 30 minutes at 4° C. PD-L1-mFc and PD-L2-mFc were detected with anti-murine-IgG secondary antibody.

FIG. 45 show that XENP20717 was able to block the binding of PD-1 to ligands PD-L1 and PD-L2 in a dose dependent manner. XENP20111 was also able to block the binding of PD-1 to ligands PD-L1 and PD-L2, while XENP20559 did not block PD-1 binding to its ligands.

b. T Cell Binding of Bispecific Anti-CTLA-4× Anti-PD-1 Bispecific Antibody on CD3$^+$ Cells Human PBMCs were stimulated with 500 ng/mL SEB for 3 days, washed twice in culture medium and then re-stimulated with 500 ng/mL SEB for an additional 24 hours. The PBMCs were then treated with XENP20717 (anti-CTLA-4×anti-PD-1) for 30 minutes at 4° C. Following treatment, PBMCs were washed and incubated with anti-human-Fc-(Fab fragment specific)-APC secondary antibody (Jackson Labs) on CD3$^+$ cells with an anti-CD3-FITC (UCHT1) mAb. PBMCs were then washed twice and analyzed by flow cytometry. FIG. 45 depicts the average MFI of 7 unique PBMC donors and shows binding of XENP20717 on CD3+ T cells and that binding was in a dose-dependent manner.

c. Assessment of Variant Anti-CTLA-4× Anti-PD-1 Bispecifics on T Cell Activation Anti-CTLA-4×anti-PD-1 bispecific antibodies with variant anti-CTLA-4 Fab arms were tested in an MLR assay. Mixed PBMCs were treated with 69.5 nM of bivalent antibodies (e.g. nivolumab) or 139 nM of bispecific antibodies (e.g. XENP16004) for equimolar PD-1 binding concentrations. The data depicted in depicts the results of some anti-CTLA-4 Fab screening. This depicts the XENP code for the Fab and scFv embodiments, the designation of the vh and vl engineered domains, the KD binding constant against human and cyno CTLA-4 as measured by OCTET®, and the Tm of the scFv and Fab. Additionally, the number of sequence 9-mers that were an exact match to at least one human VH or VL germline are depicted as a measure of humanness for the variable regions of both Fabs and scFvs.

FIG. 25B show that a number of the bispecific antibodies enable IL-2 induction superior to nivolumab alone.

In an SEB-stimulated PBMC assay, PBMCs were treated with 500 ng/mL SEB for 2 days. Cells were then washed and treated with 20 µg/mL of XENP16432 (nivolumab) or XENP20717 and 500 ng/mL SEB. Supernatant was assayed for IL-2 as an indicator of T cell activation. The data depicted in FIG. 69 show that the anti-CTLA-4×anti-PD-1 bispecific induces significantly more IL-2 release than nivolumab alone.

In another study, XENP16432, XENP20717 and one-arm combination control were tested in an SEB-stimulated PBMC assay. PBMCs were stimulated with 500 ng/mL SEB for 2 days. Cells were then washed once with PBS and then culture medium with 20 µg/mL of indicated test articles and 500 ng/mL SEB was added. Supernatants were collected after 24 hours and assayed for IL-2. In a control experiment without SEB stimulation, PBMCs were treated with indicated test articles for 3 days before supernatant was assayed for IL-2. The fold-change in IL-2 concentration is depicted in FIG. 45A-C. As shown in FIG. 45B, XENP20717 enhanced IL-2 secretion significantly more than nivolumab did. The data show that XENP20717 activates T cells more potently than both anti-PD-1 bivalent alone as well as a combination of one-arm anti-PD-1 and one-arm anti-CTLA-4 demonstrating the advantage of selectively activating T cells expressing multiple immune checkpoint receptors. Notably, and consistent with the findings described in Example 2B, the bispecific XENP20717 enhanced IL-2 secretion to a greater extent than did the combination of one-arm antibodies derived from XENP20717.

An additional bispecific antibody targeting CTLA-4 and PD-1 with an anti-CTLA-4 scFv arm and a variant 2E9 anti-PD-1 Fab arm and control test articles were tested in an SEB-stimulated PBMC assay. Human PBMCs were stimulated with 100 ng/mL SEB for 2 days. Cells were washed and restimulated with 100 ng/mL SEB in combination with 20 µg/mL of the indicated test articles. Supernatants were assayed for IL-2 and IFNγ 24 hours after treatment (depicted respectively in FIGS. 19A and B).

2. In Vitro Assessment of Anti-LAG-3× Anti-PD-1 Bispecific Checkpoint Antibodies a. Assessment of Variant Anti-LAG-3× Anti-PD-1 Bispecifics on T Cell Activation In an SEB-stimulated PBMC assay, PBMCs were treated with 500 ng/mL SEB for 2 days. Cells were then washed and treated with 20 µg/mL of XENP16432 (nivolumab) or XENP22604 and 500 ng/mL SEB. Supernatant was assayed for IL-2 as an indicator of T cell activation (depicted in FIG. 69).

Additional anti-LAG-3×anti-PD-1 bispecific antibodies with optimized 2A11 anti-LAG-3 Fab arms (derived from variant mAbs generated as described in Example 4) were also assessed for T cell activation in an SEB-stimulated PBMC assay. Human PBMCs from multiple donors were stimulated with 500 ng/ml of SEB for 2 days. Cells were then washed twice in culture medium and stimulated with 500 ng/mL SEB in combination with 10 µg/mL of indicated test articles. 24 hours after treatment, cell supernatants were assayed for IL-2 and IFNγ. Data are shown in FIG. 64 for fold increase in IL-2 and IFNγ over NUMAX® bivalent. Each point indicates a donor represented in technical singlet.

The data shows that a number of the anti-LAG-3×anti-PD-1 bispecific antibodies activate T cells more potently than either nivolumab alone or anti-LAG-3 bivalent alone.

3. In Vitro Assessment of Anti-BTLA× Anti-PD-1 Bispecific Checkpoint Antibodies a. T Cell Binding of Bispecific Anti-BTLA× Anti-PD-1 Bispecific Antibodies on CD3+ Cells Anti-BTLA×anti-PD-1 bispecific antibodies with optimized anti-BTLA Fab arms (derived from variants mAbs generated as described in Example 4) were assessed for binding on T cells. Human PBMCs were stimulated with 100 ng/mL SEB for 3 days, after which the PBMCs were treated with the indicated test articles for 30 minutes at 4° C. PBMCs were then incubated with anti-human-Fc secondary antibody for 30 minutes at 4° C. FIG. 47 shows the binding of the indicated test articles on CD3+ cells.

The data show that the anti-PD-1×anti-BTLA bispecific checkpoint antibodies of the invention (e.g. XENP20895, XENP21220 and XENP21221) bind more avidly to T-cells compared to one-armed controls (e.g. XENP21446 and XENP16011). This demonstrates that binding to human T cells is generally better with bispecific antibodies, each arm monovalently binding a different antigen, than monovalent, monospecific antibodies such as the one-armed controls.

b. Assessment of Variant Anti-BTLA× Anti-PD-1 Bispecifics on T Cell Activation

Anti-BTLA×anti-PD-1 bispecific antibodies with prototype anti-BTLA (e.g. 4C7, 8D5 and E8D9) and 9C6 Fab arms were assessed for T cell activation in an SEB-stimulated PBMC assay. Human PBMCs from multiple donors were stimulated with 10 ng/ml of SEB for 72 h with 5 µg/mL or 20 µg/mL as indicated of test articles. Following treatment, cell supernatants were assayed for IL-2 and IFNγ by ELISA, depicted respectively in FIGS. 1J and 1K. The data show that bispecific antibodies comprising the 9C6 hybridoma derived arm enhanced T cell activation not only greater than anti-PD-1 bivalent alone did but also greater than did the bispecifics with the prototype anti-BTLA Fab arms.

An exemplary anti-BTLA×anti-PD-1 XENP21220 and XENP16432 (nivolumab) were assessed in an SEB-stimulated PBMC assay. PBMCs were treated with 500 ng/mL SEB for 2 days. Cells were then washed and treated with 20 µg/mL of XENP16432 or XENP21220 and 500 ng/mL SEB. Supernatant was assayed for IL-2 as an indicator of T cell activation (depicted in FIG. 69).

Additional anti-BTLA×anti-PD-1 bispecifics with variant 9C6 anti-BTLA Fab arms and one-arm variant 9C6 antibodies (alone and in combination with one-arm anti-PD-1 antibody) were assessed for T cell activation in an SEB-stimulated PBMC assay as described above. Data are shown in FIG. 1L for fold increase in IL-2 and IFNγ secretion over treatment with PBS.

4. In Vitro Assessment of Anti-LAG-3× Anti-CTLA-4 Bispecific Checkpoint Antibodies a. T Cell Binding of Bispecific Anti-BTLA× Anti-PD-1 Bispecific Antibodies on CD3+ Cells Anti-LAG-3×anti-CTLA-4 bispecifics with variant anti-LAG-3 Fab arms and one-arm variant anti-LAG-3 antibodies were assessed for binding on T cells. Human PBMCs were stimulated with 100 ng/mL SEB for 3 days, after which the PBMCs were treated with the indicated test articles for 30 minutes at 4° C. Following treatment, PBMCs were incubated with anti-CD3-FITC and anti-human-Fc-APC antibodies for 30 minutes at 4° C. PBMCs were then washed twice and analyzed by flow cytometry. FIG. 56 shows the binding of the indicated test articles on CD3+ T cells.

The data show that a number of the anti-LAG-3×anti-CTLA-4 bispecific checkpoint antibodies of the invention (e.g. XENP22505 and XENP21896) bind more avidly to T-cells compared to one-armed controls (e.g. XENP22516). This demonstrates that binding to human T cells can be better with bispecific antibodies, each arm monovalently binding a different antigen, than monovalent, monospecific antibodies such as the one-armed controls.

b. T Cell Activation by Anti-LAG-3× Anti-CTLA-4 Bispecific Antibodies

Anti-LAG-3×anti-CTLA-4 bispecific antibodies were assessed for T cell activation in MLR and SEB-stimulated PBMC assays.

40 MLR reactions were made in the presence of 20 µg/mL of the indicated test articles, and cell supernatant were assayed 6 days after treatment for IL-2 and IFNγ. FIG. 59 depicts fold induction in IL-2 and IFNγ over anti-RSV bivalent (XENP15074).

In an SEB-stimulated PBMC assay, PBMCs were treated with 500 ng/mL SEB for 2 days. Cells were then washed and treated with 20 µg/mL of XENP16432 (nivolumab), XENP22602 or a combination of XENP16432 and XENP22602 and 500 ng/mL SEB. Supernatant was assayed for IL-2 as an indicator of T cell activation (depicted in FIG. 69).

In another SEB-stimulated PBMC assays, additional anti-LAG-3×anti-CTLA-4 bispecific were assessed. Human PBMCs from multiple donors were stimulated with 500 ng/ml of SEB for 2 days. Cells were then washed twice in culture medium and stimulated with 500 ng/mL SEB in combination with 20 µg/mL of indicated test articles. 24 hours after treatment, cell supernatants were assayed for IL-2 and IFNγ. Data are shown in FIG. 57 and FIG. 58 and FIG. 60 for fold increase in IL-2 and IFNγ over NUMAX® bivalent. Each point indicates a donor represented in technical singlet.

The data is consistent with Example 2D in showing that a combination of anti-PD-1 bivalent and anti-LAG-3× anti-CTLA-4 bispecific exerts synergistic effect in T cell activation. Further, the data show that 7G8 based anti-LAG-3×anti-CTLA-4 bispecific antibodies exhibit more selective function on PBMCs than 2A11 based anti-LAG-3×anti-CTLA-4 bispecific antibodies F. Example 6: In Vivo Assessment of Bispecific Immune Checkpoint Antibodies 1. Anti-CTLA-4× Anti-PD-1 Bispecifics Enhance Engraftment and Disease Activity in Human PBMC-Engrafted NSG Mice In several GVHD studies, exemplary anti-CTLA-4×anti-PD-1 bispecific antibodies of the invention were shown to enhance engraftment and disease activity in human PBMC-engrafted NSG mice.

In a first study, 10 million human PBMCs were engrafted into NSG mice via IV-OSP on Day 0. On day 1, the mice were dosed with XENP16432 (2.89 mg/kg), XENP20053 (2 mg/kg) and a combination of XENP16432 and XENP16433 (2.89+2.92 mg/kg). CD45+ cell counts were measured on Day 14 (depicted in FIG. 70).

Additional anti-CTLA-4×anti-PD-1 bispecifics with variant anti-CTLA-4 Fab and anti-PD-1 scFv arms were assessed. 10 million human PBMCs were engrafted into NSG mice via IV-OSP on Day 0 followed by dosing with the indicated test articles (5 mg/kg or as indicated) on Day 1. CD45+ cell counts were measured on Day 14 (FIG. 1QA, FIG. 1RA and FIG. 1S). IFNγ levels were also measured as an additional indicator of GVHD and plotted against CD45+ cell levels (depicts mixed lymphocyte reaction looking at enhancement of IL-2 release by anti-CTLA-4×anti-PD-1 bispecific antibodies with variant anti-CTLA-4 Fab arms and variant anti-PD-1 scFv arms, as well as nivolumab alone, ipilimumab alone, and a prototype anti-CTLA-4× anti-PD-1 bispecific based on the nivolumab and ipilimumab arms as controls.

FIG. 27 and FIG. 30).

The data show that the anti-PD-1×anti-CTLA-4 bispecific checkpoint antibodies of the invention enhance proliferation of CD45+ cells in human PBMC-engrafted NSG mice as compared to control (PBS+PBMC). Further, enhancement is greater using antibodies of the invention than that seen with nivolumab (XENP16432) alone. FIG. 31 shows the comparison of test article effect on CD45+ cell proliferation between studies 160314 (presented in FIG. 26) and 160331 (presented in FIG. 29). Both studies consistently demonstrate superiority of anti-PD-1×anti-CTLA-4 bispecific checkpoint antibodies over nivolumab alone.

In another study, an anti-CTLA-4×anti-PD-1 bispecific antibody with Xtend Fc was assessed. PBMC-engrafted mice were dosed with indicated test articles at indicated concentrations and CD45+, CD4+ and CD8+ events were measured on Day 14 (depicted in FIG. 20).

2. Anti-BTLA× Anti-PD-1 Bispecifics Enhance Engraftment and Disease Activity in Human PBMC-Engrafted NSG Mice In a first study, 10 million human PBMCs were engrafted into NSG mice via IV-OSP on Day 0. On day 1, the mice were dosed with XENP16432 (2.89 mg/kg) and XENP20895 (5 mg/kg). CD45+ cell counts were measured on Day 14 (depicted in FIG. 70).

Anti-BTLA×anti-PD-1 bispecific XENP20895 was assessed in a second GVHD study. 10 million human PBMCs were engrafted into NSG mice via IV-OSP on Day 0 followed by dosing with the indicated test articles (at concentrations as indicated) on Day 1. CD45+ cell counts and IFNγ were measured on Days 10, 14 and 22 (depicted respectively in FIG. 51).

3. Anti-LAG-3× Anti-PD-1 Bispecifics Enhance Engraftment and Disease Activity in Human PBMC-Engrafted NSG Mice In a GVHD, 10 million human PBMCs were engrafted into NSG mice via IV-OSP on Day 0. On day 1, the mice were dosed with XENP16432 (2.89 mg/kg) and XENP22672 (5 mg/kg). CD45+ cell counts were measured on Day 14 (depicted in FIG. 70).

In the second study described in Example 6A, another exemplary anti-LAG-3×anti-PD-1 (XENP22847) was also assessed (FIG. 20C).

4. Anti-LAG-3× Anti-CTLA-4 Bispecifics Enhance Engraftment and Disease Activity in Human PBMC-Engrafted NSG Mice In a GVHD, 10 million human PBMCs were engrafted into NSG mice via IV-OSP on Day 0. On day 1, the mice were dosed with XENP16432 (2.89 mg/kg), XENP22675 (5 mg/kg) and a combination of XENP16432 and XENP22675 (5+5 mg/kg). CD45+ cell counts were measured on Day 14 (depicted in FIG. 70).

The data shows that XENP22675 enhances engraftment and disease activity over dosing with nivolumab alone. Notably, XENP22675 in combination with nivolumab acts synergistically to further enhance engraftment.

G. Example 7: Anti-PD-1× Anti-CTLA-4 Bispecific Antibodies Exhibit Anti-Tumor Activity in NSG Mice Engrafted with KG1A-Luc Cancer Cells and Human PBMCs NOD SCID gamma (NSG) mice were engrafted with KG1A-luc cancer cells on Day 0. On Day 21, human PBMCs were engrafted into the intraperitoneally into the mice. After PBMC engraftment, indicated test articles were dosed weekly by intraperitoneal injection (control mice were dosed with PBS). Tumor growth was monitored by measuring total flux per mouse using an in vivo imaging system (IVIS® Lumina III) and data are shown (days post 1st dose) in FIG. 71.

XIII. INCORPORATION BY REFERENCE

The claim sets from "Anti-CTLA-4", claim set A1 to A30, "Anti-PD-1", claim set B1 to B30, "Anti-LAG-3", claim set C1 to C28, "Anti-TIM-3", claim set D1 to D28, "Anti-TIGIT", claim set E1 to E28, "Anti-BTLA" claim set F1 to F28, "Backbone plus Fvs", claim set Y1 to Y5, and "Specific molecules", claim set X1 to X16, from U.S. Ser. No. 62/420,500 are expressly incorporated by reference in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10787518B2). An electronic copy of the "Sequence Listing" will also be available from the USPTO upon request and payment of the fee set forth in 37 CFR 1.19(b)(3).

The invention claimed is:

1. A composition comprising a Programmed Cell Death 1 (PD-1) binding domain, the PD-1 binding domain comprising:
   a) a light chain variable domain comprising a vhCDR1 having SEQ ID NO: 37778; a vhCDR2 having SEQ ID NO: 37779, and a vhCDR3 having SEQ ID NO: 37780; and
   b) a heavy chain variable domain comprising a vlCDR1 having SEQ ID NO: 37782, a vlCDR2 having SEQ ID NO: 37783, and a vlCDR3 having SEQ ID NO: 37784.

2. The composition of claim 1, wherein the light chain variable domain has the sequence of SEQ ID NO: 37777 and the heavy chain variable domain has the sequence of SEQ ID NO: 37781.

3. The composition of claim 1, wherein the PD-1 binding domain is a single chain variable fragment (scFv).

4. The composition of claim 3, wherein the scFv has the amino acid sequence of SEQ ID NO: 37785.

5. An antibody comprising a PD-1 binding domain, the PD-1 binding domain comprising:
   a) a light chain variable domain comprising a vhCDR1 having SEQ ID NO: 37778; a vhCDR2 having SEQ ID NO: 37779, and a vhCDR3 having SEQ ID NO: 37780; and
   b) a heavy chain variable domain comprising a vlCDR1 having SEQ ID NO: 37782, a vlCDR2 having SEQ ID NO: 37783, and a vlCDR3 having SEQ ID NO: 37784.

6. The antibody of claim 5, wherein the PD-1 binding domain is an scFv.

7. A bispecific antibody comprising:
   a) a first monomer comprising an anti-PD-1 scFv-linker-CH2-CH3, wherein CH2-CH3 is a first IgG Fc domain and the anti-PD1 scFv comprises a first heavy chain variable domain having the amino acid sequence of SEQ ID NO: 37781, a first light chain variable domain having the amino acid sequence of SEQ ID NO: 37777, and a scFv linker that attaches the first variable heavy chain with the first variable light chain;
   b) a second monomer comprising a VH-CH1-hinge-CH2-CH3, wherein VH is a second heavy chain variable domain and CH2-CH3 is a second IgG Fc domain; and
   c) a light chain comprising a second light chain variable domain, wherein the second heavy chain variable domain and second light chain variable domain form an antigen binding domain.

8. The antibody of claim 7, wherein the anti-PD-1 scFv has the amino acid sequence of SEQ ID NO: 37785.

9. An antibody comprising:
   a) a first monomer comprising a VH1-CH1-linker 1-VL2-scFv linker-VH2-linker 2-CH2-CH3, wherein VL2-scFv linker-VH2 is an anti-PD1 scFV, linker 1 and linker 2 are a first linker and second linker, respectively, and CH2-CH3 is a first IgG Fc domain;
   b) a second monomer comprising a VH1-CH1-hinge-CH2-CH3, wherein VH1 is a first variable heavy domain and CH2-CH3 is a second IgG Fc domain;
   c) a common light chain comprising a first variable light domain (VL1); and
   wherein the first variable heavy domain on the first monomer and the first variable light domain form a first binding domain, and the first variable heavy domain on the second monomer and the first variable light domain form a second binding domain, and
   wherein the VH2 is a second variable heavy domain having the amino acid sequence of SEQ ID NO: 37781 and the VL2 is a second variable light domain having the amino acid sequence of SEQ ID NO: 37777.

10. The heterodimeric antibody of claim 9, wherein the anti-PD-1 scFv has the amino acid sequence of SEQ ID NO: 37785.

11. A nucleic acid composition comprising:
    a) a first nucleic acid encoding the heavy chain variable domain of claim 1; and
    b) a second nucleic acid encoding the light chain variable domain of claim 1.

12. An expression vector composition comprising:
    a) a first expression vector comprising the first nucleic acid of claim 11; and
    b) a second expression vector comprising the second nucleic acid of claim 11.

13. A host cell comprising the expression vector composition of claim 12.

14. A nucleic acid composition comprising:
    a) a first nucleic acid encoding the first monomer of claim 7;
    b) a second nucleic acid encoding the second monomer of claim 7; and
    c) a third nucleic acid encoding the light chain of claim 7.

15. An expression vector composition comprising:
    a) a first expression vector comprising the first nucleic acid of claim 14;
    b) a second expression vector comprising the second nucleic acid of claim 14; and
    c) a third expression vector comprising the third nucleic acid of claim 14.

16. A host cell comprising the expression vector composition of claim 15.

17. A nucleic acid composition comprising:
a) a first nucleic acid encoding the first monomer of claim 9;
b) a second nucleic acid encoding the second monomer of claim 9; and
c) a third nucleic acid encoding the common light chain of claim 9.

18. An expression vector composition comprising:
a) a first expression vector comprising the first nucleic acid of claim 17;
b) a second expression vector comprising the second nucleic acid of claim 17; and
c) a third expression vector comprising the third nucleic acid of claim 17.

19. A host cell comprising the expression vector composition of claim 18.

* * * * *